United States Patent
Stansfield et al.

(10) Patent No.: US 11,001,569 B2
(45) Date of Patent: May 11, 2021

(54) 6-MEMBERED HETEROAROMATIC SUBSTITUTED CYANOINDOLINE DERIVATIVES AS NIK INHIBITORS

(71) Applicant: Janssen Pharmaceutica NV, Beerse (BE)

(72) Inventors: Ian Stansfield, Issy-les Moulineaux (FR); Olivier Alexis Georges Querolle, Issy-les Moulineaux (FR); Gerhard Max Gross, Beerse (BE); Edgar Jacoby, Beerse (BE); Lieven Meerpoel, Beerse (BE); Janusz Jozef Kulagowski, Harlow (GB); Calum Macleod, Harlow (GB); Samuel Edward Mann, Harlow (GB); Simon Richard Green, Harlow (GB); George Hynd, Harlow (GB)

(73) Assignee: Janssen Pharmaceutica NV, Beerse (BE)

( * ) Notice: Subject to any disclaimer, the term of this patent is extended or adjusted under 35 U.S.C. 154(b) by 123 days.

(21) Appl. No.: 16/071,298

(22) PCT Filed: Jan. 20, 2017

(86) PCT No.: PCT/EP2017/051160
§ 371 (c)(1),
(2) Date: Jul. 19, 2018

(87) PCT Pub. No.: WO2017/125534
PCT Pub. Date: Jul. 27, 2017

(65) Prior Publication Data
US 2020/0109129 A1  Apr. 9, 2020

(30) Foreign Application Priority Data

Jan. 22, 2016 (EP) .................................. 16152414
Jan. 22, 2016 (EP) .................................. 16152415
Mar. 10, 2016 (EP) .................................. 16159658
Mar. 10, 2016 (EP) .................................. 16159659

(51) Int. Cl.
| | | |
|---|---|---|
| *C07D 401/14* | (2006.01) | |
| *C07D 403/14* | (2006.01) | |
| *C07D 405/14* | (2006.01) | |
| *C07D 413/14* | (2006.01) | |
| *A61P 35/00* | (2006.01) | |

(52) U.S. Cl.
CPC ......... *C07D 401/14* (2013.01); *C07D 403/14* (2013.01); *C07D 405/14* (2013.01); *C07D 413/14* (2013.01)

(58) Field of Classification Search
CPC ........................... C07D 401/14; C07D 403/14
See application file for complete search history.

(56) References Cited

U.S. PATENT DOCUMENTS

2019/0119299 A1   4/2019  Stansfield et al.

FOREIGN PATENT DOCUMENTS

| WO | WO-0160816 A1 | 8/2001 |
|---|---|---|
| WO | WO-0164643 A2 | 9/2001 |
| WO | WO-02079197 A1 | 10/2002 |
| WO | WO-02102313 A2 | 12/2002 |
| WO | WO-03030909 A1 | 4/2003 |
| WO | WO-2009158011 A1 | 12/2009 |
| WO | WO-2009158571 A1 | 12/2009 |
| WO | WO-2010042337 A1 | 4/2010 |
| WO | WO-2011022440 A2 | 2/2011 |
| WO | WO-2011153553 A2 | 12/2011 |
| WO | WO-2012016217 A1 | 2/2012 |
| WO | WO-2014174021 A1 | 10/2014 |
| WO | WO-2015030847 A1 | 3/2015 |
| WO | WO-2015044267 A1 | 4/2015 |
| WO | WO-2015044269 A1 | 4/2015 |

(Continued)

OTHER PUBLICATIONS

Herrington et al. Journal of Biomolecular Screening 2016, vol. 21(3) 223-242. (Year: 2016).*
Vrabel et al. Blood Reviews vol. 34 p. 56-66. (Year: 2019).*
Cancer [online]; Retrieved from the Internet, URL: http://www.nim.nih.gov/medlineplus/cancer.html (2007). (pp. 1-10).
Golub et al.: Molecular Classification of Cancer: Class Discovery and Class Prediction by Gene Expression Monitoring; Science 286; 531-537 (1999).
International Application No. PCT/EP2017/066120 International Preliminary Report on Patentability dated Jan. 1, 2019.

(Continued)

*Primary Examiner* — Emily A Bernhardt

(57) ABSTRACT

The present invention relates to pharmaceutical agents of formula (I), useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, and to the use of such compounds or pharmaceutical compositions for the prevention or treatment of diseases such as a cancer, inflammatory disorders, metabolic disorders including obesity and diabetes, and autoimmune disorders.

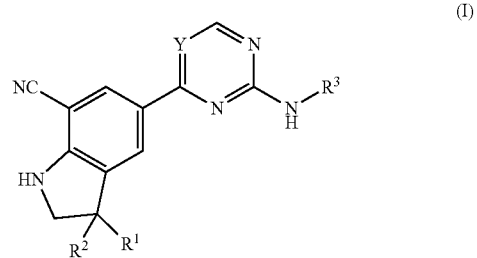

(I)

8 Claims, No Drawings

(56) References Cited

FOREIGN PATENT DOCUMENTS

| WO | WO-2015154039 A2 | 10/2015 |
|---|---|---|
| WO | WO-2015176135 A1 | 11/2015 |
| WO | WO-2016022645 A1 | 2/2016 |
| WO | WO-2017114510 A1 | 7/2017 |
| WO | WO-2017125530 A1 | 7/2017 |
| WO | WO-2017125534 A1 | 7/2017 |
| WO | WO-2017161028 A1 | 9/2017 |
| WO | WO-2018002217 A1 | 1/2018 |
| WO | WO-2018002219 A1 | 1/2018 |

OTHER PUBLICATIONS

Lala et al.: Role of nitric oxide in tumor progression: Lessons from experimental tumors; Cancer and Metastasis Reviews; 17; 91-106 (1999).
International Application No. PCT/EP2017/066125 International Preliminary Report on Patentability dated Jan. 1, 2019.
U.S. Appl. No. 16/309,080 Office Action dated May 29, 2019.
Allen et al. NLRP12 suppresses colon inflammation and tumorigenesis through the negative regulation of noncanonical NF-kB signaling. Immunity. 36: 742-754 (2012).
Annuziata et al. Frequent engagement of the classical and alternative NF-kB pathways by diverse genetic abnormalities in multiple myeloma. Cancer Cell. 12: 115-130 (2007).
Aya et al. NF-κB-inducing kinase controls lymphocyte and osteoclast activities in inflammatory arthritis. J. Clin. Invest. 115: 1848-1854 (2005).
Bhattacharyya et al. Tumor necrosis factor-induced inflammation is increased but apoptosis is inhibited by common food additive carrageenan. J Biol. Chem. 285: 39511-39522 (2011).
Bitar et al. Inflammation and apoptosis in aortic tissues of aged type II diabetes: Amelioration with α-lipoic acid through phosphatidylinositol 3-kinase/Akt-dependent mechanism. Life Sci. 86: 844-853 (2010).
Bushell et al., Genetic inactivation of TRAF3 in canine and human B-cell lymphoma. Blood. 125: 999-1005 (2015).
Choudhary et al. NF-B-Inducing Kinase (NIK) mediates skeletal muscle insulin resistance: blockade by adiponectin. Endocrinology. 152: 3622-3627 (2011).
Chung et al. NF-kB Inducing Kinase, NIK mediates cigarette smoke/ TNFa-induced histone acetylation and inflammation through differential activation of IKKs. PLoS One. 6(8): e23488. doi:10.1371/journal.pone.0023488 (2011). (14 pages).
Demchenko et al. Classical and/or alternative NF-κB pathway activation in multiple myeloma. Blood. 115: 3541-3552 (2010).
Gennaro et al. Remington's Pharmaceutical Sciences (18th ed., Mack Publishing Company, 1990, see especially Part 8 : Pharmaceutical preparations and their Manufacture (1990). (284 pages).
Hughes et al., 4-Aryl-5-cyano-2-aminopyrimidines as VEGF-R2 inhibitors: synthesis and biological evaluation.Bioorg Med Chem Lett. 17(12):3266-3270 (2007).
Keats et al. Promiscuous mutations activate the noncanonical NF-kB pathway in multiple myeloma. Cancer Cell. 12: 131-144 (2007).
Nishina et al. Biochem. Bioph. Res. Co. NIK is involved in constitutive activation of the alternative NF-jB pathway and proliferation of pancreatic cancer cells. 388: 96-101 (2009).
Pham et al. Constitutive BR3 receptor signaling in diffuse, large B-cell lymphomas stabilizes nuclear factor-B-inducing kinase while activating both canonical and alternative nuclear factor-B pathways. Blood. 117: 200-210 (2011).
Rahal et al., Pharmacological and genomic profiling identifies NF-κB-targeted treatment strategies for mantle cell lymphoma. Nature Med. 1: 87-92 (2014).
Ranuncolo et al. Hodgkin lymphoma requires stabilized NIK and constitutive RelB expression for survival. Blood First Edition Paper. DOI 10.1182/blood-2012-01-405951 (2012).
Rosebeck et al. Cleavage of NIK by the API2-MALT1 fusion oncoprotein leads to noncanonical NF-kB activation. Science. 331: 468-472 (2011).
Saitoh et al. Overexpressed NF-B-inducing kinase contributes to the tumorigenesis of adult T-cell leukemia and Hodgkin Reed-Sternberg cells. Blood. 111: 5118-5129 (2008).
Shuto et al. Activation of NF-kB by nontypeable Hemophilus influenzae is mediated by toll-like receptor 2-TAK1-dependent NIK-IKKayb-IkBa and MKK3y6-p38 MAP kinase signaling pathways in epithelial cells. PNAS. 98: 8774-8779 (2001).
PCT/EP2017/066125 International Search Report and Written Opinion dated Jul. 27, 2017.
PCT/EP2017/051150 International Preliminary Report on Patentability dated Jul. 24, 2018.
PCT/EP2017/051150 International Search Report and Written Opinion dated Mar. 2, 2017.
PCT/EP2017/051160 International Preliminary Report on Patentability dated Jul. 24, 2018.
PCT/EP2017/051160 International Search Report and Written Opinion dated Sep. 3, 2017.
PCT/EP2017/066120 International Search Report and Written Opinion dated Aug. 23, 2017.
T. W. Greene and P. G. M. Wuts, Protective Groups in Organic Synthesis, 4th ed., Wiley, Hoboken, New Jersey, 2007. (112 pages).
Thu and Richmond, NF-κB inducing kinase: a key regulator in the immune system and in cancer. Cytokine Growth F. R. 21: 213-226 (2010).
Thu et al. NF-jB inducing kinase (NIK) modulates melanoma tumorigenesis by regulating expression of pro-survival factors through the b-catenin pathway. Oncogene. 31(20), 2580-2592 (2012).
Wixted et al. A model to identify novel targets involved in oxidative stress-induced apoptosis in human lung epithelial cells by RNA interferenceToxicol. In Vitro. 24: 310-318 (2010).
Yamamoto et al. Epigenetic alteration of the NF-jB-inducing kinase (NIK) gene is involved in enhanced NIK expression in basal-like breast cancer. Cancer Sci. 101: 2391-2397 (2010).
Yang et al. NIK stabilization in osteoclasts results in osteoporosis and enhanced inflammatoryosteolysis. PLoS One. 5(11): e15383. doi:10.1371/journal.pone.0015383 (2010). (9 pages).
Zhao et al. NF-κB-Inducing kinase increases renal tubule epithelial inflammation associated with diabetes. Exp. Diabetes Res. 2011: 1-9 (2011).
G. McMahon, "VEGF Receptor Signaling in Tumor Angiogenesis", The Oncologist, (2000), vol. 5, suppl. 1, pp. 3-10.
H.M. Pinedo, et al., "Translational Research: The Role of VEGF in Tumor Angiogenesis", The Oncologist, (2000), vol. 5, suppl. 1, pp. 1-2.

\* cited by examiner

6-MEMBERED HETEROAROMATIC SUBSTITUTED CYANOINDOLINE DERIVATIVES AS NIK INHIBITORS

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer (in particular B-cell malignancies including leukemias, lymphomas and myeloma), inflammatory disorders, metabolic disorders including obesity and diabetes, and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, adhesion, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK is indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF2 and TRAF3), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226)

Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *Cancer Cell* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129). It has been demonstrated that the API2-MALT1 fusion oncoprotein created by the recurrent translocation t(11; 18)(q21; q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11; 18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210). More recently, also loss-of-function mutations in TRAF3 have been characterized in human and canine DLBCL (Bushell et al., *Blood* 2015, 125, 999-1005).

Recently, similar mutations in the non-cannonical NFkB signaling pathway (TRAF2, TRAF3, NIK, BIRC3) were found in ibrutinib-refractory mantle cell lymphoma cell lines (Rahal et al., *Nat Med* 2014, 1, 87-92).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010, 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2012, 31(20), 2580-92). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable Hemophilus influenza (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al. *PLoS ONE* 2011, 6(8): e23488. doi:10.1371/journal.pone.0023488). A shRNA screen was used in an in vitro model of oxidative stress induced cell death (as a model of COPD) to interrogate a human druggable genome siRNA library in order to identify genes that modulate the cellular response to stress. NIK was one of the genes identified in this screen as a potential new therapeutic target to modulate epithelial apoptosis in chronic lung diseases (Wixted et al. *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2 g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS ONE* 2010, 5(11): e15383. doi:10.1371/journal.pone.0015383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune responses and alloresponses, like GVHD (Graft Versus Host Disease) and transplant rejection, without crippling the immune system as severely as do inhibitors of canonical NF-κB activation.

WO2003030909 describes the preparation of 2- and 4-aminopyrimidines N-substituted by a bicyclic ring for use as kinase inhibitors in the treatment of cancer.

WO2002079197 describes 4-aryl-substituted 2-pyrimidinamines and 2-pyridinamines, useful as inhibitors of c-Jun N-terminal kinases (JNK) and other protein kinases.

DESCRIPTION OF THE INVENTION

The present invention concerns novel compounds of Formula (I):

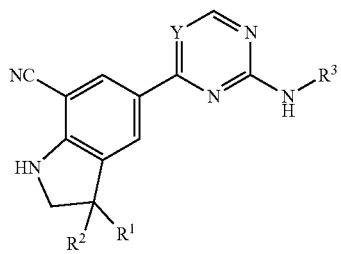

(I)

tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$ or N;

$R^4$ represents hydrogen or halo;

$R^5$ represents halo, $Het^{3a}$, $-NR^{6a}R^{6b}$, or $-OR^7$;

$R^{6a}$ represents hydrogen or $C_{1-4}$alkyl;

$R^{6b}$ represents hydrogen; $C_{1-4}$alkyl; $C_{3-6}$cycloalkyl; $-C(=O)-C_{1-4}$alkyl; $-C(=O)-Het^4$; $-S(=O)_2-C_{1-4}$alkyl; $-C(=O)-C_{1-4}$alkyl substituted with one substituent selected from the group consisting of $-OH$ and $-NR^{16a}R^{16b}$; or $C_{1-4}$alkyl substituted with one substituent selected from the group consisting of $-OH$ and $-S(=O)_2-C_{1-4}$alkyl;

$R^7$ represents hydrogen, $C_{1-4}$alkyl, $-C_{1-4}$alkyl-$NR^{8a}R^{8b}$, $-C(=O)-R^9$, $-S(=O)_2-OH$, $-P(=O)_2-OH$, $-(C=O)-CH(NH_2)-C_{1-4}$alkyl-$Ar^1$, or $-C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of $-NH_2$, $-COOH$, and $Het^6$;

$R^{16a}$ and $R^{16b}$ each independently represents hydrogen, $C_{1-4}$alkyl or $C_{3-6}$cycloalkyl;

$R^3$ represents a 6-membered heteroaromatic ring containing 1 or 2 N-atoms, optionally substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-S(=O)(=N-R^{20a})-C_{1-4}$alkyl; $-O-C_{1-4}$alkyl substituted with one, two or three halo atoms; $-O-C_{1-4}$alkyl-$R^{12}$; $C_{3-6}$cycloalkyl; $-O-C_{3-6}$cycloalkyl; $Het^{1a}$; $-O-Het^{1b}$; $R^{18}$; $R^{21}$; $-P(=O)-(C_{1-4}$alkyl$)_2$; $-NH-C(=O)-C_{1-4}$alkyl; $-NH-C(=O)-Het^{1g}$; $-NR^{17a}R^{17b}$; $C_{1-4}$alkyl substituted with one, two or three halo atoms; $C_{1-4}$alkyl substituted with one, two or three $-OH$ substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$; or $R^3$ represents 2-oxo-1,2-dihydropyridin-3-yl, wherein said 2-oxo-1,2-dihydropyridin-3-yl may optionally be substituted on the N-atom with a substituent selected from the group consisting of $C_{1-6}$alkyl; $C_{3-6}$cycloalkyl; $Het^{1a}$; $R^{18}$; $R^{21}$; $C_{1-4}$alkyl substituted with one, two or three halo atoms; $C_{1-4}$alkyl substituted with one, two or three $-OH$ substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 2-oxo-1,2-dihydropyridin-3-yl, said $Het^{1a}$ or $R^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-S(=O)(=N-R^{20a})-C_{1-4}$alkyl; $-O-C_{1-4}$alkyl substituted with one, two or three halo atoms; $-O-C_{1-4}$alkyl-$R^{12}$; $C_{3-6}$cycloalkyl; $-O-C_{3-6}$cycloalkyl; $Het^{1a}$; $-O-Het^{1b}$; $R^{18}$; $R^{21}$; $-P(=O)-(C_{1-4}$alkyl$)_2$; $-NH-C(=O)-C_{1-4}$alkyl; $-NH-C(=O)-Het^{1a}$; $-NR^{17a}R^{17b}$; $C_{1-4}$alkyl substituted with one, two or three halo atoms; $C_{1-4}$alkyl substituted with one, two or three $-OH$ substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$;

$R^{10}$ represents $-OH$, $-O-C_{1-4}$alkyl, $-NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of $-OH$ and $-O-C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of $-OH$, halo, $C_{1-4}$alkyl, cyano, $-C(=O)-C_{1-4}$alkyl, $-O-C_{1-4}$alkyl, $-NH_2$, $-NH(C_{1-4}$alkyl), and $-N(C_{1-4}$alkyl$)_2$;

$Het^{1b}$, $Het^{1e}$, $Het^{1g}$, $Het^4$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^4$, $Het^7$ and $Het^8$ containing one or two heteroatoms each independently selected from O, S, $S(=O)_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of $-OH$ and $-O-C_{1-4}$alkyl; and wherein said 4- to 7-membered monocyclic saturated heterocyclyl may optionally be substituted on one, two or three ring C-atoms with one or two substituents each independently selected from the group consisting of $-OH$, halo, $C_{1-4}$alkyl, cyano, —C(═O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1):

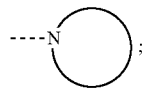
(b-1)

(b-1) represents a N-linked 4- to 7-membered monocyclic saturated heterocyclyl optionally containing one additional heteroatom selected from O, S, S(═O)$_p$ and N, or a N-linked 6- to 11-membered bicyclic saturated heterocyclyl, including fused, spiro and bridged cycles, optionally containing one or two additional heteroatoms each independently selected from O, S, S(═O)$_p$ and N;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and Het$^7$; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

R$^{11b}$ represents hydrogen; Het$^{1e}$; $C_{1-4}$alkyl; —$C_{1-4}$alkyl-Het$^5$; —$C_{1-4}$alkyl-Het$^8$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

R$^{13}$ represents —O—$C_{1-4}$alkyl, —C(═O)NR$^{15a}$R$^{15b}$, —NR$^{19a}$R$^{19b}$, $C_{3-6}$cycloalkyl, Het$^{1d}$, or —C(═O)—Het$^{1f}$;

R$^{12}$ represents —OH, —O—$C_{1-4}$alkyl, —NR$^{14a}$R$^{14b}$, —C(═O)NR$^{14c}$R$^{14d}$, —S(═O)$_2$—$C_{1-4}$alkyl, —S(═O)(═N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

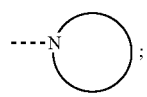
(c-1)

(c-1) represents a N-linked 4- to 7-membered monocyclic saturated heterocyclyl optionally containing one additional heteroatom selected from O, S, S(═O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

R$^{11a}$, R$^{14n}$, R$^{14c}$, R$^{15a}$, R$^{17a}$ and R$^{19a}$ each independently represents hydrogen or $C_{1-4}$alkyl;

R$^{14b}$, R$^{14d}$, R$^{15b}$, R$^{17b}$ and R$^{19b}$ each independently represents hydrogen; $C_{1-4}$alkyl; $C_{3-6}$cycloalkyl; —C(═O)—$C_{1-4}$alkyl; $C_{1-4}$alkyl substituted with one substituent selected from the group consisting of halo, —OH and —O—$C_{1-4}$alkyl; —C(═O)—$C_{1-4}$alkyl substituted with one substituent selected from the group consisting of halo, —OH and —O—$C_{1-4}$alkyl; or —S(═O)$_2$—$C_{1-4}$alkyl;

R$^{20a}$ and R$^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention also relates to a pharmaceutical composition comprising a therapeutically effective amount of a compound of Formula (I), a pharmaceutically acceptable addition salt, or a solvate thereof, and a pharmaceutically acceptable carrier or excipient.

Additionally, the invention relates to a compound of Formula (I), a pharmaceutically acceptable addition salt, or a solvate thereof, for use as a medicament, and to a compound of Formula (I), a pharmaceutically acceptable addition salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable addition salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable addition salt, or a solvate thereof, in combination with an additional pharmaceutical agent for use in the treatment or prevention of cancer, inflammatory disorders, autoimmune disorders, and metabolic disorders such as diabetes and obesity. Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable addition salt, or a solvate thereof.

The invention also relates to a product comprising a compound of Formula (I), a pharmaceutically acceptable addition salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity. Additionally, the invention relates to a method of treating or preventing a cell proliferative disease in a warm-blooded animal which comprises administering to the said animal an effective amount of a compound of Formula (I), a pharmaceutically acceptable addition salt, or a solvate thereof, as defined herein, or a pharmaceutical composition or combination as defined herein.

Some of the compounds of the present invention may undergo metabolism to a more active form in vivo (prodrugs).

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term "$C_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term "$C_{2-6}$alkynyl" as used herein as a group or part of a group represents a straight or branched chain hydrocarbon group having from 2 to 6 carbon atoms and containing a carbon carbon triple bond.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In general, whenever the term "substituted" is used in the present invention, it is meant, unless otherwise is indicated or is clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, where possible and unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent), for example in saturated heterocyclyl groups or 5-membered aromatic rings as used in the definition of $R^{18}$.

C(O) or C(=O) represents a carbonyl moiety.

S(=O)$_2$ or SO$_2$ represents a sulfonyl moiety.

The skilled person will understand that —S(=O)(=N—$R^{20a}$)—$C_{1-4}$alkyl corresponds with

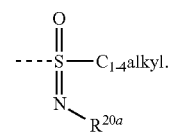

Within the context of this invention 'saturated' means 'fully saturated', if not otherwise specified.

Het$^{1a}$, Het$^{1c}$ and Het$^{1d}$, may be attached to the remainder of the molecule of Formula (I) through any available ring carbon or nitrogen atom as appropriate, if not otherwise specified.

The 5-membered aromatic ring containing one, two or three N-atoms as referred to in the definition of $R^{18}$, may be attached to the remainder of the molecule of Formula (I) through any available ring carbon or nitrogen atom as, if not otherwise specified.

It will be clear that in case a saturated cyclic moiety is substituted on two ring carbon atoms with one substituent, in total two carbon-linked substituents are present on the saturated cyclic moiety (one substituent on each carbon atom).

It will be clear that in case a saturated cyclic moiety is substituted on two ring carbon atoms with two substituents, in total four carbon-linked substituents are present on the saturated cyclic moiety (two substituents on each carbon atom).

It will be clear that in case a saturated cyclic moiety is substituted on three ring carbon atoms with two substituents, in total six carbon-linked substituents are present on the saturated cyclic moiety (two substituents on each carbon atom).

It will be clear that in case a saturated cyclic moiety is substituted on two ring N-atoms with a substituent, in total two N-linked substituents are present on the saturated cyclic moiety (a substituent on each N-atom).

It will be clear that a saturated cyclic moiety may, where possible, have substituents on both carbon and N-atoms, unless otherwise is indicated or is clear from the context.

It will also be clear that $R^3$ representing 2-oxo-1,2-dihydropyridin-3-yl, may have substituents on both carbon and N-atoms, unless otherwise is indicated or is clear from the context.

Within the context of this invention, bicyclic saturated heterocyclyl groups include fused, spiro and bridged saturated heterocycles.

Fused bicyclic groups are two cycles that share two atoms and the bond between these atoms.

Spiro bicyclic groups are two cycles that are joined at a single atom.

Bridged bicyclic groups are two cycles that share more than two atoms.

Examples of N-linked 6- to 11-membered fused bicyclic saturated heterocyclyl groups, include, but are not limited to

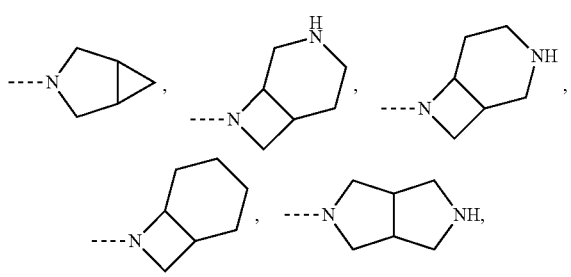

and the like.

Examples of N-linked 6- to 11-membered spiro bicyclic saturated heterocyclyl groups, include, but are not limited to

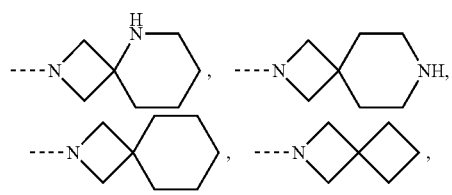

and the like.

Examples of N-linked 6- to 11-membered bridged bicyclic saturated heterocyclyl groups, include, but are not limited to

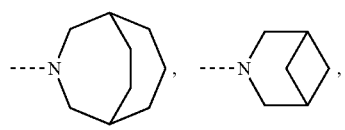

and the like.

The skilled person will realize that the definition of $Het^{1a}$, $Het^{1c}$ and $Het^{1d}$ also includes C-linked bicycles (attached to the remainder of the molecule of Formula (I) through any available ring carbon atom).

It should be understood that the exemplified bicyclic saturated heterocyclyl groups referred to above may optionally be substituted, where possible, on carbon and/or nitrogen atoms according to any of the embodiments.

Non-limiting examples of 4- to 7-membered monocyclic saturated heterocyclyl moieties containing one or two heteroatoms each independently selected from O, S, S(=O) and N (as in the definition of $Het^{1a}$, $Het^{1c}$, and $Het^{1d}$) are shown below:

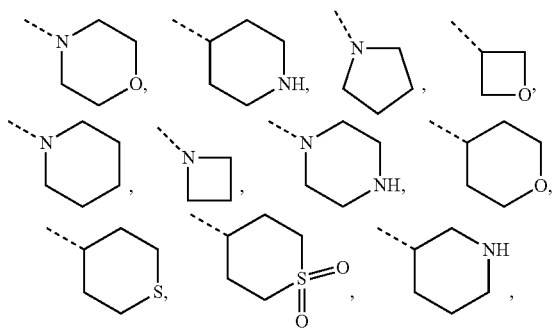

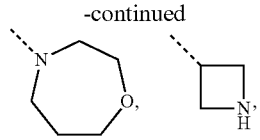

and the like.

Each of which may optionally be substituted, where possible, on carbon and/or nitrogen atoms according to any of the embodiments.

Non-limiting examples of 4- to 7-membered monocyclic saturated heterocyclyl moieties, attached to the remainder of the molecule of Formula (I) through any available ring carbon atom (C-linked), and containing one or two heteroatoms each independently selected from O, S, S(=O), and N (as in the definition of $Het^{1b}$, $Het^{1e}$, $Het^{1g}$, $Het^4$, $Het^7$ and $Het^8$) are shown below:

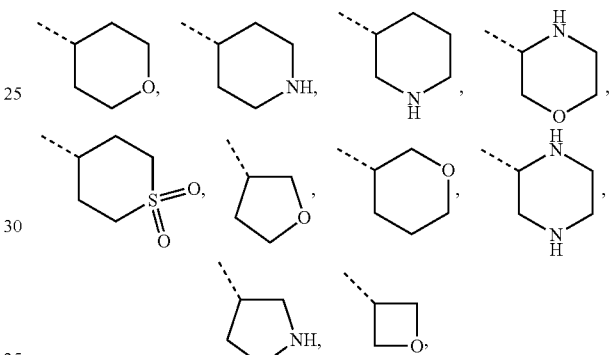

and the like.

Each of which may optionally be substituted, where possible, on carbon and/or nitrogen atoms according to any of the embodiments.

Non-limiting examples of N-linked 4- to 7-membered monocyclic saturated heterocyclyl moieties optionally containing one additional heteroatom selected from O, S, $S(=O)_p$ and N (as in the definition of (b-1) and (c-1)) are shown below:

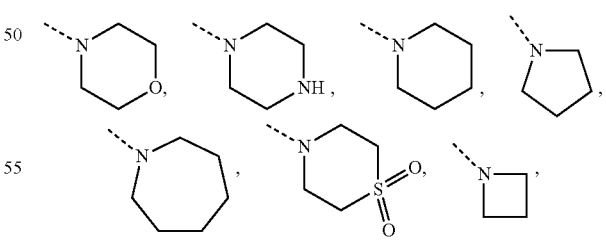

and the like.

Each of which may optionally be substituted, where possible, on carbon and/or nitrogen atoms according to any of the embodiments.

Non-limiting examples of 5-membered aromatic ring containing one, two or three N-atoms as referred to in the definition of $R^{18}$ are shown below:

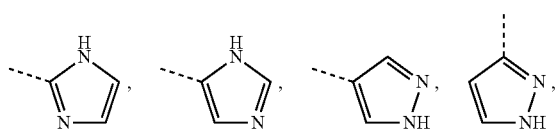

and the like.

Each of which may optionally be substituted, where possible, on carbon and/or nitrogen atoms according to any of the embodiments.

Non-limiting examples of 6-membered heteroaromatic rings containing 1 or 2 N-atoms (as in the definition of $R^3$) are pyridinyl, pyrimidinyl, pyridazinyl or pyrazinyl; particular non-limiting examples are 2-pyridinyl, 3-pyridinyl, 4-pyridinyl, 5-pyrimidinyl, 4-pyrimidinyl, 4-pyridazinyl or 2-pyrazinyl; each of which may optionally be substituted according to any of the embodiments.

Whenever substituents are represented by chemical structure, "- - -" represents the bond of attachment to the remainder of the molecule of Formula (I).

Lines (such as "- - -") drawn into ring systems indicate that the bond may be attached to any of the suitable ring atoms.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable addition salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention.

It follows that a single compound may exist in both stereoisomeric and tautomeric form.

Pharmaceutically-acceptable addition salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl, or $C_{1-6}$alkyl substituted with one $R^5$;
Y represents $CR^4$ or N;
$R^4$ represents hydrogen or halo;
$R^5$ represents halo, $Het^{3a}$, —$NR^{6a}R^{6b}$, or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —$NH_2$, —COOH, and $Het^6$;
$R^{16a}$ and $R^{16b}$ each independently represents hydrogen, $C_{1-4}$alkyl or $C_{3-6}$cycloalkyl;
$R^3$ represents 2-oxo-1,2-dihydropyridin-3-yl,
wherein said 2-oxo-1,2-dihydropyridin-3-yl may optionally be substituted on the N-atom with a substituent selected from the group consisting of $C_{1-6}$alkyl; $C_{3-6}$cycloalkyl; $Het^{1a}$; $R^{18}$; $R^{21}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 2-oxo-1,2-dihydropyridin-3-yl, said $Het^{1a}$ or $R^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—$(C_{1-4}$alkyl$)_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^{1b}$, $Het^{1e}$, $Het^{1g}$, $Het^4$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^4$, $Het^7$ and $Het^8$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^2$ represents a heterocyclyl of formula (b-1):

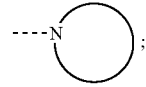

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; —$C_{1-4}$alkyl-$Het^5$; —$C_{1-4}$alkyl-$Het^8$; $C_{1-4}$alkyl substituted with one, two or three substituents each independently selected from the group consisting of halo, —OH and —O—$C_{1-4}$ alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1):

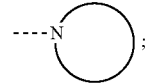

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17b}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$ or N;

$R^4$ represents hydrogen or halo;

$R^5$ represents halo, $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-Ar, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, —COOH, and $Het^6$;

$R^{16a}$ and $R^{16b}$ each independently represents hydrogen, $C_{1-4}$alkyl or $C_{3-6}$cycloalkyl;

$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^{1b}$, $Het^{1e}$, $Het^{1g}$, $Het^4$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^4$, $Het^7$ and $Het^8$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^2$ represents a heterocyclyl of formula (b-1):

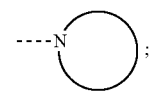

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; —$C_{1-4}$alkyl-$Het^5$; —$C_{1-4}$alkyl-$Het^8$; $C_{1-4}$alkyl substituted with one, two or three substituents each independently selected from the group consisting of halo, —OH and —O—$C_{1-4}$ alkyl; $C_{3-6}$cycloalkyl; or $C_{3-6}$cycloalkyl substituted with one, two or three substituents each independently selected from the group consisting of halo,
—OH and —O—$C_{1-4}$alkyl;
$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;
$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$, or $Het^{1c}$;
$Ar^1$ represents phenyl optionally substituted with one hydroxy;
$Ar^2$ represents phenyl optionally substituted with one $C_{1-4}$alkyl;
$Het^{3a}$, $Het^{3b}$, $Het^5$, $Het^6$ and $Het^{1f}$ each independently represents a heterocyclyl of formula (c-1):

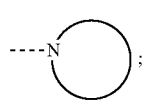

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and
wherein (c-1) may optionally be substituted on one or two ring C-atoms atoms with one or two substituents each independently selected from the group consisting of halo, $C_{1-4}$alkyl, and $C_{3-6}$cycloalkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;
$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —$NH_2$, —COOH, and $Het^6$;
$R^{16a}$ and $R^{16b}$ each independently represents hydrogen, $C_{1-4}$alkyl or $C_{3-6}$cycloalkyl;
$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; or
$R^3$ represents 2-oxo-1,2-dihydropyridin-3-yl,
wherein said 2-oxo-1,2-dihydropyridin-3-yl may optionally be substituted on the N-atom with a substituent selected from the group consisting of $C_{1-6}$alkyl; $C_{3-6}$cycloalkyl; $Het^{1a}$; $R^{18}$; $R^{21}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 2-oxo-1,2-dihydropyridin-3-yl, said $Het^{1a}$ or $R^{18}$ are attached to the N-atom via a ring carbon atom; and
wherein said 2-oxo-1,2-dihydropyridin-3-yl may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$ alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;
$R^{10}$ represents —OH, —O—$C_{1-4}$alkyl, —NR $11^a R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;
$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, $S(=O)_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^2$ represents a heterocyclyl of formula (b-1):

(b-1) represents a N-linked 4- to 7-membered monocyclic saturated heterocyclyl optionally containing one additional heteroatom selected from O, S, $S(=O)_p$ and N, or a N-linked 6- to 11-membered bicyclic saturated heterocyclyl, including fused, spiro and bridged cycles, optionally containing one or two additional heteroatoms each independently selected from O, S, $S(=O)_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; —$C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, $Het^{1d}$, or —C(=O)—$Het^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O) (=N—R$^{20b}$)—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1):

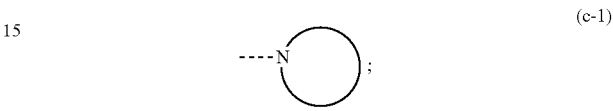

(c-1) represents a N-linked 4- to 7-membered monocyclic saturated heterocyclyl optionally containing one additional heteroatom selected from O, S, $S(=O)_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents $Het^{3a}$, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, —COOH, and Het$^6$;

$R^{16a}$ and $R^{16b}$ each independently represents hydrogen, $C_{1-4}$alkyl or $C_{3-6}$cycloalkyl;

$R^3$ represents 2-oxo-1,2-dihydropyridin-3-yl, wherein said 2-oxo-1,2-dihydropyridin-3-yl may optionally be substituted on the N-atom with a substituent selected from the group consisting of $C_{1-6}$alkyl; $C_{3-6}$cycloalkyl; Het$^{1a}$; $R^{18}$; $R^{21}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of the 2-oxo-1,2-dihydropyridin-3-yl, said Het$^{1a}$ or $R^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; $R^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1):

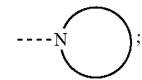

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; Het$^{1e}$; $C_{1-4}$alkyl; —$C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

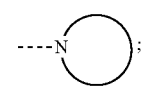

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with C$_{1-4}$alkyl or C$_{3-6}$cycloalkyl; and wherein (c-1) may optionally be substituted on one or two ring C-atoms atoms with one or two substituents each independently selected from the group consisting of halo, C$_{1-4}$alkyl, and C$_{3-6}$cycloalkyl;

R$^{11a}$, R$^{14a}$, R$^{14c}$, R$^{15a}$, R$^{17a}$ and R$^{19a}$ each independently represents hydrogen or C$_{1-4}$alkyl;

R$^{14b}$, R$^{14d}$, R$^{15b}$, R$^{17b}$ and R$^{19b}$ each independently represents hydrogen; C$_{1-4}$alkyl; C$_{3-6}$cycloalkyl; or C$_{1-4}$alkyl substituted with one substituent selected from the group consisting of halo, —OH and —O—C$_{1-4}$alkyl;

R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^1$ represents C$_{1-4}$alkyl;

R$^2$ represents C$_{1-6}$alkyl, or C$_{1-6}$alkyl substituted with one R$^5$;

Y represents CR$^4$;

R$^4$ represents hydrogen or halo;

R$^5$ represents Het$^{3a}$, —NR$^{6a}$R$^{6b}$, or —OR$^7$;

R$^{6a}$ represents hydrogen or C$_{1-4}$alkyl;

R$^{6b}$ represents hydrogen; C$_{1-4}$alkyl; C$_{3-6}$cycloalkyl; —C(=O)—C$_{1-4}$alkyl; —C(=O)—Het$^4$; —S(=O)$_2$—C$_{1-4}$alkyl; —C(=O)—C$_{1-4}$alkyl substituted with one substituent selected from the group consisting of —OH and —NR$^{16a}$R$^{16b}$; or C$_{1-4}$alkyl substituted with one substituent selected from the group consisting of —OH and —S(=O)$_2$—C$_{1-4}$alkyl;

R$^7$ represents hydrogen, C$_{1-4}$alkyl, —C$_{1-4}$alkyl-NR$^{8a}$R$^{8b}$, —C(=O)—R$^9$, —S(=O)$_2$—OH, —P(=O)$_2$—OH, —(C=O)—CH(NH$_2$)—C$_{1-4}$alkyl-Ar$^1$, or —C$_{1-4}$alkyl-Het$^{3b}$;

R$^{8a}$ represents hydrogen or C$_{1-4}$alkyl;

R$^{8b}$ represents hydrogen, C$_{1-4}$alkyl, or C$_{3-6}$cycloalkyl;

R$^9$ represents C$_{1-6}$alkyl, or C$_{1-6}$alkyl substituted with one substituent selected from the group consisting of —NH$_2$, —COOH, and Het$^6$;

R$^{16a}$ and R$^{16b}$ each independently represents hydrogen, C$_{1-4}$alkyl or C$_{3-6}$cycloalkyl;

R$^3$ represents a 6-membered heteroaromatic ring containing 1 or 2 N-atoms, optionally substituted with one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$;

R$^{10}$ represents —OH, —O—C$_{1-4}$alkyl, —NR 11$^a$R$^{1b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1e}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^2$ represents a heterocyclyl of formula (b-1):

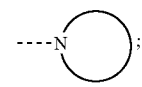

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with C$_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; Het$^{1e}$; $C_{1-4}$alkyl; —$C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents CR$^4$;

$R^4$ represents hydrogen or halo;

$R^5$ represents Het$^{3a}$, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —NH$_2$, —COOH, and Het$^6$;

$R^{16a}$ and $R^{16b}$ each independently represents hydrogen, $C_{1-4}$alkyl or $C_{3-6}$cycloalkyl;

$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$, and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$, and Het$^{1g}$ containing one or two heteroatoms each independently selected from O, S, S(=O)$_p$ and N; wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1):

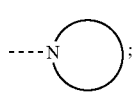

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

R$^{11b}$ represents hydrogen; Het$^{1e}$; $C_{1-4}$alkyl; —$C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

R$^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

R$^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

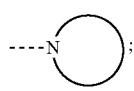

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

R$^{11a}$, R$^{14a}$, R$^{14c}$, R$^{15a}$, R$^{17a}$ and R$^{19a}$ each independently represents hydrogen or $C_{1-4}$alkyl;

R$^{14b}$, R$^{14d}$, R$^{15b}$, R$^{17b}$ and R$^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

R$^{20a}$ and R$^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^1$ represents $C_{1-4}$alkyl;

R$^2$ represents $C_{1-6}$alkyl, or $C_{1-6}$alkyl substituted with one R$^5$;

Y represents CR$^4$;

R$^4$ represents hydrogen or halo;

R$^5$ represents Het$^{3a}$, —NR$^{6a}$R$^{6b}$, or —OR$^7$;

R$^{6a}$ represents hydrogen or $C_{1-4}$alkyl;

R$^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

R$^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

R$^{8a}$ represents hydrogen or $C_{1-4}$alkyl;

R$^{8b}$ represents hydrogen, $C_{1-4}$alkyl, or $C_{3-6}$cycloalkyl;

R$^9$ represents $C_{1-4}$alkyl, or $C_{1-4}$alkyl substituted with one substituent selected from the group consisting of —NH$_2$, —COOH, and Het$^6$;

R$^{16a}$ and R$^{16b}$ each independently represents hydrogen, $C_{1-4}$alkyl or $C_{3-6}$cycloalkhyl;

R$^3$ represents 2-oxo-1,2-dihydropyridin-3-yl, wherein said 2-oxo-1,2-dihydropyridin-3-yl may optionally be substituted on the N-atom with a substituent selected from the group consisting of $C_{1-6}$alkyl; $C_{3-6}$cycloalkyl; Het$^{1a}$; R$^{18}$; R$^{21}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$; provided that when Het$^{1a}$ or R$^{18}$ are directly attached to the N-atom of the 2-oxo-1,2-dihydropyridin-3-yl, said Het$^{1a}$ or R$^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$;

R$^{10}$ represents —OH, —O—C$_{1-4}$alkyl, —NR 11$^{a}$R$^{11b}$ or Het$^{2}$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one or two ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1e}$ and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$ and Het$^{1g}$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{2}$ represents a heterocyclyl of formula (b-1):

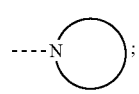

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with C$_{1-4}$alkyl; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH; R$^{11b}$ represents hydrogen; Het$^{1e}$; C$_{1-4}$alkyl; —C$_{1-4}$alkyl-Het$^{5}$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;

R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{2b}$)—C$_{1-4}$alkyl, C$_{3-6}$cycloalkyl, Ar$^{2}$, or Het$^{1c}$;

Ar$^{1}$ represents phenyl optionally substituted with one hydroxy;

Ar$^{2}$ represents phenyl optionally substituted with one C$_{1-4}$alkyl;

Het$^{3a}$, Het$^{3b}$, Het$^{5}$, Het$^{6}$ and Het$^{1f}$ each independently represents a heterocyclyl of formula (c-1):

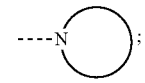

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with C$_{1-4}$alkyl or C$_{3-6}$cycloalkyl; and wherein (c-1) may optionally be substituted on one or two ring C-atoms atoms with one or two substituents each independently selected from the group consisting of halo, C$_{1-4}$alkyl, and C$_{3-6}$cycloalkyl;

R$^{11a}$, R$^{14a}$, R$^{14c}$, R$^{15a}$, R$^{17a}$ and R$^{19a}$ each independently represents hydrogen or C$_{1-4}$alkyl;

R$^{14b}$, R$^{14d}$, R$^{15b}$, R$^{17b}$ and R$^{19b}$ each independently represents hydrogen; C$_{1-4}$alkyl; C$_{3-6}$cycloalkyl; or C$_{1-4}$alkyl substituted with one substituent selected from the group consisting of halo, —OH and —O—C$_{1-4}$alkyl;

R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^{1}$ represents C$_{1-4}$alkyl;

R$^{2}$ represents C$_{1-6}$alkyl, or C$_{1-6}$alkyl substituted with one R$^{5}$;

Y represents CR$^{4}$ or N;

R$^{4}$ represents hydrogen or halo;

R$^{5}$ represents halo, Het$^{3a}$, —NR$^{6a}$R$^{6b}$, or —OR$^{7}$;

R$^{6a}$ represents hydrogen or C$_{1-4}$alkyl;

$R^{6b}$ represents hydrogen; $C_{1-4}$alkyl; $C_{3-6}$cycloalkyl; —C(=O)—$C_{1-4}$alkyl; —C(=O)—Het$^4$; —S(=O)$_2$—$C_{1-4}$alkyl; —C(=O)—$C_{1-4}$alkyl substituted with one substituent selected from the group consisting of —OH and —NR$^{6a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —NH$_2$, —COOH, and Het$^6$;

$R^{16a}$ and $R^{16b}$ each independently represents hydrogen, $C_{1-4}$alkyl or $C_{3-6}$cycloalkyl;

$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; $C_{2-6}$alkenyl substituted with one R$^{13}$; $C_{2-6}$alkynyl; and $C_{2-6}$alkynyl substituted with one R$^{13}$; or $R^3$ represents 2-oxo-1,2-dihydropyridin-3-yl,
wherein said 2-oxo-1,2-dihydropyridin-3-yl may optionally be substituted on the N-atom with a substituent selected from the group consisting of $C_{1-6}$alkyl; $C_{3-6}$cycloalkyl; Het$^{1a}$; R$^{18}$; R$^{21}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$; provided that when Het$^{1a}$ or R$^{18}$ are directly attached to the N-atom of the 2-oxo-1,2-dihydropyridin-3-yl, said Het$^{1a}$ or R$^{18}$ are attached to the N-atom via a ring carbon atom; and
wherein said 2-oxo-1,2-dihydropyridin-3-yl may optionally be substituted on the ring carbon atoms with in total one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; $C_{2-6}$alkenyl substituted with one R$^{13}$; $C_{2-6}$alkynyl; and $C_{2-6}$alkynyl substituted with one R$^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;
wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl or said 6- to 11-membered bicyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$, Het$^{1g}$, Het$^4$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^4$, Het$^7$ and Het$^8$ containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1):

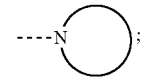

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with a substituent each independently selected from the group consisting of $C_{1-4}$alkyl, $C_{3-6}$cycloalkyl and Het$^7$; and wherein (b-1) may optionally be substituted on one, two or three ring C-atoms with one substituent each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; Het$^{1e}$; $C_{1-4}$alkyl; —$C_{1-4}$alkyl-Het$^5$; —$C_{1-4}$alkyl-Het$^8$; $C_{1-4}$alkyl substituted with one, two or three substituents each independently selected from the group consisting of halo, —OH and —O—$C_{1-4}$ alkyl; $C_{3-6}$cycloalkyl; or $C_{3-6}$cycloalkyl substituted with one, two or three substituents each independently selected from the group consisting of halo,
—OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

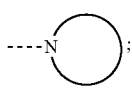

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one substituent each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents CR$^4$;

$R^4$ represents hydrogen or halo;

$R^5$ represents Het$^{3a}$, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—Het$^4$; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —NH$_2$, —COOH, and Het$^6$;

$R^{16a}$ and $R^{16b}$ each independently represents hydrogen, $C_{1-4}$alkyl or $C_{3-6}$cycloalkyl;

$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$; or $R^3$ represents 2-oxo-1,2-dihydropyridin-3-yl, wherein said 2-oxo-1,2-dihydropyridin-3-yl may optionally be substituted on the N-atom with a substituent selected from the group consisting of $C_{1-6}$alkyl; $C_{3-6}$cycloalkyl; Het$^{1a}$; R$^{18}$; R$^{21}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$; provided that when Het$^{1a}$ or R$^{18}$ are directly attached to the N-atom of the 2-oxo-1,2-dihydropyridin-3-yl, said Het$^{1a}$ or R$^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; $C_{1}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetra-hydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —$NH_2$, —$NH(C_{1-4}$alkyl), and —$N(C_{1-4}$alkyl$)_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, $S(=O)_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —$NH_2$, —$NH(C_{1-4}$alkyl), and —$N(C_{1-4}$alkyl$)_2$;

$Het^2$ represents a heterocyclyl of formula (b-1):

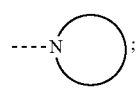

(b-1)

(b-1) represents a N-linked 4- to 7-membered monocyclic saturated heterocyclyl optionally containing one additional heteroatom selected from O, S, $S(=O)_p$ and N, or a N-linked 6- to 11-membered bicyclic saturated heterocyclyl, including fused, spiro and bridged cycles, optionally containing one or two additional heteroatoms each independently selected from O, S, $S(=O)_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one substituent each independently selected from the group consisting of halo, —OH, cyano, $C_{1-4}$alkyl, —O—$C_{1-4}$alkyl, —$NH_2$, —$NH(C_{1-4}$alkyl), —$N(C_{1-4}$alkyl$)_2$, and $C_{1-4}$alkyl-OH;

$R^{11b}$ represents hydrogen; $Het^{1e}$; $C_{1-4}$alkyl; —$C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

$R^{12}$ represents —OH, —O—$C_{1-4}$alkyl, —$NR^{14a}R^{14b}$, —C(=O)$NR^{14c}R^{14d}$, —$S(=O)_2$—$C_{1-4}$alkyl, —$S(=O)(=N$—$R^{20b})$—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1):

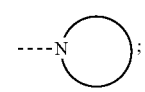

(c-1)

(c-1) represents a N-linked 4- to 7-membered monocyclic saturated heterocyclyl optionally containing one additional heteroatom selected from O, S, $S(=O)_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one substituent each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$ or N;

$R^4$ represents hydrogen or halo;

$R^5$ represents halo, $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —$S(=O)_2$—$C_{1-4}$alkyl; —C(=O)—$C_{1-4}$alkyl substituted with one substituent selected from the group consisting of —OH and —NR$^{16a}$R$^{16b}$; or C$_{1-4}$alkyl substituted with one substituent selected from the group consisting of —OH and —S(=O)$_2$—C$_{1-4}$alkyl;

R$^7$ represents hydrogen, C$_{1-4}$alkyl, —C$_{1-4}$alkyl-NR$^{8a}$R$^{8b}$, —C(=O)—R$^9$, —S(=O)$_2$—OH, —P(=O)$_2$—OH, —(C=O)—CH(NH$_2$)—C$_{1-4}$alkyl-Ar$^1$, or —C$_{1-4}$alkyl-Het$^{3b}$;

R$^{8a}$ represents hydrogen or C$_{1-4}$alkyl;

R$^{8b}$ represents hydrogen, C$_{1-4}$alkyl, or C$_{3-6}$cycloalkyl;

R$^9$ represents C$_{1-4}$alkyl, or C$_{1-4}$alkyl substituted with one substituent selected from the group consisting of —NH$_2$, —COOH, and Het$^6$;

R$^{16a}$ and R$^{16b}$ each independently represents hydrogen, C$_{1-4}$alkyl or C$_{3-6}$cycloalkyl;

R$^3$ represents 2-oxo-1,2-dihydropyridin-3-yl, wherein said 2-oxo-1,2-dihydropyridin-3-yl may optionally substituted on the N-atom with a substituent selected from the group consisting of C$_{1-6}$alkyl; C$_{3-6}$cycloalkyl; Het$^{1a}$; R$^{18}$; R$^{21}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$; provided that when Het$^{1a}$ or R$^{18}$ are directly attached to the N-atom of the 2-oxo-1,2-dihydropyridin-3-yl, said Het$^{1a}$ or R$^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; C$_{2-6}$alkenyl substituted with one R$^{13}$; C$_{2-6}$alkynyl; and C$_{2-6}$alkynyl substituted with one R$^{13}$;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one or two ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1e}$, Het$^{1g}$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^7$ and Het$^8$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^2$ represents a heterocyclyl of formula (b-1):

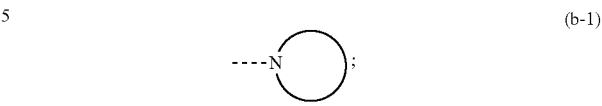

(b-1) represents a N-linked 4- to 7-membered monocyclic saturated heterocyclyl optionally containing one additional heteroatom selected from O, S, S(=O)$_p$ and N; wherein in case (b-1) contains one additional N-atom, said N-atom may optionally be substituted with a substituent each independently selected from the group consisting of C$_{1-4}$alkyl, C$_{3-6}$cycloalkyl and Het$^7$; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;

R$^{11b}$ represents hydrogen; Het$^{1e}$; C$_{1-4}$alkyl; —C$_{1-4}$alkyl-Het$^5$; —C$_{1-4}$alkyl-Het$^8$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;

R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{2b}$)—C$_{1-4}$alkyl, C$_{3-6}$cycloalkyl, Ar$^2$, or Het$^{1c}$;

Ar$^1$ represents phenyl optionally substituted with one hydroxy;

Ar$^2$ represents phenyl optionally substituted with one C$_{1-4}$alkyl;

Het$^{3a}$, Het$^{3b}$, Het$^5$, Het$^6$ and Het$^{1f}$ each independently represents a heterocyclyl of formula (c-1):

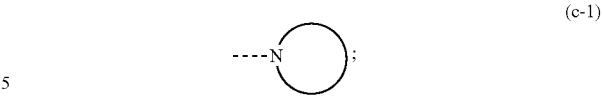

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents Het$^{3a}$, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —NH$_2$, —COOH, and Het$^6$;

$R^{16a}$ and $R^{16b}$ each independently represents hydrogen, $C_{1-4}$alkyl or $C_{3-6}$cycloalkyl;

$R^3$ represents 2-oxo-1,2-dihydropyridin-3-yl, wherein said 2-oxo-1,2-dihydropyridin-3-yl may optionally substituted on the N-atom with a substituent selected from the group consisting of $C_{1-6}$alkyl; $C_{3-6}$cycloalkyl; Het$^{1a}$; $R^{18}$; $R^{21}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of the 2-oxo-1,2-dihydropyridin-3-yl, said Het$^{1a}$ or $R^{18}$ are attached to the N-atom via a ring carbon atom; and wherein said 2-oxo-1,2-dihydropyridin-3-yl may optionally be substituted on the ring carbon atoms with in total one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; $R^{18}$; $R^{21}$; —P(=O)—(C$_{1-4}$alkyl)$_2$; —NH—C(=O)—$C_{1-4}$alkyl; —NH—C(=O)—Het$^{1g}$; —NR$^{7a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one or two ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$ and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$ and Het$^{1g}$ containing one or two heteroatoms each independently selected from O, S, S(=O)$_p$ and N; wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocycyl of formula (b-1):

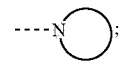

(b-1)

(b-1) represents a N-linked 4- to 7-membered monocyclic saturated heterocyclyl optionally containing one additional heteroatom selected from O, S, S(=O)$_p$ and N; wherein in case (b-1) contains one additional N-atom, said N-atom may optionally be substituted with C$_{1-4}$alkyl; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;

R$^{11b}$ represents hydrogen; Het$^{1e}$; C$_{1-4}$alkyl; —C$_{1-4}$alkyl-Het$^5$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;

R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{20b}$)—C$_{1-4}$alkyl, C$_{3-6}$cycloalkyl, Ar$^2$, or Het$^{1c}$;

Ar$^1$ represents phenyl optionally substituted with one hydroxy;

Ar$^2$ represents phenyl optionally substituted with one C$_{1-4}$alkyl;

Het$^{3a}$, Het$^{3b}$, Het$^5$, Het$^6$ and Het$^{1f}$ each independently represents a heterocyclyl of formula (c-1):

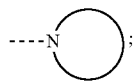

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with C$_{1-4}$alkyl or C$_{3-6}$cycloalkyl; and wherein (c-1) may optionally be substituted on one or two ring C-atoms atoms with one or two substituents each independently selected from the group consisting of halo, C$_{1-4}$alkyl, and C$_{3-6}$cycloalkyl;

R$^{11a}$, R$^{14a}$, R$^{14c}$, R$^{15a}$, R$^{17a}$ and R$^{19a}$ each independently represents hydrogen or C$_{1-4}$alkyl;

R$^{14b}$, R$^{14d}$, R$^{15b}$, R$^{17b}$ and R$^{19b}$ each independently represents hydrogen; C$_{1-4}$alkyl; C$_{3-6}$cycloalkyl; or C$_{1-4}$alkyl substituted with one substituent selected from the group consisting of halo, —OH and —O—C$_{1-4}$alkyl;

R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^1$ represents C$_{1-4}$alkyl;

R$^2$ represents C$_{1-6}$alkyl, or C$_{1-6}$alkyl substituted with one R$^5$;

Y represents CR$^4$ or N;

R$^4$ represents hydrogen or halo;

R$^5$ represents Het$^{3a}$, —NR$^{6a}$R$^{6b}$, or —OR$^7$;

R$^{6a}$ represents hydrogen or C$_{1-4}$alkyl;

R$^{6b}$ represents C$_{1-4}$alkyl; C$_{3-6}$cycloalkyl; —C(=O)—C$_{1-4}$alkyl; or C$_{1-4}$alkyl substituted with one substituent selected from the group consisting of —OH and —S(=O)$_2$—C$_{1-4}$alkyl;

R$^7$ represents hydrogen, C$_{1-4}$alkyl, —C$_{1-4}$alkyl-NR$^{8a}$R$^{8b}$, —C(=O)—R$^9$, or —C$_{1-4}$alkyl-Het$^{3b}$;

R$^{8a}$ represents hydrogen;

R$^{8b}$ represents C$_{1-4}$alkyl, or C$_{3-6}$cycloalkyl;

R$^9$ represents C$_{1-4}$alkyl, or C$_{1-4}$alkyl substituted with one substituent selected from the group consisting of —NH$_2$;

R$^3$ represents a 6-membered heteroaromatic ring containing 1 or 2 N-atoms, optionally substituted with one, two or three substituents each independently selected from the group consisting of halo; cyano; C$_{1-6}$alkyl; —O—C$_{1-4}$alkyl; —C(=O)—R$^{10}$; —O—C$_{1-4}$alkyl-R$^{12}$; C$_{3-6}$cycloalkyl; —O—C$_{3-6}$cycloalkyl; Het$^{1a}$; —O-Het$^{1b}$; C$_{1-4}$alkyl substituted with one, two or three —OH substituents; R$^{18}$; R$^{21}$; —P(=O)—(C$_{1-4}$alkyl)$_2$; —NR$^{17a}$R$^{17b}$; C$_{1-4}$alkyl substituted with one, two or three halo atoms; C$_{1-4}$alkyl substituted with one R$^{13}$; C$_{2-6}$alkenyl; and C$_{2-6}$alkenyl substituted with one R$^{13}$;

or R$^3$ represents 2-oxo-1,2-dihydropyridin-3-yl, wherein said 2-oxo-1,2-dihydropyridin-3-yl may optionally substituted on the N-atom with a substituent selected from the group consisting of C$_{1-6}$alkyl; C$_{1-4}$alkyl substituted with one, two or three —OH substituents; C$_{1-4}$alkyl substituted with one R$^{13}$; C$_{1-4}$alkyl substituted with one R$^{18}$; and wherein said 2-oxo-1,2-dihydropyridin-3-yl may optionally be substituted on the ring carbon atoms with in total one, two or three substituents each independently selected from the group consisting of halo; C$_{1-6}$alkyl; —C(=O)—Ro; and Het$^{1a}$;

R$^{10}$ represents —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl;

Het$^{1a}$, Het$^{1c}$ and Het$^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one —OH substituent; and wherein said 4- to 7-membered monocyclic saturated heterocyclyl may optionally be substituted on one, two or three ring C-atoms with one or two substituents each independently selected from the group consisting of halo and C$_{1-4}$alkyl;

Het$^{1b}$ represents a 4- to 7-membered monocyclic saturated heterocyclyl, attached to the remainder of the molecule of Formula (I) through any available ring carbon atom, said Het$^{1b}$ containing one or two heteroatoms each independently selected from O and N; wherein said 4- to 7-membered monocyclic saturated heterocyclyl may optionally be substituted, where possible, on one or two ring N-atoms with a substituent each independently selected from the group consisting of C$_{1-4}$alkyl and C$_{3-6}$cycloalkyl; wherein said 4- to 7-membered monocyclic saturated heterocyclyl may optionally be substituted on one, two or three ring C-atoms with one or two halo substituents; Het² represents a heterocyclyl of formula (b-1):

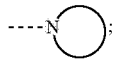

(b-1) represents a N-linked 4- to 7-membered monocyclic saturated heterocyclyl optionally containing one additional N-atom;
wherein in case (b-1) contains one additional N-atom, said one N-atom may optionally be substituted with $C_{1-4}$alkyl;
wherein (b-1) may optionally be substituted on one, two or three ring C-atoms with one or two —OH substituents;
$R^{11b}$ represents $C_{1-4}$alkyl;
$R^{13}$ represents —O—$C_{1-4}$alkyl, —C(=O)NR$^{15a}$R$^{15b}$, —NR$^{19a}$R$^{19b}$, $C_{3-6}$cycloalkyl, or Het$^{1d}$;
$R^{12}$ represents —OH, —O—$C_{1-4}$alkyl, —C(=O)NR$^{14c}$R$^{14d}$, $C_{3-6}$cycloalkyl, or Het$^{1c}$;
Het$^{3a}$ and Het$^{3b}$ each independently represents a heterocyclyl of formula (c-1):

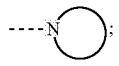

(c-1) represents a N-linked 4- to 7-membered monocyclic saturated heterocyclyl optionally containing one additional heteroatom selected from O and N;
$R^{11a}$, $R^{14c}$, $R^{15a}$, $R^{17a}$ and $R^{19a}$ each independently represents hydrogen or $C_{1-4}$alkyl;
$R^{14d}$, $R^{15b}$, $R^{17b}$ and $R^{19b}$ each independently represents $C_{1-4}$alkyl; $C_{3-6}$cycloalkyl; or $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents CR$^4$ or N;
$R^4$ represents hydrogen or halo;
$R^5$ represents halo, —NR$^{6a}$R$^{6b}$, or —OR$^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl;
—S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-NR$^{8a}$R$^{8b}$, —C(=O)—R$^9$, —S(=O)$_2$—OH,
—P(=O)$_2$—OH, or —(C=O)—CH(NH$_2$)—$C_{1-4}$alkyl-Ar$^1$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-4}$alkyl, or $C_{1-4}$alkyl substituted with one substituent selected from the group consisting of —NH$_2$ and —COOH;
$R^{16a}$ and $R^{16b}$ each independently represents hydrogen, $C_{1-4}$alkyl or $C_{3-6}$cycloalkyl;

$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; —P(=O)—(C$_{1-4}$alkyl)$_2$; —NH—C(=O)—$C_{1-4}$alkyl; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{2-6}$alkenyl; $C_{2-6}$alkenyl substituted with one R$^{13}$; $C_{2-6}$alkynyl; and $C_{2-6}$alkynyl substituted with one R$^{13}$;
$R^{10}$ represents —OH, —O—$C_{1-4}$alkyl or —NR$^{11a}$R$^{11b}$;
$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)NR$^{15a}$R$^{15b}$, —NR$^{19a}$R$^{19b}$, $C_{3-6}$cycloalkyl;
$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$;
Ar$^1$ represents phenyl optionally substituted with one hydroxy;
Ar$^2$ represents phenyl optionally substituted with one $C_{1-4}$alkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl; $R^{20a}$ and $R^{20b}$ each independently represents hydrogen; $C_{1-4}$alkyl; $C_{3-6}$cycloalkyl; or
$C_{1-4}$alkyl substituted with one substituent selected from the group consisting of —OH and —O—$C_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents CR$^4$;
$R^4$ represents hydrogen or halo;
$R^5$ represents —NR$^{6a}$R$^{6b}$, or —OR$^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl;
—S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, or —(C=O)—CH(NH$_2$)—$C_{1-4}$alkyl-Ar$^1$;
$R^{8a}$ represents hydrogen or $C_{1-4}$alkyl;

$R^{8b}$ represents hydrogen, $C_{1-4}$alkyl, or $C_{3-6}$cycloalkyl;
$R^9$ represents $C_{1-4}$alkyl, or $C_{1-4}$alkyl substituted with one substituent selected from the group consisting of —$NH_2$ and —COOH;
$R^{16a}$ and $R^{16b}$ each independently represents hydrogen, $C_{1-4}$alkyl or $C_{3-6}$cycloalkyl;
$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; —P(=O)—($C_{1-4}$alkyl)$_2$; —NH—C(=O)—$C_{1-4}$alkyl; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$;
$R^{10}$ represents —OH, —O—$C_{1-4}$alkyl or —$NR^{11a}R^{11b}$;
$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)$NR^{15a}R^{15b}$, —$NR^{19a}R^{19b}$, $C_{3-6}$cycloalkyl;
$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$;
$Ar^1$ represents phenyl optionally substituted with one hydroxy;
$Ar^2$ represents phenyl optionally substituted with one $C_{1-4}$alkyl;
$R^{11a}$, $R^{14a}$, $R^{14c}$, $R^{15a}$, $R^{17a}$ and $R^{19a}$ each independently represents hydrogen or $C_{1-4}$alkyl;
$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;
$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents $C_{1-4}$alkyl; $C_{3-6}$cycloalkyl; —C(=O)—$C_{1-4}$alkyl; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, or —$C_{1-4}$alkyl-$Het^{3b}$;
$R^{8a}$ represents hydrogen;
$R^{8b}$ represents $C_{1-4}$alkyl, or $C_{3-6}$cycloalkyl;

$R^9$ represents $C_{1-4}$alkyl, or $C_{1-4}$alkyl substituted with one substituent selected from the group consisting of —$NH_2$;
$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —$NR^{17a}R^{17b}$; $C_{1-4}$alkyl substituted with one, two or three halo atoms; $C_{1-4}$alkyl substituted with one $R^{13}$; $C_{2-6}$alkenyl; and $C_{2-6}$alkenyl substituted with one $R^{13}$;
$R^{10}$ represents —O—$C_{1-4}$alkyl, —$NR^{11a}R^{11b}$ or $Het^2$;
$R^{18}$ represents a 5-membered aromatic ring containing one, two or three N-atoms; wherein said 5-membered aromatic ring may optionally be substituted with one $C_{1-4}$alkyl substituent;
$R^{21}$ represents 3,6-dihydro-2H-pyran-4-yl;
$Het^{1a}$ and $Het^{1c}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, and $C_{1-4}$alkyl substituted with one —OH substituent; and
wherein said 4- to 7-membered monocyclic saturated heterocyclyl may optionally be substituted on one, two or three ring C-atoms with one or two $C_{1-4}$alkyl substituents;
$Het^{1b}$ represents a 4- to 7-membered monocyclic saturated heterocyclyl, attached to the remainder of the molecule of Formula (I) through any available ring carbon atom, said $Het^{1b}$ containing one or two heteroatoms each independently selected from O and N; wherein said 4- to 7-membered monocyclic saturated heterocyclyl may optionally be substituted, where possible, on one or two ring N-atoms with a $C_{1-4}$alkyl substituent;
$Het^2$ represents a heterocyclyl of formula (b-1):

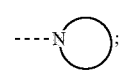

(b-1) represents a N-linked 4- to 7-membered monocyclic saturated heterocyclyl optionally containing one additional N-atom;
wherein in case (b-1) contains one additional N-atom, said one N-atom may optionally be substituted with $C_{1-4}$alkyl;
$R^{11b}$ represents $C_{1-4}$alkyl;
$R^{13}$ represents —O—$C_{1-4}$alkyl, —C(=O)$NR^{15a}R^{15b}$, or $C_{3-6}$cycloalkyl;
$R^{12}$ represents —OH, —O—$C_{1-4}$alkyl, —C(=O)$NR^{14c}R^{14d}$, $C_{3-6}$cycloalkyl, or $Het^{1c}$;
$Het^{3a}$ and $Het^{3b}$ each independently represents a heterocyclyl of formula (c-1):

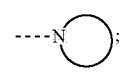

(c-1) represents a N-linked 4- to 7-membered monocyclic saturated heterocyclyl optionally containing one additional heteroatom selected from O and N;

$R^{11a}$, $R^{14c}$, $R^{15a}$, $R^{17a}$ each independently represents hydrogen or $C_{1-4}$alkyl;
$R^{14d}$, $R^{15b}$, $R^{17b}$ each independently represents $C_{1-4}$alkyl; or $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents $C_{1-4}$alkyl; $C_{3-6}$cycloalkyl; —C(=O)—$C_{1-4}$alkyl; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, or —$C_{1-4}$alkyl-$Het^{3b}$;
$R^{8a}$ represents hydrogen;
$R^{8b}$ represents $C_{1-4}$alkyl, or $C_{3-6}$cycloalkyl;
$R^9$ represents $C_{1-4}$alkyl, or $C_{1-4}$alkyl substituted with one substituent selected from the group consisting of —$NH_2$;
$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —$NR^{17a}R^{17b}$; $C_{1-4}$alkyl substituted with one, two or three halo atoms; $C_{1-4}$alkyl substituted with one $R^{13}$; $C_{2-6}$alkenyl; and $C_{2-6}$alkenyl substituted with one $R^{13}$;
$R^{10}$ represents —O—$C_{1-4}$alkyl, or —$NR^{11a}R^{11b}$;
$R^{18}$ represents a 5-membered aromatic ring containing one, two or three N-atoms; wherein said 5-membered aromatic ring may optionally be substituted with one $C_{1-4}$alkyl substituent;
$R^{21}$ represents 3,6-dihydro-2H-pyran-4-yl;
$Het^{1a}$ a and $Het^{1c}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one, two or three ring N-atoms with a substituent each independently selected from the group consisting of $C_{1-4}$alkyl, and $C_{1-4}$alkyl substituted with one —OH substituent; and
wherein said 4- to 7-membered monocyclic saturated heterocyclyl may optionally be substituted on one, two or three ring C-atoms with one or two $C_{1-4}$alkyl substituents;
$Het^{1b}$ represents a 4- to 7-membered monocyclic saturated heterocyclyl, attached to the remainder of the molecule of Formula (I) through any available ring carbon atom, said $Het^{1b}$ containing one or two heteroatoms each independently selected from O and N; wherein said 4- to 7-membered monocyclic saturated heterocyclyl may optionally be substituted, where possible, on one or two ring N-atoms with a $C_{1-4}$alkyl substituent;
$R^{11b}$ represents $C_{1-4}$alkyl;
$R^{13}$ represents —O—$C_{1-4}$alkyl, —C(=O)$NR^{15a}R^{15b}$, or $C_{3-6}$cycloalkyl;

$R^{12}$ represents —OH, —O—$C_{1-4}$alkyl, —C(=O)$NR^{14c}R^{14d}$, $C_{3-6}$cycloalkyl, or $Het^{1c}$;
$Het^{3a}$ and $Het^{3b}$ each independently represents a heterocyclyl of formula (c-1):

(c-1) represents a N-linked 4- to 7-membered monocyclic saturated heterocyclyl optionally containing one additional heteroatom selected from O and N;
$R^{11a}$, $R^{14c}$, $R^{15a}$, $R^{17a}$ each independently represents hydrogen or $C_{1-4}$alkyl;
$R^{14d}$, $R^{15b}$, $R^{17b}$ each independently represents $C_{1-4}$alkyl; or $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen or halo;
$R^5$ represents —$NR^{6a}R^{6b}$, or —$OR^7$;
$R^{6a}$ represents hydrogen;
$R^{6b}$ represents —C(=O)—$C_{1-4}$alkyl;
$R^7$ represents hydrogen;
$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $Het^{1a}$; —$NR^{17a}R^{17b}$; $C_{1-4}$alkyl substituted with one $R^{13}$;
$R^{10}$ represents —$NR^{11a}R^{11b}$;
$Het^{1a}$ represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, and $C_{1-4}$alkyl substituted with one —OH substituent;
$R^{11a}$ represents hydrogen or $C_{1-4}$alkyl;
$R^{11b}$ represents $C_{1-4}$alkyl;
$R^{13}$ represents —O—$C_{1-4}$alkyl;
$R^{12}$ represents —O—$C_{1-4}$alkyl;
$R^{17a}$ represents hydrogen;
$R^{17b}$ represents $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen or halo;
$R^5$ represents —$NR^{6a}R^{6b}$, or —$OR^7$;
$R^{6a}$ represents hydrogen;
$R^{6b}$ represents —C(=O)—$C_{1-4}$alkyl;
$R^7$ represents hydrogen;

R³ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R¹⁰; —O—$C_{1-4}$alkyl-R¹²; —NR¹⁷ᵃR¹⁷ᵇ; $C_{1-4}$alkyl substituted with one R¹³;
R¹⁰ represents —NR¹¹ᵃR¹¹ᵇ;
R¹¹ᵃ represents hydrogen or $C_{1-4}$alkyl;
R¹¹ᵇ represents $C_{1-4}$alkyl;
R¹³ represents —O—$C_{1-4}$alkyl;
R¹² represents —O—$C_{1-4}$alkyl;
R¹⁷ᵃ represents hydrogen;
R¹⁷ᵇ represents $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
R¹ represents $C_{1-4}$alkyl;
R² represents $C_{1-6}$alkyl substituted with one R⁵;
Y represents CR⁴;
R⁴ represents hydrogen;
R⁵ represents-OR⁷;
R⁷ represents hydrogen;
R³ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R¹⁰; —O—$C_{1-4}$alkyl-R¹²; Het¹ᵃ; —NR¹⁷ᵃR¹⁷ᵇ; $C_{1-4}$alkyl substituted with one R¹³;
R¹⁰ represents —NR¹¹ᵃR¹¹ᵇ;
Het¹ᵃ represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, and $C_{1-4}$alkyl substituted with one —OH substituent;
R¹¹ᵃ represents hydrogen or $C_{1-4}$alkyl;
R¹¹ᵇ represents $C_{1-4}$alkyl;
R¹³ represents —O—$C_{1-4}$alkyl;
R¹² represents —O—$C_{1-4}$alkyl;
R¹⁷ᵃ represents hydrogen;
R¹⁷ᵇ represents $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
R¹ represents $C_{1-4}$alkyl;
R² represents $C_{1-6}$alkyl substituted with one R⁵;
Y represents CR⁴;
R⁴ represents hydrogen;
R⁵ represents-OR⁷;
R⁷ represents hydrogen;
R³ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—R¹⁰; —O—$C_{1-4}$alkyl-R¹²; —NR¹⁷ᵃR¹⁷ᵇ; $C_{1-4}$alkyl substituted with one R¹³; R¹⁰ represents —NR¹¹ᵃR¹¹ᵇ;
R¹¹ᵃ represents hydrogen or $C_{1-4}$alkyl;
R¹¹ᵇ represents $C_{1-4}$alkyl;

R¹³ represents —O—$C_{1-4}$alkyl;
R¹² represents —O—$C_{1-4}$alkyl;
R¹⁷ᵃ represents hydrogen;
R¹⁷ᵇ represents $C_{1-4}$alkyl substituted with one —O—$C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
R¹ represents $C_{1-4}$alkyl;
R² represents $C_{1-6}$alkyl substituted with one R⁵;
Y represents CR⁴;
R⁴ represents hydrogen;
R⁵ represents —OR⁷;
R⁷ represents hydrogen;
R³ represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one, two or three —OH substituents; $C_{1-4}$alkyl substituted with one R¹³; $C_{1-4}$alkyl substituted with one R¹⁸; and
wherein said 2-oxo-1,2-dihydropyridin-3-yl may optionally be substituted on the ring carbon atoms with in total one, two or three substituents each independently selected from the group consisting of halo; $C_{1-6}$alkyl; and Het¹ᵃ;
R¹⁸ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
Het¹ᵃ and Het¹ᵈ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with $C_{1-4}$alkyl; and wherein said 4- to 7-membered monocyclic saturated heterocyclyl may optionally be substituted on one or two ring C-atoms with one or two substituents each independently selected from the group consisting of halo and $C_{1-4}$alkyl;
R¹³ represents —O—$C_{1-4}$alkyl, —C(=O)NR¹⁵ᵃR¹⁵ᵇ, $C_{3-6}$cycloalkyl, or Het¹ᵈ;
R¹⁵ᵃ represents $C_{1-4}$alkyl;
R¹⁵ᵇ represents $C_{1-4}$alkyl;
and the pharmaceutically acceptable addition salts, and the solvates thereof.

The present invention relates in particular to compounds of Formula (I) as defined herein, tautomers and stereoisomeric forms thereof, wherein
R¹ represents $C_{1-4}$alkyl;
R² represents $C_{1-6}$alkyl substituted with one R⁵;
Y represents CR⁴;
R⁴ represents hydrogen;
R⁵ represents —OR⁷;
R⁷ represents hydrogen;
R³ represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one, two or three —OH substituents; $C_{1-4}$alkyl substituted with one R¹³; $C_{1-4}$alkyl substituted with one R¹⁸; and
wherein said 2-oxo-1,2-dihydropyridin-3-yl may optionally be substituted on the ring carbon atoms with in total one, two or three substituents each independently selected from the group consisting of halo and $C_{1-6}$alkyl;

R[18] represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
Het[1d] represents a 4- to 7-membered monocyclic saturated heterocyclyl containing one or two heteroatoms each independently selected from O and N; wherein said 4- to 7-membered monocyclic saturated heterocyclyl may optionally be substituted on one or two ring C-atoms with one or two substituents each independently selected from the group consisting of halo and $C_{1-4}$alkyl;
R[13] represents —O—$C_{1-4}$alkyl, —C(=O)NR[15a]R[15b], $C_{3-6}$cycloalkyl, or Het[1d];
R[15a] represents $C_{1-4}$alkyl;
R[15b] represents $C_{1-4}$alkyl;
and the pharmaceutically acceptable addition salts, and the solvates thereof.

The present invention relates in particular to compounds of Formula (I) as defined herein, tautomers and stereoisomeric forms thereof, wherein
R[1] represents $C_{1-4}$alkyl;
R[2] represents $C_{1-6}$alkyl substituted with one R[5];
Y represents CR[4];
R[4] represents hydrogen;
R[5] represents —OR[7];
R[7] represents hydrogen;
R[3] represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one R[13]; $C_{1-4}$alkyl substituted with one R[18]; and
wherein said 2-oxo-1,2-dihydropyridin-3-yl may optionally be substituted on the ring carbon atoms with in total one, two or three substituents each independently selected from the group consisting of halo and $C_{1-6}$alkyl;
R[18] represents a 5-membered aromatic ring containing one, two or three N-atoms; wherein said 5-membered aromatic ring may optionally be substituted with one $C_{1-4}$alkyl substituent;
Het[1d] represents a 4- to 7-membered monocyclic saturated heterocyclyl containing one or two heteroatoms each independently selected from O and N;
wherein said 4- to 7-membered monocyclic saturated heterocyclyl may optionally be substituted on one or two ring C-atoms with one or two substituents each independently selected from the group consisting of halo and $C_{1-4}$alkyl;
R[13] represents Het[1d];
and the pharmaceutically acceptable addition salts, and the solvates thereof.

The present invention relates in particular to compounds of Formula (I) as defined herein, tautomers and stereoisomeric forms thereof, wherein
R[1] represents $C_{1-4}$alkyl;
R[2] represents $C_{1-6}$alkyl substituted with one R[5];
Y represents CR[4];
R[4] represents hydrogen;
R[5] represents —OR[7];
R[7] represents hydrogen;
R[3] represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one R[18]; and
wherein said 2-oxo-1,2-dihydropyridin-3-yl may optionally be substituted on the ring carbon atoms with in total one, two or three substituents each independently selected from the group consisting of halo and $C_{1-6}$alkyl;
R[18] represents or three substituents each independently selected from the group consisting of halo and $C_{1-6}$alkyl;
R[18] represents a 5-membered aromatic ring containing one, two or three N-atoms; wherein said 5-membered aromatic ring may optionally be substituted with one $C_{1-4}$alkyl substituent;
and the pharmaceutically acceptable addition salts, and the solvates thereof.

The present invention relates in particular to compounds of Formula (I) as defined herein, tautomers and stereoisomeric forms thereof, wherein
R[1] represents $C_{1-4}$alkyl;
R[2] represents $C_{1-6}$alkyl substituted with one R[5];
Y represents CR[4];
R[4] represents hydrogen;
R[5] represents —OR[7];
R[7] represents hydrogen;
R[3] represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one R[13]; $C_{1-4}$alkyl substituted with one R[18]; and
wherein said 2-oxo-1,2-dihydropyridin-3-yl may optionally be substituted on the ring carbon atoms with in total one, two or three substituents each independently selected from the group consisting of halo and $C_{1-6}$alkyl;
R[18] represents

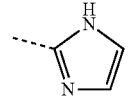

wherein the NH moiety is substituted with $C_{1-4}$alkyl;
Het[1d] represents 1-morpholinyl;
R[13] represents Het[1d];
and the pharmaceutically acceptable addition salts, and the solvates thereof.

The present invention relates in particular to compounds of Formula (I) as defined herein, tautomers and stereoisomeric forms thereof, wherein
R[1] represents $C_{1-4}$alkyl;
R[2] represents $C_{1-6}$alkyl substituted with one R[5];
Y represents CR[4];
R[4] represents hydrogen;
R[5] represents —OR[7];
R[7] represents hydrogen;
R[3] represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one R[18]; and
wherein said 2-oxo-1,2-dihydropyridin-3-yl may optionally be substituted on the ring carbon atoms with in total one, two or three substituents each independently selected from the group consisting of halo and $C_{1-6}$alkyl;
R[18] represents

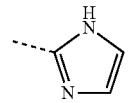

wherein the NH moiety is substituted with $C_{1-4}$alkyl;

and the pharmaceutically acceptable addition salts, and the solvates thereof.

In an embodiment, the present invention relates to those compounds of Formula (I) and the pharmaceutically acceptable addition salts, and the solvates thereof, or any subgroup thereof as mentioned in any of the other embodiments, wherein
$R^5$ represents —$NR^{6a}R^{6b}$, or —$OR^7$;
$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, or —(C=O)—CH(NH$_2$)—$C_{1-4}$alkyl-Ar$^1$.

Another embodiment of the present invention relates to those compounds of Formula (I) and the pharmaceutically acceptable addition salts, and the solvates thereof, or any subgroup thereof as mentioned in any of the other embodiments wherein $R^3$ represents a 6-membered heteroaromatic ring containing 1 or 2 N-atoms, optionally substituted as mentioned in any of the other embodiments, wherein Y represents $CR^4$ or N, in particular wherein Y represents $CR^4$; and
wherein one or more of the following restrictions apply:
(a) $R^{6b}$ represents $C_{1-4}$alkyl; $C_{3-6}$cycloalkyl; —C(=O)—$C_{1-4}$alkyl; or $C_{1-4}$alkyl substituted with one substituent selected from the group consisting of —OH and —S(=O)$_2$—$C_{1-4}$alkyl;
(b) $R^7$ represents hydrogen, $C_{1-4}$alkyl, —$C_{1-4}$alkyl-$NR^{8a}R^{8b}$, —C(=O)—$R^9$, or —$C_{1-4}$alkyl-Het$^{3b}$;
(c) $R^{8a}$ represents hydrogen;
(d) $R^{8b}$ represents $C_{1-4}$alkyl, or $C_{3-6}$cycloalkyl;
(e) $R^9$ represents $C_{1-4}$alkyl, or $C_{1-4}$alkyl substituted with one substituent selected from the group consisting of —NH$_2$;
(f) $R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $C_{3-6}$cycloalkyl; —O—$C_{3-6}$cycloalkyl; Het$^{1a}$; —O-Het$^{1b}$; $C_{1-4}$alkyl substituted with one, two or three —OH substituents; $R^{18}$; $R^{21}$; —P(=O)—($C_{1-4}$alkyl)$_2$; —$NR^{7a}R^{17b}$; $C_{1-4}$alkyl substituted with one, two or three halo atoms; $C_{1-4}$alkyl substituted with one $R^{13}$; $C_{2-6}$alkenyl; and $C_{2-6}$alkenyl substituted with one $R^{13}$; in particular, $R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; $R^{21}$; —P(=O)—($C_{1-4}$alkyl)$_2$; —$NR^{17a}R^{17b}$; $C_{1-4}$alkyl substituted with one, two or three halo atoms; $C_{1-4}$alkyl substituted with one $R^{13}$; $C_{2-6}$alkenyl; and $C_{2-6}$alkenyl substituted with one $R^{13}$; (g) $R^{10}$ represents —O—$C_{1-4}$alkyl, —$NR^{11a}R^{11b}$ or Het$^2$;
(h) $R^{18}$ represents a 5-membered aromatic ring containing one, two or three N-atoms; wherein said 5-membered aromatic ring may optionally be substituted with one $C_{1-4}$alkyl substituent; (i) $R^{21}$ represents 3,6-dihydro-2H-pyran-4-yl;
(j) Het$^{1a}$, Het$^{1c}$ and Het$^{1d}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —OH substituent; and
wherein said 4- to 7-membered monocyclic saturated heterocyclyl may optionally be substituted on one, two or three ring C-atoms with one or two substituents each independently selected from the group consisting of halo and $C_{1-4}$alkyl;
in particular Het$^{1a}$ and Het$^1$c each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, and $C_{1-4}$alkyl substituted with one —OH substituent; and
wherein said 4- to 7-membered monocyclic saturated heterocyclyl may optionally be substituted on one, two or three ring C-atoms with one or two $C_{1-4}$alkyl substituents;
(k) Het$^{1b}$ represents a 4- to 7-membered monocyclic saturated heterocyclyl, attached to the remainder of the molecule of Formula (I) through any available ring carbon atom, said Het$^{1b}$ containing one or two heteroatoms each independently selected from O and N; wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; wherein said 4- to 7-membered monocyclic saturated heterocyclyl may optionally be substituted on one, two or three ring C-atoms with one or two halo substituents;
in particular Het$^{1b}$ represents a 4- to 7-membered monocyclic saturated heterocyclyl, attached to the remainder of the molecule of Formula (I) through any available ring carbon atom, said Het$^{1b}$ containing one or two heteroatoms each independently selected from O and N;
wherein said 4- to 7-membered monocyclic saturated heterocyclyl may optionally be substituted, where possible, on one or two ring N-atoms with a $C_{1-4}$alkyl substituent;
(l) Het$^2$ represents a heterocyclyl of formula (b-1):

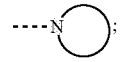
(b-1)

(b-1) represents a N-linked 4- to 7-membered monocyclic saturated heterocyclyl optionally containing one additional N-atom;
wherein in case (b-1) contains one additional N-atom, said one N-atom may optionally be substituted with $C_{1-4}$alkyl;
wherein (b-1) may optionally be substituted on one, two or three ring C-atoms with one or two —OH substituents;
in particular Het$^2$ represents a heterocyclyl of formula (b-1):

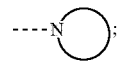
(b-1)

(b-1) represents a N-linked 4- to 7-membered monocyclic saturated heterocyclyl optionally containing one additional N-atom;
wherein in case (b-1) contains one additional N-atom, said one N-atom may optionally be substituted with $C_{1-4}$alkyl;
(m) $R^{11b}$ represents $C_{1-4}$alkyl;
(n) $R^{13}$ represents —O—$C_{1-4}$alkyl, —C(=O)$NR^{15a}R^{15b}$, —$NR^{19a}R^{19b}$, $C_{3-6}$cycloalkyl, or $Het^{1d}$; in particular $R^{13}$ represents —O—$C_{1-4}$alkyl, —C(=O)$NR^{15a}R^{15b}$, or $C_{3-6}$cycloalkyl;
(o) $R^{12}$ represents —OH, —O—$C_{1-4}$alkyl, —C(=O)$NR^{14c}R^{14d}$, $C_{3-6}$cycloalkyl, or $Het^{1c}$;
(p) $Het^{3a}$ and $Het^{3b}$ each independently represents a heterocyclyl of formula (c-1):

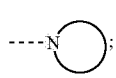

(c-1) represents a N-linked 4- to 7-membered monocyclic saturated heterocyclyl optionally containing one additional heteroatom selected from O and N;
(q) $R^{11a}$, $R^{14c}$, $R^{15a}$, $R^{17a}$ each independently represents hydrogen or $C_{1-4}$alkyl;
(r) $R^{14d}$, $R^{15b}$, $R^{17b}$ and $R^{19b}$ each independently represents $C_{1-4}$alkyl; $C_{3-6}$cycloalkyl; or $C_{1-4}$alkyl substituted with one —O—$C_{1-4}$alkyl substituent; in particular $R^{14d}$, $R^{15b}$, $R^{17b}$ each independently represents $C_{1-4}$alkyl; or $C_{1-4}$alkyl substituted with one —O—$C_{1-4}$alkyl substituent.

Another embodiment of the present invention relates to those compounds of Formula (I) and the pharmaceutically acceptable addition salts, and the solvates thereof, or any subgroup thereof as mentioned in any of the other embodiments wherein $R^3$ represents a 6-membered heteroaromatic ring containing 1 or 2 N-atoms, optionally substituted as mentioned in any of the other embodiments, wherein Y represents $CR^4$ or N, in particular wherein Y represents $CR^4$; and wherein one or more of the following restrictions apply:
(a) $R^2$ represents $C_{1-6}$alkyl substituted with one $R^5$;
(b) $R^5$ represents —$NR^{6a}R^{6b}$, or —$OR^7$;
(c) $R^{6a}$ represents hydrogen;
(d) $R^{6b}$ represents —C(=O)—$C_{1-4}$alkyl;
(e) $R^7$ represents hydrogen;
(f) $R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $Het^{1a}$; —$NR^{17a}R^{17b}$; $C_{1-4}$alkyl substituted with one $R^{13}$;
(g) $R^{10}$ represents —$NR^{11a}R^{11b}$;
(h) $Het^{1a}$ represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, and $C_{1-4}$alkyl substituted with one —OH substituent;
(i) $R^{11b}$ represents $C_{1-4}$alkyl;
(j) $R^{13}$ represents —O—$C_{1-4}$alkyl;
(k) $R^{12}$ represents —O—$C_{1-4}$alkyl;
(l) $R^{7a}$ represents hydrogen;
(m) $R^{17b}$ represents $C_{1-4}$alkyl substituted with one —O—$C_{1-4}$alkyl substituent.

Another embodiment of the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, wherein Y represents $CR^4$ or N, in particular wherein Y represents $CR^4$; and wherein one or more of the following restrictions apply:
(a) $R^1$ represents $C_{1-4}$alkyl;
(b) $R^2$ represents $C_{1-6}$alkyl substituted with one $R^5$;
(c) $R^4$ represents hydrogen;
(d) $R^5$ represents $Het^3a$, —$NR^{6a}R^{6b}$, or —$OR^7$; in particular $R^5$ represents —$OR^7$;
(e) $R^7$ represents hydrogen, $C_{1-4}$alkyl, —$C_{1-4}$alkyl-$NR^{8a}R^{8b}$, —C(=O)—$R^9$, or —$C_{1-4}$alkyl-$Het^{3b}$; in particular $R^7$ represents hydrogen;
(f) $R^3$ represents 2-oxo-1,2-dihydropyridin-3-yl,
wherein said 2-oxo-1,2-dihydropyridin-3-yl may optionally substituted on the N-atom with a substituent selected from the group consisting of $C_{1-6}$alkyl; $C_{1-4}$alkyl substituted with one, two or three —OH substituents; $C_{1-4}$alkyl substituted with one $R^{13}$; $C_{1-4}$alkyl substituted with one $R^{18}$; and
wherein said 2-oxo-1,2-dihydropyridin-3-yl may optionally be substituted on the ring carbon atoms with in total one, two or three substituents each independently selected from the group consisting of halo; $C_{1-6}$alkyl; —C(=O)—$R^{10}$; and $Het^{1a}$;
in particular $R^3$ represents 2-oxo-1,2-dihydropyridin-3-yl, wherein said 2-oxo-1,2-dihydropyridin-3-yl may optionally substituted on the N-atom with a substituent selected from the group consisting of $C_{1-6}$alkyl; $C_{1-4}$alkyl substituted with one, two or three —OH substituents; $C_{1-4}$alkyl substituted with one $R^{13}$; $C_{1-4}$alkyl substituted with one $R^{18}$; and
wherein said 2-oxo-1,2-dihydropyridin-3-yl may optionally be substituted on the ring carbon atoms with in total one, two or three substituents each independently selected from the group consisting of halo; $C_{1-6}$alkyl; and $Het^{1a}$;
(g) $R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
(h) $Het^{1a}$, $Het^{1e}$ and $Het^{1d}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —OH substituent; and
wherein said 4- to 7-membered monocyclic saturated heterocyclyl may optionally be substituted on one, two or three ring C-atoms with one or two substituents each independently selected from the group consisting of halo and $C_{1-4}$alkyl;
in particular $Het^{1a}$ and $Het^{1d}$ each independently represents a 4- to 7-membered monocyclic saturated heterocyclyl containing one or two heteroatoms each independently selected from O and N;
wherein said 4- to 7-membered monocyclic saturated heterocyclyl may optionally be substituted, where possible, on one or two ring N-atoms with $C_{1-4}$alkyl; and wherein said 4- to 7-membered monocyclic saturated heterocyclyl may optionally be substituted on one or two ring C-atoms with one or two substituents each independently selected from the group consisting of halo and $C_{1-4}$alkyl;

(i) $R^{13}$ represents —O—$C_{1-4}$alkyl, —C(=O)$NR^{15a}R^{15b}$, —$NR^{19a}R^{19b}$, $C_{3-6}$cycloalkyl, or $Het^{1d}$; in particular $R^{13}$ represents —O—$C_{1-4}$alkyl, —C(=O)$NR^{15a}R^{15b}$, $C_{3-6}$cycloalkyl, or $Het^{11d}$ (j) $R^{15a}$ represents $C_{1-4}$alkyl;

(k) $R^{15b}$ represents $C_{1-4}$alkyl; $C_{3-6}$cycloalkyl; or $C_{1-4}$alkyl substituted with one —O—$C_{1-4}$alkyl substituent; in particular $R^{15b}$ represents $C_{1-4}$alkyl.

Another embodiment of the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, wherein Y represents $CR^4$ or N, in particular wherein Y represents $CR^4$; and wherein one or more of the following restrictions apply:

(a) $R^1$ represents $C_{1-4}$alkyl;
(b) $R^2$ represents $C_{1-6}$alkyl substituted with one $R^5$;
(c) $R^4$ represents hydrogen;
(d) $R^5$ represents —$OR^7$;
(e) $R^7$ represents hydrogen;
(f) $R^3$ represents 2-oxo-1,2-dihydropyridin-3-yl, wherein said 2-oxo-1,2-dihydropyridin-3-yl may optionally substituted on the N-atom with a substituent selected from the group consisting of $C_{1-6}$alkyl; $C_{1-4}$alkyl substituted with one $R^{13}$; $C_{1-4}$alkyl substituted with one $R^{18}$; and wherein said 2-oxo-1,2-dihydropyridin-3-yl may optionally be substituted on the ring carbon atoms with in total one, two or three substituents each independently selected from the group consisting of halo and $C_{1-6}$alkyl;

(g) $R^{18}$ represents a 5-membered aromatic ring containing one, two or three N-atoms; wherein said 5-membered aromatic ring may optionally be substituted with one $C_{1-4}$alkyl substituent;

(h) $Het^{1d}$ represents a 4- to 7-membered monocyclic saturated heterocyclyl containing one or two heteroatoms each independently selected from O and N; wherein said 4- to 7-membered monocyclic saturated heterocyclyl may optionally be substituted on one or two ring C-atoms with one or two substituents each independently selected from the group consisting of halo and $C_{1-4}$alkyl;

(i) $R^{13}$ represents $Het^{1d}$

In an embodiment, the present invention relates to a subgroup of Formula (I), hereby named compounds of Formula (I'), and the pharmaceutically acceptable addition salts, and the solvates thereof:

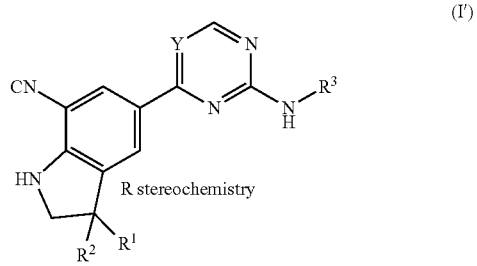

(I')

wherein $R^1$ represents $C_{1-4}$alkyl;
$R^2$ represents $C_{1-6}$alkyl substituted with one $R^5$;
in particular wherein $R^1$ represents $C_{1-4}$alkyl;
$R^2$ represents $C_{1-6}$alkyl substituted with one $R^5$;
$R^5$ represents —$OR^7$;
more in particular wherein $R^1$ represents $C_{1-4}$alkyl;
$R^2$ represents $C_{1-6}$alkyl substituted with one $R^5$;
$R^5$ represents —$OR^7$;
$R^7$ represents hydrogen;
and wherein all other variables are defined according to any of the other embodiments.

In an embodiment, the present invention relates to a subgroup of Formula (I), hereby named compounds of Formula (I"), and the pharmaceutically acceptable addition salts, and the solvates thereof:

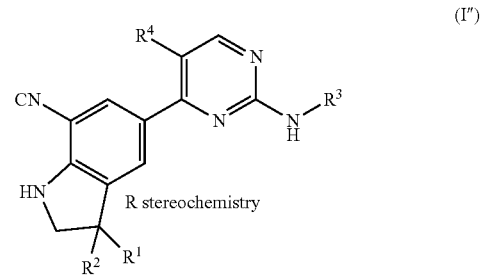

(I")

wherein $R^1$ represents $C_{1-4}$alkyl;
$R^2$ represents $C_{1-6}$alkyl substituted with one $R^5$;
in particular wherein $R^1$ represents $C_{1-4}$alkyl;
$R^2$ represents $C_{1-6}$alkyl substituted with one $R^5$;
$R^5$ represents —$OR^7$;
more in particular wherein $R^1$ represents $C_{1-4}$alkyl;
$R^2$ represents $C_{1-6}$alkyl substituted with one $R^5$;
$R^5$ represents —$OR^7$;
$R^7$ represents hydrogen;
and wherein all other variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents methyl;
$R^2$ represents methyl or —$CH_2$—OH.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents methyl; $R^2$ represents —$CH_2$—OH.

In an embodiment, the present invention relates to those compounds of Formula (I) and the pharmaceutically acceptable addition salts, and the solvates thereof, or any subgroup thereof as mentioned in any of the other embodiments, wherein $R^3$ represents pyridinyl, pyrimidinyl, pyridazinyl or pyrazinyl, each of which may optionally be substituted according to any of the other embodiments;
in particular $R^3$ represents 2-pyridinyl, 3-pyridinyl, 4-pyridinyl, 5-pyrimidinyl, 4-pyrimidinyl, 4-pyridazinyl or 2-pyrazinyl, each of which may optionally be substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^3$ represents pyridinyl, pyrimidinyl or pyridazinyl, each of which may optionally be substituted according to any of the other embodiments;

in particular R³ represents 2-pyridinyl, 3-pyridinyl, 4-pyridinyl, 5-pyrimidinyl, 4-pyrimidinyl, or 4-pyridazinyl, each of which may optionally be substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R³ represents a 6-membered heteroaromatic ring containing 1 or 2 N-atoms, substituted with one, two or three substituents according to any of the other embodiments, provided however that the substituents are not selected from the group consisting of —S(=O)$_2$—C$_{1-4}$alkyl; —S(=O)(=N—R$^{20a}$)—C$_{1-4}$alkyl; and —P(=O)—(C$_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein
R³ represents 2-oxo-1,2-dihydropyridin-3-yl optionally substituted according to any of the other embodiments, provided however that the substituents on the carbon atoms are not selected from the group consisting of —S(=O)$_2$—C$_{1-4}$alkyl; —S(=O)(=N—R$^{20a}$)—C$_{1-4}$alkyl; and —P(=O)—(C$_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein R⁴ is hydrogen or fluoro.

In an embodiment, the present invention relates to those compounds of Formula (I) and the pharmaceutically acceptable addition salts, and the solvates thereof, or any subgroup thereof as mentioned in any of the other embodiments, wherein R⁴ is hydrogen.

In an embodiment, the present invention relates to those compounds of Formula (I) and the pharmaceutically acceptable addition salts, and the solvates thereof, or any subgroup thereof as mentioned in any of the other embodiments, wherein R⁷ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
R⁵ represents —OR⁷; and
R⁷ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
R⁹ represents C$_{1-4}$alkyl, or C$_{1-4}$alkyl substituted with one substituent selected from the group consisting of —NH$_2$, —COOH, and Het⁶;

In an embodiment, the present invention relates to those compounds of Formula (I) and the pharmaceutically acceptable addition salts, and the solvates thereof, or any subgroup thereof as mentioned in any of the other embodiments, wherein R¹⁸ is attached to the remainder of the molecule of Formula (I) via a carbon atom.

In an embodiment, the present invention relates to those compounds of Formula (I) and the pharmaceutically acceptable addition salts, and the solvates thereof, or any subgroup thereof as mentioned in any of the other embodiments, wherein R¹⁸ represents

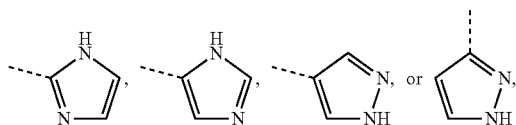

in particular

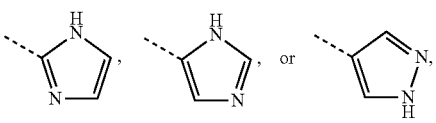

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R¹⁸ represents

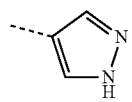

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R¹⁸ represents

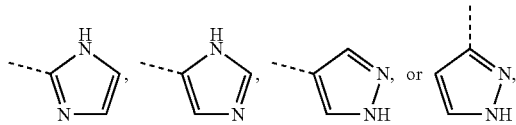

in particular

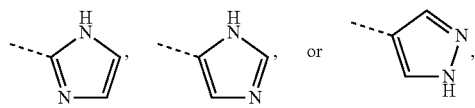

each substituted on the NH with C$_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein R¹⁸ represents

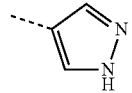

substituted on the NH with C$_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein Het$^{1a}$, Het$^{1c}$ and Het$^{1d}$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents a 6-membered heteroaromatic ring containing 1 or 2 N-atoms, optionally substituted as mentioned in any of the other embodiments, wherein Het$^{1a}$, Het$^{1c}$ and Het$^{1d}$ each independently represents morpholinyl, piperidinyl, oxetanyl, piperazinyl, tetrahydro-2H-pyranyl, or tetrahydrofuranyl,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents a 6-membered heteroaromatic ring containing 1 or 2 N-atoms, optionally substituted as mentioned in any of the other embodiments, wherein Het$^{1a}$, Het$^{1c}$ and Het$^{1d}$ each independently represents

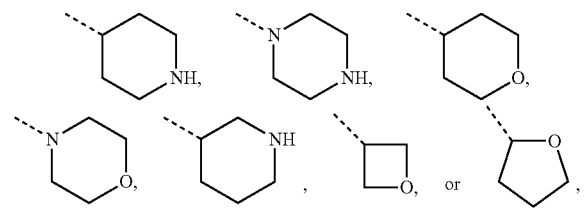

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents a 6-membered heteroaromatic ring containing 1 or 2 N-atoms, optionally substituted as mentioned in any of the other embodiments, wherein Het$^{1a}$ represents

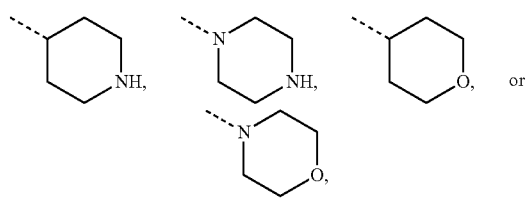

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents a 6-membered heteroaromatic ring containing 1 or 2 N-atoms, optionally substituted as mentioned in any of the other embodiments, and wherein Het$^{1c}$ represents

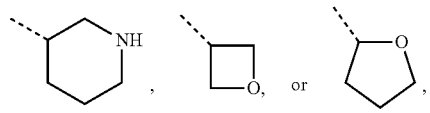

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents a 6-membered heteroaromatic ring containing 1 or 2 N-atoms, optionally substituted as mentioned in any of the other embodiments, and wherein Het$^{1d}$ represents

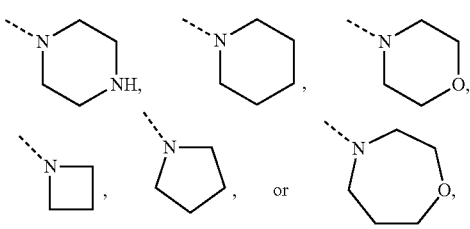

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents 2-oxo-1,2-dihydropyridin-3-yl, optionally substituted as mentioned in any of the other embodiments, and wherein Het$^{1a}$, Het$^{1c}$ and Het$^{1d}$ each independently represents morpholinyl, piperidinyl, pyrrolidinyl, oxetanyl, azetidinyl, piperazinyl, tetrahydro-2H-pyranyl, or hexahydro-1,4-oxazepinyl,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R$^3$ represents 2-oxo-1,2-dihydropyridin-3-yl, optionally substituted as mentioned in any of the other embodiments, and wherein Het$^{1a}$, Het$^{1c}$ and Het$^{1d}$ each independently represents

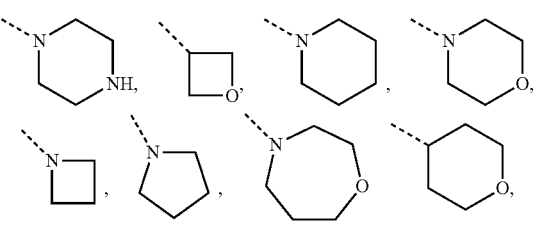

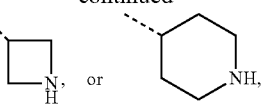 or each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, and wherein $Het^{1a}$, $Het^{1c}$ and $Het^{1d}$ each independently represents

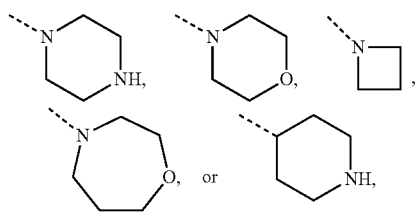

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, and wherein $Het^{1a}$ represents

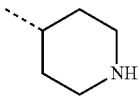

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, and wherein $Het^{1c}$ represents

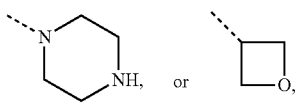

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, and wherein $Het^{1d}$ represents

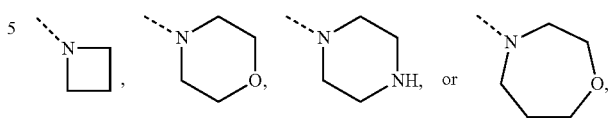

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1b}$, $Het^{1e}$, $Het^{1g}$ and $Het^4$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein $R^3$ represents a 6-membered heteroaromatic ring containing 1 or 2 N-atoms, optionally substituted as mentioned in any of the other embodiments, and wherein $Het^{1b}$, $Het^{1e}$, $Het^{1g}$ and $Het^4$ each independently represents piperidinyl, tetrahydro-2H-pyranyl, or tetrahydrofuranyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^3$ represents a 6-membered heteroaromatic ring containing 1 or 2 N-atoms, optionally substituted as mentioned in any of the other embodiments, and wherein $Het^{1b}$, $Het^{1e}$, $Het^{1g}$ and $Het^4$ each independently represents

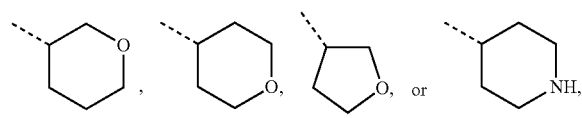

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein $R^3$ represents 2-oxo-1,2-dihydropyridin-3-yl, optionally substituted as mentioned in any of the other embodiments, and wherein $Het^{1b}$, $Het^{1e}$, $Het^{1g}$ and $Het^4$ each independently represents piperidinyl, tetrahydro-2H-pyranyl, or pyrrolidinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R³ represents 2-oxo-1,2-dihydropyridin-3-yl, optionally substituted as mentioned in any of the other embodiments, and wherein Het¹ᵇ, Het¹ᵉ, Het¹ᵍ and Het⁴ each independently represents

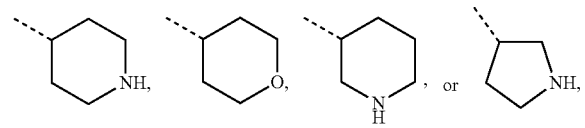

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het¹ᵍ represents

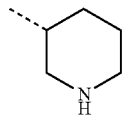

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het¹ᵉ represents

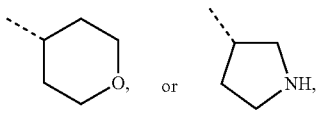

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R³ represents a 6-membered heteroaromatic ring containing 1 or 2 N-atoms, optionally substituted as mentioned in any of the other embodiments, and wherein Het¹ᵇ represents

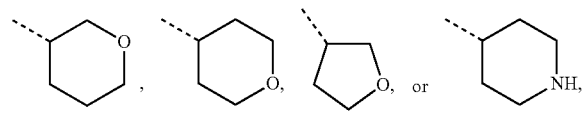

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments wherein R³ represents 2-oxo-1,2-dihydropyridin-3-yl, optionally substituted as mentioned in any of the other embodiments, and wherein Het¹ᵇ represents

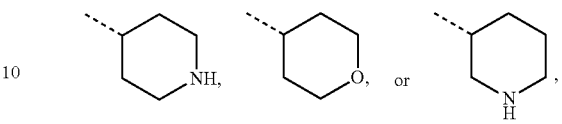

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het⁴ represents pyrrolidinyl, piperidinyl, tetrahydropyranyl, azetidinyl, or 1,1-dioxidethiopyranyl; each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het² represents

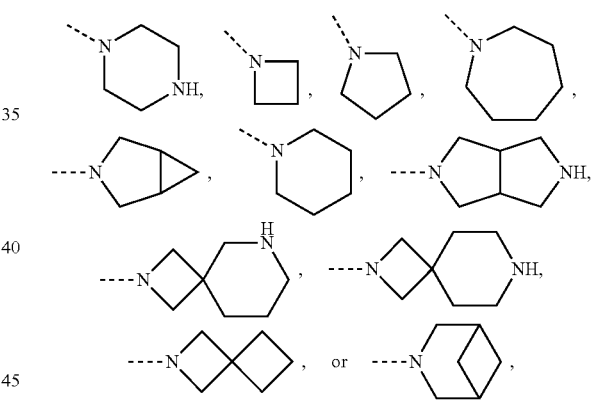

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R³ represents a 6-membered heteroaromatic ring containing 1 or 2 N-atoms, optionally substituted as mentioned in any of the other embodiments, and wherein Het² represents

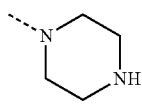

optionally substituted on carbon and/or nitrogen atoms according to any of the other embodiments; in particular the hydrogen on the nitrogen atom is replaced by $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein Het$^{3a}$, Het$^{3b}$, Het$^5$, Het$^6$ and Het$^{1f}$ each independently represents

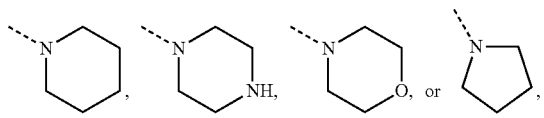

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R$^3$ represents 2-oxo-1,2-dihydropyridin-3-yl, optionally substituted as mentioned in any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents CR$^4$; and wherein R$^3$ represents 2-oxo-1,2-dihydropyridin-3-yl, optionally substituted as mentioned in any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R$^3$ represents a 6-membered heteroaromatic ring containing 1 or 2 N-atoms, optionally substituted as mentioned in any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents CR$^4$; and wherein R$^3$ represents a 6-membered heteroaromatic ring containing 1 or 2 N-atoms, optionally substituted as mentioned in any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R$^3$ represents a 6-membered heteroaromatic ring containing 1 or 2 N-atoms, optionally substituted as mentioned in any of the other embodiments, wherein Het$^{3a}$ represents

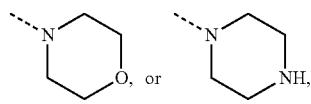

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R$^3$ represents a 6-membered heteroaromatic ring containing 1 or 2 N-atoms, optionally substituted as mentioned in any of the other embodiments, and wherein Het$^{3b}$ represents

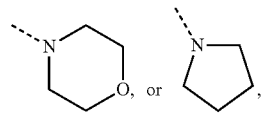

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^5$ represents

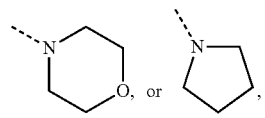

each optionally substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^6$ represents

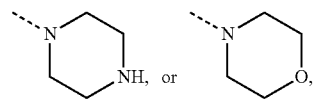

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1f}$ represents

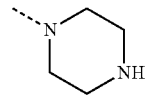

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^7$ and Het$^8$ each independently represent

optionally substituted on carbon atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein $Het^2$ represents a heterocyclyl of formula (b-1):

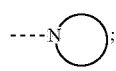   (b-1)

(b-1) represents a N-linked 4- to 7-membered monocyclic saturated heterocyclyl optionally containing one additional heteroatom selected from O, S, $S(=O)_p$ and N; wherein in case (b-1) contains one additional N-atom, said N-atom may optionally be substituted with $C_{1-4}$alkyl; and
wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH.

In an embodiment, the present invention relates to those compounds of Formula (I) and the pharmaceutically acceptable addition salts, and the solvates thereof, or any subgroup thereof as mentioned in any of the other embodiments, wherein
$Het^{1a}$ represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;
wherein said 4- to 7-membered monocyclic saturated heterocyclyl or said 6- to 11-membered bicyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;
$Het^{1c}$ and $Het^{1d}$ each independently represents a 4- to 7-membered monocyclic saturated heterocyclyl containing one or two heteroatoms each independently selected from O, S, $S(=O)_p$ and N; or in case $Het^{1c}$ and $Het^{1d}$ are attached to the remainder of the molecule of Formula (I) through an N-atom, $Het^{1c}$ and $Het^{1d}$ may also represent a N-linked 6- to 11-membered bicyclic saturated heterocyclyl, including fused, spiro and bridged cycles, optionally containing one or two additional heteroatoms each independently selected from O, S, $S(=O)_p$ and N;
wherein said 4- to 7-membered monocyclic saturated heterocyclyl or said N-linked 6- to 11-membered bicyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said N-linked 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein Y represents $CR^4$.

In an embodiment, the present invention relates to a subgroup of Formula (I), hereby named compounds of Formula (I-x), and the pharmaceutically acceptable addition salts, and the solvates thereof:

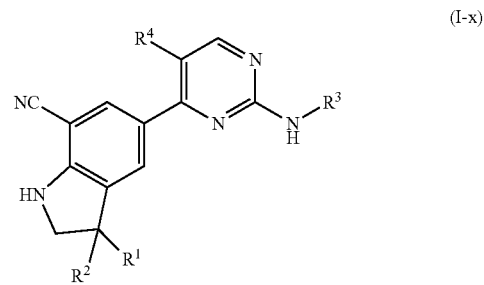   (I-x)

wherein all variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents N.

In an embodiment, the present invention relates to a subgroup of Formula (I), hereby named compounds of Formula (I-y), and the pharmaceutically acceptable addition salts, and the solvates thereof:

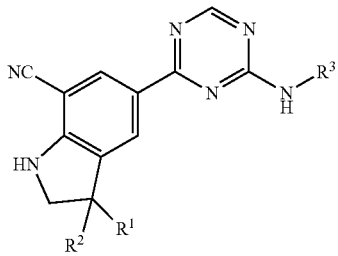

(I-y)

wherein all variables are defined according to any of the other embodiments.

In an embodiment, the present invention relates to a subgroup of Formula (I) as defined in the general reaction schemes.

In an embodiment the compound of Formula (I) is selected from the group consisting of compounds 3, 4, 6, 10, 33, 50, 59, 65, 93, 103, 115, 124, 140, 4i, 7i and 13i, tautomers and stereoisomeric forms thereof,
and the pharmaceutically acceptable addition salts, and the solvates thereof.

In an embodiment the compound of Formula (I) is selected from the group consisting of compounds 3, 4, 6, 10, 33, 50, 59, 65, 93, 103, 115, 124, 140, 4i, 7i and 13i.

In an embodiment the compound of Formula (I) is selected from the group consisting of any of the exemplified compounds,
tautomers and stereoisomeric forms thereof,
and the free bases, any pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realise that functionalization reactions illustrated in the Schemes below for compounds of Formula (I) wherein Y is $CR^4$, may also be carried out for compounds wherein Y is N. The skilled person will realise this applies, for example and without limitation, to steps 3 and 4 of scheme 2 and scheme 18.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 6, the NH moiety on the pyrimidinyl can be protected with a t-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art.

In the general schemes below, $R^3$ being a C-linked 6-membered heteroaromatic ring containing 1 or 2 N-atoms is represented as

Scheme 1

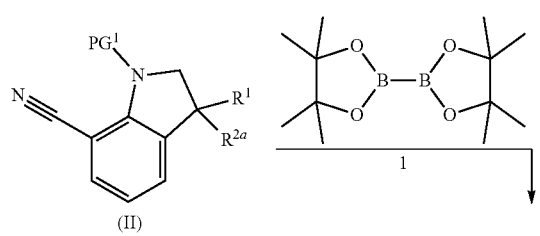

(II)

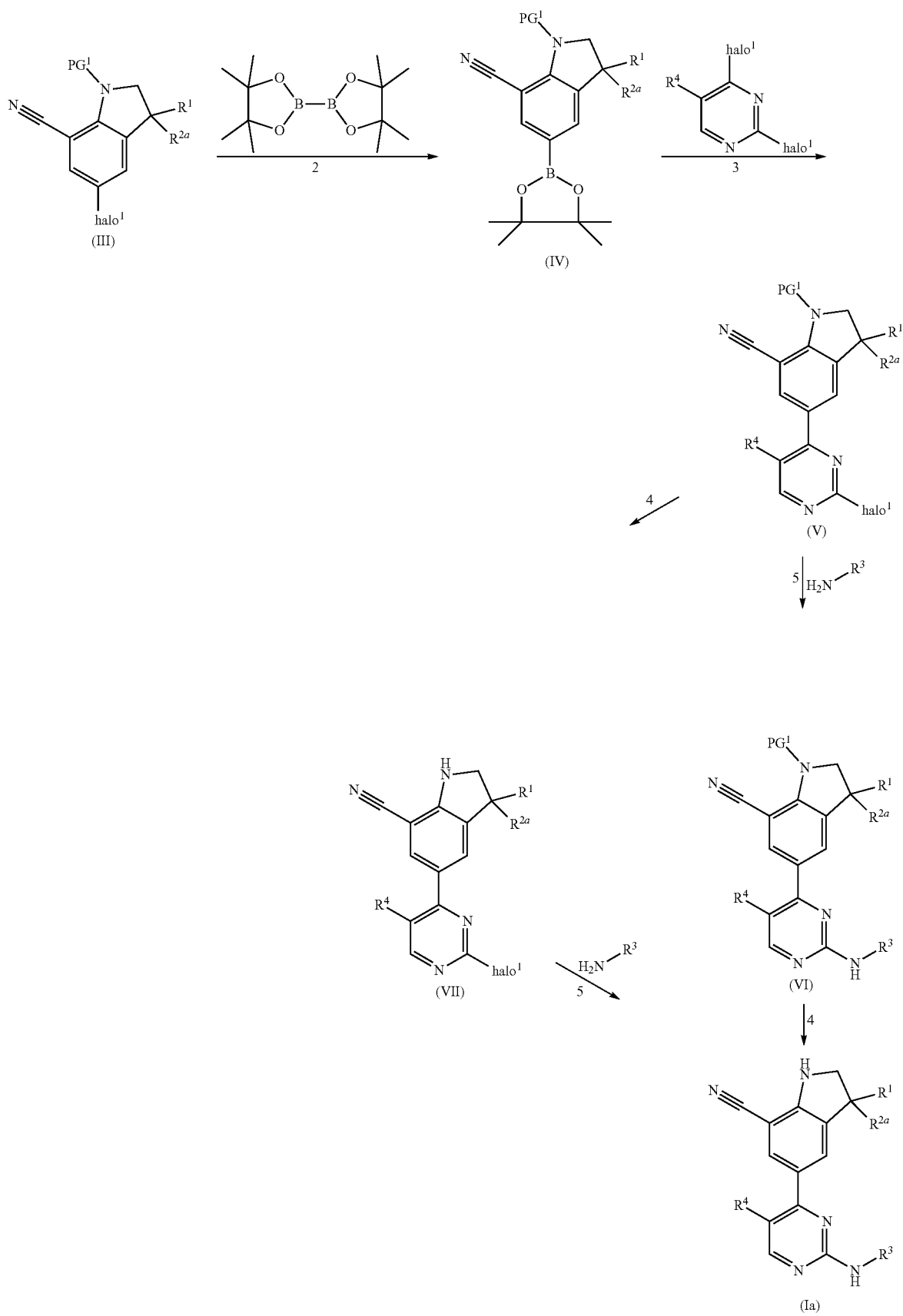

-continued

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-μ-methoxydiiridium (I) ([Ir(OCH₃)(C₈H₁₂)]₂), and a suitable solvent such as for example heptane;

2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh₃)₄), a suitable base such as for example sodium carbonate, and a suitable solvent such as for example 1,4-dioxane;

4: at a suitable temperature such as for example 0° C. or room temperatire or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

5: at a suitable temperature such as for example 100° C., in the presence of a suitable catalyst such as for example palladium acetate (Pd(OAc)₂), a suitable ligand such as for example 2,2'-bis(diphenylphosphino)-1,1'-binaphthyl (BINAP), a suitable base such as for example cesium carbinate, and a suitable solvent such as for example 1,4-dioxane, optionally under microwave activation.

In general, compounds of Formula (I) wherein $R^2$ is $R^{2a}$ being $C_{1-6}$alkyl, Y is $CR^4$, and wherein all the other variables are defined according to the scope of the present invention, hereby named compounds of Formula (Ia), can be prepared according to the following reaction Scheme 1. In Scheme 1 halo¹ is defined as Cl, Br or I; and $PG^1$ represents a suitable protecting group, such as for example tert-(butoxycarbonyl). All other variables in Scheme 1 are defined according to the scope of the present invention.

In Scheme 1, the following reaction conditions apply:

Scheme 2

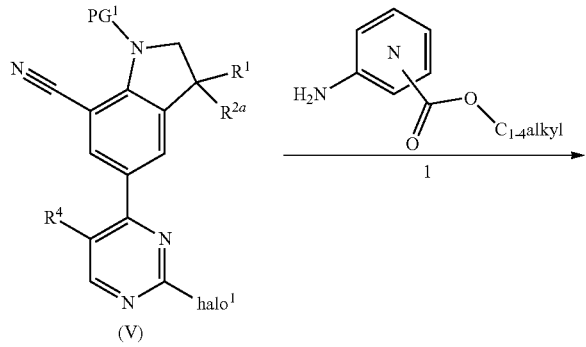

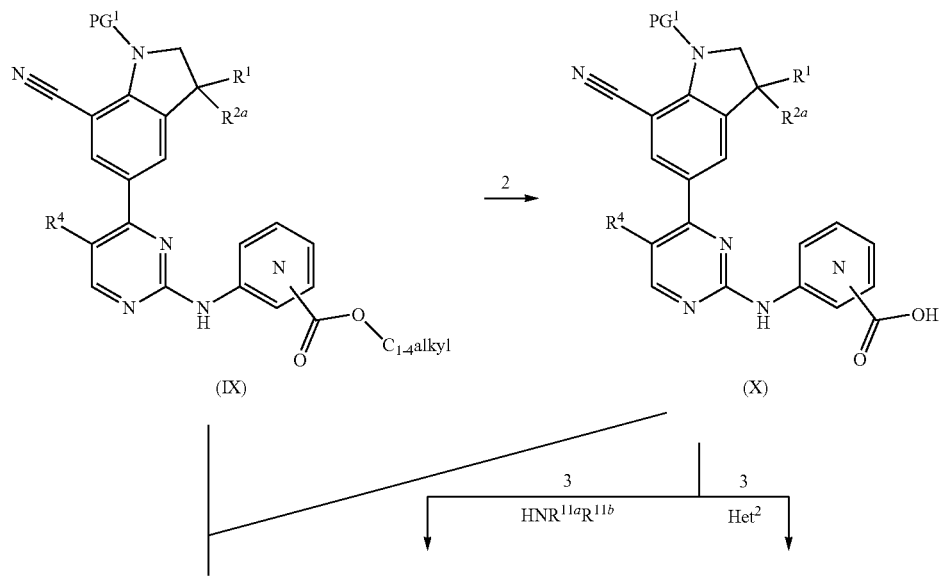

-continued

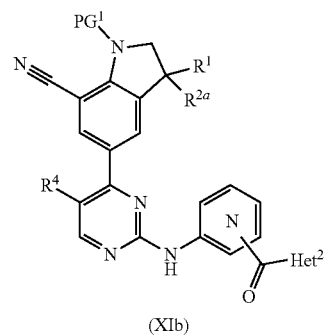

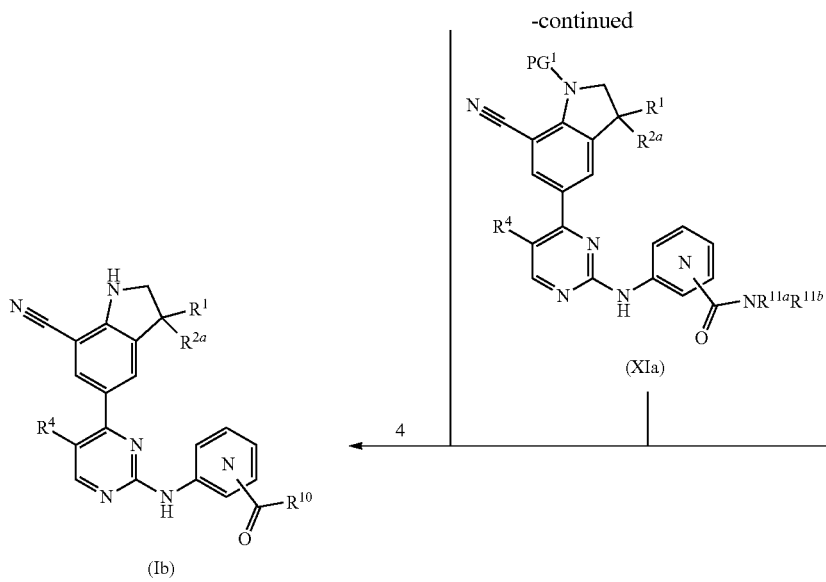

1: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

2: at a suitable temperature such as for example 70° C., in the presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;

4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethylacetate, or 1,4-dioxane, and a suitable time such as for example 3 hours.

In general, compounds of Formula (I) wherein $R^2$ is $R^{2a}$ being $C_{1-6}$alkyl, $R^3$ is a C-linked 6-membered heteroaromatic ring containing 1 or 2 N-atoms, which is substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ib), can be prepared according to the following reaction Scheme 2. In Scheme 2 halo$^1$ is defined as Cl, Br or I; $PG^1$ represents a suitable protecting group, such as for example tert-(butoxycarbonyl). All other variables in Scheme 2 are defined according to the scope of the present invention.

In Scheme 2, the following reaction conditions apply:

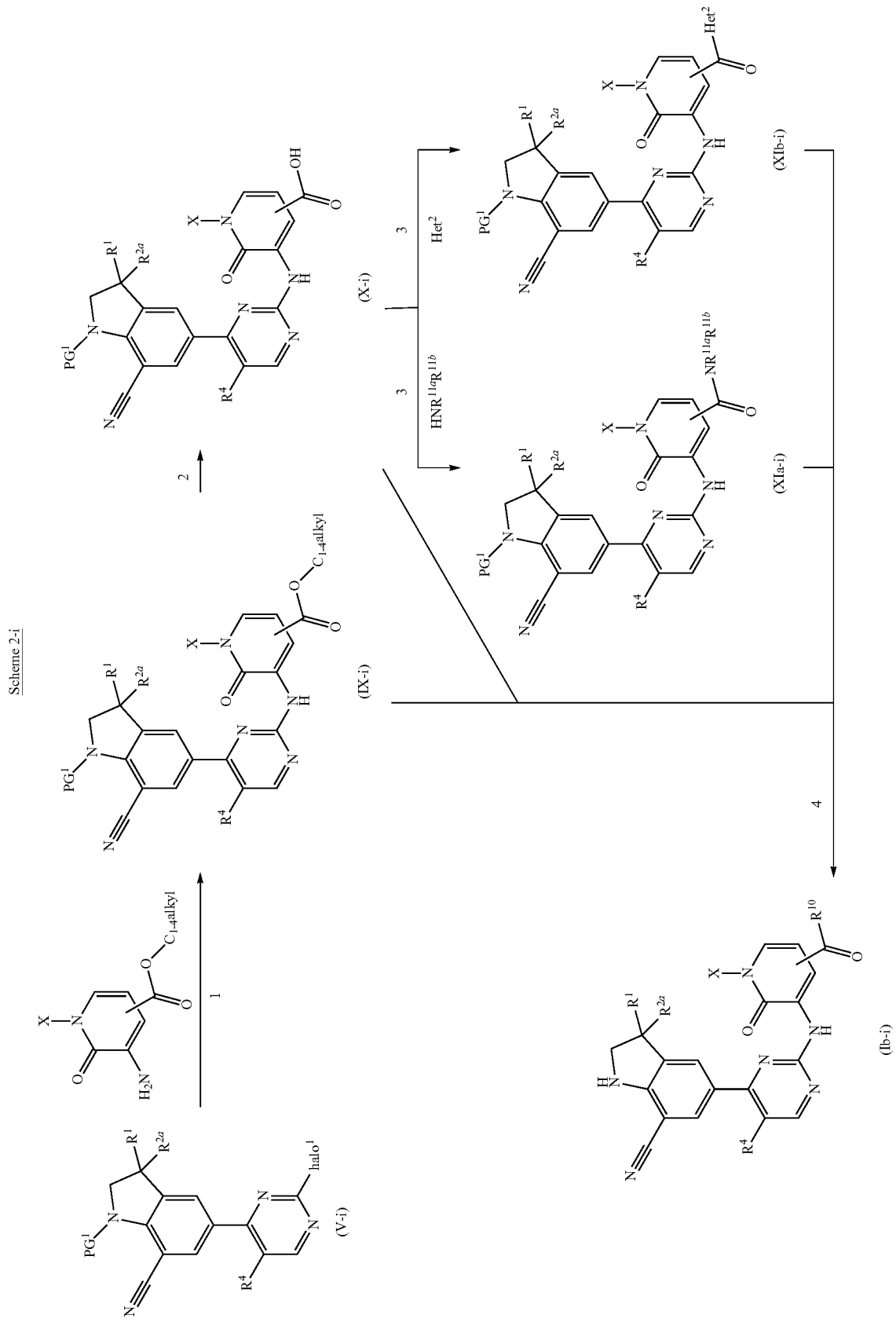

In general, compounds of Formula (I) wherein $R^2$ is $R^{2a}$ being $C_{1-6}$alkyl, $R^3$ is a 2-oxo-1,2-dihydropyridin-3-yl substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ib-i), can be prepared according to the following reaction Scheme 2-i. In Scheme 2-i, X is defined as an optional substituent on the N-atom of the 2-oxo-1,2-dihydropyridin-3-yl (according to the scope), $halo^1$ is defined as Cl, Br or I; $PG^1$ represents a suitable protecting group, such as for example tert-(butoxycarbonyl). All other variables in Scheme 2-i are defined according to the scope of the present invention.

Scheme 2-i is shown below and the same reaction conditions as mentioned for Scheme 2 above apply:

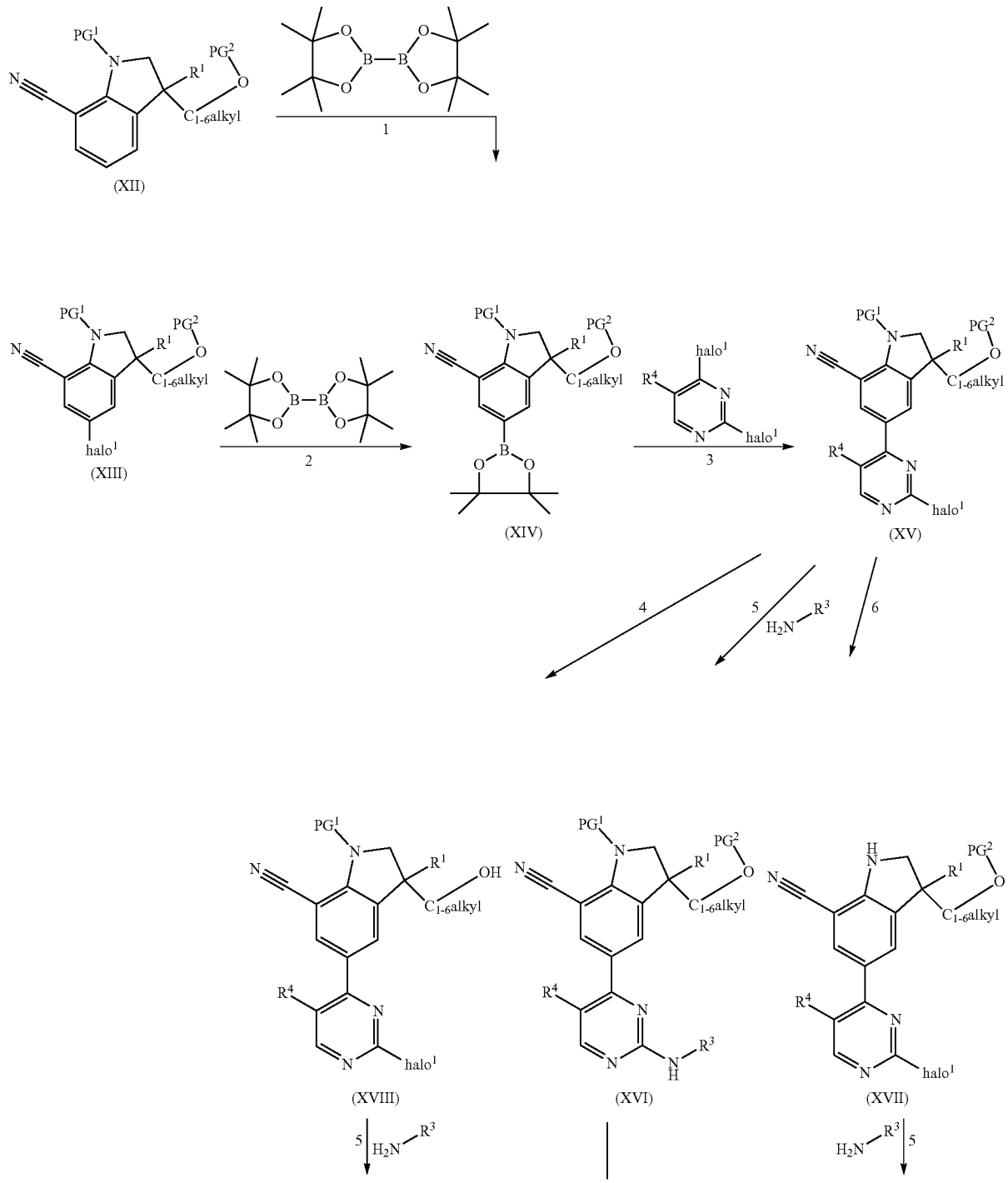

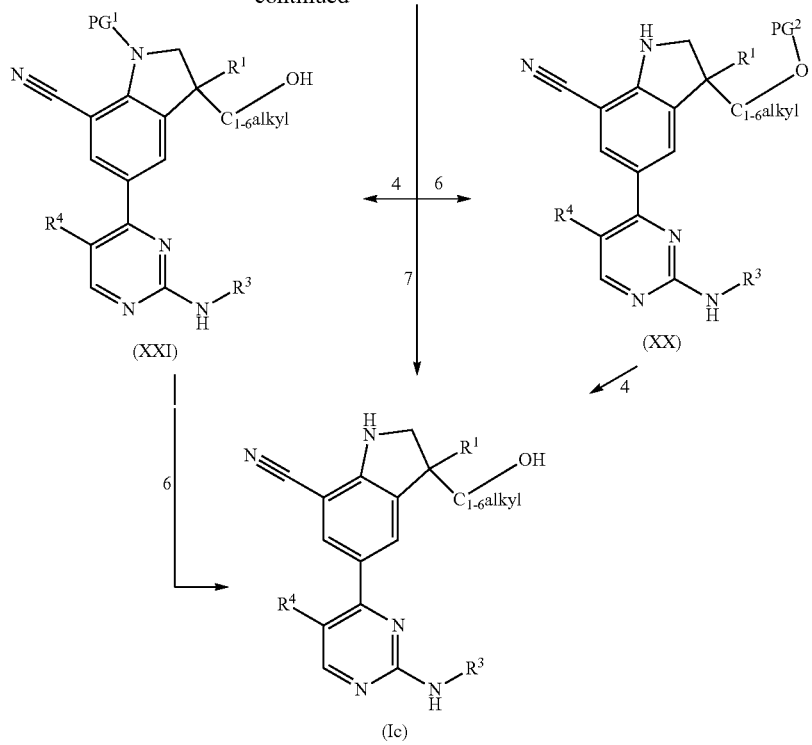

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-μ-methoxydiiridium (I) ([Ir(OCH$_3$)(C$_8$H$_{12}$)]$_2$), and a suitable solvent such as for example heptane;

2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;

4: at a suitable temperature such as for example room temperature, in presence of a suitable desilylating agent such as for example tetra-n-butylammonium fluoride and a suitable solvent such as for example 2-methyltetrahydrofuran or tetrahydrofuran;

5: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

7: at a suitable temperature such as for example reflux, in the presence of a suitable acid such as for example aqueous hydrochloric acid with a suitable solvent such as for example dichloromethane, methanol, ethyl acetate or 1,4-dioxane, and a suitable time such as for example 6 hours.

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 3. In Scheme 3 halo$^1$ is defined as Cl, Br or I; PG$^1$ represents a suitable protecting group, such as for example tert-(butoxycarbonyl) and PG$^2$ represents a suitable protecting group, such as for example tert-butyl-dimethylsilyl. All other variables in Scheme 3 are defined according to the scope of the present invention.

In Scheme 3, the following reaction conditions apply:

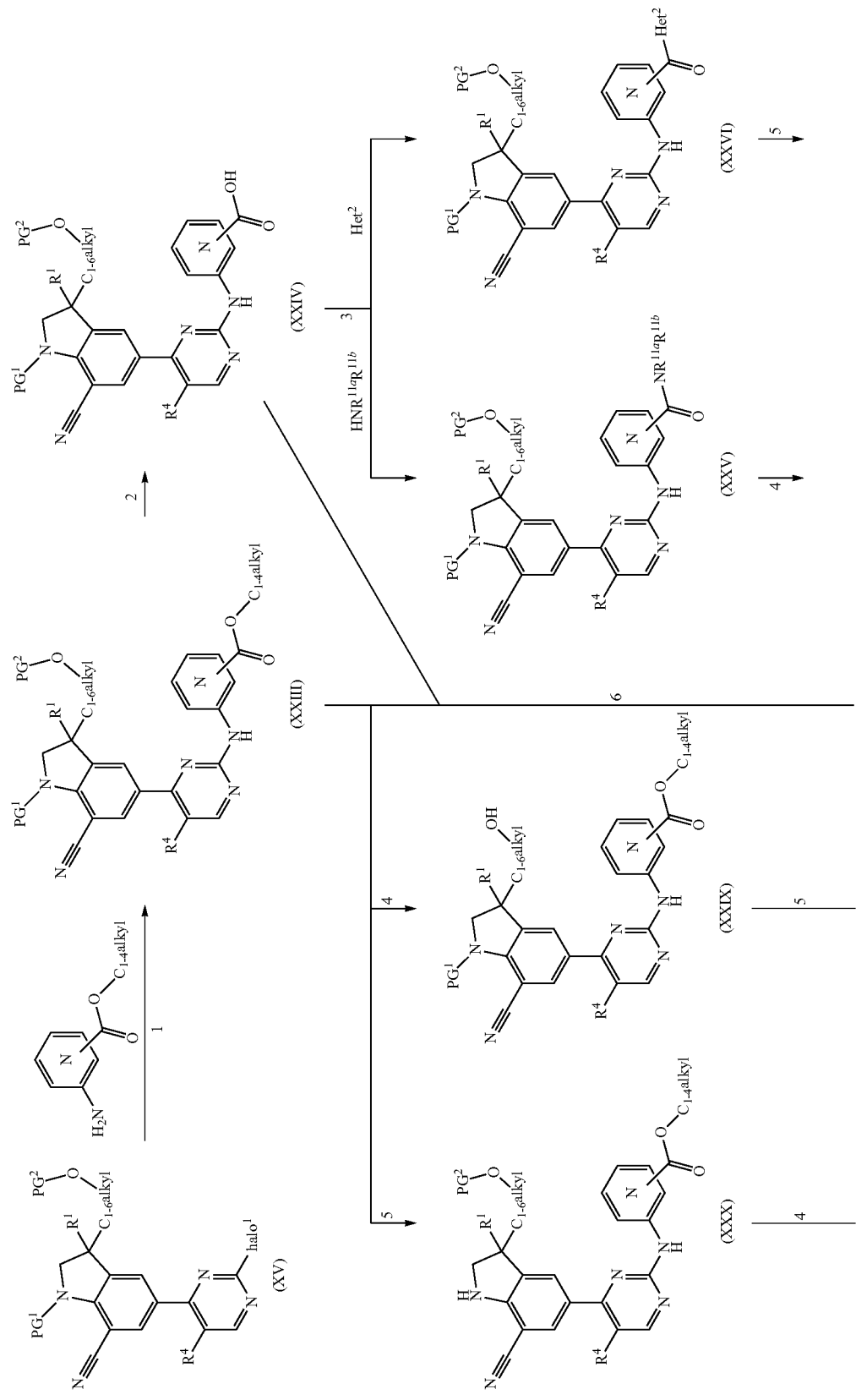

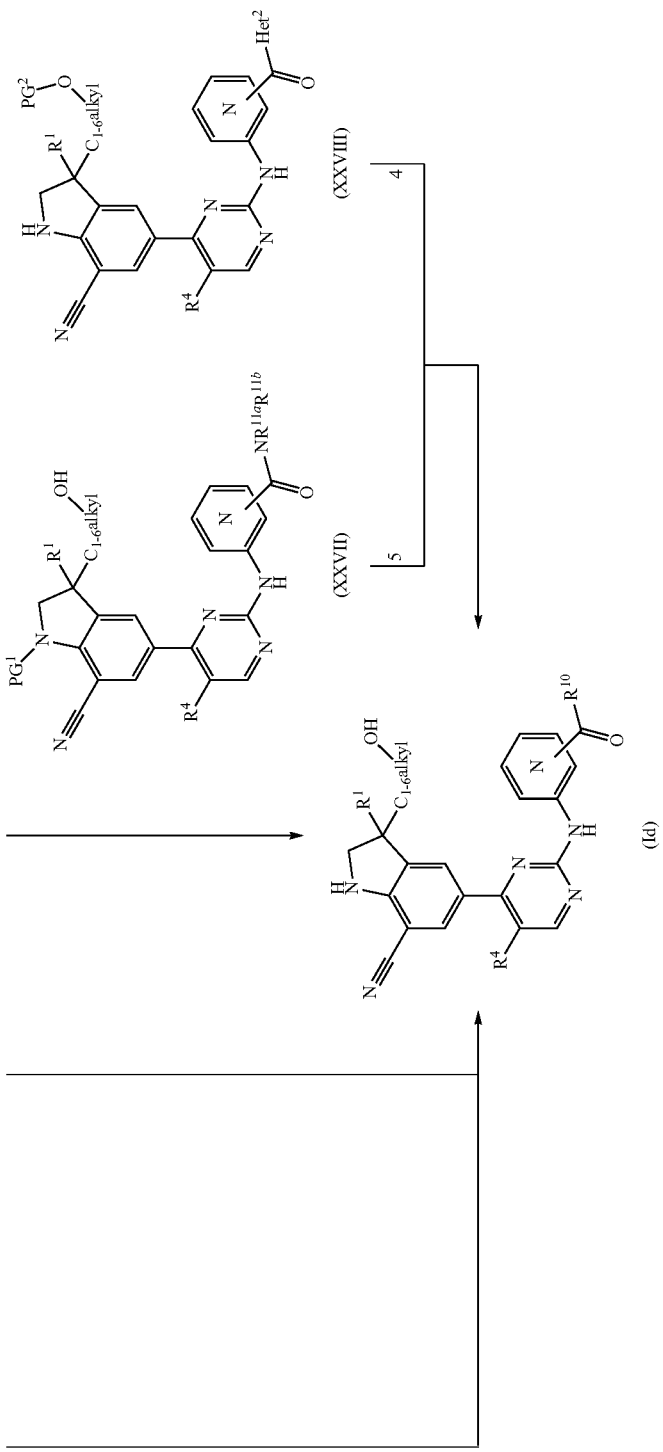

1: at a suitable temperature such as for example 100° C., in the presence of a suitable catalyst such as for example palladium acetate (Pd(OAc)₂), a suitable ligand such as for example 2,2′-bis(diphenylphosphio)-1,1′-binaphthyl (BINAP), a suitable base such as for example cesium carbonate, and a suitable solvent such as for example 1,4-dioxane, optionally under microwave activation;

2: at a suitable temperature such as for example 70° C., in presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;

4: at a suitable temperature such as for example room temperature, in presence of a suitable desilylating agent such as for example tetra-n-butylammonium fluoride and a suitable solvent such as for example 2-methyltetrahydrofuran or tetrahydrofuran;

5: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene as a sutiabel temperature such as for example 125° C., and a suitable time such as for example 3 hours;

6: at a suitable temperature such as for example reflux, in presence of a suitable acid such as for example aqueous hydrochloric acid with a suitable solvent such as for example dichloromethane, methanol, ethyl acetate or 1,4-dioxane, and a suitable time such as for example 6 hours.

In general, compounds of Formula (I) wherein $R^2$ is $R^{2b}$ being $C_{1-6}$alkyl substituted with one OH, Y is $CR^4$, $R^3$ is a C-linked 6-membered heteroaromatic ring containing 1 or 2 N-atoms, which is substituted with —C(=O)—$R^{10}$ and optionally substituted with other substituents according to the scope of the present invention and wherein all the other variables are as defined according to the scope of the present invention, hereby named compounds of Formula (Id), can be prepared according to the following reaction Scheme 4. In Scheme 4 halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 4 are defined according to the scope of the present invention.

In Scheme 4, the following reaction conditions apply:

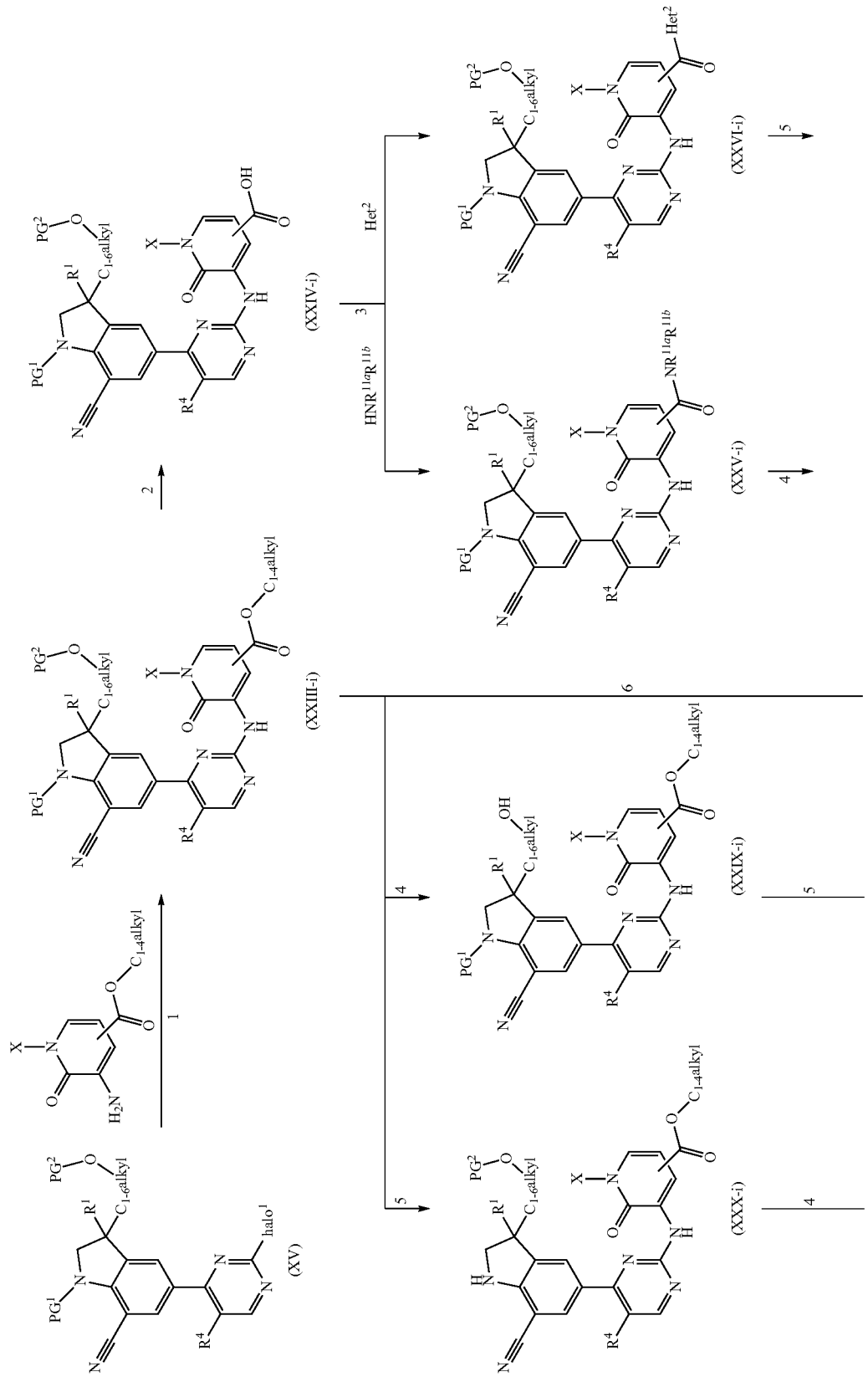

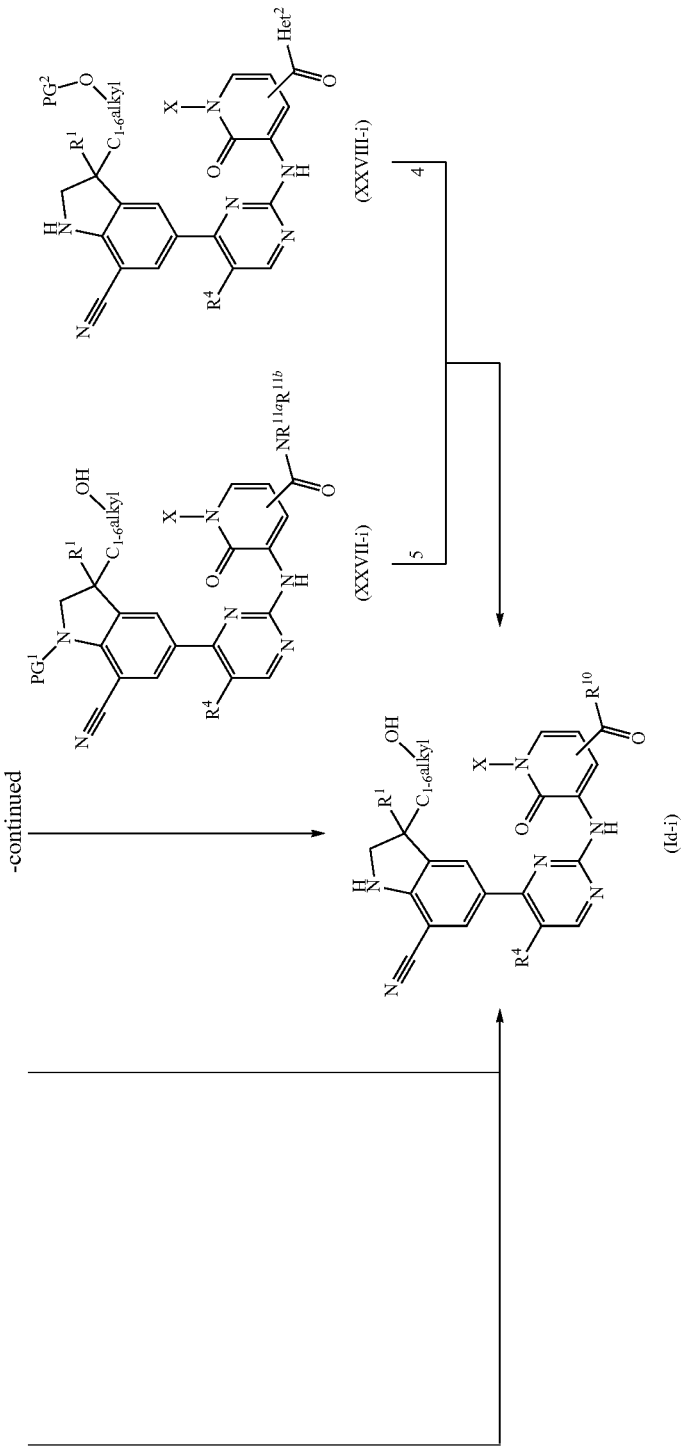

In general, compounds of Formula (I) wherein $R^2$ is $R^{2b}$ being $C_{1-6}$alkyl substituted with one OH, $R^3$ is 2-oxo-1,2-dihydropyridin-3-yl substituted with —C(=O)—$R^{10}$ on a carbon atom and optionally substituted with other substituents according to the scope of the present invention, Y is $CR^4$, and wherein all the other variables are as defined according to the scope of the present invention, hereby named compounds of Formula (Id-i), can be prepared according to the following reaction Scheme 4-i. In Scheme 4-i, X is defined as an optional subsistent on the N-atom of the 2-oxo-1,2-dihydropyridin-3-yl, $halo^1$ is defined as Cl, Br or I; $PG^1$ represents a suitable protecting group, such as for example tert-(butoxycarbonyl) and $PG^2$ represents a suitable protecting group, such as for example tert-butyl-dimethyl-silyl. All other variables in Scheme 4-i are defined according to the scope of the present invention.

Scheme 4-i is shown below and the same reaction conditions as mentioned for Scheme 4 above apply:

Scheme 5

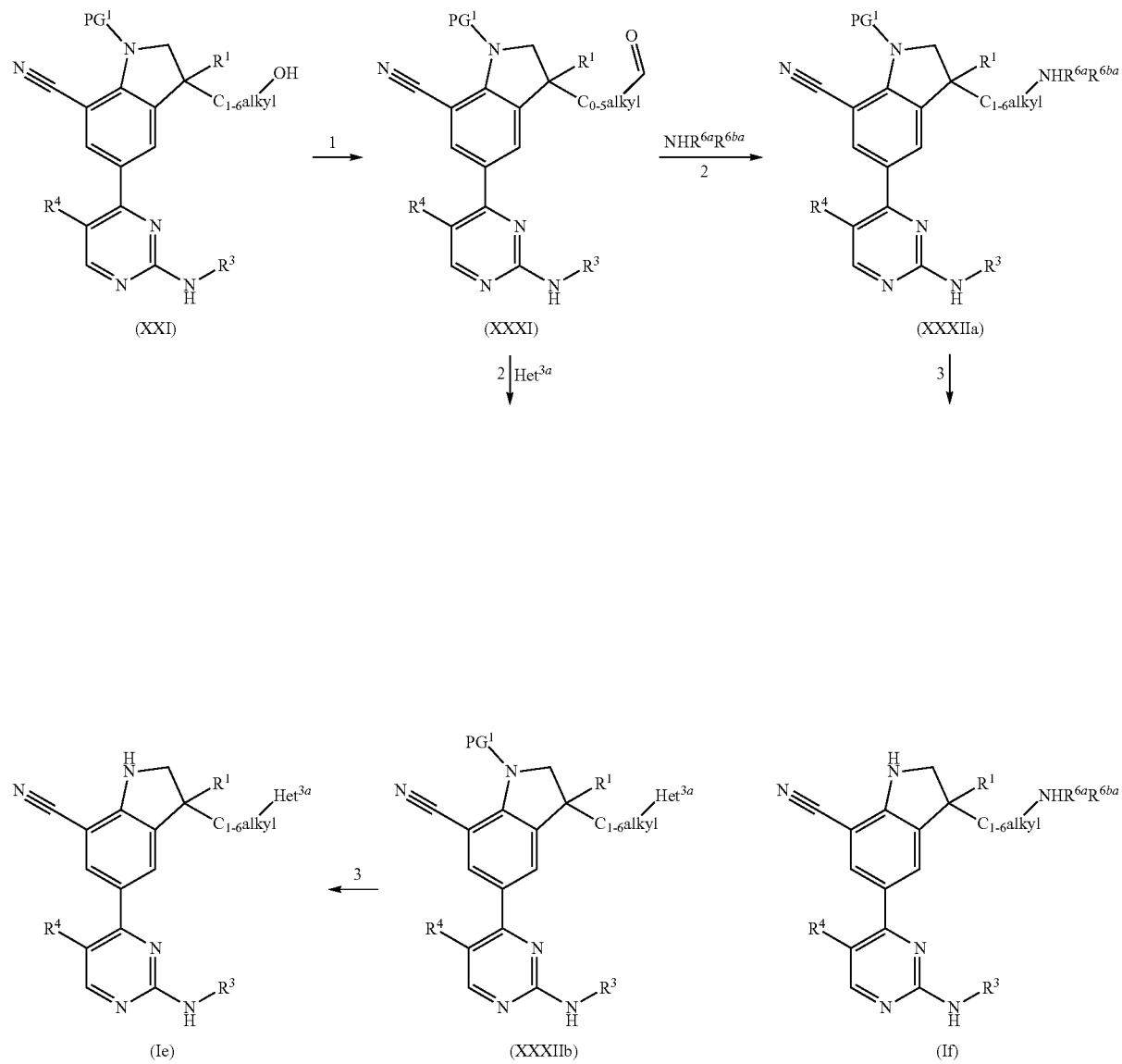

1: at a suitable temperature such as for example -78° C., in the presence of oxalyl chloride and dimethyl sulfoxide as reagents, a suitable base such as for example N,N-diisopropylethylamine, and a suitable solvent such as for example dichloromethane;
2: at a suitable temperature such as for example room temperature, in the presence of a suitable acid such as for example acetic acid, a suitable reducing agent such as for example sodium triacetoxyborohydride, and a suitable solvent such as for example dichloroethane;
3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $R^{2c}$ being $C_{1-6}$alkyl substituted with one $Het^{3a}$ or —$NR^{6a}R^{6b}$, wherein $R^{6b}$ is $R^{6ba}$ being H, $C_{1-4}$alkyl and $C_{3-6}$cycloalkyl, Y is $CR^4$, and wherein all the other variables are as defined according to the scope of the present invention, hereby named compounds of Formula (Ie) and Formula (If), can be prepared according to the following reaction Scheme 5. In Scheme 5 $PG^1$ represents a suitable protecting group, such as for example tert-(butoxycarbonyl). All other variables in Scheme 5 are defined according to the scope of the present invention.

In Scheme 5, the following reaction conditions apply:

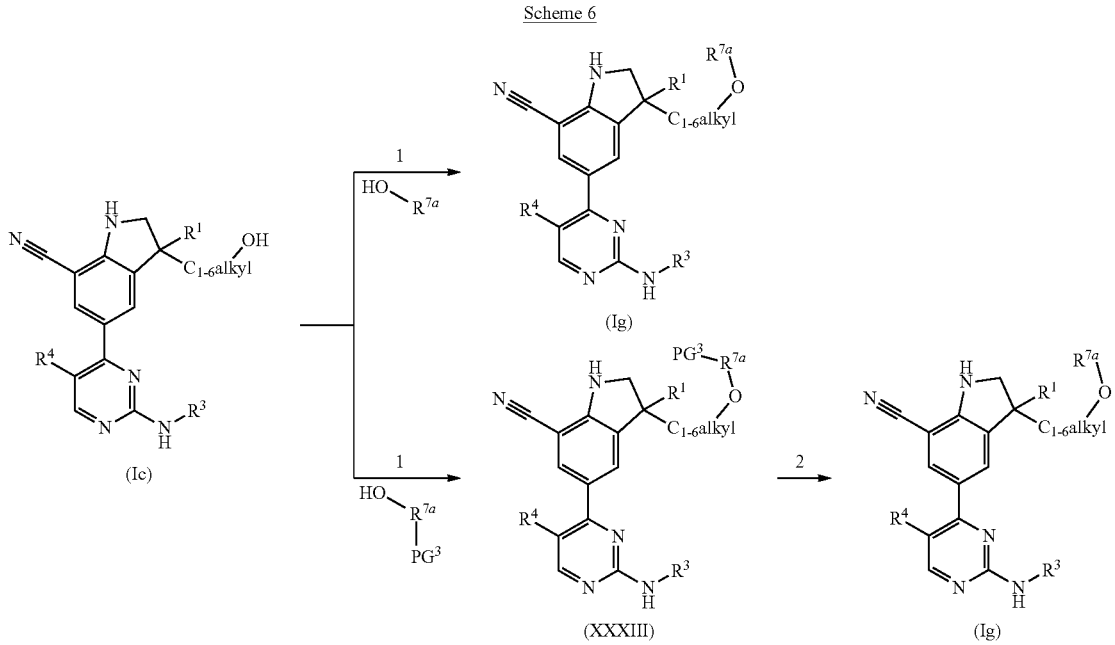

Scheme 6

1: at a suitable temperature such as for example room temperature, in the prescence of a suitable coupling reagent such as for example 1-[bis(dimethylamino)methylene]-1H-1,2,3-triazolo[4,5-b]pyridinium 3-oxid hexafluorophosphate (HATU), in the presence of a suitable base as for example N,N-diisopropylethylamine, and a suitable solvent such as for example a mixture of tetrahydrofuran and dimethylformamide, and optionally followed by a deprotection step using a suitable acid such as for example hydrochloric acid in a suitable solvent such as for example 1,4-dioxane;
2: at a suitable temperature such as for example 0° C. or room temperature, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7a}$, $R^{7a}$ being —C(=O)—$R^9$ or —(C=O)—CH($NH_2$)—$C_{1-4}$alkyl-$Ar^1$), Y is $CR^4$, and wherein all the other variables are as defined according to the scope of the present invention, hereby named compounds of Formula (Ig), can be prepared according to the following reaction Scheme 6. In Scheme 6 $PG^3$ represents a suitable protecting group, such as for example a tert-(butoxycarbonyl), a tert-butyl or a benzyl. All other variables in Scheme 6 are defined according to the scope of the present invention.

In Scheme 6, the following reaction conditions apply:

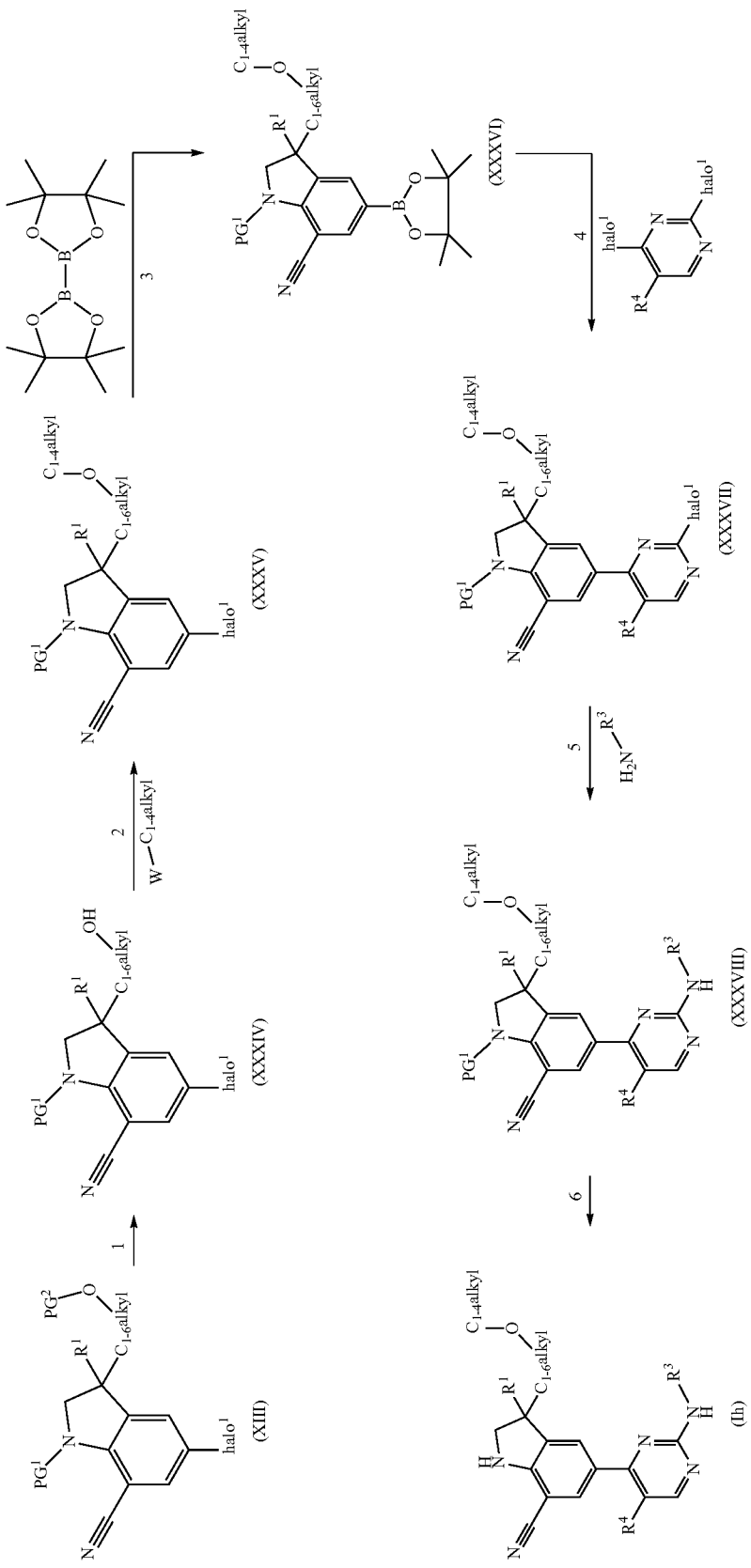

In general, compounds of Formula (I) wherein $R^2$ is $C_{1-6}$alkyl substituted with one $OR^{7b}$, $R^{7b}$ being $C_{1-4}$alkyl, Y is $CR^4$, and wherein all the other variables are as defined according to the scope of the present invention, hereby named compounds of Formula (Ih), can be prepared according to the following reaction Scheme 7. In Scheme 7 halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl; W represents a leaving group, such as for example a methane sulfonate or toluene sulfonate or an halogen (Cl, Br or I). All other variables in Scheme 7 are defined according to the scope of the present invention.

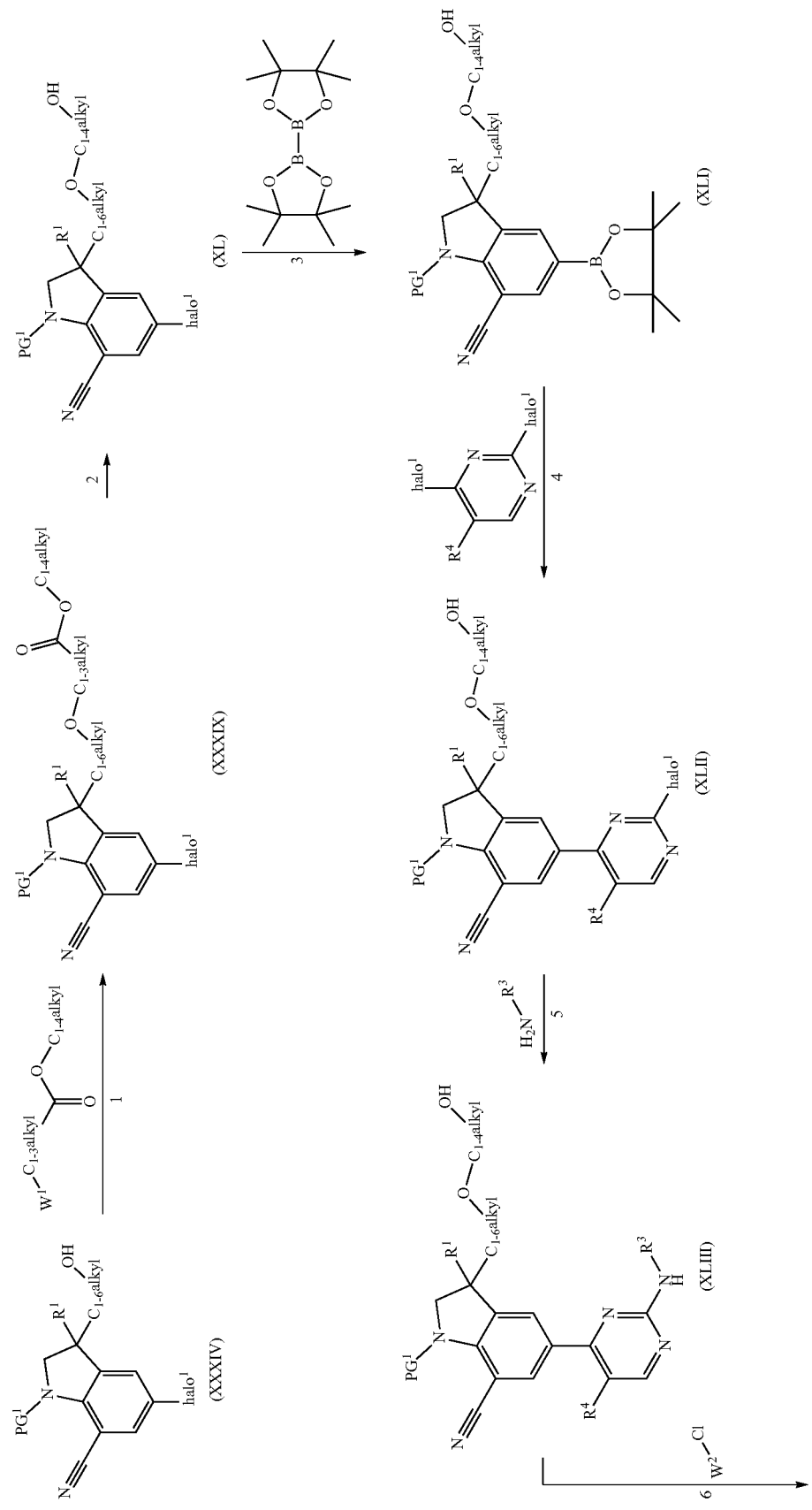

-continued

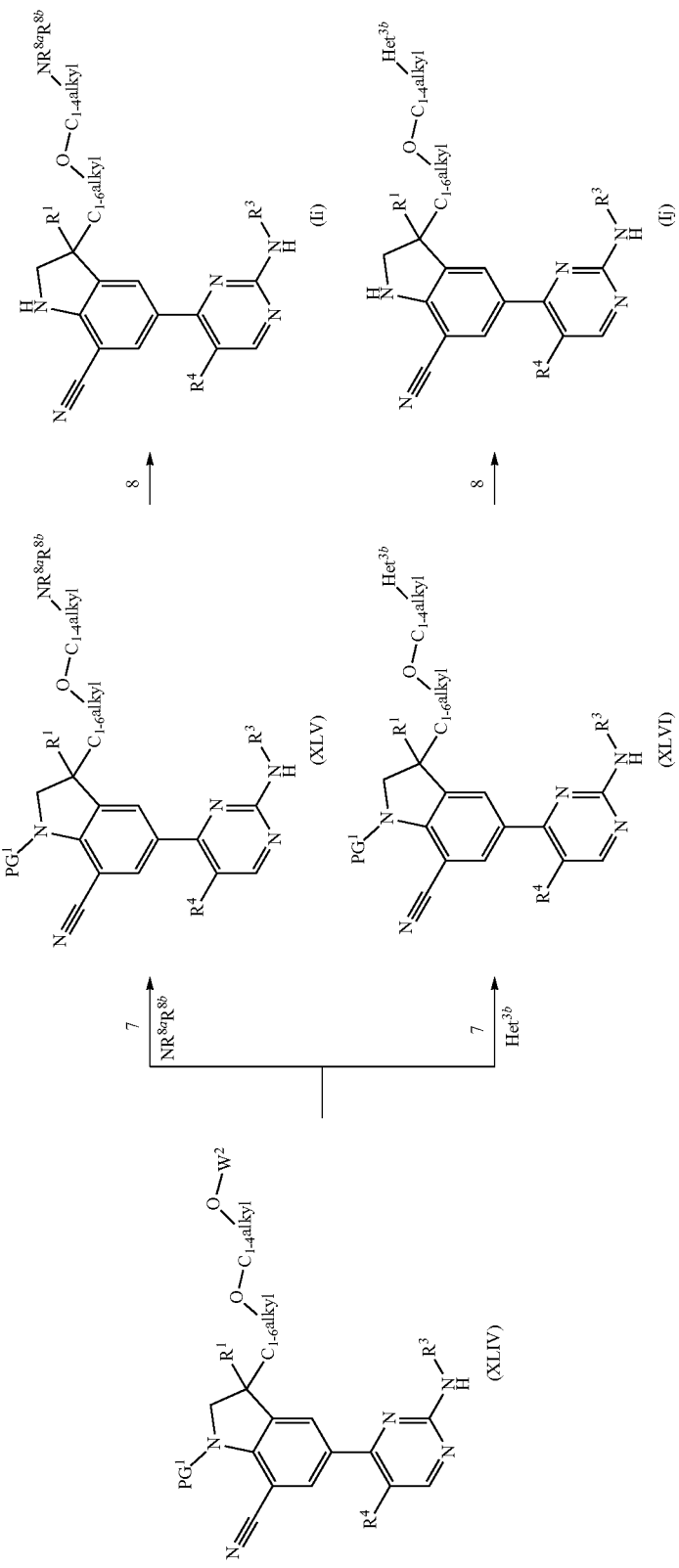

1: at a suitable temperature such as for example room temperature, in the presence of a suitable base as for example sodium hydride, and a suitable solvent such as for example dimethylformamide;
2: at a suitable temperature such as for example 55° C., in presence of reducing agent such as for example sodium borohydride and a suitable solvent such as for example a mixture of tetrahydrofuran and methanol;
3: at a suitable temperature such as for example 100° C., in the presence of a suitable catalyst such as for example [1,1′-bis(diphenylphosphino)ferrocene]dichloropalladium (II), optionally with dichloromethane complex, a suitable base such as for example potassium acetate and a suitable solvent such as for example 1,4-dioxane;
4: at a suitable temperature such as for example 85° C., in the presence of a suitable catalyst such as for example palladium tetrakis (Pd(PPh₃)₄), a suitable base such as for example sodium carbonate, and a suitable solvent such as for example 1,4-dioxane;
5: at a suitable temperature such as for example 120° C., in the presence of a suitable catalyst such as for example palladium acetate (Pd(OAc)₂), a suitable ligand such as for example 2,2′-bis(diphenylphosphino)-1,1′-binaphthyl (BINAP), a suitable base such as for example cesium carbonate, and a suitable solvent such as for example 1,4-dioxane, optionally under microwave activation;
6: at a suitable temperature such as for example 5° C., in the presence of a suitable base such as for example triethylamine, and a suitable solvent such as for example dichloromethane;
7: at a suitable temperature such as for example 80° C., and a suitable solvent such as for example acetonitrile;
8: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperture such as for example 125° C., and a suitable time such as for example 3 hours.

In general, compounds of Formula (I) wherein $R^2$ is $C_{1-6}$alkyl substituted with one $OR^7$, $R^{7c}$ being $C_{1-4}$alkyl-$NR^{8a}R^{8b}$ or $C_{1-4}$alkyl-$Het^{3b}$, Y is $CR^4$, and wherein all the other variables are as defined according to the scope of the present invention, hereby named compounds of Formula (Ii) and Formula (Ij), can be prepared according to the following reaction Scheme 8. In Scheme 8 $halo^1$ is defined as Cl, Br or I; $PG^1$ represents a suitable protecting group, such as for example tert-(butoxycarbonyl); $W^1$ represents a leaving group, such as for example a methane sulfonate or toluene sulfonate or an halogen (Cl, Br or I); $W^2$ represents a leaving group, such as for example a mesyl or a tosyl. All other variables in Scheme 8 are defined according to the scope of the present invention.

In Scheme 8, the following reaction conditions apply:

Scheme 9

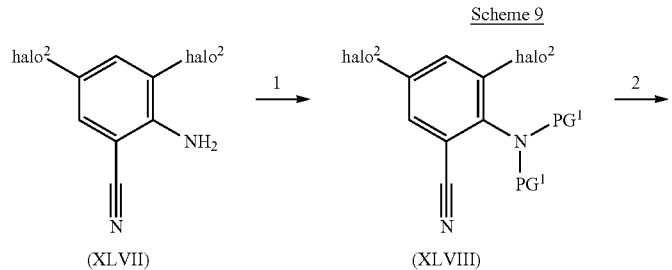

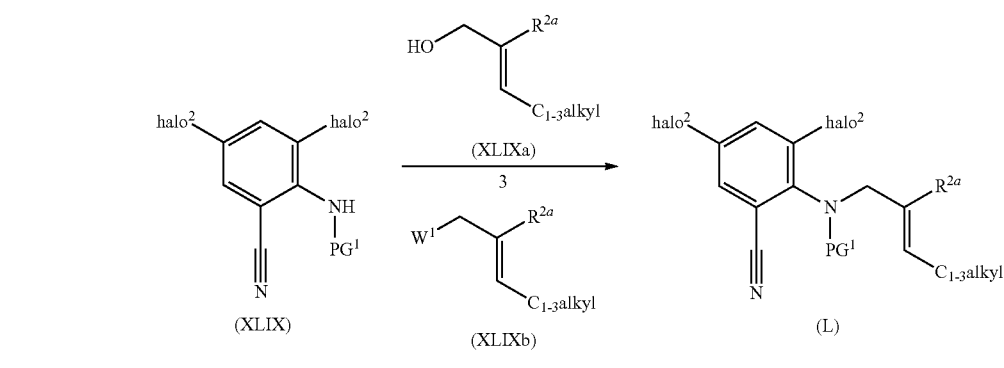

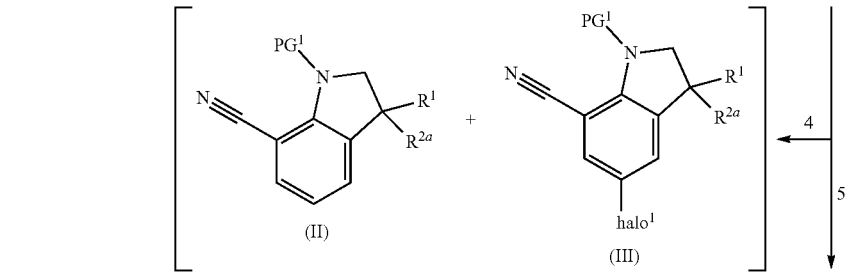

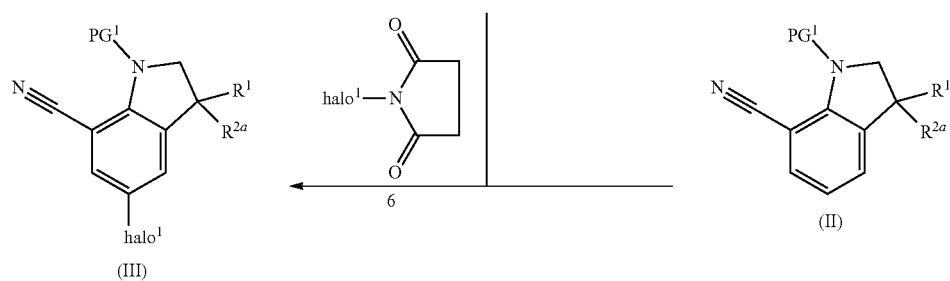

-continued

1: at a suitable temperature such as for example 45° C., in the presence of a suitable reagent such as for example di-tert-butyl dicarbonate, in the presence of a suitable catalyst such as for example 4-dimethylaminopyridine (DMAP), and a suitable solvent such as for example dichloromethane;
2: at a suitable temperature such as for example 65° C. and a suitable solvent such as for example methanol;
3: in case of (XLIXa), at a suitable temperature such as for example at room temperature, in the presence of tri-n-butylphosphine and 1,1'-(azodicarbonyl)piperidine and a suitable solvent such as for example 2-methyltetrahydrofuran;
In case of (XLIXb), at a suitable temperature such as for example 80° C., in the presence of a suitable base such as for example potassium carbonate, a suitable additive such as for example sodium iodide, in a suitable solvent such as for example acetonitrile;
4: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example dimethylformamide;
5: at a suitable temperature such as for example 60° C., in the presence of sodium acetate, sodium formate dehydrate and tetraethylammonium chloride, a suitable catalyst such as for example [1,1'-bis(diphenylphosphino)ferrocene]palladium, (II) chloride optionally with dichloromethane complex, and a suitable solvent such as for example dimethylformamide;
6: at a suitable temperature such as for example 40° C., in the presence of N-halogeno-succinimide, and a suitable solvent such as for example acetonitrile. Alternatively, in the presence of a suitable reagent such as for example 1,3-dibromo-5,5-dimethylhydantoin, in a suitable solvent such as for example acetonitrile.

In general, intermediates of Formula (II) and (III) wherein $R^2$ is $R^{2a}$ being $C_{1-6}$alkyl, and wherein all the other variables are as defined according to the scope of the present invention, hereby named compounds of Formula (II) and (III), can be prepared according to the following reaction Scheme 9. In Scheme 9 halo$^1$ is defined as Cl, Br, I; halo$^2$ is defined as Cl, Br, I; PG$^1$ represents a suitable protecting group, such as for example tert-(butoxycarbonyl); W$^1$ represents a leaving group, such as for example a methane sulfonate or toluene sulfonate or an halogen (Cl, Br or I). All other variables in Scheme 9 are defined according to the scope of the present invention.

In Scheme 9, the following reaction conditions apply:

Scheme 10

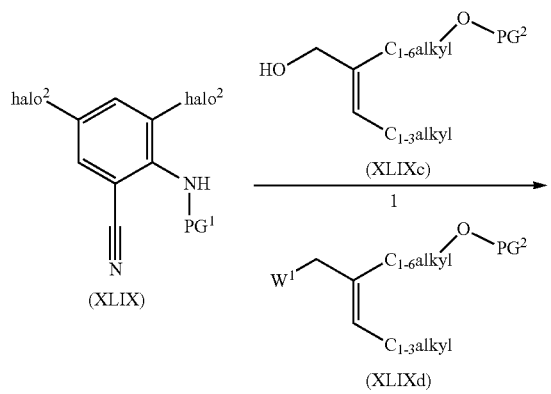

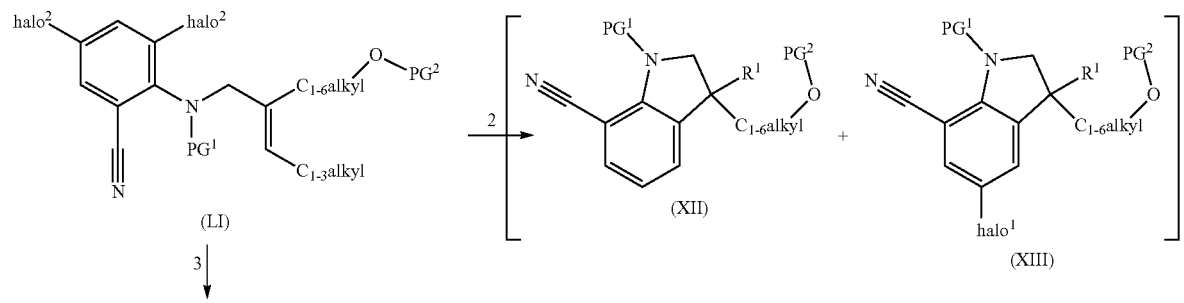

-continued

(XII)

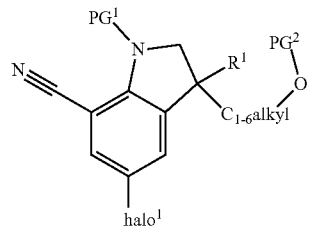

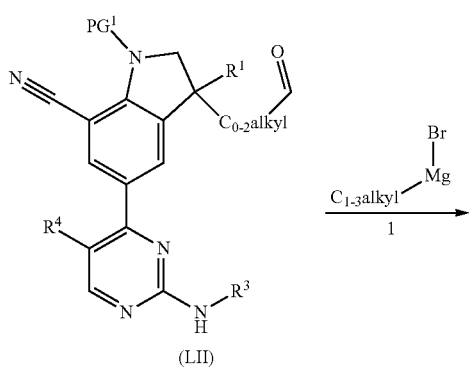

(XIII)

1: in case of (XLIXc), at a suitable temperature such as for example at room temperature, in the presence of tri-n-butylphosphine and 1,1'-(azodicarbonyl)piperidine and a suitable solvent such as for example 2-methyltetrahydrofuran;
In case of (XLIXd), at a suitable temperature such as for example 80° C., in the presence of a suitable base such as for example potassium carbonate, a suitable additive such as for example sodium iodide, in a suitable solvent such as for example acetonitrile;
2: at a suitable temperature such as for example 85° C., in the presence of soidum acetate, sodium formate and tetraethylammonium chloride, a suitable catalyst such as for example palladium acetate (Pd(OAc)₂), and a suitable solvent such as for example dimethylformamide;
3: at a suitable temperature such as for example 60°C., in the presence of soidum acetate, sodium formate dehydrate and tetaethylammonium chloride, a suitable catalyst such as for example [1,1'-bis(diphenylphosphino) ferrocene] palladium, (II) chloride optionally with dichloromethane complex, and a suitable solvent such as for example dimethylformamide;
4: at a suitable temperature such as for example 40° C., in the presence of N-halogeno-succinimide, and a suitable solvent such as for example acetonitrile. Alternatively, in the presence of a suitable reagent such as for example 1,3-dibromo-5,5- dimethylhydantoin, in suitable solvent such as for example acetonitrile.

In general, intermediates of Formula (XII) and (XIII) wherein $R^2$ is $R^{2b}$ being $C_{1-6}$alkyl substituted with one OH, and wherein all the other variables are as defined according to the scope of the present invention, hereby named compounds of Formula (XII) and (XIII), can be prepared according to the following reaction Scheme 10. In Scheme 10 halo$^1$ is defined as Cl, Br, I; halo$^2$ is defined as Cl, Br, I; PG$^1$ represents a suitable protecting group, such as for example tert-(butoxycarbonyl) and PG$^2$ represents a suitable protecting group, such as for example tert-butyl-dimethylsilyl; W$^1$ represents a leaving group, such as for example a methane sulfonate or toluene sulfonate or an halogen (Cl, Br or I). All other variables in Scheme 10 are defined according to the scope of the present invention.

In Scheme 10, the following reaction conditions apply:

Scheme 11

-continued

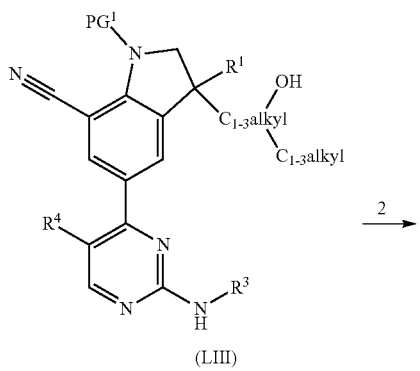

(LIII)

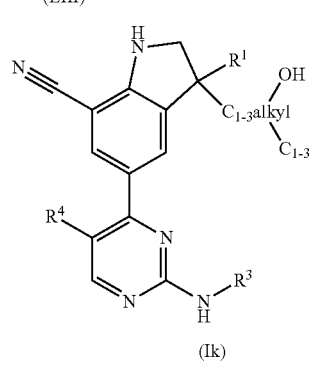

(Ik)

1: at a suitable temperature such as for example at room temperature, and a suitable solvent such as for example tetrahydofuran;
2: at a suitable temperature such as for example 0° C. or room temperature or reflux, in presence of a suitable acid such as for example trifluoracetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is as shown in the scheme 11, Y is $CR^4$, and wherein all the other variables are as defined according to the scope of the present invention, hereby named compounds of Formula (Ik) can be prepared according to the following reaction Scheme 11. In Scheme 11 $PG^1$ represents a suitable protecting group, such as for example tert-(butoxycarbonyl). All other variables in Scheme 11 are defined according to the scope of the present invention.

In Scheme 11, the following reaction conditions apply:

Scheme 12

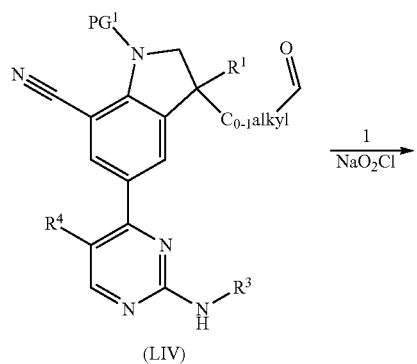

(LIV)

-continued

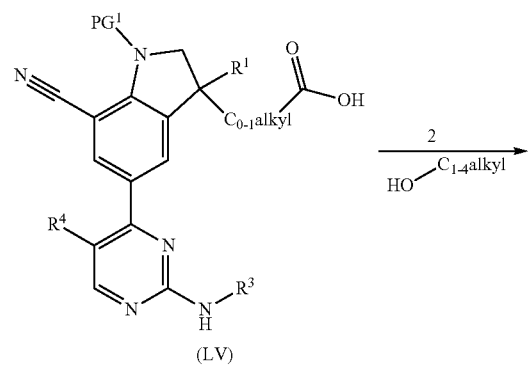

(LV)

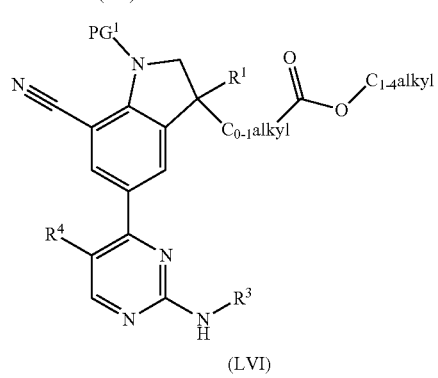

(LVI)

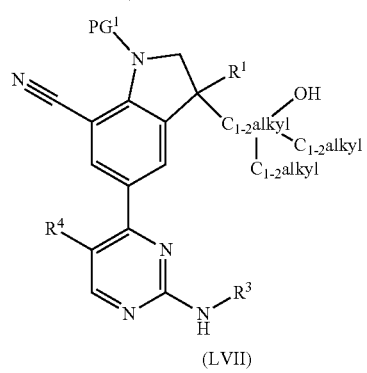

(LVII)

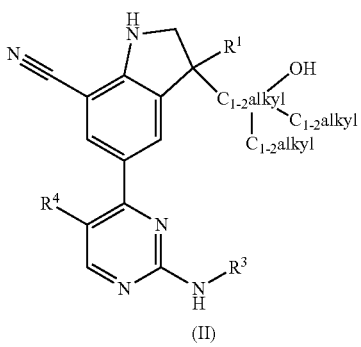

(II)

119
-continued

1: at a suitable temperature such as for example at room temperature, in the presence of tert-butyl alcohol, 2-methyl-2-butene, sodium dihydrogenophosphate and distilled water;
2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;
3: at a suitable temperature such as for example at room temperature, and a suitable solvent such as for example tetrahydrofuran;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is as shown in the scheme 12, Y is $CR^4$, and wherein all the other variables are as defined according to the scope of the present invention, hereby named compounds of Formula (Il) can be prepared according to the following reaction Scheme 12. In Scheme 12 $PG^1$ represents a suitable protecting group, such as for example tert-(butoxycarbonyl). All other variables in Scheme 12 are defined according to the scope of the present invention.

In Scheme 12, the following reaction conditions apply:

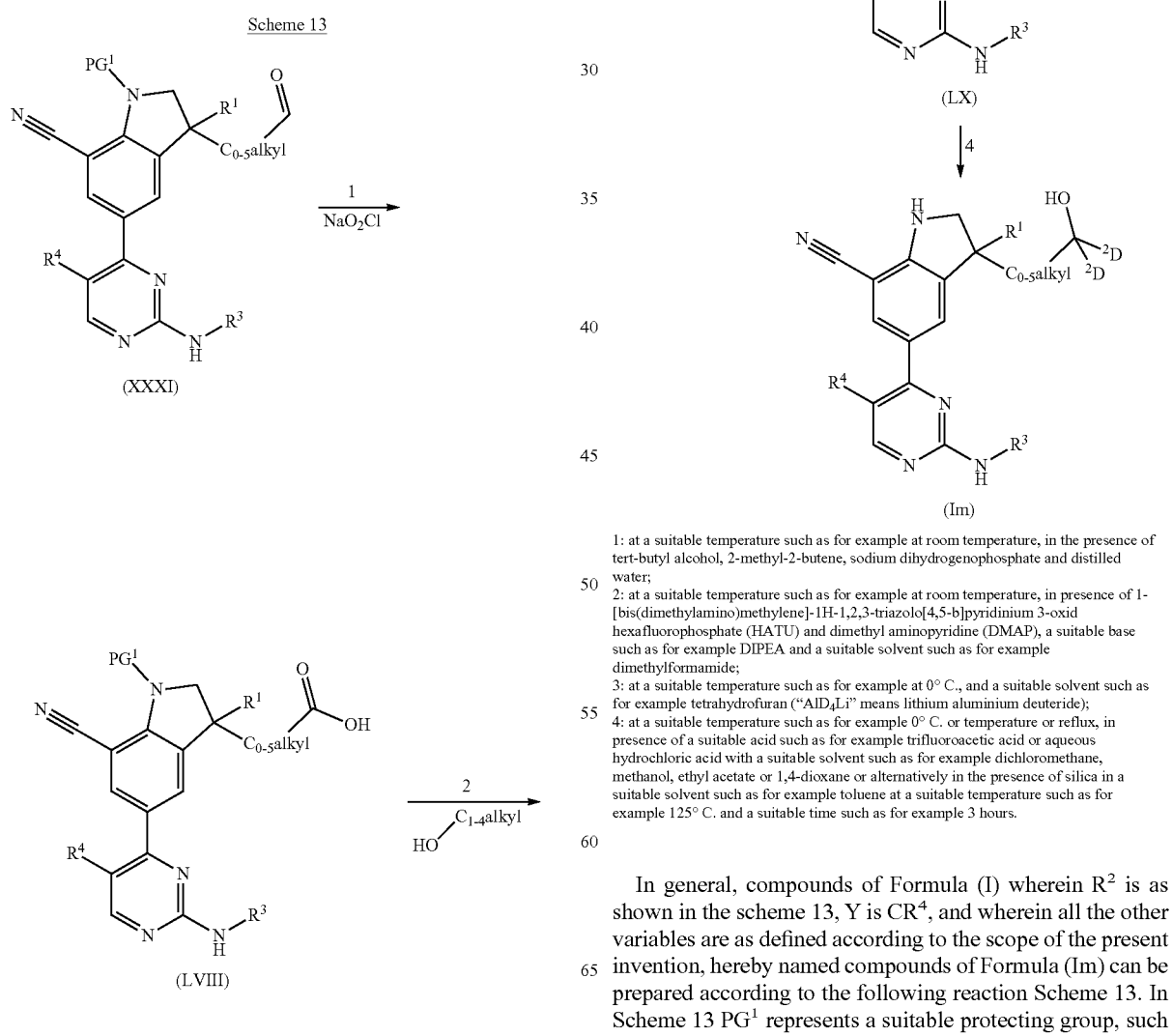

120
-continued (LIX)

(LX)

(Im)

1: at a suitable temperature such as for example at room temperature, in the presence of tert-butyl alcohol, 2-methyl-2-butene, sodium dihydrogenophosphate and distilled water;
2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;
3: at a suitable temperature such as for example at 0° C., and a suitable solvent such as for example tetrahydrofuran ("AlD$_4$Li" means lithium aluminium deuteride);
4: at a suitable temperature such as for example 0° C. or temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is as shown in the scheme 13, Y is $CR^4$, and wherein all the other variables are as defined according to the scope of the present invention, hereby named compounds of Formula (Im) can be prepared according to the following reaction Scheme 13. In Scheme 13 $PG^1$ represents a suitable protecting group, such as for example tert-(butoxycarbonyl). All other variables in Scheme 13 are defined according to the scope of the present invention.

In Scheme 13, the following reaction conditions apply:

Scheme 14
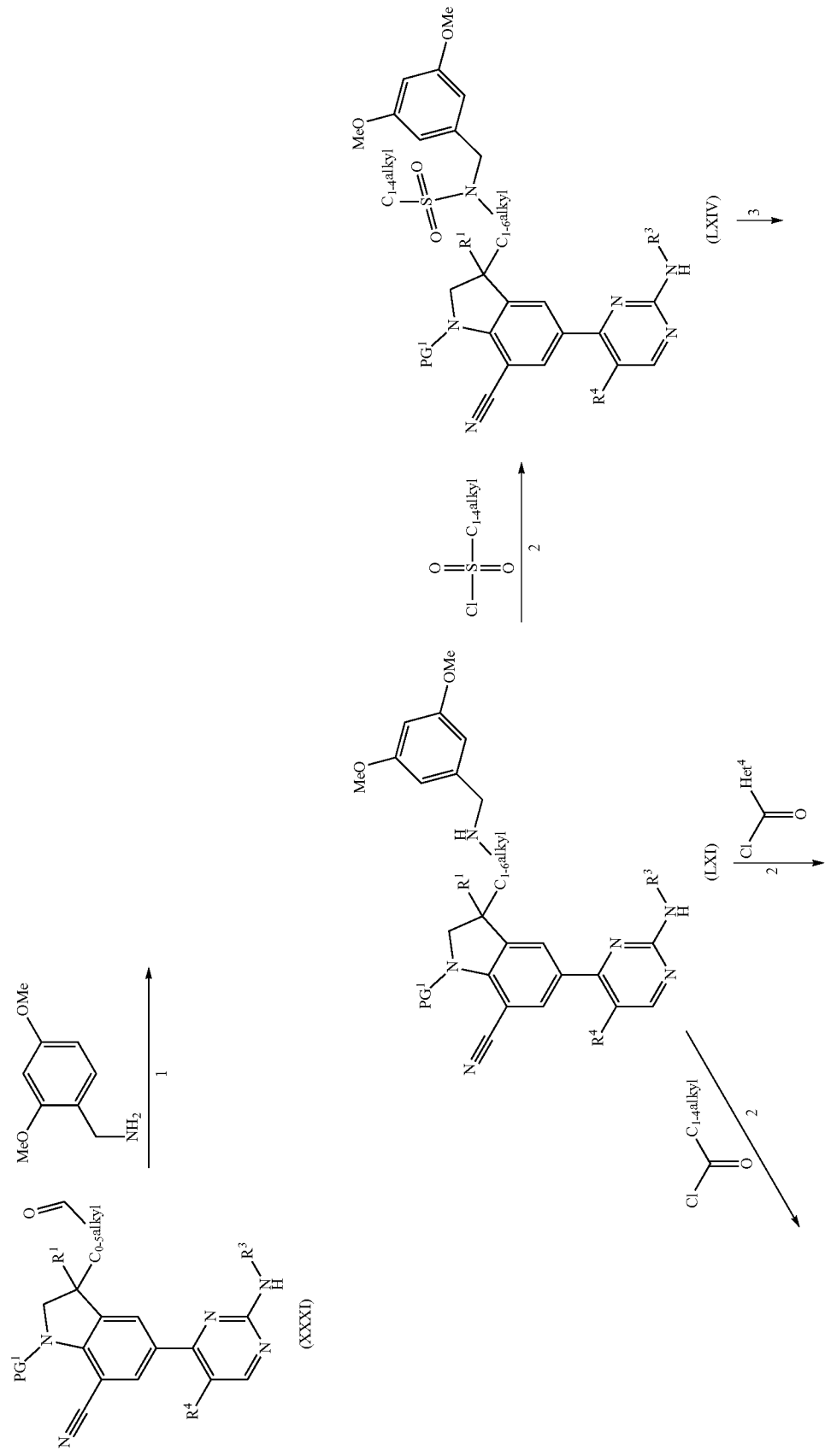

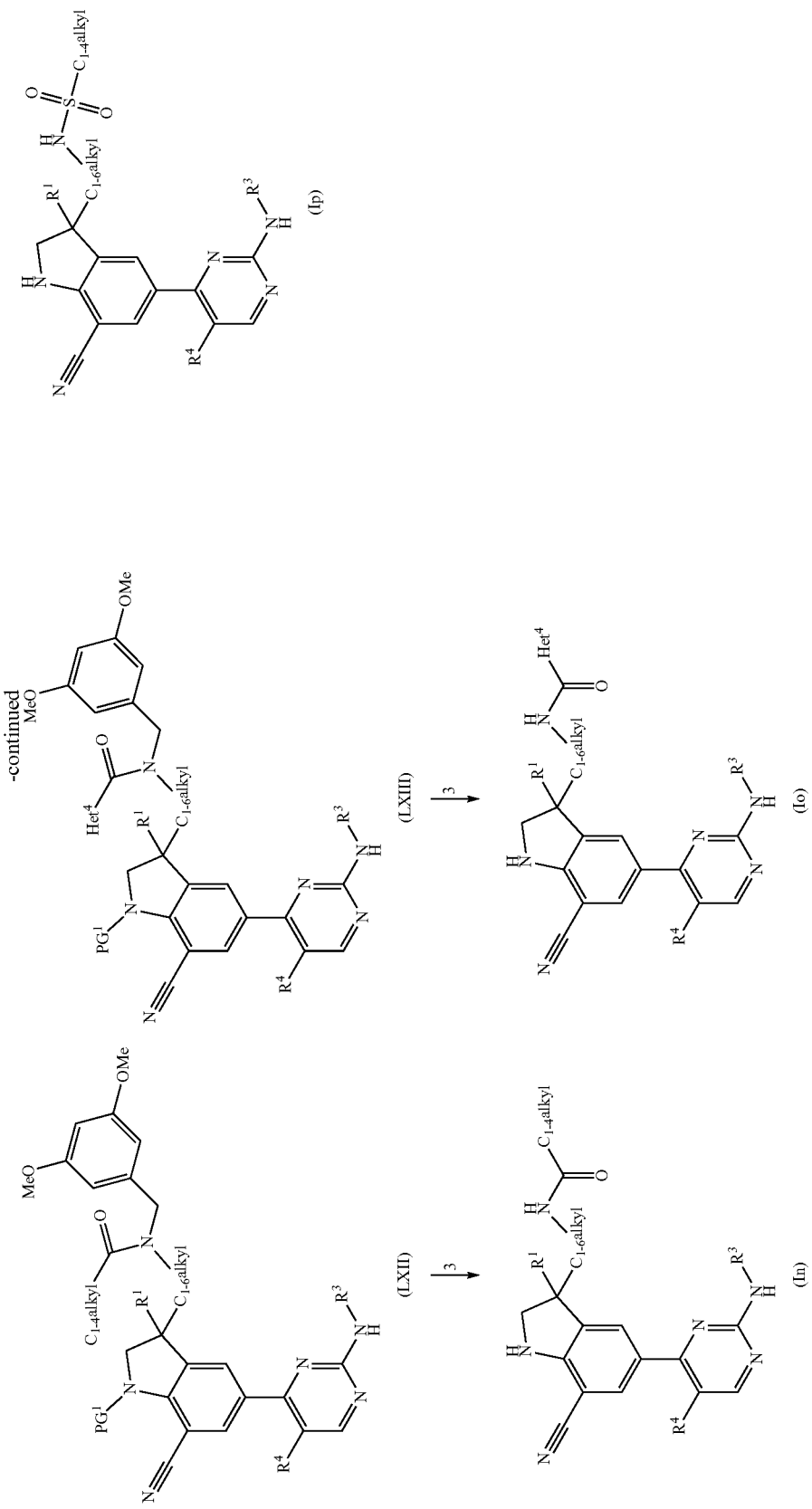

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;
2: at a suitable temperature such as for example at room temperature, in the presence of a suitable base such as for example triethylamine, in a suitable solvent such as for example tetrahydrofuran;
3: at a suitable temperature such as for example at room temperature, in the presence of a suitable acid such as for example trifluoroacetic acid, in a suitable solvent such as for example dichloromethane.

In general, compounds of Formula (I) wherein $R^2$ is being $C_{1-6}$alkyl substituted with one $Het^{3a}$ or $-NR^{6a}R^{6b}$, wherein $R^{6a}$ is being H, $R^{6b}$ is being $-C(=O)-C_{1-4}$alkyl; $-C(=O)-Het^4$; $-S(=O)_2-C_{1-4}$alkyl, Y is $CR^4$, and wherein all the other variables are as defined according to the scope of the present invention, hereby named compounds of Formula (In), Formula (Io) and Formula (Ip), can be prepared according to the following reaction Scheme 14. In Scheme 14, $PG^1$ represents a suitable protecting group, such as for example tert-(butoxycarbonyl). All other variables in Scheme 14 are defined according to the scope of the present invention.

In Scheme 14, the following reaction conditions apply:

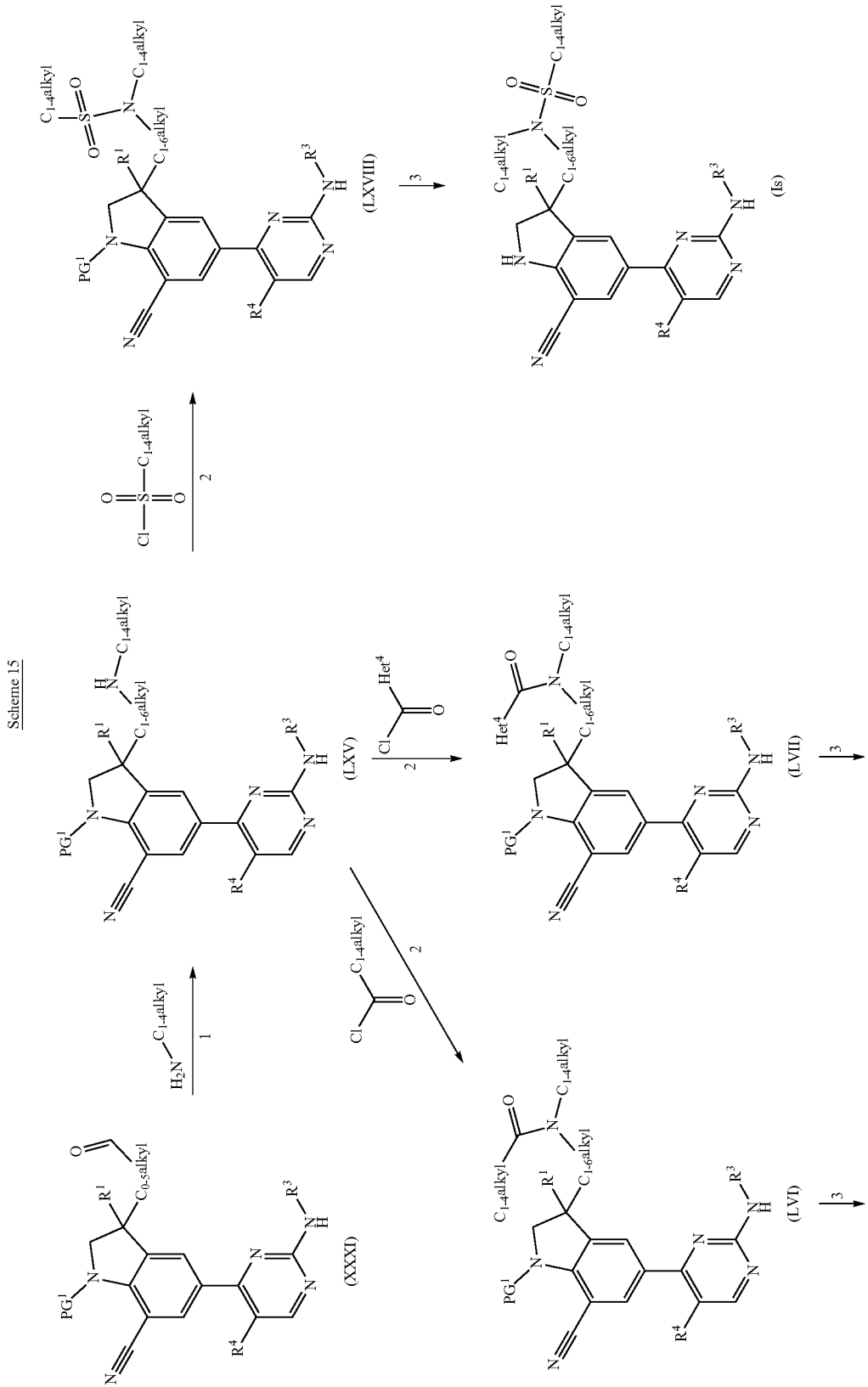

-continued

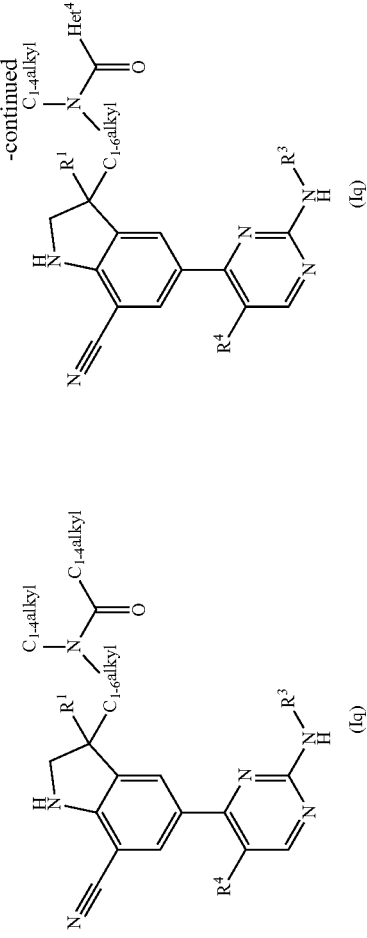

(Iq)

(Iq)

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;
2: at a suitable temperature such as for example at room temperature, in the presence of a suitable base such as for example triethylamine, in a suitable solvent such as for example tetrahydrofuran;
3: at a suitable temperature such as for example at room temperature, in the presence of a suitable acid such as for example trifluoroacetic acid, in a suitable solvent such as for example dichloromethane;

In general, compounds of Formula (I) wherein $R^2$ is being $C_{1-6}$alkyl substituted with one $Het^{3a}$ or $-NR^{6a}R^{6b}$, wherein $R^{6a}$ is being $C_{1-4}$alkyl, $R^{6b}$ is being $-C(=O)-C_{1-4}$alkyl; $-C(=O)-Het^4$; $-S(=O)_2-C_{1-4}$alkyl, Y is $CR^4$, and wherein all the other variables are as defined according to the scope of the present invention, hereby named compounds of Formula (Iq), Formula (Ir°) and Formula (Is), can be prepared according to the following reaction Scheme 15. In Scheme 15, $PG^1$ represents a suitable protecting group, such as for example tert-(butoxycarbonyl). All other variables in Scheme 15 are defined according to the scope of the present invention.

In Scheme 15, the following reaction conditions apply:

Scheme 16

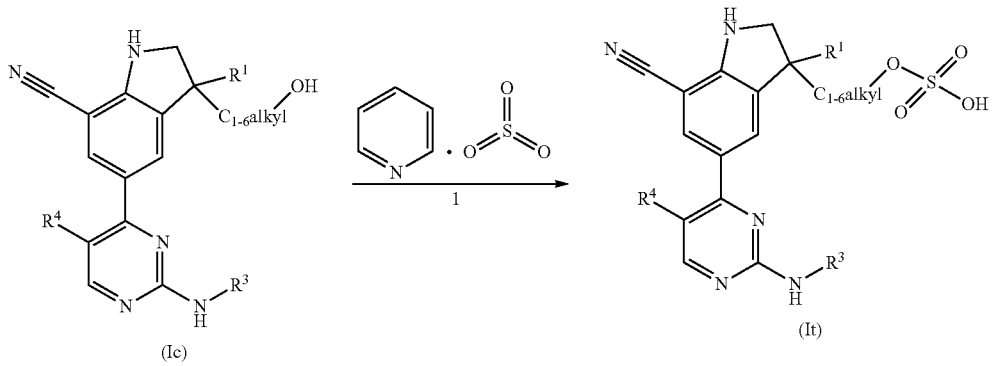

(Ic)            (It)

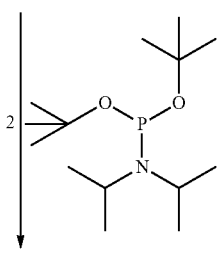

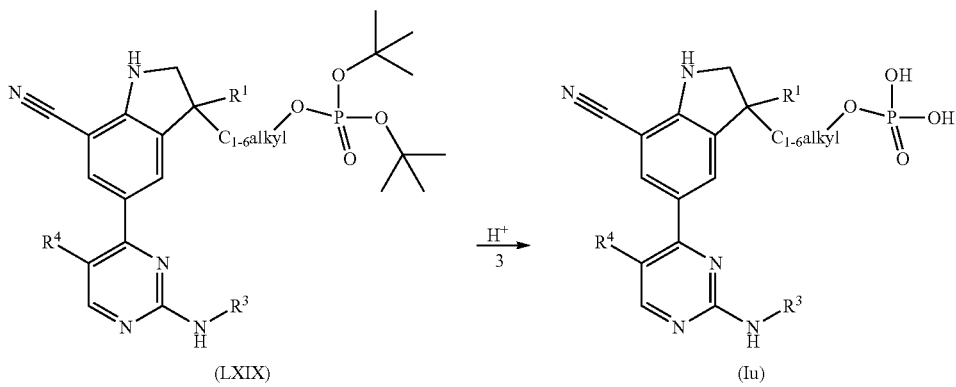

(LXIX)            (Iu)

1: at suitable temperature such as for example at room temperature, in a suitable solvent such as for example tetrahydrofuran, in the presence of a suitable base such as for example sodium hydroxide;
2: in the presence of a suitable reagent such as for example tetrazole, in the presence of a suitable oxidizing agent such as for example meta-chloroperbenzoic acid, in a suitable solvent such as for example acetonitrile;
3: at a suitable temperature such as for example at room temperature, in the presence of a suitable acid such as for example hydrochloric acid, in a suitable solvent such as for example acetonitrile.

In general, compounds of Formula (I) wherein $R^2$ is $C_{1-6}$alkyl substituted with one $OR^{7d}$, $R^{7d}$ being —S(=O)$_2$—OH or —P(=O)—(OH)$_2$, Y is $CR^4$, and wherein all the other variables are as defined according to the scope of the present invention, hereby named compounds of Formula (It) and Formula (Iu), can be prepared according to the following reaction Scheme 16. All other variables in Scheme 16 are defined according to the scope of the present invention.

In Scheme 16, the following reaction conditions apply:

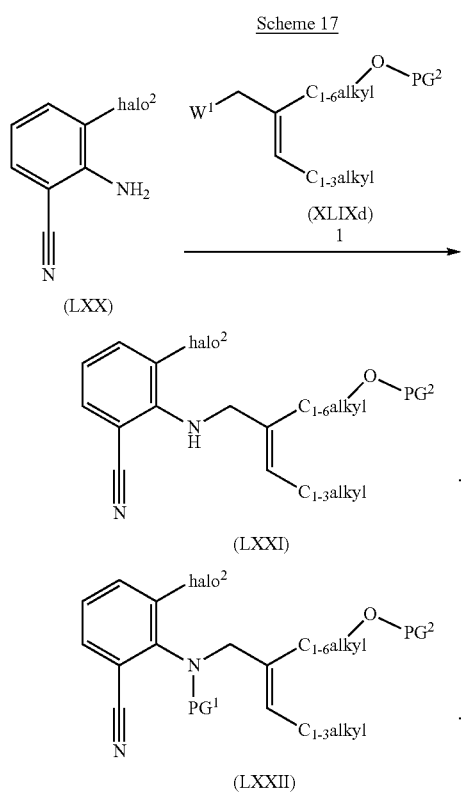

1: At a suitable temperature range between -5° C. and 5° C., in the presence of a suitable base such as for example sodium tert-butoxide in a suitable solvent such as for example tetrahydrofuran;
2: at a suitable temperature ranged between 65 and 70° C., in te presence of a suitable reagent such as for example di-tert-butyl dicarbonate, in the presence of a suitable catalyst such as for example 4-dimethylaminopyridine (DMAP), and a suitable solvent such as for example tetrhydrofuran;
3: at a suitable temperature ranged between 45 and 50° C., in the presence of sodium acetate, sodium formate dehydrate and tetraethylammonium chloride, a suitable catalyst such as for example palladium acetate or [1,1'-bis(diphenylphosphino) ferrocene] palladium, (II) chloride optionally with dichloromethane complex, and a suitable solvent such as for example dimethylformamide.

In general, intermediates of Formula (XII) wherein all the variables are as defined according to the scope of the present invention can be prepared according to the following reaction Scheme 17.

In Scheme 17, the following reaction conditions apply:

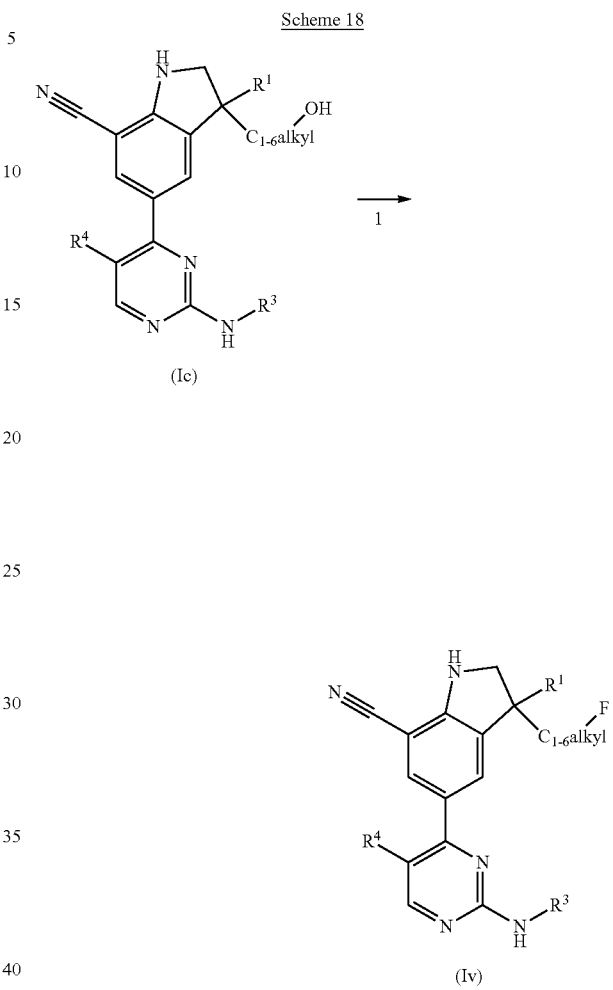

1: in the presence of a suitable fluorinating reagent such as for example diethylaminosulfur trifluoride, a suitable solvent such as for example dichloromethane, at a suitable temperature such as for example room temperature.

In general, compounds of Formula (I) wherein $R^2$ is $C_{1-6}$alkyl substituted with one $R^5$, $R^5$ being a fluorine, Y is $CR^4$, and wherein all the other variables are as defined according to the scope of the present invention, hereby named compounds of Formula (Iv), can be prepared according to the following reaction Scheme 18. All other variables in Scheme 18 are defined according to the scope of the present invention.

In Scheme 18, the following reaction conditions apply:

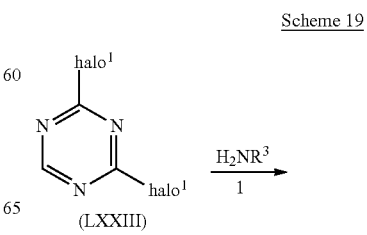

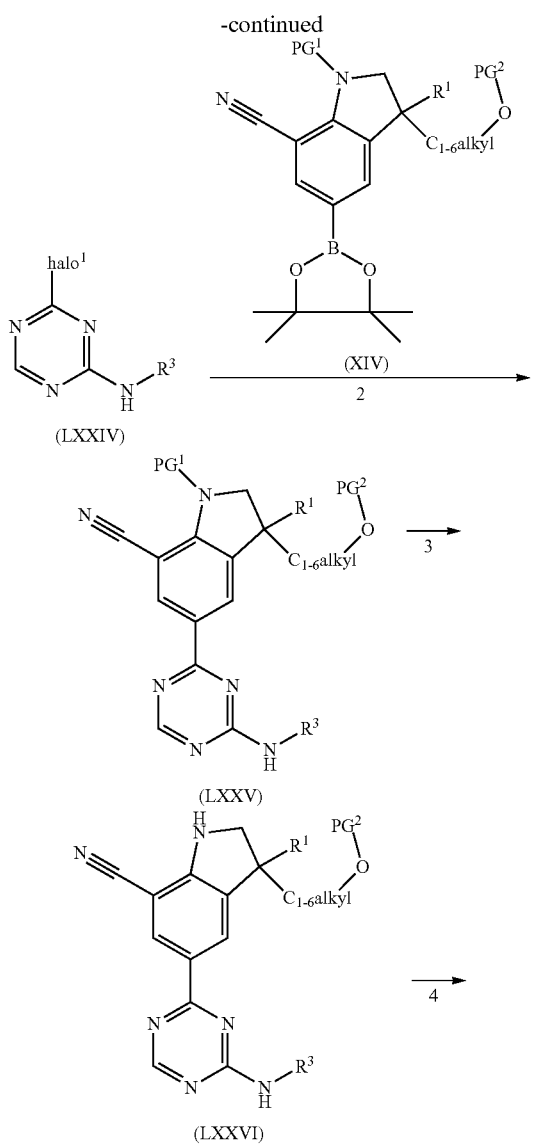

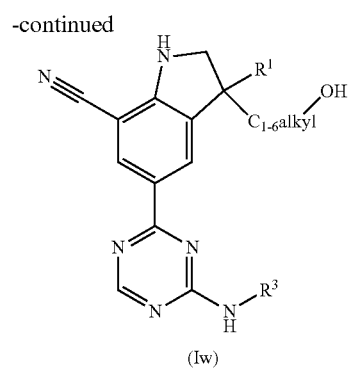

1: in the presence of a suitable base such as for example diisopropylethylamine, in a suitable solvent such as for example acetonitrile;
2: in the presence of suitable catalyst such as for example [1,1'-bis(diphenylphosphino)ferrocene] dichloropalladium (II), optionally with dichloromethane complex, a suitable base such as an aqueous solution of hydrogenocarbonate at a suitable temperature such as 80° C.;
3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitbale temperature such as for example 125° C., and a suitable time such as for example 3 hours;
4: at a suitable temperature such as for example room temperature, in presence of a suitable desilylating agent such as for e example tetra-n-butylammonium fluoride and suitable solvent such as for example 2-methyltetrahydrofuran or tetrahydrofuran.

In general, compounds of Formula (I) wherein $R^2$ is $R^{2b}$ being $C_{1-6}$alkyl substituted with one OH, Y is N, and wherein all the other variables are as defined according to the scope of the present invention, hereby named compounds of Formula (Iw), can be prepared according to the following reaction Scheme 19. In Scheme 19, halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 19 are defined according to the scope of the present invention.

In Scheme 19, the following reaction conditions apply:

Scheme 20

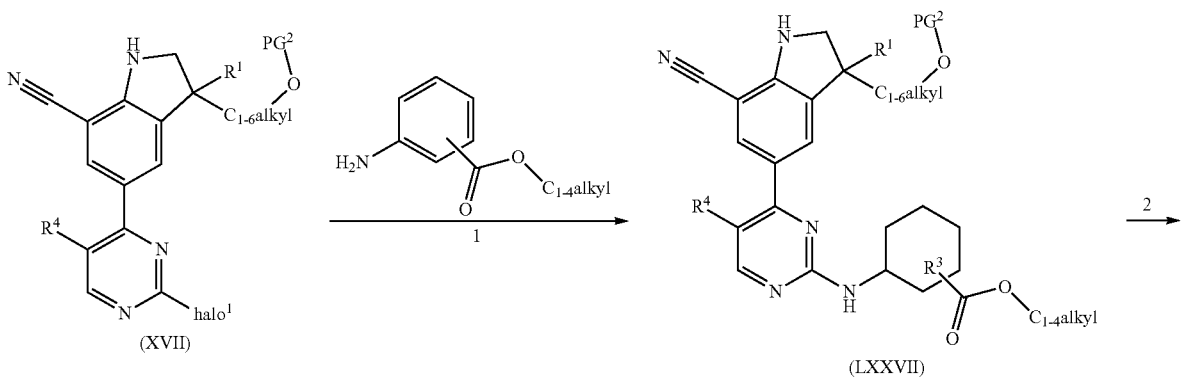

-continued

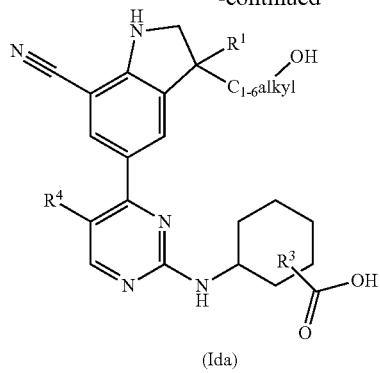

(Ida)

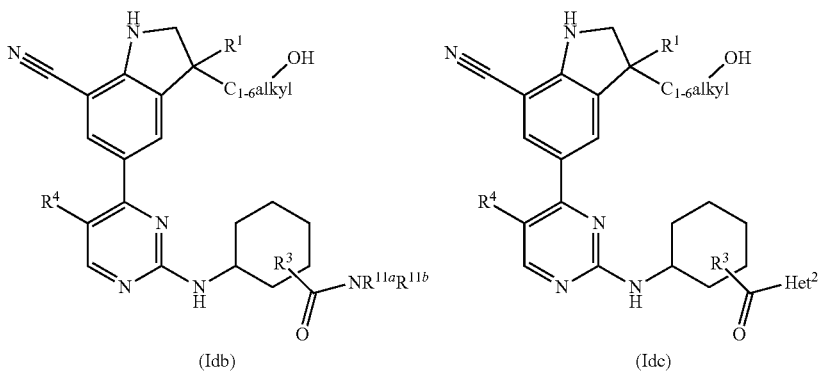

(Idb) (Idc)

1: at a suitable temperature such as for example 120° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbinate, and a suitable solvent such as for example 1,4-dioxane, optionally under microwave activation;

2: at a suitable temperature such as for example 60° C., in presence of a suitable base such as for example lithium hydroxide, and a suitable solvent such as for example a mixture of tetrahydrofuran and water;

3: at a suitabe temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dmethylformamide or dichloromethane.

In general, compounds of Formula (I) wherein $R^2$ is $R^{2b}$ being $C_{1-6}$alkyl substituted with one OH, R is a ring system according to the scope (represented as

in Scheme 20) substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ida), (Idb) and (Idc) can be prepared according to the following reaction Scheme 20. In Scheme 20, halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 20 are defined according to the scope of the present invention.

In Scheme 20, the following reaction conditions apply:

Scheme 21

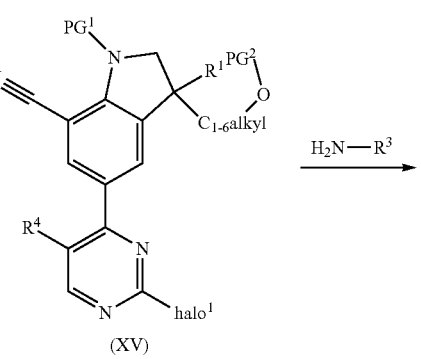

(XV)

-continued

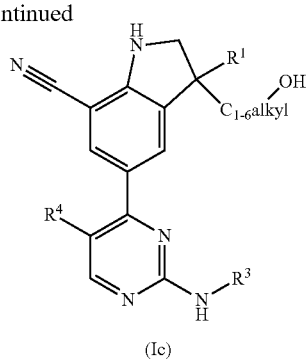

(Ic)

1: at a suitable temperature such as for example 90° C., in the presence of a suitable acid such as for example p-toluenesulfonic acid and a suitable solvent such as for example 1,4-dioxane.

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 21. All other variables in Scheme 21 are defined according to the scope of the present invention or as above.

In Scheme 21, the following reaction conditions apply:

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention inhibit NF-κB-inducing kinase (NIK—also known as MAP3K14). Some of the compounds of the present invention may undergo metabolism to a more active form in vivo (prodrugs). Therefore the compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, non-Hodgkin's lymphoma, Hodgkin lymphoma, T-cell leukaemia, mucosa-associated lymphoid tissue lymphoma, diffuse large B-cell lymphoma and mantle cell lymphoma, in a particular embodiment mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Particular examples of cancers which may be treated (or inhibited) include B-cell malignancies, such as multiple myeloma, hodgkins lymphoma, mantle cell lymphoma, diffuse large B-cell lymphoma or chronic lymphocytic leukemia, with mutations in the non-canonical NFkB signalling pathway (eg in NIK (MAP3K14), TRAF3, TRAF2, BIRC2 or BIRC3 genes).

Hence, the invention relates to compounds of Formula (I), the tautomers and the stereoisomeric forms thereof, and the pharmaceutically acceptable addition salts, and the solvates thereof, for use as a medicament.

The invention also relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable addition salt, or a solvate thereof, or a pharmaceutical composition according to the invention, for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase.

Also, the present invention relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof, or a pharmaceutically acceptable addition salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable addition salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable addition salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof, or a pharmaceutically acceptable addition salt, or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable addition salt, or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 10 mg/kg body weight to 40 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable addition salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. *Remington's Pharmaceutical Sciences* (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more medicinal agent, more particularly, with one or more anticancer agent or adjuvant, as a combined preparation for simultaneous, separate or sequential use in the treatment of patients suffering from cancer.

Accordingly, for the treatment of the conditions mentioned hereinbefore, the compounds of the invention may be advantageously employed in combination with one or more other medicinal agents (also referred to as therapeutic agents), more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacytidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;

Inhibitors of the ubiquitin-proteasome pathway for example PS-341, Velcade (MLN-341) or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-199;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. Unless otherwise noted, all starting materials were obtained from commercial suppliers and used without further purification. Hereinafter, the term 'ACN' or 'MeCN' means acetonitrile, 'AcOH' means acetic acid, 'Ar' means argon, 'BINAP' means 2,2'-bis(diphenylphosphino)-1,1'-binaphthyl, 'BOC' means tert-butyloxycarbonyl, 'ACN' or 'MeCN' means acetonitrile, 'Boc$_2$O' means di-tert-butyl dicarbonate, 'Celite®' means diatomaceous earth, 'CMBP' means (cyanomethylene)tributylphosphorane, 'DCM' means dichloromethane, 'DIEA' or 'DIPEA' means diisopropylethylamine, 'DiPE' means diisopropylether, 'DMAP' means dimethylaminopyridine, 'DMF' means dimethylformamide, 'dppf' means [1,1'-Bis(diphenylphosphino)ferrocene], 'Et$_2$O' means diethylether, 'EtOH' means ethanol, 'EtOAc' or 'AcOEt' means ethyl acetate, 'ee' means enantiomeric excess, 'HATU' means 1-[bis(dimethylamino)methylene]-1H-[1,2,3]triazolo [4,5-b]pyridin-1-ium 3-oxide hexafluorophosphate, 'HPLC' means High-performance Liquid Chromatography, 'iPrOH' means isopropyl alcohol, 'iPrNH$_2$' means isopropyl amine, 'LC/MS' means Liquid Chromatography/Mass Spectrometry, 'LiHMDS' means Lithium bis(trimethylsilyl)amide, 'Me-THF' means 2-methyl-tetrahydrofuran, 'MeNH$_2$' means monomethylamine, 'MeOH' means methanol, 'MsCl' means methanesulfonyl chloride, 'MTBE' means methyl tert-butyl ether 'NBS' means N-bromosuccinimide, 'NCS' means N-chlorosuccinimide, 'NMR' means Nuclear Magnetic Resonance, 'o/n' means overnight, 'OR' means optical rotation, 'Pd/C 10%' means palladium on carbon loading 10%, 'Pd-118' means dichloro [1,1'-bis (di-tert-butylphosphino)ferrocene] palladium(II), 'PdCl$_2$(dppf).DCM' means [1,1'-Bis(diphenylphosphino)ferrocene] dichloropalladium(II) complex with DCM, 'Pd(OAc)$_2$' means palladium (II) acetate, 'Pd(PPh$_3$)$_4$' means tetrakis (triphenylphosphine)palladium (0), 'Pd(t-Bu$_3$P)$_2$' means bis (tri-tert-butyl-phosphine) palladium (0), 'PdCl$_2$dppf' or 'Pd (dppf)Cl$_2$' means [1,1'-bis(diphenylphosphino)ferrocene] dichloropalladium(II), 'Pd(OH)$_2$/C' means palladium hydroxide on carbon, 'Psi' means Pounds per Square Inch (pressure), 'Pybrop' means bromotripyrrolidinophosphonium hexafluorophosphate, 'rt' means room temperature, 'SFC' means supercritical fluid chromatography, 'T' means temperature, 'TBAF' means tetrabutylammonium fluoride, 'TBDMS' or 'SMDBT' means tert-butyldimethylsilyl, 'TEA' or 'Et$_3$N' means triethylamine, 'TFA' means trifluoroacetic acid, 'THF' means tetrahydrofuran, CV' means column volumes, 'Quant.' means quantitative, 'min' or 'mn' means minute(s), 'W' means microwave, 'equiv.' means equivalent(s), 'M.P.' or 'm.p.' means melting point, 'v/v' means volume/volume %.

When a stereocenter is indicated with 'RS' this means that a racemic mixture was obtained.

It is well known to one skilled in the art that protecting groups such as TBDMS can routinely be removed with TBAF in a variety of solvents such as for example THF.

Similarly, conditions for removal of BOC protecting groups are well known to one skilled in the art, commonly including for example TFA in a solvent such as for example DCM, or HCl in a solvent such as for example dioxane.

The skilled person will realize that in some cases where an organic layer was obtained at the end of an experimental protocol, it was necessary to dry the organic layer with a typical drying agent such as for example MgSO$_4$, or by azeotropic distillation, and to evaporate the solvent before using the product as a starting material in the next reaction step.

A. Preparation of the Intermediates

Example A1

Preparation of Intermediate 1

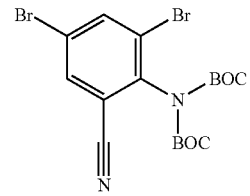 [SMILES: CC(C)(C)OC(=O)N(C(=O)OC(C)(C)C)c1c(Br)cc(Br)cc1C#N]

To a solution of 2,4-dibromo-6-cyanoaniline (200.00 g, 724.82 mmol) and DMAP (17.71 g, 144.96 mmol) in DCM (3 L), Boc$_2$O (474.58 g, 2.17 mol) was added and the reaction mixture was stirred at 45° C. for 4 h. The crude mixture was successively washed with saturated NaHCO$_3$ (2×1 L) and brine (2×1 L), dried over MgSO$_4$, filtered and concentrated under vacuum to give 323 g of intermediate 1

(56% yield, yellow solid, 86% purity evaluated by LC/MS). The product was used in the next step without any further purification.

Preparation of Intermediate 2

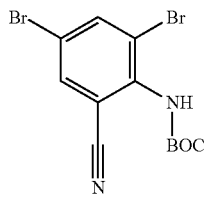 [SMILES: CC(C)(C)OC(=O)Nc1c(Br)cc(Br)cc1C#N]

A mixture of intermediate 1 (620.00 g, 1.30 mol) and $K_2CO_3$ (539.02 g, 3.90 mol) in MeOH (6 L) was stirred at 65° C. for 3 h. The reaction mixture was cooled to 25° C. filtered and concentrated under vacuum. Then, the residue was dissolved in EtOAc (4 L) and the organic layer was washed with brine (2 L), dried over $MgSO_4$, and filtered. The filtrate was evaporated under vacuum to 1/8 solvent, filtered to collect the solid and dried under reduced pressure to give 300 g of intermediate 2 (60% yield, yellow solid). The product was used in the next step without any further purification.

Preparation of Intermediate 3

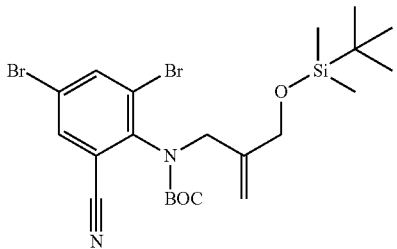 [SMILES: C=C(CO[Si](C)(C)C(C)(C)C)CN(C(=O)OC(C)(C)C)c1c(Br)cc(Br)cc1C#N]

Intermediate 2 (100.00 g, 265.93 mmol), 2-(((tert-butyl-dimethyl-silanyl)oxy) methyl) prop-2-en-1-ol (80.72 g, 398.90 mmol) and tributylphosphane (107.61 g, 531.86 mmol) were dissolved in THF (2 L) and cooled to 0° C. A solution of 1,1'-(azodicarbonyl)-dipiperidine (147.61 g, 585.05 mmol) in THF (50 mL) was added dropwise under $N_2$ and stirred at 0° C. for 1 h, then 25° C. for 12 h. The resulting mixture was triturated with petroleum ether (3 L), filtered and concentrated under vacuum. Then, the residue was dissolved in EtOAc (6 L), washed successively with water (2×2 L) and brine (2×2 L), dried over $MgSO_4$, filtered and concentrated under vacuum. Three reactions (each 100 g) were carried out in parallel. The resulting residues were purified by column chromatography on silica gel ($SiO_2$, mobile phase: petroleum ether/EtOAc, 10:1). The desired fractions were collected and the solvent was concentrated to dryness under vacuum to give 350 g of intermediate 3 (78% yield, yellow oil).

Preparation of Intermediate 3a

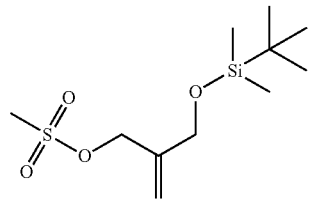 [SMILES: C=C(CO[Si](C)(C)C(C)(C)C)COS(C)(=O)=O]

Triethylamine (196.3 mL; 1.408 mol) was added to a solution of 2-(((tert-butyl-dimethyl-silanyl)oxy) methyl) prop-2-en-1-ol (114 g, 563.3 mmol) in DCM (1 L) at 0° C. Methanesulfonylchloride (56.0 mL; 704.2 mmol) was slowly added to the mixture and this mixture was stirred for 2 h at 0° C. The reaction was quenched with saturated aqueous solution of $NaHCO_3$ (100 ml) and extracted with DCM (500 ml*2). The organic layer was dried over $MgSO_4$, filtered, and concentrated under vacuum. The residue was purified by silica gel chromatography (Petroleum ether/ethyl acetate from 0/100 to 5/1) to give 50 g (32%; light yellow oil) of intermediate 3a.

Alternative Preparation of Intermediate 3

Intermediate 2 (140 g; 372.3 mmol) was dissolved in acetonitrile (1.3 L). Intermediate 3a (104.4 g; 372.3 mmol), potassium carbonate (128.6 g; 930.7 mmol sodium iodide (5.58 g; 37.2 mmol) were added. The mixture was stirred at 80° C. for 12 h, cooled and concentrated under reduced pressure. The residue was dissolved in water (1 L) and extracted with ethyl acetate (1 L*2).

The combined organic phase was washed with brine (1 L), dried over $Na_2SO_4$ and filtered. The filtrate was concentrated under vacuum to give a crude product. The residue was purified by silica gel chromatography (Petroleum ether/ethyl acetate from 100/0 to 40/1) to give 180 g (86%; clear oil) of intermediate 3.

Preparation of Intermediate 4 and Intermediate 4'

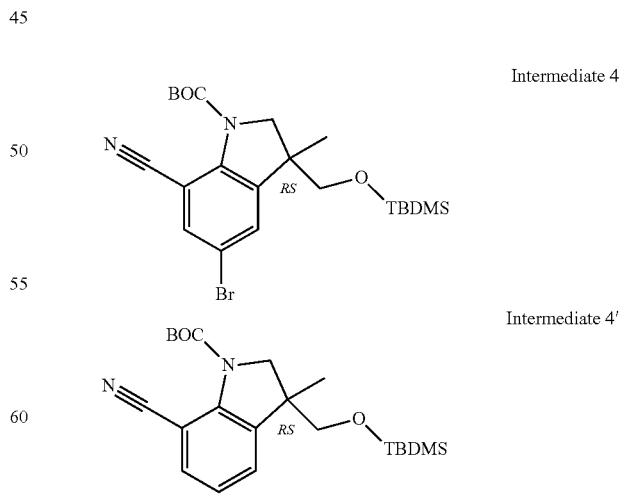

A suspension of intermediate 3 (120.00 g, 214.14 mmol), sodium acetate (45.67 g, 556.76 mmol), sodium formate (37.86 g, 556.76 mmol), $Pd(OAc)_2$ (4.81 g, 21.41 mmol) and tetraethylammonium chloride (44.35 g, 267.67 mmol) in DMF (1.26 L) was degassed under vacuum, purged with Ar three times, and stirred at 85° C. for 2 h. The resulting mixture was filtered through a pad of Celite® and the solid was washed with DCM (2 L). The filtrate was concentrated under vacuum. The residue was dissolved in ethyl acetate (4 L), washed successively with water (2×2 L) and brine (2×2 L), dried over MgSO₄, filtered and concentrated under vacuum. Then, the residue was purified by column chromatography on silica gel (SiO₂, mobile phase: petroleum ether/EtOAc, 15:1). The desired fractions were collected and the solvent was concentrated to dryness under vacuum to give a mixture of intermediates 5 and 5'. Three reactions (each on 100-120 g of intermediate 3) were carried out in parallel which gave in total 160 g of a mixture of intermediates 4 and 4' (38:62).

Alternative Preparation of Intermediate 4

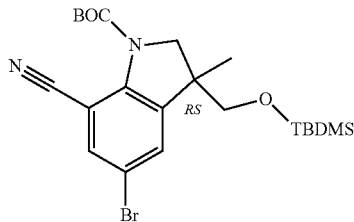

To a mixture of intermediates 4 and 4' in CH₃CN (1.60 L), 1-bromopyrrolidine-2,5-dione (212.20 g, 1.19 mol) was added and stirred at 40° C. for 16 h. The solvent was removed by evaporation under reduced pressure. The residue was dissolved in ethyl acetate (2 L), washed successively with NaHCO₃ (2×1 L) and brine (2×1 L), dried over MgSO₄ and filtered. The filtrate was evaporated under vacuum and purified by column chromatography on silica gel (SiO₂, mobile phase: petroleum ether/EtOAc, 50:1). The desired fractions were collected and the solvent was concentrated to dryness under vacuum to give 110.00 g of intermediate 4 (56% yield, yellow oil, 97% purity evaluated by LC/MS).

Alternative Preparation of Intermediate 4R

Intermediate 4R

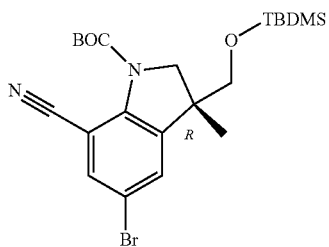

To a solution of intermediate 4'R (10.0 g) in ACN (100 mL) 1,3-dibromo-5,5-dimethylhydantoin (0.75 eq.) was added and the mixture was stirred at 20° C. for 24-28 hours, monitoring the conversion by HPLC. After complete conversion aqueous 5% NaHCO₃ was added (250 mL) and the mixture was stirred for 30 minutes. Toluene (250 mL) was then added and, after 30 min stirring at room temperature, the mixture was allowed to settle and the layers were separated. The organic layer was washed twice with water (100 mL) and used directly in the next reaction step (conversion 99.6%).

Alternative Preparation a of Intermediate 4'

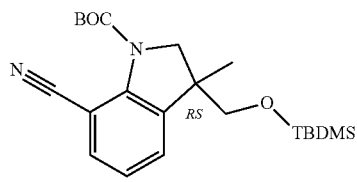

To a solution of intermediate 3 (295.00 g, 473.70 mmol), sodium acetate (101.05 g, 1.23 mol), sodium formate dihydrate (128.15 g, 1.23 mol) and [1,1'-bis(diphenylphosphino)ferrocene] palladium, (II) chloride complex with dichloromethane (19.34 g, 23.70 mmol) in DMF (2 L), tetra-N-butylammonium chloride (164.60 g, 592.20 mmol) was added under N₂ at rt. The reaction mixture was stirred overnight at 60° C., then, filtered through a pad of Celite® and the solid was washed with DCM (400 mL). The filtrate was concentrated under vacuum. The resulting residue was dissolved in EtOAc (4 L) and the organic layer was washed successively with water (2 L) and brine (2 L), dried over Na₂SO₄, filtered and concentrated to give the crude product as black oil. This residue was purified by column chromatography on silica gel (SiO₂, mobile phase: petroleum ether/EtOAc, gradient from 100:0 to 10:1). The desired fractions were collected and the solvent was concentrated to dryness under vacuum to give 155 g of intermediate 4' (70% yield, yellow oil).

Alternative Preparation B of Intermediate 4'

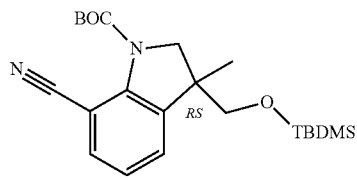

Intermediate 583 (50.0 g) was dissolved in DMF (250 mL). Sodium formate dehydrate (2.6 eq.), sodium acetate (2.6 eq.), tetraethylammonium chloride (1.25 eq.) and palladium acetate (0.05 eq.) were added. The mixture was degassed with nitrogen (3 times) and was then warmed at 45-50° C. until complete conversion (approximately 24 hours monitored by HPLC). Water (350 mL) was then added followed by heptane (350 mL). The mixture was filtered and, after phase separation, the aqueous layer was extracted with heptane (350 mL). The combined organic layers were washed with water (250 mL) and then filtered on a diatomite pad (25 g; diatomaceous earth). The filtrate was concentrated to 100-150 mL, cooled to −10 to −5° C. for 2 hours and filtered to afford 37.6 g of intermediate 4'. An additional amount of intermediate 4' could be recovered by filtering the mother liquors on a silica gel pad to remove impurities, and subsequently cool down the filtrate to −10° C. to crystallize out an additional amount of intermediate 4'.

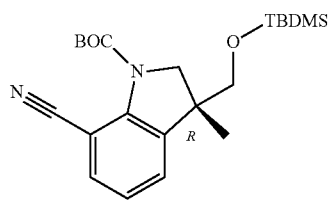

Preparation of Intermediate 4'R Intermediate 4'R

Intermediate 4'R was obtained from a chiral chromatography separation of intermediate 4' (column CHIRALPAK IC 5 cm*25 cm; mobile phase: hexane/EtOH:80/20; Flow rate: 60.0 mL/min; Wavelenght: UV 254 nm; Temperature: 35° C.).

Preparation of Intermediate 4R and Intermediate 4S

Intermediate 4R

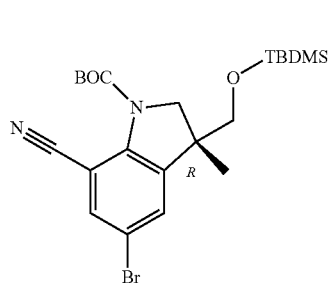

Intermediate 4S

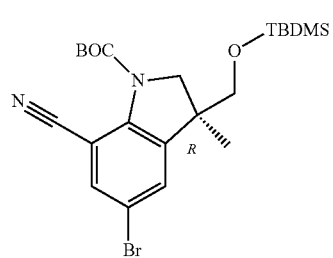

Intermediate 4 (500 g) was purified via Normal Phase Chiral separation (Stationary phase: Daicel Chiralpak IC 2000 gram 10 microhm, mobile phase: heptane/EtOH, Isocratic 80% heptane, 20% EtOH). The fractions containing the products were mixed and concentrated to afford 266 g of intermediate 4R (53% yield, ee>98%) and 225 g of intermediate 4S (45% yield, ee>98%).

Alternatively, intermediate 4 (10 g) was purified by chiral SFC (Stationary phase: CHIRALPAK IC 5 μm 250×30 mm, mobile phase: 85% CO$_2$, 15% iPrOH). The pure fractions were collected and evaporated to dryness yielding 4.3 g of intermediate 4R (43% yield, ee=100%) and 4.5 g of intermediate 4S (45% yield, ee=100%).

Example A2

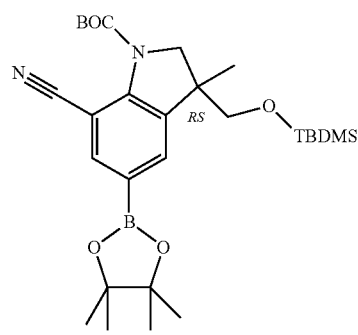

Preparation of Intermediate 5

To a solution of intermediate 4 (127.00 g, 234.70 mmol) in 1,4-dioxane (1.2 L), bis(pinacolato)diboron (74.50 g, 293.40 mmol) and potassium acetate (69.11 g, 704.24 mmol) were added. Then, [1,1'-bis(diphenylphosphino) ferrocene] palladium, (II) chloride (8.59 g, 11.74 mmol) was added and stirred for 4 h at 85° C. under N$_2$ atmosphere. The mixture was cooled, partitioned between EtOAc (2 L) and water (500 mL) and filtered through a pad of Celite®. The organic and aqueous layers were separated. The organic layer was washed successively with water (300 mL), brine (300 mL), dried over Na$_2$SO$_4$ and concentrated under vacuum. The residue was dissolved in a mixture of DCM/EtOAc (90:10, 600 mL), filtered through a plug of flash silica gel, washed with DCM/EtOAc (90:10, 3 L). The filtrate was evaporated to give 125 g of crude intermediate 5 (brown oil) which was directly engaged in the next step.

Preparation of Intermediate 5R

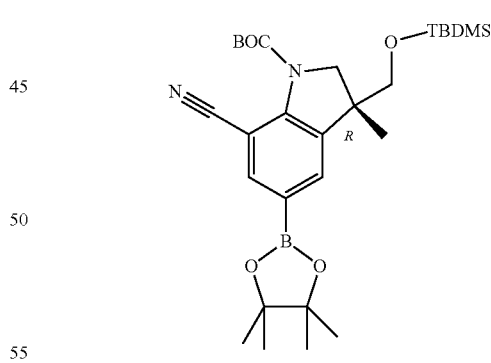

To a solution of intermediate 4R (20.00 g, 41.50 mmol) in 1,4-dioxane (200 mL), bis(pinacolato)diboron (13.20 g, 51.90 mmol) and potassium acetate (12.20 g, 124.60 mmol) were added. Then, [1,1'-bis(diphenylphosphino) ferrocene] palladium, (II) chloride complex with dichloromethane (1.70 g, 2.08 mmol) was added and stirred for 4 h at 85° C. under N$_2$. The mixture was cooled, partitioned between EtOAc (200 mL) and water (100 mL), and filtered through a pad of Celite®. The organic and aqueous layers were separated. The organic layer was washed successively with water (100 mL), brine (100 mL), dried over Na$_2$SO$_4$, and concentrated under vacuum. The residue was dissolved in a mixture of DCM/EtOAc (90:10, 200 mL), filtered through a plug of flash silica gel and washed with a mixture of DCM/EtOAc (90:10, 1 L). The filtrate was evaporated to give 25 g of crude intermediate 5R (brown oil) which was directly engaged in the next step.

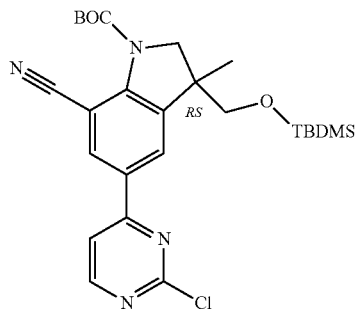

Preparation of Intermediate 6

A solution of intermediate 5 (160.00 g, 302.70 mmol) in 1,4-dioxane (1.2 L) was treated with a solution of NaHCO$_3$ (76.30 g, 908.10 mmol) in water (400 mL). Then, 2,4-dichloropyrimidine (67.64 g, 545.06 mmol) and Pd(PPh$_3$)$_4$ (17.50 g, 15.13 mmol) were added under N$_2$. The reaction mixture was stirred at 80° C. under N$_2$. The mixture was cooled, partitioned between EtOAc (2 L) and water (800 mL), and the mixture was filtered through a pad of Celite®. The organic and aqueous layers were separated. The organic layer was washed successively with water (800 mL) and brine (500 mL), dried over Na$_2$SO$_4$ and concentrated under vacuum. The residue was purified by flash column chromatography on silica gel (SiO$_2$, mobile phase: petroleum ether/EtOAc, gradient from 100:0 to 10:1). The desired fractions were collected and the solvent was concentrated to dryness under vacuum to give 100 g of intermediate 6 (71% yield in 2 steps, yellow solid).

Preparation of Intermediate 6R and intermediate 6S

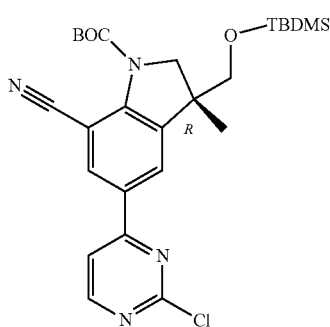

Intermediate 6R

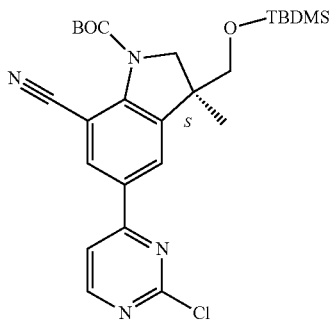

Intermediate 6S

Intermediate 6 (52.00 g) was purified by chiral SFC (stationary phase: CHIRALPAK IC 5 μm 250×30 mm, mobile phase: 60% CO$_2$, 40% MeOH). The desired fractions were collected and the solvent was concentrated to dryness under vacuum to give 25 g of intermediate 6R (48% yield) and 25.1 g of intermediate 6S (48% yield).

Intermediate 6R (50.10 g) was further purified by chiral SFC (stationary phase: CHIRALPAK IA 5 μm 250*20 mm, mobile phase: 87.5% CO$_2$, 12.5% MeOH). The pure fractions were mixed and the solvent was evaporated to afford 49.10 g of intermediate 6R.

Alternative Preparation A of Intermediate 6R

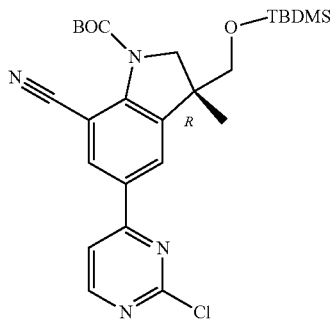

A solution of intermediate 5R (25.00 g, 41.90 mmol) in 1,4-dioxane (1.2 L) was treated with a solution of NaHCO$_3$ (10.50 g, 125.72 mmol) in water (80 mL). Then, 2,4-dichloropyrimidine (9.36 g, 62.86 mmol) and Pd(PPh$_3$)$_4$ (2.42 g, 2.09 mmol) were added under N$_2$. The reaction mixture was stirred at 80° C. under N$_2$. The mixture was cooled, partitioned between EtOAc (300 mL) and water (100 mL), and filtered through a pad of Celite®. The organic layer was washed with water (100 mL), brine (100 mL), dried over Na$_2$SO$_4$ and concentrated under vacuum. The resulting residue was combined with 3 other batches coming from reactions performed on 25 g of intermediate 5R. The residue was purified by flash column chromatography on silica gel (SiO$_2$, mobile phase: petroleum ether/EtOAc, gradient from 100:0 to 10:1). The desired fractions were collected and the solvent was concentrated to dryness under vacuum to give 63 g of intermediate 6R (70% yield over 2 steps, yellow solid).

Alternative Preparation B of Intermediate 6R

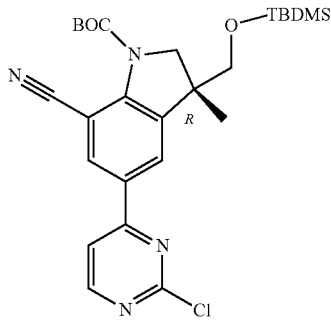

To a solution of intermediate 4R (50.0 g) in toluene (400 mL) was added bis(pinacolato)diboron (1.3 eq.), potassium acetate (3.0 eq.) and Pd(dppf)Cl$_2$ (0.05 eq.). The mixture was degassed 3 times with nitrogen and heated to 90° C. for 12-14 hours. Subsequently, the mixture was cooled to room temperature and filtered on a celite pad which was washed with toluene (150 mL). The filtrate was washed with water (250 mL) and was then filtered on a silica pad (10 g) to afford a toluene solution containing 49 g of intermediate 5R. To this solution was added 2,4-dichloropyrimidine (1.5 eq.), NaHCO$_3$ (3.0 eq.), water (25 mL) and Pd(PPh$_3$)$_4$ (0.05 eq.). After degassing three times with nitrogen, the mixture was stirred at 90° C. monitoring the conversion by HPLC. After complete conversion (24-48 hours), the mixture was cooled to room temperature, filtered on a celite pad and washed with water (250 mL). To the organic layer was added silica thiol scavenging resin (10 g; resin used to scavenge metals) and the mixture was stirred at 90° C. for 3 hours, then cooled to room temperature and filtered. The solvent was switched completely to isopropanol by repeated distillation until about 100 mL of isopropanol solution remained. The solution was warmed to 50° C. and 250 mL of methanol were added. After stirring at 50° C. for 4 hours, the mixture was cooled to 0° C. in 4 h, held at the same temperature for 16 hours and finally filtered to obtain 26 g of intermediate 6R.

The intermediate in the Table below was prepared by using an analogous method to that described as the alternative method A for intermediate 6R, starting from the respective starting materials indicated. The most relevant minor deviations to the referenced method are indicated as additional information in the column 'Yield (%)'.

| Intermediate number | Structure | Mass (mg) | Yield (%) |
|---|---|---|---|
| Intermediate 104i | 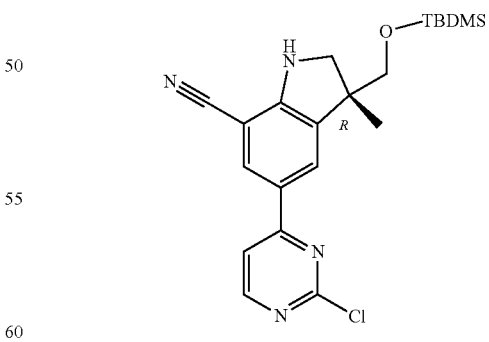<br>From intermediate 5R and intermediate 103i | 320<br>LCMS 88% | 28<br>Procedure with PdCl$_2$(dppf).DCM, 80° C., o.n |

Example A3
Preparation of Intermediate 7R

In a three neck round bottom flask, SiO$_2$ (35-70 μm) (200 g) was added to a solution of intermediate 6R (45.00 g, 87.36 mmol) in toluene (640 mL) at rt. The reaction mixture was reflux (bath temperature 125° C.) for 6 h under mechanical agitation. Then, SiO$_2$ (35-70 μm) was filtered off, washed successively with THF and EtOAc, and the filtrate was evaporated to dryness to give 37.2 g of crude intermediate 7R which was directly engaged in the next steps.

Alternative Preparation of Intermediate 7R

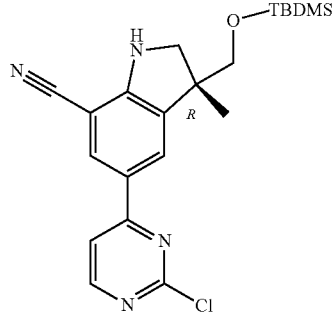

TFA (135 mL, 1.76 mol) was added dropwise at −10° C. (over 50 min) to a solution of intermediate 6R (20.00 g, 38.82 mmol) in DCM (550 mL). The reaction mixture was stirred below 0° C. for 15 min more, then poured in a mixture of crushed ice and a saturated aqueous solution of $K_2CO_3$. After extraction with DCM (twice), the organic layers were combined, washed with an aqueous solution of $K_2CO_3$, dried over $MgSO_4$ and evaporated to dryness. The residue (17.40 g) was purified by chromatography on silica gel (irregular SiOH, 80 g, mobile phase: $NH_4OH$/MeOH/DCM, gradient from 0% $NH_4OH$, 0% MeOH, 100% DCM to 0.2% $NH_4OH$, 2% MeOH, 98% DCM). The desired fractions were collected and the solvent was concentrated to dryness under vacuum to give 12.1 g of intermediate 7R (75% yield).

Preparation of Intermediate 7

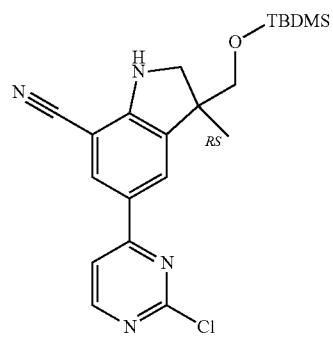

To a solution of intermediate 7 (1.50 g, 2.91 mmol) in DCM (30 mL), TFA (7 mL, 91.50 mmol) was added at 0-5° C. and stirred at 0-5° C. for 1 h, then rt for 1 h. The crude product was poured in a mixture of crushed ice and a saturated aqueous solution of $NaHCO_3$. After extraction with DCM (twice), the organic layers were combined, washed with a saturated solution of $NaHCO_3$, dried over $MgSO_4$ and concentrated under vacuum. The residue was purified by column chromatography on silica gel (Irregular SiOH, 40 μm, mobile phase: $NH_4OH$/MeOH/DCM, gradient from 0% $NH_4OH$, 0% MeOH, 100% DCM to 0.1% $NH_4OH$, 2% MeOH, 98% DCM). The desired fractions were collected and the solvent was concentrated to dryness under vacuum to give 524 mg of intermediate 7 (65% yield).

Example A4

Preparation of Intermediate 331

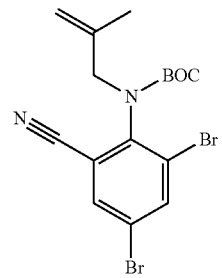 [SMILES: C=C(C)CN(C(=O)OC(C)(C)C)c1c(Br)cc(Br)cc1C#N]

A solution of intermediate 2 (10.00 g, 26.59 mmol) and 2-methyl-2-propen-1-ol (4.50 mL, 53.69 mmol) in Me-THF (200 mL) was cooled with EtOH/ice bath under $N_2$ to an internal temperature of −5° C. Tri-n-butylphosphine (13.30 mL, 53.19 mmol) was added. Then a solution of 1,1'-(azodicarbonyl)piperidine (14.80 g, 58.62 mmol) in Me-THF (120 mL) was added dropwise over 25 min. The solution was stirred for 5 min more at this temperature then the cooling bath was removed and the solution stirred at rt for 18 h. The reaction mixture was poured onto a 10% aqueous solution of $K_2CO_3$ and extracted with DCM. The organic layer was decanted, dried over $MgSO_4$, filtered and evaporated to dryness. The residue (20 g) was taken up with heptane and the insoluble material was removed by filtration. The filtrate was concentrated to 20 mL and purified by column chromatography on silica gel (irregular SiOH, 80 g, mobile phase: heptane/EtOAc, gradient from 100:0 to 88:12). The pure fractions were collected and evaporated to dryness to give 10.80 g of intermediate 331 (94% yield).

Preparation of Intermediate 332 and intermediate 332'

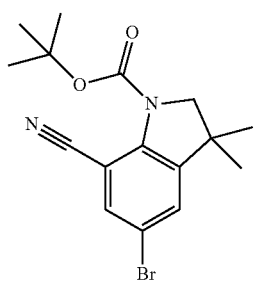

Intermediate 332

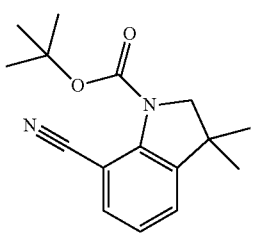

Intermediate 332'

A mixture of intermediate 331 (10.80 g, 25.11 mmol), sodium acetate (5.35 g, 65.28 mmol), sodium formate (4.44

163 g, 65.28 mmol) and tetraethylammonium chloride (5.20 g, 31.38 mmol) in DMF (100 mL) was de-gassed by sonication for 10 min under a stream of Ar. Pd(OAc)$_2$ (563.00 mg, 2.51 mmol) was added and the resulting orange suspension was then stirred at 85° C. (block temperature) for 4 h. The residue was diluted with EtOAc and water, then filtered through a plug of Celite®. The organic layer was decanted, washed successively with a saturated aqueous solution of NaHCO$_3$ and brine, dried over MgSO$_4$, filtered and evaporated to dryness. The residue (8.3 g, mixture of intermediates 332 and 332') was dissolved in CH$_3$CN (230 mL) and NBS (4.47 g, 25.11 mmol) was added. The reaction mixture was heated at 55° C. (block temp) for 18 h. The reaction mixture was evaporated to dryness and the residue was taken up with heptane/DCM. The precipitate was filtered off (1 g derivative) and the filtrate (10 g) was purified by column chromatography on silica gel (irregular SiOH, 120 g, injection in DCM, mobile phase: heptane/EtOAc, gradient from 100:0 to 80:20). The pure fractions were collected and evaporated to dryness to give 4 g of intermediate 332 (45% yield).

Preparation of Intermediate 333

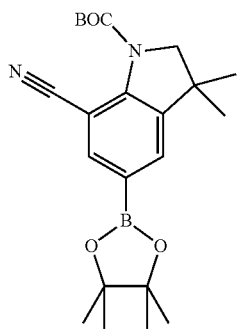 [SMILES: CC(C)(C)OC(=O)N1CC(C)(C)c2cc(B3OC(C)(C)C(C)(C)O3)cc(C#N)c21]

[1,1'-Bis(diphenylphosphino)ferrocene]dichloropalladium (II), complex with dichloromethane (243.00 mg, 0.30 mmol) was added to a solution of intermediate 332 (2.09 g, 5.95 mmol), bis(pinacolato)diboron (1.90 g, 7.44 mmol) and potassium acetate (1.75 g, 17.85 mmol) in 1,4-dioxane (45 mL) and the reaction mixture was heated for 18 h at 85° C. The reaction mixture was diluted with EtOAc and filtered through a pad of Celite®. The filtrate was washed with water, and the organic layer was decanted, dried over MgSO$_4$, filtered and evaporated to dryness. The residue was crystallized from DiPE and the precipitate was filtered and dried to give 1.85 g of intermediate 333 (78% yield).

164

Preparation of Intermediate 334

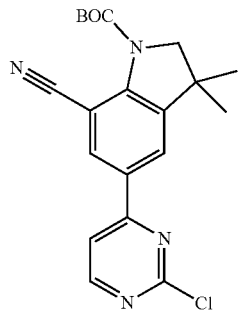 [SMILES: CC(C)(C)OC(=O)N1CC(C)(C)c2cc(-c3ccnc(Cl)n3)cc(C#N)c21]

A degassed suspension of intermediate 333 (1.12 g, 2.81 mmol), 2,4-dichloropyridine (502.00 mg, 3.37 mmol), Pd(PPh$_3$)$_4$ (162.00 mg, 0.14 mmol) and a solution of Na$_2$CO$_3$ 2M (4.20 mL, 8.14 mmol) in 1,4-dioxane (24 mL) was heated to 85° C. for 18 h. The reaction mixture was partitioned between DCM and saturated aqueous NaHCO$_3$. The organic layer was decanted, dried over MgSO$_4$, filtered and evaporated to dryness. The residue (2 g) was purified by column chromatography on silica gel (irregular SiOH, 40 g, mobile phase: heptane/EtOAc, gradient from 70:30 to 50:50). The pure fractions were collected and evaporated to dryness to give 933 mg of intermediate 334 (86% yield, 85% purity based on LC/MS).

Example A5

Preparation of Intermediate 343

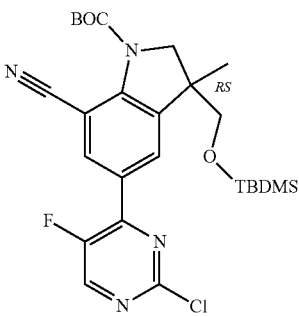

To a solution of intermediate 5 (3.89 g, 4.92 mmol), 5-fluoro-2,4-dichloropyrimidine (1.07 g, 6.40 mmol) and Cs$_2$CO$_3$ (4.81 g, 14.80 mmol) in 1,4-dioxane (25 mL) and distilled water (2.5 mL), Pd(PPh$_3$)$_4$ (0.28 g, 0.25 mmol) was added and the reaction mixture was heated overnight at 95° C. The mixture was poured into ice and extracted with EtOAc. The organic layer was washed with brine, dried over MgSO$_4$, filtered and the solvent was evaporated. The residue was purified by column chromatography on silica gel (240 g, 15-40 μm, mobile phase: heptane/EtOAc, gradient from 1:0 to 0:1). The pure fractions were mixed and the solvent was evaporated to give 1.92 g of intermediate 343 (73% yield).

The intermediates in the Table below were prepared by using an analogous starting from the respective starting materials.

| Intermediate number | Structure | Mass (mg) | Yield (%) |
|---|---|---|---|
| Intermediate 348 | 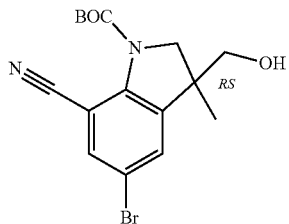 [SMILES: CC(C)(C)OC(=O)N1CC(C)(CO)c2cc(Br)cc(C#N)c21] From intermediate 5R and 5-fluoro-2,4-dichloropyrimidine | 1820 | 83 |

Example A6

Preparation of Intermediate 372

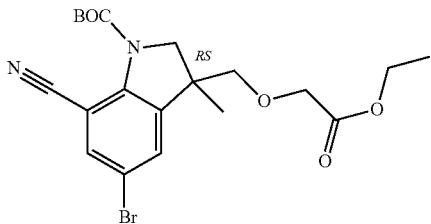 [SMILES: CCOC(=O)COCC1(C)CN(C(=O)OC(C)(C)C)c2c(C#N)cc(Br)cc21]

Intermediate 4 (4.00 g, 8.31 mmol) was dissolved in THF (81 mL) and a TBAF solution in THF (1M, 16.60 mL, 16.60 mmol) was added. After stirring at rt for 4 h, the solvent was evaporated under vacuum. The residue was extracted with EtOAc/water and the organic phase was washed twice with water, once with brine, dried over anhydrous $MgSO_4$ and evaporated to dryness under vacuum to provide a yellow oil. The residue (4.5 g) was purified by column chromatography on silica gel (irregular SiOH, 80 g, mobile phase: heptane/EtOAc, gradient from 80:20 to 50:50). The fractions containing the product were combined and evaporated to provide 2.54 g of intermediate 372 (83% yield, white powder).

Preparation of Intermediate 373

A solution of intermediate 372 (2.00 g, 5.45 mmol) and ethylbromoacetate (722.80 μL, 6.53 mmol) in dry DMF (15 mL) was cooled to 0° C. After stirring for 5 min, NaH (60% dispersed in mineral oil) (261.40 mg, 6.53 mmol) was then added and the reaction mixture was stirred at 0° C. for 1 h. The reaction was poured onto a mixture of $Et_2O$ and aqueous $NaHCO_3$. The organic layer was decanted, washed thrice with brine, dried over $MgSO_4$ and evaporated to dryness. The residue was purified by column chromatography on silica gel (irregular SiOH, 80 g, mobile phase: heptane/EtOAc, gradient from 80:20 to 50:50). The pure fractions were collected and evaporated to dryness to give 2.04 g of intermediate 373 (82% yield, 95% purity based on LC/MS).

Preparation of Intermediate 374

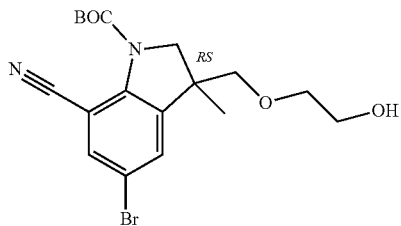 [SMILES: CC(C)(C)OC(=O)N1CC(C)(COCCO)c2cc(Br)cc(C#N)c21]

$NaBH_4$ (250.40 mg, 6.62 mmol) was added portionwise to a solution of intermediate 373 (2.00 g, 4.41 mmol) in a mixture of THF (24 mL) and MeOH (8 mL) and the reaction mixture was heated at 55° C. for 45 min. The reaction mixture was cooled to rt, poured onto water and extracted with $Et_2O$. The organic layer was decanted, dried over $MgSO_4$, filtered and evaporated to dryness. The residue was purified by column chromatography on silica gel (irregular SiOH, 40 g, mobile phase: heptane/EtOAc, gradient from 80:20 to 50:50). The pure fractions were collected and evaporated to dryness to give 810 mg of intermediate 374 (45% yield).

Preparation of Intermediate 375 and intermediate 375'

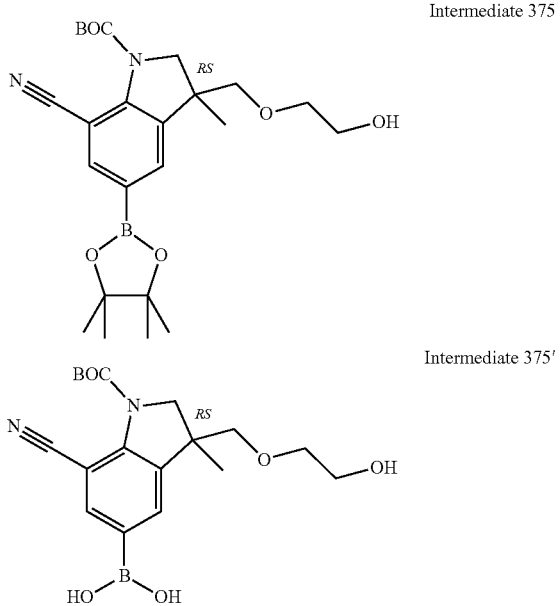

Intermediate 375

Intermediate 375'

A mixture of intermediate 374 (1.50 g, 3.65 mmol), bis(pinacolato)diboron (1.15 g, 4.56 mmol) and acetic acid potassium salt (715.90 mg, 7.29 mmol) in Me-THF (30 mL) was purged with $N_2$. [1,1'-bis(diphenylphosphino)ferrocene]dichloropalladium (II), complex with dichloromethane (298.60 mg, 0.36 mmol) was added and the mixture was purged with $N_2$ and stirred for 18 h at 100° C. The reaction mixture was diluted with EtOAc, washed with water then brine, dried over $MgSO_4$ and evaporated to dryness to give 2.76 g of intermediate 375 in a mixture with intermediate 375' (75:20+5% of impurities not defined) and used as it in the next step.

Preparation of Intermediate 376

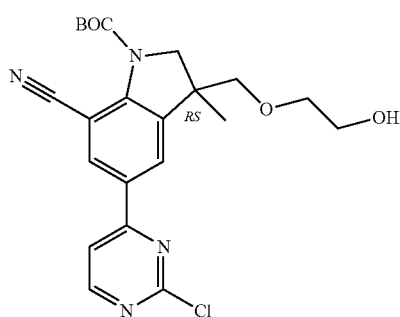 [SMILES: CC(C)(C)OC(=O)N1CC(C)(COCCO)c2cc(-c3ccnc(Cl)n3)cc(C#N)c21]

A solution of intermediate 375 (1.67 g, 3.65 mmol), 2,4-dichloropyrimidine (652.00 mg, 4.38 mmol) and $K_3PO_4$ (1.80 g, 7.29 mmol) in a mixture of Me-THF (30 mL) and distilled water (6.5 mL) was degassed with $N_2$. [1,1'-Bis(diphenylphosphino)ferrocene]dichloropalladium (II), complex with dichloromethane (238.85 mg, 0.29 mmol) was added and the reaction mixture was heated at 85° C. for 18 h. The reaction mixture was diluted with EtOAc, washed with water then with brine, dried over $MgSO_4$ and evaporated to dryness. The residue (2.4 g) was purified by column chromatography on silica gel (irregular SiOH, 40 g, mobile phase: heptane/EtOAc, gradient from 50:50 to 0:100). The pure fractions were collected and evaporated to dryness to give 1.1 g of intermediate 376 (68% yield).

Example A7

Preparation of Intermediate 387

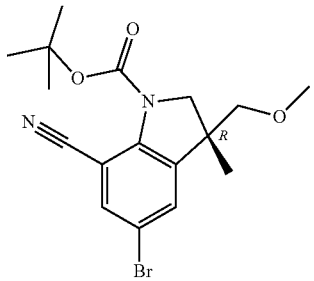

In a round bottom flask, intermediate 372 (665.00 mg, 1.81 mmol) was diluted in DMF (7.29 mL). Then, NaH (60% dispersed in mineral oil) (79.70 mg, 1.99 mmol) was added and the mixture was become yellow. Then methyl methanesulfonate (1.84 mL, 21.73 mmol) was added and the reaction mixture was stirred at rt for 5 h. Then, a diluted solution of $NH_4Cl$ was added and the aqueous layer was extracted twice with DCM and the combined layers were dried over $MgSO_4$. After filtration and careful removal of the solvent in vacuo, the residue (800 mg, yellow oil) was purified by column chromatography on silica gel (irregular SiOH, 40 g, mobile phase: heptane/EtOAc, gradient from 100:0 to 80:20). The fractions containing the product were collected and evaporated to dryness to give 573 mg of intermediate 387 (83% yield, colorless oil).

Preparation of Intermediate 388

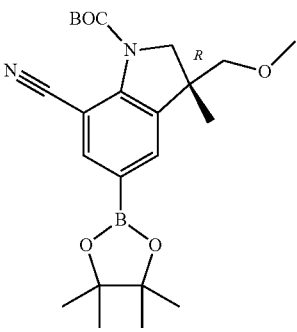

$N_2$ was bubbled into a solution of intermediate 387 (50 mg, 0.13 mmol) and bis(pinacolato)diboron (41.60 mg, 0.16 mmol) in Me-THF (0.505 mL). [1,1'-bis(diphenylphosphino)ferrocene]dichloropalladium (II), complex with dichloromethane (5.35 mg, 0.066 mmol) and $Pd(OAc)_2$ (38.60 mg, 0.39 mmol) were added. The reaction mixture was degassed with $N_2$ and heated at 85° C. overnight. The reaction mixture was cooled to rt. The reaction mixture was filtered through a pad of Celite®. The organic layer was decanted and washed twice with water, brine, dried over MgSO₄, filtered and evaporated to dryness. The residue was used as it is for the next step (79% purity based on LC/MS).

Preparation of Intermediate 389

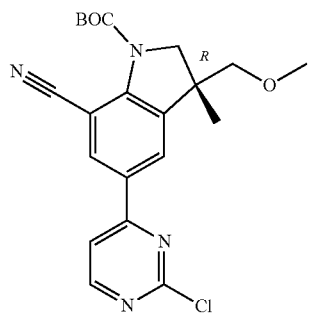

A solution of intermediate 388 (0.77 g, 1.79 mmol) in 1,4-dioxane (20 mL) was treated with Na₂CO₃ (2M, 2.68 mL, 5.36 mmol), 2,4-dichloropyrimidine (399.60 mg, 2.68 mmol) and Pd(PPh₃)₄ (103.30 mg, 0.09 mmol) and the mixture evacuated and purged thrice with N₂ and then heated to 80° C. overnight. The mixture was cooled and partitioned between EtOAc and water and the organic layer washed with water, brine, dried over Na₂SO₄ and evaporated to to dryness. The residue (1.15 g, brown oil) was purified by column chromatography on silica gel (irregular SiOH, 80 g, mobile phase: heptane/EtOAc, gradient from 100:0 to 80:20). The pure fractions were collected and evaporated to dryness to give 273 mg of intermediate 389 (37% yield, 79% purity based on LC/MS).

Example A8

Preparation of Intermediate 8

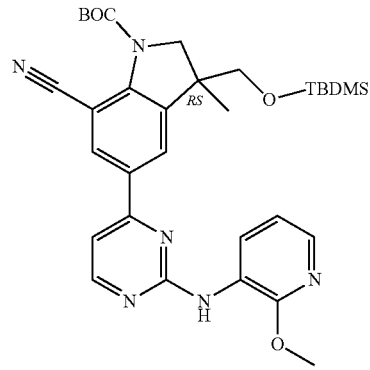

To a solution of intermediate 6 (0.15 g, 0.29 mmol), 3-amino-2-methoxypyridine (43.30 mg, 0.35 mmol), BINAP (18.10 mg, 30.00 µmol) and Cs₂CO₃ (284.00 mg, 0.87 mmol) in 1,4-dioxane (3 mL), Pd(OAc)₂ (6.51 mg, 30.00 µmol) was added and the reaction mixture was heated for 30 min at 85° C. The reaction mixture was left stirring at 95° C. for a further 1 h. The reaction mixture was then diluted with EtOAc, washed successively with water and brine. The organic layer was dried over Na₂SO₄ and concentrated in vacuo to give 235 mg of intermediate 8 as a dark brown oil used as it is in the next step.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 15 | From intermediate 6 and 3-amino-5-chloro-2-methoxypyridine | 433 | Quant. procedure with T = 95° C. |

-continued

| Intermediate number | Structure | Mass (mg) | Yield (%) |
|---|---|---|---|
| Intermediate 17 | 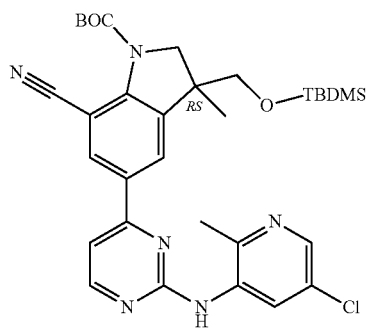<br>From intermediate 6 and 3-amino-5-chloro-2-methylpyridine | 1400 (60% purity based on LC/MS) brown solid | 100 procedure with T = 95° C. |
| Intermediate 22 | 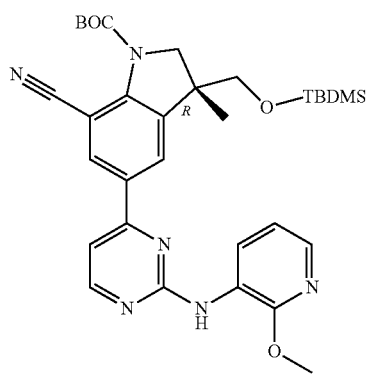<br>From intermediate 6R and 3-amino-2-methoxypyridine | 110 (49% purity based on LC/MS) light yellow oil<br><br>340 (97% purity based on LC/MS) white powder | 18<br><br><br><br><br>55 procedure with T = 95° C. |
| Intermediate 23 | 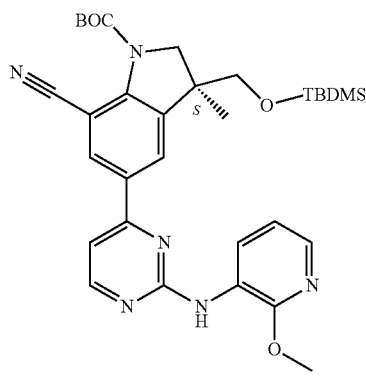<br>From intermediate 6S and 3-amino-2-methoxypyridine | 524 yellow oil | 80 procedure with T = 95° C. |

| Intermediate number | Structure | Mass (mg) | Yield (%) |
|---|---|---|---|
| Intermediate 56 | 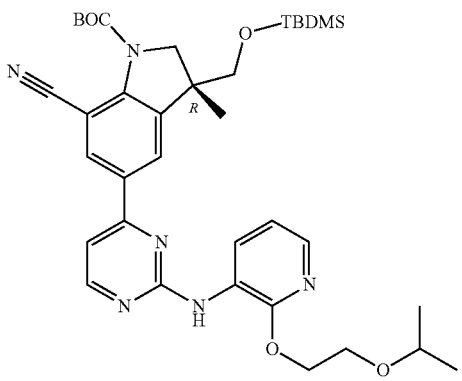<br>From intermediate 6R and intermediate 55 | 603 | 92 procedure with T = 120° C. |
| Intermediate 62 | 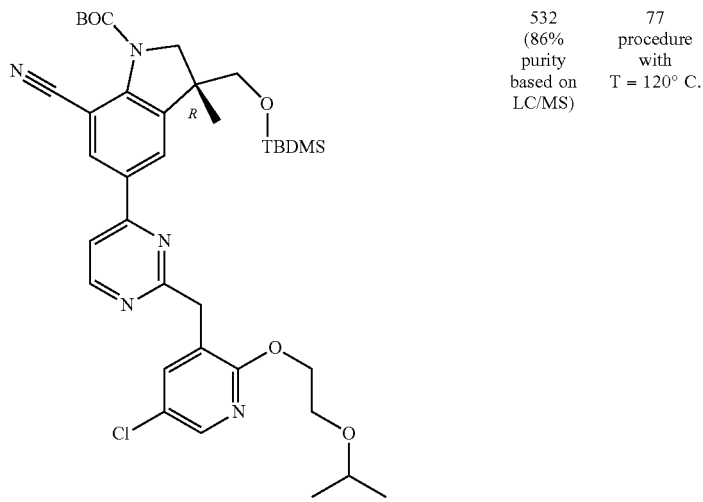<br>From intermediate 6R and intermediate 61 | 532 (86% purity based on LC/MS) | 77 procedure with T = 120° C. |
| Intermediate 66 | 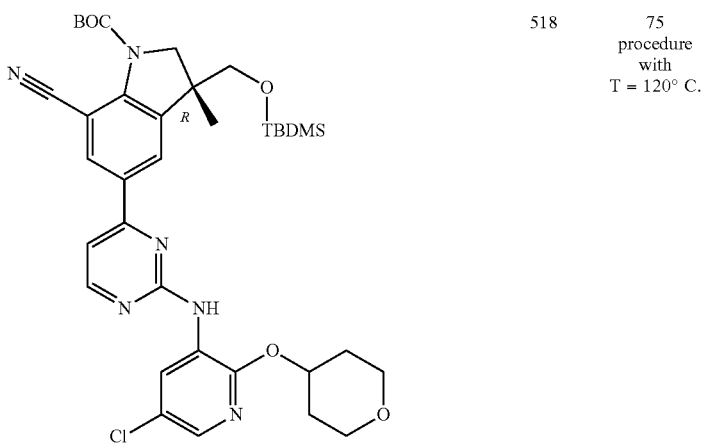<br>From intermediate 6R and intermediate 65 | 518 | 75 procedure with T = 120° C. |

-continued
| Intermediate number | Structure | Mass (mg) | Yield (%) |
|---|---|---|---|
| Intermediate 70 | 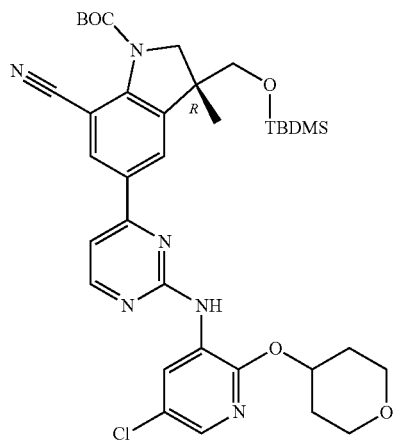<br>From intermediate 6R and intermediate 69 | 518 | 79 |
| Intermediate 72 | 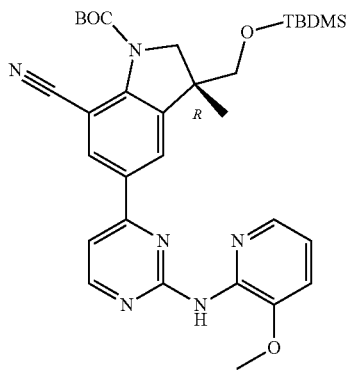<br>From intermediate 6R and 2-amino-3-methoxypyridine | 281 | 48 procedure with T = 120° C. |
| Intermediate 76 | 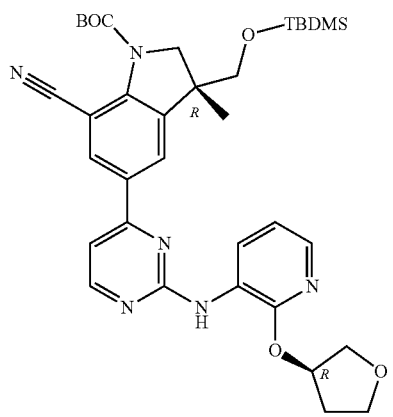<br>From intermediate 6R and intermediate 75 | 523 | 82 procedure with T = 120° C. |

| Intermediate number | Structure | Mass (mg) | Yield (%) |
|---|---|---|---|
| Intermediate 80 | 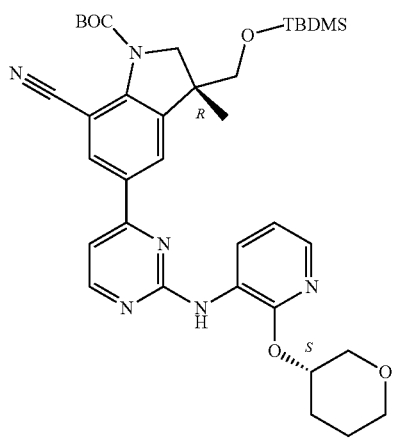<br>From intermediate 6R and intermediate 79 | 511 | 78 procedure with T = 120° C. |
| Intermediate 84 | 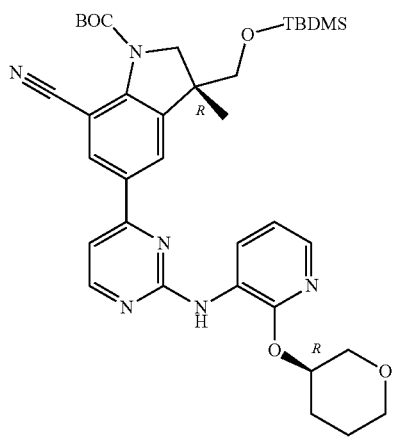<br>From intermediate 6R and intermediate 83 | 521 | 80 procedure with T = 120° C. |
| Intermediate 88 | 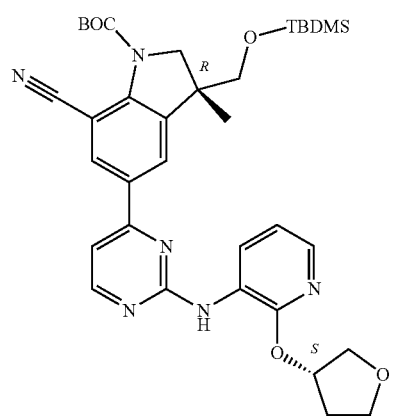<br>From intermediate 6R and intermediate 87 | 476 | 74 procedure with T = 120° C. |

| Intermediate number | Structure | Mass (mg) | Yield (%) |
|---|---|---|---|
| Intermediate 90 | 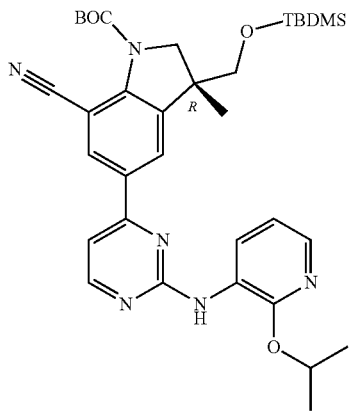<br>From intermediate 6R and 2-(1-methylethoxy)-3-aminopyridine | 495 | 81 procedure with T = 120° C. |
| Intermediate 94 | 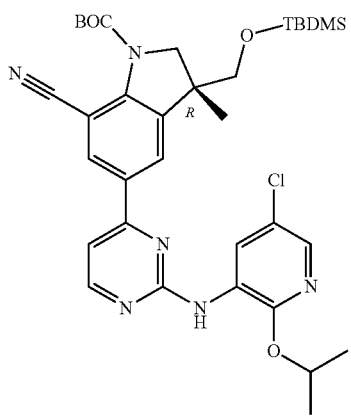<br>From intermediate 6R and intermediate 92 | 430 | 67 procedure with T = 120° C. |
| Intermediate 98 | 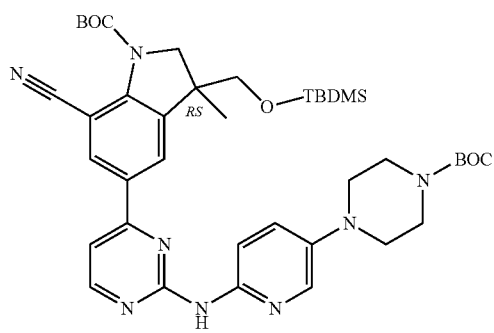<br>From intermediate 6 and tert-butyl-4-(6-aminopyridin-3-yl)piperazine-1-carboxylate | 498 | Quant. procedure with T = 100° C. |

-continued

| Intermediate number | Structure | Mass (mg) | Yield (%) |
|---|---|---|---|
| Intermediate 102 | 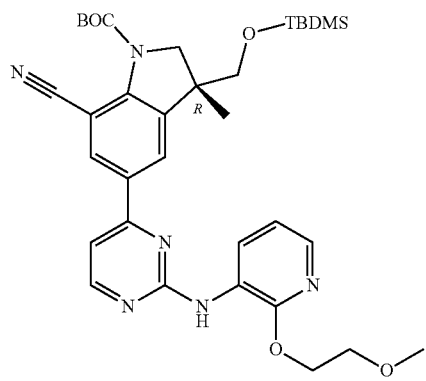<br>From intermediate 6R and intermediate 101 | 441<br>(97% purity based on (LC/MS) | 70<br>procedure with T = 120° C. |
| Intermediate 104 | 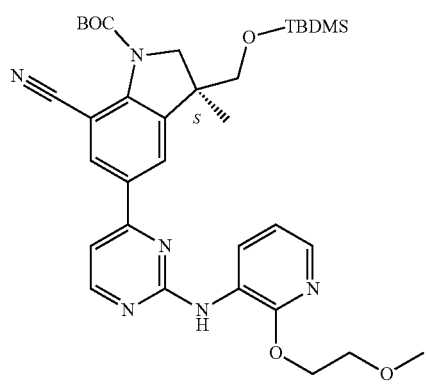<br>From intermediate 6S and intermediate 101 | 450<br>(97% purity based on LC/MS) | 72<br>procedure with T = 120° C. |
| Intermediate 116 | 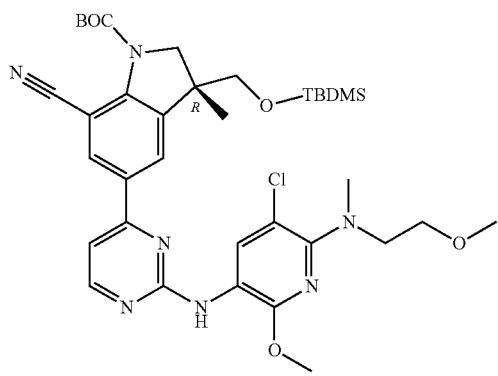<br>From intermediate 6R and intermediate 115 | 492<br>(73% purity based on LC/MS)<br>yellow oil | Quant.<br>procedure with T = 95° C. |

-continued

| Intermediate number | Structure | Mass (mg) | Yield (%) |
|---|---|---|---|
| Intermediate 120 | From intermediate 6R and intermediate 119 | 607 | 92 procedure with T = 120° C. |
| Intermediate 124 | From intermediate 6R and intermediate 123 | 398 (94% purity based on LC/MS) | 64 procedure with T = 120° C. |
| Intermediate 132 | From intermediate 6R and intermediate 131 | 571 | 87 procedure with T = 120° C. |

-continued
| Intermediate number | Structure | Mass (mg) | Yield (%) |
|---|---|---|---|
| Intermediate 136 | 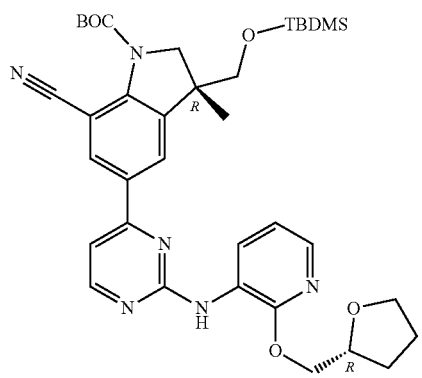  From intermediate 6R and intermediate 135 | 554 | 85 procedure with T = 120° C. |
| Intermediate 140 | 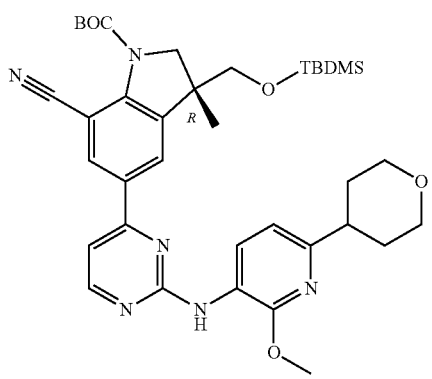  From intermediate 6R and intermediate 139 | 685 pale yellow foam | Quant. procedure with T = 100° C. |
| Intermediate 144 | 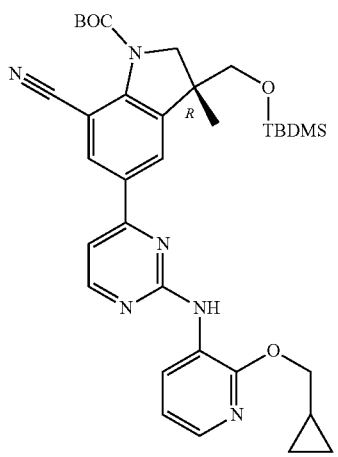  From intermediate 6R and intermediate 143 | 504 (77% purity based on LC/MS) | 81 procedure with T = 120° C. |

-continued

| Intermediate number | Structure | Mass (mg) | Yield (%) |
|---|---|---|---|
| Intermediate 148 | 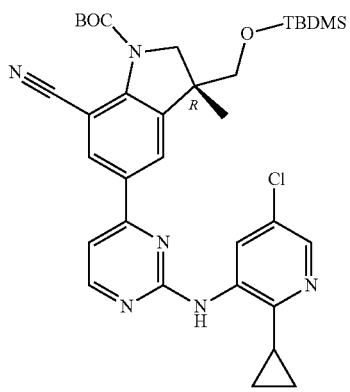 From intermediate 6R and intermediate 147 | 413 (91% purity based on LC/MS) | — procedure with T = 120° C. |
| Intermediate 156 | 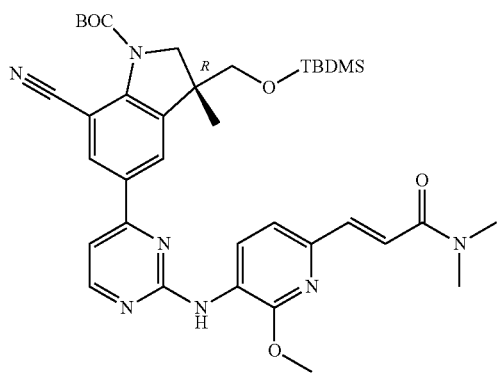 From intermediate 6R and intermediate 155 | 467 (95% purity based on LC/MS) orange foam | 89 procedure with T = 90° C. |
| Intermediate 160 | 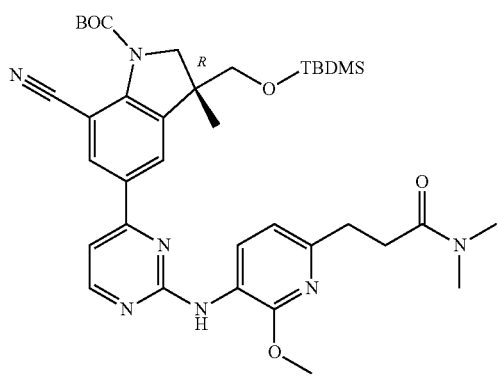 From intermediate 6R and intermediate 159 | 366 (99% purity based on LC/MS) orange foam | 75 procedure with T = 90° C. |

| Intermediate number | Structure | Mass (mg) | Yield (%) |
|---|---|---|---|
| Intermediant 163 | 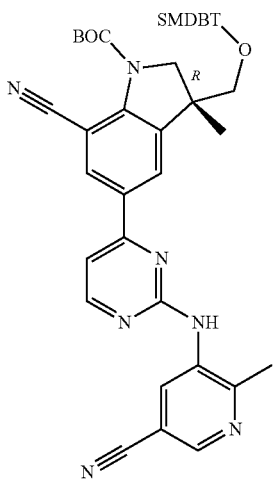<br>From intermediate 6R and 5-amino-6-methylnicotinonitrile | 1078 (82% purity based on LC/MS) | 79 procedure with T = 120° C. |
| Intermediate 176 | 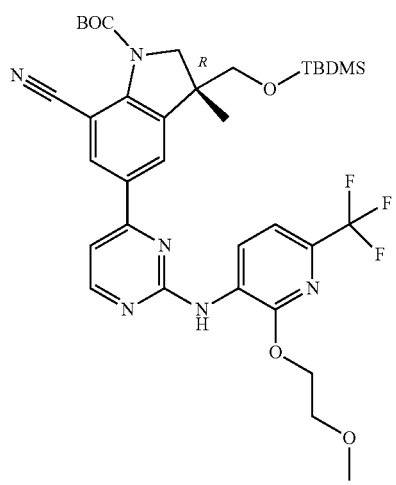<br>From intermediate 6R and intermediate 175 | 534 orange foam | 96 |
| Intermediate 180 | 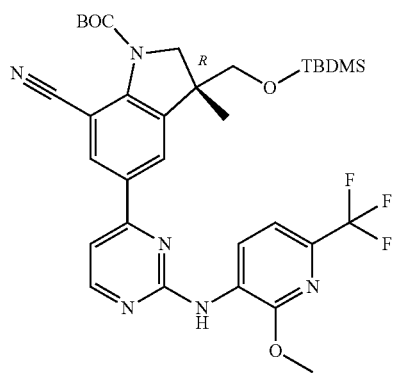<br>From intermediate 6R and intermediate 179 | 454 off-white foam | — |

-continued

| Intermediate number | Structure | Mass (mg) | Yield (%) |
|---|---|---|---|
| Intermediate 184 | From intermediate 6R and intermediate 183 | 545 beige residue | 76 procedure with T = 90° C. |
| Intermediate 189 | From intermediate 6R and intermediate 188 | 537 (93% purity based on LC/MS) | Quant. procedure with T = 90° C. |
| Intermediate 193 | From intermediate 6R and intermediate 192 | 280 (59% purity based on LC/MS) brown oil | — procedure with T = 90° C. |

-continued

| Intermediate number | Structure | Mass (mg) | Yield (%) |
|---|---|---|---|
| Intermediate 195 | 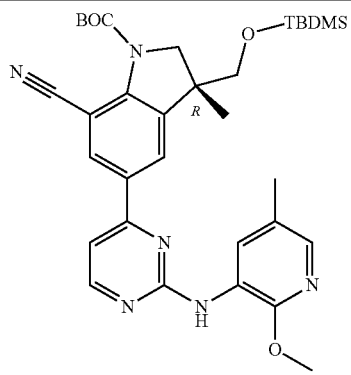<br>From intermediate 6R and 2-methoxy-5-methyl-3-aminopyridine | 587 (67% purity based on LC/MS) | 66 procedure with T = 120° C. |
| Intermediate 200 | 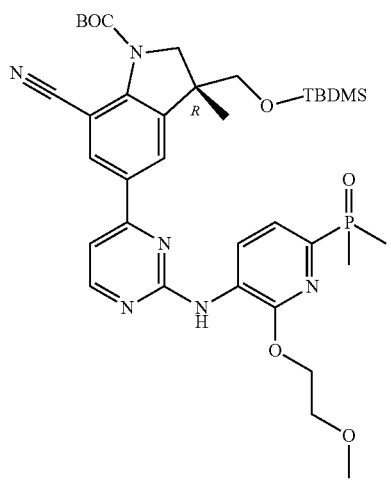<br>From intermediate 6R and intermediate 199 | 575 brown oil | 89 procedure with T = 90° C. |
| Intermediate 204 | 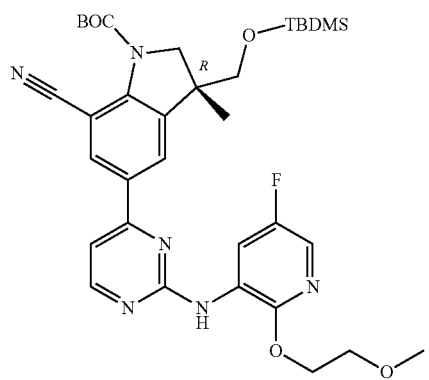<br>From intermediate 6R and intermediate 203 | 586 (93% purity based on LC/MS) | 91 procedure with T = 120° C. |

-continued

| Intermediate number | Structure | Mass (mg) | Yield (%) |
|---|---|---|---|
| Intermediate 208 | 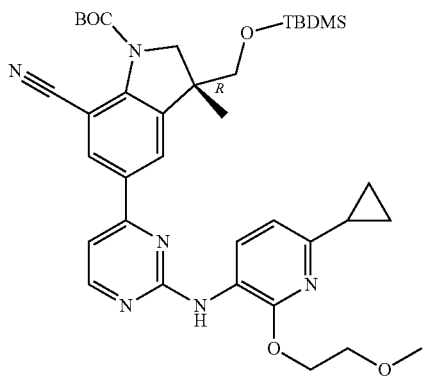<br>From intermediate 6R and intermediate 207 | 509<br>(90% purity based on LC/MS) | 76<br>procedure with T = 120° C. |
| Intermediate 211 | 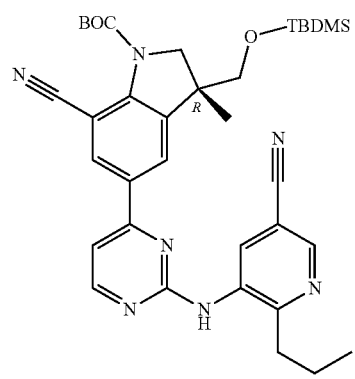<br>From intermediate 6R and intermediate 210 | 218<br>(89% purity based on LC/MS) | 29<br>procedure with T = 120° C. |
| Intermediate 216 | 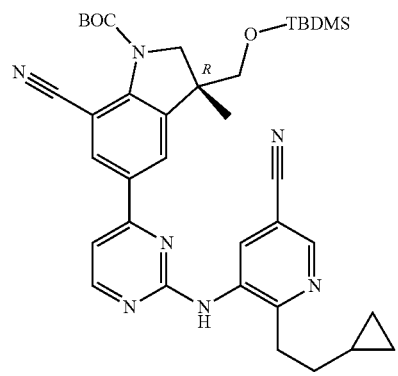<br>From intermediate 6R and intermediate 215 | 323<br>(84% purity based on LC/MS) | 37<br>procedure with T = 120° C. |

-continued
| Intermediate number | Structure | Mass (mg) | Yield (%) |
|---|---|---|---|
| Intermediate 220 | 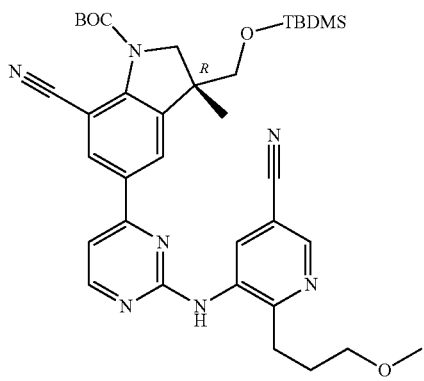<br>From intermediate 6R and intermediate 219 | 418 (92% purity based on LC/MS) | 68 procedure with T = 120° C. |
| Intermediate 227 | 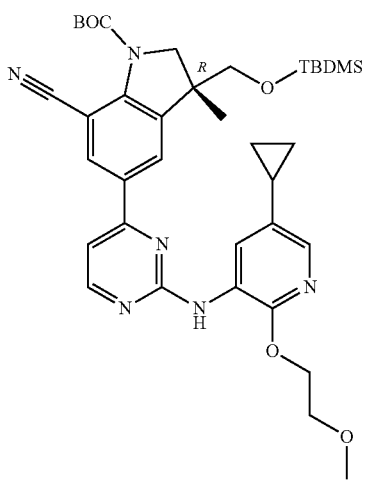<br>From intermediate 6R and intermediate 226 | 1000 pale yellow oil | 75 |
| Intermediate 231 | 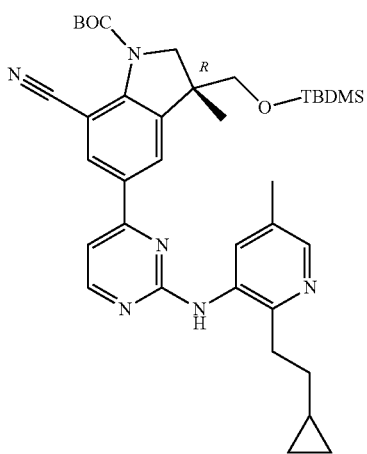<br>From intermediate 6R and intermediate 230 | 587 (98% purity based on LC/MS) white foam | 79 |

-continued

| Intermediate number | Structure | Mass (mg) | Yield (%) |
|---|---|---|---|
| Intermediate 235 | 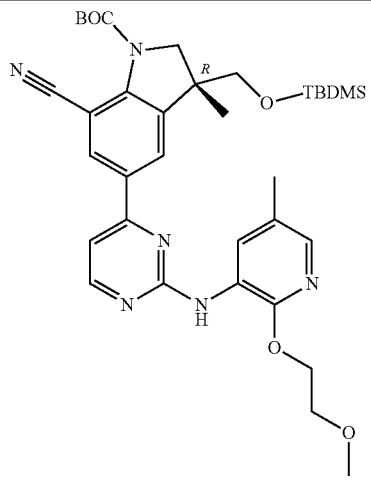 From intermediate 6R and intermediate 234 | 1090 (88% purity based on LC/MS) pale yellow foam | 87 |
| Intermediate 248 | 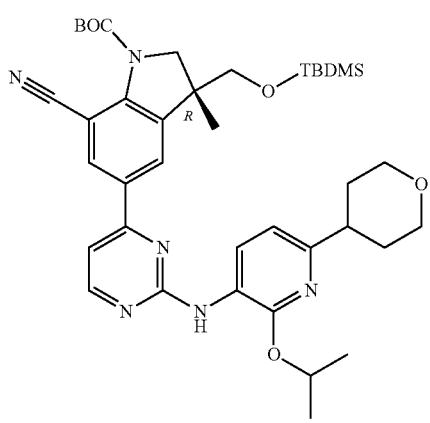 From intermediate 6R and intermediate 247 | 701 (99% purity based on LC/MS) yellow solid<br>652 (60% purity based on LC/MS) yellow oil | 59<br><br>33 |
| Intermediate 251 | 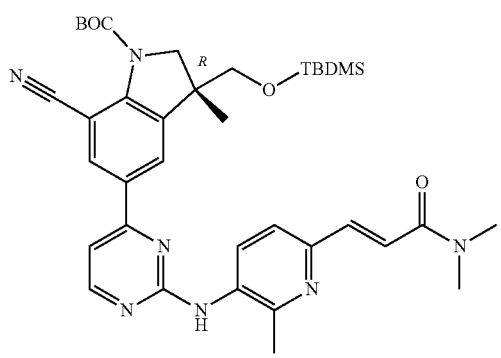 From intermediate 6R and intermediate 250 | 967 (96% purity based on LC/MS) light yellow solid | 73 |

-continued

| Intermediate number | Structure | Mass (mg) | Yield (%) |
|---|---|---|---|
| Intermediate 273 | From intermediate 6R and intermediate 272 | 457 (94% purity based on NMR) yellow foam | 81 |
| Intermediate 291 | From intermediate 6R and intermediate 290 | 446 white foam | 70 procedure with T = 90° C. |
| Intermediate 297 | From intermediate 6R and intermediate 296 | 484 (98% purity based on LCMS) pale yellow solid | 91 |

-continued
| Intermediate number | Structure | Mass (mg) | Yield (%) |
|---|---|---|---|
| Intermediate 300 | 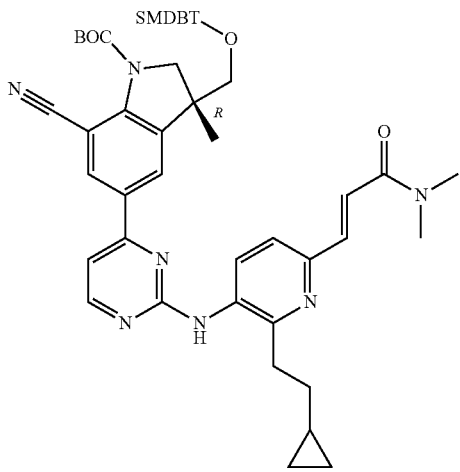 From intermediate 6R and intermediate 299 | 405 (66% purity based on LCMS) orange solid | 60 |
| Intermediate 303 | 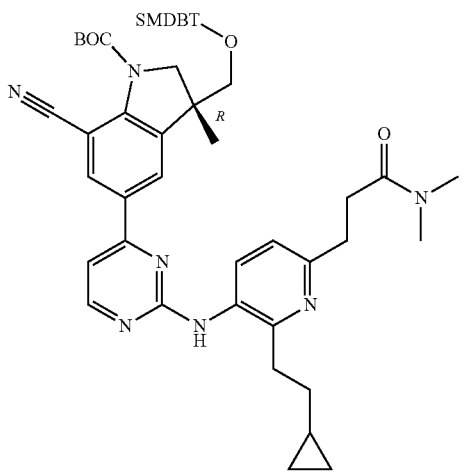 From intermediate 6R and intermediate 302 | 226 (92% purity based on LCMS) yellow solid | 73 |
| Intermediate 307 | 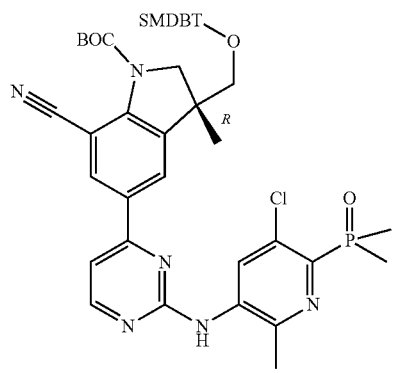 From intermediate 6R and intermediate 306 | 311 (74% purity based on LCMS) yellow solid | 41 |

| Intermediate number | Structure | Mass (mg) | Yield (%) |
|---|---|---|---|
| Intermediate 318 | 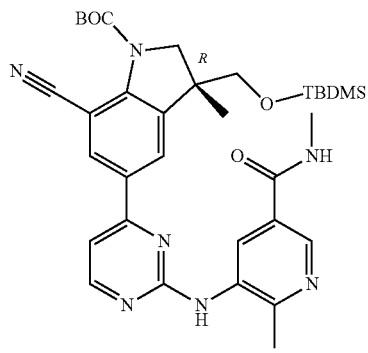
From intermediate 6R and intermediate 317 | 372 yellow foam | 99 |
| Intermediate 329 | 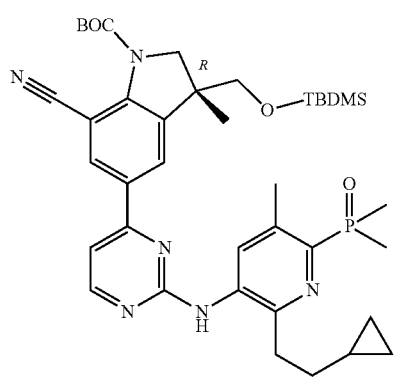
From intermediate 6R and intermediate 328 | 810 (84% purity based on LC/MS) brown gum | Quant. |
| Intermediate 362 | 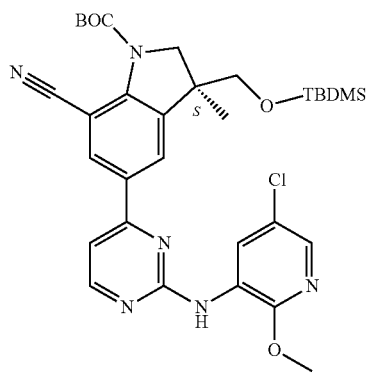
From intermediate 6S and 5-chloro-3-amino-2-methoxypyridin | 2371 (96% purity based on LC/MS) yellow powder | 64 |

| Intermediate number | Structure | Mass (mg) | Yield (%) |
|---|---|---|---|
| Intermediate 401 | 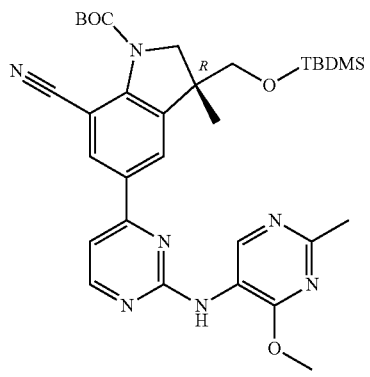 From intermediate 6R and 4-methoxy-2-methylpyrimidin-5-amine | 360 foam | Quant. procedure with T = 100° C. |
| Intermediate 403 | 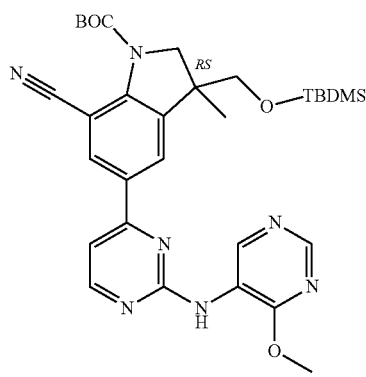 From intermediate 6 and 4-methoxy-pyrimidin-5-amine | 540 yellow solid | 89 procedure with T = 95° C. |
| Intermediate 405 | 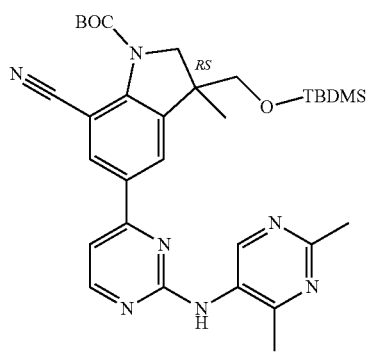 From intermediate 6 and 2,4-dimethyl-5-pyrimidinamine | 720 | — procedure with T = 95° C. |

-continued

| Intermediate number | Structure | Mass (mg) | Yield (%) |
|---|---|---|---|
| Intermediate 407 | 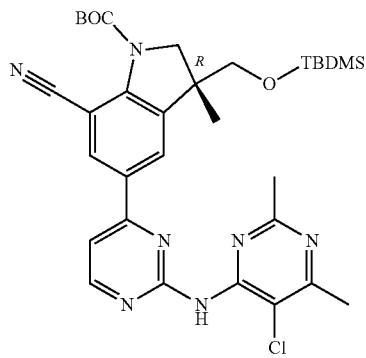<br>From intermediate 6R and 4-amino-5-chloro-2,6-dimethylpyrimidine | 272 foam | 73 procedure with T = 100° C. |
| Intermediate 409 | 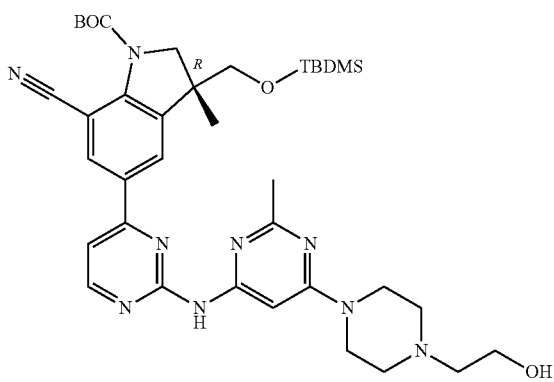<br>From intermediate 6R and 2-[4-(6-Amino-2-methylpyrimidin-4-yl)piperazin-1-yl]ethanol | 610 grey solid | 88 procedure with T = 100° C. |
| Intermediate 411 | 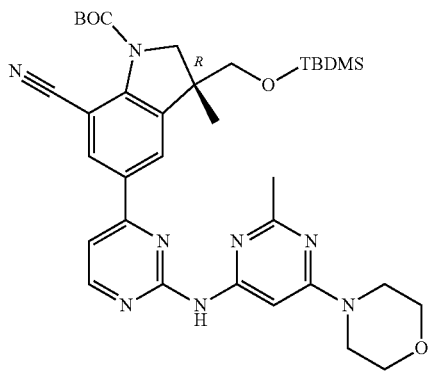<br>From intermediate 6R and 2-methyl-6-(4-morpholinyl)-4-Pyrimidinamine | 688 yellow residue | Quant. procedure with T = 95° C. |

| Intermediate number | Structure | Mass (mg) | Yield (%) |
|---|---|---|---|
| Intermediate 413 | 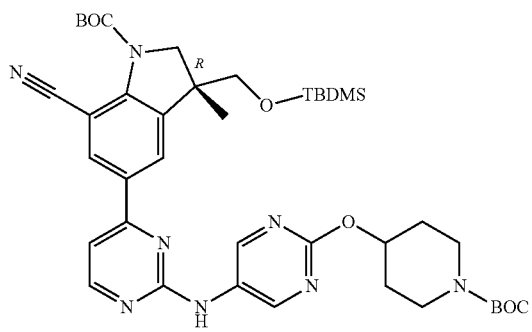<br>From intermediate 6R and 4-[(5-amino-2-pyrimidinyl)oxy]-1,1-dimethylethylester-1-piperidine carboxylic acid | 308 (54% purity based on LC/MS) yellow oil | 86 procedure with T = 95° C. |
| Intermediate 417 | 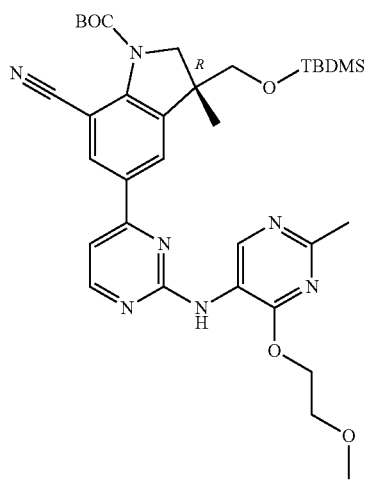<br>From intermediate 6R and intermediate 416 | 748 yellow foam | 83 procedure with T = 100° C. |
| Intermediate 421 | 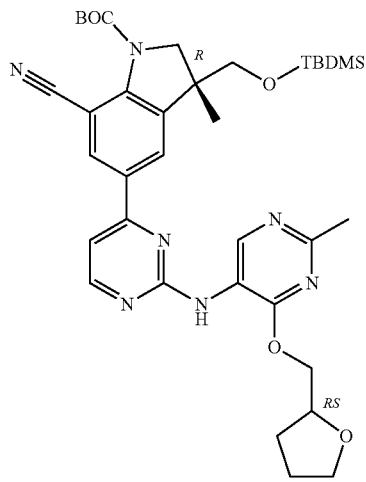<br>From intermediate 6R and intermediate 420 | 936 yellow foam | 70 procedure with T = 100° C. |

| Intermediate number | Structure | Mass (mg) | Yield (%) |
|---|---|---|---|
| Intermediate 425 | 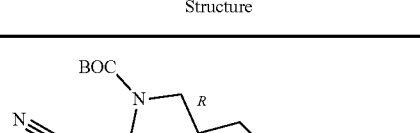 From intermediate 6R and intermediate 424 | 400 (81% purity based on LC/MS) brown solid | Quant. |
| Intermediate 429 | From intermediate 6R and intermediate 428 | 780 (77% purity based on LC/MS) yellow solid | Quant. |
| Intermediate 433 | From intermediate 6R and intermediate 432 | 700 (71% purity based on LC/MS) brown solid | Quant. |

-continued

| Intermediate number | Structure | Mass (mg) | Yield (%) |
|---|---|---|---|
| Intermediate 437 | From intermediate 6R and intermediate 436 | 235 pale yellow oil | 44 |
| Intermediate 439 | From intermediate 6R and intermediate 427 | 800 (5% purity based on LC/MS) black foam | Quant. |
| Intermediate 443 | From intermediate 6R and intermediate 442 | 414 yellow foam | 77 |

-continued
| Intermediate number | Structure | Mass (mg) | Yield (%) |
|---|---|---|---|
| Intermediate 545 | 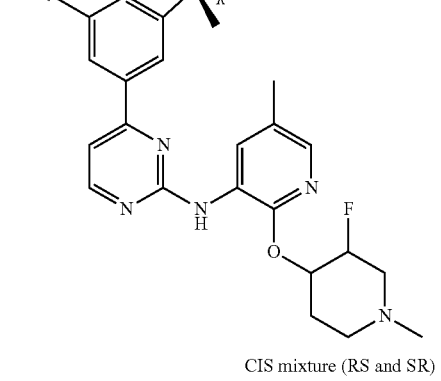<br>CIS mixture (RS and SR)<br>From intermediate 6R and intermediate 544 | 144 | 70 procedure with T = 100° C. |
| Intermediate 548 | From intermediate 6R and intermediate 547 | 163 | 42 procedure with T = 120° C., 30 min μw |
| Intermediate 567 | TRANS mixture (RR and SS)<br>From intermediate 6R and intermediate 566 | 600 | 88 procedure with T = 120° C., 3 h |

| Intermediate number | Structure | Mass (mg) | Yield (%) |
|---|---|---|---|
| Intermediate 561 | From intermediate 348 and 2,5-dimethylpyridine-4-amine | 400 yellow solid | 86 procedure with T = 120° C. |
| Intermediate 551 | From intermediate 6R and intermediate 550 | 625 (89% purity based on LC/MS) | 68 |
| Intermediate 529 | From intermediate 6R and intermediate 528 | 300 (90% purity based on LC/MS) | 54 procedure with T = 80° C. o/n |
| Intermediate 572 | From intermediate 6R and intermediate 571 | 360 yellow solid | 20 procedure with T = 95° C. 2 h |

Example A9

Preparation of intermediate 12

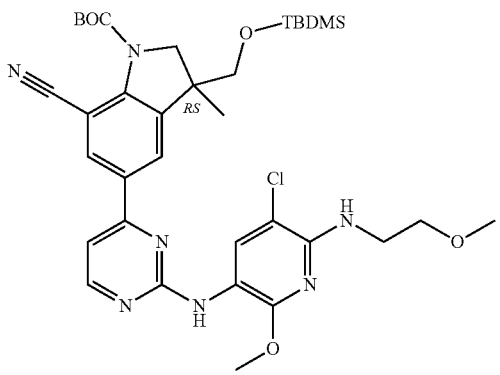

A degassed suspension of intermediate 6 (445.00 mg, 0.86 mmol), intermediate 11 (220.00 mg, 0.95 mmol), Pd(OAc)$_2$ (10.00 mg, 0.044 mmol), BINAP (27.00 mg, 0.043 mmol) and Cs$_2$CO$_3$ (844.00 mg, 2.59 mmol) in 1,4-dioxane (10 mL) was heated at 85° C. for 1 h 30 min. The reaction mixture was transferred in a MW sealed tube. Pd(OAc)$_2$ (5.00 mg, 0.020 mmol) and BINAP (14.00 mg, 0.022 mmol) were added and the reaction mixture was heated at 120° C. for 20 min using one single mode microwave (Biotage Initiator EXP 60) with a power output ranging from 0 to 400 W [fixed hold time]. The reaction mixture was cooled to rt, diluted with EtOAc and poured onto a 10% aqueous solution of K$_2$CO$_3$. The organic layer was decanted, washed with brine, dried over MgSO$_4$, filtered and evaporated to dryness. The residue was purified by column chromatography on silica gel (irregular SiOH, 40 g, mobile phase: heptane/MeOH/EtOAc, gradient from 0% MeOH, 40% EtOAc, 60% heptane to 2% MeOH, 58 EtOAc, 40% heptane). The pure fractions were collected and evaporated to dryness to give 390 mg of intermediate 12 (63% yield, 81% purity based on LC/MS). The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 26 | *(structure shown; From intermediate 6 and ethyl-5-aminopicolinate)* | 535 | 85 procedure with T = 120° C. |
| Intermediate 28 | *(structure shown; From intermediate 6R and intermediate 11)* | 426 (81% purity based on LC/MS) | 69 procedure With T = 120° C. |

-continued
| Intermediate number | Structure | Mass (mg) | Yield (%) |
|---|---|---|---|
| Intermediate 30 | 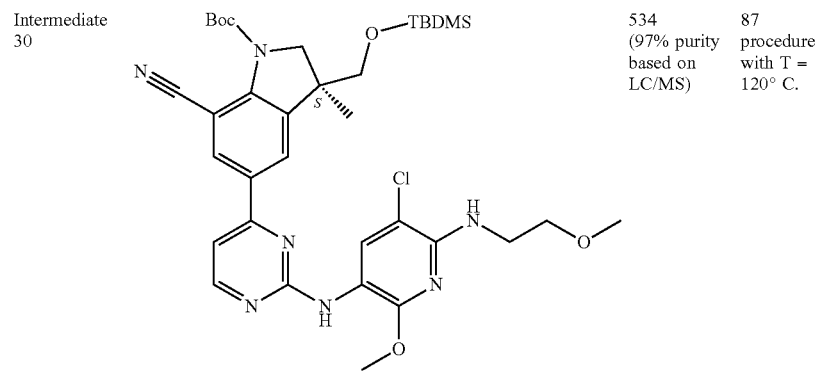 From intermediate 6S and intermediate 11 | 534 (97% purity based on LC/MS) | 87 procedure with T = 120° C. |
| Intermediate 33 | 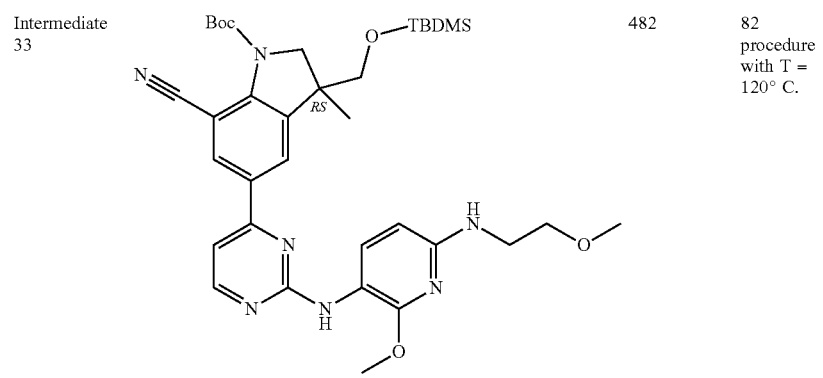 From intermediate 6 and intermediate 32 | 482 | 82 procedure with T = 120° C. |
| Intermediate 39 | 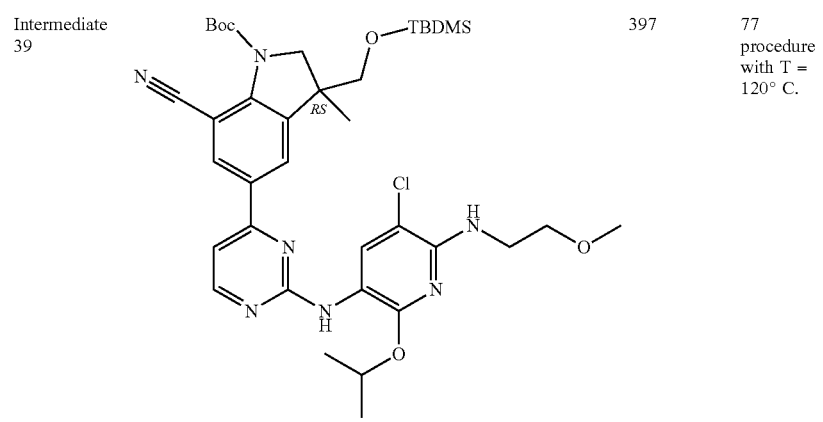 From intermediate 6 and intermediate 38 | 397 | 77 procedure with T = 120° C. |

-continued
| Intermediate number | Structure | Mass (mg) | Yield (%) |
|---|---|---|---|
| Intermediate 41 | 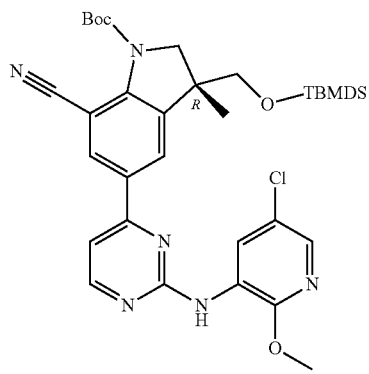<br>From intermediate 6 and 3-amino-5-chloro-2-methoxypyridine | 730 (85% purity based on LC/MS) brown foam | Quant. procedure with T = 95° C. |
| Intermediate 47 | 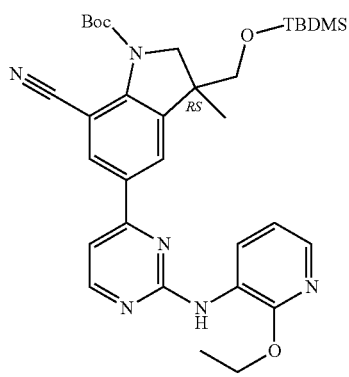<br>From intermediate 6 and 3-amino-2-ethoxypyridine | 271 | 50 procedure with T = 120° C. |
| Intermediate 50 | 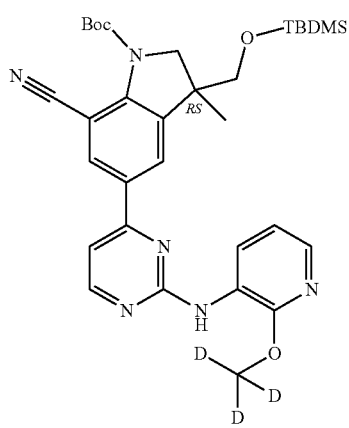<br>From intermediate 6 and intermediate 49 | 421 | 79 procedure with T = 120° C. |

-continued

| Intermediate number | Structure | Mass (mg) | Yield (%) |
|---|---|---|---|
| Intermediate 52 | From intermediate 6 and 2-(1-methylethoxy)-3-pyridinamine | 220 | 40 procedure with T = 120° C. |
| Intermediate 58 | From intermediate 6R and 4-amino-3-methoxypyridine | 310 | 66 procedure with T = 120° C. |
| Intermediate 96 | From intermediate 6R and 2-trifluoromethyl-3-aminopyridine | 382 | 68 procedure with T = 120° C. |

-continued
| Intermediate number | Structure | Mass (mg) | Yield (%) |
|---|---|---|---|
| Intermediate 107 | 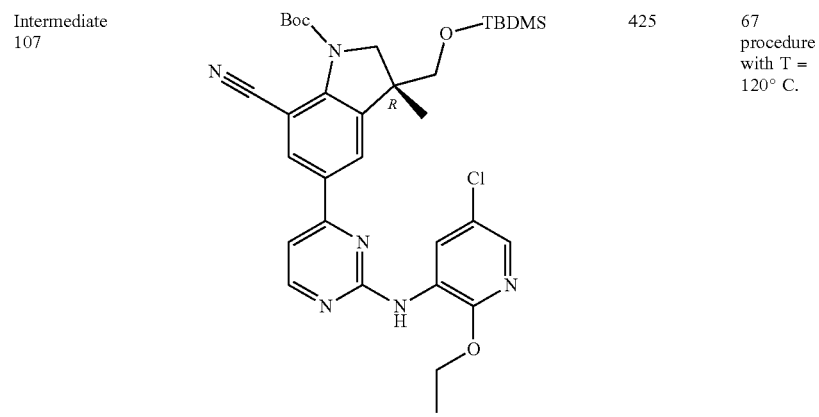 From intermediate 6R and intermediate 106 | 425 | 67 procedure with T = 120° C. |
| Intermediate 109 | 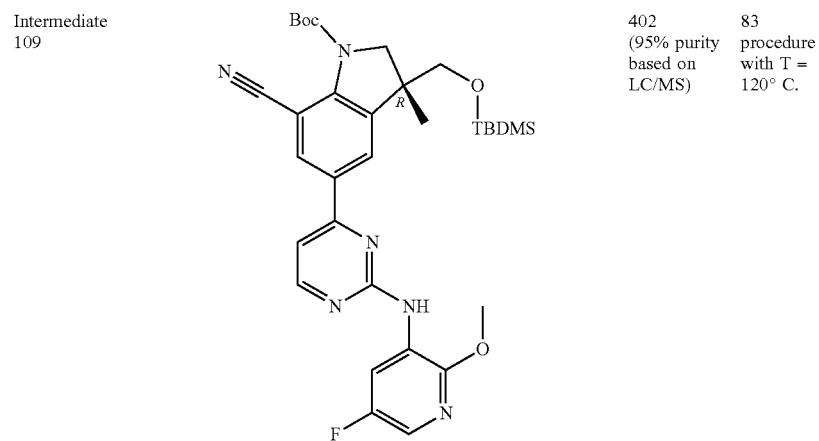 From intermediate 6R and 5-fluoro-2-methoxy-pyridin-3-amide | 402 (95% purity based on LC/MS) | 83 procedure with T = 120° C. |
| Intermediate 111 | 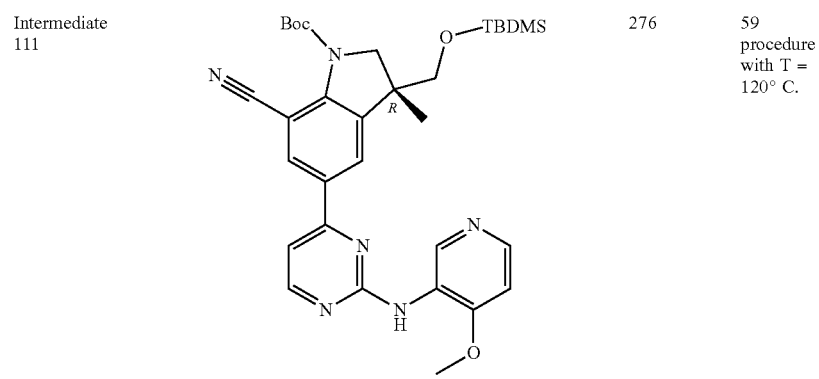 From intermediate 6R and 3-amino-4-methoxypyridine | 276 | 59 procedure with T = 120° C. |

| Intermediate number | Structure | Mass (mg) | Yield (%) |
|---|---|---|---|
| Intermediate 152 | 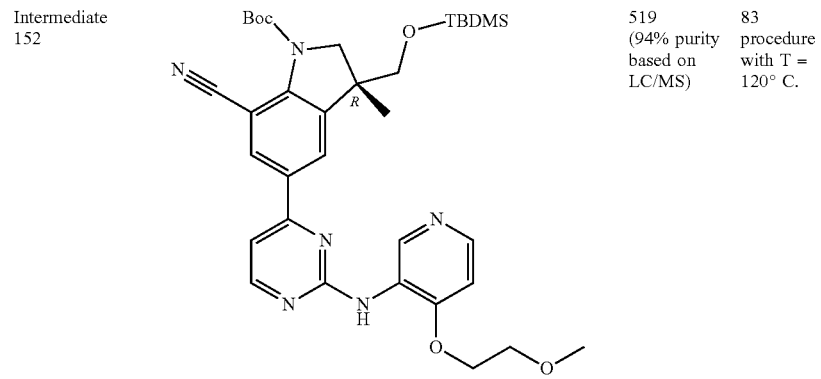 From intermediate 6R and intermediate 151 | 519 (94% purity based on LC/MS) | 83 procedure with T = 120° C. |
| Intermediate 168 | 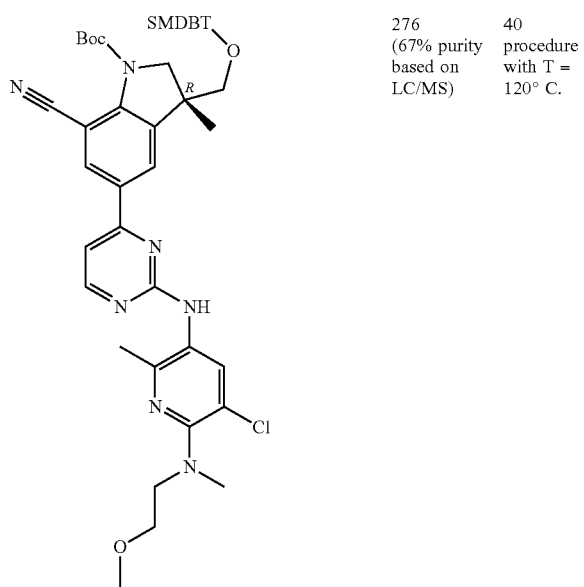 From intermediate 6R and intermediate 167 | 276 (67% purity based on LC/MS) | 40 procedure with T = 120° C. |

-continued
| Intermediate number | Structure | Mass (mg) | Yield (%) |
|---|---|---|---|
| Intermediate 172 | 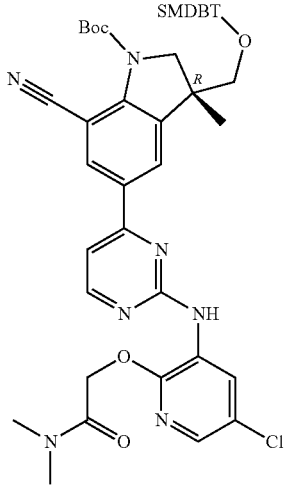<br>From intermediate 6R and intermediate 171 | 747 (87% purity based on LC/MS) | Quant. procedure with T = 120° C. |
| Intermediate 517 | 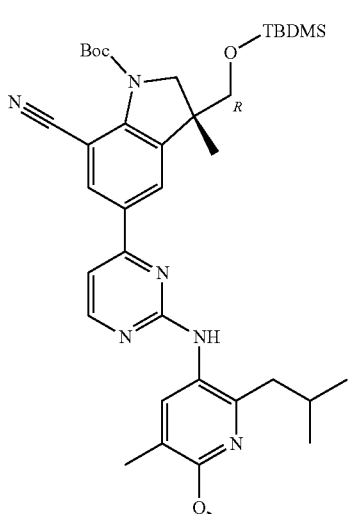<br>From intermediate 6R and intermediate 516 | 770 | 84 procedure with T = 120° C. 30 min |

| Intermediate number | Structure | Mass (mg) | Yield (%) |
|---|---|---|---|
| Intermediate 525 | 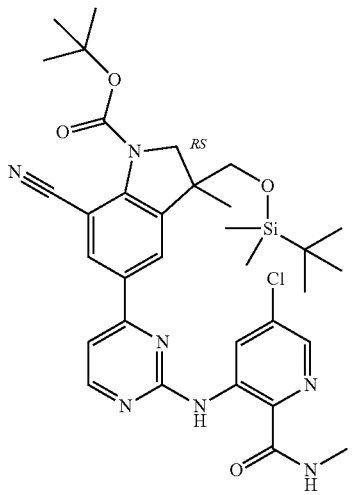 From intermediate 6 and intermediate 524 | 620 | Quant. procedure with T = 120° C. 30 min |
| Intermediate 519 | 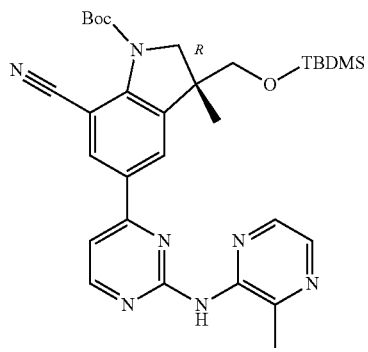 From intermediate 6R and aniline 2-amino-3-methylpyrazine | 456 (90% purity based on LC/MS) | Quant. procedure with T = 100° C. 2 h |
| Intermediate 505 | 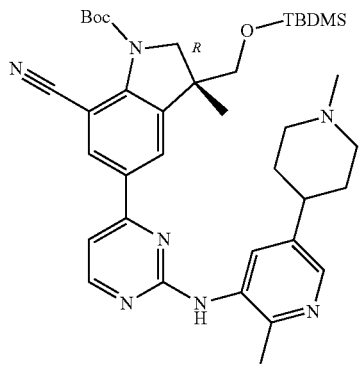 From intermediate 6R and intermediate 504 | 380 (83% purity based on LC/MS) | 51 procedure with T = 80° C. o/n |

| Intermediate number | Structure | Mass (mg) | Yield (%) |
|---|---|---|---|
| Intermediate 508 | 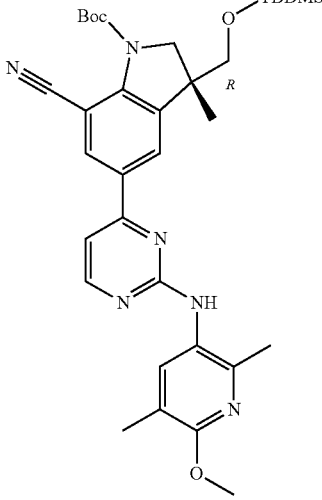 From intermediate 6R and intermediate 507 | 427 | 50 procedure with T = 120° C. 30 min μw |
| Intermediate 587 | 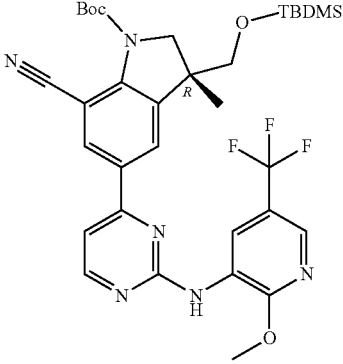 From intermediate 6R and 2-methoxy-5-(trifluoromethyl)-3-pyridinamine | 425 | 73 Procedure with T = 120° C. 30 min μw |

Example A10

Preparation of Intermediate 14

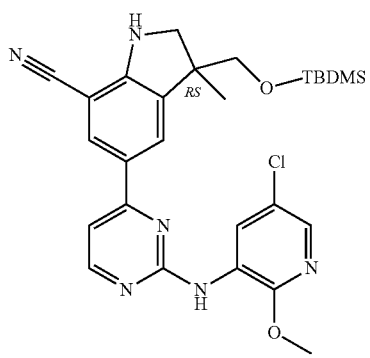

In a sealed tube, a mixture of intermediate 7 (400.00 mg, 0.96 mmol), 5-chloro-2-methoxypyridin-3-amine (168.00 mg, 1.06 mmol) and $Cs_2CO_3$ (942.00 mg, 2.89 mmol) in dry 1,4-dioxane (14 mL) was purged with $N_2$. Then, $Pd(OAc)_2$ (22.00 mg, 96.40 μmol) and BINAP (60.00 mg, 96.40 μmol) were added. The mixture was purged with $N_2$ and stirred at 95° C. for 2 h. The reaction mixture was combined with another batch (from 20 mg of int. 7) and the mixture was diluted with EtOAc and $H_2O$. The layers were separated. The organic layer was dried ($MgSO_4$), filtered and the solvent was removed under reduced pressure. The residue was purified by column chromatography on silica gel (irregular SiOH 15-40 μm, 24 g, liquid injection (DCM), mobile phase: DCM/MeOH, gradient from 100:0 to 80:20). The pure fractions were combined and concentrated under vacuum to give 420 mg of intermediate 14 (77% yield, yellow solid).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 46 | 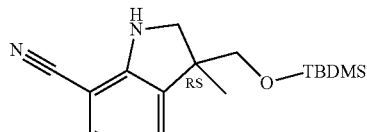<br>From intermediate 7 and intermediate 44 | 281 | — |
| Intermediate 162 | From intermediate 7R and 5-amino-6 methylnicotinonitrile | 2070 (99% purity based on LC/MS) | 56 procedure with T = 120° C. |
| Intermediate 223 | From intermediate 7R and intermediate 222 | 352 (99% purity based on LC/MS) | 49 procedure with T = 120° C. |

| Intermediate number | Structure | Mass (mg) | Yield (%) |
|---|---|---|---|
| Intermediate 255 | 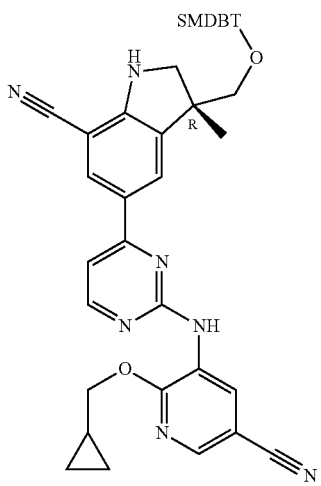<br>From intermediate 7R and intermediate 254 | 389 (91% purity based on LC/MS) | 65 procedure with T = 120° C. |
| Intermediate 258 | 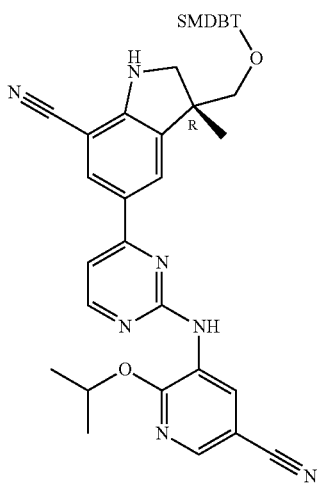<br>From intermediate 7R and intermediate 257 | 93 | 38 procedure with T = 120° C. |

-continued
| Intermediate number | Structure | Mass (mg) | Yield (%) |
|---|---|---|---|
| Intermediate 261 | 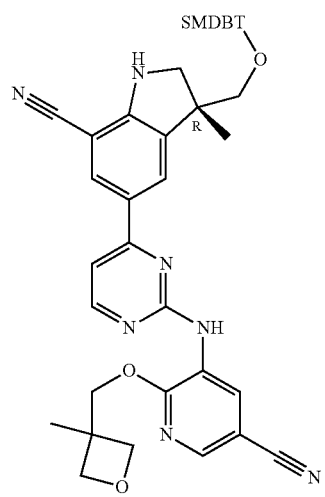<br>From intermediate 7R and intermediate 260 | 186 (58% purity based on LC/MS) | 70 procedure with T = 120° C. |
| Intermediate 264 | 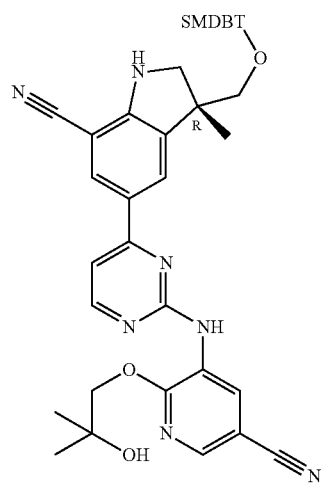<br>From intermediate 7R and intermediate 263 | 231 | 83 procedure with T = 120° C. |

| Intermediate number | Structure | Mass (mg) | Yield (%) |
|---|---|---|---|
| Intermediate 267 | 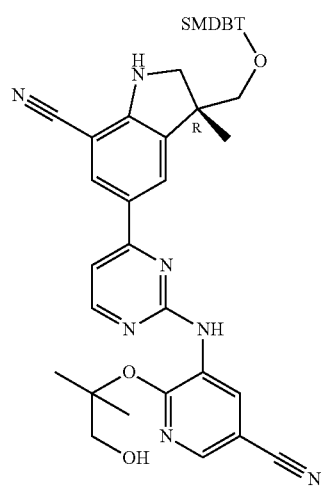<br>From intermediate 7R and intermediate 266 | 90 | 46 procedure with T = 120° C. |
| Intermediate 279 | 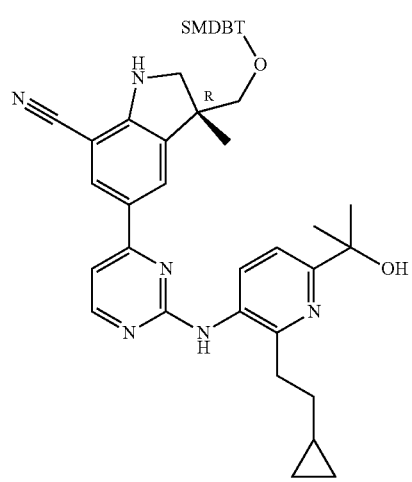<br>From intermediate 7R and intermediate 266 | 458 (80% purity based on LC/MS) off-white solid | 78 procedure with T = 85° C. |

| Intermediate number | Structure | Mass (mg) | Yield (%) |
|---|---|---|---|
| Intermediate 285 | 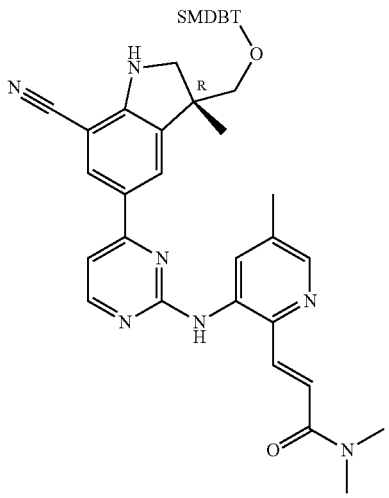<br>From intermediate 7R and intermediate 271 | 36 yellow oil | 10 procedure with T = 85° C. |
| Intermediate 288 | 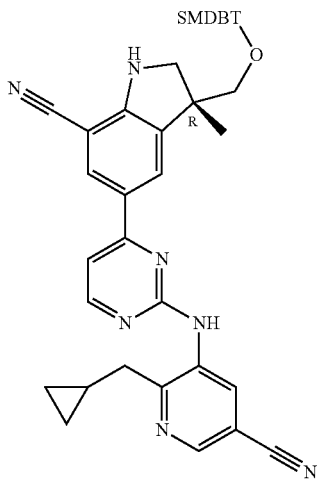<br>From intermediate 7R and intermediate 287 | 146 | 43 procedure with T = 120° C. |

-continued
| Intermediate number | Structure | Mass (mg) | Yield (%) |
|---|---|---|---|
| Intermediate 314 | 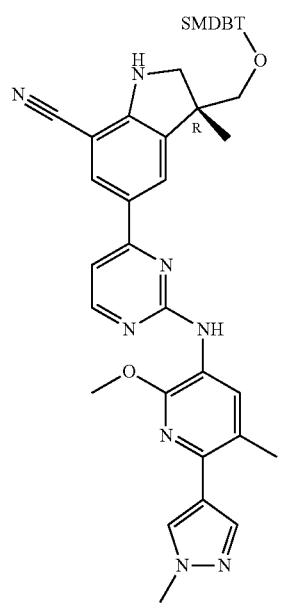<br>From intermediate 7R and intermediate 313 | 449 (91% purity based on LC/MS) | 70 procedure with T = 120° C. |
| Intermediate 398 | 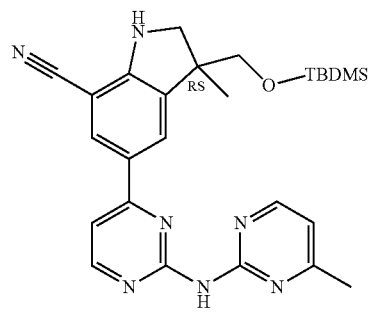<br>From intermediate 7 and 2-amino-4-methylpyrimidine | 236 orange oil | 57 procedure with T = 95° C. |
| Intermediate 399 | 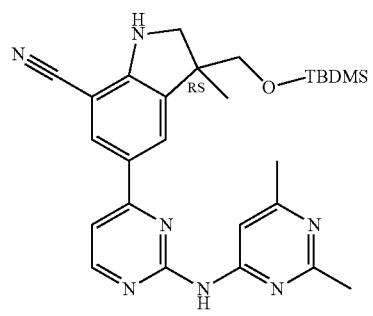<br>From intermediate 7 and 4-amino-2,6-dimethylpyrimidine | 220 brown residue | 45 procedure with T = 95° C. |

| Intermediate number | Structure | Mass (mg) | Yield (%) |
|---|---|---|---|
| Intermediate 400 | 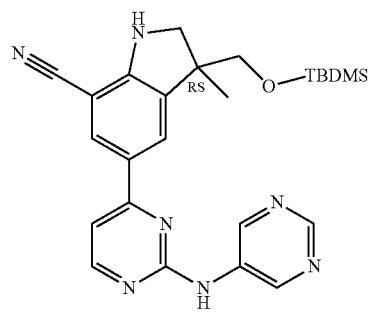<br>From intermediate 7 and 5-aminopyrimidine | 268 brown oil | 67 with T = 95° C. |
| Intermediate 470 | 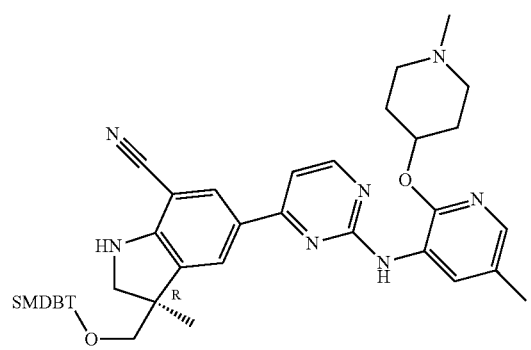<br>From intermediate 7R and intermediate 469 | 135 | 40 procedure with T = 120° C. 5 h |
| Intermediate 449 | 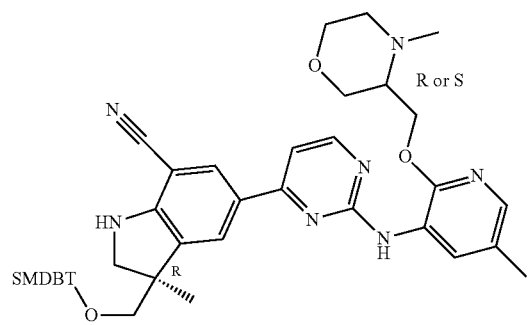<br>From intermediate 7R and intermediate 448 | 91 yellow oil | 33 procedure with T = 120° C. 3 h |
| Intermediate 451 | 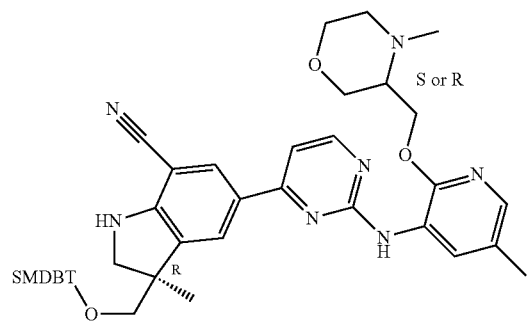<br>From intermediate 7R and intermediate 450 | 163 yellow solid | 56 procedure with T = 120° C. 3 h |

| Intermediate number | Structure | Mass (mg) | Yield (%) |
|---|---|---|---|
| Intermediate 477 | 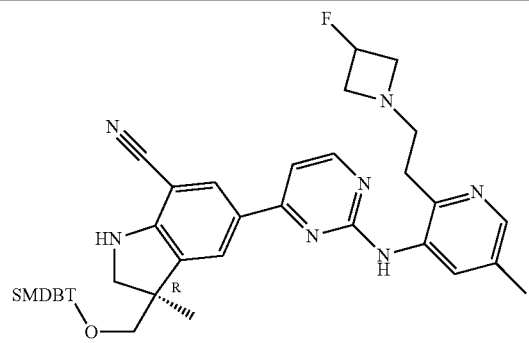<br>From intermediate 7R and intermediate 476 | 307 | 65 procedure with T = 120° C. 4 h |
| Intermediate 465 | 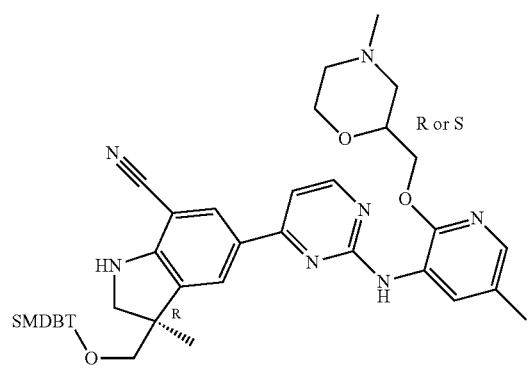<br>From intermediate 7R and intermediate 464 | 394 | 72 procedure with T = 120° C. 3 h |
| Intermediate 467 | 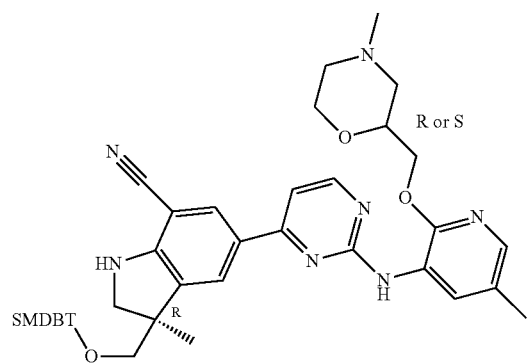<br>From intermediate 7R and intermediate 466 | 210 | 41 procedure with T = 120° C. 3 h |
| Intermediate 456 | 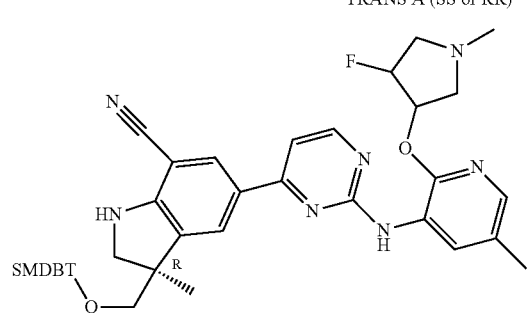<br>From intermediate 7R and intermediate 455 | 180 | 75 procedure with T = 120° C. 3 h |

| Intermediate number | Structure | Mass (mg) | Yield (%) |
|---|---|---|---|
| Intermediate 458 | 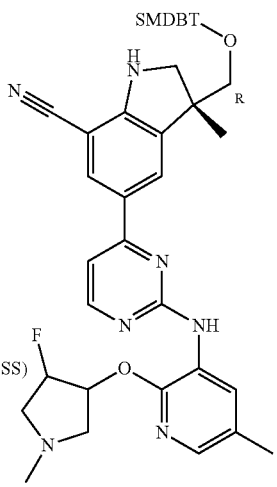<br>From intermediate 7R and intermediate 457 | 90 yellow oil | 46 procedure with T = 120° C. 3 h |
| Intermediate 479 | 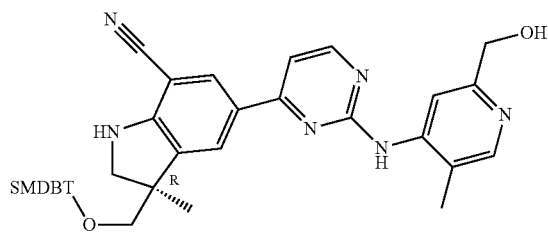<br>From intermediate 7R and intermediate 478 | 125 | 41 procedure with T = 120° C. 3 h |
| Intermediate 502 | 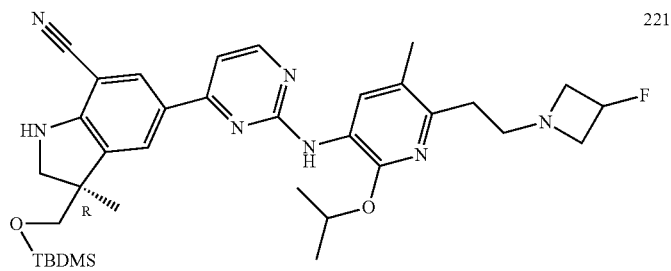<br>From intermediate 7R and intermediate 501 | 221 | 35 procedure with T = 120° C. 3 h |
| Intermediate 497 | 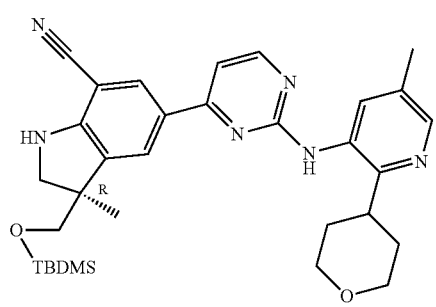<br>From intermediate 7R and intermediate 496 | 470 | 72 procedure with T = 120° C. 15 min, μw |

-continued

| Intermediate number | Structure | Mass (mg) | Yield (%) |
|---|---|---|---|
| Intermediate 473 | 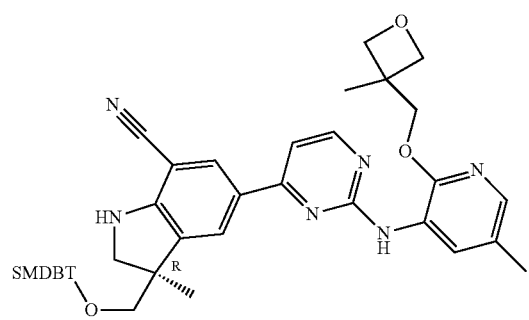<br>From intermediate 7R and intermediate 472 | 100 | 45<br>procedure with T = 120° C.<br>3 h |
| Intermediate 558 | 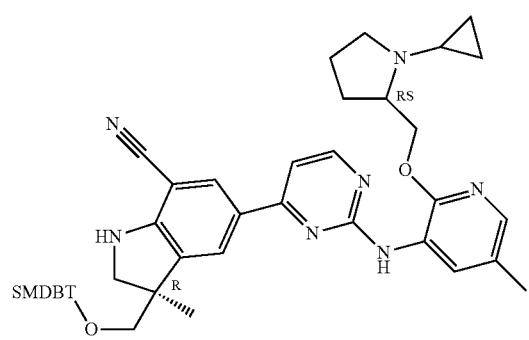<br>From intermediate 7R and intermediate 557 | 47 | 65<br>procedure with T = 100° C.<br>6 h |
| Intermediate 492 | 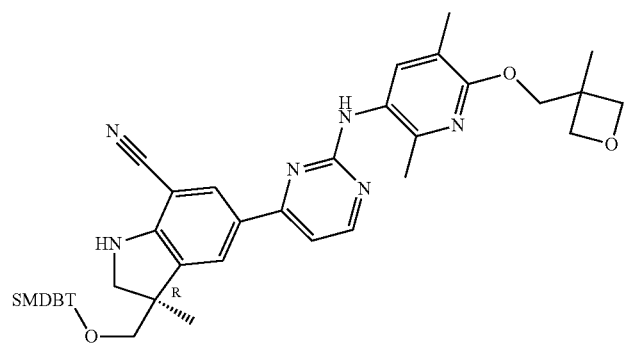<br>From intermediate 7R and intermediate 491 | 428<br>(81% purity based on LC/MS) | 78<br>procedure with T = 120° C.<br>30 min, μw |
| Intermediate 494 | 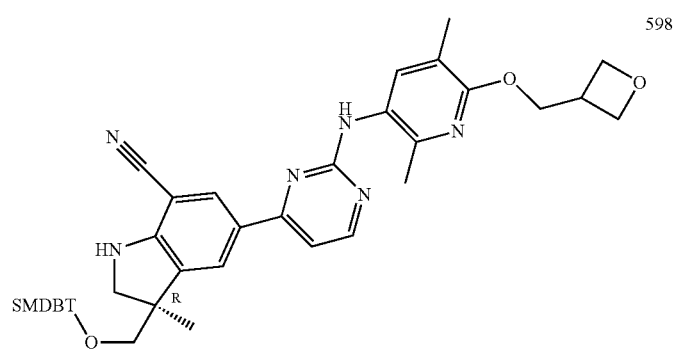<br>From intermediate 7R and intermediate 493 | 598 | 75<br>procedure with T = 120° C.<br>30mn, μw |

| Intermediate number | Structure | Mass (mg) | Yield (%) |
|---|---|---|---|
| Intermediate 512 | 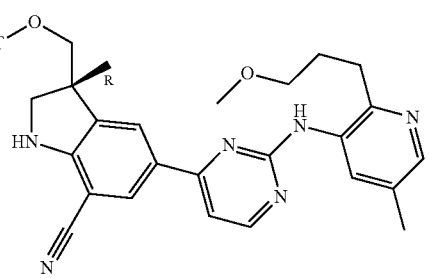 From intermediate 7R and intermediate 511 | 662 | 52 procedure with T = 120° C. 1 h |
| Intermediate 560 | 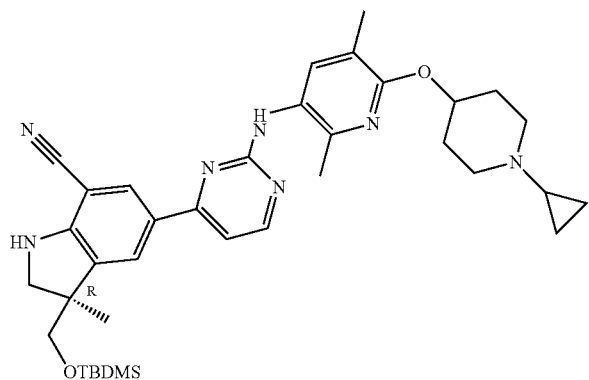 From intermediate 7R and intermediate 559 | 100 | 32 procedure with T = 120° C. μw 30 min |
| Intermediate 539 | 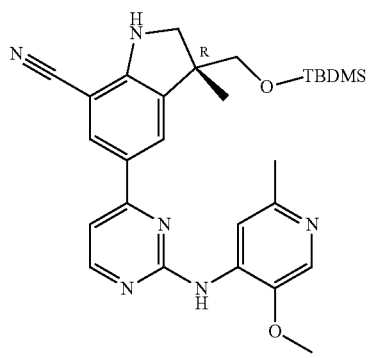 From intermediate 7R and intermediate 538 | 10 | 7 procedure with T = 120° C. 3 h |

-continued
| Intermediate number | Structure | Mass (mg) | Yield (%) |
|---|---|---|---|
| Intermediate 536 | 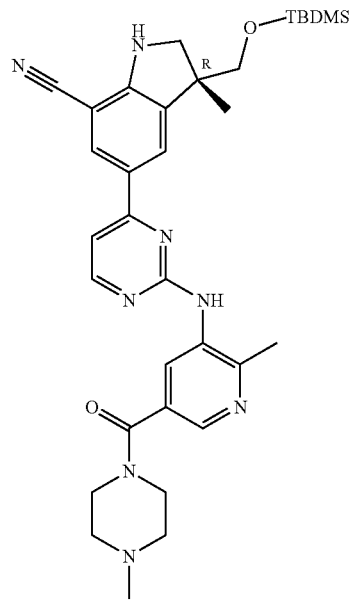<br>From intermediate 7R and intermediate 535 | 248 (80% purity based on LC/MS) | 39 procedure with T = 120° C. 15 min μw |
| Intermediate 540 | 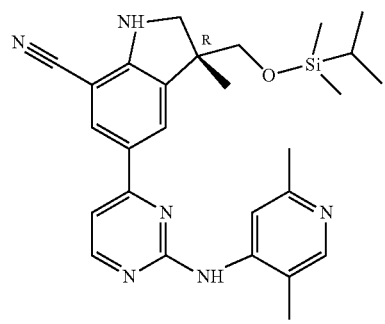<br>From intermediate 7R and 2,5-dimethylpyridin-4-amine | 188 | 52 procedure with T = 120° C. 3 h |
| Intermediate 534 | 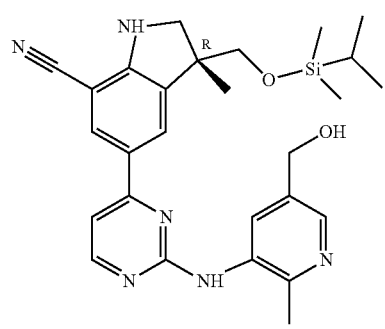<br>From intermediate 7R and intermediate 533 | 1280 | 66 procedure with T = 120° C. 3 h |

-continued

| Intermediate number | Structure | Mass (mg) | Yield (%) |
|---|---|---|---|
| Intermediate 532 | 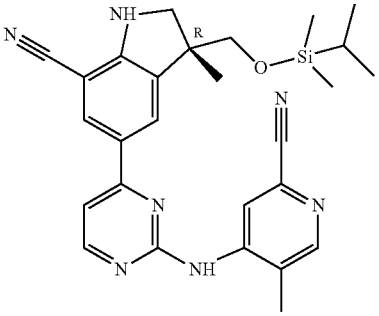<br>From intermediate 7R and intermediate 531 | 160 | 92<br>procedure with T = 120° C.<br>3 h |
| Intermediate 586 | 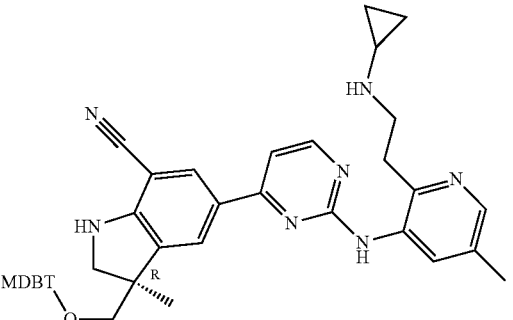<br>From intermediate 7R and intermediate 585 | 77 | 31<br>procedure with T = 120° C.<br>4 h |

Example A11

Preparation of Intermediate 20

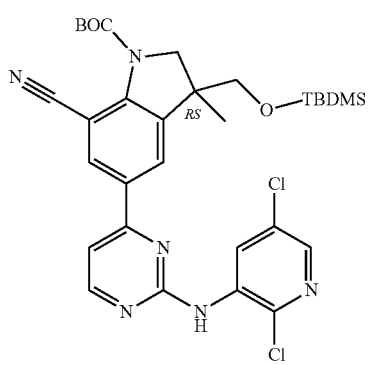

A mixture of intermediate 6 (300.00 mg, 0.58 mmol), 3-amino-2,5-dichloropyridine (237.00 mg, 1.46 mmol) and $Cs_2CO_3$ (569.00 mg, 1.75 mmol) in THF (6 mL) was purged with $N_2$. Then (BrettPhos) palladium (II) phenethylamine chloride (47.00 mg, 58.20 μmol) and BrettPhos (31.00 mg, 58.20 μmol) were added. The mixture was purged with $N_2$ and stirred at 95° C. for 18 h. An extraction was performed with AcOEt and water. The organic layer was washed with brine, dried and evaporated to give 450 mg of intermediate 20 (quant. yield, black solid) used as such for the next step.

The intermediates in the Table below were prepared by using an analogous method starting from the respective starting materials.

| Intermediate number | Structure | Mass (mg) | Yield (%) |
|---|---|---|---|
| Intermediate 395 | ![structure] From intermediate 6 and 6-chloro-3-methoxypyridazin-4-amine | 800 (62% purity based on LC/MS) brown solid | Quant. procedure with THF as solvent |

Example A12

Preparation of Intermediate 13

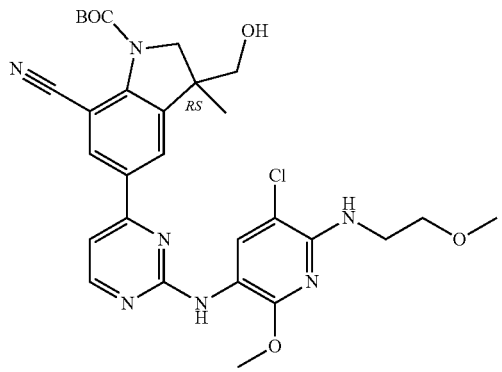 [SMILES: COCCNc1nc(OC)c(Nc2nccc(-c3cc(C#N)c4c(c3)C(C)(CO)CN4C(=O)OC(C)(C)C)n2)cc1Cl]

A solution of TBAF (1.0 M in THF) (576.00 μL, 0.58 mmol) was added to a solution of intermediate 12 (390.00 mg, 0.55 mmol) in Me-THF (5 mL) and the mixture was stirred at rt for 1 h. The reaction mixture was poured onto a 10% aqueous solution of $K_2CO_3$ and extracted with EtOAc. The organic layer was decanted, washed with brine, dried over $MgSO_4$, filtered and evaporated to dryness. The residue was taken up with $Et_2O$ and the precipitate was filtered and dried to give 274 mg of intermediate 13 (84% yield, 98% purity based on LC/MS).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 16 | ![structure] From intermediate 15 | 355 black oil | Quant. procedure with THF as solvent |

-continued

| Intermediate number | Structure | Mass (mg) | Yield (%) |
|---|---|---|---|
| Intermediate 19 | 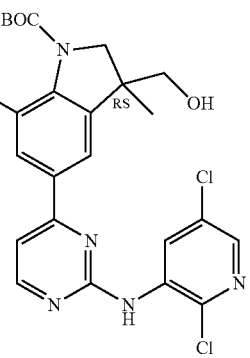<br>From intermediate 17 | 360<br>yellow solid | — procedure with THF as solvent |
| Intermediate 21 | 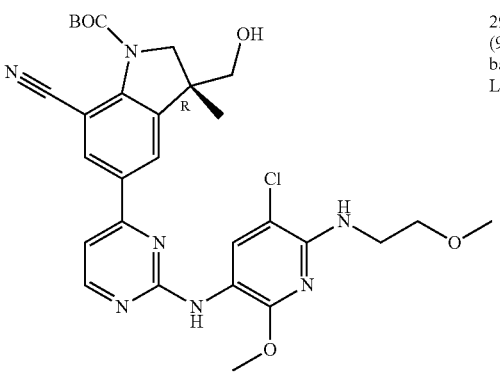<br>From intermediate 20 | 420<br>(73% purity based on LC/MS)<br>black oil | Quant. procedure with THF as solvent |
| Intermediate 29 | 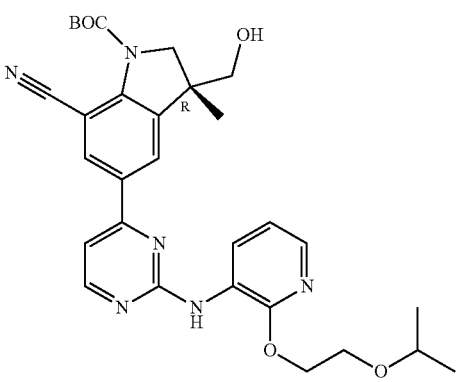<br>From intermediate 28 | 290<br>(98% purity based on LC/MS) | 81 |
| Intermediate 57 | <br>From intermediate 56 | 449 | 89 procedure with 3 equiv. of TBAF |

| Intermediate number | Structure | Mass (mg) | Yield (%) |
|---|---|---|---|
| Intermediate 71 | 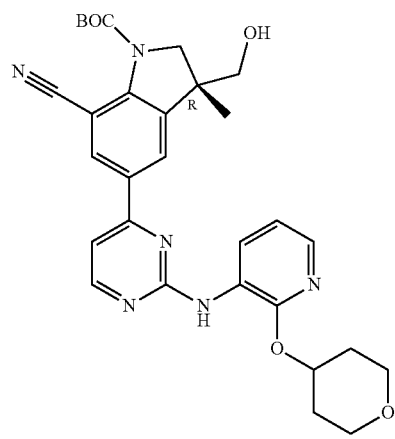<br>From intermediate 70 | 295 | 69 procedure with 3 equiv. of TBAF |
| Intermediate 73 | 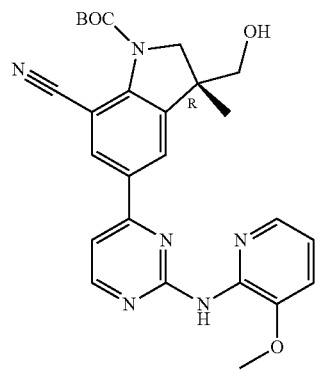<br>From intermediate 72 | 200 | 88 procedure with 3 equiv. of TBAF |
| Intermediate 164 | 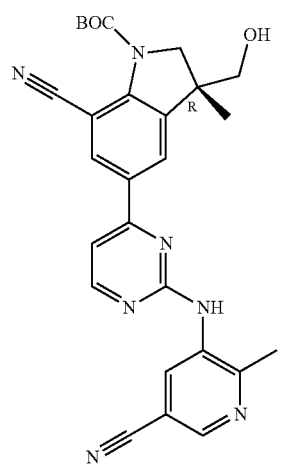<br>From intermediate 163 | 622 | 71 |

-continued
| Intermediate number | Structure | Mass (mg) | Yield (%) |
|---|---|---|---|
| Intermediate 190 | 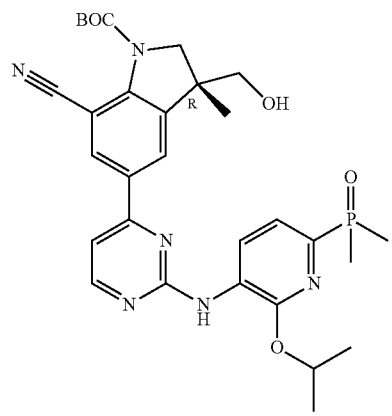<br>From intermediate 189 | 420<br>yellow oil | 93 |
| Intermediate 194 | 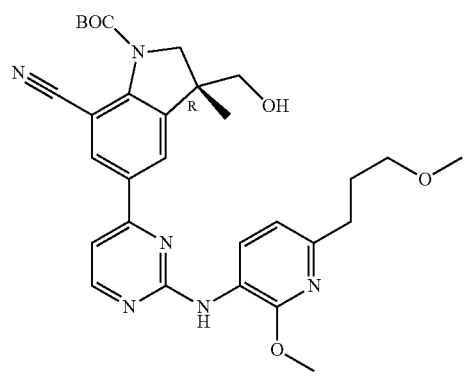<br>From intermediate 193 | 190<br>(85% purity based on LC/MS)<br>yellow oil | — |
| Intermediate 201 | 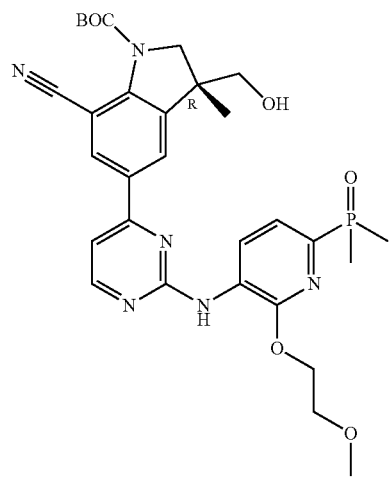<br>From intermediate 200 | 386<br>(96% purity based on LC/MS)<br>brown oil | 80 |

| Intermediate number | Structure | Mass (mg) | Yield (%) |
|---|---|---|---|
| Intermediate 209 | 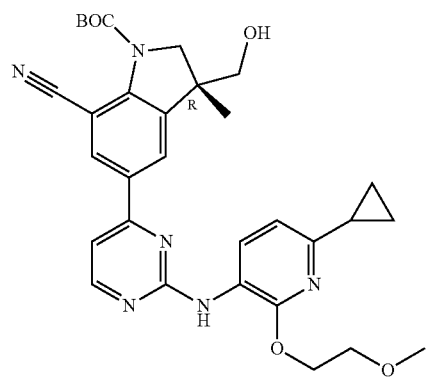<br>From intermediate 208 | 300 | 71 procedure with 2 equiv. of TBAF |
| Intermediate 212 | 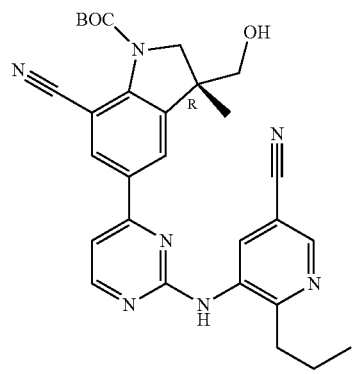<br>From intermediate 211 | 165 | 95 procedure with 2 equiv. of TBAF |
| Intermediate 217 | 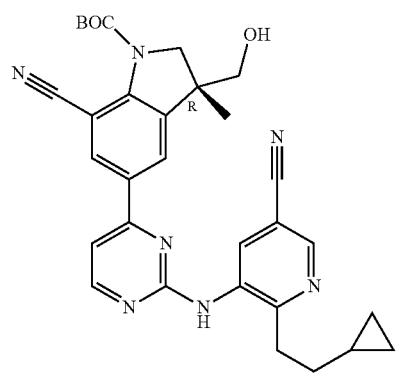<br>From intermediate 216 | 236 (95% purity based on LC/MS) | 88 procedure with 2 equiv. of TBAF |

-continued
| Intermediate number | Structure | Mass (mg) | Yield (%) |
|---|---|---|---|
| Intermediate 221 | 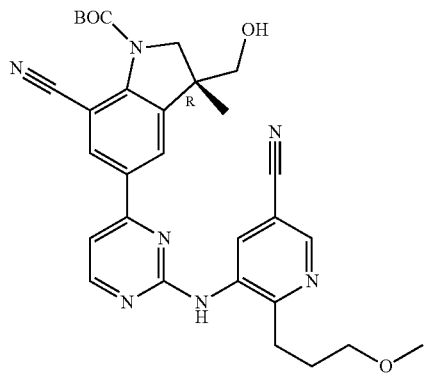<br>From intermediate 220 | 269 | 78 procedure with 2 equiv. of TBAF |
| Intermediate 228 | 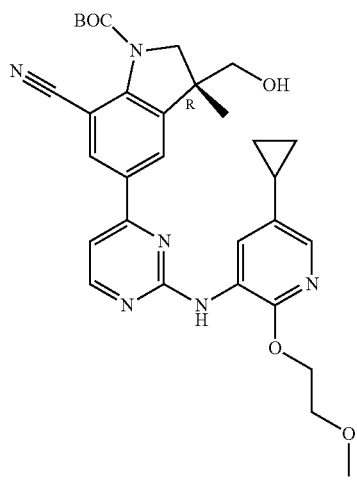<br>From intermediate 227 | 600 yellow foam | 76 |
| Intermediate 359 | 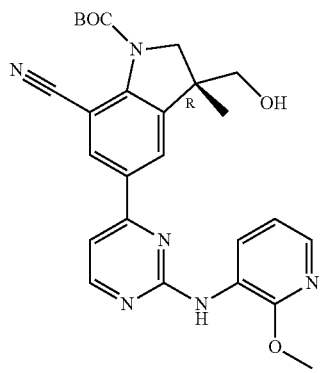<br>From intermediate 8 | 2200 yellow solid | — procedure with THF as solent with 2 equiv.of TBAF |

| Intermediate number | Structure | Mass (mg) | Yield (%) |
|---|---|---|---|
| Intermediate 363 | 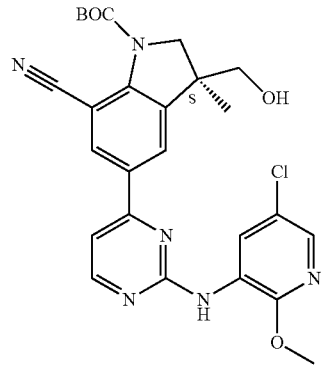<br>From intermediate 362 | 1680<br>(96% purity based on LC/MS)<br>red powder | 86<br>procedure with THF as solent with 2 equiv. of TBAF |
| Intermediate 426 | 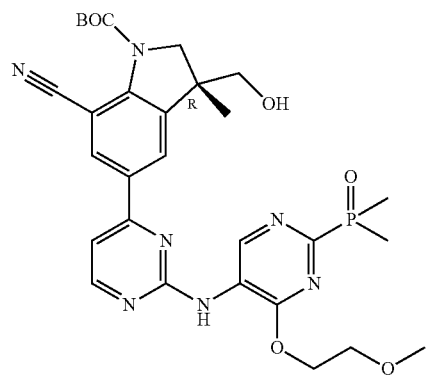<br>From intermediate 425 | 40<br>yellow solid | 14 |
| Intermediate 430 | 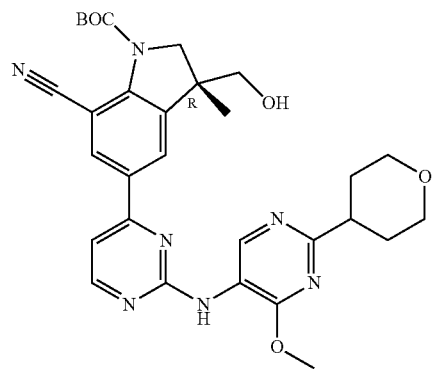<br>From intermediate 429 | 418<br>white foam<br>(87% purity based on NMR) | 72 |

-continued
| Intermediate number | Structure | Mass (mg) | Yield (%) |
|---|---|---|---|
| Intermediate 434 | 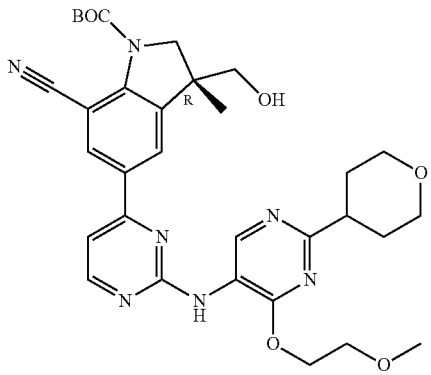 From intermediate 433 | 295 pale yellow foam | 70 procedure with 1.8 equiv. of TBAF |
| Intermediate 440 | 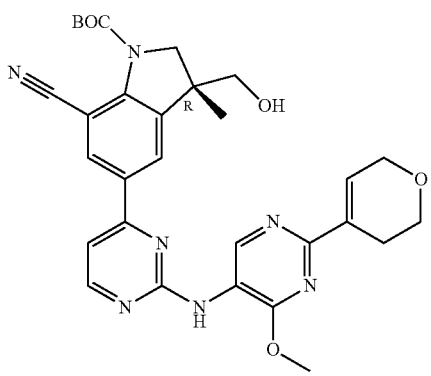 From intermediate 439 | 432 white solid | 86 procedure with 1.7 equiv. of TBAF |
| Intermediate 573 | 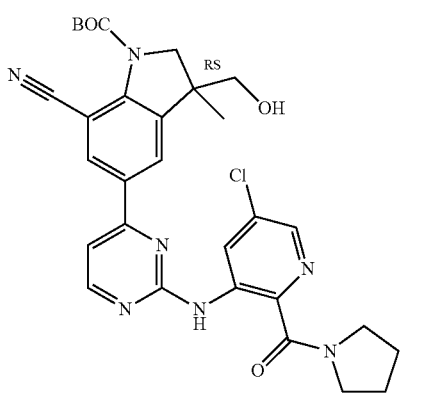 From intermediate 572 | 260 yellow solid | 98 procedure with 7.8 equiv. of TBAF 30 min |

Example A13

Preparation of Intermediate 59

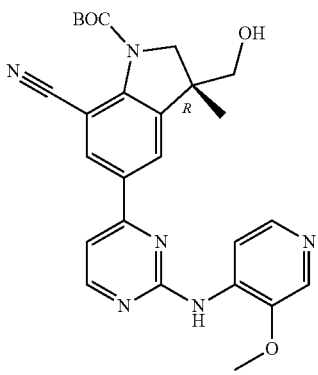

TBAF (on silica gel 1.5 mmol/g) (2.22 g, 3.33 mmol) was added to a solution of intermediate 58 (335.00 mg, 0.56 mmol) in Me-THF (15 mL) and the reaction mixture was stirred at rt for 18 h. The reaction mixture was diluted with DCM, filtered through paper and poured onto a 10% aqueous solution of $K_2CO_3$. The organic layer was decanted, washed with water, dried over $MgSO_4$, filtered and evaporated to dryness. The residue was purified by column chromatography on silica gel (irregular SiOH, 24 g, mobile phase: DCM/MeOH, gradient from 97:3 to 92:8). The pure fractions were collected and evaporated to dryness to give 196 mg of intermediate 59 (72% yield).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 77 | From intermediate 76 | 278 | 64 |
| Intermediate 81 | From intermediate 80 | 298 | 70 |

| Intermediate number | Structure | Mass (mg) | Yield (%) |
|---|---|---|---|
| Intermediate 85 | 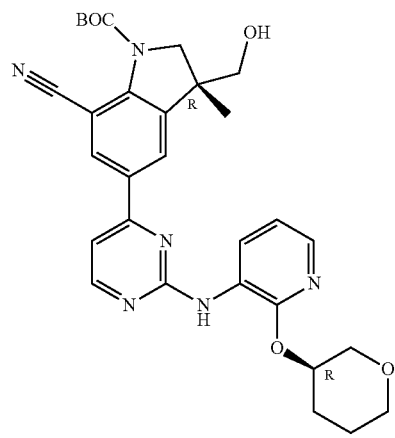  From intermediate 84 | 334 | 77 |
| Intermediate 89 | 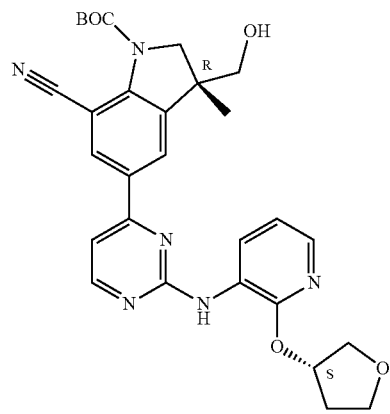  From intermediate 88 | 247 | 63 |
| Intermediate 91 | 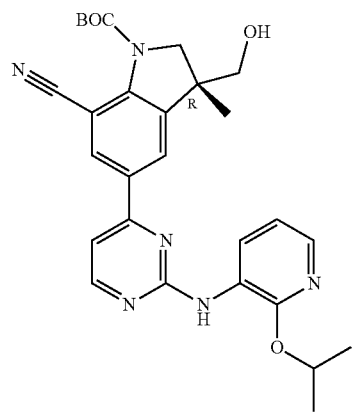  From intermediate 90 | 287 | 71 |

-continued
| Intermediate number | Structure | Mass (mg) | Yield (%) |
|---|---|---|---|
| Intermediate 95 | 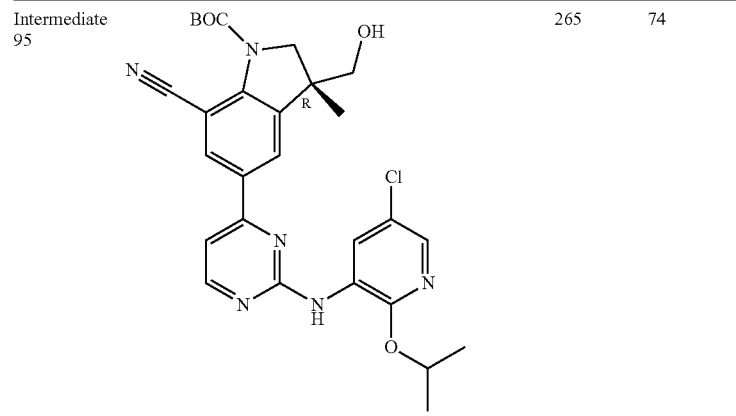<br>From intermediate 94 | 265 | 74 |
| Intermediate 112 | 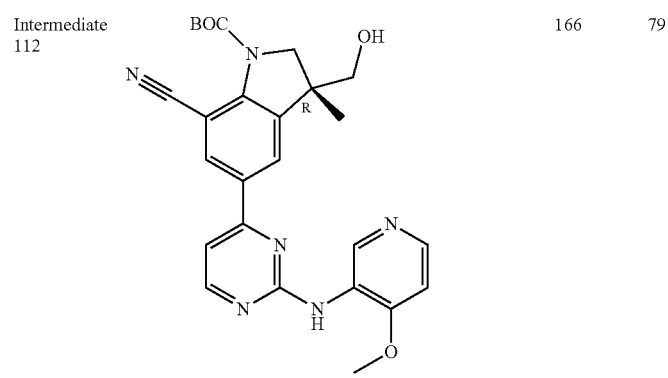<br>From intermediate 111 | 166 | 79 |
| Intermediate 121 | 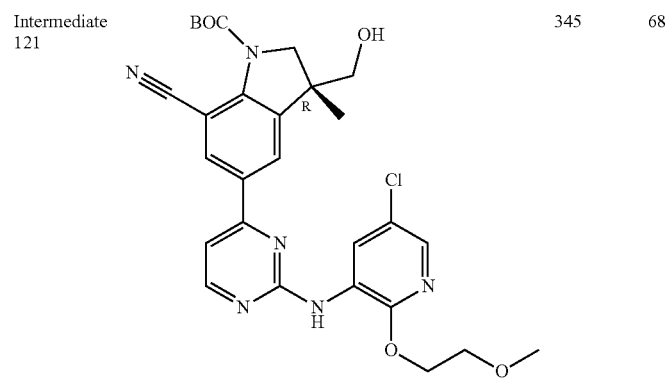<br>From intermediate 90 | 345 | 68 |

-continued

| Intermediate number | Structure | Mass (mg) | Yield (%) |
|---|---|---|---|
| Intermediate 196 | 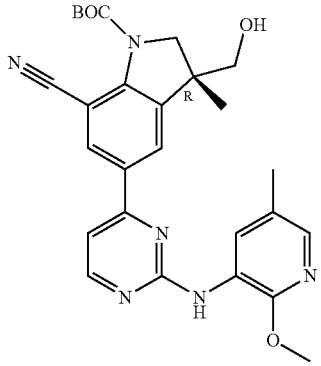<br>From intermediate 195 | 265 | 84 procedure with 4 equiv. of TBAF |
| Intermediate 205 | 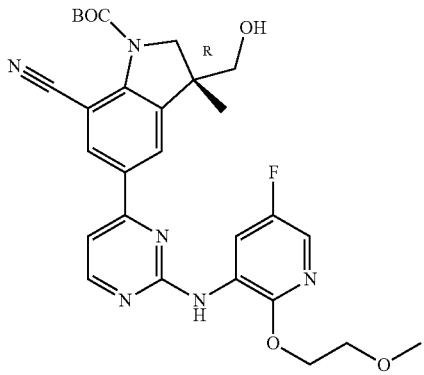<br>From intermediate 204 | 254 | 79 procedure with 4 equiv. of TBAF |

Example A14

Preparation of Intermediate 18

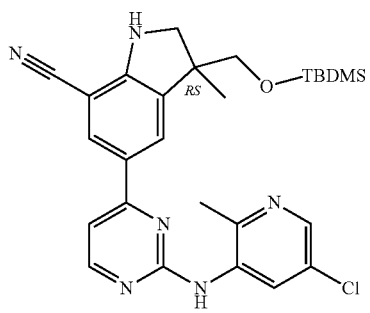

A mixture of intermediate 17 (1.40 g, 1.35 mmol) in TFA (3 mL) and DCM (15 mL) was stirred at rt for 1 h 30 min. The mixture was basified with saturated aq. NaHCO₃. An extraction was performed with DCM. The organic layer was washed with brine, dried over MgSO₄, evaporated and purified by column chromatography on silica gel (irregular SiOH 15-40 μm, 120 g, liquid injection (DCM), mobile phase: heptane/AcOEt, gradient from 100:0 to 0:100 in 15 CV). The fractions containing the product was concentrated under vacuum to give 480 mg of intermediate 18 (68% yield, yellow solid).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 27 | 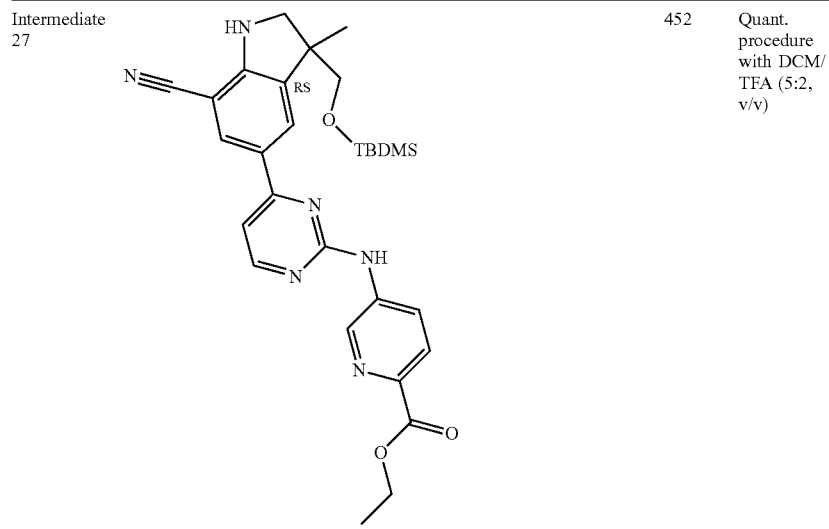<br>From intermediate 26 | 452 | Quant. procedure with DCM/TFA (5:2, v/v) |
| Intermediate 31 | 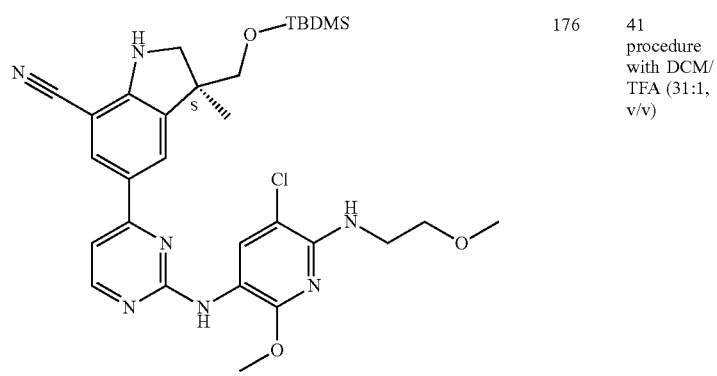<br>From intermediate 30 | 176 | 41 procedure with DCM/TFA (31:1, v/v) |
| Intermediate 34 | 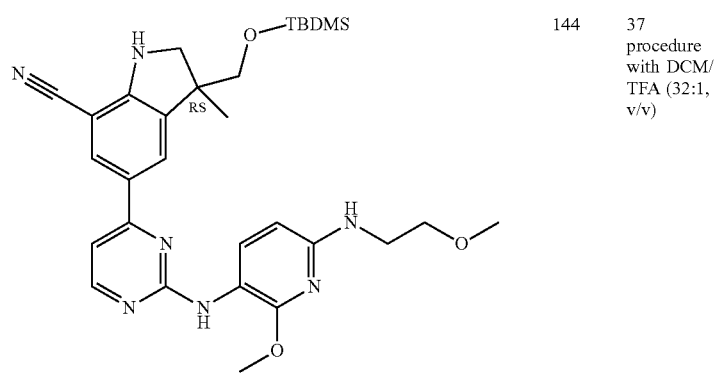<br>From intermediate 33 | 144 | 37 procedure with DCM/TFA (32:1, v/v) |

| Intermediate number | Structure | Mass (mg) | Yield (%) |
|---|---|---|---|
| Intermediate 40 | 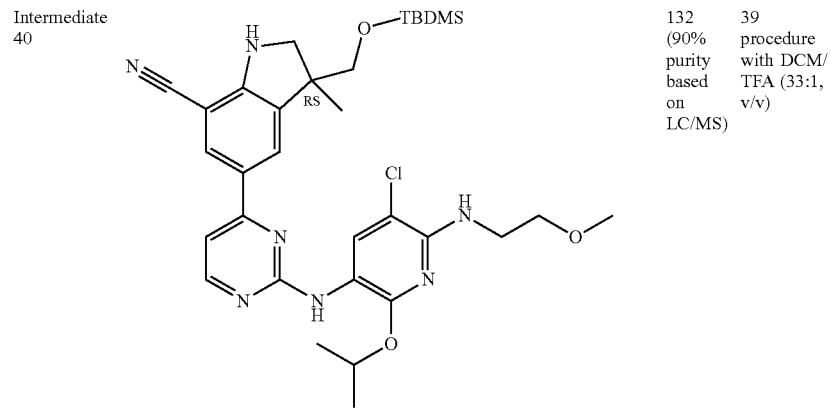<br>From intermediate 39 | 132 (90% purity based on LC/MS) | 39 procedure with DCM/ TFA (33:1, v/v) |
| Intermediate 42 | 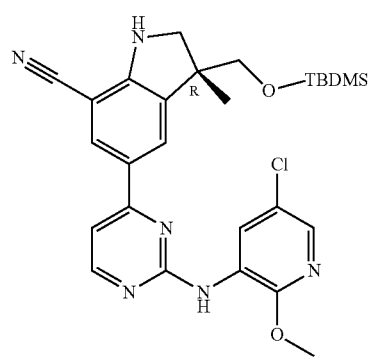<br>From intermediate 41 | 274 | 52 |
| Intermediate 48 | 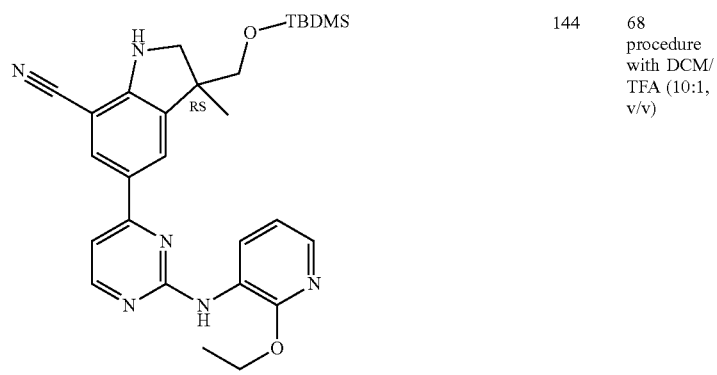<br>From intermediate 47 | 144 | 68 procedure with DCM/ TFA (10:1, v/v) |

| Intermediate number | Structure | Mass (mg) | Yield (%) | |
|---|---|---|---|---|
| Intermediate 51 | 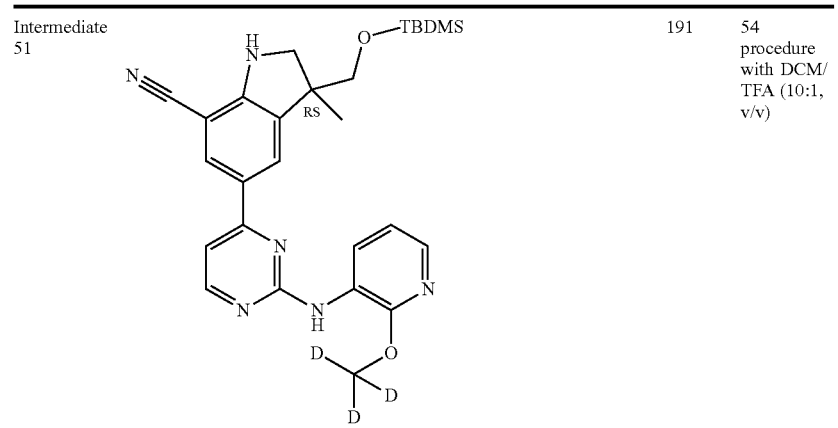<br>From intermediate 50 | 191 | 54 | procedure with DCM/TFA (10:1, v/v) |
| Intermediate 53 | 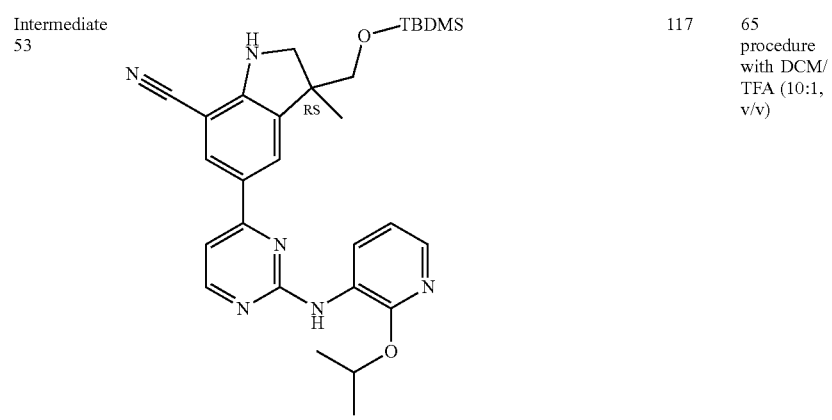<br>From intermediate 52 | 117 | 65 | procedure with DCM/TFA (10:1, v/v) |
| Intermediate 63 | 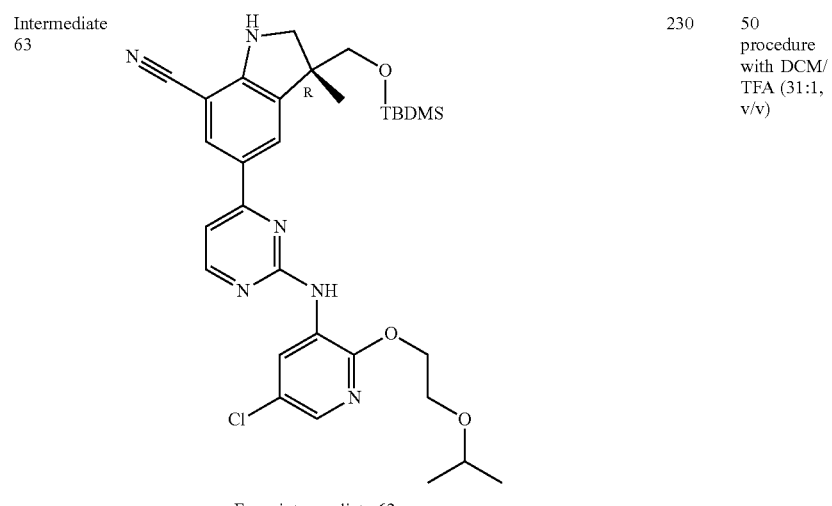<br>From intermediate 62 | 230 | 50 | procedure with DCM/TFA (31:1, v/v) |

| Intermediate number | Structure | Mass (mg) | Yield (%) |
|---|---|---|---|
| Intermediate 67 | 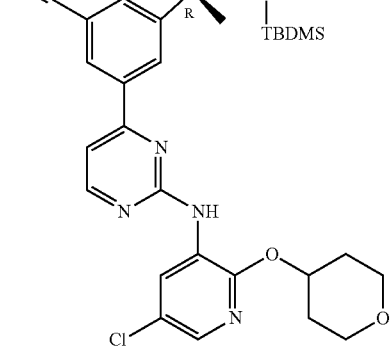<br>From intermediate 66 | 273 (78% purity based on LC/MS) | 63 procedure with DCM/ TFA (31:1, v/v) |
| Intermediate 97 | 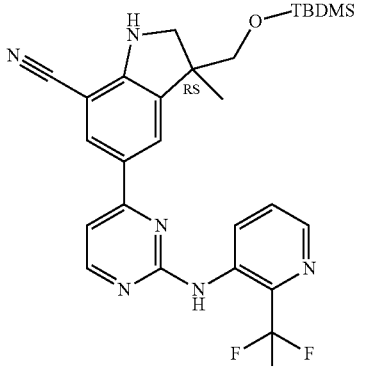<br>From intermediate 96 | 250 | 86 procedure with DCM/ TFA (32:1, v/v) |
| Intermediate 99 | 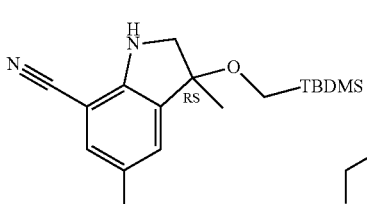<br>From intermediate 98 | 366 | Quant. procedure with DCM/ TFA (4:1, v/v) |

| Intermediate number | Structure | Mass (mg) | Yield (%) |
|---|---|---|---|
| Intermediate 103 | 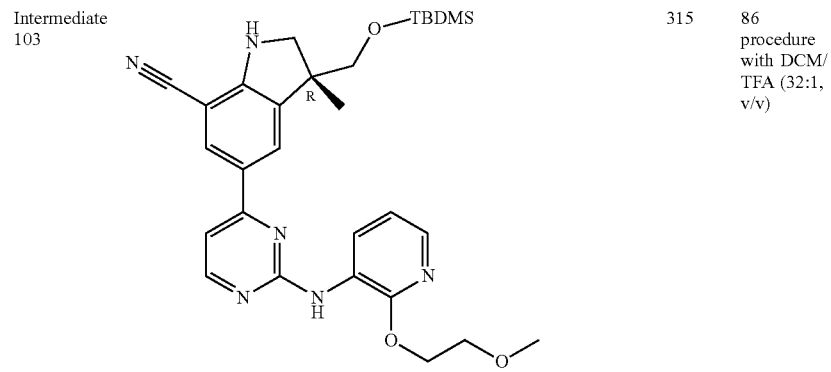<br>From intermediate 102 | 315 | 86 procedure with DCM/TFA (32:1, v/v) |
| Intermediate 105 | 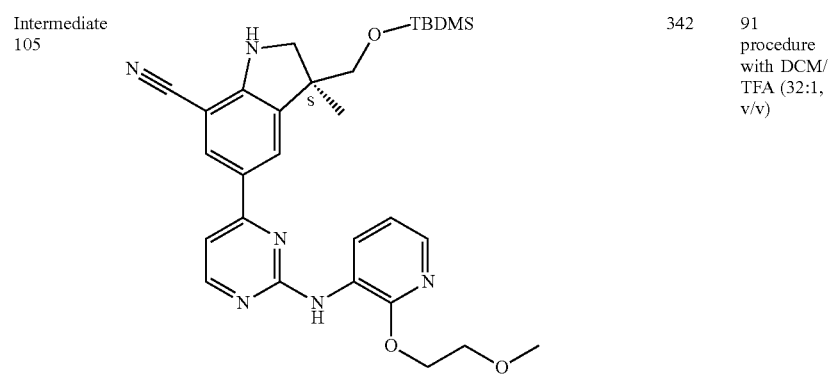<br>From intermediate 104 | 342 | 91 procedure with DCM/TFA (32:1, v/v) |
| Intermediate 108 | 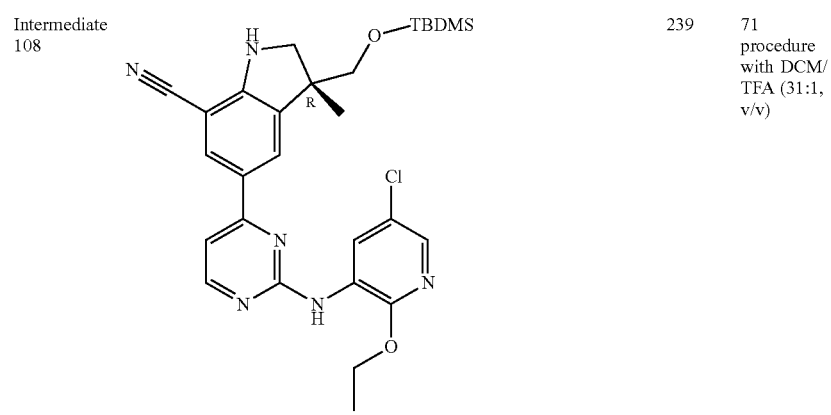<br>From intermediate 107 | 239 | 71 procedure with DCM/TFA (31:1, v/v) |

-continued
| Intermediate number | Structure | Mass (mg) | Yield (%) | |
|---|---|---|---|---|
| Intermediate 110 | 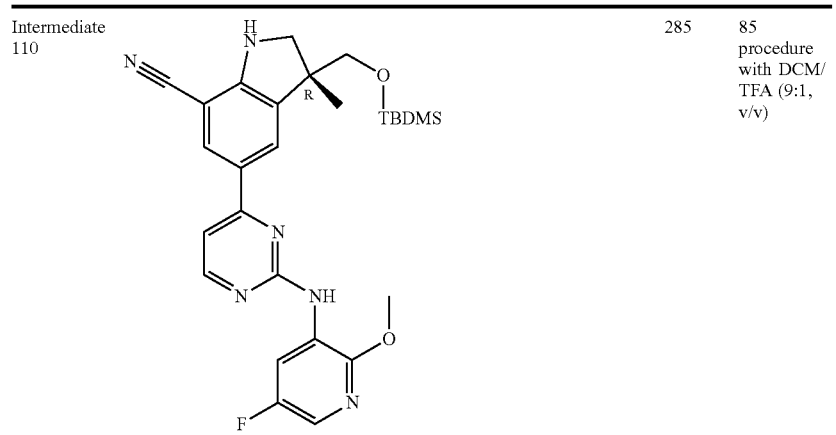<br>From intermediate 109 | 285 | 85 | procedure with DCM/ TFA (9:1, v/v) |
| Intermediate 117 | 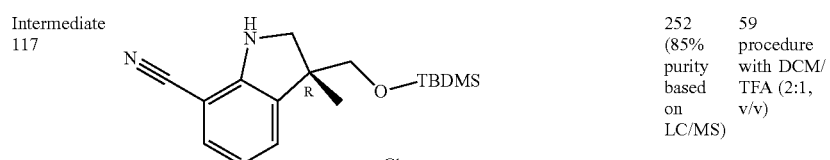<br>From intermediate 116 | 252 (85% purity based on LC/MS) | 59 | procedure with DCM/ TFA (2:1, v/v) |
| Intermediate 125 | 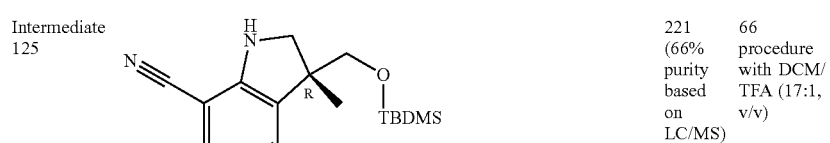<br>From intermediate 124 | 221 (66% purity based on LC/MS) | 66 | procedure with DCM/ TFA (17:1, v/v) |

| Intermediate number | Structure | Mass (mg) | Yield (%) | |
|---|---|---|---|---|
| Intermediate 133 | 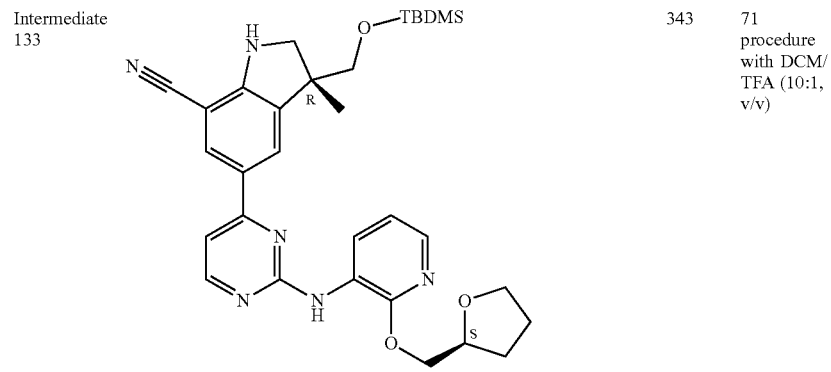<br>From intermediate 132 | 343 | 71 | procedure with DCM/ TFA (10:1, v/v) |
| Intermediate 137 | 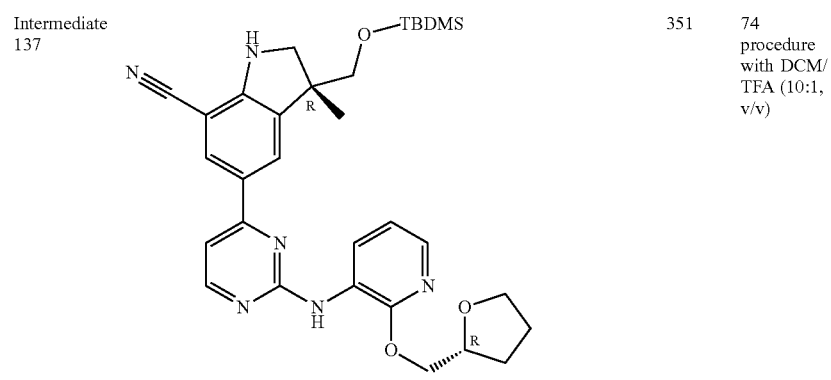<br>From intermediate 136 | 351 | 74 | procedure with DCM/ TFA (10:1, v/v) |
| Intermediate 141 | 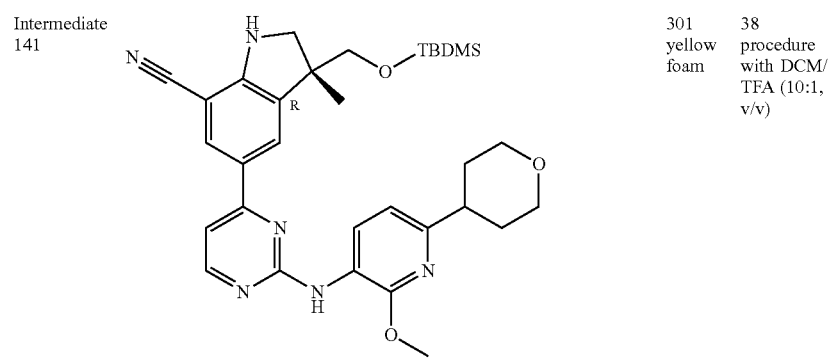<br>From intermediate 141 | 301 yellow foam | 38 | procedure with DCM/ TFA (10:1, v/v) |

-continued
| Intermediate number | Structure | Mass (mg) | Yield (%) |
|---|---|---|---|
| Intermediate 145 | 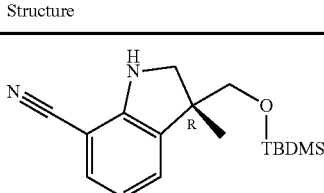 From intermediate 144 | 150 | 35 procedure with DCM/TFA (17:1, v/v) |
| Intermediate 149 | From intermediate 148 | 219 | 63 procedure with DCM/TFA (20:1, v/v) |
| Intermediate 153 | From intermediate 152 | 169 | 39 procedure with DCM/TFA (17:1, v/v) |

-continued
| Intermediate number | Structure | Mass (mg) | Yield (%) |
|---|---|---|---|
| Intermediate 157 | 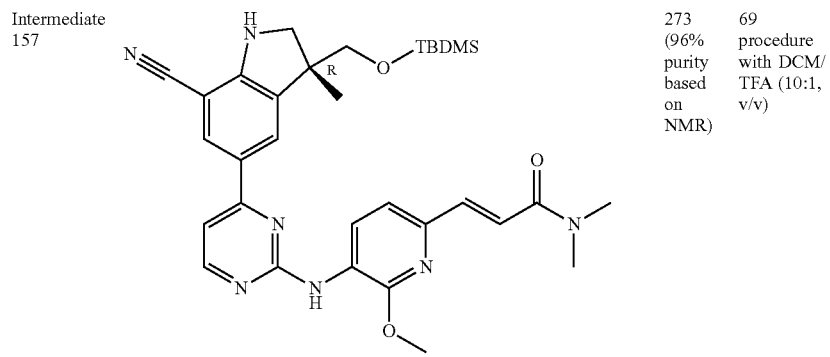 From intermediate 156 | 273 (96% purity based on NMR) | 69 procedure with DCM/TFA (10:1, v/v) |
| Intermediate 161 | 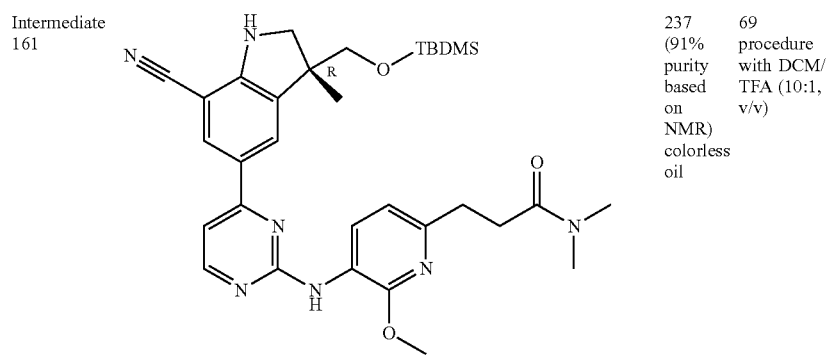 From intermediate 160 | 237 (91% purity based on NMR) colorless oil | 69 procedure with DCM/TFA (10:1, v/v) |
| Intermediate 173 | 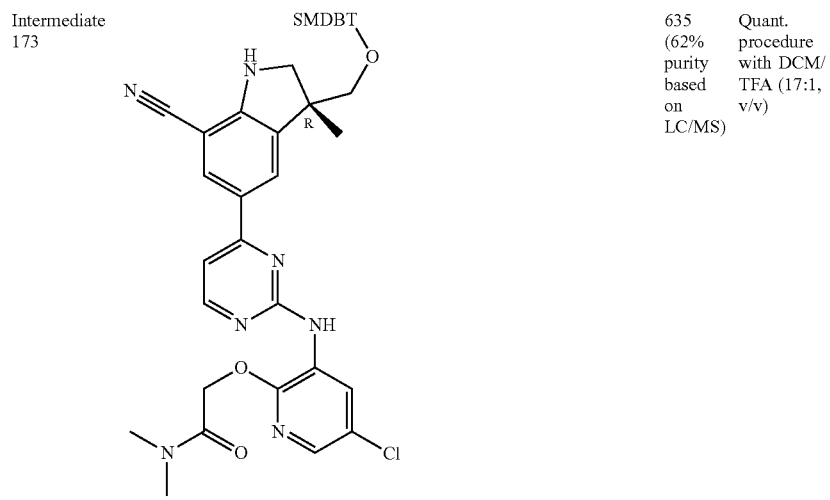 From intermediate 172 | 635 (62% purity based on LC/MS) | Quant. procedure with DCM/TFA (17:1, v/v) |

-continued
| Intermediate number | Structure | Mass (mg) | Yield (%) |
|---|---|---|---|
| Intermediate 169 | 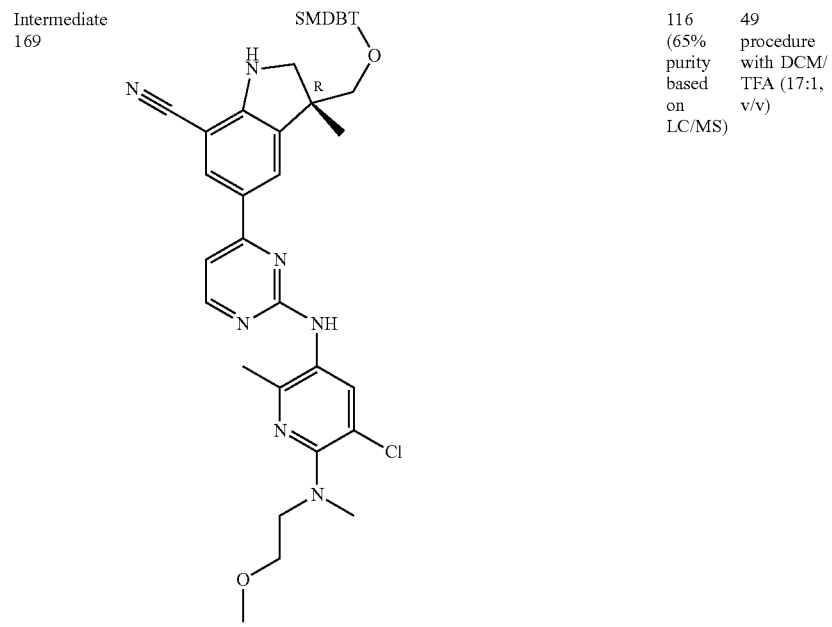 From intermediate 168 | 116 (65% purity based on LC/MS) | 49 procedure with DCM/ TFA (17:1, v/v) |
| Intermediate 177 | 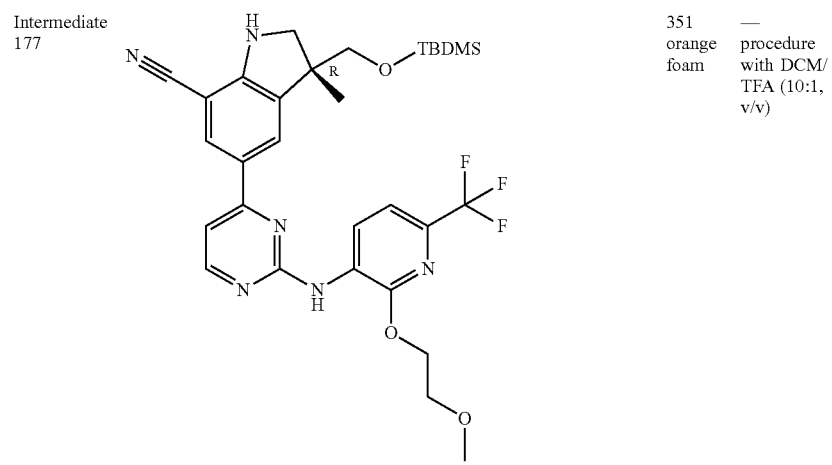 From intermediate 176 | 351 orange foam | — procedure with DCM/ TFA (10:1, v/v) |
| Intermediate 181 | 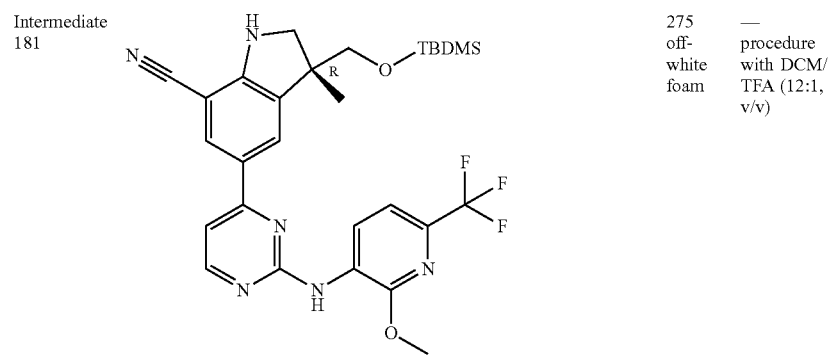 From intermediate 180 | 275 off-white foam | — procedure with DCM/ TFA (12:1, v/v) |

-continued
| Intermediate number | Structure | Mass (mg) | Yield (%) |
|---|---|---|---|
| Intermediate 185 | 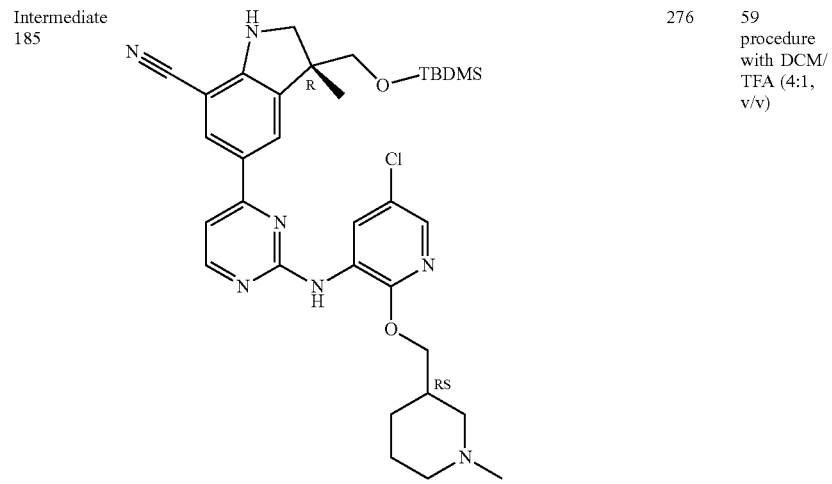<br>From intermediate 184 | 276 | 59 procedure with DCM/ TFA (4:1, v/v) |
| Intermediate 232 | 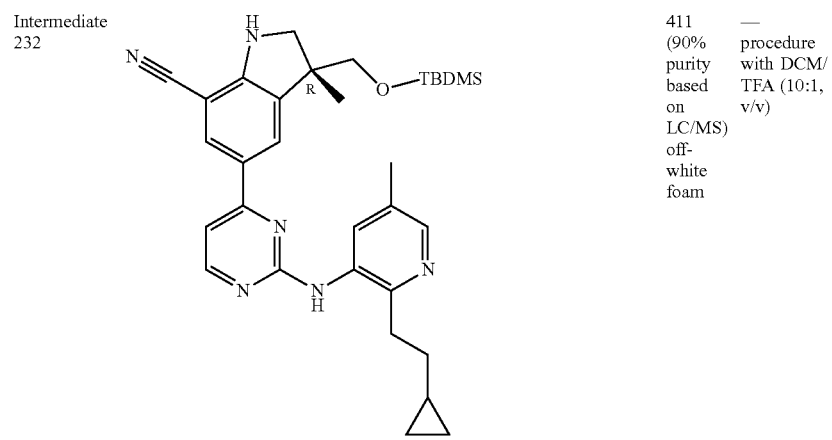<br>From intermediate 231 | 411 (90% purity based on LC/MS) off-white foam | — procedure with DCM/ TFA (10:1, v/v) |
| Intermediate 236 | 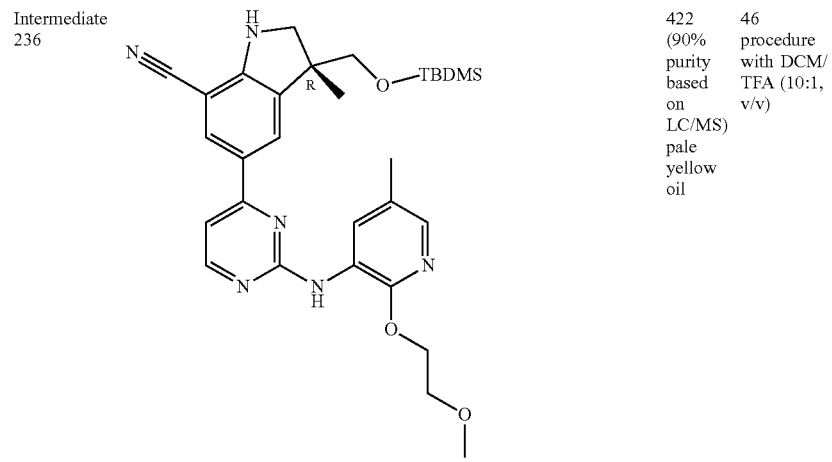<br>From intermediate 235 | 422 (90% purity based on LC/MS) pale yellow oil | 46 procedure with DCM/ TFA (10:1, v/v) |

| Intermediate number | Structure | Mass (mg) | Yield (%) |
|---|---|---|---|
| Intermediate 249 | 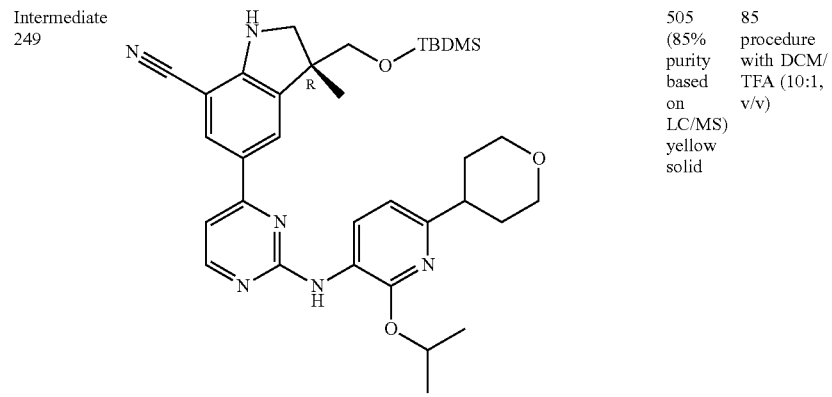<br>From intermediate 248 | 505 (85% purity based on LC/MS) yellow solid | 85 procedure with DCM/ TFA (10:1, v/v) |
| Intermediate 252 | 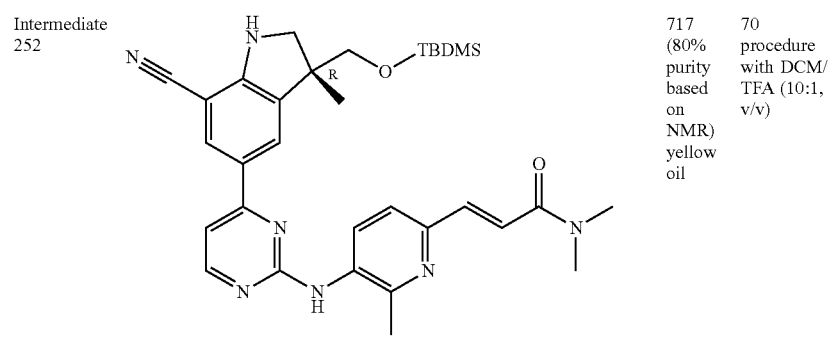<br>From intermediate 251 | 717 (80% purity based on NMR) yellow oil | 70 procedure with DCM/ TFA (10:1, v/v) |
| Intermediate 274 | 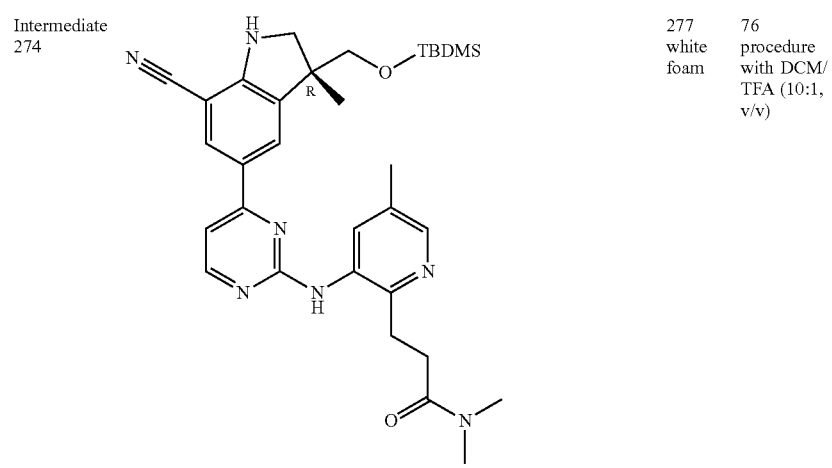<br>From intermediate 273 | 277 white foam | 76 procedure with DCM/ TFA (10:1, v/v) |

-continued
| Intermediate number | Structure | Mass (mg) | Yield (%) |
|---|---|---|---|
| Intermediate 298 | 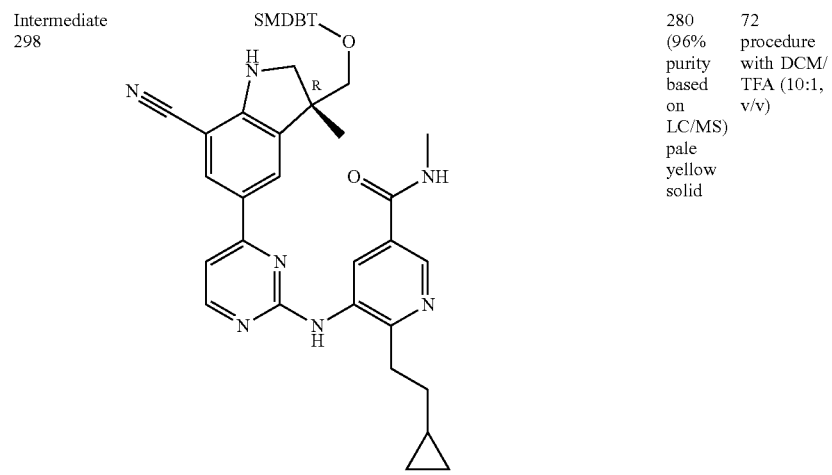From intermediate 297 | 280 (96% purity based on LC/MS) pale yellow solid | 72 procedure with DCM/ TFA (10:1, v/v) |
| Intermediate 301 | 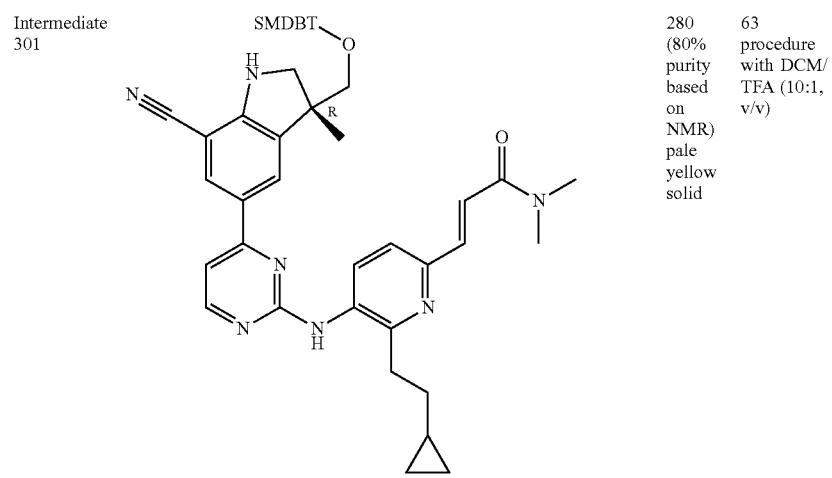From intermediate 300 | 280 (80% purity based on NMR) pale yellow solid | 63 procedure with DCM/ TFA (10:1, v/v) |
| Intermediate 304 | 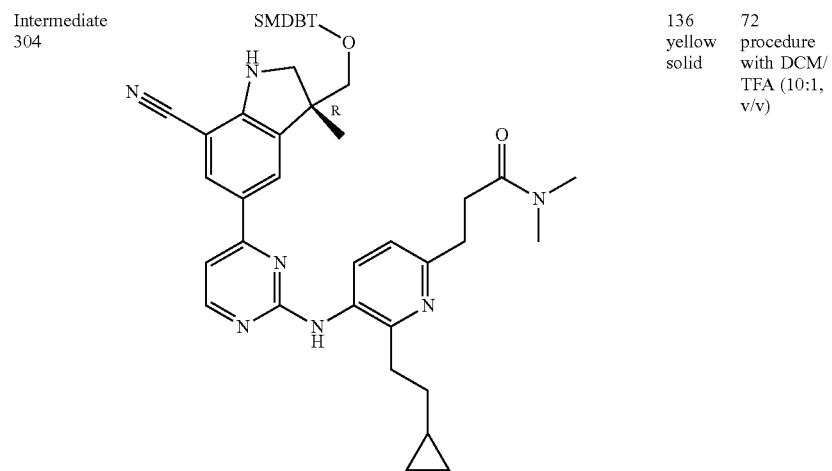From intermediate 303 | 136 yellow solid | 72 procedure with DCM/ TFA (10:1, v/v) |

-continued

| Intermediate number | Structure | Mass (mg) | Yield (%) |
|---|---|---|---|
| Intermediate 308 | From intermediate 307 | 179 (85% purity based on NMR) pale yellow solid | — procedure with DCM/ TFA (10:1, v/v) |
| Intermediate 330 | From intermediate 329 | 441 yellow solid | 73 procedure with DCM/ TFA (10:1, v/v) |
| Intermediate 396 | From intermediate 395 | 50 (100% purity based on LC/MS) white solid | 12 procedure with DCM/ TFA (8:3, v/v) |
| Intermediate 402 | From intermediate 401 | 147 white solid | 50 procedure with DCM/ TFA (10:1, v/v) |

-continued

| Intermediate number | Structure | Mass (mg) | Yield (%) |
|---|---|---|---|
| Intermediate 404 | From intermediate 403 | 450 brown oil | Quant. procedure with DCM/TFA (8:3, v/v) |
| Intermediate 406 | From intermediate 405 | 590 brown oil | — procedure with DCM/TFA (8:3, v/v) |
| Intermediate 408 | From intermediate 407 | 139 (90% purity based on LC/MS) yellow solid | 62 procedure with DCM/TFA (10:1, v/v) |
| Intermediate 410 | From intermediate 409 | 478 | 91 procedure with DCM/TFA (10:1, v/v) |

| Intermediate number | Structure | Mass (mg) | Yield (%) |
|---|---|---|---|
| Intermediate 412 | 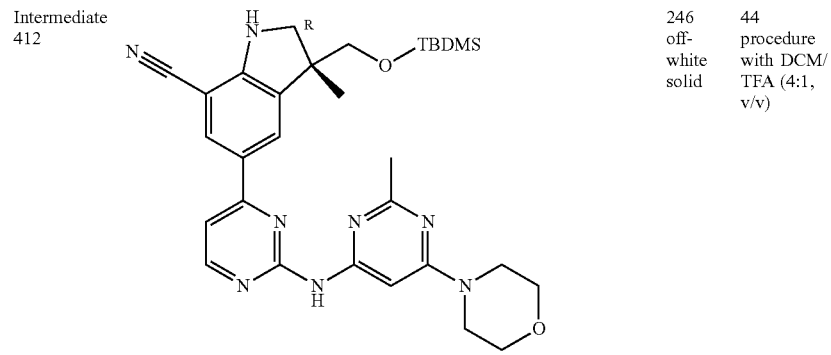<br>From intermediate 411 | 246 off-white solid | 44 procedure with DCM/ TFA (4:1, v/v) |
| Intermediate 414 | 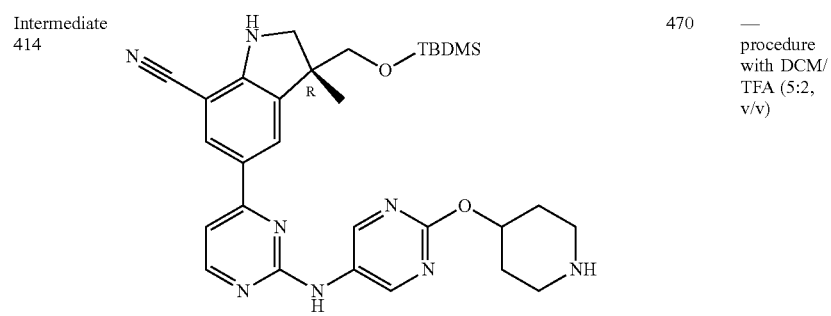<br>From intermediate 413 | 470 | — procedure with DCM/ TFA (5:2, v/v) |
| Intermediate 418 | 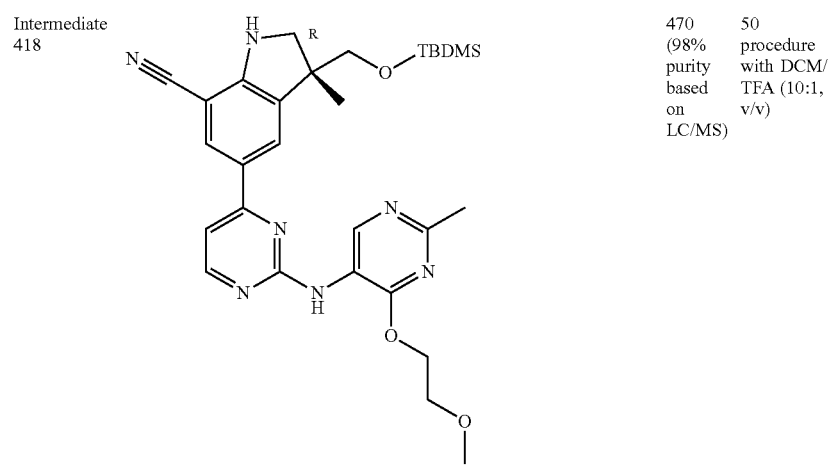<br>From intermediate 417 | 470 (98% purity based on LC/MS) | 50 procedure with DCM/ TFA (10:1, v/v) |

| Intermediate number | Structure | Mass (mg) | Yield (%) |
|---|---|---|---|
| Intermediate 422 | 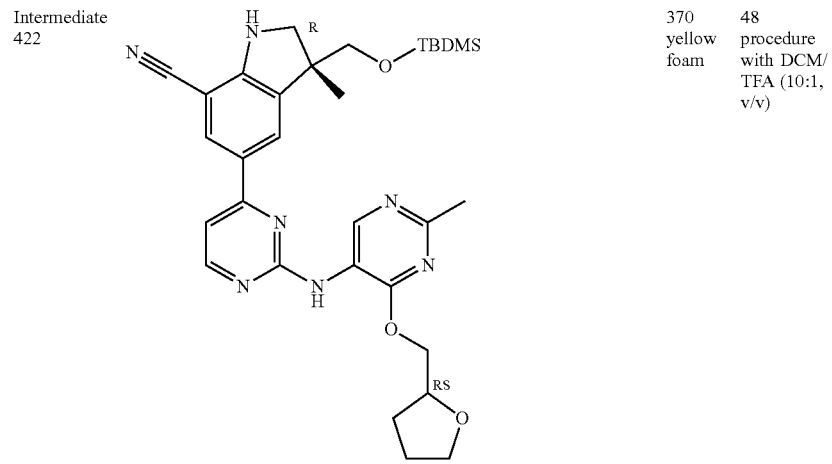<br>From intermediate 421 | 370 yellow foam | 48 procedure with DCM/ TFA (10:1, v/v) |
| Intermediate 438 | 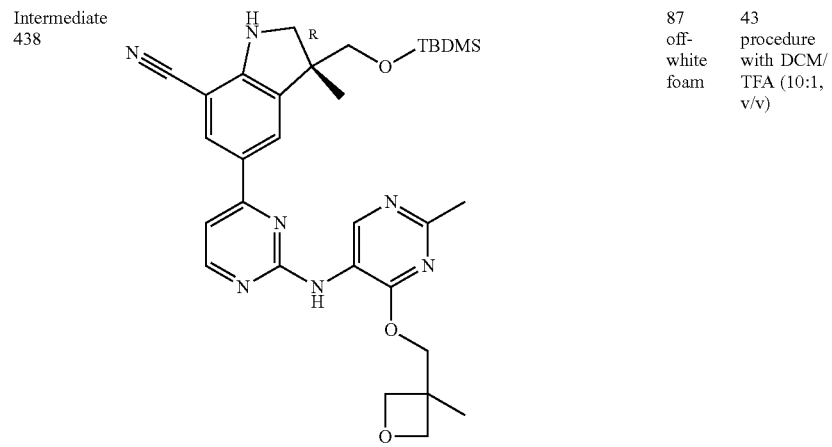<br>From intermediate 437 | 87 off- white foam | 43 procedure with DCM/ TFA (10:1, v/v) |
| Intermediate 444 | 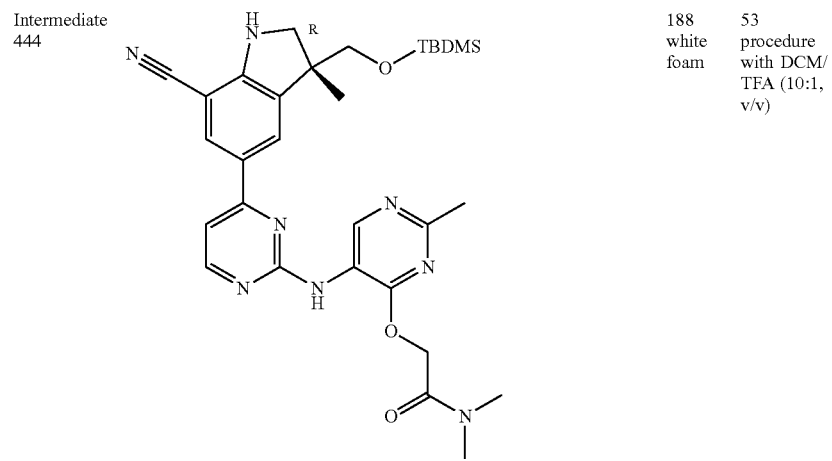<br>From intermediate 443 | 188 white foam | 53 procedure with DCM/ TFA (10:1, v/v) |

-continued

| Intermediate number | Structure | Mass (mg) | Yield (%) | |
|---|---|---|---|---|
| Intermediate 520 | 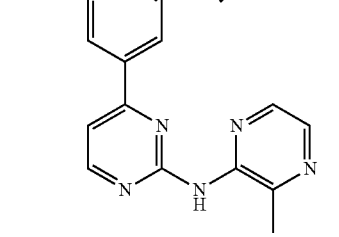<br>From intermediate 519 | 378 | 100 | procedure with DCM/ TFA (12:1, v/v) |
| Intermediate 506 | 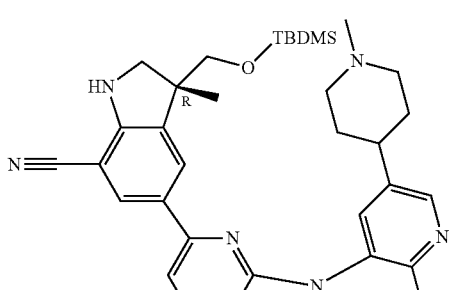<br>From intermediate 505 | 280 (49% purity based on LC/MS) | 47 | procedure with DCM/ TFA (5:1, v/v) |
| Intermediate 530 | 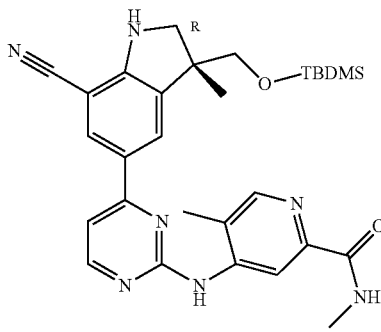<br>From intermediate 529 | 435 (65% purity based on LC/MS) | 100% | procedure with DCM/ TFA (6:1, v/v) |
| Intermediate 588 | 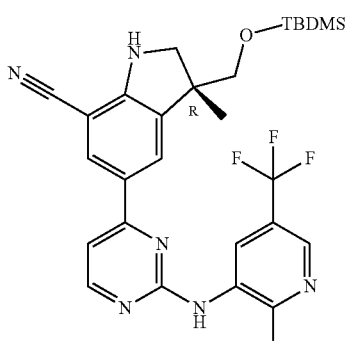<br>From intermediate 587 | 277 | 92 | procedure with DCM/ TFA (17:1, v/v) 5° C.; 1 h |

Example A15

Preparation of Intermediate 292

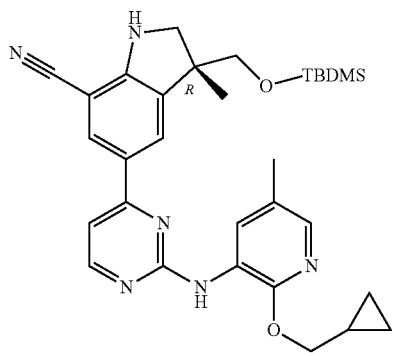

In a sealed tube, $SiO_2$ (40-63 µm) (1.00 g, 5 equiv. wt) was added to a solution of intermediate 291 (200.00 mg, 0.30 mmol) in toluene (2 mL). The mixture was refluxed for 2 h. Some Celite® was added and the resulting mixture was evaporated in vacuo. The residue was purified by column chromatography on silica gel (irregular SiOH 15-40 µm, grace 80 g, dry loading, mobile phase: heptane/AcOEt, gradient: from 70:30 to 30:70 in 10 CV). The pure fractions were combined and evaporated to dryness to give 160 mg of intermediate 292 (94% yield, white solid).

The intermediates in the Table below were prepared by using an analogous method starting from the respective starting materials.

| Intermediate number | Structure | Mass (mg) | Yield (%) |
|---|---|---|---|
| Intermediate 319 | 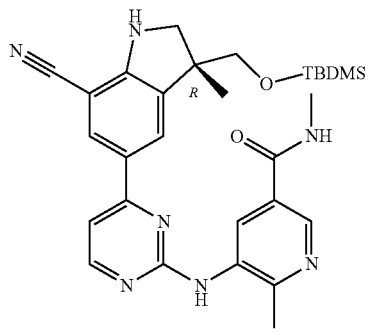<br>From intermediate 318 | 49 | 16 |
| Intermediate 518 | 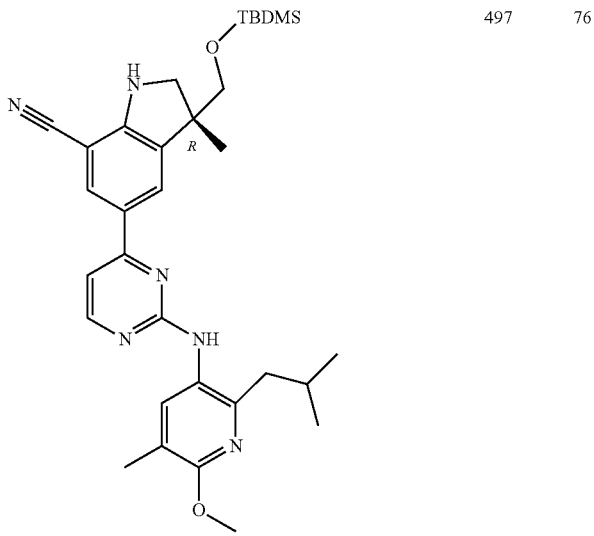<br>From intermediate 517 | 497 | 76 |

-continued
| Intermediate number | Structure | Mass (mg) | Yield (%) |
|---|---|---|---|
| Intermediate 509 | 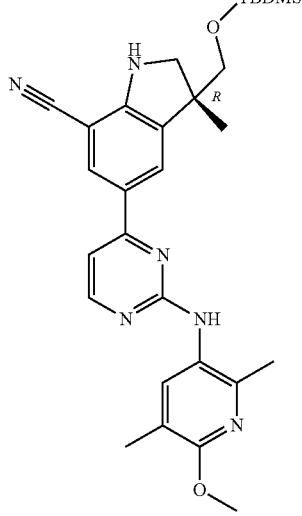<br>From intermediate 508 | 287 | 80 |
| Intermediate 546 | CIS mixture (RS and SR)<br>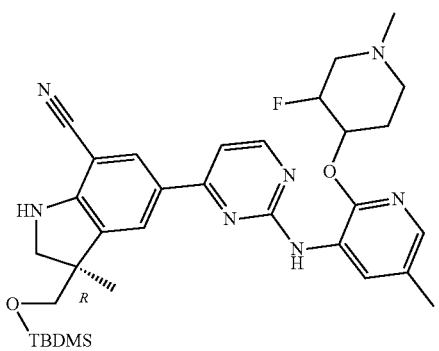<br>From intermediate 545 | 108 | 87<br>LC-MS: 95% |
| Intermediate 549 | 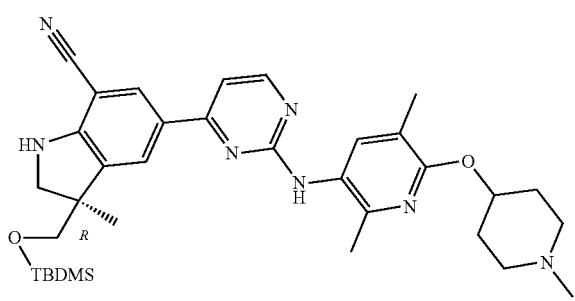<br>From intermediate 548 | 124 | 90 |

-continued
| Intermediate number | Structure | Mass (mg) | Yield (%) |
|---|---|---|---|
| Intermediate 568 | TRANS mixture (RR and SS) 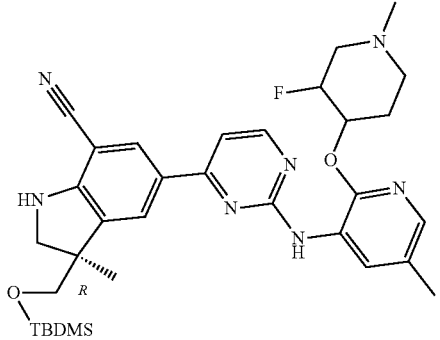 From intermediate 567 | 500 | 97 LC-MS: 60% |
| Intermediate 562 | 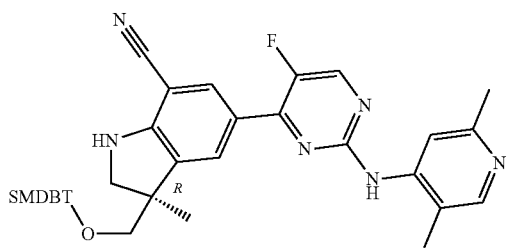 From intermediate 561 | 320 | 95 |
| Intermediate 552 | 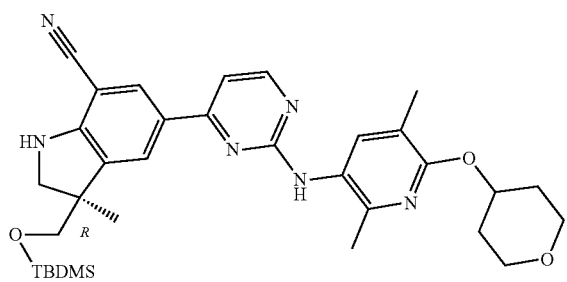 From intermediate 551 | 640 | 100% |

Example A16

Preparation of Intermediate 335

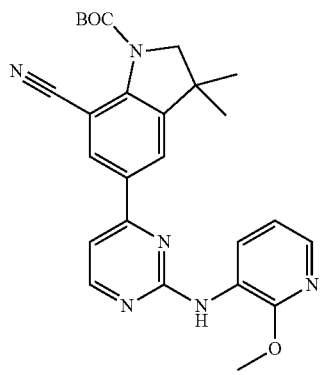 [SMILES: COc1ncccc1Nc1nccc(-c2cc(C#N)c3c(c2)C(C)(C)CN3C(=O)OC(C)(C)C)n1]

A degassed suspension of intermediate 334 (73.00 mg, 0.19 mmol), 3-amino-2-methoxy pyridine (26.10 mg, 0.21 mmol), Pd(OAc)$_2$ (4.27 mg, 0.019 mmol), BINAP (11.83 mg, 0.019 mmol) and Cs$_2$CO$_3$ (185.72 mg, 0.57 mmol) in 1,4-dioxane (2 mL) was heated to 85° C. for 1 h. The reaction mixture was partitioned between EtOAc and diluted with a solution of NaHCO$_3$. The organics layers were washed with brine, dried over Na$_2$SO$_4$ and concentrated in vacuo. This residue (89 mg, quant. yield, 73% purity based on LC/MS) was used in the next step without further purification.

The intermediates in the Table below were prepared by using an analogous method starting from the respective starting materials.

| Intermediate number | Structure | Mass (mg) | Yield (%) |
|---|---|---|---|
| Intermediate 336 | 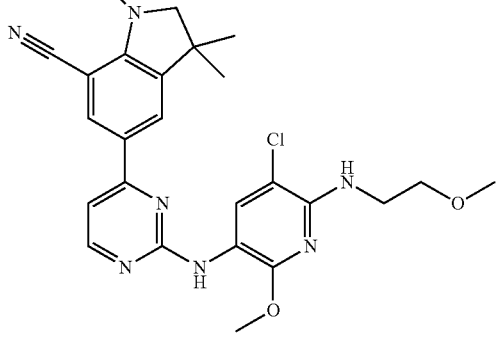<br>From intermediate 334 and intermediate 11 | 150<br>brown oil | Quant. |
| Intermediate 340 | 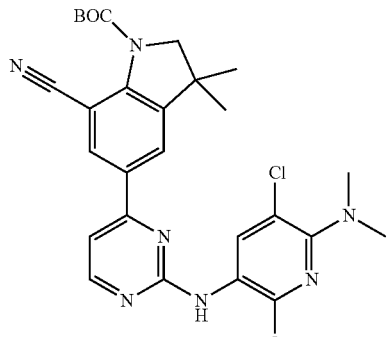<br>From intermediate 334 and intermediate 339 | 171<br>brown oil | Quant. |

| Intermediate number | Structure | Mass (mg) | Yield (%) |
|---|---|---|---|
| Intermediate 397 | 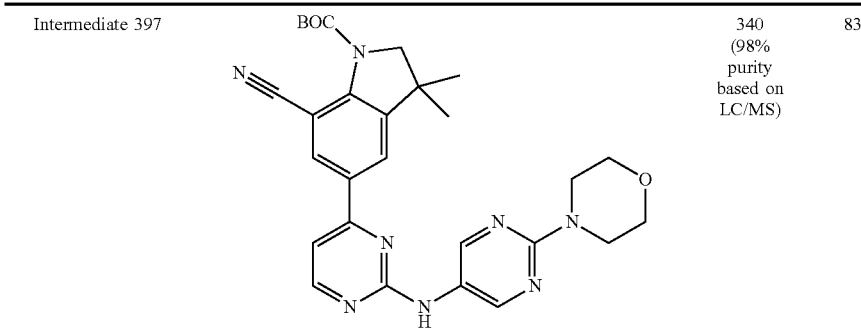<br>From intermediate 334 and 2-(4-morpholinyl)-5-Pyrimidinamine | 340<br>(98% purity based on LC/MS) | 83 |
| Intermediate 578 | 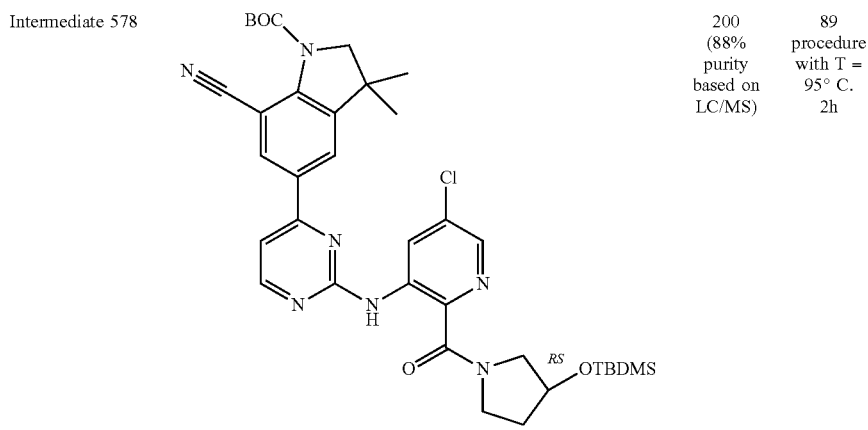<br>From intermediate 334 and intermediate 577 | 200<br>(88% purity based on LC/MS) | 89<br>procedure with T = 95° C.<br>2h |

Example A17

Preparation of Intermediate 344

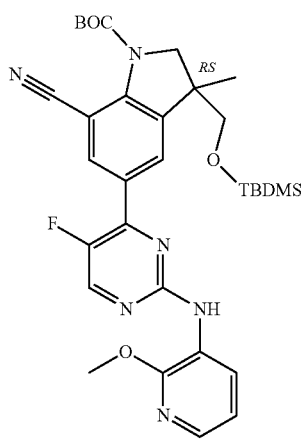

Intermediate 343 (0.35 g, 0.66 mmol), 3-amino-2-methoxypyridine (81.50 mg, 0.66 mmol) and $Cs_2CO_3$ (0.64 g, 1.97 mmol) in 1,4-dioxane (6.3 mL) was degassed with $N_2$. Then, $Pd(OAc)_2$ (14.70 mg, 0.066 mmol) and BINAP (40.88 mg, 0.066 mmol) were added together and the resulting mixture was heated at 120° C. for 20 min using one single mode microwave (Biotage Initiator EXP 60) with a power output ranging from 0 to 400 W [fixed hold time]. The reaction mixture was cooled down to rt, and partitionned between water and EtOAc. The organic layer was separated, dried over $MgSO_4$ and concentrated. The residue was purified by column chromatography on silica gel (irregular $SiO_2$, 40 g, mobile phase: heptane/EtOAc, gradient from 9:1 to 0:1). The fractions containing the products were mixed and the solvent was concentrated to give 0.408 g of intermediate 344 (100% yield, 92% purity based on LC/MS).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 346 | From intermediate 343 and 5-chloro-2-methoxypyridine-3-amine | 552 (75% purity based on LC/MS) | 96 procedure without microwave activation |
| Intermediate 349 | From intermediate 348 and 3-amino-2-methoxypyridine | 378 (97% purity based on LC/MS) | 93 |
| Intermediate 351 | From intermediate 348 and 5-chloro-2-methoxypyridine-3-amine | 402 (65% purity based on LC/MS) | 61 procedure without microwave activation with T = 95° C. |

-continued

| Intermediate number | Structure | Mass (mg) | Yield (%) |
|---|---|---|---|
| Intermediate 353 | (structure with BOC-protected indoline bearing CN, methyl, CH2-O-TBDMS (RS), linked to fluoropyrimidine-NH-chloropyridine-O-tetrahydropyran) From intermediate 343 and intermediate 65 | 429 (95% purity based on LC/MS) | 83 procedure without microwave activation |
| Intermediate 355 | (structure with BOC-protected indoline bearing CN, methyl (R), CH2-O-TBDMS, linked to fluoropyrimidine-NH-pyridine-O-CH2CH2-OCH3) From intermediate 348 and intermediate 101 | 442 | 75 procedure without microwave activation |
| Intermediate 357 | (structure with BOC-protected indoline bearing CN, methyl, CH2-O-TBDMS (RS), linked to fluoropyrimidine-NH-pyridine-O-tetrahydropyran) From intermediate 348 and intermediate 69 | 430 | 66 procedure without microwave activation |

Example A18

Preparation of Intermediate 345

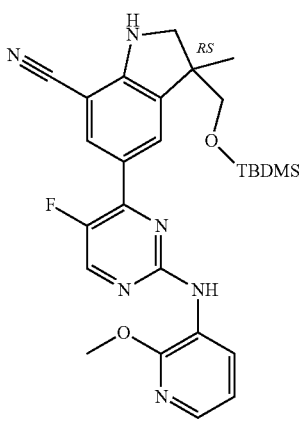

TFA (0.82 mL) was added at 5° C. to a solution of intermediate 344 (443.00 mg, 0.71 mmol) in DCM (7 mL). The reaction mixture was stirred at 5° C. for 1 h. The mixture was diluted with DCM (50 mL) and poured onto a 10% aqueous solution of $K_2CO_3$. More DCM/MeOH was added (80:20, 200 mL) The organic layer was decanted, washed with a 10% aqueous solution of $K_2CO_3$, dried over $MgSO_4$, filtered and evaporated to dryness. The residue was purified by column chromatography on silica gel (15-40 μm, 40 g, mobile phase: heptane/EtOAc/MeOH, gradient from 100:0:0 to 80:20:0 to 0:98:2). The pure fractions were collected and evaporated to dryness to give 0.248 g of intermediate 345 (67% yield).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 347 | *(structure)* From intermediate 346 | 86 (89% purity based on LC/MS) | 23 |
| Intermediate 350 | *(structure)* From intermediate 349 | 213 (98% purity based on LC/MS) | 67 |

-continued
| Intermediate number | Structure | Mass (mg) | Yield (%) |
|---|---|---|---|
| Intermediate 352 | 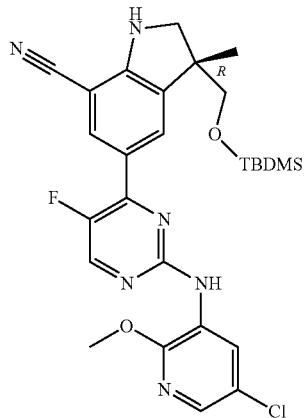<br>From intermediate 351 | 216<br>(83% purity based on LC/MS) | 64 |
| Intermediate 354 | 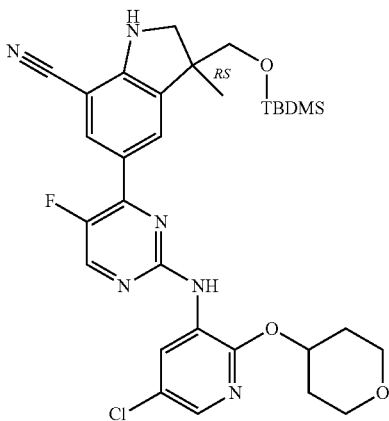<br>From intermediate 353 | 276 | 75<br>procedure with DCM/TFA (31:1, v/v) |
| Intermediate 356 | 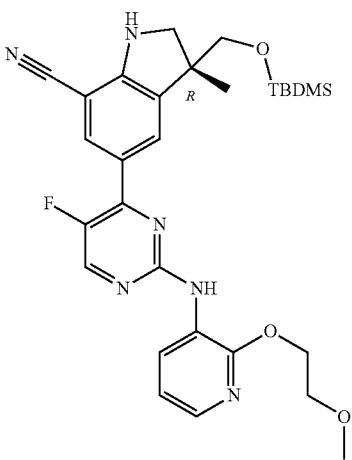<br>From intermediate 355 | 316<br>(87% purity based on LC/MS) | 84<br>procedure with DCM/TFA (31:1, v/v) |

| Intermediate number | Structure | Mass (mg) | Yield (%) |
|---|---|---|---|
| Intermediate 358 | From intermediate 357 | 247 | 67 procedure with DCM/TFA (17:1, v/v) |
| Intermediate 526 | From intermediate 525 | 340 | 65% procedure with DCM/TFA (6:1, v/v) with T = 0° C. 30 min |

Example A19

Preparation of Intermediate 360

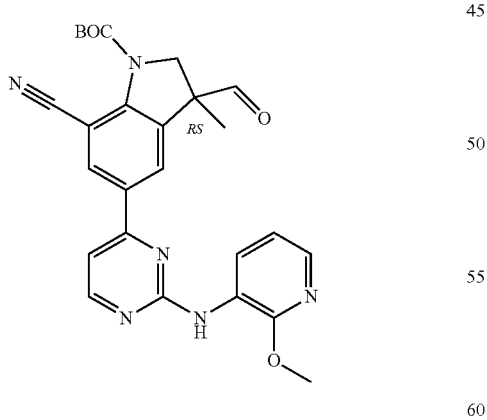

A dry three neck round bottom flask (25 mL) was charged with DCM (1 mL), cooled to −78° C., and oxalyl chloride (2.55 mL, 5.11 mmol) was added followed by DMSO (0.73 mL, 10.21 mmol). After 1 h, a solution of intermediate 359 (1.66 g, 3.40 mmol) in solution in DCM (4 mL) was added dropwise. The mixture was stirred for 1 h at −78° C., before DIPEA (3.52 mL, 20.42 mmol) was added. Stirring was continued and then the mixture was allowed to warm to rt over 5 h. A diluted solution of $NH_4Cl$ was added and the aqueous layer was extracted twice with DCM and the combined layers were dried with $MgSO_4$. After filtration and careful removal of the solvent in vacuo, 1.73 g of intermediate 360 was obtained (14% purity based on LC/MS, yellow solid).

Preparation of Intermediate 365

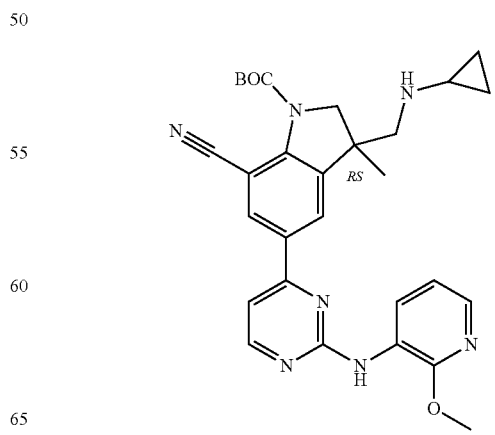

A solution of intermediate 360 (0.20 g, 0.41 mmol), cyclopropylamine (0.30 mL, 4.93 mmol), AcOH (141.00 μL, 2.47 mmol) and NaBH(OAc)₃ (87.20 mg, 4.11 mmol) in dichloroethane (8.3 mL) was stirred at rt over the weekend. A saturated NaHCO₃ solution was added and the aqueous layer was extracted with DCM. The organic layer was dried over MgSO₄ and evaporated to dryness. The residue (420 mg, colorless oil) was purified by column chromatography on silica gel (irregular SiOH, 24 g, mobile phase: heptane/ EtOAc, gradient from 100:0 to 60:40). The fractions containing the product were evaporated to provide 139 mg of intermediate 365 (64% yield, 98% purity based on LC/MS, colorless oil).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 361 | From intermediate 360 and methylamine | 93 white solid | 45 |
| Intermediate 366 | From intermediate 360 and N-Boc piperazine | 126 (99% purity based on LC/MS) white powder 278 (98% purity based on LC/MS) colorless oil | 16 34 |

| Intermediate number | Structure | Mass (mg) | Yield (%) |
|---|---|---|---|
| Intermediate 367 | 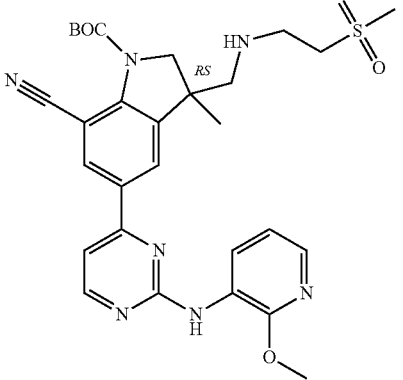<br>From intermediate 360 and 2-(methylsulfonyl)ethanamine | 172 colorless oil | 47 |
| Intermediate 368 | 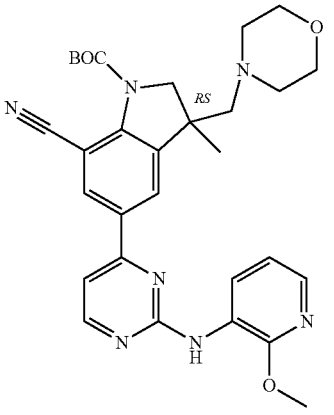 [SMILES: COc1ncccc1Nc1nccc(-c2cc(C#N)c3c(c2)C(C)(CN2CCOCC2)CN3C(=O)OC(C)(C)C)n1]<br>From intermediate 360 and morpholine | 82 colorless oil | 24 |
| Intermediate 369 | 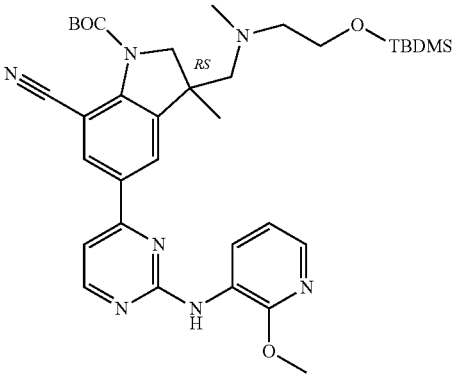<br>From intermediate 360 and 2-[[(1,1-dimethylethyl)dimethylsilyl]oxy]-N-methyl-ethanalamine | 154 (87% purity based on LC/MS) colorless oil | 41 |

| Intermediate number | Structure | Mass (mg) | Yield (%) |
|---|---|---|---|
| Intermediate 370 |  From intermediate 360 and 2,4-dimethoxybenzylamine | 630 (81% purity based on LC/MS) yellow oil | 86 |

Example A20

Preparation of intermediate 364

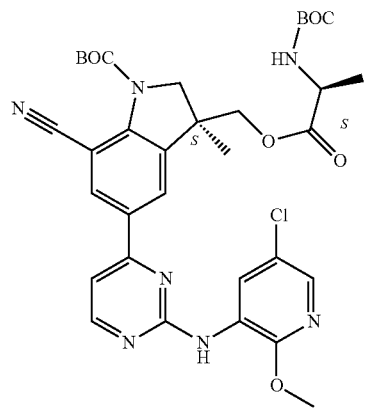

To a solution of intermediate 363 (0.20 g, 0.38 mmol) and L-BOC-alanine (79.60 mg, 0.42 mmol) in DCM (0.64 mL) at 0° C., HATU (523.50 mg, 1.38 mmol), DIPEA (132.00 µL, 0.76 mmol) and DMAP (2.34 mg, 19.10 µmol) were added. The resulted mixture was stirred at rt over the weekend. The organic layer was washed with 1 N HCl, water and brine, dried over MgSO₄, filtered and evaporated to provide a purple oil. The residue (300 mg) was purified by column chromatography on silica gel (Irregular SiOH, 12 g, mobile phase: heptane/EtOAc, gradient from 100:0 to 60:40). The fractions containing the products were combined and evaporated to provide 270 mg of intermediate 364 (Quant. yield, white powder).

Example A21

Preparation of Intermediate 371

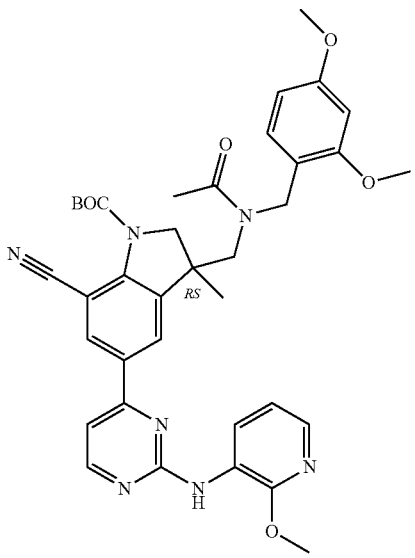

To a solution of intermediate 370 (630.00 mg, 0.99 mmol) in CH₃CN (3.1 mL), Ac₂O (0.103 mL, 1.09 mmol) and pyridine (88.00 µL, 1.09 mmol) were added and stirring overnight. The mixture was concentrated to dryness. The residue was purified by column chromatography on silica gel (irregular SiOH, 40 g, mobile phase: NH₄OH/DCM/MeOH, gradient from 100% DCM to 95% DCM 5% MeOH, 0.5% NH₄OH). Fractions containing the products were collected and evaporated to dryness to give three batches as a colorless oil (batch 1: 42 mg, batch 2: 15 mg, batch 3: 727 mg). Batch 3 was purified another time by column chromatography on silica gel (irregular SiOH, 40 g, mobile phase: heptane/EtOAc/MeOH, gradient from 100% Heptane 0% EtOAc 1% MeOH to 0% Heptane 100% EtOAc 1% MeOH). The fractions containing the product were gathered and evaporated to dryness to provide 457 mg of intermediate 371 (68% yield, 86% purity based on LC/MS, yellow oil) and 79 mg of intermediate 371 (12% yield, 93% purity based on LC/MS, white powder).

Example A22

Preparation of Intermediate 377

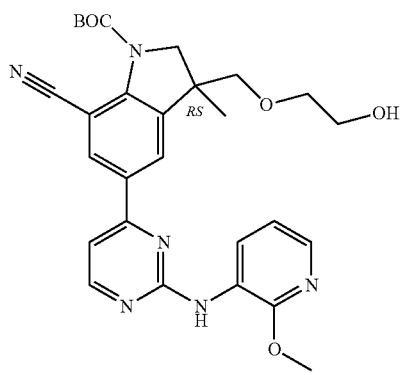

A degassed suspension of intermediate 376 (339.00 mg, 0.76 mmol), 2-methoxypyridin-3-amine (189.20 mg, 1.52 mmol), Pd(OAc)₂ (8.50 mg, 0.038 mmol), BINAP (23.70 mg, 0.038 mmol) and Cs₂CO₃ (744.80 mg, 2.29 mmol) in 1,4-dioxane (10 mL) was heated at 120° C. for 30 min using one single mode microwave (Biotage Initiator EXP 60) with a power output ranging from 0 to 400 W [fixed hold time]. The reaction mixture was cooled to rt, diluted with EtOAc and poured onto a 10% aqueous solution of K₂CO₃. The organic layer was decanted, washed with brine, dried over MgSO₄, filtered and evaporated to dryness. The residue was purified by column chromatography on silica gel (irregular SiOH, 24 g, mobile phase: heptane/EtOAc/MeOH, gradient from 20% EtOAc, 80% heptane to 1% MeOH, 60% EtOAc, 39% heptane). The pure fractions were collected and evaporated to dryness to give 350 mg of intermediate 377 (86% yield, 95% purity based on LC/MS).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
| --- | --- | --- | --- |
| Intermediate 382 | ![structure] From intermediate 376 and 2-methoxy-4-chloropyridin-3-amine | 1200 (93% purity based on LC/MS) | 65 procedure without microwave activation |

Preparation of Intermediate 378

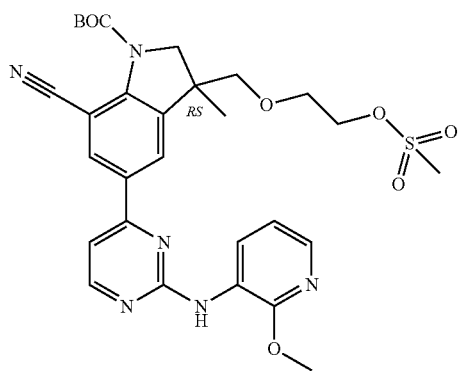

MsCl (41.00 µL, 0.53 mmol) was added dropwise at 5° C. to a solution of intermediate 377 (237.00 mg, 0.44 mmol) and TEA (148.00 µL, 1.07 mmol) in DCM (5 mL) and the reaction mixture was stirred at this temperature for 1 h. The reaction mixture was diluted with DCM and water was added. The organic layer was filtered through Chromabond® and evaporated to dryness to give 298 mg of intermediate 378 (quant. yield) and used as it is for the next step.

The intermediates in the Table below were prepared by using an analogous method starting from the respective starting materials.

| Intermediate number | Structure | Mass (mg) | Yield (%) |
|---|---|---|---|
| Intermediate 383 | 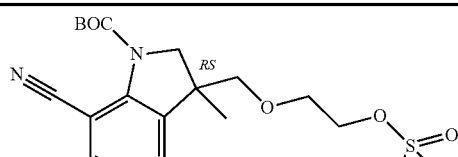<br>From intermediate 382 | 1360 | Quant. |

Preparation of Intermediate 379

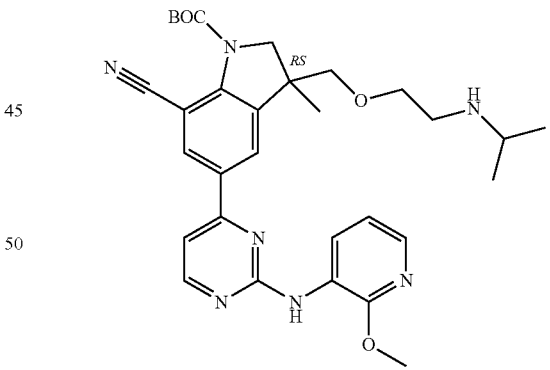

A mixture of intermediate 378 (270.00 mg, 0.44 mmol) and isopropylamine (1.90 mL, 22.11 mmol) in CH$_3$CN (5 mL) was heated at 80° C. for 3 h. The reaction mixture was gathered with another batch (from 55 mg of intermediate 378) for the work up. The resulting crude mixture was diluted with DCM and poured onto water. The organic layer was decanted, dried over MgSO$_4$, filtered and evaporated to dryness to give 282 mg of intermediate 379 (92% yield, 98% purity based on LC/MS) used as it is for the next step.

The intermediates in the Table below were prepared by using an analogous method starting from the respective starting materials.

| Intermediate number | Structure | Mass (mg) | Yield (%) |
|---|---|---|---|
| Intermediate 380 | 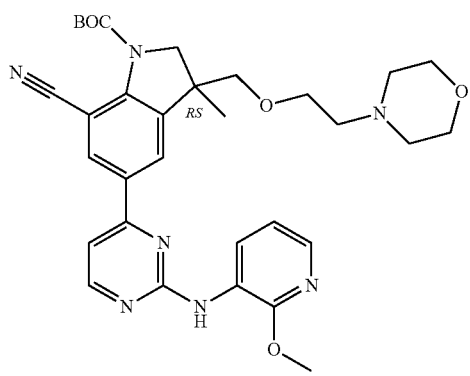 [SMILES: COc1ncccc1Nc1nccc(-c2cc(C#N)c3c(c2)C(C)(COCCN2CCOCC2)CN3C(=O)OC(C)(C)C)n1]<br>From intermediate 378 and morpholine | 402 | 88 |
| Intermediate 381 | 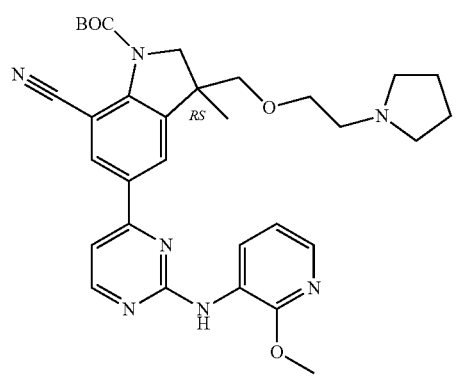 [SMILES: COc1ncccc1Nc1nccc(-c2cc(C#N)c3c(c2)C(C)(COCCN2CCCC2)CN3C(=O)OC(C)(C)C)n1]<br>From intermediate 378 and pyrrolidine | 395 | 89 |
| Intermediate 384 | 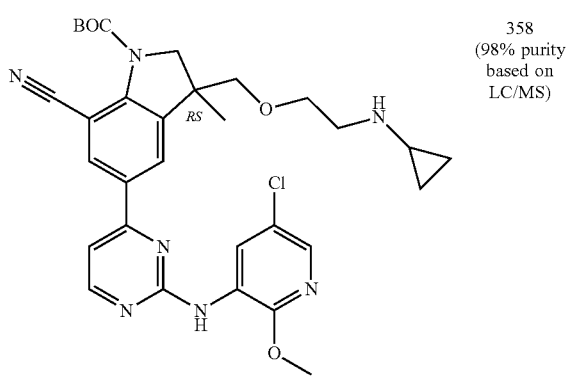<br>From intermediate 383 and cyclopropylamine | 358<br>(98% purity based on LC/MS) | 84 |

-continued

| Intermediate number | Structure | Mass (mg) | Yield (%) |
|---|---|---|---|
| Intermediate 385 | 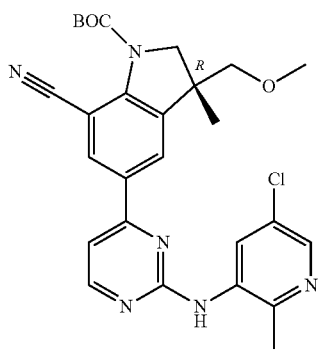  From intermediate 383 and pyrrolidine | 340 (99% purity based on LC/MS) | 78 |
| Intermediate 386 | From intermediate 383 and morpholine | 400 (91% purity based on LC/MS) | 90 |

Example A23

Preparation of Intermediate 390

A mixture of intermediate 389 (0.27 g, 0.65 mmol), $Cs_2CO_3$ (636.10 mg, 1.95 mmol) and 3-amino-5-chloropicoline (139.20 mg, 0.98 mmol) in 1,4-dioxane (6.70 mL) was purged with $N_2$. Then $Pd(OAc)_2$ (14.60 mg, 0.065 mmol) and BINAP (40.50 mg, 0.065 mmol) were added. The mixture was purged with $N_2$ and stirred at 90° C. for 9 h. An extraction was performed with EtOAc and water. The organic layer was washed with brine, dried and evaporated to give a black oil. The residue (450 mg) was purified on silica gel (irregular SiOH, 40 g, mobile phase: heptane/EtOAc/MeOH, gradient from 0% EtOAc, 100% heptane to 60% EtOAc, 40% heptane, 1% MeOH). The fractions containing the product were collected and evaporated to dryness to give 201 mg of intermediate 390 (59% yield, 95% purity based on LC/MS, yellow oil).

Example A24

Preparation of Intermediate 9

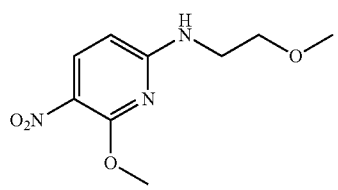

A mixture of 6-chloro-2-methoxy-3-nitropyridine (0.50 g, 2.65 mmol), 2-methoxyethanolamine (277.00 μL, 3.19 mmol) and DIPEA (1.40 mL, 8.04 mmol) in 2-propanol (5 ml) was heated at 120° C. for 30 min using one single mode microwave (Biotage Initiator EXP 60) with a power output ranging from 0 to 400 W for 15 min [fixed hold time]. The reaction mixture was cooled to rt, partitioned between water and EtOAc. The organic layer was dried over MgSO$_4$, filtered and concentrated to afford 460 mg of intermediate 9 (76% yield) which was directly engaged in the next step without any further purification.

The intermediates in the Table below were prepared by using an analogous method starting from the respective starting materials.

| Intermediate number | Structure | Mass (mg) | Yield (%) |
|---|---|---|---|
| Intermediate 36 | (structure) From intermediate 35 | 885 | 67 |
| Intermediate 113 | (structure) 6-chloro-2-methoxy-3-nitropyridine | 780 | 76 |
| Intermediate 165 | (structure) 2-fluoro-5-nitro-6-picoline | 2630 | 91 |

Preparation of Intermediate 10

A mixture of intermediate 9 (1.00 g, 4.40 mmol) and NCS (705.00 mg, 5.28 mmol) in CH$_3$CN (13 mL) was heated at 85° C. for 30 min using one single mode microwave (Biotage Initiator EXP 60) with a power output ranging from 0 to 400 W [fixed hold time]. The reaction was performed three times on the same quantity of intermediate 9 (1.00, 4.40 mmol; 3.00 g, 13.20 mmol). The reaction mixtures were combined and partitioned between water and EtOAc. The organic layer was decanted, dried over MgSO$_4$, filtered and evaporated to dryness. The residue was purified by column chromatography on silica gel (irregular SiOH, 40 g, mobile phase: heptane/MeOH/EtOAc, gradient from 0% MeOH, 30% EtOAc, 70% heptane to 2% MeOH, 48% EtOAc, 50% heptane). The pure fractions were collected and evaporated to dryness to give 1.9 g of intermediate 10 (55% yield).

The intermediates in the Table below were prepared by using an analogous method starting from the respective starting materials

| Intermediate number | Structure | Mass (mg) | Yield (%) |
|---|---|---|---|
| Intermediate 37 | (structure) From intermediate 36 | 459 | 66 |

| Intermediate number | Structure | Mass (mg) | Yield (%) |
|---|---|---|---|
| Intermediate 114 | 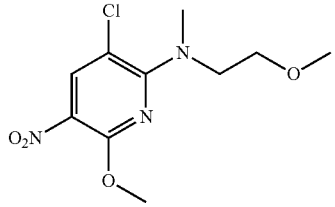<br>From intermediate 113 | 990<br>yellow oil | — |
| Intermediate 166 | 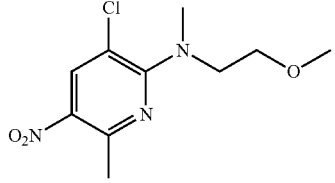<br>From intermediate 165 | 2950<br>yellow oil | Quant. |

Preparation of Intermediate 11

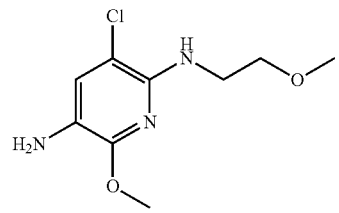

A mixture of intermediate 10 (500.00 mg, 1.91 mmol), NH$_4$Cl (409.00 mg, 7.64 mmol) and Iron powder (534.00 mg, 9.55 mmol) in EtOH (6 mL) and distilled water (9 mL) was heated at 75° C. for 1 h. The reaction mixture was cooled to rt, diluted with DCM and filtered through a pad of Celite®. The solution was poured onto a 10% aqueous solution of K$_2$CO$_3$. The organic layer was decanted, dried over MgSO$_4$, filtered and evaporated to dryness to give 456 mg of intermediate 11 used immediately as it is for the next step.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 32 | 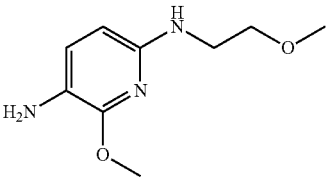 [SMILES: COCCNc1ccc([N+](=O)[O-])c(OC)n1]<br>From intermediate 9 | 206 | 95 |
| Intermediate 38 | 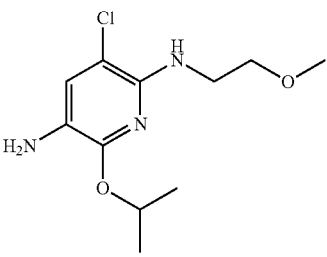<br>From intermediate 37 | 198<br>(>97%<br>purity based<br>on LC/MS) | 98 |

-continued
| Intermediate number | Structure | Mass (mg) | Yield (%) |
|---|---|---|---|
| Intermediate 49 | 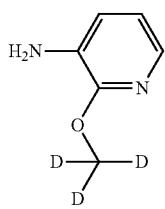 [SMILES: [2H]C([2H])([2H])Oc1ncccc1N] From 2-methoxy-3-nitropyridine | 600 | Quant. |
| Intermediate 55 | 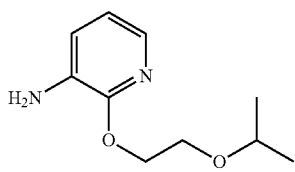 From intermediate 54 | 1026 | 77 |
| Intermediate 61 | 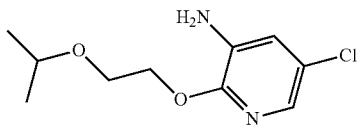 From intermediate 60 | 1668 | 91 |
| Intermediate 65 | 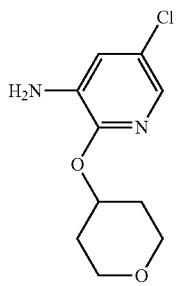 [SMILES: Nc1cc(Cl)cnc1OC1CCOCC1] From intermediate 64 | 1096 | 93 |
| Intermediate 69 | 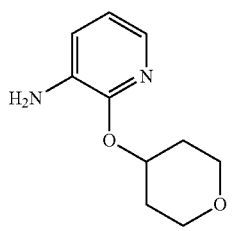 [SMILES: Nc1cccnc1OC1CCOCC1] From intermediate 68 | 1569 (85% purity based on NMR) 1334 | 43 31 |
| Intermediate 75 | 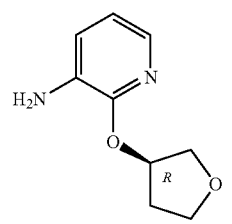 From intermediate 74 | 1150 | 93 |

-continued

| Intermediate number | Structure | Mass (mg) | Yield (%) |
|---|---|---|---|
| Intermediate 79 | From intermediate 78 | 768 | 95 |
| Intermediate 83 | From intermediate 82 | 727 | 89 |
| Intermediate 87 | From intermediate 86 | 1040 | 91 |
| Intermediate 93 | From intermediate 92 | 940 | Quant. |
| Intermediate 101 | From intermediate 100 | 1650 | 76 |
| Intermediate 106 | 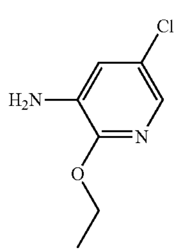 | 298 | 70 |

-continued
| Intermediate number | Structure | Mass (mg) | Yield (%) |
|---|---|---|---|
| | From 5-chloro-2-ethoxy-3-nitropyridine | | |
| Intermediate 115 | 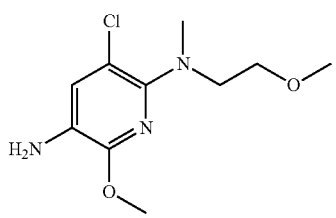 | 438 | 55 procedure with T = 85° C. |
| | From intermediate 114 | | |
| Intermediate 119 | 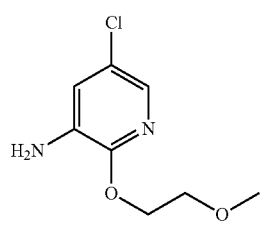 | 536 (82% purity based on LC/MS) | 80 |
| | From intermediate 118 | | |
| Intermediate 123 | 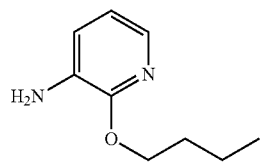 | 606 | 97 |
| | From intermediate 122 | | |
| Intermediate 131 | 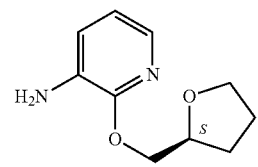 | 649 | 92 |
| | From intermediate 122 | | |
| Intermediate 135 | 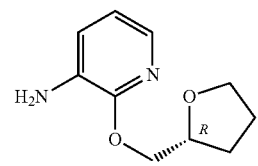 | 884 | 94 |
| | From intermediate 134 | | |
| Intermediate 143 | 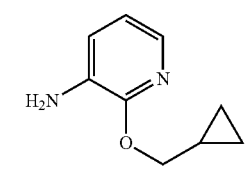 [SMILES: Nc1cccnc1OCC1CC1] | 882 | 97 |
| | From intermediate 142 | | |

| Intermediate number | Structure | Mass (mg) | Yield (%) |
|---|---|---|---|
| Intermediate 147 | 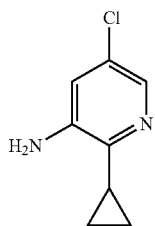<br>From intermediate 146 | 207 | 94 |
| Intermediate 151 | 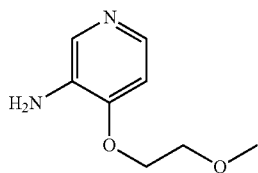<br>From intermediate 150 | 484 | Quant. |
| Intermediate 155 | 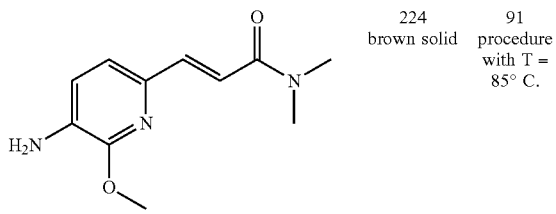<br>From intermediate 154 | 224<br>brown solid | 91<br>procedure with T = 85° C. |
| Intermediate 167 | 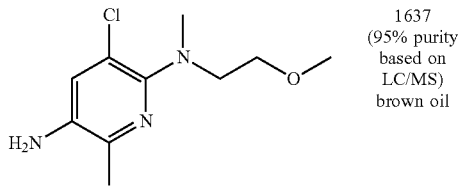<br>From intermediate 166 | 1637<br>(95% purity based on LC/MS)<br>brown oil | 63 |
| Intermediate 171 | 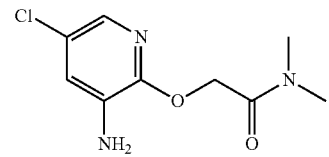<br>From intermediate 170 | 725 | 78 |
| Intermediate 183 | 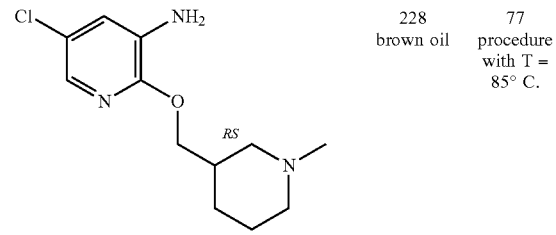<br>From intermediate 182 | 228<br>brown oil | 77<br>procedure with T = 85° C. |

-continued

| Intermediate number | Structure | Mass (mg) | Yield (%) |
|---|---|---|---|
| Intermediate 203 | 5-fluoro-2-(2-methoxyethoxy)pyridin-3-amine<br>From intermediate 202 | 489 | 95 |
| Intermediate 207 | 6-cyclopropyl-2-(2-methoxyethoxy)pyridin-3-amine<br>From intermediate 206 | 435 | 90 |
| Intermediate 254 | 5-amino-6-(cyclopropylmethoxy)nicotinonitrile<br>From intermediate 253 | 230 | 87 |
| Intermediate 257 | 5-amino-6-isopropoxynicotinonitrile<br>From intermediate 256 | 78 | 68 |
| Intermediate 260 | 5-amino-6-((3-methyloxetan-3-yl)methoxy)nicotinonitrile<br>From intermediate 259 | 102 | 48 |
| Intermediate 263 | 5-amino-6-(2-hydroxy-2-methylpropoxy)nicotinonitrile<br>From intermediate 262 | 160<br>(80% purity based on LC/MS) | 100 |
| Intermediate 266 | 5-amino-6-((1-hydroxy-2-methylpropan-2-yl)oxy)nicotinonitrile<br>From intermediate 265 | 94<br>(85% purity based on LC/MS) | 59 |

-continued

| Intermediate number | Structure | Mass (mg) | Yield (%) |
|---|---|---|---|
| Intermediate 287 | 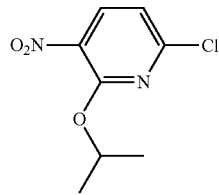<br>From intermediate 286 | 108<br>(99% purity based on LC/MS) | 77 |
| Intermediate 339 | 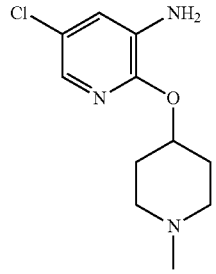<br>From intermediate 338 | 68<br>(90% purity based on LC/MS)<br>dark purple oil | 76 |

Example A25

Preparation of Intermediate 35

NaH (60% dispersed in mineral oil) (269.00 mg, 6.7 mmol) was added portionwise at 5° C. to a solution of 2,6-dichloro-3-nitropyridine (1.00 g, 5.18 mmol) and iPrOH (476.00 µL, 6.22 mmol) in toluene (50 mL). The reaction mixture was allowed to warm to rt and stirred overnight. The reaction mixture was poured onto a 10% aqueous solution of $K_2CO_3$ and extracted thrice with EtOAc. The organic layer was decanted, washed with brine, dried over $MgSO_4$, filtered and evaporated to dryness to give 1.15 g of intermediate 35 (quant. yield).

The intermediates in the Table below were prepared by using an analogous method starting from the respective starting materials.

| Intermediate number | Structure | Mass (mg) | Yield (%) |
|---|---|---|---|
| Intermediate 43 | 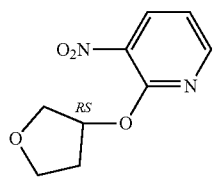<br>From 2,5-dichloro-3-nitropyridine | 385<br>brown oil | — |

Example A26

Preparation of Intermediate 44

Intermediate 43 (385.00 mg, 1.42 mmol) was diluted in EtOAc (10.5 mL), and platinum (553.00 mg, 142.00 µmol) and $ZnBr_2$ (64.00 mg, 284.00 µmol) were added. The mixture was hydrogenated under an atmosphere of $H_2$ (1 bar) at rt for 17 h. The reaction mixture was filtered on a pad of Celite® and the filtrate was concentrated under reduced pressure to give 290 mg of intermediate 44 (85% yield, 95% purity based on LC/MS).

Example A27

Preparation of Intermediate 54

3-hydroxytetrahydrofuran (869.00 µL, 10.56 mmol) was diluted in THF (33.5 mL). Then, the solution was cooled to 0° C. and LiHMDS (10.00 mL, 10.56 mmol) was added. After 30 min, 2-fluoro-3-nitropyridine (1.50 g, 10.56 mmol) was quickly added and the reaction mixture was stirred overnight allowing the temperature to reach rt. The reaction mixture was mixed with another batch (from 100 mg of 2-fluoro-3-nitropyridine) and partitioned between water and EtOAc. The organic layer was separated, dried over MgSO$_4$, filtered and concentrated to afford 2.03 g of intermediate 54 (91% yield) which was directly engaged in the next steps without any further treatment.

The intermediates in the Table below were prepared by using an analogous method starting from the respective starting materials.

| Intermediate number | Structure | Mass (mg) | Yield (%) |
|---|---|---|---|
| Intermediate 60 | 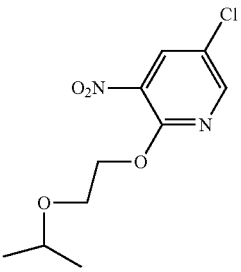<br>From 5-Chloro-2-fluoro-3-nitropyridine | 2000 | 95 |
| Intermediate 64 | 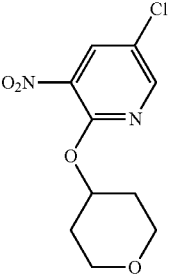<br>From 5-Chloro-2-fluoro-3-nitropyridine | 1340 | Quant. |
| Intermediate 68 | 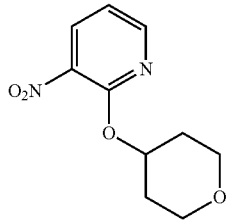<br>From 2-fluoro-3-nitropyridine | 1540 | 98 |
| Intermediate 74 | 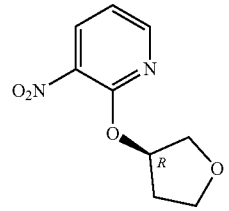<br>From 2-fluoro-3-nitropyridine | 1440 | 97 |
| Intermediate 78 | 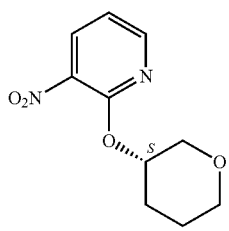<br>From 2-fluoro-3-nitropyridine | 936 | 99 |

-continued

| Intermediate number | Structure | Mass (mg) | Yield (%) |
|---|---|---|---|
| Intermediate 82 | (3-nitro-2-((R)-tetrahydro-2H-pyran-3-yloxy)pyridine) From 2-fluoro-3-nitropyridine | 944 | Quant. |
| Intermediate 86 | (3-nitro-2-((S)-tetrahydrofuran-3-yloxy)pyridine) From 2-fluoro-3-nitropyridine | 1340 | 91 |
| Intermediate 92 | (5-chloro-2-isopropoxy-3-nitropyridine) From 5-chloro-2-fluoro-3-nitropyridine | 1090 | 89 |
| Intermediate 122 | (2-butoxy-3-nitropyridine) From 2-fluoro-3-nitropyridine | 737 | 53 |
| Intermediate 130 | (3-nitro-2-(((S)-tetrahydrofuran-2-yl)methoxy)pyridine) From 2-fluoro-3-nitropyridine | 816 | 96 |
| Intermediate 134 | (3-nitro-2-(((R)-tetrahydrofuran-2-yl)methoxy)pyridine) From 2-fluoro-3-nitropyridine | 1090 | Quant. |

-continued

| Intermediate number | Structure | Mass (mg) | Yield (%) |
|---|---|---|---|
| Intermediate 142 | 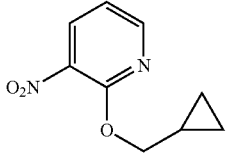<br>From 2-fluoro-3-nitropyridine | 1070 | 78 |
| Intermediate 150 | 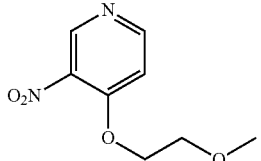<br>From 4-chloro-3-nitropyridine | 560 | 45 |
| Intermediate 170 | 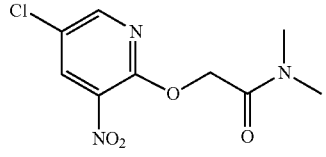<br>From 5-chloro-2-fluoro-3-nitropyridine | 1051 | 71 |
| Intermediate 202 | 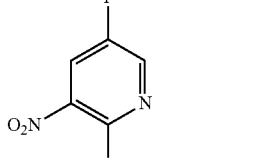<br>From 2-chloro-5-fluoro-3-nitropyridine | 613 | 50 |
| Intermediate 253 | 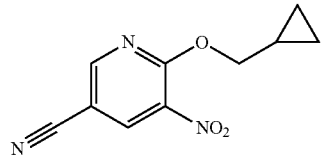 [SMILES: N#Cc1cnc(OCC2CC2)c(N)c1]<br>From 6-bromo-5-nitropyridine-3-carbonitrile | 278 | 43 |
| Intermediate 256 | 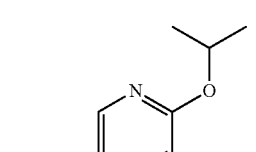<br>From 6-bromo-5-nitropyridine-3-carbonitrile | 142 | 24 |

-continued

| Intermediate number | Structure | Mass (mg) | Yield (%) |
|---|---|---|---|
| Intermediate 259 | 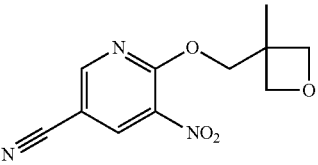 [SMILES: CC1(COc2ncc(C#N)cc2N)COC1]<br>From 6-bromo-5-nitropyridine-3-carbonitrile | 242 | 35 |
| Intermediate 262 | 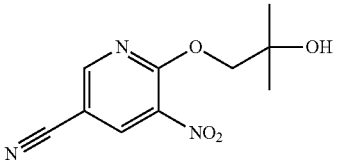<br>From 6-bromo-5-nitropyridine-3-carbonitrile | 183 | 28 |
| Intermediate 265 | 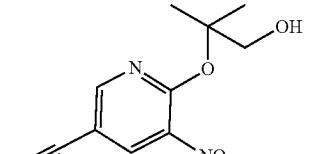<br>From 6-bromo-5-nitropyridine-3-carbonitrile | 133 | 20 |
| Intermediate 286 | 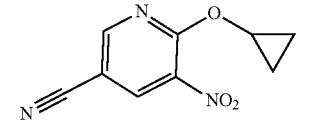<br>From 6-bromo-5-nitropyridine-3-carbonitrile | 165 | 23 |
| Intermediate 289 | 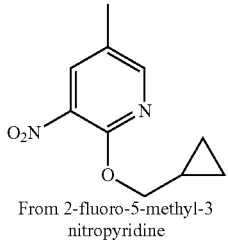<br>From 2-fluoro-5-methyl-3 nitropyridine | 1260 (98% purity based on LC/MS) | 94 |
| Intermediate 309/ Intermediate 310 | 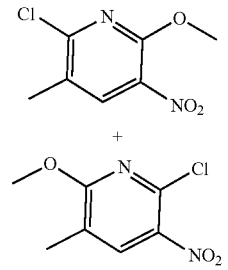<br>From 2,6-dichloro-3-methyl-5-nitropyridine | 1549 | 79 |

383

Example A28

Preparation of Intermediate 100

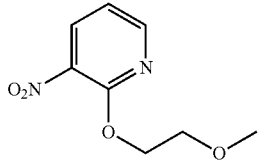

A mixture of 2-chloro-3-nitropyridine (2.00 g, 12.61 mmol), 2-methoxyethanol (1.20 mL, 15.14 mmol) and $Cs_2CO_3$ (7.81 g, 23.97 mmol) in DMF (32 mL) was stirred all over the week end at rt. Additional 2-methoxyethanol (1.20 mL, 15.14 mmol) was added and the reaction mixture was heated at 80° C. overnight. The reaction mixture was poured into ice and extracted with EtOAc and $Et_2O$. The organic layer was washed with brine, dried over $MgSO_4$, filtered and evaporated to dryness to give 2.15 g of intermediate 100 (86% yield) used as it for the next step.

The intermediates in the Table below were prepared by using an analogous method starting from the respective starting materials.

| Intermediate number | Structure | Mass (mg) | Yield (%) |
|---|---|---|---|
| Intermediate 118 | ![structure] From 2,5-dichloro-3-nitropyridine | 629 | 15 |

384

Example A29

Preparation of Intermediate 138

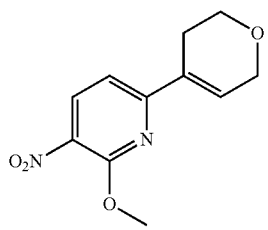 [SMILES: COc1nc(C2=CCOCC2)ccc1[N+](=O)[O-]]

In a Shlenck reactor, a solution of 6-chloro-2-methoxy-3-nitropyridine (1.00 g, 5.30 mmol), 3,6-dihydro-2H-pyran-4-boronic acid pinacol ester (1.23 g, 5.83 mmol) and $K_3PO_4$ (3.38 g, 15.90 mmol) in 1,4-dioxane (44 mL) and distilled water (9 mL) was degassed under $N_2$. [1,1'-bis(diphenylphosphino)ferrocene]dichloropalladium (II), complex with dichloromethane (434.00 mg, 0.53 mmol) was added, the mixture was degassed again under $N_2$ and heated at 80° C. for 4 h. The mixture was extended with EtOAc and filtered on a pad of Celite®. The cake was washed with EtOAc and water. The layers were separated and the organic layer was dried over $MgSO_4$, filtered off and evaporated in vacuo to give a brown solid. The residue was purified by column chromatography on silica gel (irregular SiOH, 15-40 µm, 50 g, dry loading on Celite®, mobile phase: heptane/EtOAc, gradient: 95:5 to 60:40) to give 922 mg of intermediate 138 (74% yield, yellow solid).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 427 | From 2-chloro-4-methoxy-5 pyrimidinamine | 540 brown solid | 83 procedure with T = 90° C. |

-continued

| Intermediate number | Structure | Mass (mg) | Yield (%) |
|---|---|---|---|
| Intermediate 431 | 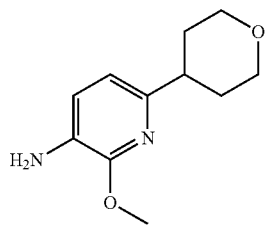<br>From 2-chloro-4-methoxy-5 pyrimidinamine | 244<br>brown solid | 99<br>procedure with T = 90° C. |

Preparation of Intermediate 139

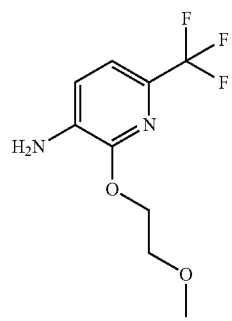

Pd/C (10 wt. %, 208.00 mg, 0.19 mmol) was added to a solution of intermediate 138 (922.00 mg, 3.90 mmol) in EtOH (20 mL) under $N_2$. The mixture was stirred at rt under an $H_2$ atmosphere ($P_{atm}$) overnight. The mixture was filtered on a pad of Celite® and the filtrate was evaporated in vacuo to give 800 mg of intermediate 139 (98% yield, white solid).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 159 | From intermediate 154 | 230<br>orange oil | 90 |
| Intermediate 175 | From intermediate 174 | 352 | 97 |

-continued

| Intermediate number | Structure | Mass (mg) | Yield (%) |
|---|---|---|---|
| Intermediate 179 | From intermediate 178 | 740 | 92 |
| Intermediate 192 | From intermediate 191 | 350 colourless oil | 99 procedure with 4 bars pressure of $H_2$ |
| Intermediate 215 | From intermediate 214 | 300 | 11 |
| Intermediate 219 | From intermediate 218 | 35 | 18 |
| Intermediate 226 | From intermediate 225 | 774 (91% purity based on LC/MS) orange oil | 88 |

-continued

| Intermediate number | Structure | Mass (mg) | Yield (%) |
|---|---|---|---|
| Intermediate 234 | From intermediate 233 | 968 pale brown oil | 96 |
| Intermediate 247 | From intermediate 246 | 1330 pale pink solid | 85 |
| Intermediate 272 | From intermediate 271 | 344 pale yellow cristals | 97 procedure with (EtOAc/ Me—THF, 1:1, v/v) as solvent |
| Intermediate 294 | From intermediate 294 | 930 white solid | 41 procedure with MeOH as solvent |
| Intermediate 302 | From intermediate 299 | 196 (93% purity based on LC/MS) brown oil | 70 procedure with MeOH as solvent |

-continued
| Intermediate number | Structure | Mass (mg) | Yield (%) |
|---|---|---|---|
| Intermediate 416 | 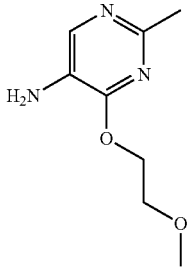<br>From intermediate 415 | 306<br>pink oil | 73 |
| Intermediate 420 | 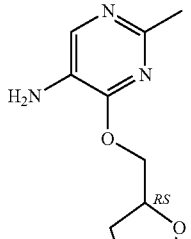<br>From intermediate 419 | 770<br>orange oil | 76 |
| Intermediate 428 | 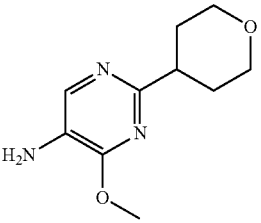<br>From intermediate 427 | 256<br>brown solid | 99 |
| Intermediate 432 | 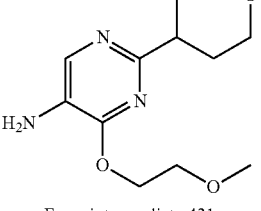<br>From intermediate 431 | 212<br>black solid | 86 |
| Intermediate 436 | 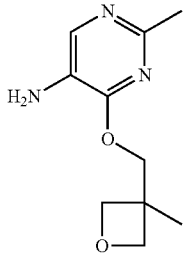<br>From intermediate 435 | 374<br>(97% purity based on LC/MS)<br>orange crystals | Quant. |

| Intermediate number | Structure | Mass (mg) | Yield (%) |
|---|---|---|---|
| Intermediate 442 | From intermediate 441 | 318 pink solid | — |

Example A30

Preparation of Intermediate 146

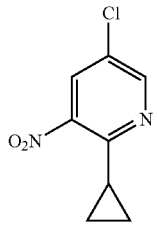 [SMILES: O=[N+]([O-])c1cc(Cl)cnc1C1CC1]

Di-(1-adamantyl)-N-butylphosphine (143.00 mg, 0.40 mmol) and Pd(OAc)$_2$ (89.00 mg, 0.40 mmol) were added to a degassed (N$_2$) solution of 2,5-dichloro-3-nitropyridine (770.00 mg, 4.00 mmol), potassium cyclopropyltrifluoroborate (767.00 mg, 5.19 mmol) and Cs$_2$CO$_3$ (2.60 g, 7.98 mmol) in a mixture of 1,4-dioxane (18 mL) and distilled water (4 mL). The reaction mixture was then heated at 100° C. for 18 h, cooled to rt, poured onto water and extracted with DCM. The organic layer was decanted, dried over MgSO$_4$, filtered and evaporated to dryness. The residue was purified by column chromatography on silica gel (irregular SiOH, 24 g, mobile phase: heptane/DCM, gradient from 70:30 to 20:80). The pure fractions were collected and evaporated to dryness to give 190 mg of intermediate 146 (24% yield).

The intermediates in the Table below were prepared by using an analogous method starting from the respective starting materials.

| Intermediate number | Structure | Mass (mg) | Yield (%) |
|---|---|---|---|
| Intermediate 206 | From intermediate 197 | 566 | 55 |

Example A31

Preparation of Intermediate 154

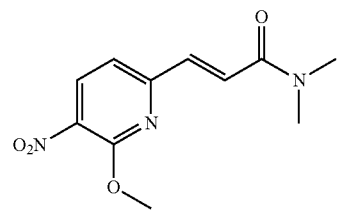

In a Shlenck reactor, to a solution of 6-chloro-2-methoxy-3-nitropyridine (1.00 g, 5.30 mmol) in DMF (50 mL), N,N-dimethylacrylamide (820.00 µL, 7.96 mmol) and TEA (2.21 mL, 15.90 mmol) were added. The mixture was degassed under N$_2$ and [1,1'-bis(diphenylphosphino)ferrocene]dichloropalladium (II), complex with dichloromethane (434.00 mg, 0.53 mmol) was added. The mixture was degassed again with N$_2$ and stirred at 100° C. overnight. The mixture was evaporated in vacuo. The residue was taken-up in EtOAc and brine and filtered on a pad of Celite®. The cake was washed with EtOAc. The layers were separated and the organic layer was washed with brine. The organic layer was dried over MgSO$_4$, filtered off and evaporated in vacuo to give a black solid. The residue (2.4 g) was purified by column chromatography on silica gel (irregular SiOH, 15-40 µm, 50 g, dry loading on Celite®, mobile phase: heptane/EtOAc/MeOH, gradient: from heptane 70%, EtOAc 27%, MeOH 3% to heptane 40%, EtOAc 54%, MeOH 6%). The pure fractions were combined and evaporated to dryness to give 566 mg of intermediate 154 (43% yield, orange solid).

The intermediates in the Table below were prepared by using an analogous method starting from the respective starting materials.

| Intermediate number | Structure | Mass (mg) | Yield (%) |
|---|---|---|---|
| Intermediate 250 | ![structure] From 3-amino-6-chloro-2-picoline | 762 (91% purity based on LC/MS) dark grey powder | 26 procedure with T = 120° C. |
| Intermediate 299 | ![structure] From intermediate 276 | 600 (94% purity based on LC/MS) brown oil | 47 procedure with T = 120° C. |

Example A32

Preparation of Intermediate 174

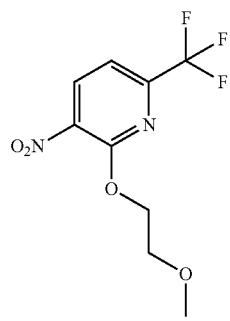 [SMILES: COCCOc1nc(C(F)(F)F)ccc1[N+](=O)[O-]]

NaH (60% dispersed in mineral oil) (111.00 mg, 2.78 mmol) was added slowly to dry 2-methoxyethanol (6 mL) at 0° C. (bubbling in the mixture). The mixture was stirred at 0° C. for 10 min and then, a solution of 2-chloro-3-nitro-6-(trifluoromethyl)pyridine (450.00 mg, 1.99 mmol) in 2-methoxyethanol (1 mL) was added dropwise (yellow coloration). The mixture was stirred at 0° C. for 1 h. The mixture was quenched with water and stirred for 1 h. EtOAc and brine were added and the layers were separated. The aqueous layer was extracted with EtOAc and the combined organic layers were dried over MgSO$_4$, filtered off and evaporated in vacuo to give an orange oil. The residue was purified by column chromatography on silica gel (irregular SiOH, 15-40 μm, 24 g, mobile phase: heptane/EtOAc, gradient: from 95:5 to 70:30). The fractions containing the product were combined and concentrated in vacuo to give 410 mg of intermediate 174 (78% yield, colorless liquid).

The intermediates in the Table below were prepared by using an analogous method starting from the respective starting materials.

| Intermediate number | Structure | Mass (mg) | Yield (%) |
|---|---|---|---|
| Intermediate 178 | ![structure] From 2-chloro-3-nitro-6-(trifluoromethyl)pyridine | 303 | 69 |

-continued

| Intermediate number | Structure | Mass (mg) | Yield (%) |
|---|---|---|---|
| Intermediate 182 | ![structure] From 2,5-dichloro-3-nitropyridine | 332 brown oil | 22 with toluene as solvent |
| Intermediate 186 | ![structure] From 2,6-dichloro-3-nitropyridine | 4700 brown residue | Quant with toluene as solvent |
| Intermediate 197 | ![structure] From 2,6-dichloro-3-nitropyridine | 1460 yellow oil | 61 with toluene as solvent |
| Intermediate 224 | ![structure] From 5-bromo-2-chloro-3-nitropyridine | 1630 orange liquid | 67 with Me—THF as solvent |
| Intermediate 233 | ![structure] From 2-fluoro-5-methyl-3-nitropyridine | 1170 yellow oil | 86 |

Example A33

Preparation of Intermediate 187

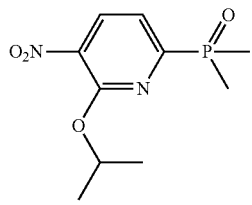

In a sealed tube, a mixture of intermediate 186 (800.00 mg, 3.69 mmol), dimethylphosphine oxide (341.00 mg, 4.06 mmol, purity 93%) and $K_3PO_4$ (862.00 mg, 4.06 mmol) in DMF (14.6 mL) was purged with $N_2$. $Pd(OAc)_2$ (83.00 mg, 0.37 mmol) and 4,5-bis(diphenylphosphino)-9,9-dimethylxanthene (214.00 mg, 0.37 mmol) were added. The mixture was purged with $N_2$ and stirred at 150° C. for 16 h. The mixture was evaporated in vacuo. The residue was diluted with DCM and water. The aqueous layer was extracted twice with DCM and the layers were separated. The combined organic layers were washed twice with brine, dried with $MgSO_4$, filtered and the solvent was removed under reduced pressure to give a brown oil. The residue was purified by column chromatography on silica gel (irregular SiOH 15-40 μm, 24 g, dry load on Celite®, mobile phase: DCM/MeOH (+10% aq. $NH_3$), gradient: from 100:0 to 80:20). The pure fractions were combined and evaporated under vacuum to give 330 mg of intermediate 187 (35% yield).

The intermediates in the Table below were prepared by using an analogous method starting from the respective starting materials.

| Intermediate number | Structure | Mass (mg) | Yield (%) |
|---|---|---|---|
| Intermediate 198 | From intermediate 197 | 439 (81% purity based on LC/MS) | 27% (over 2 steps) |
| Intermediate 306 | From intermediate 305 | 1194 orange solid | 60 |
| Intermediate 328 | From intermediate 327 | 405 pale red solid | 65 |
| Intermediate 424 | From intermediate 423 | 130 (94% purity based on LC/MS) brown solid | 35 |

Preparation of Intermediate 188

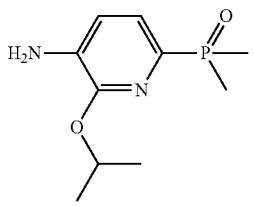 [SMILES: CC(C)Oc1nc(P(C)(C)=O)ccc1[N+](=O)[O-]]

A mixture of intermediate 187 (310.00 mg, 1.20 mmol), Zn (785.00 mg, 12.00 mmol) and AcOH (0.69 mL, 12.00 mmol) in MeOH (5.70 mL) was stirred at rt for 16 h. The mixture was filtered on a pad of Celite® and the filtrate was diluted with DCM/MeOH (9/1) and water. The aqueous layer was saturated with $K_2CO_3$ powder and the layers were separated. The aqueous layer was extracted twice with DCM/MeOH (9/1). The combined organic layers were washed with brine, dried with $MgSO_4$, filtered and the solvent was removed under reduced pressure to give 260 mg of intermediate 188 (95% yield, brown oil).

The intermediates in the Table below were prepared by using an analogous method starting from the respective starting materials.

| Intermediate number | Structure | Mass (mg) | Yield (%) |
|---|---|---|---|
| Intermediate 199 | From intermediate 198 | 337 brown oil | 86 |

-continued

| Intermediate number | Structure | Mass (mg) | Yield (%) |
|---|---|---|---|
| Intermediate 290 | 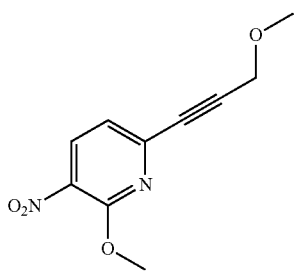 [SMILES: COCC#Cc1ccc([N+](=O)[O-])c(OC)n1]<br>From intermediate 289 | 1010 | 94 |

Example A34

Preparation of Intermediate 191

In a sealed glassware, a mixture of 6-chloro-2-methoxy-3-nitropyridine (0.70 g, 3.71 mmol), methyl propargyl ether (0.31 mL, 3.71 mmol) and $Cs_2CO_3$ (3.63 g, 11.10 mmo) in dry $CH_3CN$ (7.40 mL) was purged with $N_2$. Then dichlorobis(acetonitrile)palladium (II) (48.00 mg, 0.19 mmol) and XPhos (177.00 mg, 0.37 mmol) were added. The mixture was purged with $N_2$ and stirred at 95° C. for 2 h. An extraction was performed with EtOAc and water and the layers were separated. The organic layer was dried over $MgSO_4$, filtered and the solvent was removed under reduced pressure to give a brown oil. The residue was purified by column chromatography on silica gel (irregular SiOH 15-40 µm, 40 g, dry loading on Celite®, mobile phase: heptane/EtOAc, gradient from 80:20 to 50:50). The pure fractions were combined and evaporated to dryness to give 440 mg of intermediate 191 (53% yield, pale brown solid).

Example A35

Preparation of Intermediate 210

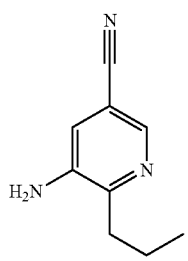

A solution of 5-amino-6-bromo-3-pridinecarbonitrile (500.00 mg, 2.53 mmol) in THF (12 mL), was added to a premixed degassed solution of bis(tri-tert-butyl-phosphine)palladium (0) (129.00 mg, 0.25 mmol) in n-propyl bromide/THF (0.5 M, 10 mL) and the reaction mixture was stirred at rt for 3 h. The reaction mixture was poured onto a 10% aqueous solution of $K_2CO_3$ and EtOAc was added. The mixture was filtered through a pad of Celite® and the organic layer was decanted, washed with water, dried over $MgSO_4$, filtered and evaporated to dryness. The residue was purified by column chromatography on silica gel (irregular SiOH, 24 g, mobile phase: heptane/EtOAc, gradient from 90:10 to 70:30). The pure fractions were collected and evaporated to dryness to give 311 mg of intermediate 210 (76% yield).

The intermediates in the Table below were prepared by using an analogous method starting from the respective starting materials.

| Intermediate number | Structure | Mass (mg) | Yield (%) |
|---|---|---|---|
| Intermediate 222 | 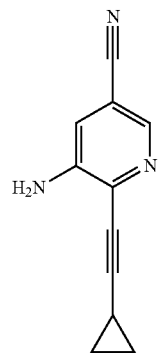<br>From 5-amino-6-bromo-3-pridinecarbonitrile | 309 | 70 |

Example A36

Preparation of Intermediate 214

In a sealed vessel, 5-amino-6-bromo-3-pridinecarbonitrile (5.00 g, 25.25 mmol), cyclopropylacetylen (4.50 mL, 53.17 mmol) and TEA (10.80 mL, 75.75 mmol) were diluted in DMF (150 mL). The reaction mixture was degassed ($N_2$ bubbling) and $PdCl_2(PPh_3)_2$ (886.00 mg, 1.26 mmol) and CuI (967.00 mg, 5.05 mmol) were added. The reaction mixture was degassed with $N_2$ and stirred at rt for 2 h. The reaction mixture was quenched with water and extracted with a mixture of $Et_2O$ and EtOAc. The organic layer was decanted, washed with brine, dried over $MgSO_4$, filtered over a pad of Celite® and evaporated to dryness. The residue was purified by column chromatography on silica gel (irregular SiOH, 80 g, mobile phase: heptane/EtOAc, gradient from 80:20 to 40:60). The pure fractions were collected and evaporated to dryness to give 2.81 g of intermediate 214 (61% yield).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 218 | 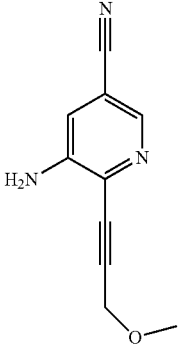<br>From 5-amino-6-bromo-3-pridinecarbonitrile | 193 | 41 |
| Intermediate 229 | 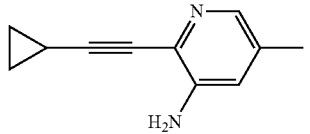<br>From 3-amino-2-bromo-5-methylpyridine | 674<br>pale brown solid | 73<br>procedure with T = 85° C. |
| Intermediate 275 | 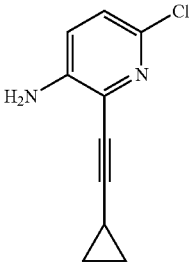<br>From 2-bromo-6-chloro-3-aminopyridine | 2970<br>(99% purity based on LC/MS)<br>beige powder<br>498<br>(93% purity based on LC/MS)<br>orange solid | 64<br>11<br>procedure with T = 90° C. |

Example A37

Preparation of Intermediate 225

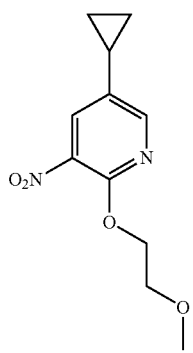 [SMILES: COCCOc1ncc(C2CC2)cc1[N+](=O)[O-]]

In a Shlenck reactor, to a solution of intermediate 224 (1.60 g, 5.78 mmol) in a mixture of 1,4-dioxane (50 mL) and distilled water (12.5 mL), cyclopropylboronic acid (1.24 g, 14.40 mmol) and 1,1'-bis(diphenylphosphino)ferrocene-palladium (ii) dichloride, DCM complex (475.00 mg, 0.58 mmol) were added. The mixture was purged with $N_2$ and $K_2CO_3$ (2.39 g, 17.30 mmol) was added. The mixture was purged again with $N_2$ and stirred at 80° C. overnight. The mixture was combined with an other batch (from 20 mg of intermediate 224), filtered on a pad of Celite® and the cake was washed with EtOAc. The filtrate was evaporated in vacuo to give a black gum. The residue (3.1 g) was purified by column chromatography on silica gel (irregular SiOH, 15-40 μm, 80 g, dry loading on Celite®, mobile phase: heptane/EtOAc, gradient from 95:5 to 70:30). The pure fractions were combined and concentrated under vacuum to give 916 mg of intermediate 225 (66% yield, yellow liquid).

Example A38

Preparation of Intermediate 230

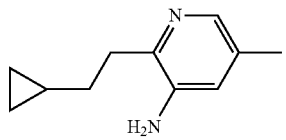

To a solution of intermediate 229 (527.00 mg, 3.06 mmol) in MeOH (11.8 mL), $CoCl_2$ (79.50 mg, 0.61 mmol) was added. The mixture was stirred at rt for 30 min then cooled down to 0° C. $NaBH_4$ (463.00 mg, 12.20 mmol) in DMF (6.6 mL) was slowly added and the mixture was stirred at 0° C. for 10 min then allowed to warm to rt and stirred for 30 min. The crude mixture was diluted with water and EtOAc. The aqueous layer was extracted twice with EtOAc. The combined organic layers were dried over $MgSO_4$, filtered off and evaporated in vacuo to give a brown oil. The residue (629 mg) was purified by column chromatography on silica gel (Irregular SiOH, 15-40 μm, 24 g, dry loading on Celite®, mobile phase: heptane/(EtOAc/MeOH (90:10)), gradient from 90:10 to 50:50). The pure fractions were combined and evaporated to dryness to give 334 mg of intermediate 230 (62% yield, 78% purity based on LC/MS, brown oil) and used as it in the next step.

The intermediates in the Table below were prepared by using an analogous method starting from the respective starting materials.

| Intermediate number | Structure | Mass (mg) | Yield (%) |
|---|---|---|---|
| Intermediate 276 | 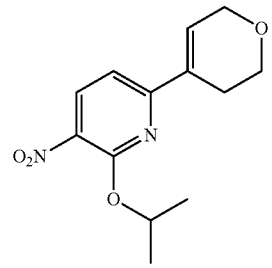 [SMILES: CC(C)Oc1nc(C2=CCOCC2)ccc1[N+](=O)[O-]]<br>From intermediate 275 | 3400 yellow oil | 40 Procedure: cooled down to −50° C. before addition of $NaBH_4$ |

Example A39

Preparation of Intermediate 246

A mixture of intermediate 186 (2.00 g, 9.23 mmol), 3,6-dihydro-2H-pyran-4-boronic acid pinacol ester (3.88 g, 18.50 mmol) and $K_2CO_3$ (1.63 g, 11.80 mmol) in a mixture of 1,4-dioxane (112 mL) and distilled water (28 mL) was purged with $N_2$. 1,1'-bis(di-tert-butylphosphino)ferrocene palladium dichloride (300.90 mg, 461.60 μmol) was added and the mixture was purged with $N_2$ and was stirred at 90° C. for 15 h. The mixture was evaporated and extracted, then water and EtOAc were added. The layers were separated and the aqueous layer was extracted thrice with EtOAc. The organic layer was washed with brine, dried over $MgSO_4$ and concentrated. The residue was purified by column chromatography on silica gel (irregular SiOH 15-40 μm, 120 g, liquid loading in DCM, mobile phase: DCM). The fractions containing the product were combined and evaporated to dryness to give 1.85 g of intermediate 246 (76% yield, pale yellow solid).

Example A40

Preparation of Intermediate 271

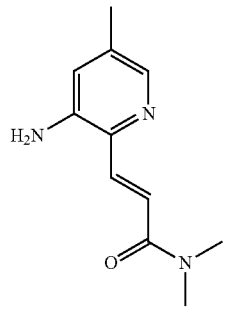

In a microwave vial, a suspension of 3-amino-2-bromo-5-methylpyridine (500.00 mg, 2.67 mmol), N,N-dimethylacrylamide (689.00 µL, 6.68 mmol), bis(di-tert-butyl(4-dimethylaminophenyl)phosphine) palladium (II) dichloride (94.60 mg, 0.13 mmol) and TEA (1.12 mL, 8.02 mmol) in DMF (12.5 mL) was purged with $N_2$ and was heated at 140° C. using one single mode microwave (Biotage Initiator) with a power output ranging from 0 to 400 W for 30 min [fixed hold time]. This reaction was performed in two batches from 500 mg of 3-amino-2-bromo-5-methylpyridine each. These two batches were combined and evaporated in vacuo. The residue was taken-up in EtOAc and water. The layers were separated and the aqueous layer was extracted twice with EtOAc and twice with DCM. The aqueous layer was saturated with $K_2CO_3$ and extracted twice with a mixture of DCM/MeOH (9:1). The combined organic layers were dried over $MgSO_4$, filtered off and evaporated in vacuo to give a brown solid. The residue (2.2 g) was purified by column chromatography on silica gel (irregular SiOH, 15-40 µm, 80 g, dry loading on Celite®, mobile phase: heptane/(EtOAc/MeOH (9:1)), gradient: from 70:30 to 15:85). The pure fractions were combined to give 815 mg of intermediate 271 (71% yield, yellow solid).

Example A41

Preparation of Intermediate 277

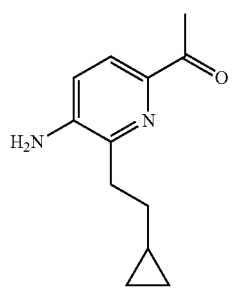

The reaction was performed in 2 batches.
In a sealed tube, a mixture of intermediate 276 (500.00 mg, 2.54 mmol), butyl vinyl ether (1.02 mL, 7.63 mmol) and $NaHCO_3$ (427.00 mg, 5.08 mmol) in MeOH (5 mL) was purged with $N_2$. $Pd(OAc)_2$ (11.40 mg, 50.80 µmol) and DPPP (31.50 mg, 76.20 µmol) was added. Then, the mixture was purged again with $N_2$ and heated at 130° C. for 1 h 30 min. This reaction was performed in 2 batches from 500 mg of intermediate 276 each. After cooling down to rt, the 2 batches were combined, cooled to 0° C. and quenched with a 3N aqueous solution of HCl. The solution was warmed to rt, stirred for 10 min, then neutralized with a 10% aqueous solution of $K_2CO_3$. EtOAc were added, the organic layer was separated and the aqueous layer was extracted thrice with EtOAc. The combined organic layers were dried over $MgSO_4$, filtered off and evaporated in vacuo to give pale brown oil which crystallized. The residue (1.14 g) was purified by column chromatography on silica gel (Irregular SiOH 15-40 µm, 50 g, liquid injection (DCM), mobile phase: heptane/EtOAc, gradient: from 90:10 to 70:30). The pure fractions were combined and evaporated to dryness to give 854 mg of intermediate 277 (82% yield, yellow solid).

Preparation of Intermediate 278

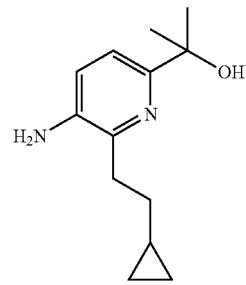 [SMILES: CC(C)(O)c1ccc(N)c(CCC2CC2)n1]

To a solution of methyl magnesium bromide (13.10 mL, 41.80 mmol) in Me-THF (50 mL) at −78° C. under $N_2$, intermediate 277 in Me-THF (35 mL) (854.00 mg, 4.18 mmol) was slowly added. The solution was allowed to warm to rt, stirred for 18 h then slowly quenched with water. EtOAc was added, the organic layer was separated, dried over $MgSO_4$, filtered off and evaporated in vacuo to give a yellow oil. The residue (968 mg) was purified by column chromatography on silica gel (Irregular SiOH 15-40 µm, 10 g, mobile phase: heptane/(EtOAc/MeOH (90:10)), gradient: from 90:10 to heptane 70:30). The fractions containing the product were combined and concentrated under vacuum to give a yellow oil. The residue (648 mg) was further purified by column chromatography on silica gel (Irregular SiOH 15-40 µm, 10 g, mobile phase: DCM/iPrOH, gradient: from 100:0 to 95:5). The pure fractions were combined and concentrated under vacuum to give 218 mg of intermediate 278 (23% yield, 97% purity based on NMR, pale yellow oil). This intermediate was used as it in the next step.

Example A42

Preparation of Intermediate 293

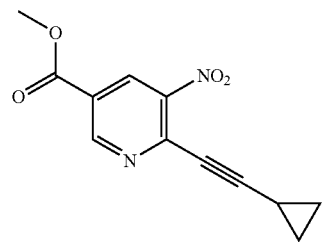 [SMILES: COC(=O)c1cnc(C#CC2CC2)c([N+](=O)[O-])c1]

A flask was charged with methyl-6-chloro-5-nitronicotinate (2.00 g, 9.23 mmol), PdCl$_2$(PPh$_3$)$_2$ (324.00 mg, 461.70 µmol) and CuI (87.90 mg, 461.70 µmol). The system was evacuated and filled thrice with N2 before addition of TEA (44 mL) and DMF (88 mL) and the resulting solution was degassed with N$_2$ for 10 min. Then cyclopropylacetylene (1.56 mL, 18.49 mmol) was added and the reaction mixture was stirred at rt for 18 h. Then, the reaction mixture was concentrated. The residue was purified by column chromatography on silica gel (Irregular SiOH 15-40 µm, 80 g, dry loading on Celite®, mobile phase: heptane/DCM, gradient from 50:50 to 0:100). The fractions containing the product were combined and concentrated under vacuum to give 1.3 g of intermediate 293 (58% yield, brown solid).

Example A43

Preparation of Intermediate 295

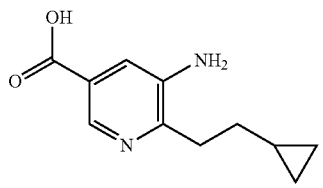 [SMILES: Nc1cc(C(=O)O)cnc1CCC1CC1]

To a solution of intermediate 294 (500.00 mg, 2.27 mmol) in Me-THF (10 mL) and MeOH (10 mL), NaOH (1M in H$_2$O) (13.60 mL, 13.60 mmol) was added. The mixture was heated at 50° C. for 15 min. After cooling down to rt, the mixture was concentrated in vacuo. The residue was slowly acidified with a 1N aqueous solution of HCl (until pH=4). The resulting mixture was extracted with DCM/i-PrOH (3/1) (4 times). The combined organic layers were dried over Na$_2$SO$_4$ filtered and concentrated to give 322 mg of intermediate 295 (69% yield, 98% purity based on LC/MS, beige powder).

Preparation of Intermediate 296

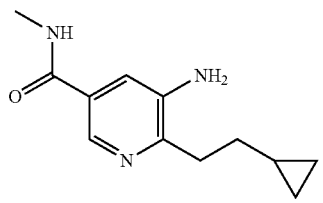 [SMILES: CNC(=O)c1cnc(CCC2CC2)c(N)c1]

To a solution of intermediate 295 (322.00 mg, 1.56 mmol) in DMF (15 mL), DIPEA (538.00 µL, 3.12 mmol), methylamine (3.12 mL, 6.25 mmol) and COMU(R) (1.67 g, 3.90 mmol) were added. The reaction mixture was stirred at rt for 24 h then concentrated to dryness. The residue was purified by column chromatography on silica gel (irregular SiOH 15-40 µm, 120 g, dry loading on Celite®, mobile phase: DCM/MeOH, gradient from 100:0 to 90:10). The fractions containing the product were combined and evaporated to dryness to give 282 mg of intermediate 296 (82% yield, white solid).

The intermediates in the Table below were prepared by using an analogous method starting from the respective starting materials.

| Intermediate number | Structure | Mass (mg) | Yield (%) |
|---|---|---|---|
| Intermediate 317 | 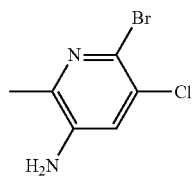 From 3-amino-2-methylpyridine-5-carboxilic aid | 275 pale brown solid | 84 |

Example A44

Preparation of Intermediate 305

To a solution of 5-chloro-2-methylpyridin-3-amine (2.00 g, 14.00 mmol) in CH$_3$CN (140 mL), NBS (2.62 g, 14.70 mmol) was added at 0° C. The solution was stirred 1 h at 0° C. The reaction mixture was diluted with water and EtOAc. The layers were separated. The aqueous layer was extracted twice with EtOAc, the combined organic layers were washed with brine, dried over MgSO$_4$, filtered and concentrated to give a brown solid. The residue was purified by column chromatography on silica gel (Irregular SiOH 15-40 µm, 80 g, dry loading on Celite®, mobile phase: DCM/MeOH, gradient from 100:0 to 95:5). The fractions containing the product were combined and concentrated under vacuum to give 2.88 g of intermediate 305 (93% yield, orange powder).

The intermediates in the Table below were prepared by using an analogous method starting from the respective starting materials.

| Intermediate number | Structure | Mass (mg) | Yield (%) |
|---|---|---|---|
| Intermediate 327 | From intermediate 230 | 632 brown solid | 87 |

Example A45

Preparation of Intermediate 311 and Intermediate 312

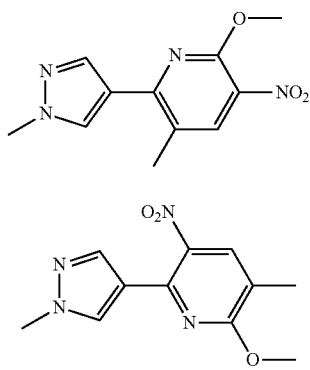

intermediate 311 intermediate 312

A mixture of intermediates 309/310 (1.00 g, 4.94 mmol), 1-methyl-4-(4,4,5,5-tetramethyl-1,3,2-dioxaborolan-2-yl)-1H-pyrazole (1.03 g, 4.94 mmol) and $K_3PO_4$ (2.10 mg, 9.87 mmol) in 1,4-dioxane (17 mL) and F (9 mL) was degassed with $N_2$. [1,1'-bis(diphenylphosphino)ferrocene]dichloropalladium (II), complex with dichloromethane (404.00 mg, 0.49 mmol) was added and the reaction mixture was heated at 120° C. for 15 min using one single mode microwave (Biotage Initiator EXP 60) with a power output ranging from 0 to 400 W [fixed hold time]. The mixture was poured into ice and extracted with EtOAc. The organic layer was washed with brine, dried over $MgSO_4$, filtered and the solvent was evaporated. The residue was purified by column chromatography on silica gel (15-40 µm, 80 g, mobile phase: DCM/MeOH, gradient from 100:0 to 90:10). The pure fractions were mixed and the solvent was evaporated to give 0.338 g of intermediate 312 (28% yield) and 0.338 g of intermediate 311 (28% yield).

Preparation of Intermediate 313

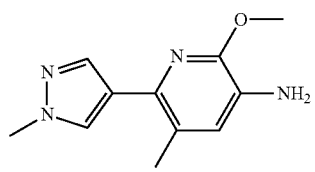 [SMILES: COc1nc(-c2cnn(C)c2)c(C)cc1N]

Intermediate 311 (0.33 g, 1.35 mmol) with RaNi (0.055 g, 0.94 mmol) as a catalyst in MeOH (10 mL) was hydrogenated at rt overnight under 1.5 bar of $H_2$. The catalyst was filtered off and the filtrate was evaporated to give 0.298 g of intermediate 313 (100% yield).

Example A46

Preparation of Intermediate 337

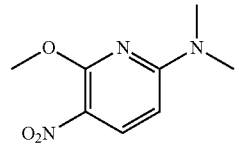

To a solution of 6-chloro-2-methoxy-3-nitropyridine (100.00 mg, 0.53 mmol) in EtOH (2 mL), dimethylamine (40% in $H_2O$, 134 µL, 1.06 mmol) was added and the resulting mixture was stirred at rt for 1 h. The precipitate was collected by filtration, washed with EtOH and dried under high vacuum at 50° C. for 1 h to give 94 mg of intermediate 337 (90% yield, 47% purity based on LC/MS, off-white solid).

Example A47

Preparation of Intermediate 338

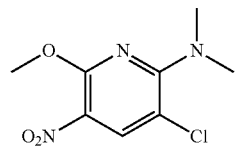

Intermediate 337 (94.00 mg, 0.48 mmol) and NCS (70.10 mg, 0.52 mmol) were added together in DMF (3.2 mL) and the resulting mixture was heated at 50° C. under $N_2$ for 30 min. The reaction was allowed to cool to rt, diluted with EtOAc and washed with saturated $NaHCO_3$ solution and brine. The organic layer was separated, dried over $Na_2SO_4$ and evaporated under reduced pressure to give 103 mg of intermediate 338 (93% yield, yellow solid).

Example A48

Preparation of Intermediate 415

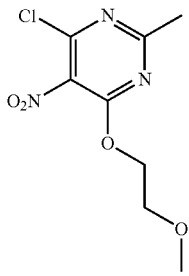

To a solution of 2-methoxyethanol (266.76 µL, 3.37 mmol) in dry Me-THF (10 mL) under $N_2$, NaH (60% dispersed in mineral oil) (148.06 mg, 3.70 mmol) was added and the mixture was stirred at rt for 1 h. This suspension was added dropwise to a solution of 4,6-dichloro-2-methyl-5- nitropyrimidine (700.00 mg, 3.37 mmol) in dry Me-THF (25 mL) under $N_2$ at 0° C. The mixture was stirred at 0° C. for 2 h. The mixture was quenched with a sat. solution of $NH_4Cl$ and extended with EtOAc. The layers were separated and the organic layer was washed with brine, dried over $MgSO_4$, filtered off and evaporated in vacuo to give an orange oil. The residue (1.1 g) was purified by column chromatography on silica gel (irregular SiOH, 15-40 µm, 50 g, dry loading on Celite®, mobile phase: heptane/EtOAc, gradient from 80:20 to 50:50). The fractions containing the product were combined and evaporated to dryness to give 570 mg of intermediate 415 which crystallized on standing (68% yield, yellow oil).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 419 | 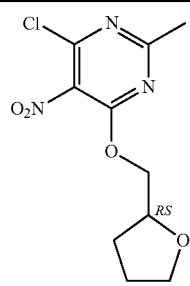<br>From 4,6-dichloro-2-methyl-5-nitropyrimidine and tetrahydrofurfuryl alcohol | 1.34 yellow oil | 68 |
| Intermediate 423 | 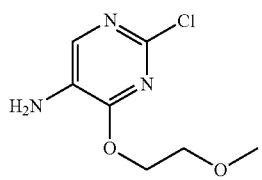<br>From 5-amino-2,4-dichloropyrimidine and 2-methoxyethanol | 310 white solid | 25 procedure with DMF as solvent |
| Intermediate 435 | 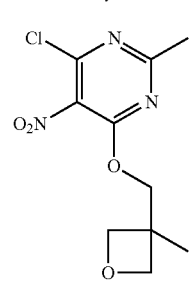<br>From 4,6-dichloro-2-methyl-5-nitropyrimidine and 3-hydroxymethyl-3-methyloxetane | 425 orange oil | 65 |
| Intermediate 441 | 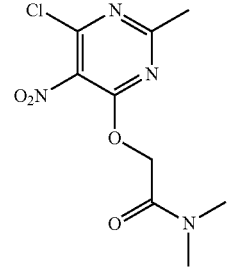 [SMILES: Cc1nc(Cl)c([N+](=O)[O-])c(OCC(=O)N(C)C)n1]<br>From 4,6-dichloro-2-methyl-5-nitropyrimidine and 2-hydroxy-N,N-dimethylacetamide | 360 beige solid | 55 |

Example A49

Preparation of Intermediate 445

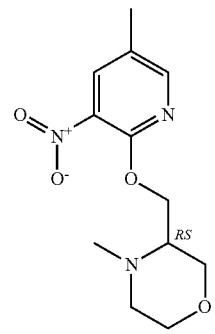 [SMILES: Cc1cnc(OCC2COCCN2C)c([N+](=O)[O-])c1]

LiHMDS 1.5M in THF (2.6 mL; 3.84 mmol) was added dropwise at 5° C. to a solution of 4-methyl-3-(hydroxymethyl)morpholine (420 mg; 3.20 mmol) in Me-THF (12 mL). After 30 min, 2-fluoro-5-methyl-3-nitropyridine (500 mg; 3.20 mmol) was quickly added and the reaction mixture was allowed to warm to room temperature and stirred at rt overnight. LiHMDS 1.5M in THF (854 µL; 1.28 mmol) was added at 0° C. and the mixture was stirred at rt for 5 h. The reaction mixture was poured onto iced water, a 10% aqueous solution of $K_2CO_3$ and extracted with EtOAc. The organic layer was decanted, washed with water, dried over $MgSO_4$, filtered and evaporated to give 733 mg of crude. The crude was purified by chromatography over silica gel (SiOH, GraceResolv®, 12 g, Mobile phase DCM/MeOH/$NH_4OH$, Gradient from: 99% DCM, 1% MeOH, 0.1% $NH_4OH$ to 97% DCM, 3% MeOH, 0.3% $NH_4OH$). The pure fractions were collected and the solvent was evaporated to give 544 mg of intermediate 445 (64% yield, yellow solid).

Chiral separation of intermediate 445 was performed via chiral SFC (Stationary phase: CHIRALPAK AD-H 5 µm 250×20 mm, Mobile phase: 70% $CO_2$, 30% MeOH). The pure fractions were collected and the solvent was evaporated to give 254 mg of intermediate 446 (30% yield, yellow solid) and 262 mg of intermediate 447 (31% yield, yellow solid).

| Intermediate number | Structure | Mass (mg) | Yield (%) |
|---|---|---|---|
| Intermediate 446 | (structure) From 4-methyl-3-(hydroxymethyl)morpholine and 2-fluoro-5-methyl-3-nitropyridine | 254 | 30 procedure with T = rt o/n |
| Intermediate 447 | (structure) From 4-methyl-3-(hydroxymethyl)morpholine and 2-fluoro-5-methyl-3-nitropyridine | 262 | 31 procedure with T = rt o/n |

The intermediates in the Table below were prepared by using an analogous method starting from the respective starting materials. The most relevant minor deviations to the referenced method are indicated as additional information in the column 'Yield (%)'. Chiral SFC could optionally be used for the separation of diastereoisomers, with minor modifications to either the stationary phase and/or the mobile phase that would be readily achieved by one skilled in the art.

| Intermediate number | Structure | Mass (mg) | Yield (%) |
|---|---|---|---|
| Intermediate 541 | (structure) | 302 | 75 |
| Intermediate 459 | (structure) CIS mixture (RS and SR) From 2-Fluoro-5-methyl-3-nitropyridine and cis-1-boc-3-fluoro-4-hydroxypiperidine | 2.1 g | 84 |
| Intermediate 453 | (structure) From 2-fluoro-5-methyl-3-nitropyridine and (r,s)-tert-butyl 2-(hydroxymethyl)morpholine-4-carboxylate. TRANS A (SS or RR) From 2-fluoro-5-methyl-3-nitropyridine and intermediate 452 | 193 contains 5-10% of intermediate 454 | 28 |
| Intermediate 454 | (structure) TRANS B (RR or SS) From 2-fluoro-5-methyl-3-nitropyridine and Intermediate 452 | 191 | 28 |

418

Example A50

Preparation of Intermediate 448

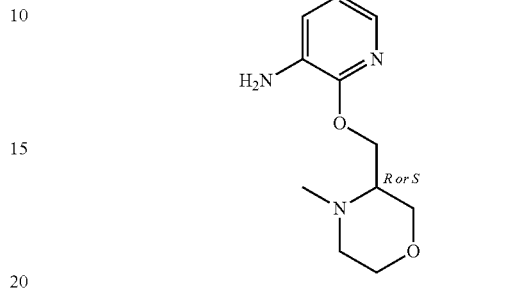

A mixture of intermediate 446 (250 mg; 0.94 mmol), NH$_4$Cl (200 mg; 3.74 mmol) and Iron Powder (261 mg; 4.68 mmol) in EtOH (3.5 mL) and water, distilled (1.5 mL) was heated at 75° C. for 4 h. The reaction mixture was cooled to room temperature, poured onto a mixture of 10% aqueous K$_2$CO$_3$ and DCM, then filtered through a pad of Celite®. The organic layer was decanted, dried over MgSO$_4$, filtered and the solvent was evaporated to give 204 mg of crude (orange oil). The crude was purified by chromatography over silica gel (SiOH, Biotage, SNAP 10 g, Mobile phase DCM/MeOH/NH$_4$OH, Gradient from 98% DCM, 2% MeOH, 0.2% NH$_4$OH to 95% DCM, 5% MeOH, 0.5% NH$_4$OH). The pure fractions were collected and the solvent was evaporated to give 160 mg of intermediate 448 (72% yield, yellow oil).

The intermediates in the Table below were prepared by using an analogous method starting from the respective starting materials. The most relevant minor deviations to the referenced method are indicated as additional information in the column 'Yield (%)'. Chiral SFC could optionally be used for the separation of diastereoisomers, with the appropriate choice of either the stationary phase and/or the mobile phase that would be readily achieved by one skilled in the art.

| Intermediate number | Structure | Mass (mg) | Yield (%) |
|---|---|---|---|
| Intermediate 450 | 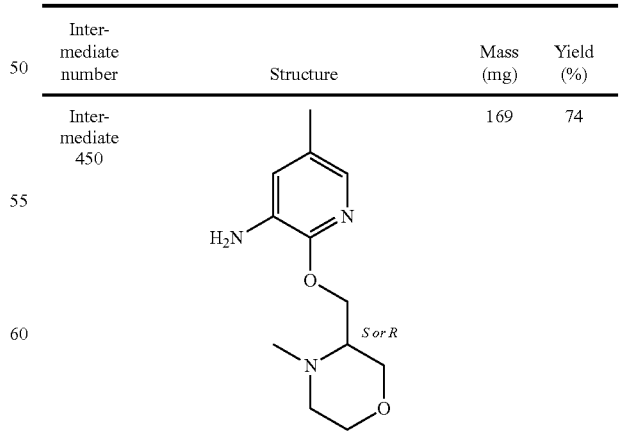<br>From intermediate 447 | 169 | 74 |

417
-continued

| Intermediate number | Structure | Mass (mg) | Yield (%) |
|---|---|---|---|
| Intermediate 498 | 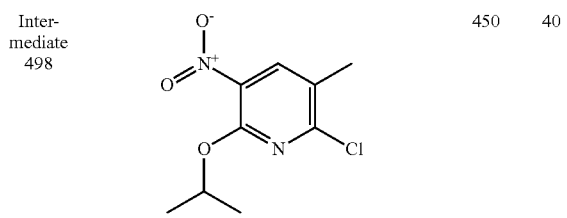<br>From 2,6-dichloro-3-methyl-5-nitro-pyridine and isopropyl alcohol | 450 | 40 |
| Intermediate 556 | 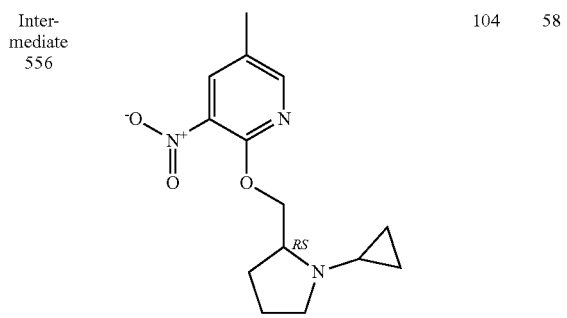<br>From 2-fluoro-5-methyl-3-nitropyridine and intermediate 555 | 104 | 58 |
| Intermediate 563 | 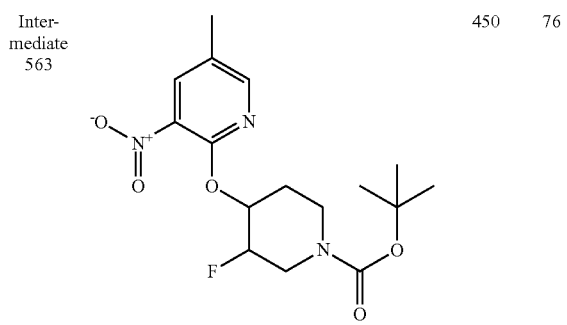<br>TRANS mixture (RR and SS)<br>From 2-fluoro-5-methyl-3-nitropyridine and trans-1-boc-3-fluoro-4-hydroxypiperidine | 450 | 76 |

| Intermediate number | Structure | Mass (mg) | Yield (%) |
|---|---|---|---|
| Intermediate 544 | CIS mixture (RS and SR) From intermediate 543 | 73 | 68 procedure with T = 70° C. o/n |
| Intermediate 476 | From intermediate 475 | 349 | 97 procedure with T = 65° C. 1 h |
| Intermediate 464 | From intermediate 462 | 318 | 80 |
| Intermediate 466 | From intermediate 463 | 283 | 71 |

| Intermediate number | Structure | Mass (mg) | Yield (%) |
|---|---|---|---|
| Intermediate 455 | TRANS A (SS or RR) From intermediate 453 | 134 | 79 procedure with T = 75° C. 3 h |
| Intermediate 457 | TRANS B (RR or SS) From intermediate 454 | 109 | 65 procedure with T = 75° C. 3 h |
| Intermediate 469 | From intermediate 468 | 181 | 66 procedure with T = 80° C. 1 h |
| Intermediate 472 | From intermediate 471 | 91 | 30 procedure with T = 80° C. 2 h |

-continued

| Intermediate number | Structure | Mass (mg) | Yield (%) |
|---|---|---|---|
| Intermediate 557 | 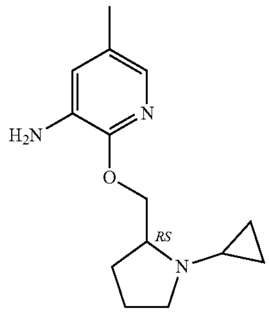 [SMILES: Cc1cnc(OCC2CCCN2C2CC2)c(N)c1] | 31 | 34 procedure with T = 70° C. 30 mn |
| | From intermediate 556 | | |
| Intermediate 566 | 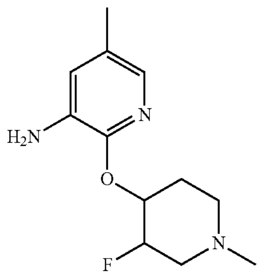 [SMILES: Cc1cnc(OC2CCN(C)CC2F)c(N)c1] | 250 | 97 procedure with T = 70° C. 1 h |
| | TRANS mixture (RR and SS) From intermediate 565 | | |
| Intermediate 559 | 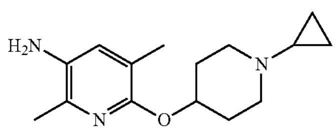 [SMILES: Cc1cc(N)c(C)nc1OC1CCN(C2CC2)CC1] | 159 | Quant. procedure with T = 80° C. 1 h 30 |
| | From intermediate 488 | | |
| Intermediate 585 | 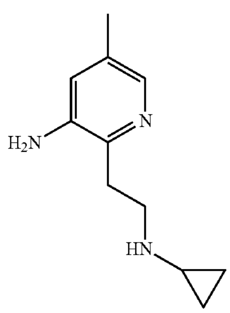 | 174 | 65% Procedure with T = 80° C. 1 hr |
| | From intermediate 584 | | |

Example A51

Preparation of Intermediate 547

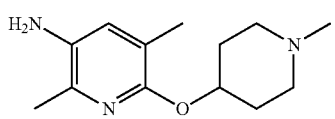

Intermediate 484 (0.160 g; 0.60 mmol) was hydrogenated at atmospheric pressure and at rt in MeOH (4.00 mL) and EtOAc (2.00 mL) with Pd/C (10% w/w, 0.060 g; 0.06 mmol) as a catalyst. After 2 hours the catalyst was filtered over Celite® and the solvent was evaporated until dryness to give: 160 mg of intermediate 547 (100% yield)

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 501 | 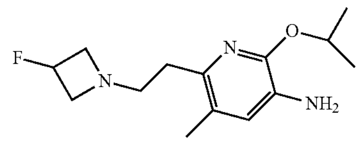 [SMILES: Cc1cc(N)c(OC(C)C)nc1CCN1CC(F)C1] | 270 | 91 |
| | From intermediate 500 | | |
| Intermediate 496 | 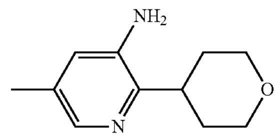 | 837 | 100 Procedure with 2 bars pressure of H$_2$, rt, o/n |
| | From intermediate 495 | | |
| Intermediate 550 | 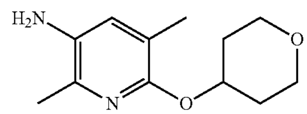 [SMILES: Cc1cc(N)c(C)nc1OC1CCOCC1] | 470 | 99 Procedure with atmospheric pressure H$_2$ 2 h |
| | From intermediate 485 | | |
| Intermediate 491 | 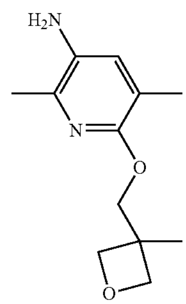 | 590 | 100 Procedure with atmospheric pressure H$_2$ 3 h |
| | From intermediate 489 | | |
| Intermediate 493 | 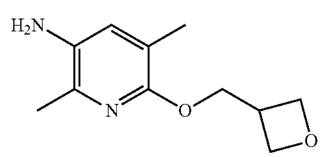 | 403 | 93 Procedure with atmospheric pressure H$_2$ 12 h |
| | From intermediate 490 | | |
| Intermediate 507 | 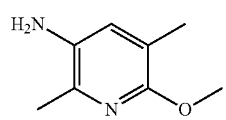 | 388 | 96 Procedure with atmospheric pressure H$_2$ 7 h |
| | From intermediate 482 | | |

423

Example A52

Preparation of Intermediate 542

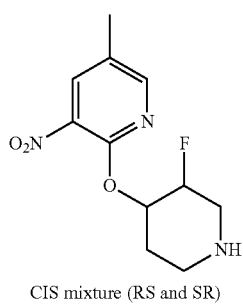 [SMILES: Cc1cnc(OC2CCNCC2F)c([N+](=O)[O-])c1]

CIS mixture (RS and SR)

In a round bottom flask containing intermediate 541 and dioxane (5 mL) was added HCl (6.3 mL) and the reaction was left stirring at room temperature overnight.

The crude was concentrated in vacuo before being quenched with a saturated solution of NaHCO$_3$ and extracted with DCM. The organic layer was dried over anhydrous sodium sulfate and concentrated under vacuum to give a crude that was purified by flash chromatography eluting with [DCM:MeOH 75:25] to give intermediate 542 (187 mg; 87% yield)

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 564 | ![structure] TRANS mixture (RR and SS) From intermediate 563 | 320 | 99 |
| Intermediate 487 | ![structure] From intermediate 486 | 500 | 83 |

424

Example A53

Preparation of Intermediate 460

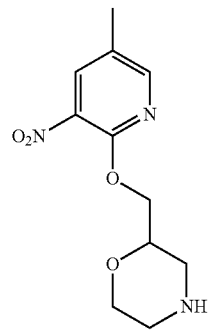 [SMILES: Cc1cnc(OCC2CNCCO2)c([N+](=O)[O-])c1]

TFA (4.2 mL; 54.33 mmol) was added dropwise at 5° C. to a suspension of intermediate 459 (1.92 g; 5.43 mmol) in DCM (38 mL) and the reaction mixture was stirred at rt for 2 h. The reaction mixture was diluted with ice-water, a 10% aqueous solution of K$_2$CO$_3$ and DCM. The mixture was extracted with DCM (5×). The layers were separated and the organic layer was dried over MgSO$_4$, filtered and the solvent was evaporated. The residue was combined with that from a parallel experiment and the solvent was evaporated to give in total 1.48 g of intermediate 460 as a yellow oil. The product was used without purificaton for subsequent reactions.

Example A54

Preparation of Intermediate 452

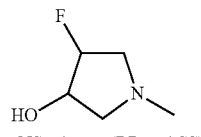

TRANS mixture (RR and SS)

Formaldehyde (10 mL; 134.21 mmol) was added to a mixture of trans-4-fluoro-3-hydroxypyrrolidine hydrochloride (950 mg; 6.71 mmol) and AcOH (768 µL; 13.42 mmol) in MeOH (54 mL) at rt. The reaction mixture was stirred at rt for 30 min, then sodium triacetoxyborohydride (3.56 g; 16.78 mmol) was added and the reaction mixture was stirred at rt for 3 h. The mixture was basified with a saturated aqueous NaHCO$_3$ solution at 5° C. and the solvent was evaporated. The mixture was diluted with EtOAc and washed with saturated aqueous NaHCO$_3$ solution, then extracted with EtOAc (3×). Then, the aqueous layer was extracted with DCM (3×). The organic layer was combined, dried over MgSO$_4$, filtered and the solvent was evaporated to give 445 mg of intermediate 452 as a pale brown volatile oil.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 462 | From intermediate 460 | 450 | 29 SFC separation of racemate into enantiomers |
| Intermediate 463 | From intermediate 460 | 450 | 29 SFC separation of racemate into enantiomers |

Example A55

Preparation of Intermediate 543

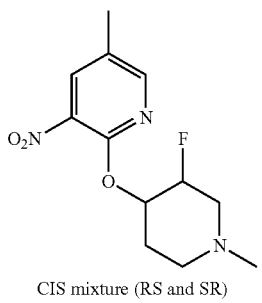 [SMILES: Cc1cnc(OC2CCN(C)CC2F)c([N+](=O)[O-])c1]

CIS mixture (RS and SR)

To a solution of intermediate 542 in MeOH (8 mL, 1.528 mmol) was added formaldehyde (124 µL) and then Formic acid (288 µL, 0.00764 mmol). The reaction mixture was stirred at room temperature for 1 hour. Then, sodium triacetoxyborohydride (202 mg, 0.955 mmol) was added and the stirring was continued for 1 hour. Then, the reaction mixture was carefully quenched by addition of NaHCO₃ sat. (2 mL) and extracted with ethyl acetate.

The organic layer was evaporated to dryness and was purified by silica gel column chromnatography [DCM: MeOH 9:1 30%] to afford intermediate 543 (121 mg; 59% yield).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 565 Trans | TRANS mixture (RR and SS) From intermediate 564 | 290 | 86 |

Example A56

Preparation of Intermediate 488

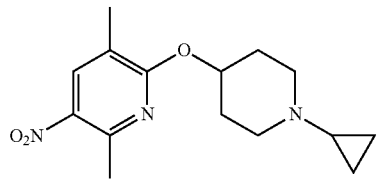 [SMILES: Cc1cc([N+](=O)[O-])c(C)nc1OC1CCN(C2CC2)CC1]

In a sealed tube, a mixture of intermediate 487 (0.500 g; 1.99 mmol); ethoxycyclopropoxy)trimethyl silane (0.41 mL; 2.04 mmol) and NaBH₃CN (0.175 g; 2.79 mmol) in AcOH (5.50 mL) and MeOH (0.16 mL; 2.80 mmol) was stirred at 60° C. overnight. The reaction was cooled down to room temperature. Water was added and this mixture was extracted twice with EtOAc. The organic layer was decanted and evaporated until dryness to give: 0.455 g of crude intermediate 488. This crude was purified by preparative LC (Irregular SiOH 15-40 µm 40 g GraceResolv®, mobile phase gradient from: 99% DCM, 1% MeOH, 0.1% NH₄OH to 94% DCM, 6% MeOH, 0.6% NH₄OH). The pure fractions were collected and the solvent was evaporated until dryness to give a combined yield of 295 mg (51%) of intermediate 488

Example A57

Preparation of Intermediate 471

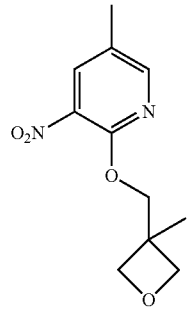 [SMILES: Cc1cnc(OCC2(C)COC2)c([N+](=O)[O-])c1]

In a sealed tube, a mixture of 2-hydroxy-5-methyl-3-nitropyridine (463 mg; 3.00 mmol), 3-bromomethyl-3-methyloxetane (991 mg; 6.01 mmol) and $K_2CO_3$ (1.25 g; 9.01 mmol) in DMF (6 mL) was stirred at 60° C. for 2 h. The reaction mixture was cooled down to room temperature. The insoluble material was filtered off and the filtrate was concentrated. The residue poured onto a mixture of water and brine, then extracted with EtOAc. The organic layer was decanted, washed with brine, dried over $MgSO_4$, filtered and the solvent was evaporated to give 750 mg of crude product as a yellow oil. The crude was purified by chromatography over silica gel (irregular SiOH, 24 g; gradient: from 100% DCM to 98% DCM, 2% MeOH). The pure fractions were collected and the solvent was evaporated to give intermediate 471 in 2 fractions: 287 mg of a yellow oil (40% yield) and 365 mg of a yellow solid (51% yield).

Example A58

Preparation of Intermediate 474

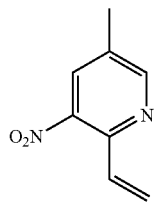

Tetrakis(triphenylphosphine)palladium(0) (167 mg; 0.145 mmol) was added to a stirred suspension of 2-chloro-3-nitro-5-picoline (500 mg; 2.897 mmol) and vinylboronic acid pinacol ester (516 µL; 3.042 mmol) in 1,4-dioxane (15 mL) and $Na_2CO_3$ 2M (4 mL). The mixture was stirred at 100° C. for 4 hours. Then, water was added and the mixture was extracted with AcOEt. The organic layer was decanted, dried over $MgSO_4$, filtered and evaporated to dryness. The crude product was purified by chromatography over silica gel (irregular SiOH, 12 g; Mobile phase: gradient from 10% EtOAc, 90% heptane to 20% EtOAc, 80% heptane). The desired fractions were collected and evaporated to dryness yielding 403 mg of intermediate 474 (85% yield).

Preparation of Intermediate 475

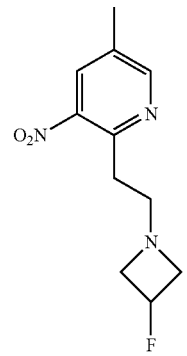 [SMILES: Cc1cnc(CCN2CC(F)C2)c([N+](=O)[O-])c1]

In a sealed tube, a mixture of intermediate 474 (403 mg; 2.455 mmol), 3-fluoroazetidine hydrochloride (821 mg; 7.365 mmol) and $Et_3N$ (1.36 mL; 9.819 mmol) in EtOH (10 mL) was refluxed for 1 hour. The reaction mixture was evaporated to dryness and purified by chromatography over silica gel (irregular SiOH, 24 g; mobile phase: gradient from 3% MeOH, 97% DCM to 5% MeOH, 95% DCM). The pure fractions were collected and evaporated to dryness yielding 410 mg of intermediate 475 (70% yield).

The intermediate in the Table below was prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 584 | From intermediate 474 and cyclopropylamine | 298 | 72 Procedure with MeOH; no $Et_3N$; refluxed 18 hrs |

Example A59

Preparation of Intermediate 478

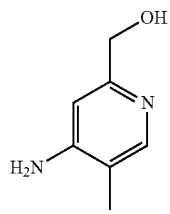

Lithium aluminium hydride in solution 1M THF (5.4 mL; 5.40 mmol) was added dropwise to a solution of 4-amino-5-methylpyridine-2-carboxylate methyl ester HCl salt (300 mg; 1.48 mmol) in Me-THF (4.2 mL) at 0° C. and under $N_2$ flow. The reaction mixture was stirred at rt overnight. The mixture was cooled to 0° C. and ice-water then cooled solution of NaOH 3N and ice-water were successively added dropwise at 0° C. The material was combined with that from a parallel reaction for the treatment. EtOAc was added and the reaction mixture was filtered on a short pad of Celite®. The Celite® was washed with AcOEt and water was added. The filtrate was extracted with EtOAc (3×). The organic layer was washed with water then brine, dried over $MgSO_4$, filtered and the solvent was evaporated to give 80 mg of intermediate 478 as an orange oil.

NaCl solid was added to the aqueous layer and the product was extracted with EtOAc (3×). As the product was found to persist in the aqueous layer, this was evaporated to dryness and the residue was taken up with 50 mL of solution of DCM/MeOH (90/10). The mixture was stirred at rt for 5 min and then filtered. The cake was treated a further 2 times in the same fashion before combining all the organic fractions, drying over $MgSO_4$, filtering and evaporating the solvent in vacuo. The residue was combined with 80 mg initially isolated to give after evaporation 391 mg of crude intermediate 478 as a brown solid. The crude was purified by chromatography over silica gel (SiO2, Grace, 12 g, eluent: from 96% DCM, 4% MeOH, 0.4% $NH_4OH$ to 90% DCM, 10% MeOH, 1% $NH_4OH$). The pure fractions were collected and the solvent was evaporated to give 69 mg of intermediate 478 as a white solid (28% yield).

Example A60

Preparation of Intermediate 480

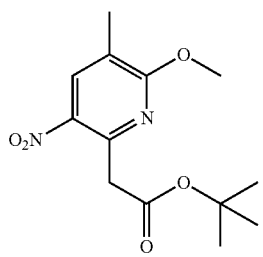 [SMILES: COc1nc(CC(=O)OC(C)(C)C)c([N+](=O)[O-])cc1C]

2-methoxy-3-methyl-5-nitropyridine (4.30 g; 25.57 mmol) and tert-butyl chloroacetate (4.50 mL; 31.37 mmol) in THF (60 mL) was stirred and cooled at −20° C. Then potassium tert-butoxide (6.80 g; 60.60 mmol) was added portionwise to this mixture (temperature keep below −14° C.). After complete addition, this reaction was stirred at rt for 1 h. Water and an aqueous solution of HCl 3N were added and this mixture was extracted twice with EtOAc. The organic layer was decanted and the solvent was evaporated until dryness to give 7.35 g of intermediate 480 (100% yield).

Preparation of Intermediate 481

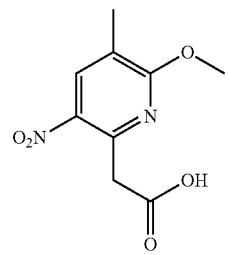 [SMILES: COc1nc(CC(=O)O)c([N+](=O)[O-])cc1C]

At rt, TFA (3.50 mL; 45.74 mmol) was added slowly to a solution of intermediate 480 (1.00 g; 3.54 mmol) in DCM (3.00 mL). This reaction was stirred at 100° C. for 1 h. The solvent was evaporated until dryness to give 863 mg of intermediate 481 (100% yield)

Preparation of Intermediate 482

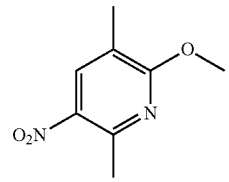

A mixture of intermediate 481 (0.860 g; 3.80 mmol) and $K_2CO_3$ powder (0.350 g; 2.53 mmol) in DMF (2.90 mL) was stirred at 90° C. for 2 h, before being allowed to cool down to rt. The reaction was poured onto a mixture of ice and water and this mixture was stirred for 15 minutes. The precipitate was filtered and dried until dryness to give: 485 mg of intermediate 482 (70% yield)

Preparation of Intermediate 483

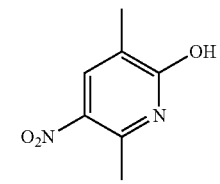

Intermediate 482 (100 mg, 0.55 mmol) in $CH_3CN$ (7.20 mL) was treated with sodium iodide (123 mg, 0.82 mmol) and chlorotrimethyl silane (0.14 mL, 1.10 mmol). The reaction was stirred at 80° C. overnight. Water was added and this mixture was extracted twice with EtOAc. The organic layer was decanted and the solvent was evaporated until dryness. The crude was taken up into diethyl ether, triturated and filtered. This precipitate was dried until dryness to give: 70 mg of intermediate 483 (76% yield), which was used as is for the next step.

Preparation of Intermediate 484

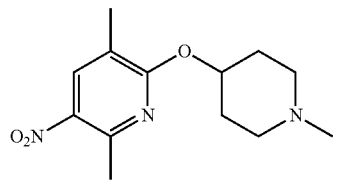 [SMILES: Cc1cc([N+](=O)[O-])c(C)nc1OC1CCN(C)CC1]

A mixture of intermediate 483 (0.241 g; 1.43 mmol), 4-hydroxy-1-methylpiperidine (0.198 g; 1.72 mmol) in toluene (4.10 mL) and CMPB (0.66 mL; 2.52 mmol) was stirred in a sealed tube at 110° C. using one single mode microwave (Anton Parr monowave 300) with a power output ranging from 0 to 850 W for 15 min. [fixed hold time]. Water was added and this mixture was extracted twice with EtOAc. The crude was purified by preparative LC (Irregular SiOH 40 µm 24 g GraceResolv®, mobile phase Gradient from: 98% DCM, 2% MeOH, 0.2% $NH_4OH$ to 90% DCM, 10% MeOH, 1% $NH_4OH$). The pure fractions were collected and the solvent was evaporated until dryness to give: 125 mg of intermediate 484 (33% yield).

(The product was combined with another batch from a parallel experiment and used as is in subsequent reactions.)

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
| --- | --- | --- | --- |
| Intermediate 485 | ![structure] From intermediate 483 and tetrahydro-4-pyranol | 540 | 60 Procedure at 110° C., 15 mn, µw |
| Intermediate 468 | ![structure] From 2-hydroxy-5-methyl-3-nitropyridine and 4-hydroxy-1-methylpiperidine | 241 | 37 Procedure at 110° C., 20 mn, µw |
| Intermediate 486 | ![structure] From intermediate 483 and 1-BOC-4-hydroxy-piperidine | 785 | 37 Procedure at 110° C., 15 mn, µw |

| Intermediate number | Structure | Mass (mg) | Yield (%) |
|---|---|---|---|
| Intermediate 489 | ![structure] From 3-methyl-3-oxetanemethanol and 483 | 630 | 76 |
| Intermediate 490 | ![structure] From 483 and 3-oxetanemethanol | 495 | 82 |

Example A61

Preparation of Intermediate 513

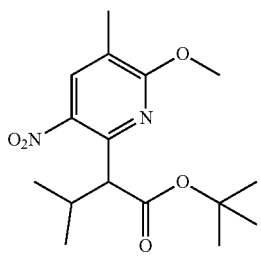 [SMILES: COc1nc(C(C(=O)OC(C)(C)C)C(C)C)c([N+](=O)[O-])cc1C]

At rt, NaH (60% dispersion in mineral oil) (264 mg; 6.60 mmol) was added portionwise to a mixture of intermediate 480 (1.20 g; 4.25 mmol) in DMF (30.00 mL). Then 2-iodopropane (0.55 mL; 5.50 mmol) was added to this mixture. The reaction was stirred at rt overnight. Water was added and this mixture was extracted twice with EtOAc. The organic layer was decanted and the solvent was evaporated until dryness. The crude was purified by preparative LC (Irregular SiOH, 15-40 μm, 80 g GraceResolv®, Mobile phase Heptane/EtOAc, Gradient from: 90:10 to 60:40). The pure fractions were collected and the solvent was evaporated until dryness to give 0.984 g of intermediate 513 (71% yield).

Preparation of Intermediate 514

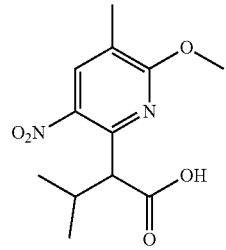 [SMILES: COc1nc(C(C(=O)O)C(C)C)c([N+](=O)[O-])cc1C]

TFA (2.40 mL; 31.36 mmol) was added to a solution of intermediate 513 (0.980 g; 3.02 mmol) in DCM (3.50 mL). This reaction was stirred at 110° C. for 2 h. The solvent was evaporated until dryness to give 984 mg of intermediate 514 (100% yield).

Preparation of Intermediate 515

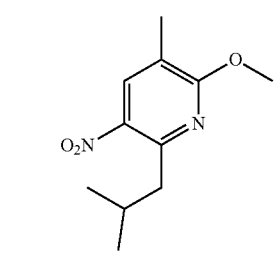 [SMILES: COc1nc(CC(C)C)c([N+](=O)[O-])cc1C]

A mixture of intermediate 514 (0.98 g; 3.67 mmol) in DMF (40.00 mL) and K$_2$CO$_3$ (1.00 g; 7.24 mmol) was stirred at 90° C. for 3 h. The reaction was cooled down to room temperature. This mixture was poured onto a mixture of ice/water, an aqueous solution of HCl 3N was added. This mixture was extracted twice with EtOAc. The organic layer was decanted and the solvent was evaporated until dryness. This crude was purified by preparative LC (Irregular SiOH 40 µm, 80 g, GraceResolv®, Mobile phase Heptane/EtOAc, Gradient from: 90:10 to 70:30). The pure fractions were evaporated until dryness to give 0.476 g of intermediate 515 (58% yield).

Preparation of Intermediate 513

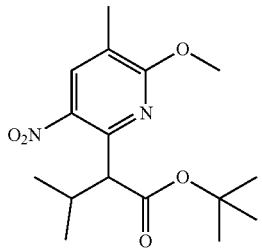 [SMILES: COc1nc(C(C(=O)OC(C)(C)C)C(C)C)c([N+](=O)[O-])cc1C]

Intermediate 515 (0.47 g; 2.11 mmol) was hydrogenated at rt in EtOAc (4.00 mL) and MeOH (6.00 mL) with Pd/C (10% wt., 0.12 g; 0.11 mmol) as a catalyst at atmospheric pressure of H$_2$. After overnight the catalyst was filtered over Celite® and the solvent was evaporated until dryness to give 0.402 g of intermediate 516 (98% yield).

Example A62

Preparation of Intermediate 495

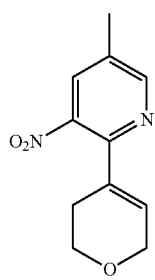

A mixture of 2-bromo-5-methyl-3-nitropyridine (1 g; 4.61 mmol), 3,6-dihydro-2H-pyran-4-boronic acid pinacol ester (2.42 g; 6.91 mmol), tetrakis(triphenylphosphine)palladium (0) (160 mg; 0.138 mmol) in 1,4-dioxane (19 mL) and 2M Na$_2$CO$_3$ (6.3 mL; 12.6 mmol) under N$_2$ atmosphere was stirred and heated at 100° C. for 1 h. Then, water was added and the mixture was extracted with DCM. The organic layer was separated, dried (MgSO$_4$) filtered and concentrated. The residue was purified by flash chromatography over silica gel (eluent: gradient from DCM to DCM/MeOH: 100/0 to 95/5).

The desired fractions were collected and concentrated till dryness, yielding: 0.988 g of intermediate 495 (97% yield).

Example A63

Preparation of Intermediate 499

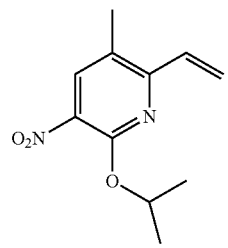 [SMILES: C=Cc1nc(OC(C)C)c([N+](=O)[O-])cc1C]

In a sealed tube, intermediate 498 (1.5 g; 0.065 mol), potassium vinyltrifluoroborate (1.22 g; 0.009 mol), PdCl$_2$dppf (106.4 mg; 0.13 mmol) and Et$_3$N (0.904 mL; 0.0065 mol) in n-propanol (15.8 mL) under a N$_2$ flow were heated at 120° C. for 3 h. The mixture was partitioned between water and EtOAc. The organic layer was dried over MgSO$_4$, filtered and concentrated in vacuo. The residue was purified by chromatography over silica gel (15-40 µm, 40 g, eluent: heptane/EtOAc: 95/5 to 90/10). The pure fractions were mixed and the solvent was evaporated yielding 0.317 g (22%) of the pure intermediate 499 as a yellow oil, and an impure second fraction which was purified again by chromatography over silica gel (15-40 µm, 40 g, eluent: heptane/EtOAc: 95/5). The pure fractions were mixed and evaporated to give a second pure batch of intermediate 499 (240 mg; 13% yield). Combined yield 35%.

Preparation of Intermediate 500

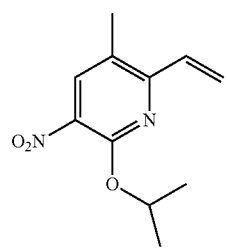 [SMILES: C=Cc1nc(OC(C)C)c([N+](=O)[O-])cc1C]

In a sealed tube, a mixture of intermediate 499 (0.317 g; 1.43 mmol), Et$_3$N (1.021 mL; 7.13 mmol) and 3-fluoroazetidine hydrochloride (535 mg; 7.13 mmol) in ethanol (10.69 mL) were stirred at 100° C. for 4 h. The reaction mixture was cooled down to room temperature and partitioned between DCM and a saturated solution of NaHCO$_3$. The organic layer dried over MgSO$_4$, filtered and concentrated to afford intermediate 500 (0.431 mg) which were directly engaged in subsequent reactions without any further treatement.

Example A64

Preparation of Intermediate 503

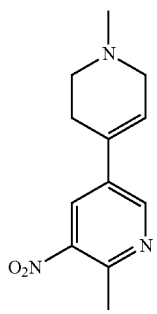

To a solution of 2-(1-methyl-1,2,3,6-tetrahydropyridin-4-yl)-4,4,5,5-tetramethyl-1,3,2-dioxaborolane (1.542 g; 6.912 mmol) in water (4.00 mL) and 1,4 dioxane (20 mL) was added $K_3PO_4$ (4.40 g; 20.74 mmol), tetrakis(triphenylphosphine)palladium(0) ($Pd(PPh_3)_4$) (798.70 mg, 0.69 mmol), 5-bromo-2-methyl-3-nitropyridine (1.50 g; 6.91 mmol) under $N_2$. The mixture was stirred at 80° C. overnight under $N_2$. The mixture was then poured into water (20 mL) and extracted three times with EtOAc (30 mL). The organic layer was washed with water (15 mL) and then brine (15 mL), dried over $Na_2SO_4$, filtered and the solvent was evaporated under vacuum. The residue was purified by flash column chromatography over silica gel (Mobile phase: petroleum ether/EtOAc Gradient from: 100:0 to 31:69 then EtOAc/MeOH Gradient from 100:0 to 90:10). The desired fractions were collected and the solvent was concentrated to dryness under vacuum to give 900 mg (56% yield) of intermediate 503 as a yellow oil

Preparation of Intermediate 504

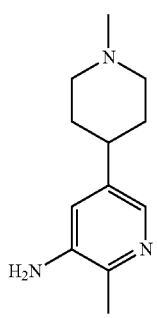

A mixture of intermediate 503 (0.90 g; 3.86 mmol) in MeOH (30 mL) was hydrogenated at rt (20 Psi) with $Pd(OH)_2/C$ (20 wt. %, 0.10 g) as a catalyst. After uptake of $H_2$ (4 equivalent), the mixture was stirred overnight at 30° C.

The catalyst was filtered off through Celite® and the filtrate was evaporated to give 650 mg of intermediate 504 (81% yield) as a black oil.

Example A65

Preparation of Intermediate 510

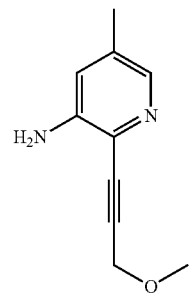

In a sealed tube, 3-amino-2-bromo-5-methylpyridine (2 g; 10.7 mmol), methyl propargyl ether (2.71 mL; 32.4 mmol) and $Et_3N$ (4.59 mL; 32.1 mmol) were diluted in DMF (64 mL). The reaction mixture was degassed ($N_2$ bubbling) and $PdCl_2(PPh_3)_2$ (375 mg; 0.535 mmol) and CuI (409 mg; 2.14 mmol) were added. The reaction mixture was stirred at 50° C. overnight. The reaction mixture was poured onto water and extracted with $EtOAc/Et_2O$. The organic layer was decanted, washed with brine, dried over $MgSO_4$, filtered and evaporated to dryness. The residue was purified by chromatography over silica gel (irregular SiOH, 90 g; mobile phase: gradient from 20% EtoAc, 80% heptane to 100% EtOAc, 0% heptane). The pure fractions were collected and evaporated to dryness. yielding: 1.45 g intermediate 510 (77% yield).

Preparation of Intermediate 511

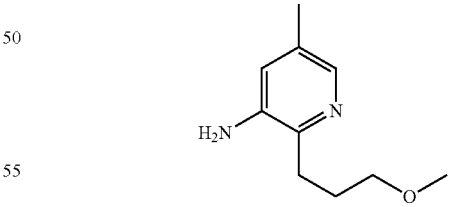

A solution of intermediate 510 (1.45 g, 8.228 mmol) in MeOH was hydrogenated under 2 bars of $H_2$ at rt in presence of Pd/C (10%) (242.85 mg, 0.228 mmol) overnight. The mixture was filtered over Celite®. To the filtrate was added again MeOH. The mixture was hydrogenated under 2 bars of $H_2$ at rt overnight. The mixture was filtered over Celite®. The filtrate was evaporated, yielding: 1.325 g of intermediate 511 (89% yield).

Example A66

Preparation of Intermediate 521

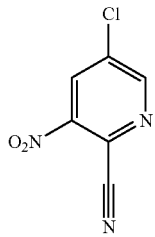

A mixture of 2-bromo-5-chloro-3-nitropyridine (2.8 g; 11.79 mmol) and copper(I) cyanide (1.40 g, 15.63 mmol) in DMF (30 mL) was stirred at 110° C. for 1.5 h. The mixture was concentrated. The residue was diluted with water (60 mL), extracted three times with EtOAc (50 mL). The organic phase was washed with brine, dried over $Na_2SO_4$, filtered and concentrated. The residue was purified by column chromatography (elution: DCM/Petroleum ether 1/1). The desired fractions were collected and concentrated to give 1.10 g of intermediate 521 (51% yield) as a yellow solid.

Preparation of Intermediate 522

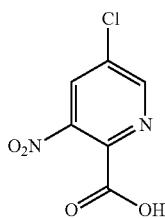 [SMILES: O=C(O)c1ncc(Cl)cc1[N+](=O)[O-]]

A mixture of intermediate 521 (1.01 g; 5.50 mmol) in $H_2SO_4$ cc (5 mL) was stirred at 120° C. for 90 min. The mixture was cooled to rt. A solution of $NaNO_2$ (996.2 mg; 14.44 mmol) in water (1.8 mL) was added dropwise at −5° C. for 15 min. The resulting mixture was warmed to rt and stirred for 30 min. Then the mixture was stirred at 80° C. for 60 min. The mixture was cooled to rt and poured into ice/water, extracted three times with EtOAc (3*15 mL). The organic phase was dried over $Na_2SO_4$, filtered and concentrated to give 1.11 g of intermediate 522 (100% yield) as a yellow solid

Preparation of Intermediate 523

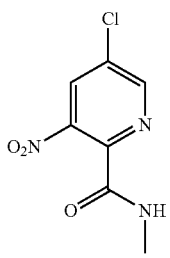

Intermediate 522 (1.10 g, 5.43 mmol) was dissolved in DMF (25.0 mL). HATU (3.10 g, 8.15 mmol) and DIPEA (3.51 g, 27.15 mmol) were added. The mixture was stirred at rt for 5 min. Methylamine hydrochloride (0.92 g; 13.58 mmol) was added. The reaction was stirred at rt overnight. The mixture was diluted with water (20 mL), extracted three times with EtOAc (20 mL). The organic phase was washed with brine, dried over $Na_2SO_4$, filtered and concentrated. The residue was purified by column chromatography (Mobile phase:Petroleum ether/EtOAc 1:1). The desired fractions were collected and concentrated to give 670 mg of intermediate 523 (57% yield) as a solid.

Preparation of Intermediate 524

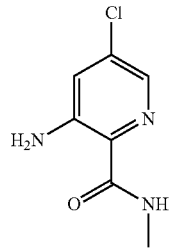

Intermediate 523 (0.67 g, 3.11 mmol) was dissolved in MeOH (24.0 mL) and water (6.00 mL). Iron (0.87 g; 15.54 mmol) and $NH_4Cl$ powder (1.66 g; 31.08 mmol) were added. This reaction was refluxed for 2 h. The mixture was cooled to rt and filtered. The filtrate was diluted with DCM (100 mL), washed with brine. The organic layer was dried over $Na_2SO_4$, filtered and concentrated to give 0.428 g intermediate 524 (74% yield) as a solid.

Example A67

Preparation of Intermediate 527

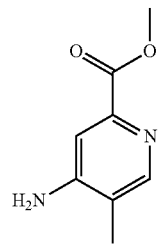

A mixture of 2-bromo-5-methylpyridin-4-amine (2.70 g; 14.44 mmol), $Et_3N$ (4.38 g; 43.30 mmol) and [1,1'-bis(diphenylphosphino)ferrocene]palladium(II) chloride dichloromethane complex (1.18 g; 1.44 mmol) in MeOH (100 mL) was stirred at 80° C. under an atmosphere of carbon monoxide (0.5 MPa) overnight. The mixture was filtered through Celite®, and the solvent was evaporated in vacuum to give 2.4 g of crude material. The crude was purified by column chromatography over silica gel (Mobiled phase: Ethyl acetate/MeOH 5:1). The desired fractions were evaporated in vacuum to give 1.53 g of intermediate 527 (64% yield) as a brown solid.

Preparation of Intermediate 528

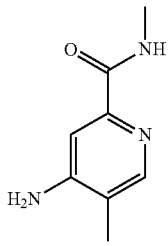

A solution of intermediate 527 (1.53 g; 9.21 mmol) and methylamine 2M in THF (51.00 mL; 102 mmol) in MeOH (50.00 mL) was stirred at 60° C. overnight. The mixture was evaporated in vacuum to give 1.50 g of crude material. The crude was purified by column chromatography over silica gel (Mobile phase: EtOAc/MeOH 10:1). The desired fractions were evaporated in vacuum to give 1.17 g of intermediate 528 (77% yield) as a brown solid.

Example A68

Preparation of Intermediate 531

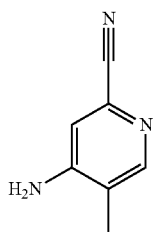

A solution 2-bromo-5-methylpyridin-4-amine (750 mg; 4.01 mmol) in DMF (15 mL) was purged with $N_2$. Copper(I) cyanide (1.08 g; 12.03 mmol) was added, the solution was purged again with $N_2$ and heated at 180° C. using one single mode microwave (Parr) with a power output ranging from 0 to 400W for 3 h [fixed old time]. The reaction mixture was poured onto an aqueous solution of $K_2CO_3$ 10% and EtOAc. The mixture was filtered through a pad of Celite® and the filtrate was extracted with EtOAc. The organic layer was decanted, washed with brine, dried over $MgSO_4$, filtered and the solvent was evaporated. The cake of Celite® was washed three times with DCM/MeOH (90:10), filtered and the solvent was evaporated to give 82 mg of crude material as a green solid. The crude material was combined with that from a parallel reaction for the purification. The residue was purified by chromatography over silica gel (SiOH, GraceResolv®, 4 g, solid deposit (Celite®); Mobile phase: Heptane/EtOAc 60:40). The pure fractions were collected and the solvent was evaporated to give 73 mg of intermediate 531 (10% yield) as an off-white solid.

Example A69

Preparation of Intermediate 533

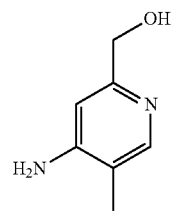

At 0° C. and under $N_2$, lithium aluminum hydride 1M in THF (22.2 mL; 22.20 mmol) was added dropwise to a solution of ethyl 5-amino-6-methylnicotinate (1.00 g; 5.55 mmol) in Me-THF (5 mL). The reaction mixture was stirred at 0° C. for 30 min, then at rt for 3 h. The mixture was cooled to 0° C. and ice-water (590 µL) was added then a cooled solution of NaOH 3N (590 µL) and ice-water (1.77 mL) were successively added dropwise at 0° C. DCM was added, then $MgSO_4$ and the mixture was stirred at room temperature overnight. The mixture was filtered through a pad of Celite® and the filtrate was evaporated to give 579 mg of intermediate 533 (76% yield) as a white solid.

Example A70

Preparation of Intermediate 535

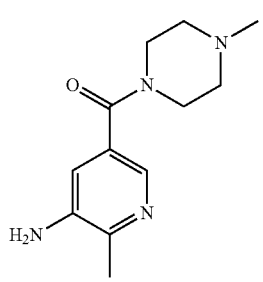 [SMILES: Cc1ncc(C(=O)N2CCN(C)CC2)cc1N]

To a solution of 3-amino-2-methylpyridine-5-carboxylic acid (400 mg; 2.63 mmol) in DCM (22 mL) were added DIPEA (906 µL; 5.26 mmol), 1-methylpiperazine (0.448 ml; 3.94 mmol) and COMU® ((1-Cyano-2-ethoxy-2-oxoethylidenaminooxy)dimethylamino-morpholino-carbenium hexafluorophosphate) (2.82 g; 6.57 mmol). The reaction was stirred at rt for 2 h. The mixture was evaporated in vacuo. The residue was crystallized with DCM, filtered and dried to give 0.53 g of intermediate 535 (86% yield).

Example A71

Preparation of Intermediate 537

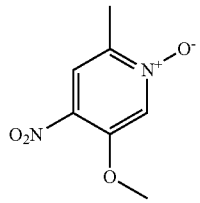

Sodium methoxide, 30 wt % solution in MeOH, (2.10 mL; 11.04 mmol) was added to a solution of 5-fluoro-2-methyl-4-nitropyridine-1-oxide (950 mg; 5.52 mmol) in Me-THF (13 mL). The reaction mixture was heated at reflux for 2 h. The reaction was cooled down to rt, water and DCM were added. The mixture was extracted five times with DCM. The organic layer was washed with water, dried over MgSO$_4$, filtered and the solvent was evaporated to give 328 mg of crude material as a red solid. The crude was purified by chromatography over silica gel (SiOH, GraceResolv®, 4 g, Mobile Phase: DCM/MeOH/NH$_4$OH Gradient from 100:0:0 to 99:1:0.1). The pure fractions were collected and the solvent was evaporated to give 98 mg of intermediate 537 (10% yield) as a yellow solid.

Preparation of Intermediate 538

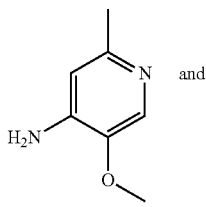

and

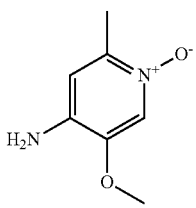

538'

A mixture of intermediate 537 (97 mg; 0.53 mmol) and Pd/C (10% wt., 24 mg; 0.23 mmol) in MeOH (12 mL) was hydrogenated at rt in a pressure vessel reactor (3 bar H$_2$) for 4 h. Hydrogenation of the reaction mixture was continued overnight. The catalyst was filtered through a pad of Celite®. The Celite® was washed with MeOH. Pd/C (10% wt., 24 mg; 0.23 mmol) was added to the filtered liquor and the reaction mixture was hydrogenated once more overnight plus 4 hours. Filtering, re-charging with fresh catalyst (Pd/C (10% wt., 24 mg; 0.23 mmol)) and hydrogenating overnight was repeated a further 2 times. The catalyst was filtered through a pad of Celite®. The Celite® was washed with DCM/MeOH and the filtrate was evaporated to give 62 mg of a mixture of intermediate 538 and 538' (85% yield) as a pale yellow oil.

Example A72

Preparation of Intermediate 553

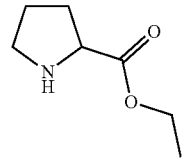

Thionyl chloride (9.46 mL, 130.288) was added dropwise to a solution of DL-Proline in EtOH (75 mL) cooled in an ice bath. The reaction mixture was allowed to reach rt and then heated to reflux for 16 h. The solvent was evaporated and the residue was diluted in EtOAc and washed with an aqueous solution of Na$_2$CO$_3$ and brine. The organic layer was separated, dried over MgSO$_4$ and removed under reduced pressure to yield intermediate 553.

Preparation of Intermediate 554

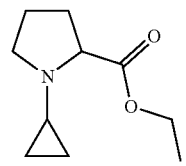

To a solution of intermediate 553 (1.00 g; 6.98 mmol) in THF:MeOH 9:1 (69.00 mL) with 3 A molecular sieves (1.00 g) was added (1-ethoxycyclopropoxy) trimethylsilane (4.21 mL; 20.95 mmol), AcOH (4.79 mL; 83.81 mmol) and sodium cyanoborohydride (1.32 g; 20.95 mmol) at room temperature. The reaction was heated to 65° C. for 16 h. The suspension was filtered and concentrated. Thre crude was diluted in saturated aqueous NaHCO$_3$ and extracted with EtOAc. The organic layer was dried over MgSO$_4$, filtered and removed under reduced pressure to give 1.07 g of intermediate 554 (84% yield, colorless oil).

Preparation of Intermediate 555

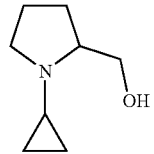

Lithium borohydride (630 mg, 28.923 mmol) was added to a solution of intermediate 554 (1.06, 5.785 mmol) in THF (30 mL) stirred at rt. The reaction mixture was stirred at 55° C. overnight. The reaction mixture was cooled, quenched with water. A solution of NaOH 10% was added and extracted with EtOAc. The organic layer was separated, dried over MgSO$_4$, filtered and removed under reduced pressure to yield intermediate 555 as a colorless oil. (678 mg, 83% yield).

Example A73

Preparation of Intermediate 569

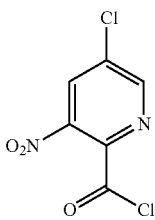 [SMILES: O=C(Cl)c1ncc(Cl)cc1[N+](=O)[O-]]

To a solution of intermediate 522 (300 mg; 1.48 mmol) in DCM (5.00 mL) was added DMF (catalytic drop) at rt. To the solution was added oxalyl chloride (0.188 mL; 2.22 mmol) at 0° C. The solution was stirred at rt for 1 hour. The reaction was concentrated to give 327 mg of intermediate 569 (100% yield) as a yellow oil.

Preparation of Intermediate 570

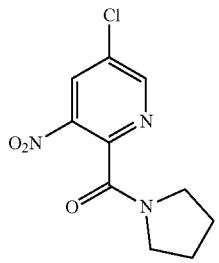

To the solution of pyrrolidine and Et$_3$N (0.62 mL; 4.44 mmol) in DCM (5.00 mL) was added intermediate 569 (327 mg; 1.48 mmol) at 0° C. The reaction was stirred at room temperature for 16 hours. To the reaction was added water (100 mL). The mixture was extracted twice with EtOAc (100 mL). The organic layer was washed with brine (100 mL). Then the organic phase was dried over anhydrous Na$_2$SO$_4$. After filtering, the organic phase was concentrated. The crude product was purified by column chromatography over silica gel (Mobile phase: petroleum ether:EtOAc, 1:1). The pure fractions were collected and the solvent was evaporated under vacuum. The aqueous layer was concentrated to give 230 mg of intermediate 570 (61% yield) as a yellow solid.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 576 | 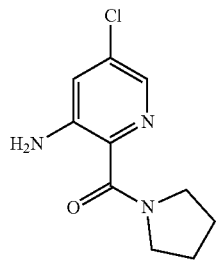 [SMILES: O=C(c1ncc(Cl)cc1[N+](=O)[O-])N1CCCC1]<br>From intermediate 569 and intermediate 575 | — | — |

Preparation of Intermediate 571

Intermediate 570 (380 mg; 1.48 mmol) was suspened in MeOH (16.00 mL) and H$_2$O (4.00 mL). Iron (413 mg; 7.41 mmol) and NH$_4$Cl (792 mg; 14.81 mmol) were added. The mixture was refluxed for 2 hours. The mixture was cooled to rt and filtered. The filtrate was concentrated. The crude product was purified by column chromatography over silica gel (mobile phase petroleum ether:EtOAc, 1:1). The combined fractions containing pure product were concentrated to give 260 mg intermediate 571 (78% yield) as a yellow solid.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 577 | From intermediate 576 | — | — |

Example A74

Preparation of Intermediate 574

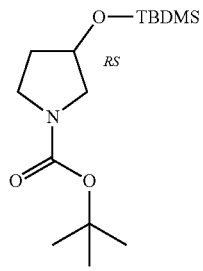

To the solution of (RS)—N—BOC-3-hydroxypyrrolidine (5.00 g, 26.704 mmol) and imidazole (4.55 g, 66.76 mmol) in DCM (50 mL) was added tert-butyldimethylchlorosilane (4.83 g, 32.045 mmol) at 0° C. The reaction was stirred at rt for 16 hours. The reaction was extracted three times with ethyl acetate (1000 mL). The combined organic layer was washed with brine (1000 mL). The organic phase was dried over anhydrous $Na_2SO_4$. The organic layer was concentrated. The crude product was purified by column chromatography over silica gel (EtOAc). The fractions containing pure product were combined and concentrated to give 7.0 g of intermediate 574 (87% yield) as a clear oil.

Preparation of Intermediate 575

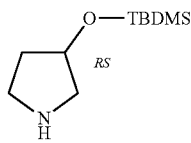

To the solution of intermediate 574 in 40 mL of DCM was added 20 mL of TFA at 0° C. The solution was stirred at 0° C. for 2 hours. To the reaction was added $NaHCO_3$ aq. to basicify to pH=8. The reaction was concentrated to give a residue. The residue was washed with EtOAc. The organic layer was concentrated to give 4.00 g of intermediate 575 (Quant. Yield) as a yellow oil. The product was used in subsequent reactions without further purification.

Example A75

Preparation of Intermediate 579

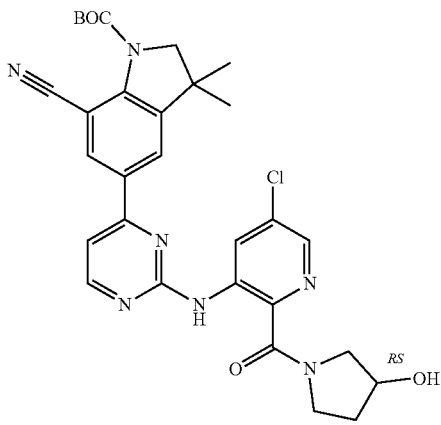 [SMILES: CC(C)(C)OC(=O)N1CC(C)(C)c2cc(-c3ccnc(Nc4cc(Cl)cnc4C(=O)N4CCC(O)C4)n3)cc(C#N)c21]

Intermediate 578 was stirred in TBAF (1M) at rt. The reaction was concentrated to give 160 mg of intermediate 579 (92% yield).

Example A76

Preparation of Intermediate 580

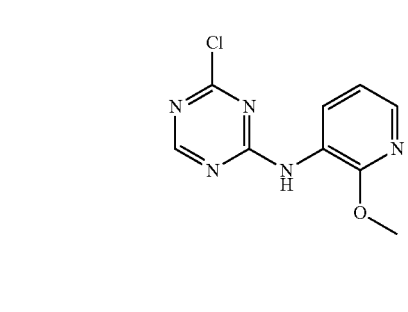 [SMILES: COc1ncccc1Nc1ncnc(Cl)n1]

DIPEA (2.50 mL; 14.50 mmol) was added to a solution of 3-amino-2-methoxypyridine (1.50 g; 12.08 mmol) and 2,4-dichloro-1,3,5-triazine (1.81 g; 12.08 mmol) in acetone at 0° C. The reaction mixture allowed to warm up to rt and stirred under nitrogen for 12 hours. The mixture was evaporated to give 3.00 g of crude material (yellow solid). This crude was combined with that from 2 parallel reactions for further purification by column chromatography (Mobile phase: Petroleum ether/ethyl acetate, Gradient from 100:0 to 20:80). The desired fractions were collected and the solvent was removed to give 780 mg intermediate 580 (27% yield) as a yellow solid.

449

Preparation of intermediate 581

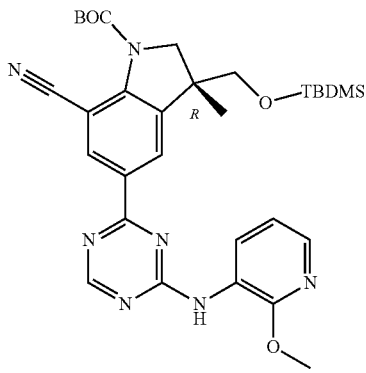

To a mixture of intermediate 5R (988 mg; 1.87 mmol), intermediate 580 (400 mg; 1.68 mmol) and NaHCO$_3$ (3.74 mL; 7.48 mmol) in 1,4-dioxane (12.00 mL) was added Pd(dppf)Cl$_2$ (137 mg; 0.19 mmol) under N$_2$. The mixture was stirred at 80° C. for 12 h. The reaction was poured into water (30 ml) and extracted four times with EtOAc (40 mL). The organic layers were dried over Mg$_2$SO$_4$, filtered and concentrated to give 1.2 g of crude material. This crude was combined with that from 2 parallel reactions for further purification by column chromatography (Mobile phase: Petroleum ether/ethyl acetate Gradient from 100:0 to 0:100). The desired fractions were collected and the solvent was removed to give 330 mg intermediate 581 (24% yield) as a yellow solid.

Example A77

Preparation of Intermediate 582

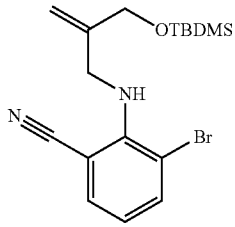 [SMILES: C=C(CNc1c(Br)cccc1C#N)CO[Si](C)(C)C(C)(C)C]

To a solution of 2-amino-3-bromobenzonitrile (30.0 g) in THF (240 mL) was added sodium tert-butoxide (1.1 eq.) and the mixture was stirred at −5 to 5° C. for 1 hour. A solution of intermediate 3a in THF (85.0 g) was then added dropwise and the mixture was stirred for 2-4 hours monitoring the conversion by HPLC. Water (210 mL) was then added dropwise and the mixture was concentrated to remove most of THF.

Heptane (300 mL) was then added and the mixture was stirred for 30 min. After phase separation, the organic layer was washed with water (210 mL), concentrated to 2-3 volumes and filtered through a pad of silica gel (60 g), washing the pad with heptane (300 mL), affording 63.3 g of intermediate 582.

450

Preparation of Intermediate 583

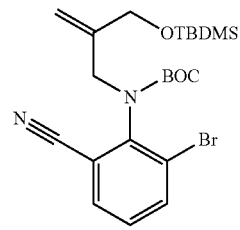 [SMILES: C=C(CO[Si](C)(C)C(C)(C)C)CN(C(=O)OC(C)(C)C)c1c(Br)cccc1C#N]

To a solution of intermediate 582 (50.0 g) in dry THF (500 mL) was added dimethylaminopyridine (0.5 eq.) and the temperature was adjusted to 65-70° C. Di-tert-butyldicarbonate (2.2 eq.) was then added and the mixture was stirred for 2 hours monitoring the conversion by HPLC. Water (350 mL) was added and the mixture was concentrated to 350-400 mL. Heptane (500 mL) was added and the pH was adjusted by addition of 20% aqueous AcOH to 4-6. The layers were separated and water (350 mL) was added. After pH adjustment to 7-8 with aqueous 8% NaHCO$_3$, the layers were separated and the organic layer was washed with water (350 mL) and concentrated to afford 64 g (quantitative) of intermediate 583.

Example A78

Preparation of Intermediate 13i

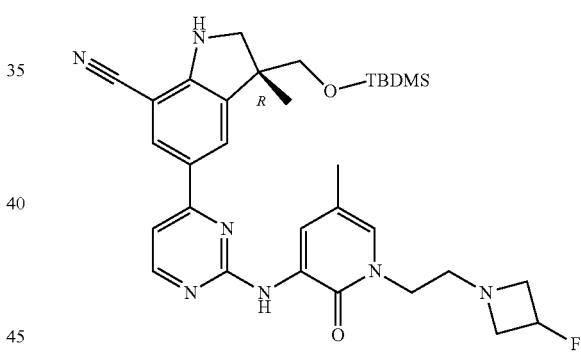

In a sealed vessel, a mixture of intermediate 7R (214.00 mg, 0.52 mmol) in 1,4-dioxane (10 mL) was purged with N$_2$. Intermediate 12i (175.00 mg, 0.78 mmol) and Cs$_2$CO$_3$ (336.02 mg, 1.03 mmol) were successively added and the suspension was degassed after each addition. Then, Pd(OAc)$_2$ (11.58 mg, 0.052 mmol) and BINAP (32.11 mg, 0.052 mmol) were added. The reaction mixture was degassed with N$_2$ and stirred at 120° C. (pre-heated bath) for 3 h, cooled to rt, poured onto iced water and extracted with EtOAc. The organic layer was decanted, washed with brine, dried over MgSO$_4$, filtered over a pad of Celite® and evaporated to dryness. The residue was purified by column chromatography on silica gel (irregular SiOH, 25 g, mobile phase: DCM/MeOH, gradient from 95:5 to 90:10). The pure fractions were collected and evaporated to dryness to give 234 mg of intermediate 13i (75% yield, 89% purity based on LC/MS) used as it for the next step.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 17i | From intermediate 7R and intermediate 16i | 107 | 66 |
| Intermediate 20i | From intermediate 7R and intermediate 19i | 668 (89% purity based on LC/MS) | 95 Procedure with Me-THF as solvent and T = 85° C. |
| Intermediate 23i | From intermediate 7R and intermediate 22i | 127 (79% purity based on LC/MS) off-white solid | 67 Procedure with Me-THF as solvent and T = 85° C. |

-continued

| Intermediate number | Structure | Mass (mg) | Yield (%) |
|---|---|---|---|
| Intermediate 36i | From intermediate 7R and 3-amino-2(1H)-pyridinone | 144 (84% purity based on LC/MS) | 24 |
| Intermediate 59i | From intermediate 7 and 3-amino-5-chloro-1-methyl-2(1H)-pyridinone | 245 brown oil | 32 Procedure with T = 95° C. |
| Intermediate 62i | From intermediate 7R and intermediate 61i | 215 | 66 |

-continued

| Intermediate number | Structure | Mass (mg) | Yield (%) |
|---|---|---|---|
| Intermediate 65i | *(structure)* From intermediate 7R and intermediate 64i | 110 | 81 |
| Intermediate 68i | *(structure)* From intermediate 7R and intermediate 67i | 500 | 73 |
| Intermediate 71i | *(structure)* From intermediate 7R and intermediate 70i | 193 | 72 |

-continued

| Intermediate number | Structure | Mass (mg) | Yield (%) |
|---|---|---|---|
| Intermediate 74i | From intermediate 7R and intermediate 73i | 203 | 85 |
| Intermediate 78i | From intermediate 7R and intermediate 77i | 700 | LC/MS purity 65% Combined with another crude |
| Intermediate 87i | From intermediate 7R and intermediate 86i | 211 | 73 Procedure at 120° C. for 18 h |
| Intermediate 100i | From intermediate 7R and intermediate 99i | 415 | 57 |

Example A79

Preparation of Intermediate 26i

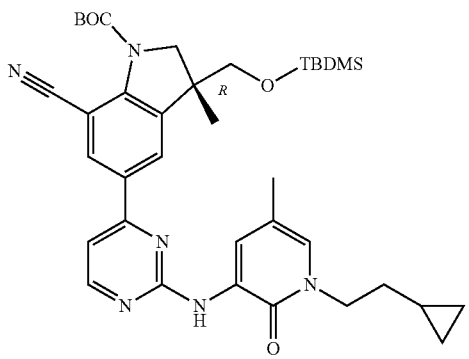

A suspension of intermediate 6R (0.45 g, 0.87 mmol), intermediate 25 (251.90 mg, 1.31 mmol), Pd(OAc)$_2$ (19.61 mg, 0.087 mmol), BINAP (54.40 mg, 0.087 mmol) and Cs$_2$CO$_3$ (853.88 mg, 2.62 mmol) in Me-THF (9 mL) was purged with N$_2$ and stirred at 85° C. for 2 h. The mixture was cooled down to rt, combined with another batch (from 50 mg of intermediate 6R) and filtered on a pad of Celite®. The cake was washed with EtOAc and the filtrate was evaporated in vacuo to give a brown foam. The residue (849 mg) was purified by column chromatography on silica gel (irregaular SiOH, 15-40 µm, 40 g, dry loading on Celite®, mobile phase: heptane/EtOAc, gradent from 85:15 to 50:50). The fractions containing the product were combined and evaporated to dryness to give 629 mg of intermediate 26i (93% yield, 94% purity based on LC/MS, off-white foam).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 30i | From intermediate 6R and intermediate 29i | 683 (98% purity based on NMR) yellow solid | 95 |
| Intermediate 34i | From intermediate 6R and intermediate 33i | 476 off-white foam | 76 |

-continued

| Intermediate number | Structure | Mass (mg) | Yield (%) |
|---|---|---|---|
| Intermediate 37i | 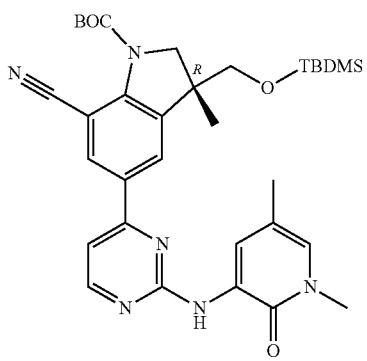<br>From intermediate 6R and 3-amino-1,5-dimethyl-2(1H)-pyridinone (intermediate 102i) | 876 clear brown foam | Quant. Procedure with 1,4-dioxane as solvent and T = 100° C. |
| Intermediate 41i | 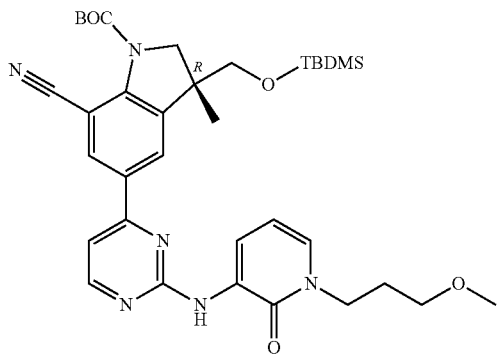<br>From intermediate 6R and intermediate 40i | 270 greenish film | 44 Procedure with 1,4-dioxane as solvent and T = 100° C. |
| Intermediate 47i | 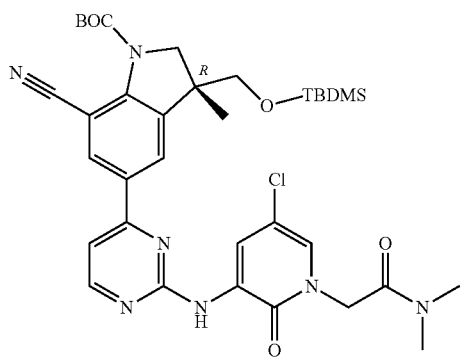<br>From intermediate 6R and intermediate 46i | 186 (56% purity based on LC/MS) green oil | — Procedure with 1,4-dioxane as solvent and T = 90° C. |

-continued

| Intermediate number | Structure | Mass (mg) | Yield (%) |
|---|---|---|---|
| Intermediate 51i | 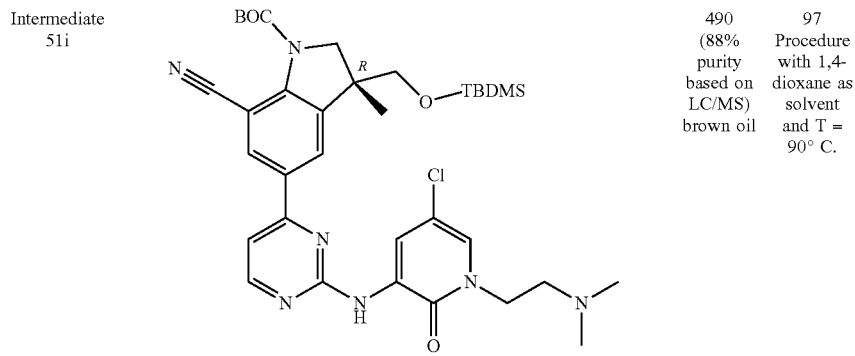<br>From intermediate 6R and intermediate 50i | 490 (88% purity based on LC/MS) brown oil | 97 Procedure with 1,4-dioxane as solvent and T = 90° C. |
| Intermediate 53i | 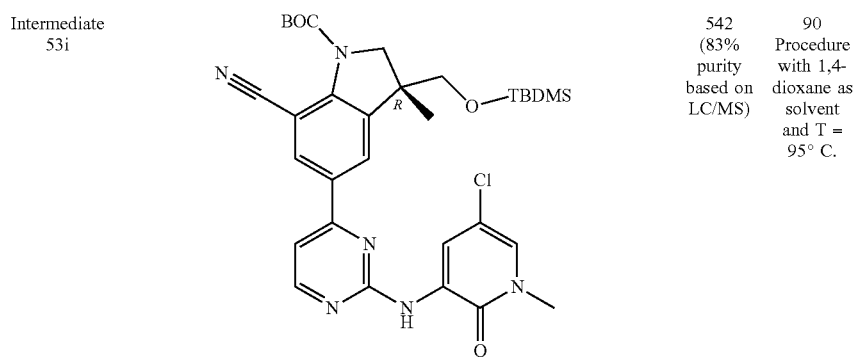<br>From intermediate 6R and 3-amino-5-chloro-1-methyl-2(1H)-pyridinone | 542 (83% purity based on LC/MS) | 90 Procedure with 1,4-dioxane as solvent and T = 95° C. |
| Intermediate 57i | 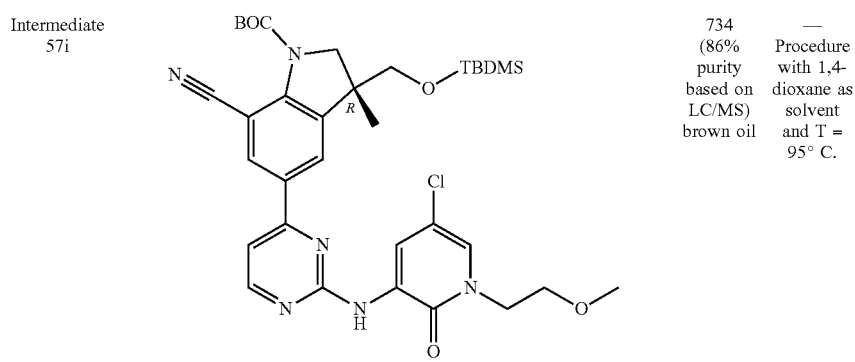<br>From intermediate 6R and intermediate 56i | 734 (86% purity based on LC/MS) brown oil | — Procedure with 1,4-dioxane as solvent and T = 95° C. |

| Intermediate number | Structure | Mass (mg) | Yield (%) |
|---|---|---|---|
| Intermediate 82i | 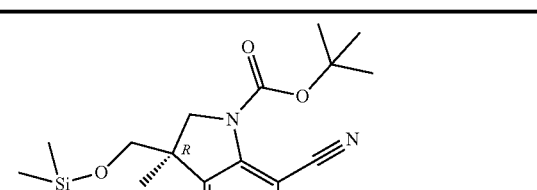 | 240 | 44% Procedure with 1,4-dioxane as solvent and T = 80° C. |

From intermediate 6R and intermediate 81i

Example A80

Preparation of Intermediate 27i

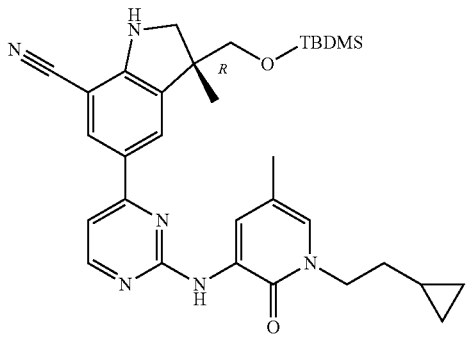

To a solution of intermediate 26i (609.00 mg, 0.89 mmol) in DCM (20 mL), TFA (2.00 mL, 26.1 mmol) was added and the mixture was stirred at rt for 20 min. The mixture was combined with another batch (from 616 mg of intermediate 26i). The mixture was poured into a saturated solution of NaHCO₃. The layers were separated and the aqueous layer was extracted with DCM. The combined organic layers were dried over MgSO₄, filtered off and evaporated in vacuo. The residue (550 mg, orange foam) was purified by column chromatography on silica gel (irregular SiOH, 15-40 μm, 40 g, dry loading on Celite®, mobile phase gradient: from heptane 95%, EtOAc/MeOH (9:1) 5% to heptane 60%, EtOAc/MeOH (9:1) 40%). The fractions containing the product were combined and concentrated under vacuum to give 429 mg of intermediate 27i (81% yield, off-white foam.

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 31i | 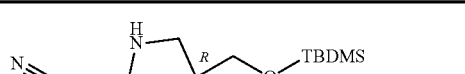 | 456 off-white solid | 79 |

From intermediate 30i

-continued

| Intermediate number | Structure | Mass (mg) | Yield (%) |
|---|---|---|---|
| Intermediate 35i | From intermediate 34i | 460 off-white solid | 84 |
| Intermediate 42i | From intermediate 41i | 220 orange oil | 96 Procedure with DCM/TFA (6:1, v/v) |
| Intermediate 48i | From intermediate 47i | 70 (72% purity based on LC/MS) | 43 Procedure with DCM/TFA (5:2, v/v) |
| Intermediate 52i | From intermediate 51i | 310 (94% purity based on LC/MS) | 74 Procedure with DCM/TFA (5:2, v/v) |

-continued

| Intermediate number | Structure | Mass (mg) | Yield (%) |
|---|---|---|---|
| Intermediate 54i | From intermediate 53i | 390 (66% purity based on LC/MS) | 85 Procedure with DCM/TFA (5:2, v/v) |
| Intermediate 58i | From intermediate 57i | 308 green oil | 73 Procedure with DCM/TFA (9:1, v/v) |
| Intermediate 83i | From intermediate 82i | 250 | 97 Procedure with DCM/TFA (5:1, v/v) |
| Intermediate 105i | From intermediate 104i | 260 LCMS 65% | quantitative |

Example A81

Preparation of Intermediate 38i

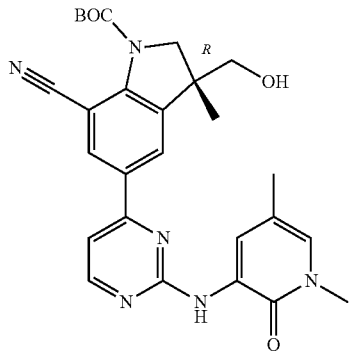

A mixture of intermediate 37i (876.00 mg, 1.35 mmol) in Me-THF (6 mL) was treated with TBAF (1M in THF) (2.10 mL, 2.10 mmol) and stirred at rt for 18 h, leading to precipitation. The precipitate was filtered off, washed with MeTHF and dried to afford 150 mg of intermediate 38i (22%). The filtrate was extended with DCM and concentrated to afford a red solution. It was purified by column chromatography on silica gel (iregular SiOH 30 µm, 80 g, liquid injection with a mixture of Me-THF/DCM, mobile phase EtOAc/MeOH, gradient from 100:0 to 95:5 in 20 CV). The fractions containing the product were combined and evaporated to dryness to give additional 439 mg of intermediate 38i (65% yield, pale yellow solid).

Example A82

Preparation of Intermediate 8i

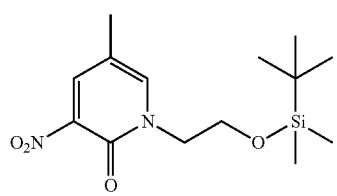 [SMILES: Cc1cc([N+](=O)[O-])c(=O)n(CCO[Si](C)(C)C(C)(C)C)c1]

In a sealed tube, a mixture of 2-hydroxy-5-methyl-3-nitropyridine (1.00 g, 6.49 mmol), (2-bromoethoxy)-tert-butyldimethylsilane (2.80 mL, 12.98 mmol) and $K_2CO_3$ (2.70 g, 19.46 mmol) in DMF (13 mL) was stirred at 60° C. for 2 h. The reaction mixture was cooled down to rt, poured onto a mixture of water and brine, then extracted with $Et_2O$. The organic layer was decanted, washed with brine, dried over $MgSO_4$, filtered and evaporated to dryness. The residue was purified by column chromatography on silica gel (irregular SiOH, 80 g, mobile phase: heptane/EtOAc, gradient from 80:20 to 60:40). The pure fractions were collected and evaporated to dryness to give 1.68 g of intermediate 8i (83% yield, 94% purity based on LC/MS).

Preparation of Intermediate 9i

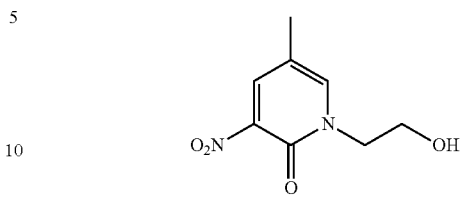

TBAF (1 M in THF) (8.64 mL, 8.64 mmol) was added to a solution of intermediate 8i (1.35 g, 4.32 mmol) in Me-THF (40 mL). The reaction mixture was stirred for 1 h and evaporated to dryness. The residue was purified by column chromatography on silica gel (irregular SiOH, 40 g, mobile phase: 5% MeOH, 95% DCM). The pure fractions were collected and evaporated to dryness. The residue was taken up with a mixture of $CH_3CN/Et_2O$ and the precipitate was filtered and dried to give 535 mg of intermediate 9i (62% yield).

The intermediate in the Table below was prepared by using an analogous method starting from the respective starting material.

| Intermediate number | Structure | Mass (mg) | Yield (%) |
|---|---|---|---|
| Intermediate 94i | 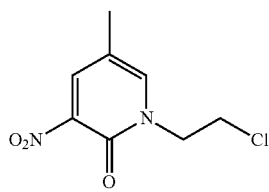 | 250 | 69 |

From intermediate 93i

Preparation of Intermediate 10i

A mixture of intermediate 9i (300.00 mg, 1.51 mmol) and $SOCl_2$ (0.22 mL, 3.03 mmol) in DCM (5 mL) was stirred at rt for 3 h and the reaction mixture was evaporated to dryness to give 300 mg of intermediate 10i (91% yield).

The intermediate in the Table below was prepared by using an analogous method starting from the respective starting material.

| Intermediate number | Structure | Mass (mg) | Yield (%) |
|---|---|---|---|
| Intermediate 95i | From intermediate 94i | 256 | 98 |

Preparation of Intermediate 11i

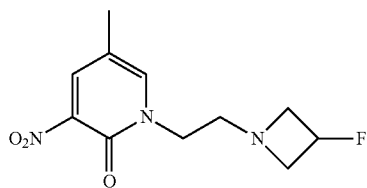 [SMILES: Cc1cc([N+](=O)[O-])c(=O)n(CCN2CC(F)C2)c1]

A mixture of intermediate 10i (300.00 mg, 1.38 mmol), 3-fluoroazetidine HCl salt (185.38 mg, 1.66 mmol) and DIEA (716.00 μL, 4.15 mmol) in CH$_3$CN (8 mL) was refluxed for 1 h in a sealed tube. The reaction mixture was evaporated to dryness and the residue was purified by column chromatography on silica gel (irregular SiOH, 12 g, mobile phase: DCM/MeOH, gradient from 100:0 to 90:10). The pure fractions were collected and evaporated to dryness to give 200 mg of intermediate 11i (57% yield).

The intermediates in the Table below were prepared by using an analogous method starting from the respective starting materials.

| Intermediate number | Structure | Mass (mg) | Yield (%) |
|---|---|---|---|
| Intermediate 15i | From intermediate 10i and cis-2,6-dimethylmorpholine | 177 (87% purity based on LC/MS) | 53 |
| Intermediate 60i | cis | 369 | 78 |
| Intermediate 63i | From intermediate 10i and cis-2,6-dimethylpiperazine | 177 | 40 |
| Intermediate 69i | From intermediate 10i and 3,3-difluoroazetidine hydrochloride | 227 Brown oil | 53 |
| Intermediate 72i | From intermediate 10i and 1-methylpiperazine | 257 | 59 |
| Intermediate 96i | From intermediate 10i and homomorpholine hydrochloride | 195 | 65 |
| | From intermediate 95i and 3-fluoroazetidine hydrochloride | | |

Preparation of Intermediate 12i

A mixture of intermediate 11i (264.00 mg, 1.03 mmol), iron powder (288.81 mg, 5.17 mmol) and NH$_4$Cl (221.30 mg, 4.14 mmol) in a mixture of EtOH (9 mL) and distilled water (4.5 mL) was heated at 80° C. for 2 h. Then, the mixture was cooled down to rt, diluted with DCM and filtered through a pad of Celite®. The organic layer was basified with a 10% aqueous solution of $K_2CO_3$, decanted, dried over $MgSO_4$, filtered and evaporated to dryness. The residue was purified by column chromatography on silica gel (irregular SiOH, 25 g, mobile phase: 5% MeOH, 95% DCM). The pure fractions were collected and evaporated to dryness to give 175 mg of intermediate 12i (75% yield, 96% purity based on LC/MS).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 16i | From intermediate 15i | 100 | 63 with EtOH/ water (5:3, v/v) |
| Intermediate 19i | From intermediate 18i | 485 | 65 with EtOH/ water (1:1, v/v) |
| Intermediate 22i | From intermediate 21i | 69 beige solid | 51 with EtOH/ water (1:1, v/v) |
| Intermediate 25i | From intermediate 24i | 603 black oil | 90 with EtOH/ water (1:1, v/v) |
| Intermediate 29i | From intermediate 28i | 504 (70% purity based on LC/MS) black solid | 68 with EtOH/ water (1:1, v/v) |

-continued

| Intermediate number | Structure | Mass (mg) | Yield (%) |
|---|---|---|---|
| Intermediate 33i | (structure: 3-amino-5-methyl-1-(2-morpholinoethyl)pyridin-2(1H)-one) From intermediate 32i | 828 brown oil | 66 with EtOH/water (1:1, v/v) |
| Intermediate 40i | (structure: 3-amino-1-(3-methoxypropyl)pyridin-2(1H)-one) From intermediate 39i | 255 dark green oil | 96 with EtOH/water (1:1, v/v) |
| Intermediate 46i | (structure: 2-(3-amino-5-chloro-2-oxopyridin-1(2H)-yl)-N,N-dimethylacetamide) From intermediate 45i | 85 green residue | 54 with EtOH/water (1:1, v/v) |
| Intermediate 50i | (structure: 3-amino-5-chloro-1-(2-(dimethylamino)ethyl)pyridin-2(1H)-one) From intermediate 49i | 235 brown oil | 54 with EtOH/water (1:1, v/v) |
| Intermediate 56i | (structure: 3-amino-5-chloro-1-(2-methoxyethyl)pyridin-2(1H)-one) From intermediate 55i | 174 (88% purity based on LC/MS) brown oil | 73 with EtOH/water (1:1, v/v) |
| Intermediate 61i | (structure: 3-amino-5-methyl-1-(2-(cis-3,5-dimethylpiperazin-1-yl)ethyl)pyridin-2(1H)-one) From intermediate 60i | 200 dark brown | 62 |

-continued

| Intermediate number | Structure | Mass (mg) | Yield (%) |
|---|---|---|---|
| Intermediate 64i | 3-amino-5-methyl-1-(2-(3,3-difluoroazetidin-1-yl)ethyl)pyridin-2(1H)-one<br>From intermediate 63i | 177 brown | 40 |
| Intermediate 70i | 3-amino-5-methyl-1-(2-(4-methylpiperazin-1-yl)ethyl)pyridin-2(1H)-one<br>From intermediate 69i | 160 | 80 |
| Intermediate 73i | 3-amino-5-methyl-1-(2-(1,4-oxazepan-4-yl)ethyl)pyridin-2(1H)-one<br>From intermediate 72i | 143 | 63 |
| Intermediate 86i | 3-amino-5-methyl-1-((4-methylmorpholin-3-yl)methyl)pyridin-2(1H)-one<br>From intermediate 85i | 175 | 86 Procedure with EtOH/ water (7:4, v/v) |
| Intermediate 97i | 3-amino-5-fluoro-1-(2-(3-fluoroazetidin-1-yl)ethyl)pyridin-2(1H)-one<br>From intermediate 96i | 60 | 36 |
| Intermediate 99i | 3-amino-5-methyl-1-((3-methyloxetan-3-yl)methyl)pyridin-2(1H)-one<br>From intermediate 98i | 307 | 80 |

Example A83

Preparation of Intermediate 14i

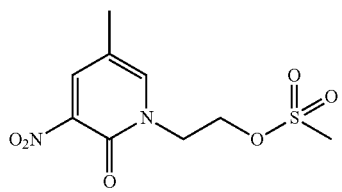 [SMILES: Cc1cc([N+](=O)[O-])c(=O)n(CCOS(C)(=O)=O)c1]

MsCl (249.24 µL, 3.21 mmol) was added at 5° C. to a suspension of intermediate 9 (530.00 mg, 2.67 mmol) and TEA (743.47 µL, 5.34 mmol) in DCM (13 mL), and the reaction mixture was stirred at 5° C. for 30 min. Then, a 10% aqueous solution of $NH_4Cl$ (2 mL) and DCM were added. The organic layer was filtered over Chromabond® and evaporated to dryness to give 631 mg of intermediate 14i (85% yield, 82% purity based on LC/MS) used as it for the next step.

Example A84

Preparation of intermediate 18i

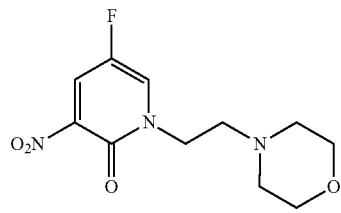 [SMILES: O=c1c([N+](=O)[O-])cc(F)cn1CCN1CCOCC1]

To a suspension of 5-fluoro-2-hydroxy-3-nitropyridine (1.03 g, 6.49 mmol) in DMF (13 mL) at rt, $K_2CO_3$ (3.59 g, 25.95 mmol) then N-(2-chloroethyl)morpholine hydrochloride (2.42 g, 12.98 mmol) were added, and the reaction mixture was stirred at 60° C. for 2 h. The mixture was cooled down to rt and filtered off. The filtrate was extracted with EtOAc. The organic layer was washed with brine, dried over $MgSO_4$, filtered and evaporated in vacuo. The residue was purified by column chromatography on silica gel (irregular SiOH, 15-40 µm, 120 g, mobile phase gradient: from heptane/EtOAc/MeOH: 100/0/0 to 0/80/20). The pure fractions were mixed and the solvent was evaporated to give and 0.846 g of intermediate 18i (48% yield).

The intermediates in the Table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 21i | 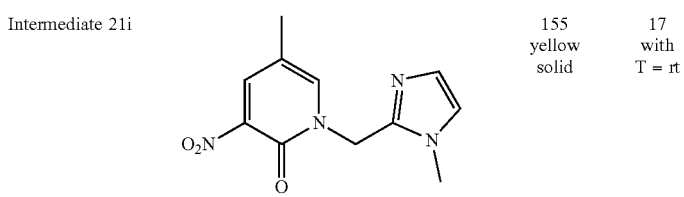 From 2-hydroxy-5-methyl-3-nitropyridine and 2-chloromethyl-1-methyl-1H-imidazole, HCl salt | 155 yellow solid | 17 with T = rt |
| Intermediate 28i | 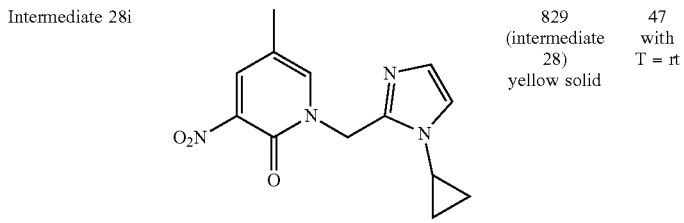 From 2-hydroxy-5-methyl-3-nitropyridine and 2-(chloromethyl)-1-cyclopropyl-1H-imidazole, HCl salt | 829 (intermediate 28) yellow solid | 47 with T = rt |

-continued

| Intermediate number | Structure | Mass (mg) | Yield (%) |
|---|---|---|---|
| Intermediate 32i | (structure) From 2-hydroxy-5-methyl-3-nitropyridine and N-(2-chloroethyl)morpholine, HCl salt | 1500 | 86 |
| Intermediate 39i | (structure) From 3-nitro-2(3H)-pyridinone and 1-Bromo-3-methoxypropane | 310 yellow oil | 51 with T = rt |
| Intermediate 49i | (structure) From 5-chloro-2-hydroxy-3-nitropyridine and 2-Bromo-N,N-dimethylethylamine hydrobromide salt | 510 yellow solid | 32 |
| Intermediate 55i | (structure) From 5-chloro-2-hydroxy-3-nitropyridine and 2-bromoethyl methyl ether | 293 brown solid | 44 with $Na_2CO_3$ as a base |
| Intermediate 66i | (structure) From 5-methyl-2-hydroxy-3-nitropyridine and 4-(2-chloro-1-methylethyl)morpholine | 483 80% purity based on $^1H$ nmr | 56 |

| Intermediate number | Structure | Mass (mg) | Yield (%) |
|---|---|---|---|
| Intermediate 85i | 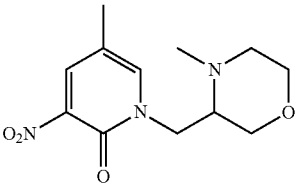 [SMILES: Cc1cc([N+](=O)[O-])c(=O)n(CC2COCCN2C)c1]<br>From 5-methyl-2-hydroxy-3-nitropyridine and intermediate 84i | 229 | 64<br>Procedure at 60° C. for 5 h |
| Intermediate 93i | 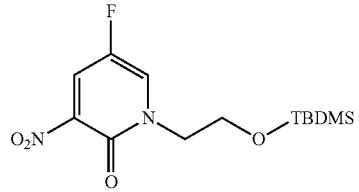<br>From 5-fluoro-2-hydroxy-3-nitropyridine and (2-bromoethoxy)-tert-butyldimethylsilane | 568 | 28 |
| Intermediate 98i | 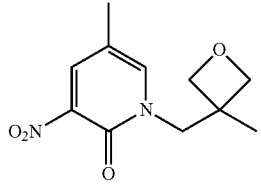 [SMILES: Cc1cc([N+](=O)[O-])c(=O)n(CC2(C)COC2)c1]<br>From 5-methyl-2-hydroxy-3-nitropyridine and 3-bromomethyl-3-methyloxetane | 365 | 51 |
| Intermediate 101i | 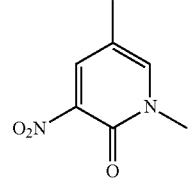<br>From 5-methyl-2-hydroxy-3-nitropyridine and iodo-methane | 500 | 91<br>Procedure with T = rt |

Example A85

Preparation of intermediate 24i

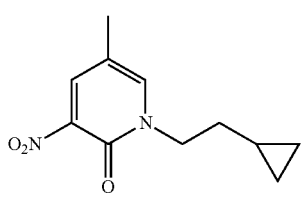

intermediate 24i

To a suspension of 2-hydroxy-5-methyl-3-nitropyridine (0.60 g, 3.89 mmol) in DMF (8 mL) at rt, $K_2CO_3$ (1.61 g, 11.7 mmol), NaI (58.40 mg, 0.39 mmol) were added then (2-bromoethyl)cyclopropane (0.87 g, 5.84 mmol) and the reaction mixture was stirred at 60° C. for 3 h. The mixture was combined with two other batches (from each 50 mg of 2-hydroxy-5-methyl-3-nitropyridine) and filtered on a pad of Celite®. The cake was washed with EtOAc and the filtrate was evaporated in vacuo to give a brown oil. The residue was purified by column chromatography on silica gel (irregular SiOH, 15-40 μm, 50 g, dry loading on Celite®, mobile phase gradient: from heptane 90%, EtOAc/MeOH (9:1) 10% to heptane 50%, EtOAc/MeOH (9:1) 50%). The fractions containing the product were combined and evaporated to dryness to give 775 mg of intermediate 24i (77% yield, orange gum).

Example A86

Preparation of Intermediate 43i

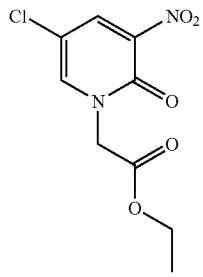 [SMILES: CCOC(=O)Cn1cc(Cl)cc([N+](=O)[O-])c1=O]

In sealed glassware, 5-chloro-2-hydroxy-3-nitropyridine (2.00 g, 11.50 mmol) and ethyl bromoacetate (1.53 mL, 13.80 mmol) were diluted in acetone (40 mL). $K_2CO_3$ (1.90 g, 13.80 mmol) was added to the solution and the mixture was refluxed for 17 h with stirring. The reaction mixture was diluted with water and extracted twice with EtOAc. The organic layers were combined and washed with brine, dried over $MgSO_4$ and filtered. The solvent was removed under reduced pressure. The residue (2.62 g, brown residue) was purified by column chromatography on silica gel (irregular SiOH 15-40 µm, 120 g, dry load on Celite®, mobile phase gradient: from DCM 100% to DCM 90%, MeOH (+aq. $NH_3$ 5%) 10%). The fractions containing the products were combined and evaporated to dryness to give 1.65 g of intermediate 43i (55% yield, yellow solid).

Preparation of Intermediate 44i

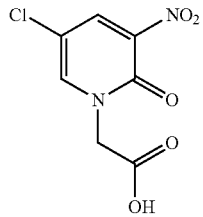 [SMILES: O=C(O)Cn1cc(Cl)cc([N+](=O)[O-])c1=O]

A mixture of intermediate 43i (700.00 mg, 2.69 mmol) and LiOH monohydrate (169.10 mg, 4.03 mmol) in a mixture of Me-THF (19 mL) and distilled water (7.7 mL) was stirred at rt for 16 h. HCl (3M in cyclopentyl methyl ether) (0.67 mL, 1.79 mmol) was added and the mixture was evaporated to dryness. The residue (brown oil) was purified by column chromatography on silica gel (irregular SiOH, 15-40 µm, 24 g, dry loading on Celite®, mobile phase gradient: from DCM 100% to DCM 80%, MeOH/AcOH (90:10) 20%). The fractions containing the product were combined and evaporated to dryness to give 380 mg of intermediate 44i (61% yield, brown solid).

Preparation of Intermediate 45i

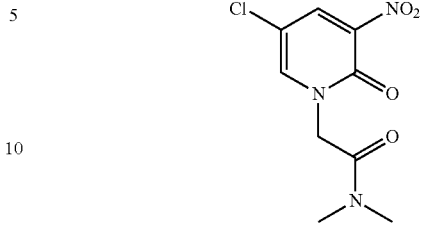

In a sealed tube, intermediate 44i (380.00 mg, 1.63 mmol) and dimethylamine (0.98 mL, 1.96 mmol) were diluted in DMF (19 mL). Then, HATU (1.37 g, 3.59 mmol) and DIEA (713.40 µL, 4.09 mmol) were added and the mixture was stirred at 70° C. for 16 h. The mixture was concentrated to dryness, diluted with DCM and basified with an aqueous saturated solution of $NaHCO_3$. The layers were separated and the organic layer was dried over $MgSO_4$, filtered and the solvent was removed under reduced pressure to give. The residue was purified by column chromatography on silica gel (irregular SiOH 15-40 µm, 24 g, dry load on Celite®, mobile phase DCM/MeOH, gradient from 100:0 to 85:15). The fractions containing the product were combined and evaporated to dryness. The residue (brown oil) was purified again by column chromatography on silica gel (irregular SiOH 15-40 µm, 24 g, dry load on Celite®, mobile phase heptane/EtOAc, gradient from 20:80 to 0:100) to give 80 mg of intermediate 45i as a pale yellow solid (19%).

Example A87

Preparation Intermediate 67i

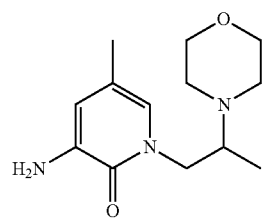 [SMILES: Cc1cc(N)c(=O)n(CC(C)N2CCOCC2)c1]

Intermediate 66i (460 mg, 1.64 mmol) with Raney Nickel (67 mg) as a catalyst in MeOH (51 mL) was hydrogenated at rt overnight under 1.5 bar of $H_2$. The catalyst was filtered off and the filtrate was evaporated, yielding: 0.411 g of intermediate 67i.

Example A88

Preparation Intermediate 75i

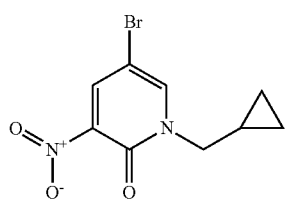 [SMILES: O=c1c([N+](=O)[O-])cc(Br)cn1CC1CC1]

To a solution of 5-bromo-2-hydroxy-3-nitropyridine (14 g, 63.9 mmol) in THF (200 mL) at room temperature was added tBuOK (7.5 g, 67.1 mmol), and stirred for 0.5 hour. (Bromomethyl)cyclopropane (8.7 mL, 92 mmol) and DMF (200 mL) were added to the suspension and the resulting mixture was warmed to 85° C. The mixture was stirred overnight at 85° C. Water (600 mL) was added, and extracted with ethyl acetate (500 mL*3). The organic phase was washed with water, brine, dried over $Na_2SO_4$, filtered, and evaporated in vacuum to give the crude compound. The crude (18 g) intermediate was purified by column chromatography over silica gel (eluent: Petrol ether/Ethyl acetate=2/3). The desired fractions were evaporated in vacuum to give the product as a brown solid: 13.0 g of intermediate 75i, yield 74.5%.

Preparation Intermediate 76i

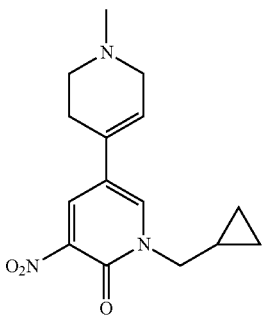 [SMILES: CN1CC=C(c2cc([N+](=O)[O-])c(=O)n(CC3CC3)c2)CC1]

To a solution of 1-methyl-1,2,3,6-tetrahydropyridine-4-boronic acid pinacol ester (1.15 g, 5.1 mmol) in water (2 mL) and 1,4-dioxane (10 mL) was added $K_3PO_4$ (3.3 g, 15.4 mmol), intermediate 75 (1.4 g, 5.1 mmol) and Pd-118 (334 mg, 0.51 mmol) under $N_2$. The mixture was stirred at 60° C. overnight under $N_2$. The mixture was poured into water (30 mL) and extracted with ethyl acetate (50 mL*3). The organic layer was washed with water (25 mL) and then brine (25 mL), dried over $MgSO_4$, and evaporated under vacuum. The residue was purified by flash column chromatography over silica gel (eluent: petroleum ether/ethyl acetate from 100/0 to 0/100; ethyl acetate/MeOH (0.1% $NH_4OH$) from 100/0 to 70/30). The desired fractions were collected and the solvent was concentrated to dryness under vacuum to give product as yellow solid. Yield: 900 mg (51% yield) of intermediate 76i.

Preparation Intermediate 77i

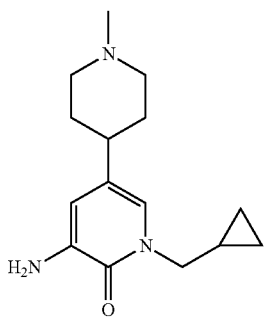 [SMILES: CN1CCC(c2cc(N)c(=O)n(CC3CC3)c2)CC1]

A mixture of intermediate 76i (800 mg, 2.3 mmol) in MeOH (50 mL) was hydrogenated at rt (20 Psi) with $Pd(OH)_2/C$ (160 mg) as a catalyst. After uptake of $H_2$ (4 equiv), the mixture was stirred overnight at 30° C. The catalyst was filtered off through celite and the filtrate was evaporated to give the product as a black oil. The crude product was combined with a another batch from 100 mg of intermediate 76i.

The residue was purified by preparative high-performance liquid chromatography over column: DuraShell 150*25 mm*5 um. Conditions: eluent A: water (+0.05% ammonia hydroxide v/v); eluent B: MeCN—starting from: A (88%) and B (12%) up to: A: (58%) and B (42%). Gradient Time (min) 10; 100% B Hold Time (min) 2.5; Flow Rate (ml/min) 25.

The pure fractions were collected and the solvent was evaporated under vacuum. The aqueous layer was lyophilized to dryness to give the product as a yellow oil. Yield: 400 mg (56.8% yield) of intermediate 77i Example A89

Preparation Intermediate 79i

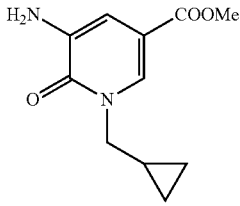 [SMILES: COC(=O)c1cc(N)c(=O)n(CC2CC2)c1]

A mixture of intermediate 75i (5 g, 18.3 mmol), TEA (5.6 g, 54.9 mmol) and $PdCl_2(dppf).DCM$ (1.5 g, 1.8 mmol) in MeOH (120 mL) was stirred at 80° C. under an atmosphere of CO (0.5 MPa) overnight. The mixture was filtered through Celite®, and evaporated in vacuum to give the crude compound. The crude compound was purified by column chromatography over silica gel (eluent: Petroleum ether/ethyl acetate=1/2). The desired fractions were evaporated in vacuum to give the compound as a brown solid. Intermediate 79i, 1.74 g, yield 39.6%.

Preparation Intermediate 80i

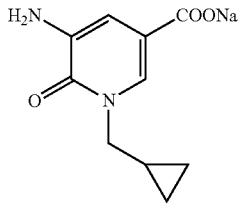

A solution of intermediate 79i (0.8 g, 3.6 mmol) and NaOH (158 mg, 3.96 mmol) in THF (50 mL) and water (5 mL) was stirred at room temperature overnight. The mixture was evaporated in vacuum to give the desired compound as a white solid. Intermediate 80i, 800.0 mg, yield 90.5%.

491

Preparation Intermediate 81i

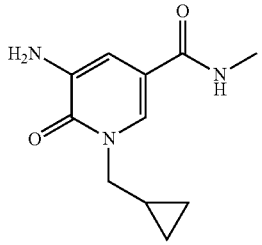 [SMILES: CNC(=O)c1cc(N)c(=O)n(CC2CC2)c1]

To a solution of intermediate 80i (0.8 g, 3.5 mmol), MeNH₂ in THF (5.2 mL, 10.4 mmol) and Pybrop (4.9 g, 10.5 mmol) in DMF (30 mL) was added DIPEA (1.35 g, 10.4 mmol). The reaction mixture was stirred at room temperature overnight. Water (60 mL) was added to the reaction mixture, and extracted with ethyl acetate (50 mL*3). The organic phase was washed with brine, dried over Na₂SO₄, filtered, and evaporated in vacuum to give the 0.9 g of crude compound. The residue was purified by high performance liquid chromatography (Column: Boston Green ODS 150*30 5 u Conditions: eluent A: water (0.05% HCl)-ACN; eluent B: MeCN—starting from: A (100%) and B (0%) up to: A: 70% and B (30%). Gradient Time (min) 12. 100% B; Hold Time (min) 2.2; Flow Rate (ml/min) 25).

The desired fraction was collected, evaporated in vacuum to give the desired compound as a white solid. Intermediate 81i, 0.59 g, yield 76.7%.

Example A90

Preparation of Intermediate 84i

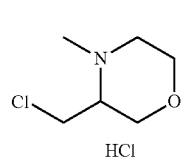

A mixture of 4-methyl-3-(hydroxymethyl)morpholine hydrochloride (500 mg; 3 mmol) and thionyl chloride (1 mL; 13.8 mmol) in DCM (10 mL) was stirred at room temperature for 3 hours. Thionyl chloride (1 mL; 13.8 mmol) was added again and the reaction mixture was stirred for 18 hours more. The reaction mixture was evaporated to dryness yielding 500 mg (99%) intermediate 84i. Used as such in the next step without further purification.

Example A91

Preparation of Intermediate 92i

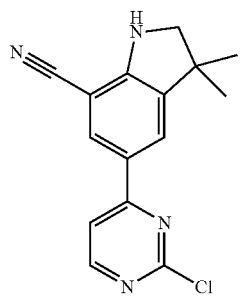 [SMILES: CC1(C)CNc2c(C#N)cc(-c3ccnc(Cl)n3)cc21]

TFA (6 mL) was added dropwise at 5° C. to a solution of intermediate 334 (3.00 g, 7.79 mmol) in DCM (60 mL) and the reaction mixture was stirred at 5° C. for 1 h. The reaction mixture was diluted with DCM and poured onto a mixture of ice and 10% aqueous K₂CO₃. The insoluble material was filtered, washed with water then Et₂O and dried to give 1.93 g of intermediate 92i (87% yield).

Example A92

Preparation of Intermediate 103i

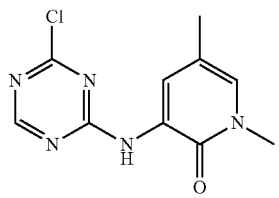 [SMILES: Cc1cc(Nc2ncnc(Cl)n2)c(=O)n(C)c1]

To a solution of intermediate 102i (370 mg, 2.68 mmol) in acetone (10 mL) was added 2,4-dichloro-1,3,5-triazine (402 mg, 2.68 mmol) and DIPEA (1 g, 8 mmol). The mixture was stirred at room temperature for 1.5 hours. The mixture was evaporated to give 1.37 g (crude product) of intermediate 103i.

Example A93

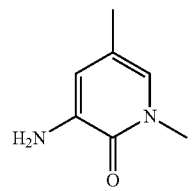

Preparation of Intermediate 102i

A mixture of intermediate 101i (500 mg, 2.97 mmol) in MeOH (10 mL) was hydrogenated at room temperature (15 psi) with Pd/C (50 mg) as a catalyst. After uptake of H₂ (1 eq, 18 hours), the catalyst was filtered off and the filtrate was evaporated to give 420 mg of a black oil (Quantitative yield).

Example A94

Preparation of Intermediate 108i

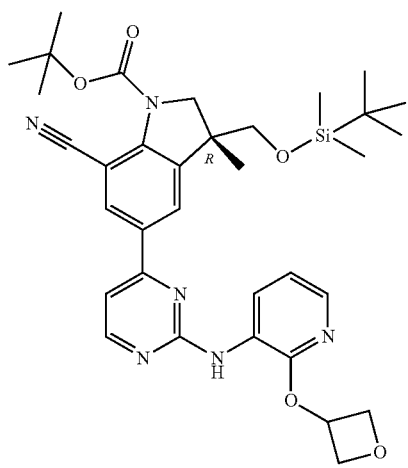

A suspension of intermediate 6R (0.4 g, 0.78 mmol), 2-(oxetan-3-yloxy)pyridin-3-amine (181 mg, 1.09 mmol), Pd(OAc)$_2$ (8.7 mg, 0.039 mmol), BINAP (24.2 mg, 0.039 mmol) and Cs$_2$CO$_3$ (759 mg, 2.33 mmol) in 1,4-dioxane (8.9 mL) in a sealed tube was purged with N$_2$ and stirred at 120° C. for 30 minutes using one single mode microwave (Biotage Initiator EXP 60) with a power output ranging from 0 to 400 W [fixed hold time]. The reaction mixture was cooled down to room temperature and partitionned between water and EtOAc. The organic layer was separated, dried over MgSO$_4$ and concentrated. The residue was purified by silica gel chromatography (irregular SiO$_2$, 40 g, gradient from heptane/EtOAc 90/10 to 0/100). The fractions containing the product were mixed and the solvent was concentrated, affording 0.538 g of intermediate 108i (83% yield, LCMS 97%).

Preparation of Intermediate 109i

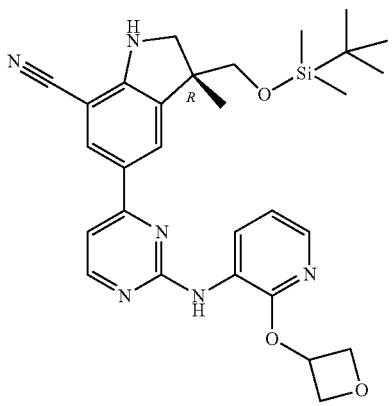

TFA (0.958 mL; 12.5 mmol) was added at 5° C. to a solution of intermediate 108i (538 mg; 0.834 mmol) in DCM (8.6 mL). The reaction mixture was stirred at 5° C. for 1 hour. The mixture was diluted with DCM (50 mL) and poured onto a 10% aqueous solution of K$_2$CO$_3$. More DCM/MeOH was added (80/20; 200 mL) The organic layer was decanted, washed with a 10% aqueous solution of K$_2$CO$_3$, dried over MgSO$_4$, filtered and evaporated to dryness to give 0.454 g of intermediate 109i (100% yield).

B. Preparation of the Final Compounds

Example B1

Preparation of Compound 1

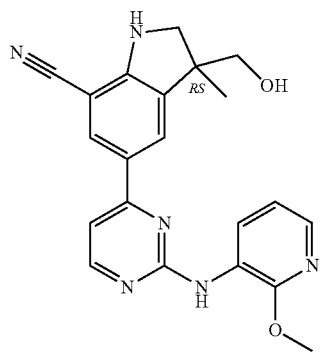

To a solution of intermediate 8 (235.00 mg, 0.29 mmol) in DCM (3 mL), TFA (3 mL) was added and the reaction mixture was stirred at rt for 2 h. Then, the solution was concentrated in vacuo and neat TFA (3 mL) was added. The reaction mixture was stirred for a further 4 h. The reaction mixture was stirred for a further 1 h and the solution was concentrated in vacuo. The residue was treated with K$_2$CO$_3$ (242.00 mg, 1.75 mmol) in DMF (2 mL) for 1 h at 50° C. After further 30 min stirring at 50° C. the reaction mixture was partitioned between EtOAc and water and the organic layer was dried with Na$_2$SO$_4$ and concentrated in vacuo. The residue was purified by column chromatography on silica gel (SiO$_2$, 10 g, mobile phase: cyclohexane/EtOAc, gradient from 100:0 to 0:100). The relevant fractions were joined and concentrated in vacuo.

This residue was submitted to mass directed auto purification system to give 43 mg of compound 1 (37% yield).

Example B2

Preparation of Compound 2

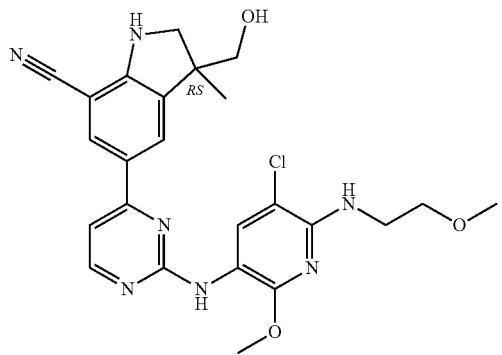 [SMILES: COCCNc1nc(OC)c(Nc2nccc(-c3cc(C#N)c4c(c3)C(C)(CO)CN4)n2)cc1Cl]

TFA (0.53 mL, 6.89 mmol) was added at 5° C. to a solution of intermediate 13 (274.00 mg, 0.46 mmol) in DCM (5 mL). The reaction mixture was stirred at 5° C. for 1 h, diluted with DCM (50 mL) and poured onto a 10% aqueous solution of $K_2CO_3$. More DCM/MeOH was added (80:20; 200 mL). The organic layer was decanted, washed with a 10% aqueous solution of $K_2CO_3$, dried over $MgSO_4$, filtered and evaporated to dryness. The residue (200 mg) was purified by column chromatography on silica gel (irregular SiOH, 25 g+5 g solid deposit; mobile phase: $NH_4OH$/MeOH/DCM, gradient from 0.2% $NH_4OH$, 2% MeOH, 98% DCM to 1% $NH_4OH$, 10% MeOH, 90% DCM). The pure fractions were collected and evaporated to dryness. The residue (170 mg) was purified again by column chromatography on silica gel (irregular SiOH, 25 g+5 g solid deposit; mobile phase: $NH_4OH$/MeOH/DCM, gradient from 0.4% $NH_4OH$, 4% MeOH, 96% DCM to 1.5% $NH_4OH$, 15% MeOH, 85% DCM). The pure fractions were collected and evaporated to dryness. The residue was taken up with $CH_3CN$ and the precipitate was filtered and dried to give 101 mg of compound 2 (44% yield). M.P.=230° C. (K).

Alternatively, this compound could be obtained by the use of a mixture of TFA/DCM (1:1, v/v).

Preparation of Compound 3

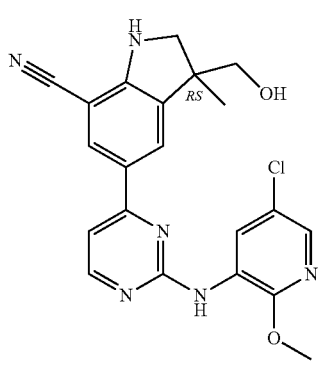

A solution of intermediate 16 (355.00 mg, 0.68 mmol) in a mixture of DCM (5 mL) and TFA (2 mL) was stirred at rt for 2 h. The reaction mixture was quenched with a saturated solution of $NaHCO_3$ and poured in a mixture DCM/MeOH (95:5). The organic layer was separated, washed with a saturated solution of $NaHCO_3$, dried over $MgSO_4$ and evaporated in vacuo to give a black oil. The residue was purified by column chromatography on silica gel (irregular SiOH 15-40 µm, 120 g, mobile phase: DCM/(MeOH (5% aq $NH_3$)), gradient from 98:2 to 95:5). The fractions containing the product were combined and evaporated to dryness to give 60 mg of a beige solid. This solid was recrystallized from EtOH. After filtration on a glass frit, the solid was washed with $Et_2O$ and dried in vacuo to give 49 mg of compound 3 (17% yield over 3 steps, off-white solid).

Preparation of Compound 4

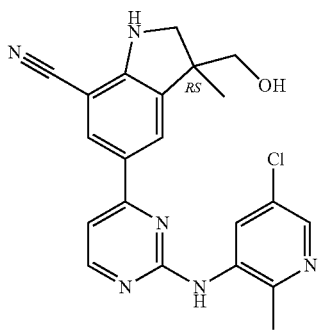 [SMILES: Cc1ncc(Cl)cc1Nc1nccc(-c2cc(C#N)c3c(c2)C(C)(CO)CN3)n1]

A mixture of intermediate 19 (294.00 mg, 0.58 mmol) in a mixture of TFA (2 mL) and DCM (5 mL) was stirred at rt for 1 h. The mixture was basified with saturated aq. $NaHCO_3$. An extraction was performed with DCM. The organic layer was washed with brine, dried over $MgSO_4$, evaporated and purified by column chromatography on silica gel (irregular SiOH 15-40 µm, 80 g, liquid injection in DCM, mobile phase: DCM/(MeOH (10% aq $NH_3$)), gradient from 100:0 to 94:6 in 15 CV). The fractions containing the product were combined and evaporated to dryness to give 45 mg of compound 4 (19% yield over 3 steps, light yellow solid). M.P.=277° C. (DSC).

Preparation of Compound 10

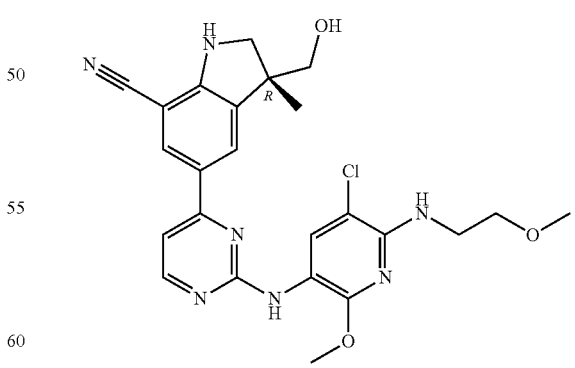

TFA (0.56 mL) was added at 5° C. to a solution of intermediate 29 (290.00 mg, 0.49 mmol) in DCM (5 mL). The reaction mixture was stirred at 5° C. for 1 h, diluted with DCM (50 mL) and poured onto a 10% aqueous solution of $K_2CO_3$. More DCM/MeOH was added (80:20, 200 mL).

The organic layer was decanted, washed with a 10% aqueous solution of $K_2CO_3$, dried over $MgSO_4$, filtered and evaporated to dryness. The residue was purified by column chromatography on silica gel (irregular SiOH, 40 g+5 g solid deposit, mobile phase: heptane/EtOAc/MeOH/DCM, gradient from 60% heptane, 1.5% MeOH, 38.5% EtOAc to 0% heptane, 3.5% MeOH, 96.5% EtOAc then 0% $NH_4OH$, 0% MeOH, 100% DCM to 1% $NH_4OH$, 10% MeOH, 90% DCM). The pure fractions were collected and evaporated to dryness to give 43 mg of compound 10 (18% yield). M.P.=231° C. (K).

Preparation of Compound 50

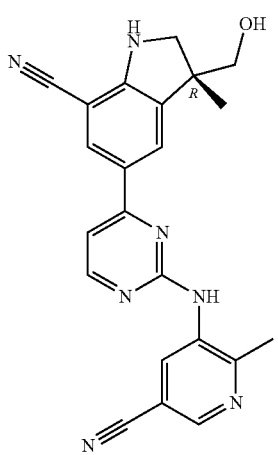

TFA (3.92 mL) was added dropwise to a solution of intermediate 164 (622.00 mg, 1.25 mmol) in DCM stabilized with amylene (21 mL) at 5° C. and the reaction mixture was stirred for 1 h at this temperature. The reaction mixture was quenched with a 10% aqueous solution of $K_2CO_3$ and extracted with DCM. The organic layer was decanted, filtered through Chromabond® and evaporated to dryness. The residue was purified by column chromatography on silica gel (irregular SiOH, 24 g, mobile phase: $NH_4OH$/MeOH/DCM gradient from 0.5% $NH_4OH$, 5% MeOH, 95% DCM to 1% $NH_4OH$, 10% MeOH, 90% DCM). The pure fractions were collected and evaporated to dryness. The residue was crystallized from $CH_3CN/Et_2O$ and the precipitate was filtered and dried to give 213 mg of compound 50 (43% yield). M.P.=242 (DSC).

Preparation of Compound 59

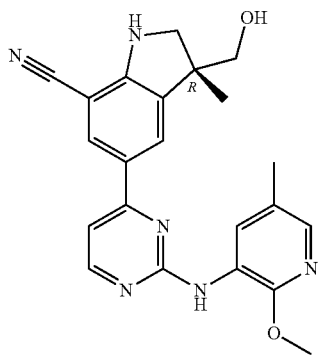

TFA (1.5 mL) was added dropwise to a solution of intermediate 196 (260.00 mg, 0.52 mmol) in DCM (10 mL) at 5° C. and the reaction mixture was stirred for 1 h at this temperature. The reaction mixture was quenched with a 10% aqueous solution of $K_2CO_3$ and extracted with DCM. The insoluble material was filtered. The organic layer was decanted, dried over $MgSO_4$, filtered and evaporated to dryness. The residue was gathered with the insoluble material. The mixture was suspended in EtOH and sonicated for 15 min. The precipitate was filtered and dried to give 138 mg of compound 59 (66% yield). M.P.=234° C. (K).

Preparation of Compound 65

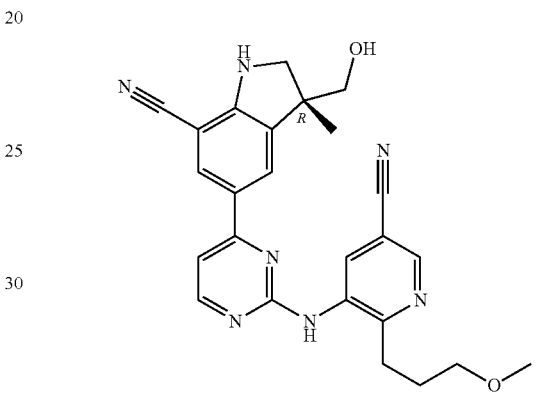

TFA (1.5 mL) was added dropwise to a solution of intermediate 221 (300.00 mg, 0.52 mmol) in DCM (10 mL) at 5° C. and the reaction mixture was stirred for 1 h at this temperature. The reaction mixture was quenched with a 10% aqueous solution of $K_2CO_3$ and extracted with DCM. The organic layer was decanted, dried over $MgSO_4$, filtered and evaporated to dryness. The residue was crystallized from $CH_3CN$ and the precipitate was filtered and dried. The residue (178 mg) was purified by column chromatography on silica gel (irregular SiOH, 24 g, mobile phase: DCM/MeOH, gradient from 100:0 to 90:10). The pure fractions were collected and evaporated to dryness. The residue was crystallized from $CH_3CN$ and the precipitate was filtered and dried. The residue (136 mg) was further purified by column chromatography on silica gel (irregular SiOH, 24 g, mobile phase: 0.5% $NH_4OH$, 10% MeOH, 50% EtOAc, 40% heptane). The pure fractions were collected and evaporated to dryness. The second filtrate was purified by column chromatography on silica gel (irregular SiOH, 24 g, mobile phase: 0.5% $NH_4OH$, 10% MeOH, 50% EtOAc, 40% heptane). The pure fractions were collected and evaporated to dryness. The residues were mixed and taken up with $Et_2O$. The precipitate was filtered and dried to give 155 mg of compound 65 (64% yield). M.P.=158° C. (K).

Preparation of Compound 140

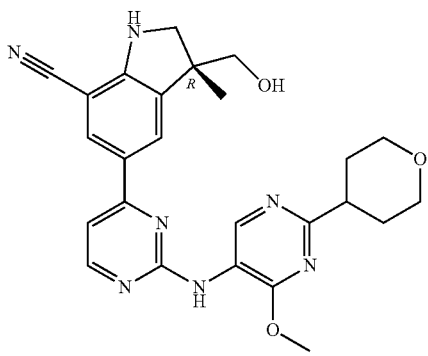

A mixture of intermediate 430 (418.00 mg, 0.63 mmol) in a mixture of TFA (0.80 mL) and DCM (6 mL) was stirred at rt for 30 min. The mixture was basified with a saturated aqueous solution of NaHCO₃. An extraction was performed with DCM. The organic layer was washed with brine, dried over MgSO₄, evaporated and purified by column chromatography on silica gel (irregular SiOH 15-40 μm, 80 g, liquid injection with DCM, mobile phase: DCM/(MeOH (10% aq. NH₃)), gradient from 100:0 to 90:10 in 10 CV). The fractions containing the product were combined and concentrated under vaccum to give as a white solid. The residue (213 mg) was purified again by column chromatography on silica gel (irregular SiOH 15-40 μm, 80 g, liquid injection with DCM, mobile phase: DCM/(MeOH (10% aq. NH₃)), gradient from 98:2 to 90:10 in 10 CV). The fractions containing the product were combined and evaporated to dryness to give a white solid. The residue (204 mg) was further purified by reverse phase (Stationary phase: X-Bridge-C18, 10 μm, 30×150 mm, mobile phase: 0.2% aq. NH₄HCO₃/MeOH, gradient from 60:40 to 0:100). The fraction of interest was evaporated, dissolved in 7 mL of a mixture of CH₃CN/water (1:4, v/v) and freeze-dried to give 113 mg of compound 140 (38% yield, white solid).

The compounds in the Table below were prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 5 | From intermediate 21 | 26 yellow solid | 10 procedure with DCM/THF (5:2, v/v) |
| Compound 19 | From intermediate 57 | 81 | 22 procedure with DCM/THF (30:1, v/v) |

-continued
| Compound number | Structure | Mass (mg) | Yield (%) |
|---|---|---|---|
| Compound 20 | 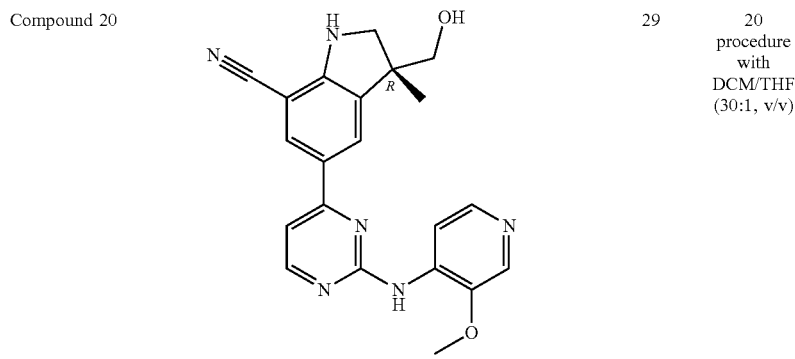<br>From intermediate 59 | 29 | 20 procedure with DCM/THF (30:1, v/v) |
| Compound 23 | 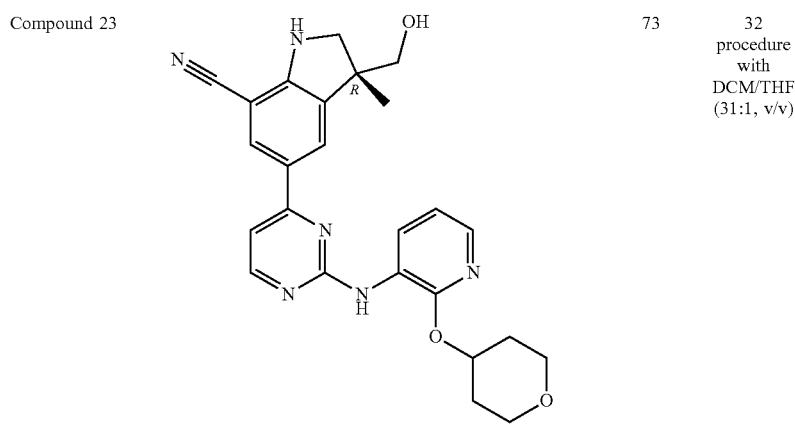<br>From intermediate 71 | 73 | 32 procedure with DCM/THF (31:1, v/v) |
| Compound 24 | 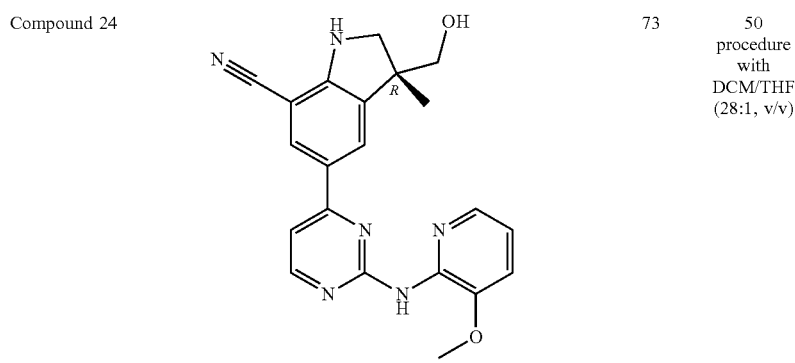<br>From intermediate 73 | 73 | 50 procedure with DCM/THF (28:1, v/v) |

| Compound number | Structure | Mass (mg) | Yield (%) |
|---|---|---|---|
| Compound 25 | 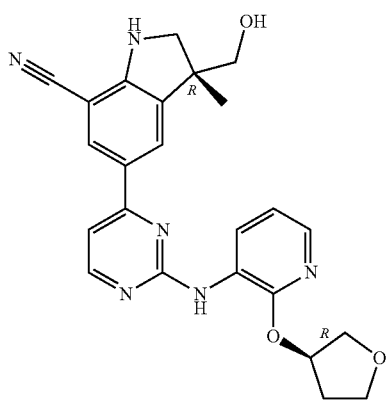<br>From intermediate 77 | 149 | 67 procedure with DCM/THF (17:1, v/v) |
| Compound 26 | 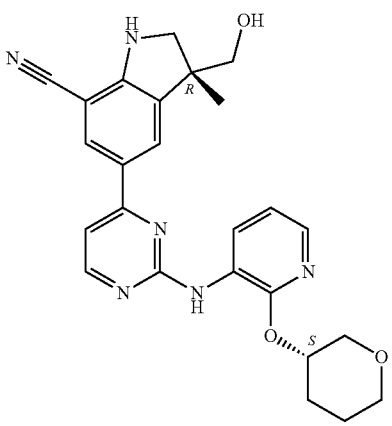<br>From intermediate 81 | 67 | 28 procedure with DCM/THF (17:1, v/v) |
| Compound 27 | 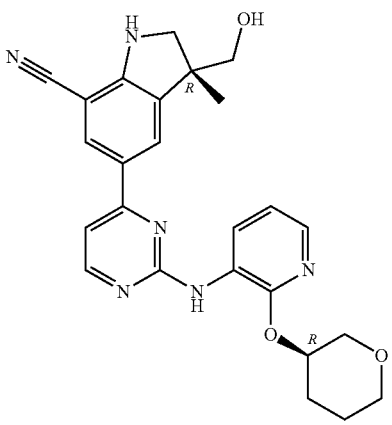<br>From intermediate 85 | 149 | 55 procedure with DCM/THF (15:1, v/v) |

-continued
| Compound number | Structure | Mass (mg) | Yield (%) |
|---|---|---|---|
| Compound 28 | 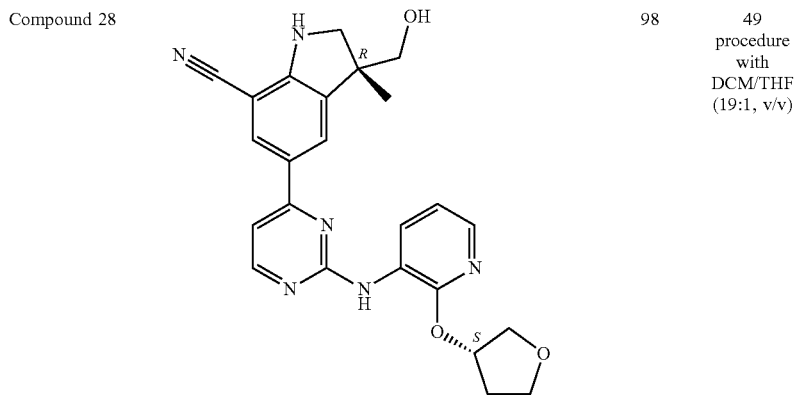<br>From intermediate 89 | 98 | 49 procedure with DCM/THF (19:1, v/v) |
| Compound 29 | 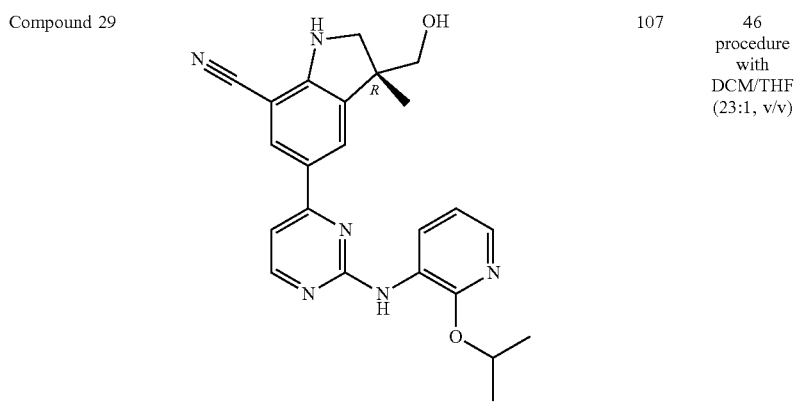<br>From intermediate 91 | 107 | 46 procedure with DCM/THF (23:1, v/v) |
| Compound 30 | 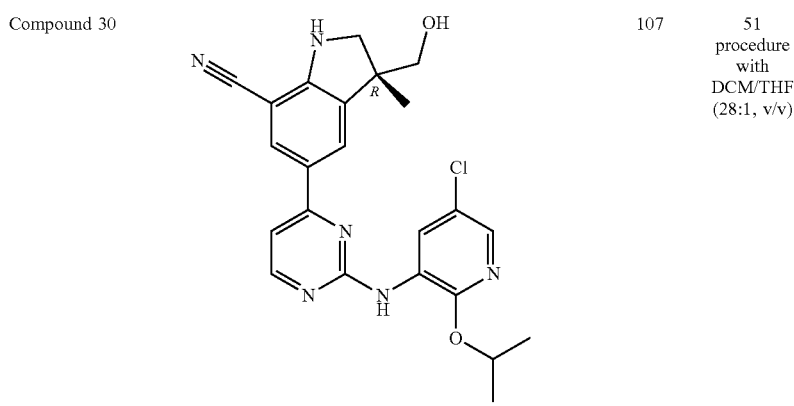<br>From intermediate 95 | 107 | 51 procedure with DCM/THF (28:1, v/v) |

-continued

| Compound number | Structure | Mass (mg) | Yield (%) |
|---|---|---|---|
| Compound 37 | From intermediate 112 | 53 | 40 procedure with DCM/THF (31:1, v/v) |
| Compound 39 | From intermediate 121 | 71 | 25 procedure with DCM/THF (29:1, v/v) |
| Compound 55 | From intermediate 185 | 84 | 37 procedure with DCM/TFA (3:1, v/v) |

-continued
| Compound number | Structure | Mass (mg) | Yield (%) |
|---|---|---|---|
| Compound 56 | 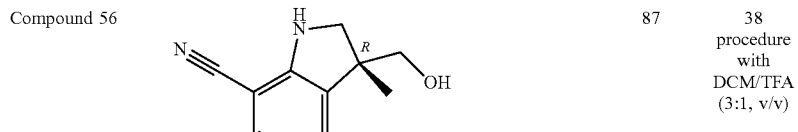<br>From intermediate 185 | 87 | 38 procedure with DCM/TFA (3:1, v/v) |
| Compound 57 | 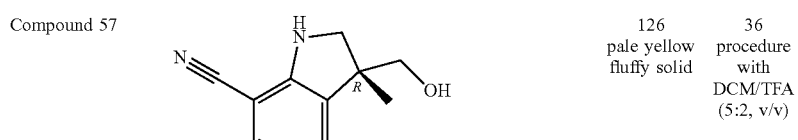<br>From intermediate 190 | 126 pale yellow fluffy solid | 36 procedure with DCM/TFA (5:2, v/v) |
| Compound 58 | 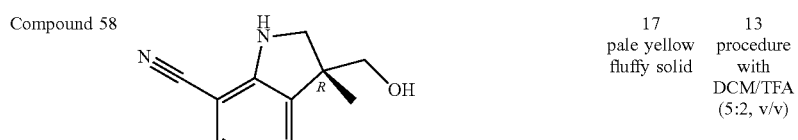<br>From intermediate 194 | 17 pale yellow fluffy solid | 13 procedure with DCM/TFA (5:2, v/v) |

-continued

| Compound number | Structure | Mass (mg) | Yield (%) |
|---|---|---|---|
| Compound 60 | From intermediate 201 | 176 pink solid | 55 procedure with DCM/TFA (5:1, v/v) |
| Compound 61 | From intermediate 205 | 138 | 68 procedure with DCM/TFA (7:1, v/v) |
| Compound 62 | From intermediate 209 | 139 | 56 procedure with DCM/TFA (7:1, v/v) |

-continued
| Compound number | Structure | Mass (mg) | Yield (%) |
|---|---|---|---|
| Compound 63 | 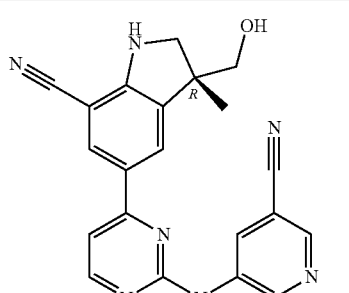<br>From intermediate 213 | 33 | 25 procedure with DCM/TFA (7:1, v/v) |
| Compound 64 | 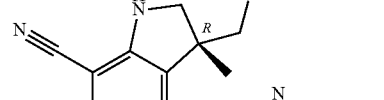<br>From intermediate 217 | 113 | 58 procedure with DCM/TFA (6:1, v/v) |
| Compound 67 | <br>From intermediate 228 | 238 yellow fluffy solid | 50 procedure with DCM/TFA (10:1, v/v) |

-continued

| Compound number | Structure | Mass (mg) | Yield (%) |
|---|---|---|---|
| Compound 139 | From intermediate 426 | 22 white solid | 66 procedure with DCM/TFA (10:1, v/v) |
| Compound 141 | From intermediate 434 | 148 white solid | 60 procedure with DCM/TFA (11:1, v/v) |
| Compound 143 | From intermediate 440 | 118 white solid | 33 procedure with DCM/TFA (10:1, v/v) |
| Compound 145 | From intermediate 390 | 201 | 59 procedure with 22 eq. TFA |

Example B3

Preparation of Compound 3

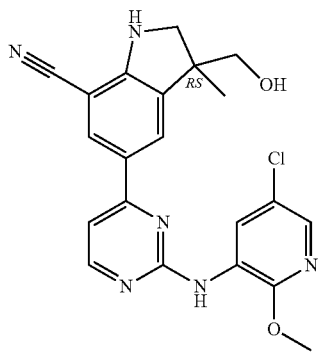

A mixture of intermediate 14 (420.00 mg, 0.78 mmol) and TBAF (1M in THF) (0.86 mL, 0.86 mmol) in Me-THF (13 mL) was stirred at rt for 2 h. The resulting mixture was directly purified (without evaporation) by column chromatography on silica gel (irregular SiOH 15-40 μm, 24 g, liquid injection, mobile phase: DCM/MeOH/(10% aq. NH$_3$), gradient from 100:0 to 80:20). The fractions containing the product were evaporated to dryness to give a brown solid. Then, the solid was recrystallized from EtOH, filtered on a glass frit and washed with EtOH. The solid was collected to give an off-white solid. This solid and its filtrate were combined. The resulting residue (280 mg, off-white solid) was taken up with a mixture of DMSO/MeOH (50:50). The mixture was filtered to give fraction A (98 mg) as an off-white solid. The filtrate was purified by RP-HPLC (Stationary phase: X-Bridge-C18 5 μm 30×150 mm, mobile phase: aq. NH$_4$HCO$_3$ (0.5%)/CH$_3$CN, gradient from 65% aq. NH$_4$HCO$_3$ (0.5%), 35% CH$_3$CN to 25% aq. NH$_4$HCO$_3$ (0.5%), 75% CH$_3$CN). The fractions containing the product were combined and concentrated to dryness to give fraction B (86 mg) as an off-white solid. Fractions A and B (98 mg and 86 mg) were combined, diluted with a mixture of CH$_3$CN/EtOH (50:50) and sonicated for 15 min. The mixture was then concentrated under reduced pressure to give a solid. This solid was recrystallized from EtOH, filtered on a glass frit, washed once with EtOH and twice with Et$_2$O. The solid was collected, dried at 50° C. for 16 h to give 112 mg of an off-white solid which was recrystallized from EtOH, directly hot-filtered on a glass frit, washed once with EtOH and twice with Et$_2$O. The solid was collected and dried at 50° C. for 16 h to give 90 mg of compound 3 (27% yield, off-white solid). MP: 254° C. (DSC)

Preparation of Compound 4

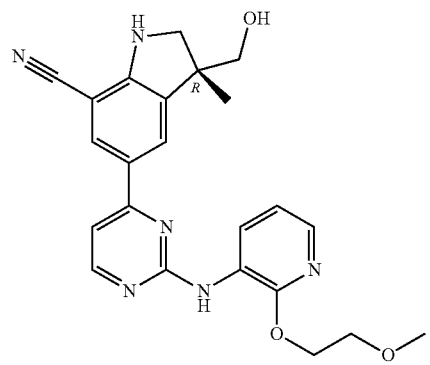

A mixture of intermediate 18 (480.00 mg, 0.92 mmol) and TBAF (1M in THF) (1.00 mL, 1.00 mmol) in THF (10 mL) was stirred at rt for 1 h. The reaction mixture was directly purified by column chromatography on silica gel (irregular SiOH 15-40 μm, 120 g, liquid injection in a mixture of THF/DCM, mobile phase: DCM/MeOH (10% aq NH$_3$), gradient from 100:0 to 90:10 in 15 CV). The fractions containing the product were combined and evaporated to dryness to give a white solid. The residue (144 mg) was dissolved in EtOH then evaporated in vacuo (3 times) and dried at 50° C. in vacuo to give 138 mg of compound 4 (37% yield, white solid).

M.P.=280° C. (DSC).

Preparation of Compound 33

TBAF (1M in THF) (5.04 mL, 5.04 mmol) was added to a solution of intermediate 103 (3.03 g, 4.20 mmol, 75% purity based on LC/MS) in Me-THF (97 mL) and the reaction mixture was stirred at rt for 4 h. The reaction mixture was partitioned between EtOAc and a 10% aqueous solution of K$_2$CO$_3$. The organic layer was separated, dried over MgSO$_4$, filtered and evaporated to dryness. The residue (4.15 g) was purified by column chromatography on silica gel (Stationary phase: irregular bare silica 80 g, mobile phase: 0.2% NH$_4$OH, 98% DCM, 2% MeOH to 1% NH$_4$OH, 90% DCM, 10% MeOH). The fractions containing the product were mixed and concentrated to afford two batches (batch 1: 1.75 g and batch 2: 1.15 g). Batch 1 was purified again by column chromatography on silica gel (Stationary phase: irregular bare silica 80 g, mobile phase: 0.2% NH$_4$OH, 98% DCM, 2% MeOH to 1% NH$_4$OH, 90% DCM, 10% MeOH). The fractions containing the product were mixed and concentrated. The residue (894 mg) was taken up with a mixture of EtOH/Et₂O and the precipitate was filtered and dried to afford 838 mg of compound 33 (46% yield, Fraction A). M.P.=118° C. (DSC).

Batch 2 was purified again by column chromatography on silica gel (Stationary phase: irregular bare silica 80 g, mobile phase: 0.2% NH₄OH, 98% DCM, 2% MeOH to 1% NH₄OH, 90% DCM, 10% MeOH). The fractions containing the product were mixed and concentrated. The residue (536 mg) was taken up with a mixture of EtOH/Et₂O. The precipitate was filtered and dried to afford 330 mg of compound 33 (18% yield, Fraction B). Then, the fractions A and B were mixed, taken up with Et₂O and stirred for 30 min. The precipitate was filtered to give 841 mg of compound 33 (46% yield, white solid). The filtrate was combined to the one coming from the filtration of batch 2 and concentrated. The residue (374 mg) was taken up with Et₂O and purified by achiral SFC (Stationary phase: NH₂, 5 µm, 150×30 mm, mobile phase: 75% CO₂, 25% MeOH (0.3% iPrNH₂)). The fractions containing the product were mixed and concentrated. The residue (287 mg) was mixed with another batch (224 mg coming from a reaction performed on 1.11 g of intermediate 103), taken up with Et₂O. The filtrate was filtered and dried to afford additional 468 mg of compound 33.

Preparation of Compound 50

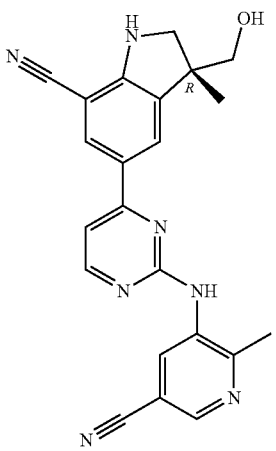

A mixture of intermediate 162 (2.00 g, 3.91 mmol) and TBAF (1M in THF) (8.01 mL, 8.01 mmol) in Me-THF (40 mL) was stirred at rt for 3 h. The reaction mixture was diluted with EtOAc washed with a solution 10% of K₂CO₃, twice with water and twice with a solution of saturated NaCl. The organic layer was decanted, dried over MgSO₄, filtered and evaporated to dryness. The residue was taken up several times with EtOH and evaporated to dryness. The residue was sonicated in CH₃CN, and the precipitate was filtered and dried to give 1.41 g of compound 50 (89% yield). M. P.=247° C. (DSC).

Preparation of Compound 93

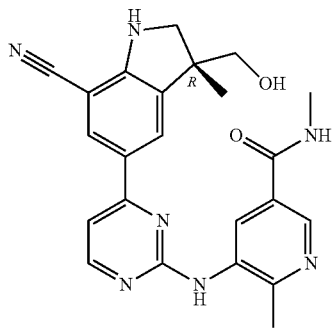

To a solution of intermediate 319 (227.00 mg, 0.42 mmol) in Me-THF (4 mL), TBAF (1M in THF) was added (450.00 µL, 0.45 mmol). The solution was stirred at rt for 18 h then TBAF (1M in THF) (210.00 µL, 0.21 mmol) was added. The solution was stirred for 4 h then evaporated in vacuo to give an orange oil. The residue (434 mg) was purified by column chromatography on silica gel (Irregular SiOH 15-40 µm, 24 g, dry loading on Celite®, mobile phase: DCM/MeOH, gradient from 100:0 to 90:10). The fractions containing the product were combined and evaporated to dryness to give a white solid. The residue (148 mg) was suspended in DCM, the solid was filtered on a glass frit and dried in vacuo to give 102 mg of compound 93 as an off-white solid (57% yield). M.P.=165 (DSC).

The compounds in the Table below were prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 9 | 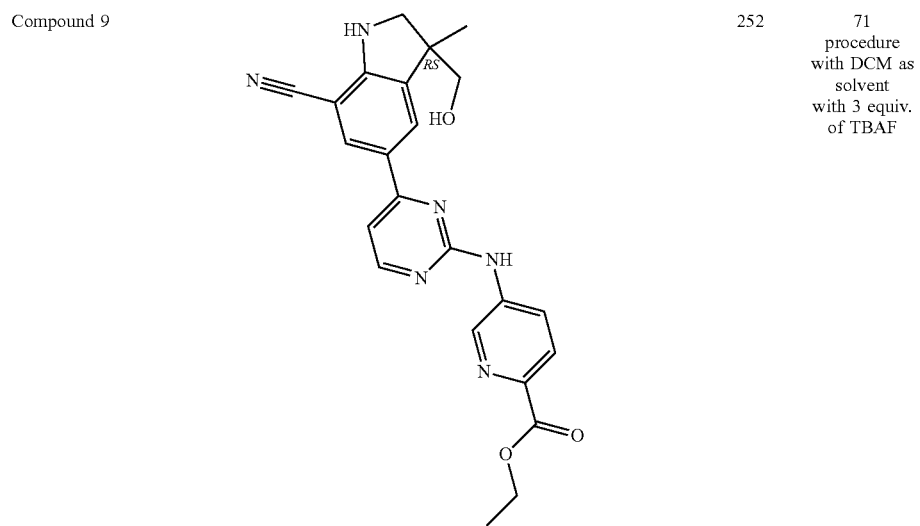<br>From Intermediate 27 | 252 | 71 procedure with DCM as solvent with 3 equiv. of TBAF |
| Compound 11 | 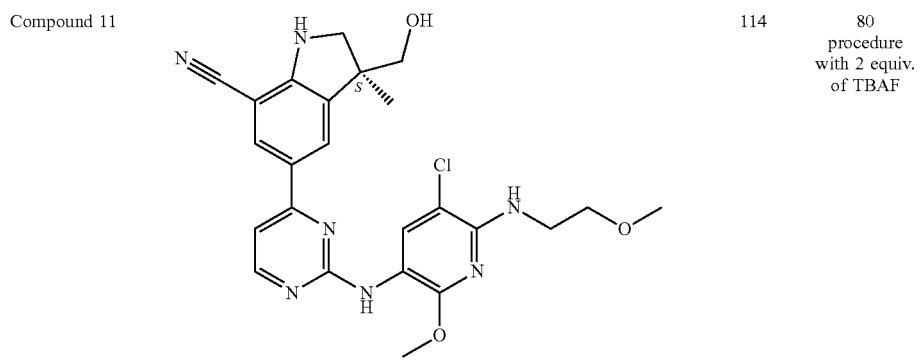<br>From Intermediate 31 | 114 | 80 procedure with 2 equiv. of TBAF |
| Compound 12 | 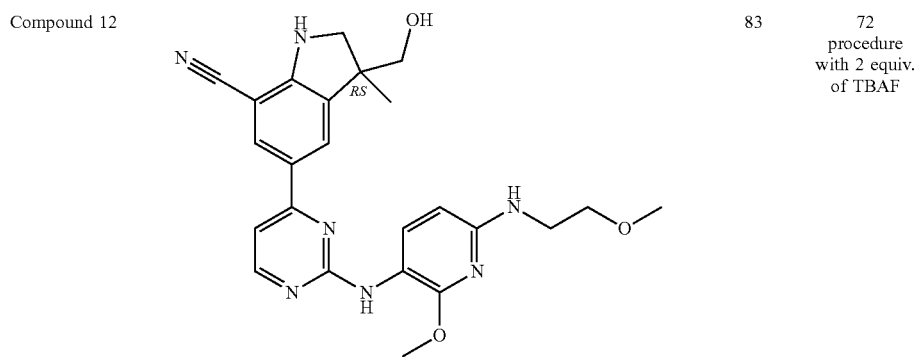<br>From Intermediate 34 | 83 | 72 procedure with 2 equiv. of TBAF |

-continued

| Compound number | Structure | Mass (mg) | Yield (%) |
|---|---|---|---|
| Compound 13 | From Intermediate 40 | 47 | 43 procedure with 2 equiv. of TBAF |
| Compound 14 | From Intermediate 42 | 200 off-white | 93 |
| Compound 15 | From Intermediate 46 | 70 yellow solid | 39 procedure with 2 equiv. of TBAF |

| Compound number | Structure | Mass (mg) | Yield (%) |
|---|---|---|---|
| Compound 16 | 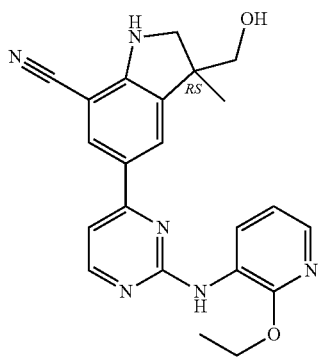<br>From Intermediate 48 | 57 | 51 procedure with 2 equiv. of TBAF |
| Compound 17 | 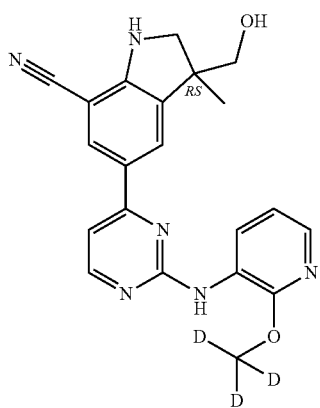<br>From Intermediate 51 | 127 | 86 procedure with 2 equiv. of TBAF |
| Compound 18 | 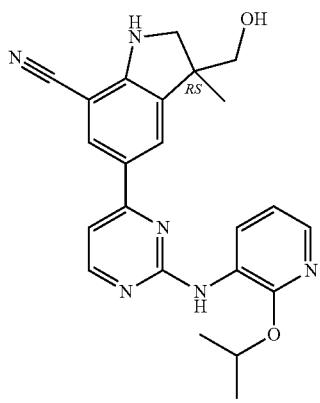<br>From Intermediate 53 | 42 | 46 procedure with 2 equiv. of TBAF |

-continued

| Compound number | Structure | Mass (mg) | Yield (%) |
|---|---|---|---|
| Compound 32 | From Intermediate 99 | 139 off-white powder | 48 |
| Compound 36 | From Intermediate 110 | 88 | 40 procedure with 1.4 equiv. of TBAF |
| Compound 38 | From Intermediate 117 | 92 | 45 |
| Compound 44 | From intermediate 141 | 125 pale yellow solid | 80 |

| Compound number | Structure | Mass (mg) | Yield (%) |
|---|---|---|---|
| Compound 48 | 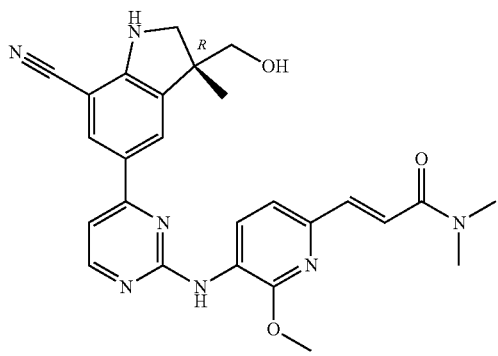<br>From intermediate 157 | 154 pale yellow solid | 73 |
| Compound 49 | 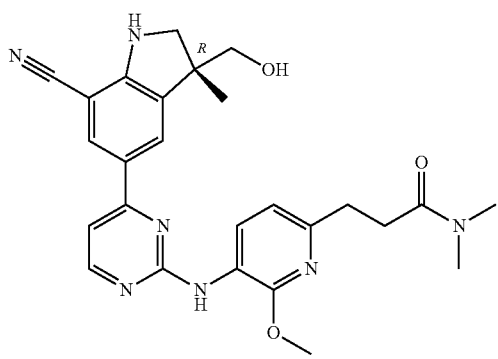<br>From intermediate 161 | 126 white solid | 72 |
| Compound 53 | 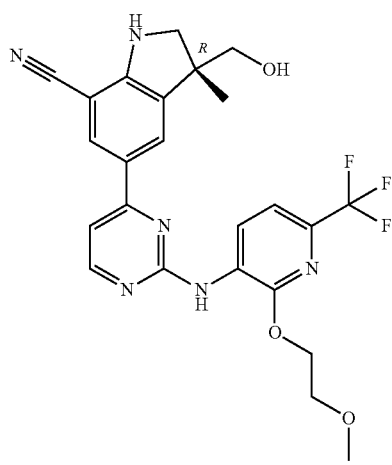<br>From intermediate 177 | 145 | 51 |

-continued
| Compound number | Structure | Mass (mg) | Yield (%) |
|---|---|---|---|
| Compound 54 | 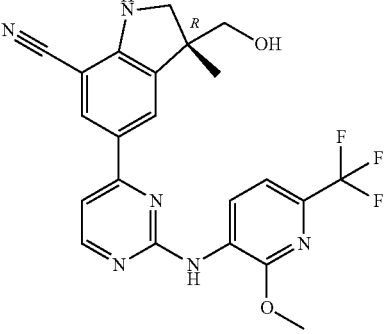 From intermediate 181 | 155 off-white solid | 70 |
| Compound 68 | 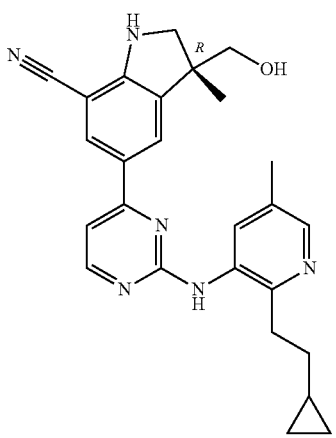 From intermediate 232 | 208 off-white solid | 64 |
| Compound 69 | 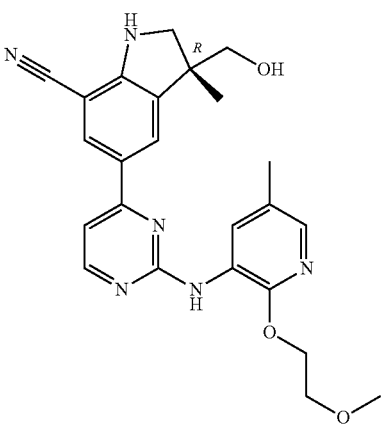 From intermediate 236 | 215 pale yellow solid | 64 |

-continued

| Compound number | Structure | Mass (mg) | Yield (%) |
|---|---|---|---|
| Compound 72 | From intermediate 249 | 383 yellow solid | 94 |
| Compound 73 | From intermediate 252 | 291 off-white powder | 63 |
| Compound 74 | From intermediate 255 | 245 | 79 |

-continued

| Compound number | Structure | Mass (mg) | Yield (%) |
|---|---|---|---|
| Compound 75 | From intermediate 258 | 25 | 34 |
| Compound 76 | From intermediate 261 | 55 | 42 |
| Compound 77 | From intermediate 264 | 93 | 50 |

-continued

| Compound number | Structure | Mass (mg) | Yield (%) |
| --- | --- | --- | --- |
| Compound 78 | From intermediate 267 | 19 | 26 |
| Compound 80 | From intermediate 274 | 110 white fluffy solid | 49 |
| Compound 81 | From intermediate 279 | 186 white solid | 63 |

-continued
| Compound number | Structure | Mass (mg) | Yield (%) |
|---|---|---|---|
| Compound 84 | 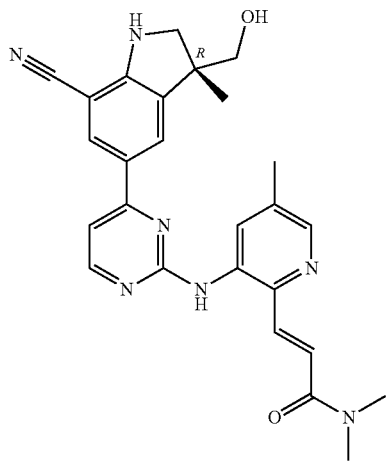<br>From intermediate 285 | 5.3 orange gum | 18 |
| Compound 85 | 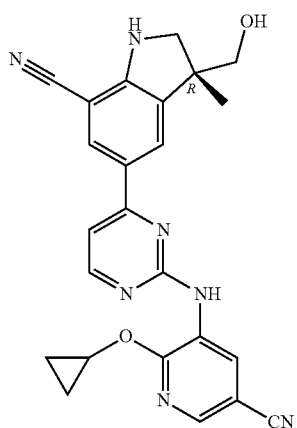<br>From intermediate 288 | 14 | 14 |
| Compound 86 | 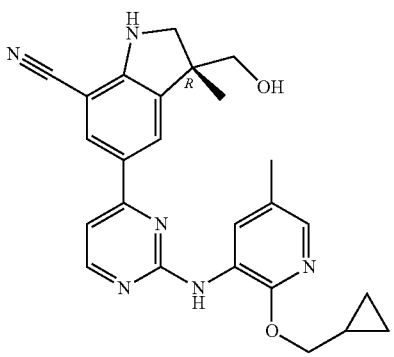<br>From intermediate 292 | 135 white solid | 57 procedure with 1.7 equiv. of TBAF |

-continued

| Compound number | Structure | Mass (mg) | Yield (%) |
|---|---|---|---|
| Compound 87 | From intermediate 298 | 210 yellow solid | 93 |
| Compound 88 | From intermediate 301 | 142 yellow solid | 62 |
| Compound 89 | From intermediate 304 | 103 yellow solid | 92 |

-continued

| Compound number | Structure | Mass (mg) | Yield (%) |
|---|---|---|---|
| Compound 90 | From intermediate 308 | 72 yellow powder | 50 |
| Compound 91 | From intermediate 314 | 254 | 72 |
| Compound 96 | From intermediate 330 | 240 white solid | 66 procedure with 2 equiv. of TBAF |
| Compound 126 | From intermediate 398 | 34 | 19 procedure with 2.2 equiv. of TBAF |

-continued

| Compound number | Structure | Mass (mg) | Yield (%) |
|---|---|---|---|
| Compound 127 | From intermediate 399 | 83 off-white solid | 49 |
| Compound 128 | From intermediate 400 | 120 orange solid | 59 procedure with 2.2 equiv. of TBAF |
| Compound 129 | From intermediate 402 | 102 white solid | 59 |
| Compound 130 | From intermediate 404 | 48 off-white solid | 28 |

-continued
| Compound number | Structure | Mass (mg) | Yield (%) |
|---|---|---|---|
| Compound 131 | 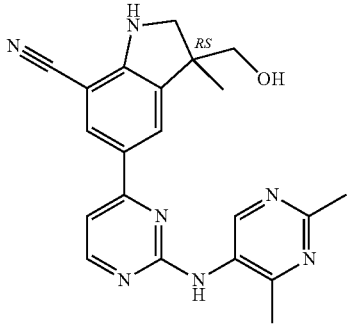 From intermediate 406 | 77 off-white solid | 20 |
| Compound 132 | 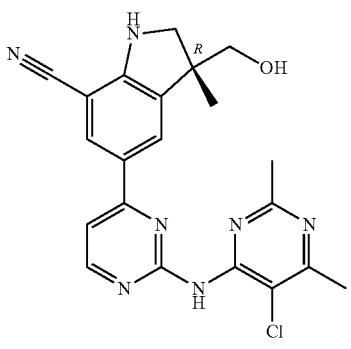 From intermediate 408 | 62 white solid | 57 |
| Compound 133 | 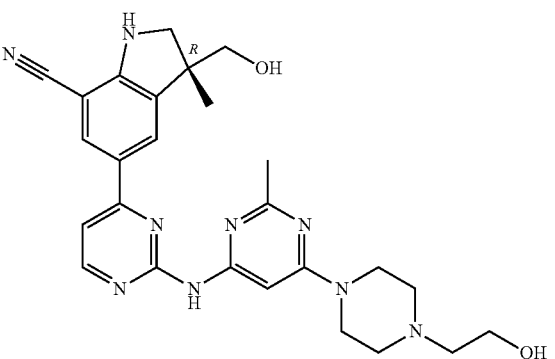 From intermediate 410 | 228 off-white solid | 59 |
| Compound 134 | 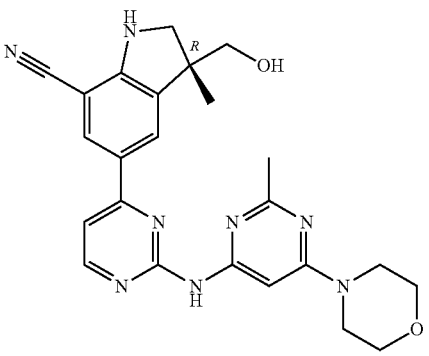 From intermediate 412 | 58 off-white solid | 29 |

-continued
| Compound number | Structure | Mass (mg) | Yield (%) |
|---|---|---|---|
| Compound 135 | 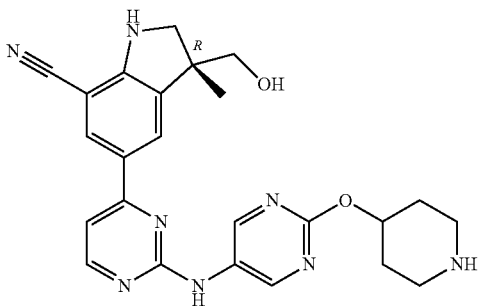<br>•CF₃COOH<br>From intermediate 414 | 19<br>off-white<br>solid | 6 |
| Compound 136 | 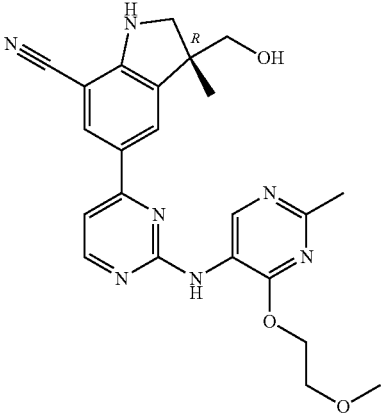<br>From intermediate 418 | 197<br>white<br>solid | 78 |
| Compound 137 | 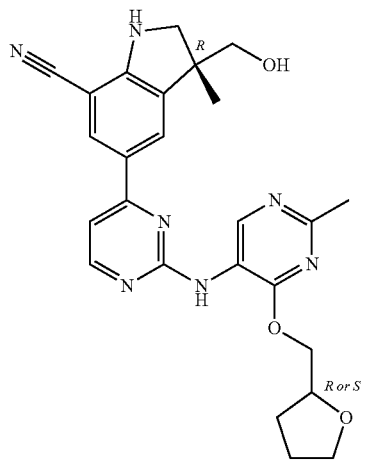<br>From intermediate 422 | 133<br>off-white<br>solid | 42 |

-continued

| Compound number | Structure | Mass (mg) | Yield (%) |
|---|---|---|---|
| Compound 138 | From intermediate 422 | 98 off-white solid | 33 |
| Compound 142 | From intermediate 438 | 47 white solid | 67 |
| Compound 144 | From intermediate 444 | 98 white fluffy solid | 65 |

-continued

| Compound number | Structure | Mass (mg) | Yield (%) |
|---|---|---|---|
| Compound 146 | From intermediate 470 | 81 | 79 |
| Compound 147 | From intermediate 473 | 57 white solid | 71 |
| Compound 148 | From intermediate 449 | 47 white solid | 63 |

| Compound number | Structure | Mass (mg) | Yield (%) |
|---|---|---|---|
| Compound 149 | 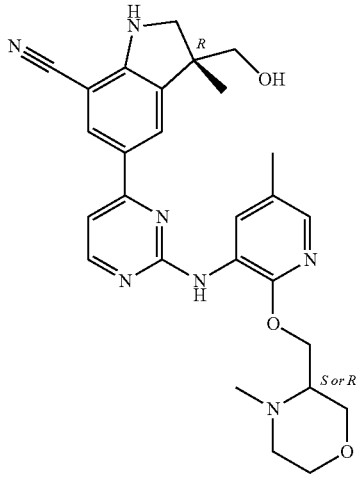 From intermediate 451 | 108 yellow solid | 81 |
| Compound 150 | 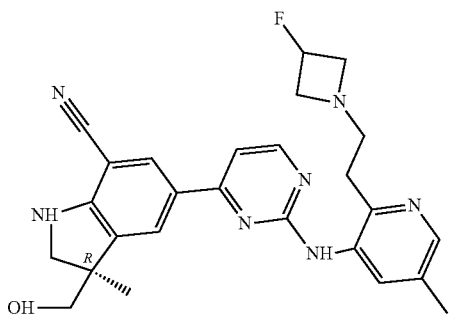 From intermediate 477 | 173 | 70 |
| Compound 151 | 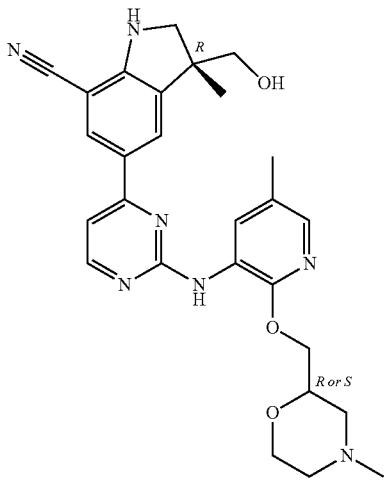 From intermediate 465 | 165 | 53 |

-continued

| Compound number | Structure | Mass (mg) | Yield (%) |
|---|---|---|---|
| Compound 152 | From intermediate 467 | 140 yellow solid | 61 |
| Compound 153 | TRANS A (SS or RR) From intermediate 456 | 115 Yellow solid | 79 |
| Compound 154 | TRANS B (RR or SS) From intermediate 458 | 52 White solid | 71 |

-continued

| Compound number | Structure | Mass (mg) | Yield (%) |
|---|---|---|---|
| Compound 155 | TRANS mixture (RR or SS)<br>From intermediate 568 | 155 | 38<br>4 h |
| Compound 156 | From intermediate 479 | 78 | 83 |
| Compound 157 | From intermediate 502 | 73 | 40 |
| Compound 158 | From intermediate 562 | 238<br>White solid | 95<br>Procedure:<br>reaction time<br>20 min |

-continued

| Compound number | Structure | Mass (mg) | Yield (%) |
|---|---|---|---|
| Compound 159 | From intermediate 492 | 138 | 40<br>Procedure:<br>reaction time<br>1 h 30 |
| Compound 160 | From intermediate 494 | 240 | 50<br>Procedure:<br>reaction time<br>2 h |
| Compound 161 | From intermediate 518 | 224 | 56<br>procedure<br>with 1.5 equiv<br>of TBAF THF<br>4 h |

-continued

| Compound number | Structure | Mass (mg) | Yield (%) |
|---|---|---|---|
| Compound 162 | From intermediate 539 | 7 | 90 procedure with 2 equiv of TBAF Me-THF 2 h |
| Compound 163 | From intermediate 520 | 64 | 22 procedure with 1.1 equiv of TBAF Me-THF 17 h |
| Compound 164 | From intermediate 506 | 112 | 50 procedure with 1.5 equiv of TBAF THF O/N |
| Compound 165 | From intermediate 530 | 94 | 40 procedure with 1.5 equiv of TBAF THF 2 h |

-continued
| Compound number | Structure | Mass (mg) | Yield (%) |
|---|---|---|---|
| Compound 166 | 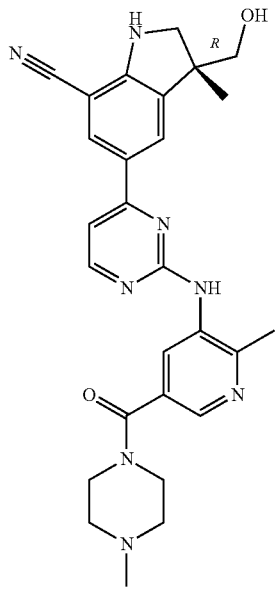 From intermediate 536 | 21 | 10 procedure with 1.1 equiv of TBAF Me-THF o/n |
| Compound 167 | 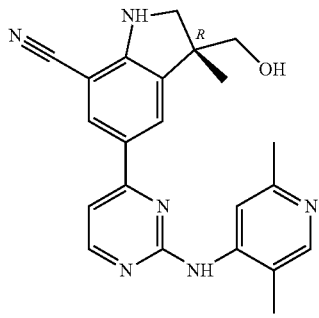 From intermediate 540 | 92 | 64 procedure with 2 equiv of TBAF Me-THF 2 h |
| Compound 168 | 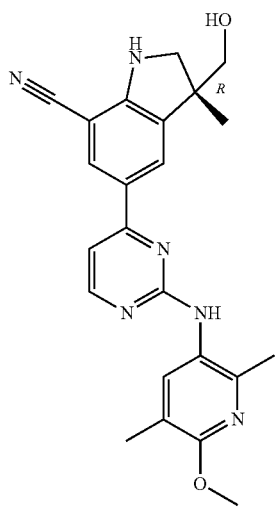 From Intermediate 509 | 172 | 76 procedure with 1.5 equiv of TBAF THF 2 h 30 |

-continued

| Compound number | Structure | Mass (mg) | Yield (%) |
| --- | --- | --- | --- |
| Compound 169 | From intermediate 534 | 790 | 77 procedure with 2 equiv of TBAF Me-THF 3 h |
| Compound 170 | From intermediate 532 | 88 | 71 procedure with 3 equiv of TBAF Me-THF 4 h |
| Compound 182 | From intermediate 586 | 42 | 68 procedure with 2 equiv of TBAF Me-THF 3 h |
| Compound 183 | From intermediate 588 | 60 | 27 procedure with 6 equiv of TBAF (TBAF on silica gel 1.55 mmol/g) Me-THF 18 h |

Example B4

Preparation of Compound 6

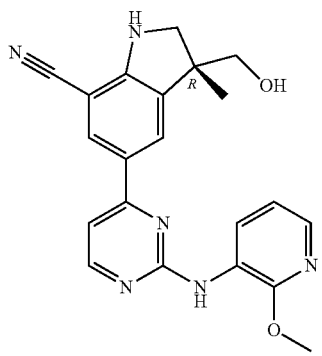

HCl (3M in H₂O) (1.88 mL, 5.64 mmol) was added to a solution of intermediate 22 (340.00 mg, 0.56 mmol) in MeOH (8.64 mL) and the reaction mixture was stirred overnight at rt. The following day, just the TBDMS was cleaved so the reaction was put at 65° C. for 4 h. After 4 h, the reaction was almost finished but there was still some NBoc product so the reaction was put at rt over the weekend. The reaction mixture was cooled to rt, poured onto a 10% aqueous solution of K₂CO₃ and extracted with DCM. The organic layer was decanted, dried over MgSO₄, filtered and evaporated to dryness.

The residue (183 mg, yellow powder) was gathered with another batch (from 110 mg of intermediate 22) and purified via achiral SFC (Stationary phase: CYANO 6 µm 150×21.2 mm, mobile phase: 80% CO₂, 20% MeOH (0.3% iPrNH₂)). The fractions containing the product were evaporated to give 139 mg of a white powder. This solid was taken up in Et₂O to provide 105 mg of compound 6 (48% yield, white solid). MP: 241° C. (K)

The compounds in the Table below were prepared by using an analogous method starting from the respective starting materials.

| Compound number | Structure | Mass (mg) | Yield (%) |
|---|---|---|---|
| Compound 7 | From Intermediate 23 | 135 white powder | 40 |

Example B5

Preparation of Compound 21

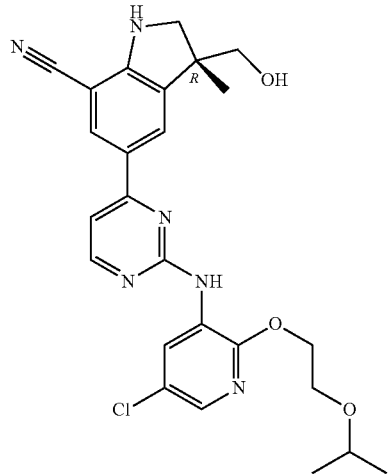

TBAF (on silica gel 1.5 mmol/g) (1.43 g, 2.15 mmol) was added to a solution of intermediate 63 (218.00 mg, 0.36 mmol) in Me-THF (10 mL) and the reaction mixture was stirred at rt for 18 h. The reaction mixture was diluted with DCM, filtered through paper and poured onto a 10% aqueous solution of K₂CO₃. The organic layer was decanted, washed with water, dried over MgSO₄, filtered and evaporated to dryness. The residue was purified by column chromatography on silica gel (irregular SiOH, 24 g, mobile phase: heptane/MeOH/EtOAc, gradient from 2% MeOH, 40% EtOAc, 60% heptane to 2% MeOH, 60% EtOAc, 40% heptane). The pure fractions were collected and evaporated to dryness. The residue was crystallized from Et₂O, filtered and dried to give 77 mg of compound 21 (43% yield).

Preparation of Compound 33

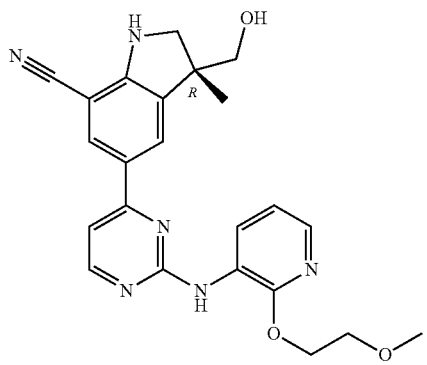

TBAF (on silica gel 1.5 mmol/g) (2.30 g, 3.46 mmol) was added to a solution of intermediate 103 (315.00 mg, 0.58 mmol) in Me-THF (14 mL) and the reaction mixture was stirred at rt for 18 h. The reaction mixture was diluted with EtOAc and poured onto a 10% aqueous solution of K₂CO₃. The organic layer was decanted, washed with brine, dried over MgSO₄, filtered and evaporated to dryness. The residue was purified by column chromatography on silica gel (irregular SiOH, 24 g, mobile phase: DCM/MeOH, gradient from 100:0 to 90:10). The pure fractions were collected and evaporated to dryness. The residue was crystallized from EtOH/Et₂O then the precipitate was filtered and dried to give 128 mg of compound 33 (51% yield). M.P.=153° C. (DSC).

The compounds in the Table below were prepared by using an analogous method starting from the respective starting materials. The most relevant minor deviations to the referenced method are indicated as additional information in the column 'Yield (%)'.

| Compound | Structure | Mass (mg) | Yield (%) |
|---|---|---|---|
| Compound 22 | 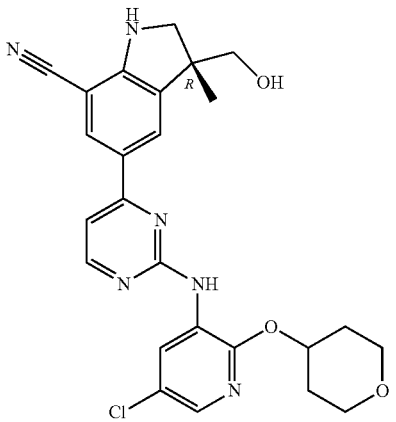<br>From Intermediate 67 | 66 | 30 |
| Compound 31 | 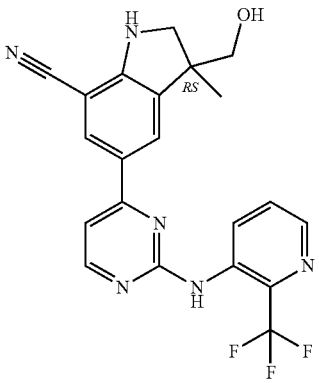<br>From Intermediate 97 | 79 | 43<br>Procedure with 3 equiv of TBAF |
| Compound 34 | 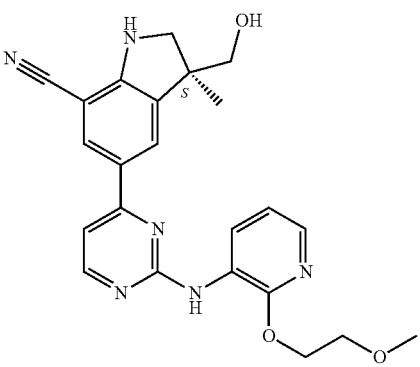<br>From Intermediate 105 | 126 | 47 |

-continued

| Compound | Structure | Mass (mg) | Yield (%) |
|---|---|---|---|
| Compound 35 | From Intermediate 108 | 98 | 52 |
| Compound 40 | From Intermediate 125 | 55 | 32 |
| Compound 42 | From Intermediate 133 | 158 | 58 |

-continued
| Compound | Structure | Mass (mg) | Yield (%) |
|---|---|---|---|
| Compound 43 | 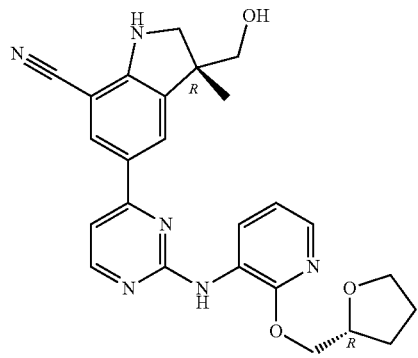 From Intermediate 137 | 88 | 31 |
| Compound 45 | 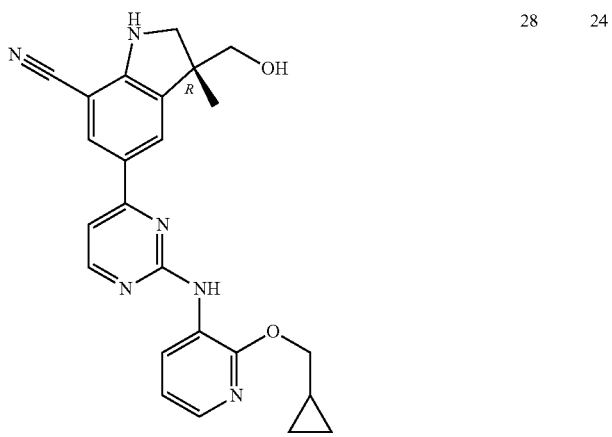 From Intermediate 145 | 28 | 24 |
| Compound 46 | 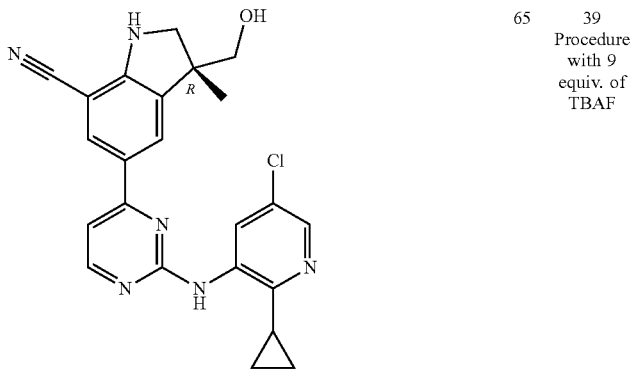 From Intermediate 149 | 65 | 39 Procedure with 9 equiv. of TBAF |

-continued

| Compound | Structure | Mass (mg) | Yield (%) |
|---|---|---|---|
| Compound 47 | From Intermediate 153 | 37 | 28 |
| Compound 51 | From Intermediate 169 | 37 | 28 |
| Compound 52 | From Intermediate 173 | 42 | 8 |

-continued

| Compound | Structure | Mass (mg) | Yield (%) |
|---|---|---|---|
| Compound 66 | From Intermediate 223 | 102 | 37 Procedure with 4 equiv. of TBAF |
| Compound 171 | CIS mixture (RS and SR)<br>From intermediate 546 | 70 | 80 |
| Compound 172 | From intermediate 549 | 14 | 17 procedure with 1.5 equiv. of TBAF |
| Compound 173 | From intermediate 497 | 159 | 42 |

-continued

| Compound | Structure | Mass (mg) | Yield (%) |
|---|---|---|---|
| Compound 174 | From intermediate 552 | 167 | 32 |
| Compound 175 | From intermediate 558 | 8 | 21 |
| Compound 176 | From intermediate 560 | 56 | 68 Procedure with 1.5 equiv. of TBAF |
| Compound 177 | From intermediate 512 | 186 | 54 procedure with 1.1 equiv. of TBAF |

Example B6

Preparation of Compound 97

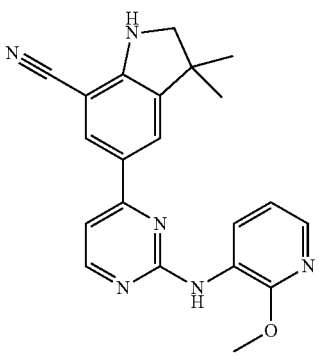 [SMILES: COc1ncccc1Nc1nccc(-c2cc(C#N)c3c(c2)C(C)(C)CN3)n1]

TFA (2 mL) was added to a solution of intermediate 335 (89.78 mg, 0.19 mmol) in DCM (5 mL) and the mixture was stirred for 3 h at rt. The reaction mixture was concentrated in vacuo and purified by column chromatography on silica gel (24 g Si-PPC, mobile phase: DCM/2 M ammonia in MeOH, gradient from 0% to 10% of MeOH) to give a yellow oil. The residue (110 mg) was further purified by prep-HPLC (Waters X-bridge, 19×250 mm, $C_{18}$ column, mobile phase: 0.1% $NH_4OH/CH_3CN$, from 10% to 98% of $CH_3CN$) and freeze-dried to give 20 mg of the desired compound (28% yield, white solid).

The compounds in the Table below were prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 98 | From intermediate 336 | 25 off-white solid | 20 Procedure with DCM/TFA (1:1, v/v) |
| Compound 99 | From intermediate 340 | 60 off-white solid | 43 Procedure with DCM/TFA (1:1, v/v) |

| Compound number | Structure | Mass (mg) | Yield (%) |
|---|---|---|---|
| Compound 125 | 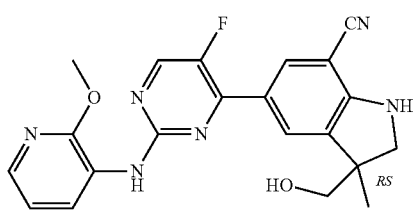 [SMILES: COc1ncccc1Nc1ncc(F)c(-c2cc(C#N)c3c(c2)C(C)(CO)CN3)n1] From intermediate 397 | 104 | 40 Procedure with DCM/TFA (3:1, v/v) |

Example B7

Preparation of Compound 101

A mixture of intermediate 345 (248.00 mg, 0.48 mmol) and TBAF (1M in THF) (0.68 mL, 0.68 mmol) in THF (5.5 mL) was stirred at rt for 18 h. The reaction mixture was directly (without evaporation) purified by column chromatography on silica gel (irregular SiOH 15-40 μm, 120 g, mobile phase: DCM/MeOH, gradient from: 100:0 to 95:5). The pure fractions were mixed and the solvent was evaporated. The residue was taken up by Et₂O, filtered and dried to give 0.127 g of compound 101 (66% yield).

Preparation of Compound 103

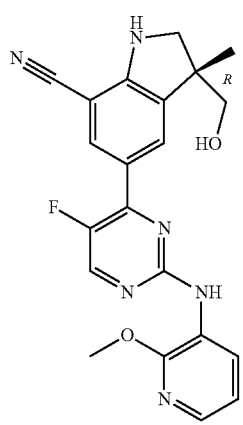

A mixture of intermediate 350 (213.00 mg, 0.41 mmol) and TBAF (1M in THF) (0.59 mL, 0.59 mmol) in THF (4.7 mL) was stirred at rt for 18 h. The reaction mixture was directly purified by column chromatography on silica gel (irregular SiOH 15-40 μm, 120 g, mobile phase: DCM/MeOH, gradient from 100:0 to 95:5). The pure fractions were mixed and the solvent was evaporated. The residue was taken up by Et₂O, filtered and dried to give 109 mg of compound 103 (66% yield).

Preparation of Compound 124

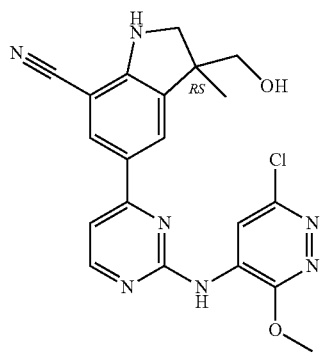

A mixture of intermediate 396 (50.00 mg, 93.00 μmol) and TBAF (1M in THF) (0.10 mL, 0.10 mmol) in THF (1 mL) was stirred at rt for 18 h. The reaction mixture was directly (without evaporation) purified by column chromatography on silica gel (irregular SiOH 15-40 μm, 40 g, liquid injection (THF/DCM), mobile phase gradient: DCM/MeOH (10% aq NH₃) from 100:0 to 90:10 in 15 CV). The fractions containing the product were combined and evaporated to dryness to give 31 mg of compound 124 (79% yield, off-white solid).

The compounds in the Table below were prepared by using an analogous method starting from the respective starting materials.

| Compound number | Structure | Mass (mg) | Yield (%) |
|---|---|---|---|
| Compound 102 | 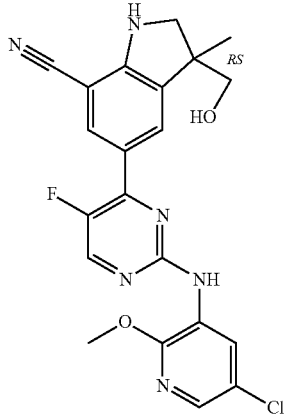<br>From intermediate 347 | 25 | 36 |
| Compound 104 | 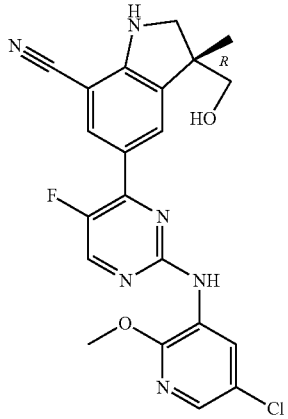<br>From intermediate 352 | 68 | 40 |
| Compound 178 | 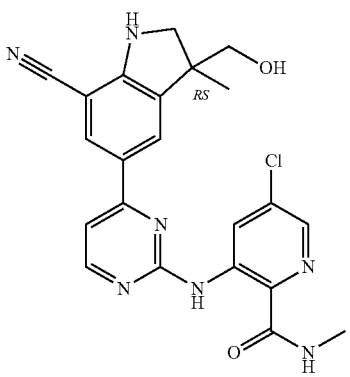<br>From intermediate 526 | 190 (70% purity based on LC/MS) | 100 procedure with 1.1 equiv. of TBAF |

Example B8

Preparation of Compound 105

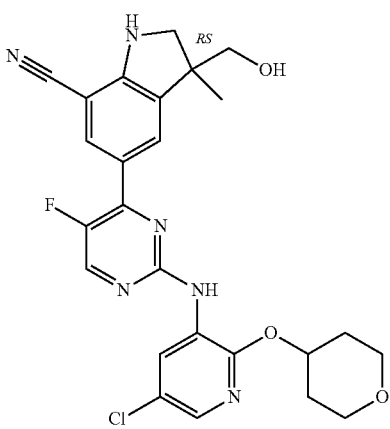

TBAF (on silica gel 1.5 mmol/g) (1.77 g, 2.65 mmol) was added to a solution of intermediate 354 (276.00 mg, 0.44 mmol) in Me-THF (12 mL) and the reaction mixture was stirred at rt for 18 h. The reaction mixture was diluted with DCM, filtered through paper and poured onto a 10% aqueous solution of $K_2CO_3$. The organic layer was decanted, washed with water, dried over $MgSO_4$, filtered and evaporated to dryness. The residue was purified by column chromatography on silica gel (irregular SiOH, 24 g, mobile phase: heptane/MeOH/EtOAc, gradient from 2% MeOH, 40% EtOAc, 60% heptane to 2% MeOH, 60% EtOAc, 40% heptane). The pure fractions were collected and evaporated to dryness. The residue was crystallized from $Et_2O$, filtered and dried to give 103 mg of compound 105 (42% yield).

The compounds in the Table below were prepared by using an analogous method starting from the respective starting materials.

| Compound number | Structure | Mass (mg) | Yield (%) |
|---|---|---|---|
| Compound 106 | 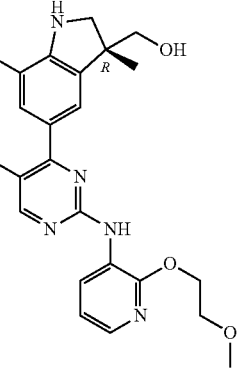<br>From intermediate 356 | 107 | 42 |
| Compound 107 | 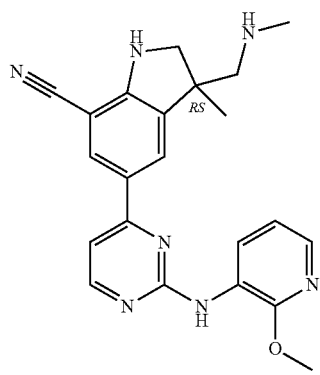<br>From intermediate 358 | 117 | 59 |

Example B9

Preparation of Compound 108

TFA (0.213 mL) was added at 5° C. to a solution of intermediate 361 (93.00 mg, 0.18 mmol) in DCM (2.0 mL). The reaction mixture was stirred at 5° C. for 1 h and 30 min. The crude was diluted with DCM and poured onto a 10% aqueous solution of $K_2CO_3$, dried over $MgSO_4$, filtered and evaporated to dryness to provide a yellow powder. The residue (120 mg) was purified by column chromatography on silica gel (deposit solid, irregular SiOH, 30 g, mobile phase: DCM/MeOH, gradient from 100:0 to 90:10). The pure fractions were collected and evaporated to dryness to give 18 mg of a white powder. The product was taken up with $Et_2O$ to give 10 mg of compound 108 (13% yield, white powder).

Preparation of Compound 115

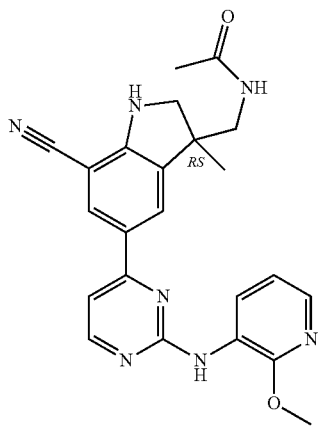

TFA (772 μL) was added at 5° C. to a solution of intermediate 371 (457.00 mg, 0.67 mmol) in DCM (7.31 mL). The reaction mixture was stirred at rt overnight. The reaction was not completed. Additional TFA (360 μL) was added at 5° C. The crude mixture was diluted with DCM and poured onto a 10% aqueous solution of K₂CO₃, dried over MgSO₄, filtered and evaporated to dryness to provide an orange powder. The residue (500 mg) was combined with another batch (100 mg coming from a reaction performed on 79 mg of intermediate 371) and purified by column chromatography on silica gel (irregular SiOH, 40 g, mobile phase: DCM/MeOH/NH₄OH, gradient from 100% DCM to 92% DCM 8% MeOH, 0.8% NH₄OH). The fractions containing the product were collected and evaporated to dryness to give a light orange powder. The residue (240 mg) was purified by reverse phase (Stationary phase: X-Bridge-C18, 5 μm, 30×150 mm, mobile phase: NH₄CO₃ (0.2%)/MeOH, gradient from 60:40 to 20:80). The fractions containing the product were combined and concentrated to provide a yellow powder. The resulting residue (78 mg) was purified again by reverse phase (Stationary phase: X-Bridge-C18, 5 μm, 30×150 mm, mobile phase: HCOONH₄ (0.6 g/L, pH=3.5)/CH₃CN, gradient from 75:25 to 35:65). The fractions containing the product were combined and concentrated to provide a light yellow powder. The residue (64 mg) was taken up with Et₂O to provide 51 mg of a yellow powder as a formiate salt. So, the residue was diluted with DCM and poured twice onto water and NaCl, dried over MgSO₄, filtered and evaporated to dryness to give a white powder. The residue (42 mg) was taken up with Et₂O to provide 38 mg of compound 115 (13% yield, white powder). M.P.=203° C.

The compounds in the Table below were prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 109 | From intermediate 364 | 65 white powder | 34 |
| Compound 110 | From intermediate 365 | 71 white powder | 39 Procedure with DCM/TFA (11:1, v/v) |

-continued
| Compound number | Structure | Mass (mg) | Yield (%) |
|---|---|---|---|
| Compound 111 | 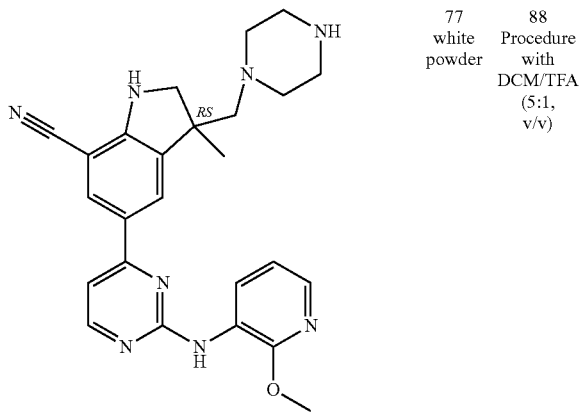 From intermediate 366 | 77 white powder | 88 Procedure with DCM/TFA (5:1, v/v) |
| Compound 112 | 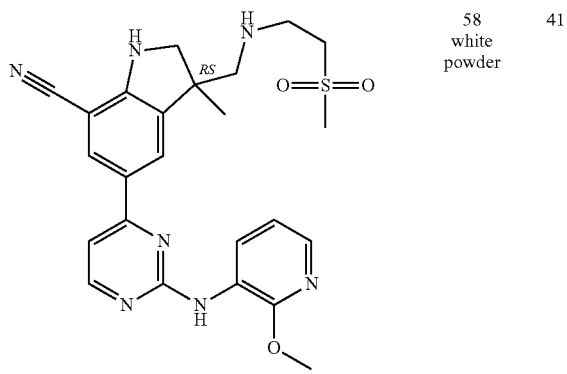 From intermediate 367 | 58 white powder | 41 |
| Compound 113 | 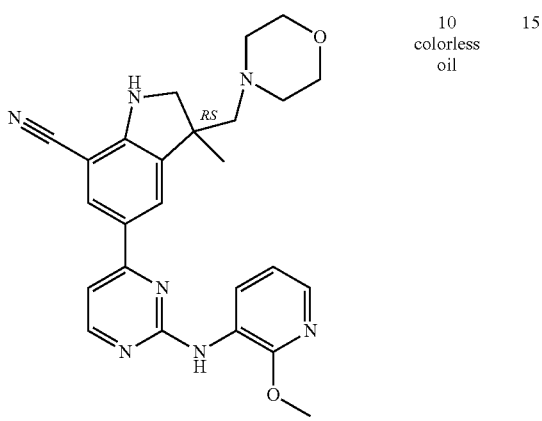 From intermediate 368 | 10 colorless oil | 15 |

-continued

| Compound number | Structure | Mass (mg) | Yield (%) |
|---|---|---|---|
| Compound 116 | From intermediate 379 | 108 | 46 Procedure with DCM/TFA (18:1, v/v) |
| Compound 117 | From intermediate 380 | 174 | 52 Procedure with DCM/TFA (10:1, v/v) |
| Compound 118 | From intermediate 381 | 101 | 31 Procedure with DCM/TFA (10:1, v/v) |
| Compound 119 | From intermediate 384 | 155 | 53 Procedure with DCM/TFA (11:1, v/v) |

-continued

| Compound number | Structure | Mass (mg) | Yield (%) |
|---|---|---|---|
| Compound 120 | From intermediate 385 | 118 | 45 Procedure with DCM/TFA (10:1, v/v) |
| Compound 121 | From intermediate 386 | 141 | 43 Procedure with DCM/TFA (10:1, v/v) |
| Compound 122 | From intermediate 390 | 43 white powder | 27 Procedure with DCM/TFA (6:1, v/v) |

Example B10

Preparation of Compound 114

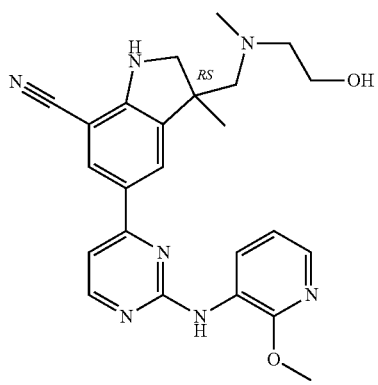

HCl (3M in H$_2$O) (0.78 mL, 2.33 mmol) was added to a solution of intermediate 369 (154.00 mg, 0.23 mmol) in MeOH (3.6 mL) and the reaction mixture was stirred several days at rt. The reaction mixture was cooled to rt, poured onto a 10% aqueous solution of K$_2$CO$_3$ and extracted with DCM. The organic layer was decanted, dried over MgSO$_4$, filtered and evaporated to dryness to provide an orange powder. The residue (300 mg) was purified by column chromatography on silica gel (Irregular SiOH, 25 g, solid deposit; mobile phaseNH$_4$OH/MeOH/DCM, gradient from 0% NH$_4$OH, 0% MeOH, 100% DCM to 0.5% NH$_4$OH, 5% MeOH, 95% DCM). The fractions containing the product were collected and evaporated to dryness to give a colorless oil. The residue (30 mg) was further purified by reverse phase (Stationary phase: X-Bridge-C18 5 µm, 30×150 mm, mobile phase: NH$_4$CO$_3$ (0.2%)/CH$_3$CN, gradient from 65:35 to 25:75). The fractions containing the product were combined and concentrated to dryness. The residue (28 mg, yellow oil) was taken up with Et$_2$O to provide 27 mg of compound 114 (26% yield, yellow oil).

Example B11

Preparation of compound 179

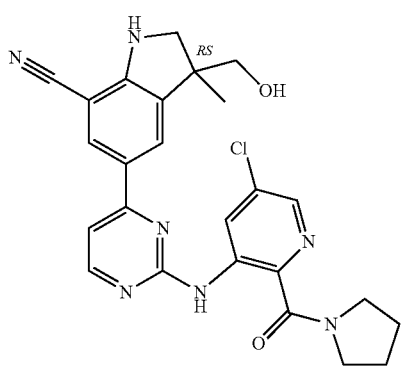

A solution of intermediate 573 (200 mg; 0.34 mmol) and silica gel (203 mg; 3.39 mmol) in toluene (10.00 mL) was stirred at 110° C. for 16 h. The reaction was filtered. The filtrate was concentrated. The crude product was purified by preparative high-performance liquid chromatography over Waters Xbridge 150*25 5 u (Mobile phase: CH$_3$CN/H$_2$O (10 mM NH$_4$HCO$_3$-ACN v/v) Gradient from 35:65 to 65:35, v/v). The pure fractions were collected and the solvent was evaporated under vacuum. The aqueous layer was lyophilized to give 40 mg of compound 179 (24% yield) as a white solid.

Example B12

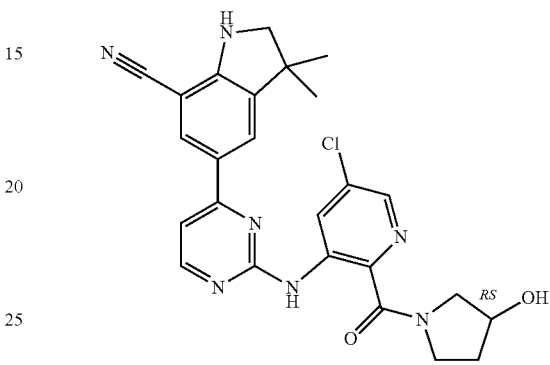

Preparation of Compound 180

To a stirred solution of intermediate 179 in toluene (10.00 mL) was added silica gel (0.13 g, 2.20 mmol) at rt. The reaction mixture was stirred at 100-105° C. for 16 h. The reaction was concentrated. The crude was purified by preparative high-performance liquid chromatography over Phenomenex Synergi C18 150*25*10 um (Mobile phase: CH$_3$CN/H$_2$O (10 mM NH$_4$HCO$_3$-ACN v/v) Gradient from 29% to 64%, v/v). The pure fractions were collected and the solvent was evaporated under vacuum. The aqueous layer was lyophilized to give 20 mg of compound 180 (18% yield) as a yellow solid.

Example B13

Preparation of Compound 181

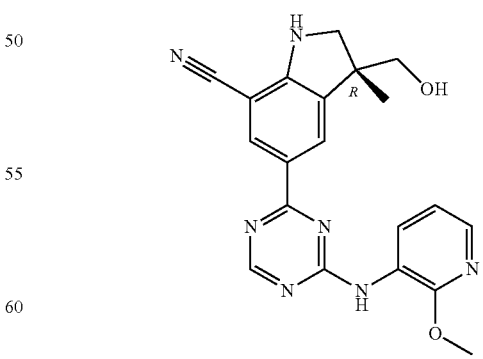

A mixture of intermediate 581 (300 mg; 0.41 mmol) in DCM (3.00 mL) was added TFA (34 µL; 0.45 mmol). The reaction mixture was stirred at rt for 1 hour. The mixture was evaporated to give 300 mg of crude material as a yellow solid. This material was combined with the crude from a parallel reaction. The combined crude product was purified by preparative high-performance liquid chromatography over Column: Kromasil 150*25 mm*10 um. Mobile phase: Water (0.05% ammonia hydroxide v/v)/ACN, Gradient from 65/35 to 35/65. Gradient Time(min) 8; 100% B Hold Time(min) 2; Flow Rate (ml/min) 30. The pure fractions were collected and the volatiles were reduced under vacuum. The remaining aqueous layer was freeze-dried to give 120 mg of compound 181 (75% yield) as a yellow solid.

Example B14

Preparation of compound 1i

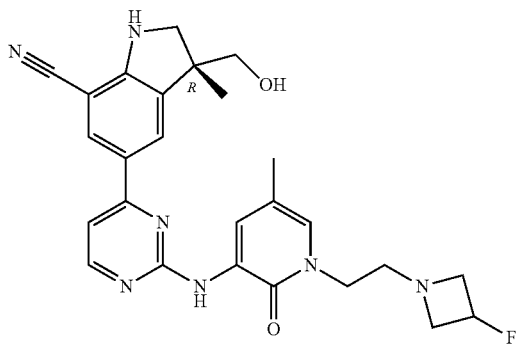

TBAF (1M in THF) (775.07 μL, 0.77 mmol) was added to a solution of intermediate 13i (234.00 g, 0.39 mmol) in Me-THF and the reaction mixture was stirred at rt for 3 h. A 10% aqueous solution of K$_2$CO$_3$ and EtOAc were added. The organic layer was decanted, washed with water then brine, dried over MgSO$_4$, filtered and evaporated to dryness. The residue was purified by column chromatography on silica gel (irregular SiOH, 25 g, mobile phase: gradient from 0.5% NH$_4$OH, 5% MeOH, 95% DCM to 1% NH$_4$OH, 10% MeOH, 90% DCM). The pure fractions were collected and evaporated to dryness. The residue was taken up with Et$_2$O and the solid was filtered and dried to give 121 mg of compound 1i (64% yield). M.P.=149° C. (K).

Preparation of Compound 4i

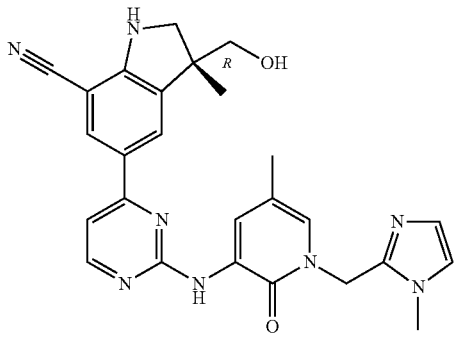

To a solution of intermediate 23i (127.00 mg, 0.17 mmol) in Me-THF (1.85 mL), TBAF (1M in THF) (0.18 mL, 0.18 mmol) was added and the mixture was stirred at rt overnight. The mixture was evaporated under vacuum to give a yellow gum. The residue was purified by column chromatography on silica gel (irregular SiOH, 15-40 μm, 4 g, dry loading on Celite®, mobile phase: DCM/MeOH, gradient from 99:1 to 94:6). The fractions containing the product were combined and concentrated under vacuum to give 69 mg of compound 4i (85% yield, white solid).

Preparation of Compound 7i

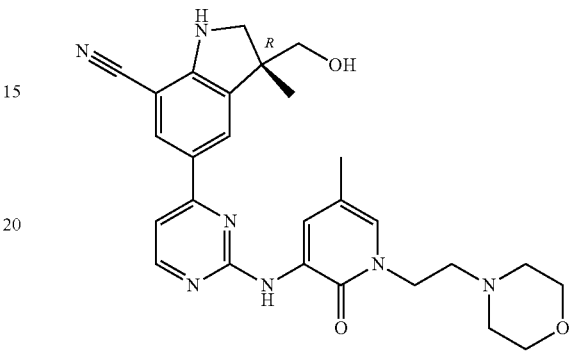

To a solution of intermediate 35i (460.00 mg, 0.75 mmol) in Me-THF (8.2 mL), TBAF (1M in THF) (0.82 mL, 0.82 mmol) was added and the mixture was stirred at rt for 4 h. The mixture was evaporated in vacuo. The residue (714 mg, orange foam) was purified by column chromatography on silica gel (irregular SiOH, 15-40 μm, 40 g, liquid loading with DCM, mobile phase: DCM/MeOH, gradient from 99:1 to 94:6). The fractions containing the product were combined and evaporated to dryness. The residue (319 mg, white solid) was dried under vacuum (50° C., 16 h) to give 280 mg of compound 7i (75% yield, white solid).

Preparation of Compound 13i

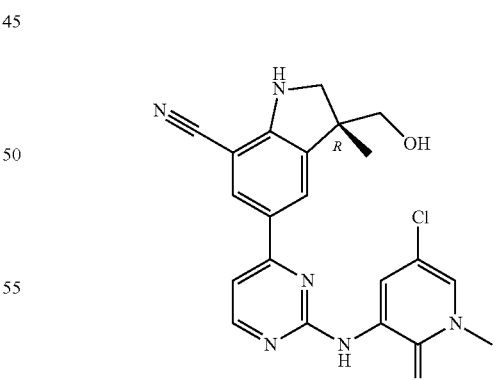

A mixture of intermediate 54i (390.00 mg, 0.73 mmol) and TBAF (1M in THF) (0.77 mL, 0.77 mmol) in Me-THF (12 mL) was stirred at rt for 20 h. The residue was directly purified by column chromatography on silica gel (irregular SiOH 15-40 μm, 24 g, dry load on Celite®, mobile phase: DCM/MeOH (+10% aq. NH₃), gradient from 98:2 to 85:15). The fractions containing the product were combined and evaporated to dryness. The residue (120 mg, brown solid) was recrystallized from EtOH, filtered on a glass frit and washed once with EtOH. The solid was collected and was dried at 50° C. under reduced pressure for 16 h to give 94 mg of compound 13i (31% yield, off-white solid).

Preparation of compounds 22i and 23i compound 22i

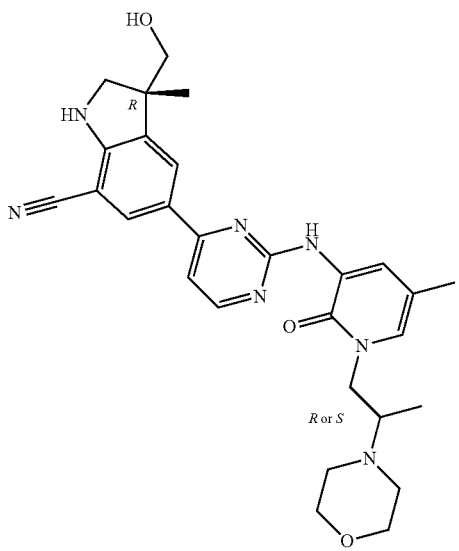

compound 23i

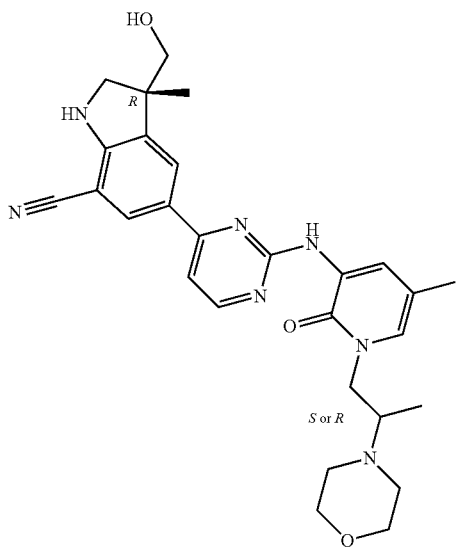

To a solution of intermediate 68i (491 mg, 0.78 mmol) in Me-THF (9 mL) was added TBAF (1M in THF) (0.86 mL, 0.86 mmol) and the mixture was stirred at rt overnight. The mixture was evaporated in vacuo. The residue was purified by preparative LC (irregular SiOH, 15-40 μm, 80 g, Grace, mobile phase gradient: from DCM/MeOH: 100/0 to 88/12). The pure fractions were mixed and the solvent was evaporated. The residue was crystallized from MeCN and aceton, filtered and dried, yielding: 0.256 g of compound 18i (64%).

0.2 g of compound 18i was purified via chiral SFC (stationary phase: Chiralcel OJ-H 5 μm 250×20 mm, mobile phase: 75% CO₂, 25% EtOH (0.3% iPrNH₂)). The pure fractions were evaporated, taken up by Et₂O, filtered and dried, yielding: 54 mg of compound 22i (13%) and 45 mg of compound 23i (11%).

The compounds in the Table below were prepared by using an analogous method starting from the respective starting materials. The most relevant minor deviations to the referenced method are indicated as additional information in the column 'Yield (%)'.

| Compound number | Structure | Mass (mg) | Yield (%) |
| --- | --- | --- | --- |
| Compound 2i | ![structure] From intermediate 13i | 56 | 63 procedure with 2 equiv. of TBAF |

-continued

| Compound number | Structure | Mass (mg) | Yield (%) |
|---|---|---|---|
| Compound 3i | From intermediate 20i | 317 | 66 procedure with 1.1 equiv. of TBAF |
| Compound 5i | From intermediate 27i | 220 pale yellow solid | 64 procedure with 1.1 equiv of TBAF |
| Compound 6i | From intermediate 31i | 275 pale yellow solid | 74 procedure with 1.1 equiv of TBAF |

-continued
| Compound number | Structure | Mass (mg) | Yield (%) |
|---|---|---|---|
| Compound 8i | 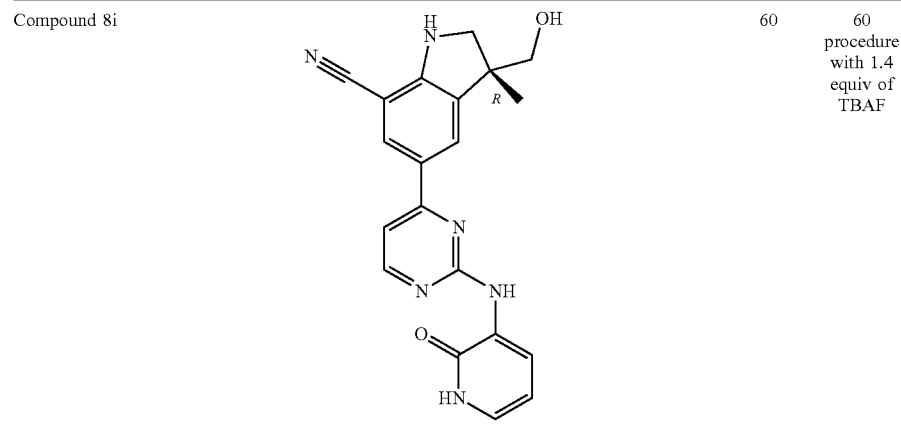 From intermediate 36i | 60 | 60 procedure with 1.4 equiv of TBAF |
| Compound 10i | 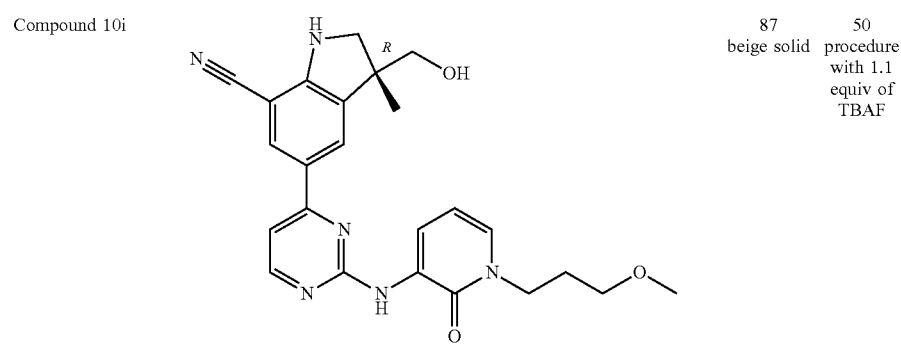 From intermediate 42i | 87 beige solid | 50 procedure with 1.1 equiv of TBAF |
| Compound 11i | 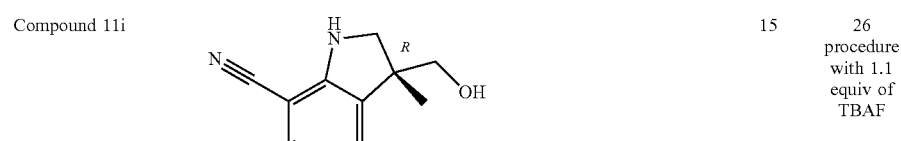 From intermediate 48i | 15 | 26 procedure with 1.1 equiv of TBAF |

-continued

| Compound number | Structure | Mass (mg) | Yield (%) |
|---|---|---|---|
| Compound 12i | From intermediate 52i | 129 white solid | 52 procedure with 1.1 equiv of TBAF |
| Compound 14i | From intermediate 58i | 136 beige solid | 55 procedure with 1.1 equiv of TBAF |
| Compound 15i | From intermediate 59i | 46 brown solid | 24 procedure with 1.1 equiv of TBAF |

-continued
| Compound number | Structure | Mass (mg) | Yield (%) |
|---|---|---|---|
| Compound 16i | 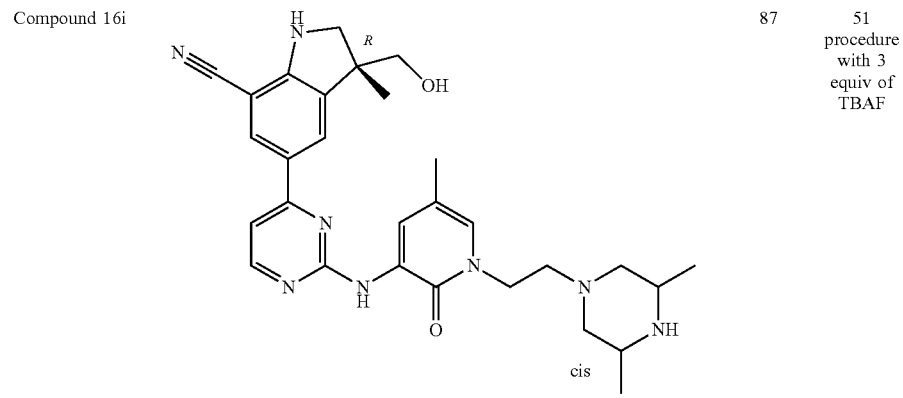<br>From intermediate 62i | 87 | 51 procedure with 3 equiv of TBAF |
| Compound 17i | 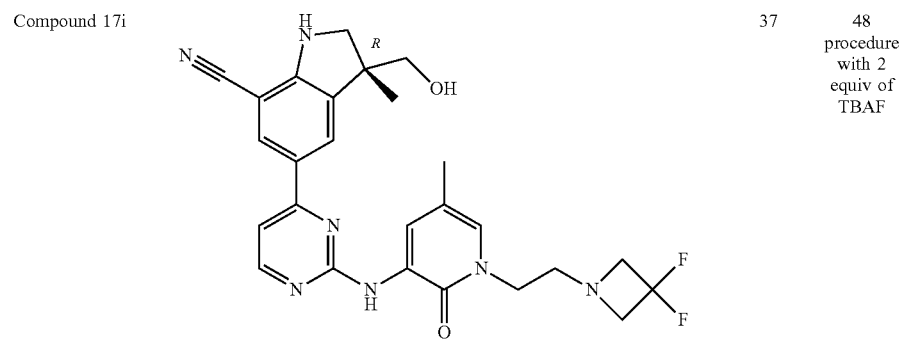<br>From intermediate 65i | 37 | 48 procedure with 2 equiv of TBAF |
| Compound 18i | 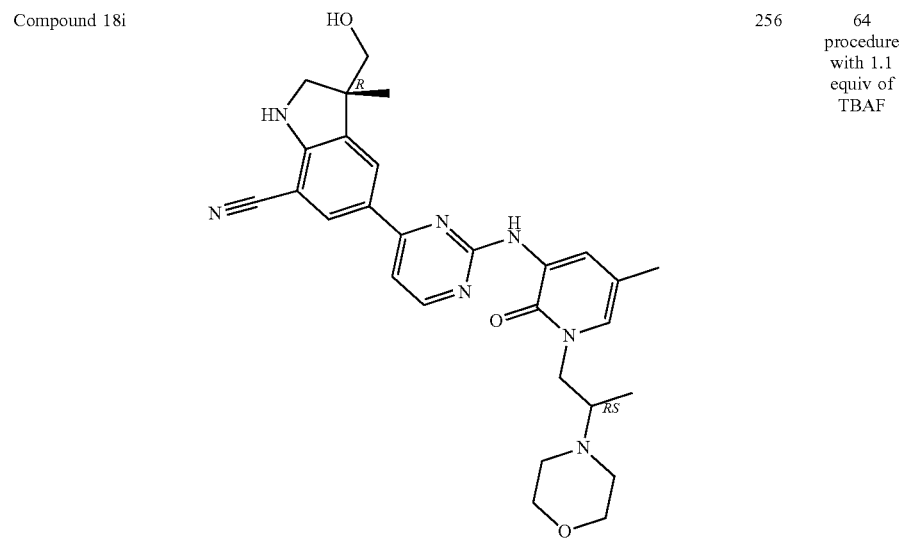<br>From intermediate 68i | 256 | 64 procedure with 1.1 equiv of TBAF |

-continued

| Compound number | Structure | Mass (mg) | Yield (%) |
|---|---|---|---|
| Compound 19i | From intermediate 71i | 73 | 46 procedure with 3 equiv of TBAF |
| Compound 20i | From intermediate 74i | 94 | 57 procedure with 3 equiv of TBAF |
| Compound 21i | From intermediate 78i | 74 | 18 procedure with 1.2 equiv of TBAF |
| Compound 25i | From intermediate 83i | 80 | 39.5 procedure with 2.8 equiv of TBAF |

-continued

| Compound number | Structure | Mass (mg) | Yield (%) |
|---|---|---|---|
| Compound 26i | From intermediate 87i | 74 | 45 procedure with 2 equiv of TBAF |
| Compound 29i | From intermediate 100i | 308 | 92 procedure with 2 equiv of TBAF |
| Compound 30i | From intermediate 105i | 65 | 48 procedure with 1.6 equiv of TBAF in THF |

Example B15

Preparation of Compound 9i

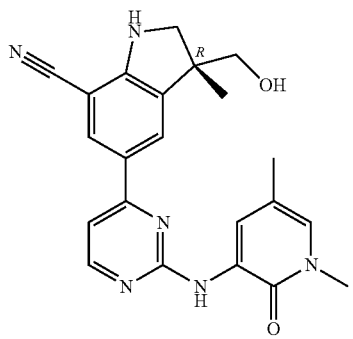

A mixture of intermediate 38i (565.0 mg 1.12 mmol) in dry DCM (stabilized with amylene) (19 mL) was treated with TFA (1.64 mL, 21.40 mmol) and stirred at rt for 30 min. The mixture was poured into a saturated aqueous solution of NaHCO₃, extracted with a mixture of DCM/MeOH (90:10, 6×100 mL). The combined organic layers were dried over MgSO₄ and filtered. Some Celite® was added and the resulting mixture was evaporated under vacuum to afford a dry load. The residue was purified by column chromatography on silica gel (irregular silica, 30 μm, 80 g, dry loading, mobile phase: DCM/MeOH, gradient from 100:0 to 95:5 in 20 CV). The fractions containing the product were combined and evaporated to dryness to afford an off-white solid. The residue was partially recrystallized from EtOH (250 mL of refluxing EtOH which did not allowed complete solubilization, no more EtOH was added). After allowing the suspension to slowly cool down to rt, the resulting solid was filtered and dried at 50° C. under high vacuum for 4 h. The residue (178 mg, white solid) was further dried at 50° C. under high vacuum for 24 h to afford 177 mg of compound 9i (39% yield, white solid).

Example B16

Preparation of Compound 24i (Cis Stereochemistry in Dimethyl Morpholine)

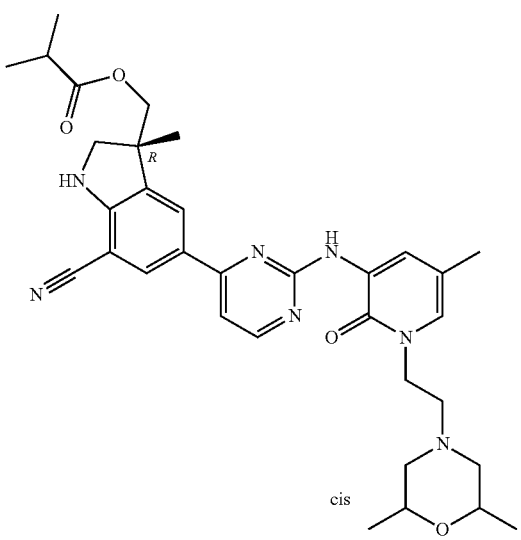

A mixture of compound 2i (0.162 g; 0.306 mmol), isobutyric acid (0.0685 mL; 9.5 mmol), HATU (0.291 g; 0.765 mmol), DIPEA (0.264 mL; 1.53 mmol) in DCM (3 mL) was stirred at room temperature for 18 hours. The solution was poured onto water and extracted with DCM. The organic layer was washed with H₂O, then brine, dried over MgSO₄, filtered and evaporated to dryness. The residue was purified by chromatography over silica gel (irregular SiOH, 60 g; mobile phase: DCM/MeOH: 100/0 to 97/3). The pure fractions were collected and evaporated to dryness yielding 0.208 g. This fraction was purified by chromatography via Reverse phase (stationary phase: YMC-actus Triart-C18 10 μm 30*150 mm, mobile phase: gradient from 60% NH₄HCO₂ 0.2%, 40% ACN to 0% NH₄HCO₂ 0.2%, 100% ACN). The pure fractions were collected and evaporated to dryness, yielding: 0.088 g of compound 24i (48%).

Example B17

Preparation of Compound 27i

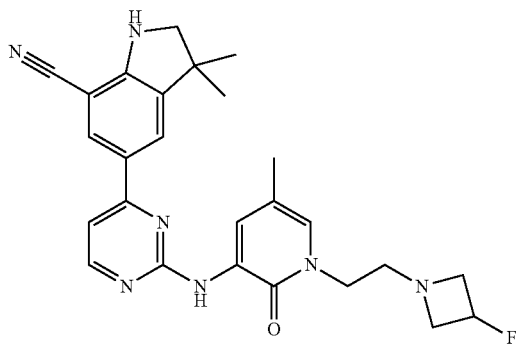 [SMILES: Cc1cc(Nc2nccc(-c3cc(C#N)c4c(c3)C(C)(C)CN4)n2)c(=O)n(CCN2CC(F)C2)c1]

A suspension of intermediate 92i (133.9 mg, 0.48 mmol), intermediate 12i (120 mg, 0.531 mmol), Pd(OAc)₂ (10.9 mg, 0.048 mmol), BINAP (30 mg, 0.048 mmol) and Cs₂CO₃ (394 mg, 1.2 mmol) in 1,4-dioxane (3.9 mL) was purged with N₂ and stirred at 120° C. for 3 h. The reaction mixture was cooled to room temperature, poured onto ice-water and extracted with EtOAc. The organic layer was decanted, washed with brine, dried over MgSO4, filtered over a pad of Celite® and evaporated to give 160 mg of brown oil. The was purified by chromatography over silica gel (Biotage, SNAP Ultra; 50 g; gradient: from 98% DCM, 2% MeOH, 0.2% NH₄OH to 95% DCM, 5% MeOH, 0.5% NH₄OH). The pure fractions were collected and the solvent was evaporated to give 96 mg of yellow oil. This fraction was purified by reverse phase (Stationary phase: YMC-actus Triart-C18 10 μm 30*150 mm, Mobile phase: Gradient from 55% NH₄HCO₂ 0.2%, 45% ACN to 0% NH₄HCO₂ 0.2%, 100% ACN). The pure fractions were collected and the solvent was evaporated to give 68 mg of yellow foam. This fraction was recrystallized from ACN. The precipitate was filtered and dried to give 62 mg of compound 27i as a yellow solid (27%). M.P.: 206° C. (Kofler). M.P.: 197° C. (DSC).

The compound in the Table below was prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 28i | From intermediate 97i | 25 | 22 |

Example B18

Preparation of Compound 31i

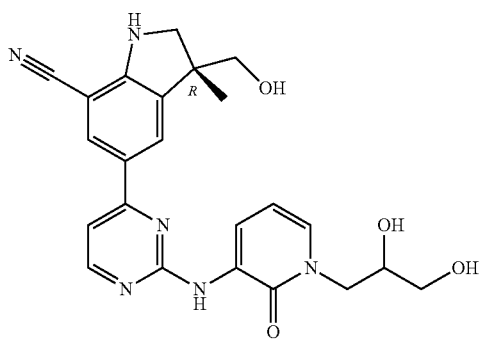

To a solution of intermediate 109i (460.00 mg, 0.75 mmol) in Me-THF (8.2 mL), TBAF (1M in THF) (0.82 mL, 0.82 mmol) was added and the mixture was stirred at rt for 4 h.

The reaction mixture was directly (without evaporation) purified by preparative LC (irregular SiOH 15-40 μm, 120 g, mobile phase gradient: DCM/MeOH from 100/0 to 95/5). The fractions containing product were mixed and the solvent was evaporated. The residue was crystallized from acetone and Et$_2$O and dried to give 0.171 g.

This fraction was purified by chromatography over silica gel by reverse phase (stationary phase: X-Bridge-C18 5 μm 30*150 mm, mobile phase: gradient from 90% NH$_4$HCO$_3$ 0.2%, 10% ACN to 50% NH$_4$HCO$_3$ 0.2%, 50% ACN). The pure fractions were mixed and the solvent was evaporated.

The residue was suspended in Et$_2$O, filtered and dried to give 0.05 g of compound 31i (13% yield).

Analytical Part

LCMS (Liquid chromatography/Mass spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (Br, Cl.), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow (mL/min) T (° C) | Run time |
|---|---|---|---|---|---|---|
| Method 1 | Waters: Acquity UPLC ®- DAD and Quattro Micro ™ | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 40 | 6.2 |

TABLE-continued

LCMS Method codes (Flow expressed in mL/min; column temperature (T) in ° C.; Run time in minutes).

| Method code | Instrument | Column | Mobile phase | gradient | Flow (mL/min) T (° C) | Run time |
|---|---|---|---|---|---|---|
| Method 2 | Waters: Acquity UPLC ® H-Class - DAD and SQD 2 | Waters: BEH C18 (1.7 µm, 2.1 × 100 mm) | A: 95% $CH_3COONH_4$ 7 mM/5% $CH_3CN$, B: $CH_3CN$ | From 84.2% A to 10.5% A in 2.18 min, held for 1.94 min, back to 84.2% A in 0.73 min, held for 0.73 min. | 0.343 40 | 6.1 |
| Method 3 | Waters: Acquity UPLC ® H-Class - DAD and QDa | BEH ®- C18 (1.7 µm, 2.1 × 100 mm) | A: 95% $CH_3COONH_4$ 7 mM/5% $CH_3CN$, B: $CH_3CN$ | 95% A to 5% A in 1 min, held for 1.6 min, back to 95% A in 1.2 min, held for 0.5 min. | 0.5 40 | 3.3 |
| Method 4 | Waters: ZMD quadripole - Waters 1525 LC system with DAD detector or Sedex 85 evaporative light scattering detector | Luna - C18 (3 µm, 30 × 4.6 mm) | A: 95% Water (with 0.1% $CH_3COOH$), B: $CH_3CN$ (with 0.1% $CH_3COOH$) | 95% A held 0.5 min, then from 95% A to 5% A 4.0 min, held for 1.0 min. | 2 40 | 5.5 |
| Method 5 | Waters: Micromass ZQ2000 - Waters Acquity UPLC system equipped with PDA detector | Acquity HST - C18 (1.8 µM, 2.1 × 100 mm) | A: 95% Water (with 0.1% $CH_3COOH$), B: $CH_3CN$ (with 0.1% $CH_3COOH$) | 95% A held 0.4 min, then from 95% A to 5% A 5.2 min, held for 0.8 min. | 0.4 40 | 6.4 |
| Method 6 | Agilent 1100 series DAD LC/MS G1956A | YMC ODS-AQ C18 (50 × 4.6 mm, 3.0 µm) | A: 0.1% HCOOH in $H_2O$ B: $CH_3CN$ | From 95% A to 5% A in 4.8 min, held for 1.0 min, to 90% A in 0.2 min. | 2.6 35 | 6.0 |
| Method 7 | Agilent 1260 series equipped with DAD and Agilent G6120B detector | ACE C18 column (3 µM, 3.0 × 50 mm) | A: 100% Water (with 0.05% TFA), B: 100% $CH_3CN$ | 95% A to 0% A in 1.5 min | 2.2 50 | 2 |
| Method 8 | Agilent 1200 equip with MSD 6110 | Phenomenex Luna- C18, 50 × 2 mm, 5 µm | A: $H_2O$ (0.1% TFA), B: $CH_3CN$ (0.05% TFA) | 90% A held for 0.8 min then 90% A to 20% A in 3.7 min, held for 2 min, back to 90% A in 2 min, held for 0.5 min. | 0.8 50 | 10 |
| Method 9 | Agilent 1200 equip with MSD 6110 | XBridge Shield RP18 (5 µm, 2.1 × 50 mm) | A: $H_2O$ (0.05% $NH_3 \cdot H_2O$), B: $CH_3CN$ | 100% A held for 1.00 min, then from 100% A to 40% A in 4.00 min, then from 40% A to 5% A in 2.50 min, back to 100% A in 2.00 min. | 0.8 40 | 10 |
| Method 10 | Agilent: 1100/1200 - DAD and MSD | Agilent: TC-C18 (5 µm, 2.1 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 50 | 10.5 |
| Method 11 | Agilent 1200 equip with MSD 6110 | Phenomenex Luna- C18, 50 × 2 mm, 5 µm | A: $H_2O$ (0.1% TFA, B: $CH_3CN$ (0.05% TFA) | 100% A held for 1 mn then 100% A to 40% A in 4 mn then 40% A to 15% A in 2.5 mn then back to 100% A in 2 mn held for 0.5 min. | 0.8 50 | 10 |

Melting Point (DSC, K, MP50 or WRS-2A)

For a number of compounds, melting points (MP) were determined with a DSCl (Mettler-Toledo). Melting points were measured with a temperature gradient of 10° C./minute. Maximum temperature was 350° C. Values are peak values. Indicated in the table as DSC.

For a number of compounds, melting points were obtained with a Kofler hot bench (indicated with (K) in the analytical table), consisting of a heated plate with linear temperature gradient, a sliding pointer and a temperature scale in degrees Celsius.

For a number of compounds, melting points were obtained with an automatic Melting Point Apparatus WRS-2A (indicated with WRS-2A in the analytical table). Melting points were measured with a temperature gradient of 5° C. per minute starting from room temperature to a maximum value of 320° C.

For a number of compounds, melting points were obtained with a Mettler Toledo MP50 apparatus (indicated with MP50 in the analytical table). Melting points were measured with a temperature gradient of 10° C. per minute starting from 50° C. (waiting time 10 second) to a maximum value of 300° C.

In the Table below, 'N°' means compound number.

| N° | MP (° C.) | MP method | Rt | [M + H]+ | LCMS Method |
|---|---|---|---|---|---|
| 1 | — | — | 4.17 | 389 | 4 |
| 2 | 230 | K | 2.75 | 496 | 2 |
| 3 | 254 | DSC | 3.18 | 423 | 1 |
| 4 | 280 | DSC | 2.59 | 407 | 1 |
|   | 277 | DSC |      |     |   |
| 5 | 261 | DSC | 3.07 | 427 | 1 |
| 6 | 241 | K | 2.75 | 389 | 1 |
| 7 | 245 | K | 2.75 | 389 | 1 |
| 9 | 238 | K | 2.45 | 431 | 1 |
| 10 | 231 | K | 2.75 | 496 | 2 |
| 11 | 236 | K | 3.04 | 496 | 1 |
| 12 | 120 (gum) | K | 2.65 | 462 | 1 |
| 13 | 125 (gum) | K | 3.34 | 524 | 1 |
| 14 | 266 | DSC | 3.18 | 423 | 1 |
| 15 | — | — | 2.64 | 506 | 1 |
| 16 | 248 | K | 2.93 | 403 | 1 |
| 17 | 248 | K | 2.73 | 392 | 1 |
| 18 | 140 | K | 3.13 | 417 | 1 |
| 19 | 154 | K | 2.95 | 461 | 1 |
| 20 | >260 | K | 2.30 | 389 | 1 |
| 21 | 170 | DSC | 3.37 | 495 | 1 |
| 22 | — | — | 3.17 | 493 | 1 |
| 23 | 213 | DSC | 2.73 | 459 | 1 |
| 24 | 145 | K | 2.11 | 389 | 1 |
| 25 | 213 | DSC | 2.73 | 459 | 1 |
| 26 | 155 | DSC | 2.82 | 459 | 1 |
| 27 | 149 | DSC | 2.80 | 459 | 1 |
| 28 | 194 | DSC | 2.62 | 445 | 1 |
| 29 | 135 | DSC | 3.09 | 418 | 1 |
| 30 | 195 | DSC | 3.51 | 451 | 1 |
| 31 | 202 | K | 2.63 | 427 | 1 |
| 32 | — | — | 1.87 | 443 | 1 |
| 33 | 153 | DSC | 2.69 | 433 | 1 |
|   | 118 | DSC |      |     |   |
| 34 | 152 | DSC | 2.69 | 433 | 1 |
| 35 | 220 | DSC | 3.38 | 437 | 1 |
| 36 | >250 | K | 2.99 | 407 | 1 |
| 37 | 210 | K | 2.24 | 389 | 1 |
| 38 | 215 | DSC | 3.26 | 510 | 1 |
| 39 | 204 | DSC | 3.01 | 467 | 1 |
| 40 | 143 | DSC | 3.29 | 431 | 1 |
| 42 | 154 | DSC | 2.67 | 459 | 1 |
| 43 | 141 | DSC | 2.67 | 459 | 1 |
| 44 | 217 | DSC | 3.08 | 473 | 1 |
| 45 | 138 | K | 3.15 | 429 | 1 |
| 46 | 234 | DSC | 2.98 | 433 | 1 |
| 47 | 215 | DSC | 2.25 | 433 | 1 |
| 48 | 192 | DSC | 2.67 | 486 | 1 |
| 49 | 195 | DSC | 2.57 | 488 | 1 |
| 50 | 247 | DSC | 2.40 | 398 | 1 |
|   | 242 | DSC |      |     |   |
| 51 | 152 | K | 2.94 | 494 | 1 |
| 52 | 281 | DSC | 2.70 | 494 | 1 |
| 53 | 190 | DSC | 3.24 | 501 | 1 |
| 54 | — | — | 3.33 | 457 | 1 |
| 55 | 204 | DSC | 2.69 | 520 | 1 |
| 56 | 126 | DSC | 2.69 | 520 | 1 |
| 57 | — | — | 2.58 | 493 | 1 |
| 58 | — | — | 3.10 | 461 | 1 |
| 59 | 237 | DSC | 2.89 | 403 | 1 |
|   | 234 | K |      |     |   |
| 60 | — | — | 2.25 | 509 | 1 |
| 61 | 186 | DSC | 2.93 | 451 | 1 |
| 62 | 117 | DSC | 3.25 | 473 | 1 |
| 63 | 193 | DSC | 2.75 | 426 | 1 |
| 64 | 145 | DSC | 2.92 | 452 | 1 |
| 65 | 158 | K | 2.62 | 456 | 1 |
| 66 | 178 | K | 1.23 | 440 | 3 |
| 67 | — | — | 2.97 | 473 | 1 |
| 68 | — | — | 2.76 | 441 | 1 |
| 69 | 186 | DSC | 2.82 | 447 | 1 |
| 72 | 224 | DSC | 3.41 | 499 | 1 |
| 73 | 231 | DSC | 2.25 | 470 | 1 |
| 74 | 206 | DSC | 3.22 | 454 | 1 |
| 75 | — | — | 3.19 | 442 | 1 |
| 76 | 162 (gum) | K | 2.78 | 484 | 1 |
| 77 | 162 (gum) | K | 2.65 | 472 | 1 |
| 78 | — | — | 2.64 | 472 | 1 |
| 80 | — | — | 2.31 | 472 | 1 |
| 81 | 318 | DSC | 2.88 | 485 | 1 |
| 84 | — | — | 2.26 | 470 | 1 |
| 85 | — | — | 2.96 | 440 | 1 |
| 86 | 206 | DSC | 3.29 | 443 | 1 |
| 87 | — | — | 2.37 | 484 | 1 |
| 88 | 198 | DSC | 2.68 | 524 | 1 |
| 89 | 301 | DSC | 2.52 | 526 | 1 |
| 90 | — | — | 2.22 | 483 | 1 |
| 91 | 166 | K | 2.81 | 483 | 1 |
| 93 | 165 | DSC | 1.97 | 430 | 1 |
| 96 | — | — | 2.67 | 517 | 1 |
| 97 | — | — | 5.24 | 373 | 5 |
| 98 | — | — | 5.43 | 480 | 5 |
| 99 | — | — | 6.31 | 450 | 5 |
| 101 | >250 | K | 2.92 | 407 | 1 |
| 102 | >250 | K | 3.33 | 441 | 1 |
| 103 | >250 | K | 2.92 | 407 | 1 |
| 104 | >250 | K | 3.33 | 441 | 1 |
| 105 | 284 | DSC | 3.32 | 511 | 1 |
| 106 | >250 | K | 2.81 | 451 | 1 |
| 107 | 226 | DSC | 2.88 | 477 | 1 |
| 108 | 173 | K | 2.49 | 402 | 1 |
| 109 | 171 | K | 3.10 | 494 | 1 |
| 110 | 116 (gum) | K | 3.35 | 428 | 1 |
| 111 | 220 | K | 2.46 | 457 | 1 |
| 112 | 146 | K | 2.76 | 494 | 1 |
| 113 | 95 (gum) | K | 3.27 | 458 | 1 |
| 114 | 60 (gum) | K | 2.90 | 446 | 1 |
| 115 | 203 | K | 2.49 | 430 | 1 |
| 116 | 95 | DSC | 2.59 | 474 | 1 |
| 117 | 108 | DSC | 2.89 | 502 | 1 |
| 118 | 88 | DSC | 2.56 | 486 | 1 |
| 119 | 106 | DSC | 3.49 | 506 | 1 |
| 120 | 152 | DSC | 3.06 | 520 | 1 |
| 121 | 104 | DSC | 3.41 | 536 | 1 |
| 122 | 182 | K | 3.06 | 421 | 1 |
| 124 | — | — | 2.60 | 424 | 1 |
| 125 | 270 | K | 2.85 | 429 | 1 |
| 126 | 227 | DSC | 2.03 | 374 | 1 |
| 127 | 333 | DSC | 2.26 | 388 | 1 |
| 128 | 307 | DSC | 2.04 | 360 | 1 |
| 129 | 223 | DSC | 2.48 | 404 | 1 |
| 130 | — | — | 2.35 | 390 | 1 |
| 131 | 234 | DSC | 2.05 | 399 | 1 |

| N° | MP (° C.) | MP method | Rt | [M + H]+ | LCMS Method |
|---|---|---|---|---|---|
| 132 | — | — | 2.32 | 422 | 1 |
| 133 | — | — | 2.07 | 502 | 1 |
| 134 | — | — | 2.40 | 459 | 1 |
| 135 | — | — | 1.86 | 459 | 1 |
| 136 | 231 | DSC | 2.46 | 448 | 1 |
| 137 | 200 | DSC | 2.56 | 474 | 1 |
| 138 | — | — | 2.57 | 474 | 1 |
| 139 | — | — | 2.08 | 510 | 1 |
| 140 | — | — | 2.64 | 474 | 1 |
| 141 | — | — | 2.57 | 518 | 1 |
| 142 | — | — | 2.46 | 474 | 1 |
| 143 | — | — | 2.79 | 472 | 1 |
| 144 | — | — | 2.19 | 475 | 1 |
| 145 | 182 | K | 3.06 | 421 | 1 |
| 146 | 135 | DSC | 2.35 | 486 | 1 |
| 147 | >260 | K | 2.75 | 473 | 2 |
| 148 | 154 | K | 2.66 | 502 | 1 |
| 149 | 146 | K | 2.56 | 502 | 2 |
| 150 | 171 | DSC | 2.40 | 474 | 1 |
| 151 | 114 | DSC | 2.63 | 502 | 1 |
| 152 | 140 | K | 2.63 | 502 | 1 |
| 153 | 180 | DSC | 2.84 | 490 | 1 |
| 154 | 185 | K | 2.84 | 490 | 1 |
| 155 | 220 | MP50 | 2.61 | 504 | 6 |
| 156 | 245 | DSC | 2.10 | 403 | 1 |
| 157 | 173 | DSC | 3.19 | 532 | 1 |
| 158 | — | — | 0.76 | 405 | 7 |
| 159 | 179 | DSC | 2.80 | 487 | 1 |
| 160 | 189 | DSC | 2.50 | 473 | 2 |
| 161 | — | DSC | 3.37 | 459 | 1 |
| 162 | >260 | K | 2.43 | 403 | 1 |
| 163 | — | DSC | 1.96 | 374 | 1 |
| 164 | 121 | WRS-2A | 2.09 | 470 | 8 |
| 165 | — | — | 4.32 | 430 | 9 |
| 166 | 150 | K | 2.00 | 499 | 1 |
| 167 | 263 | DSC | 2.29 | 387 | 1 |
| 168 | 260 | DSC | 2.83 | 417 | 1 |
| 169 | >260 | K | 1.98 | 403 | 1 |
| 170 | 279 | DSC | 2.54 | 398 | 1 |
| 171 | — | — | 2.50 | 504 | 6 |
| 172 | — | — | 2.25 | 500 | 1 |
| 173 | 225 | DSC | 2.28 | 457 | 2 |
| 174 | 199 | DSC | 2.72 | 487 | 2 |
| 175 | — | — | 2.72 | 512 | 6 |
| 176 | — | — | 3.07 | 526 | 1 |
| 177 | 115 | DSC | 2.39 | 445 | 2 |
| 178 | — | — | 0.84 | 450 | 10 |
| 179 | — | — | 5.19 | 490 | 10 |
| 180 | 143-145 | WRS-2A | 5.67 | 490 | 10 |
| 181 | — | — | 4.63 | 390 | 11 |
| 182 | 156 | K | 2.24 | 456 | 1 |
| 183 | 209 | DSC | 3.14 | 457 | 1 |
| 1i | 149 | K | 2.48 | 490 | 1 |
| 2i | 135 | K | 2.69 | 530 | 1 |
| 3i | 252 | DSC | 2.49 | 506 | 1 |
| 4i | 235 | DSC | 2.30 | 483 | 1 |
| 5i | — | — | 2.94 | 457 | 1 |
| 6i | 194 | DSC | 2.47 | 509 | 1 |
| 7i | — | — | 2.39 | 502 | 1 |
| 8i | >250 | K | 2.11 | 375 | 1 |
| 9i | 313 | DSC | 2.41 | 403 | 1 |
| 10i | 192 | DSC | 2.50 | 447 | 1 |
| 11i | 299 | DSC | 2.38 | 494 | 1 |
| 12i | 198 | DSC | 2.49 | 480 | 1 |
| 13i | 306 | DSC | 2.58 | 423 | 1 |
| 14i | — | — | 2.72 | 467 | 1 |
| 15i | 295 | DSC | 2.56 | 423 | 1 |
| 16i | 232 | DSC | 2.14 | 529 | 1 |
| 17i | 190 | K | 2.64 | 508 | 1 |
| 18i | 208 | DSC | 2.57 | 516 | 1 |
| 19i | 148 (gum) | K | 2.20 | 515 | 1 |
| 20i | 287 | DSC | 2.46 | 516 | 1 |
| 21i | Decomposition at 250° C. | WRS-2A | 3.72 | 526 | 8 |
| 22i | 138 (gum) | K | 2.57 | 516 | 1 |
| 23i | 136 (gum) | K | 2.57 | 516 | 1 |
| 24i | 120 (gum) | K | 3.19 | 600 | 2 |
| 25i | — | — | 4.33 | 486 | 8 |
| 26i | n.d. | | 2.27 | 502 | 2 |
| 27i | 197 206 | DSC K | 3.00 | 474 | 1 |
| 28i | 235 | K | 2.92 | 478 | 2 |
| 29i | 129 | DSC | 2.39 | 473 | 2 |
| 30i | 276 | WRS-2A | 4.52 | 404 | 8 |
| 31i | >250 | K | 2.00 | 449 | 1 |

NMR

The NMR experiments were carried out using a Bruker Avance 500 III using internal deuterium lock and equipped with reverse triple-resonance ($^1$H, $^{13}$C, $^{15}$N TXI) probe head or using a Bruker Avance DRX 400 spectrometer at ambient temperature, using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J values are expressed in Hz.

Compound 3:

$^1$H NMR (400 MHz, DMSO-$d_6$): δ 8.78 (d, J=2.0 Hz, 1H), 8.51 (d, J=5.0 Hz, 1H), 8.29 (s, 1H), 8.14 (d, J=1.5 Hz, 1H), 7.99 (d, J=1.0 Hz, 1H), 7.84 (d, J=2.5 Hz, 1H), 7.45-7.50 (m, 2H), 4.99 (t, J=5.3 Hz, 1H), 3.98 (s, 3H), 3.71 (d, J=10.1 Hz, 1H), 3.47 (dd, J=10.6 Hz, 5.6 Hz, 1H), 3.40 (dd, J=10.6 Hz, 5.6 Hz, 1H), 3.32-3.32 (m, 1H, partially obscured by solvent peak), 1.30 (s, 3H).

Compound 4:

$^1$H NMR (400 MHz, DMSO-$d_6$): δ 9.00 (s, 1H), 8.43 (d, J=5.0 Hz, 1H), 8.36 (d, J=2.0 Hz, 1H), 8.22 (d, J=2.5 Hz, 1H), 8.08 (d, J=1.5 Hz, 1H), 7.92 (d, J=1.0 Hz, 1H), 7.43 (s, 1H), 7.40 (d, J=5.1 Hz, 1H), 4.98 (t, J=5.3 Hz, 1H), 3.70 (d, J=10.1 Hz, 1H), 3.43 (dd, J=10.6 Hz, 5.1 Hz, 1H), 3.36 (dd, J=10.6 Hz, 5.6 Hz, 1H), 3.29 (d, J=10.6 Hz, 1H, partially obscured by solvent peak), 2.50 (s, 3H, obscured by solvent peak), 1.27 (s, 3H).

Compound 6:

$^1$H NMR (500 MHz, DMSO-$d_6$): δ 8.50 (dd, J=7.6 Hz, 1.6 Hz, 1H), 8.43 (d, J=5.4 Hz, 1H), 8.18 (s, 1H), 8.11 (d, J=1.6 Hz, 1H), 7.99 (d, J=1.3 Hz, 1H), 7.83 (dd, J=4.9 Hz, 1.7 Hz, 1H), 7.43 (s, 1H), 7.39 (d, J=5.4 Hz, 1H), 7.01 (dd, J=7.7 Hz, 4.9 Hz, 1H), 5.02 (t, J=5.2 Hz, 1H), 3.95 (s, 3H), 3.68 (d, J=9.8 Hz, 1H), 3.45 (dd, J=10.4 Hz, 5.0 Hz, 1H), 3.39 (dd, J=10.4 Hz, 5.3 Hz, 1H), 3.30 (d, J=9.8 Hz, 1H), 1.29 (s, 3H).

Compound 10:

$^1$H NMR (500 MHz, DMSO-$d_6$): δ 8.30 (d, J=5.4 Hz, 1H), 8.11 (s, 1H), 8.04 (s, 1H), 7.98 (br s, 1H), 7.91 (s, 1H), 7.38 (s, 1H), 7.23 (d, J=5.4 Hz, 1H), 6.18 (t, J=5.0 Hz, 1H), 4.99 (t, J=4.9 Hz, 1H), 3.85 (s, 3H), 3.69 (d, J=9.8 Hz, 1H), 3.49-3.60 (m, 4H), 3.44 (dd, J=10.4 Hz, 4.7 Hz, 1H), 3.34-3.38 (m, 1H, partially obscured by solvent peak), 3.25-3.32 (m, 4H), 1.27 (s, 3H).

Compound 103:

$^1$H NMR (500 MHz, DMSO-$d_6$): δ 8.52 (d, J=3.8 Hz, 1H), 8.33-8.41 (m, 2H), 7.94 (s, 1H), 7.89 (s, 1H), 7.84 (d, J=4.1 Hz, 1H), 7.59 (s, 1H), 7.00 (dd, J=7.4 Hz, 5.2 Hz, 1H), 5.05 (t, J=5.2 Hz, 1H), 3.94 (s, 3H), 3.67 (d, J=9.8 Hz, 1H), 3.41-3.47 (m, 1H), 3.35-3.39 (m, 1H, partially obscured by solvent peak), 3.34-3.38 (m, 1H, partially obscured by solvent peak), 1.27 (s, 3H).

Compound 33:
¹H NMR (500 MHz, DMSO-d₆): δ 8.55 (dd, J=7.9 Hz, 1.6 Hz, 1H), 8.45 (d, J=5.4 Hz, 1H), 8.10 (d, J=1.6 Hz, 1H), 8.07 (s, 1H), 7.98 (d, J=1.3 Hz, 1H), 7.80 (dd, J=4.7 Hz, 1.6 Hz, 1H), 7.44 (s, 1H), 7.41 (d, J=5.7 Hz, 1H), 7.02 (dd, J=7.7 Hz, 4.9 Hz, 1H), 5.03 (t, J=5.4 Hz, 1H), 4.49 (t, J=4.7 Hz, 2H), 3.72 (t, J=4.7 Hz, 2H), 3.67 (d, J=9.8 Hz, 1H), 3.44 (dd, J=10.7 Hz, 5.3 Hz, 1H), 3.39 (dd, J=10.4 Hz, 5.3 Hz, 1H), 3.29-3.32 (m, 4H), 1.29 (s, 3H).

Compound 115:
¹H NMR (500 MHz, DMSO-d₆): δ 8.51 (d, J=7.6 Hz, 1H), 8.45 (d, J=5.4 Hz, 1H), 8.20 (s, 1H), 8.13 (s, 1H), 8.02 (s, 1H), 7.97 (t, J=6.1 Hz, 1H), 7.82 (dd, J=4.7 Hz, 1.2 Hz, 1H), 7.46 (s, 1H), 7.41 (d, J=5.4 Hz, 1H), 7.03 (dd, J=7.9 Hz, 5.0 Hz, 1H), 3.96 (s, 3H), 3.64 (d, J=10.1 Hz, 1H), 3.34 (dd, J=13.6 Hz, 6.9 Hz, 1H), 3.28 (d, J=10.1 Hz, 1H), 3.21 (dd, J=13.6, 5.6 Hz, 1H), 1.81 (s, 3H), 1.28 (s, 3H).

Compound 50:
¹H NMR (500 MHz, DMSO-d₆): δ 9.16 (s, 1H), 8.61 (s, 2H), 8.43 (d, J=5.4 Hz, 1H), 8.08 (d, J=1.9 Hz, 1H), 7.92 (d, J=1.6 Hz, 1H), 7.44 (s, 1H), 7.42 (d, J=5.4 Hz, 1H), 4.98 (t, J=5.4 Hz, 1H), 3.69 (d, J=9.5 Hz, 1H), 3.44 (dd, J=10.7 Hz, 5.3 Hz, 1H), 3.34-3.39 (m, 1H, partially obscured by solvent peak), 3.29 (d, J=9.5 Hz, 1H), 2.60 (s, 3H), 1.27 (s, 3H).

Compound 59:
¹H NMR (500 MHz, DMSO-d₆): δ 8.43-8.48 (m, 2H), 8.12 (s, 1H), 8.06 (s, 1H), 7.99 (s, 1H), 7.63 (s, 1H), 7.45 (s, 1H), 7.40 (d, J=5.4 Hz, 1H), 5.02 (br s, 1H), 3.92 (s, 3H), 3.68 (d, J=10.1 Hz, 1H), 3.43-3.48 (m, 1H), 3.36-3.39 (m, 1H), 3.33-3.38 (m, 1H, partially obscured by solvent peak), 2.28 (s, 3H), 1.29 (s, 3H).

Compound 65:
¹H NMR (500 MHz, DMSO-d₆): δ 9.15 (s, 1H), 8.68 (d, J=1.9 Hz, 1H), 8.58 (d, J=1.9 Hz, 1H), 8.41 (d, J=5.7 Hz, 1H), 8.07 (d, J=1.9 Hz, 1H), 7.91 (d, J=1.6 Hz, 1H), 7.43 (s, 1H), 7.40 (d, J=5.4 Hz, 1H), 4.97 (t, J=5.4 Hz, 1H), 3.69 (d, J=9.8 Hz, 1H), 3.44 (dd, J=10.7 Hz, 5.3 Hz, 1H), 3.33-3.38 (m, 3H, partially obscured by solvent peak), 3.29 (d, J=9.5 Hz, 1H), 3.20 (s, 3H), 2.97 (t, J=7.4 Hz, 2H), 1.93 (q, J=6.6 Hz, 2H) 1.27 (s, 3H).

Compound 93:
¹H NMR (400 MHz, DMSO-d₆): δ 8.98 (s, 1H), 8.64 (s, 1H), 8.49-8.58 (m, 2H), 8.39 (d, J=5.6 Hz, 1H), 8.04 (s, 1H), 7.90 (s, 1H), 7.32-7.38 (m, 2H), 4.91 (t, J=5.3 Hz, 1H), 3.70 (d, J=10.1 Hz, 1H), 3.42 (dd, J=13.2 Hz, 6.3 Hz, 1H), 3.33-3.37 (m, 1H, partially obscured by solvent peak), 3.20-3.32 (m, 1H, partially obscured by solvent peak), 2.80 (d, J=4.0 Hz, 3H), 2.52 (s, 3H), 1.24 (s, 3H).

Compound 124:
¹H NMR (500 MHz, DMSO-d₆): δ 8.97 (s, 1H), 8.63 (br s, 2H), 8.21 (s, 1H), 8.01 (s, 1H), 7.65 (d, J=4.4 Hz, 1H), 7.57 (s, 1H), 5.02 (br s, 1H), 4.13 (s, 3H), 3.72 (d, J=9.5 Hz, 1H), 3.30-3.47 (m, 3H, partially obscured by solvent peak), 1.31 (s, 3H).

Compound 140:
¹H NMR (500 MHz, DMSO-d₆) δ ppm 8.92 (s, 1H) 8.55 (s, 1H) 8.39 (d, J=5.4 Hz, 1H) 8.07 (d, J=1.3 Hz, 1H) 7.92 (s, 1H) 7.42 (s, 1H) 7.35 (d, J=5.4 Hz, 1H) 5.00 (t, J=5.4 Hz, 1H) 3.89-4.01 (m, 5H) 3.69 (d, J=9.8 Hz, 1H) 3.40-3.54 (m, 3H) 3.35-3.40 (m, 1H) 3.30 (d, J=9.8 Hz, 1H) 2.89-3.05 (m, 1H) 1.78-1.95 (m, 4H) 1.27 (s, 3H).

Compound 4i:
¹H NMR (400 MHz, DMSO-d₆): δ 8.49 (d, J=5.6 Hz, 1H), 8.36 (d, J=2.0 Hz, 1H), 8.21 (s, 1H), 8.12 (d, J=1.5 Hz, 1H), 8.02 (d, J=1.5 Hz, 1H), 7.43-7.46 (m, 2H), 7.14 (s, 1H), 7.11 (s, 1H), 6.81 (d, J=1.0 Hz, 1H), 5.21 (s, 2H), 5.00 (t, J=5.6 Hz, 1H), 3.73 (s, 3H), 3.69 (d, J=10.1 Hz, 1H), 3.46 (dd, J=10.6 Hz, J=5.6 Hz, 1H), 3.39 (dd, J=10.6 Hz, J=5.6 Hz, 1H), 3.37-3.44 (m, 1H, partially obscured by solvent peak), 2.14 (s, 3H), 1.30 (s, 3H).

Compound 7i:
¹H NMR (400 MHz, DMSO-d₆): δ 8.49 (d, J=5.0 Hz, 1H), 8.36 (d, J=2.2 Hz, 1H), 8.23 (s, 1H), 8.13 (d, J=2.2 Hz, 1H), 8.03 (d, J=1.6 Hz, 1H), 7.41-7.48 (m, 2H), 7.13 (s, 1H), 5.00 (t, J=5.3 Hz, 1H), 4.03-4.11 (m, 2H), 3.69 (d, J=10.1 Hz, 1H), 3.55 (t, J=4.4 Hz, 4H), 3.47 (dd, J=10.6 Hz, J=5.0 Hz, 1H) 3.40 (dd, J=10.6 Hz, J=5.0 Hz, 1H), 3.37-3.44 (m, 1H, partially obscured by solvent peak), 2.60 (t, J=6.5 Hz, 2H), 2.41-2.48 (m, 4H), 2.14 (s, 3H), 1.31 (s, 3H).

Compound 13i:
¹H NMR (400 MHz, DMSO-d₆): δ 8.54 (d, J=5.6 Hz, 1H), 8.51 (d, J=2.5 Hz, 1H), 8.28 (s, 1H), 8.13 (s, 1H), 8.00 (s, 1H), 7.62 (d, J=2.5 Hz, 1H), 7.51 (d, J=5.6 Hz, 1H), 7.48 (s, 1H), 4.98 (t, J=5.3 Hz, 1H), 3.72 (d, J=10.1 Hz, 1H), 3.55 (s, 3H), 3.45 (dd, J=10.6 Hz, J=5.6 Hz, 1H) 3.40 (dd, J=10.6 Hz, J=5.6 Hz, 1H), 3.33-3.38 (m, 1H, partially obscured by solvent peak), 1.31 (s, 3H).

OR

Optical Rotation is measured with a polarimeter such as e.g. 341 Perkin Elmer, an Autopol IV automatic polarimeter (Rodolph research analytical) or a P-2000 (Jasco).

$$[\alpha]^\theta_\lambda = (100 * \alpha)/(c*1)$$

Specific rotation (OR):

α (measured rotation) is the angle through which plane polarized light is rotated by a solution of mass concentration c and path length 1. Concentration is in grams per 100 mL; path length 1 is in decimeters and is 1.000 decimeter.

θ is the temperature (° C.) and λ the wavelength of the light used.

Unless otherwise indicated, temperature is 20° C., and the sodium D line is used (589 nanometer).

| N° | OR (°) | Concentration (g/100 mL) |
|---|---|---|
| 6 | +19.53 | 0.292 |
| 7 | −20.03 | 0.314 |
| 11 | −26.6 | 0.222 |
| 14 | +34.19 | 0.31 |
| 19 | +18.92 | 0.227 |
| 20 | +13.64 | 0.22 |
| 21 | +34 | 0.25 |
| 22 | +28.4 | 0.25 |
| 23 | +16.15 | 0.26 |
| 24 | +12 | 0.25 |
| 25 | +35.17 | 0.29 |
| 26 | −5.19 | 0.27 |
| 27 | +33.67 | 0.3 |
| 28 | +35.38 | 0.26 |
| 29 | +16.72 | 0.227 |
| 30 | +35.44 | 0.245 |
| 33 | +18.65 | 0.252 |
| 34 | −17.22 | 0.331 |
| 35 | +32.53 | 0.289 |
| 36 | +22 | 0.25 |
| 37 | +21.86 | 0.247 |
| 38 | +27.72 | 0.227 |
| 39 | +33.52 | 0.254 |
| 42 | +29.63 | 0.27 |
| 43 | +47.6 | 0.25 |
| 44 | +18.45 | 0.206 |
| 45 | +15.47 | 0.278 |
| 46 | +6.27 | 0.239 |
| 47 | +11.6 | 0.25 |
| 48 | +21.88 | 0.288 |
| 49 | +14.9 | 0.255 |
| 50 | +38.97 | 0.29 |
| 51 | +13.6 | 0.25 |
| 52 | +25.91 | 0.22 |

| N° | OR (°) | Concentration (g/100 mL) |
|---|---|---|
| 53 | +8.42 | 0.285 |
| 54 | +10.31 | 0.291 |
| 55 | +9.6 | 0.25 |
| 56 | +43.33 | 0.3 |
| 57 | +9.63 | 0.27 |
| 58 | +18.08 | 0.26 |
| 59 | +20.48 | 0.293 |
| 60 | +5.93 | 0.27 |
| 61 | +17.27 | 0.249 |
| 62 | +20.77 | 0.284 |
| 63 | +40.39 | 0.255 |
| 64 | +30.74 | 0.244 |
| 65 | +24.71 | 0.263 |
| 66 | +36.12 | 0.263 |
| 67 | +16.96 | 0.283 |
| 68 | +12.93 | 0.224 |
| 69 | +19.86 | 0.252 |
| 72 | +13.96 | 0.251 |
| 73 | +20.87 | 0.288 |
| 74 | +53.77 | 0.208 |
| 75 | +46.8 | 0.25 |
| 76 | +42.31 | 0.26 |
| 77 | +57.87 | 0.233 |
| 78 | +37.69 | 0.26 |
| 80 | +10.87 | 0.23 |
| 81 | +16.94 | 0.213 |
| 86 | +16.8 | 0.25 |
| 87 | +11.54 | 0.39 |
| 88 | +17.18 | 0.39 |
| 89 | +11.76 | 0.34 |
| 90 | +16.77 | 0.31 |
| 91 | +24.33 | 0.3 |
| 93 | +16.67 | 0.258 |
| 96 | +13.33 | 0.33 |
| 103 | +18.72 | 0.262 |
| 104 | +9.2 | 0.25 |
| 109 | −50.55 | 0.275 |
| 122 | +39.16 | 0.227 |
| 129 | +25.54 | 0.255 |
| 132 | +8.4 | 0.25 |
| 133 | +13.64 | 0.33 |
| 134 | +11 | 0.227 |
| 135 | +12.96 | 0.27 |
| 136 | +21.59 | 0.245 |
| 137 | +8.01 | 0.237 |
| 138 | +31.25 | 0.256 |
| 139 | +18 | 0.25 |
| 140 | +19.67 | 0.3 |
| 141 | +18.93 | 0.28 |
| 142 | +16.98 | 0.265 |
| 143 | +26.07 | 0.28 |
| 144 | +14.29 | 0.28 |
| 145 | +39.16 | 0.227 |
| 146 | +14.29 | 0.28 |
| 147 | +18.64 | 0.279 |
| 148 | +38.46 | 0.26 |
| 149 | −8.76 | 0.251 |
| 150 | +19.16 | 0.308 |
| 151 | +20.23 | 0.262 |
| 152 | +14.7 | 0.279 |
| 153 | +41.42 | 0.268 |
| 154 | −6.45 | 0.248 |
| 156 | +16.54 | 0.254 |
| 157 | +18 | 0.25 |
| 159 | +13.39 | 0.254 |
| 160 | +15.2 | 0.25 |
| 161 | +11.59 | 0.276 |
| 163 | +11.88 | 0.227 |
| 164 | +5.55 | 0.108 (MeOH) |
| 165 | +94.67 | 0.072 (MeOH) |
| 167 | +13.01 | 0.269 |
| 168 | +8.09 | 0.346 |
| 169 | +24.92 | 0.301 |
| 170 | +55.71 | 0.28 |
| 173 | +4.62 | 0.26 |
| 174 | +14.71 | 0.272 |
| 176 | +15.83 | 0.24 |
| 177 | +9.57 | 0.282 |
| 181 | +3.53 | 0.17 (MeOH, 26.6° C.) |
| 182 | +17.52 | 0.274 |
| 1i | +21.89 | 0.37 |
| 2i | +20.37 | 0.324 |
| 3i | +22.86 | 0.28 |
| 4i | +16.95 | 0.218 |
| 5i | +22.63 | 0.234 |
| 6i | +13.05 | 0.237 |
| 7i | +19.42 | 0.232 |
| 8i | +14.81 | 0.27 |
| 9i | +17.92 | 0.24 |
| 10i | +13.08 | 0.26 |
| 11i | +32 | 0.25 |
| 12i | +25 | 0.28 |
| 13i | +39.62 | 0.26 |
| 14i | +30.35 | 0.264 |
| 16i | +20 | 0.265 |
| 17i | +16.98 | 0.265 |
| 19i | +16.67 | 0.27 |
| 20i | +13.96 | 0.265 |
| 22i | +38.52 | 0.27 |
| 23i | −12.5 | 0.28 |
| 24i | +45.19 | 0.27 |
| 26i | +20.63 | 0.286 |
| 29i | +22.9 | 0.262 |
| 30i | +6.50 | 0.123 (24.4° C.) |

OR data:
Solvent: DMF (unless otherwise indicated);
temperature: 20° C. (unless otherwise indicated);
wavelength: 589 nm; 'Conc.' means concentration of the sample in grams per 100 mL;
'OR' means optical rotation (specific rotation);
'Co. No.' means compound number SFC-MS Method The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE

Analytical SFC-MS Methods (flow expressed in mL/min; column temperature (T) expressed in ° C.; run time expressed in minutes, backpressure (BPR) expressed in bars)

| Method | column | mobile phase | gradient | Flow Col T | Run time BPR |
|---|---|---|---|---|---|
| Method 1 | Chiralpak® AS-3 column (3 μm, 100 × 4.6 mm) | A: $CO_2$ B: iPrOH (0.3% $iPrNH_2$) | 30% B hold 3 min, | 3.5 35 | 3 103 |

TABLE

Analytical SFC data ($R_t$ means retention time (in minutes), [M + H]$^+$ means the protonated mass of the compound, method refers to the method used for SFC-MS analysis of enantiomerically pure compounds).

| Compound number | Rt | [M + H]$^+$ | Chiral purity UV Area % | Method |
|---|---|---|---|---|
| 55 | 1.29 | 520 | 100.00 | 1 |
| 56 | 1.77 | 520 | 100.00 | 1 |

Pharmacological Part
Biological assay A
Inhibition of auto-phosphorylation of recombinant human NF-kappaB-inducing Kinase (NIK/MAP3K14) Activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM $Na_3VO_4$, 5 mM $MgCl_2$, 0.01% Tween® 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and $IC_{50}$'s were determined by fitting a sigmoidal curve to % inhibition of control versus $Log_{10}$ compound concentration.

Biological Assay B
Effect of Compounds on P-IKKα Levels in L363 (NIK Translocated Multiple Myeloma) Cells All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of $0.2 \times 10^6$ cells per ml-$1 \times 10^6$ cells per ml at 37° C. in a humidified 5% $CO_2$ atmosphere. Cells were passaged twice a week splitting back to obtain the low density. Cells were seeded in 96 well plates (Nunc 167008) at $2 \times 10^6$ per ml media in a volume of 75 µl per well plus 25 µl 1 µg/ml recombinant human B-cell activating factor (BAFF/BLyS/TNFSF13B). Seeded cells were incubated at 37° C. in a humidified 5% $CO_2$ atmosphere for 24 hr. Drugs and/or solvents were added (20 µl) to a final volume of 120 µl. Following 2 hr treatment plates were removed from the incubator and cell lysis was achieved by the addition of 30 µl 5x lysis buffer followed by shaking on a plate shaker at 4° C. for 10 min. At the end of this incubation lysed cells were centrifuged at 800×g for 20 min at 4° C. and the lysate was assessed for P-IKK levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 µM ADS 125117, a test concentration known to give full inhibition) were run in parallel. The blank incubation value was subtracted from all control and sample values. To determine the $IC_{50}$ a sigmoidal curve was fitted to the plot of % inhibition of control P-IKKα levels versus $Log_{10}$ compound concentration.

Biological Assay C
Determination of Antiproliferative Activity on JJN-3 (NIK Translocated) and KMS12-BM (NIK WT) Multiple Myeloma Cells All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human JJN-3 and KMS12-BM cells (DSMZ) were cultured in RPMI 1640 medium supplemented with 2 mM L-glutamine, and 10% fetal calf serum (PAA). Cells were routinely kept as suspension cells at 37° C. in a humidified 5% $CO_2$ atmosphere. Cells were passaged at a seeding density of $0.2 \times 10^6$/ml twice a week. Cells were seeded in black tissue culture treated 96-well plates (Perkin Elmer). Densities used for plating ranged from 15000 (JJN3) to 20000 (KMS12BM) cells per well in a total volume of 135 µl medium. Drugs and/or solvents were added (15 µl) to a final volume of 150 µl. Following 96 hr of treatment, plates were removed from the incubator and allowed to equilibrate to room temperature for approx 10 min. 75 µl CellTiter-Glo reagent was added to each well that was then covered (Perkin Elmer Topseal) and shaken on plate shaker for 10 min. Luminescence was measured on a HTS Topcount (Perkin Elmer). Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds of the invention in the above assays are provided in Table A (the values in Table are averaged values over all measurements on all batches of a compound; 'n.c.' means not calculated)

TABLE A

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
|---|---|---|---|---|
| 1 | n.c. | 81.3 | ~2692 | 79 |
| 2 | 13.2 | 21.4 | >10000 | 74 |
| 3 | 8.3 | n.c. | >10000 | 81 |
| 4 | 3.6 | n.c. | ~7413 | 97 |
| 5 | ~8.51 | n.c. | >10000 | 170 |
| 6 | 2.4 | n.c. | >10000 | ~245 |
| 7 | 15.5 | n.c. | >10000 | 1585 |
| 9 | 5.3 | n.c. | 427 | 219 |
| 10 | 8.5 | n.c. | >10000 | 58 |
| 11 | 10.5 | n.c. | >10000 | ~347 |
| 12 | 12.9 | n.c. | >10000 | 589 |
| 13 | 28.8 | n.c. | >10000 | 447 |
| 14 | 5.5 | n.c. | >10000 | 372 |
| 15 | 2.9 | n.c. | >10000 | 24 |
| 16 | 3.8 | n.c. | >10000 | 245 |
| 17 | 2.5 | n.c. | >10000 | 288 |

TABLE A-continued

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
|---|---|---|---|---|
| 18 | 9.1 | n.c. | >10000 | 776 |
| 19 | 14.5 | n.c. | >10000 | 912 |
| 20 | 0.9 | n.c. | >10000 | 1585 |
| 21 | 22.4 | n.c. | >10000 | 813 |
| 22 | 10.2 | n.c. | >10000 | 417 |
| 23 | 4.9 | n.c. | 7413 | 708 |
| 24 | 123.0 | n.c. | >10000 | 6918 |
| 25 | 6.2 | n.c. | >10000 | 1479 |
| 26 | 4.1 | n.c. | >10000 | 794 |
| 27 | 3.6 | n.c. | 7413 | 1514 |
| 28 | 3.2 | n.c. | 3090 | 813 |
| 29 | 6.6 | n.c. | 7244 | 1549 |
| 30 | 51.3 | n.c. | >10000 | 1259 |
| 31 | 9.8 | n.c. | >10000 | 1995 |
| 32 | 6.5 | n.c. | 437 | 89 |
| 33 | 4.2 | n.c. | >10000 | 298 |
| 34 | 38.0 | n.c. | >10000 | 2884 |
| 35 | 15.9 | n.c. | >10000 | 794 |
| 36 | 3.3 | n.c. | >10000 | 288 |
| 37 | 1.8 | n.c. | >10000 | 3467 |
| 38 | 19.5 | n.c. | >10000 | 79 |
| 39 | 8.5 | n.c. | >10000 | 324 |
| 40 | 16.6 | n.c. | 3802 | 550 |
| 42 | 6.2 | n.c. | >10000 | 347 |
| 43 | 4.0 | n.c. | >10000 | 115 |
| 44 | 9.3 | n.c. | >10000 | 81 |
| 45 | 9.1 | n.c. | >10000 | 195 |
| 46 | 3.0 | 4.7 | ~7943 | 28 |
| 47 | 13.2 | n.c. | >10000 | 1122 |
| 48 | 2.9 | 1.2 | >10000 | ~295 |
| 49 | 1.6 | 0.8 | ~9333 | 35 |
| 50 | 1.3 | 4.2 | 6607 | 145 |
| 51 | 3.0 | 2.8 | >10000 | 31 |
| 52 | ~1.48 | 0.7 | 871 | 251 |
| 53 | 95.5 | n.c. | >10000 | 3467 |
| 54 | 39.8 | n.c. | >10000 | 4074 |
| 55 | 3.8 | 67.6 | 1349 | 69 |
| 56 | 3.5 | ~7244 | ~148 | 7 |
| 57 | 4.3 | 13.8 | ~8128 | 316 |
| 58 | 6.9 | ~17 | >10000 | 200 |
| 59 | 2.5 | 13.2 | >10000 | 16 |
| 60 | 7.2 | 70.8 | >10000 | 708 |
| 61 | 3.0 | 19.5 | >10000 | 389 |
| 62 | 29.5 | n.c. | >10000 | 977 |
| 63 | 2.9 | 17.4 | >10000 | 98 |
| 64 | 4.7 | 27.5 | 6457 | 35 |
| 65 | 4.5 | 15.5 | >10000 | 263 |
| 66 | 3.3 | ~141 | >10000 | 41 |
| 67 | 12.3 | 186.2 | >10000 | 204 |
| 68 | 3.9 | ~20 | 5129 | 98 |
| 69 | 3.2 | ~129 | >10000 | 263 |
| 72 | 25.1 | 66.1 | >10000 | 1047 |
| 73 | 1.6 | ~13 | ~234 | 144 |
| 74 | 16.2 | ~120 | >10000 | 141 |
| 75 | 9.8 | 18.2 | >10000 | >10000 |
| 76 | 5.1 | 26.9 | >10000 | >10000 |
| 77 | 5.0 | 25.7 | >10000 | 60 |
| 78 | 4.7 | 28.2 | >10000 | 589 |
| 80 | 3.7 | 38.9 | >10000 | 525 |
| 81 | 4.7 | 20.9 | >10000 | 513 |
| 84 | 5.6 | 11.8 | >10000 | 4677 |
| 85 | 2.5 | 3.0 | >10000 | 372 |
| 86 | 12.0 | 53.7 | >10000 | 1175 |
| 87 | 3.8 | 27.5 | >10000 | 427 |
| 88 | 4.2 | 22.4 | >10000 | 148 |
| 89 | 3.6 | 14.8 | >10000 | 912 |
| 90 | 1.9 | 32.4 | >10000 | 5888 |
| 91 | 8.9 | 5.4 | >10000 | 81 |
| 93 | 2.1 | 5.6 | 9550 | 1445 |
| 96 | 2.2 | 1.1 | >10000 | 65 |
| 97 | 9.8 | 42.7 | >10000 | 1820 |
| 98 | 50.1 | 45.7 | >10000 | 832 |
| 99 | 123.0 | 275.4 | >10000 | 708 |
| 101 | 2.2 | n.c. | 2455 | 204 |
| 102 | 6.5 | n.c. | >10000 | 1585 |
| 103 | 1.0 | n.c. | 1585 | 120 |
| 104 | 11.2 | n.c. | >10000 | 112 |
| 105 | 30.9 | n.c. | ~3715 | 2239 |
| 106 | 3.4 | n.c. | 2630 | 275 |
| 107 | 4.8 | n.c. | 562 | 309 |
| 108 | 25.1 | n.c. | ~3981 | 2138 |
| 109 | 38.0 | n.c. | >10000 | 794 |
| 110 | 33.9 | n.c. | >10000 | 1862 |
| 111 | 14.8 | n.c. | 3163 | 669 |
| 112 | 22.9 | n.c. | >10000 | 1820 |
| 113 | 34.7 | n.c. | >10000 | 5754 |
| 114 | 32.4 | n.c. | >10000 | 3548 |
| 115 | 10.0 | n.c. | 6310 | 741 |
| 116 | 85.1 | n.c. | >10000 | 2042 |
| 117 | 45.7 | n.c. | >10000 | >10000 |
| 118 | 64.6 | n.c. | 4074 | 4571 |
| 119 | 128.8 | n.c. | 1995 | 1288 |
| 120 | 79.4 | n.c. | 1230 | 631 |
| 121 | 117.5 | n.c. | 2512 | 1413 |
| 122 | 9.5 | n.c. | 4786 | 478 |
| 124 | 3.8 | n.c. | >10000 | ~144 |
| 125 | 9.8 | n.c. | 891 | 166 |
| 126 | 147.9 | n.c. | >10000 | 2512 |
| 127 | 4.5 | n.c. | >10000 | ~7079 |
| 128 | 6.3 | n.c. | ~194.98 | 209 |
| 129 | 1.8 | n.c. | >10000 | 562 |
| 130 | 4.6 | n.c. | >10000 | 468 |
| 131 | 10.2 | n.c. | 4266 | 1318 |
| 132 | 12.9 | n.c. | >10000 | 3311 |
| 133 | 22.9 | n.c. | >10000 | ~1949 |
| 134 | 38.9 | n.c. | >10000 | >10000 |
| 135 | n.c. | n.c. | n.c. | n.c. |
| 136 | 18.2 | n.c. | >10000 | 1995 |
| 137 | 16.2 | n.c. | >10000 | 525 |
| 138 | 29.5 | n.c. | >10000 | 1514 |
| 139 | 17.8 | n.c. | >10000 | ~10000 |
| 140 | 4.8 | 12.0 | >10000 | 427 |
| 141 | 18.6 | 354.8 | 4786 | 741 |
| 142 | 15.1 | n.c. | >10000 | 6310 |
| 143 | 7.8 | n.c. | >10000 | 347 |
| 144 | 24.0 | n.c. | >10000 | >10000 |
| 145 | 9.5 | n.c. | 4786 | 479 |
| 146 | 2.8 | 4.1 | 7079 | 5.2 |
| 147 | 7.9 | n.c. | n.c. | n.c. |
| 148 | 8.5 | 13.8 | >10000 | 135 |
| 149 | 8.9 | 7.8 | >10000 | 29 |
| 150 | 12.0 | 25.7 | >10000 | 132 |
| 151 | 5.5 | 13.8 | >10000 | 66 |
| 152 | 14.1 | 85.1 | n.c. | n.c. |
| 153 | 5.8 | 9.3 | ~5888 | 240 |
| 154 | 7.2 | 3.0 | ~7943 | 148 |
| 155 | 12.0 | 19.5 | ~2884 | 81 |
| 156 | 2.3 | 6.3 | ~6457 | 105 |
| 157 | 9.3 | 25.7 | >10000 | 62 |
| 158 | 1.6 | 2.3 | >10000 | 49 |
| 159 | 5.6 | 5.9 | >10000 | 89 |
| 160 | 3.9 | 2.1 | >10000 | 115 |
| 161 | 28.2 | 46.8 | >10000 | 417 |
| 162 | 3.0 | 1.3 | >10000 | 60 |
| 163 | 34.7 | n.c. | ~5012 | 3162 |
| 164 | 102.3 | 1175 | 1660 | 1175 |
| 165 | 1.3 | 6.2 | >10000 | 117 |
| 166 | 25.7 | 229.0 | n.c. | n.c. |
| 167 | 1.7 | 2.8 | >10000 | 30 |
| 168 | 3.0 | 2.4 | >10000 | 39 |
| 169 | 2.7 | 9.9 | 4898 | 263 |
| 170 | 1.1 | 1.0 | >10000 | 5 |
| 171 | 7.4 | 6.9 | >10000 | 12 |
| 172 | 4.1 | 3.9 | ~2188 | 26 |
| 173 | 15.1 | 69.2 | >10000 | 933 |
| 174 | 6.5 | 4.0 | n.c. | n.c. |
| 175 | 19.5 | n.c. | n.c. | n.c. |
| 176 | 4.8 | n.c. | n.c. | n.c. |

TABLE A-continued

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
|---|---|---|---|---|
| 177 | 5.5 | 21.4 | >10000 | 205 |
| 178 | 18.2 | 51.3 | n.c. | n.c. |
| 179 | 93.3 | 1445 | n.c. | n.c. |
| 180 | 338.8 | 616.6 | n.c. | n.c. |
| 181 | 5.2 | 25.1 | n.c. | n.c. |
| 182 | 15.1 | 109.6 | >10000 | 49 |
| 183 | 15.8 | 40.7 | >10000 | 63 |
| 1i | 1.1 | 2.6 | 3890 | 347 |
| 2i | 1.8 | 1.1 | 5495 | 479 |
| 3i | 1.3 | 3.3 | >10000 | ~1778 |
| 4i | 1.3 | 8.9 | >10000 | 316 |
| 5i | 4.5 | 15.8 | 5012 | 282 |
| 6i | 1.0 | 10.0 | 5129 | 275 |
| 7i | 1.2 | 3.7 | 9550 | 115 |
| 8i | 4.5 | 74.1 | >10000 | 776 |
| 9i | 1.0 | 8.5 | >10000 | 120 |
| 10i | 3.0 | n.c. | 4786 | 339 |
| 11i | 1.9 | 3.2 | >10000 | ~1122 |
| 12i | 1.1 | 0.9 | 813 | 18 |
| 13i | 1.9 | 0.9 | >10000 | 31 |
| 14i | 1.4 | n.c. | >10000 | 24 |
| 15i | 3.6 | n.c. | >10000 | ~427 |
| 16i | 1.2 | 11.0 | >10000 | 25 |
| 17i | 1.9 | 1.8 | >10000 | 33 |
| 18i | 0.9 | 4.9 | >10000 | 49 |
| 19i | 0.6 | 2.5 | >10000 | 25 |
| 20i | 2.3 | 1.5 | >10000 | 41 |
| 21i | 64.6 | 550 | n.c. | n.c. |
| 22i | 3.4 | 2.1 | 9120 | 33 |
| 23i | 2.3 | 2.9 | >10000 | 30 |
| 24i | 23.4 | 5.5 | >10000 | 32 |
| 25i | 1.7 | 9.5 | >10000 | 120 |
| 26i | 2.1 | 2.3 | >10000 | 28 |
| 27i | 5.8 | 13.8 | >10000 | 148 |
| 28i | 7.6 | 21.4 | n.c. | n.c. |
| 29i | 3.0 | 3.7 | >10000 | 100 |
| 30i | 4.6 | 14.5 | n.c. | n.c. |
| 31i | 3.3 | n.c. | >10000 | ~5012 |

Prophetic Composition Examples

"Active ingredient" (a.i.) as used throughout these examples relates to a compound of Formula (I), including any tautomer or stereoisomeric form thereof, or a pharmaceutically acceptable addition salt, or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

What is claimed is:
1. A compound of Formula (I):

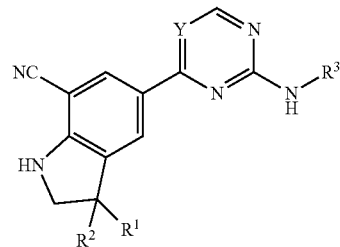

(I)

a tautomer or a stereoisomeric form thereof, wherein
$R^1$ represents $C_{1-4}$alkyl;
$R^2$ represents $C_{1-6}$alkyl, or $C_{1-6}$alkyl substituted with one $R^5$;
Y represents $CR^4$ or N;
$R^4$ represents hydrogen or halo;
$R^5$ represents $Het^{3a}$, —$NR^{6a}R^{6b}$, or —$OR^7$;
$R^{6a}$ represents or $C_{1-4}$alkyl;
$R^{6b}$ represents $C_{1-4}$alkyl; $C_{3-6}$cycloalkyl; —C(=O)—$C_{1-4}$alkyl; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, or —$C_{1-4}$alkyl-$Het^{3b}$;
$R^{8a}$ represents hydrogen;
$R^{8b}$ represents $C_{1-4}$alkyl, or $C_{3-6}$cycloalkyl;
$R^9$ represents $C_{1-6}$alkyl, or $C_{1-6}$alkyl substituted with one;
$R^3$ represents a 6-membered heteroaromatic ring containing 1 or 2 N-atoms, optionally substituted with one, two or three substituents each independently selected from the group consisting of halo; cyano; $C_{1-6}$alkyl; —O—$C_{1-4}$alkyl; —C(=O)—$R^{10}$; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$;
or $R^3$ represents 2-oxo-1,2-dihydropyridin-3-yl,
wherein said 2-oxo-1,2-dihydropyridin-3-yl may optionally be substituted on the N-atom with a substituent selected from the group consisting of $C_{1-6}$alkyl; $C_{1-4}$alkyl substituted with one, two or three —OH substituents; $C_{1-4}$alkyl substituted with one $R^{13}$; $C_{1-4}$alkyl substituted with one $R^{18}$; and
wherein said 2-oxo-1,2-dihydropyridin-3-yl may optionally be substituted on the ring carbon atoms with in total one, two or three substituents each independently selected from the group consisting of halo; $C_{1-6}$alkyl; —C(=O)—$R^{10}$;

$R^{10}$ represents —O—$C_{1-4}$alkyl, —$NR^{11a}R^{11b}$ or Het²;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl;

Het¹ᵃ, Het¹ᶜ and Het¹ᵈ each independently is selected from the group consisting of

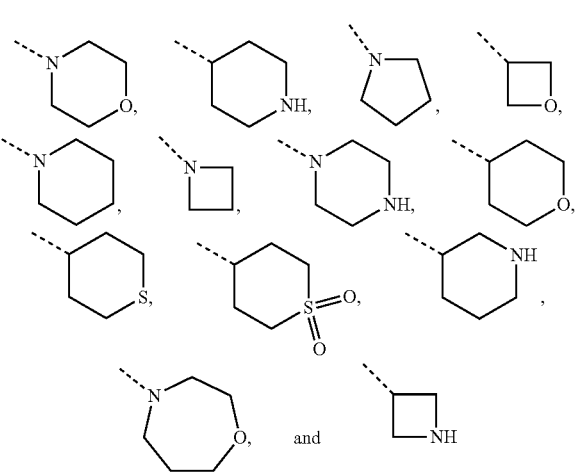

optionally substituted, on one N-atom with a substituent selected from the group consisting of $C_{1-4}$alkyl, $C_{3-6}$cycloalkyl, and $C_{1-4}$alkyl substituted with one —OH; and optionally substituted on one, two or three ring C-atoms with one or two substituents each independently selected from the group consisting of halo, and $C_{1-4}$alkyl;

Het¹ᵇ is selected from

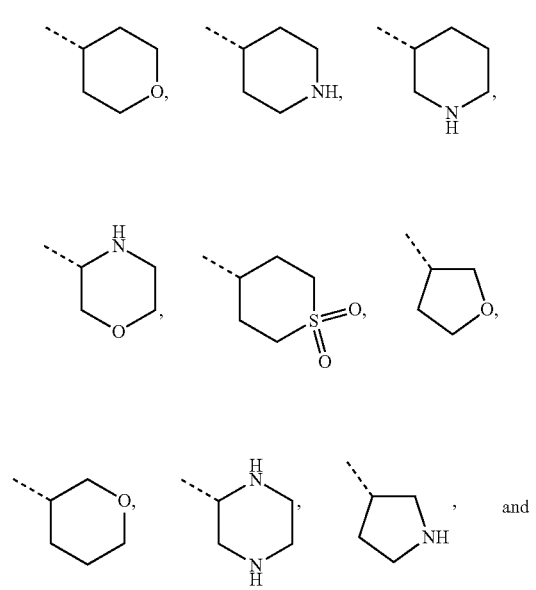

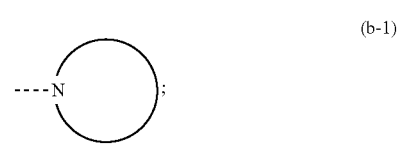

optionally substituted, on one or two ring N-atoms with a substituent each independently selected from the group consisting of $C_{1-4}$alkyl, and $C_{3-6}$cycloalkyl; and optionally substituted on one, two or three ring C-atoms with one or two halo substituents;

Het² represents a heterocyclyl of formula (b-1):

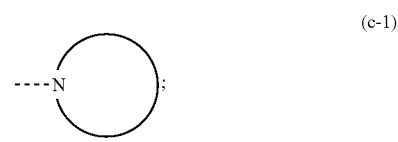

(b-1) represents a N-linked 4- to 7-membered monocyclic saturated heterocyclyl optionally containing one additional N-atom;

wherein in case (b-1) contains one additional N-atom, said one N-atom may optionally be substituted with $C_{1-4}$alkyl; and wherein (b-1) may optionally be substituted on one, two or three ring C-atoms with one or two —OH substituents;

$R^{11b}$ represents $C_{1-4}$alkyl;

$R^{13}$ represents —O—$C_{1-4}$alkyl, —C(=O)$NR^{15a}R^{15b}$, —$NR^{19a}R^{19b}$, $C_{3-6}$cycloalkyl, or Het¹ᵈ;

$R^{12}$ represents —OH, —O—$C_{1-4}$alkyl, —C(=O)$NR^{14c}R^{14d}$, $C_{3-6}$cycloalkyl, or Het¹ᶜ;

Het³ᵃ, and Het³ᵇ each independently represents a heterocyclyl of formula (c-1):

(c-1)

(c-1) represents a N-linked 4- to 7-membered monocyclic saturated heterocyclyl optionally containing one additional heteroatom selected from O and N;

$R^{11a}$, $R^{14a}$, $R^{14c}$, $R^{15a}$, $R^{17a}$ and $R^{19a}$ each independently represents hydrogen or $C_{1-4}$alkyl;

$R^{14d}$, $R^{15b}$, $R^{17b}$ and $R^{19b}$ each independently represents $C_{1-4}$alkyl; $C_{3-6}$cycloalkyl; $C_{1-4}$alkyl substituted with one —O—$C_{1-4}$alkyl substituent;

or a pharmaceutically acceptable addition salt, or a solvate thereof.

2. The compound according to claim 1, wherein
$R^1$ represents methyl;
$R^2$ represents methyl or —$CH_2$—OH.

3. The compound according to claim 1, wherein $R^4$ is hydrogen.

4. The compound according to claim 1, wherein
$R^5$ represents —$OR^7$; and
$R^7$ represents hydrogen.

5. A compound selected from:
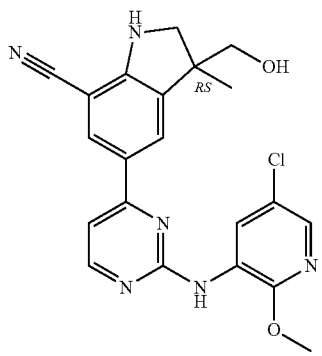
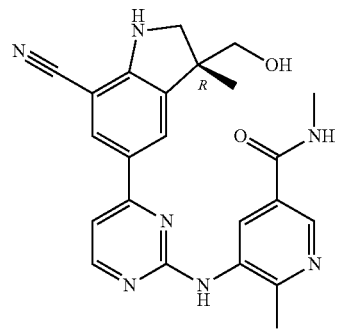
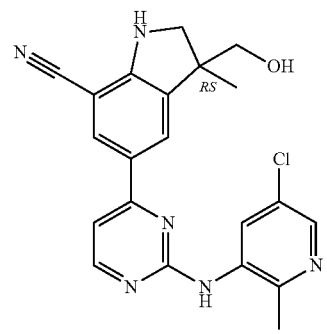
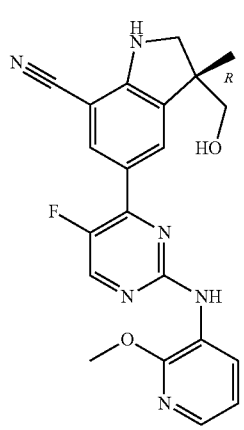
-continued
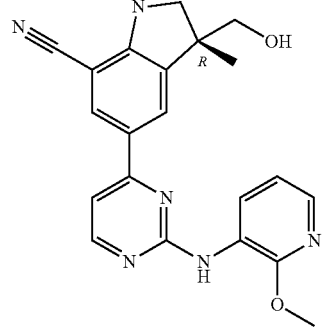
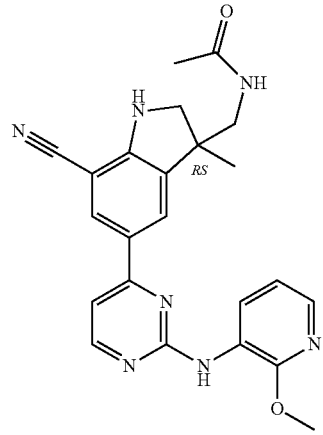
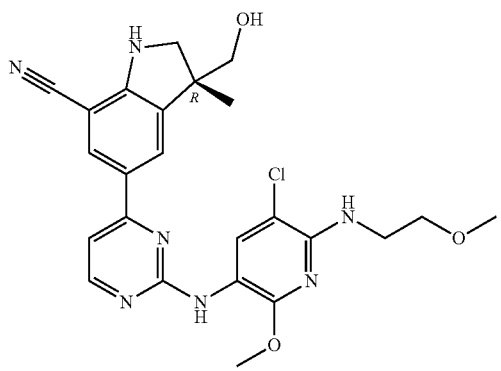
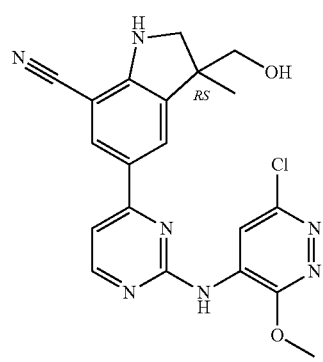

641
-continued

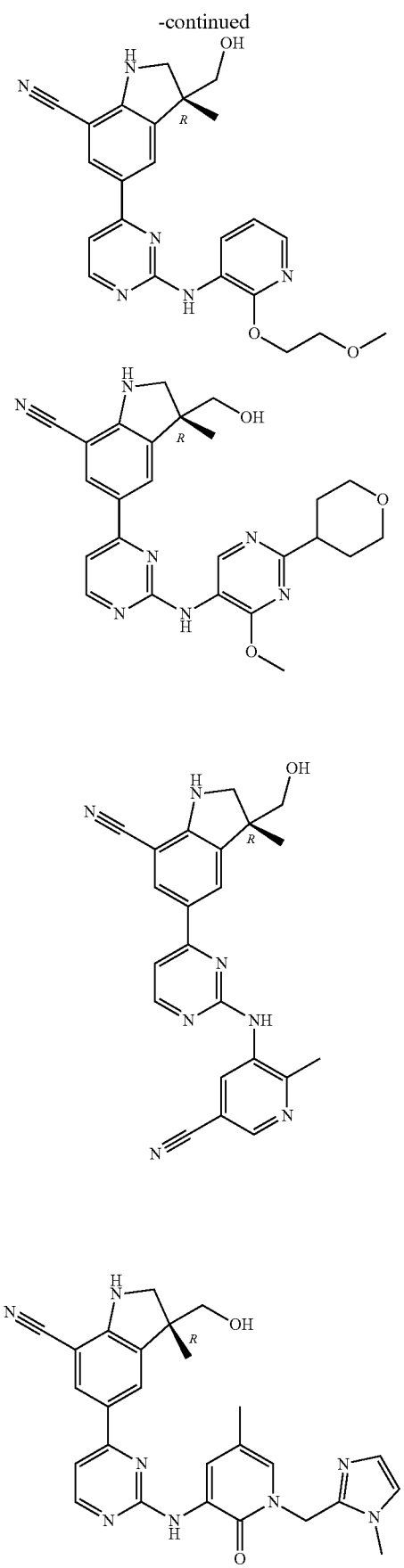

642
-continued

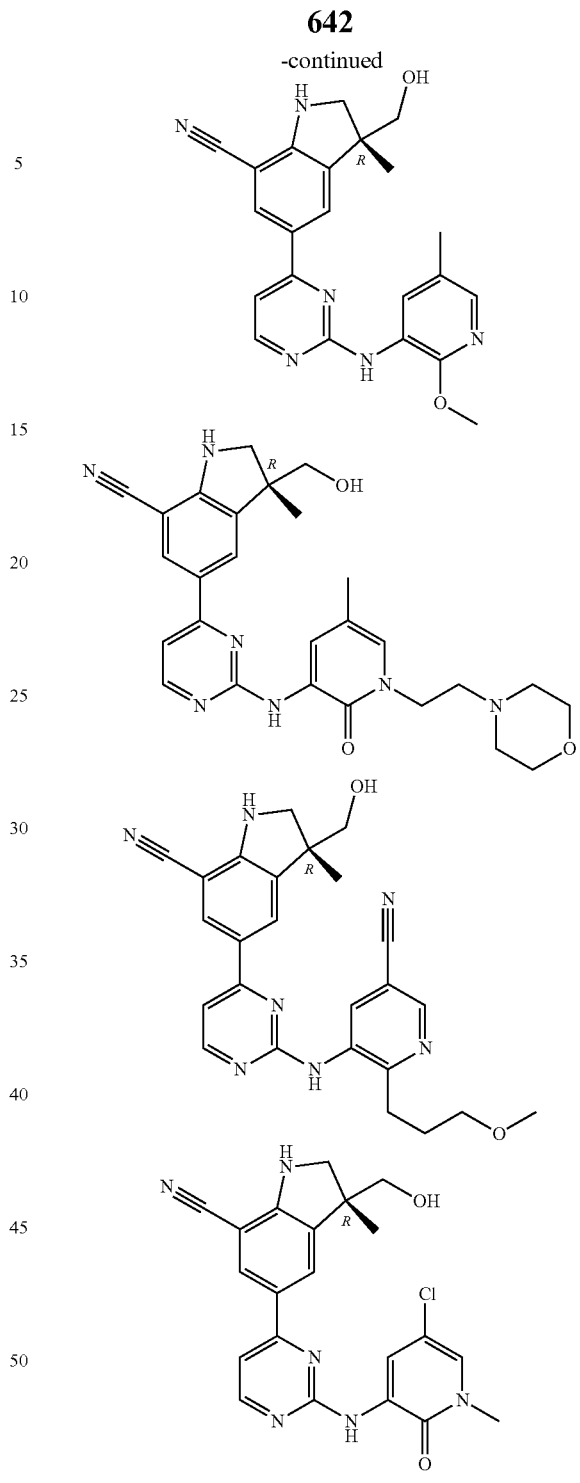

tautomers and stereoisomeric forms thereof,
and the pharmaceutically acceptable addition salts, and the solvates thereof.

6. A pharmaceutical composition comprising a compound of claim 1 or claim 5 and a pharmaceutically acceptable carrier or diluent.

7. A method of treating a B-cell malignancy selected from multiple myeloma, Hodgkin's lymphoma, mantle cell lymphoma, diffuse large B-cell lymphoma and chronic lymphocytic leukemia in a warm-blooded animal which comprises administering to said animal an effective amount of a compound of claim 1.

8. The method of claim 7, wherein the B-cell malignancy is multiple myeloma.

* * * * *